US011739157B2

(12) United States Patent
Brauer et al.

(10) Patent No.: US 11,739,157 B2
(45) Date of Patent: Aug. 29, 2023

(54) IL2RBETA/COMMON GAMMA CHAIN ANTIBODIES

(71) Applicants: Agency for Science, Technology and Research, Singapore (SG); Euchloe Bio Pte. Ltd., Singapore (SG)

(72) Inventors: Peter Brauer, Singapore (SG); John Edward Connolly, Singapore (SG); Richard Hopkins, Singapore (SG); Junyun Lai, Singapore (SG); Jianrong Lionel Low, Singapore (SG); Kar Wai Tan, Singapore (SG); Cheng-l Wang, Singapore (SG); Siok Ping Yeo, Singapore (SG)

(73) Assignees: Agency for Science, Technology and Research, Singapore (SG); Euchloe Bio Pte. Ltd., Singapore (SG)

( * ) Notice: Subject to any disclaimer, the term of this patent is extended or adjusted under 35 U.S.C. 154(b) by 461 days.

(21) Appl. No.: 16/762,895

(22) PCT Filed: Nov. 9, 2018

(86) PCT No.: PCT/EP2018/080765

§ 371 (c)(1),
(2) Date: May 8, 2020

(87) PCT Pub. No.: WO2019/092181

PCT Pub. Date: May 16, 2019

(65) Prior Publication Data

US 2022/0251221 A1 Aug. 11, 2022

Related U.S. Application Data

(60) Provisional application No. 62/735,347, filed on Sep. 24, 2018, provisional application No. 62/652,501, filed on Apr. 4, 2018.

(30) Foreign Application Priority Data

Nov. 10, 2017 (SG) ............................ 10201709289S

(51) Int. Cl.

| | |
|---|---|
| ***A61K 39/395*** | (2006.01) |
| ***A61K 39/00*** | (2006.01) |
| ***C07K 16/42*** | (2006.01) |
| ***C07K 16/46*** | (2006.01) |
| ***C07K 16/28*** | (2006.01) |
| ***A61P 35/00*** | (2006.01) |

(52) U.S. Cl.

CPC .......... *C07K 16/2866* (2013.01); *A61P 35/00* (2018.01); *C07K 16/468* (2013.01); *C07K 2317/565* (2013.01); *C07K 2317/75* (2013.01)

(58) Field of Classification Search

None

See application file for complete search history.

(56) References Cited

U.S. PATENT DOCUMENTS

| | | | | |
|---|---|---|---|---|
| 6,323,027 B1 | | 11/2001 | Burkly et al. | |
| 10,167,338 B2 | * | 1/2019 | Wang | C07K 16/1036 |
| 10,246,512 B2 | * | 4/2019 | Wang | C07K 16/1036 |
| 10,472,421 B2 | * | 11/2019 | Wang | C12N 5/0646 |
| 10,472,423 B2 | * | 11/2019 | Wang | A61P 31/00 |
| 10,696,747 B2 | * | 6/2020 | Wang | C07K 16/1036 |

FOREIGN PATENT DOCUMENTS

| | | |
|---|---|---|
| WO | WO 96/21732 A1 | 7/1996 |
| WO | WO 97/43416 A1 | 11/1997 |
| WO | WO 2011/127324 A2 | 10/2011 |
| WO | WO 2017/021540 A1 | 2/2017 |

OTHER PUBLICATIONS

Berretta, F. et al. (2011) IL-2 contributes to maintaining a balance between CD4+ Foxp3+ regulatory T cells and effector CD4+ T cells required for immune control of blood-stage malaria infection. J. Immunol. 186, 4862-4871. (Year: 2011).*

Benson, A. et al. (2012) Microbial infection-induced expansion of effector T cells overcomes the suppressive effects of regulatory T cells via an IL-2 deprivation mechanism. J. Immunol. 188, 800-810. (Year: 2012).*

Shevach. Application of IL-2 therapy to target T regulatory cell function. Trends in Immunology, Dec. 2012, vol. 33, No. 12. (Year: 2012).*

International Search Report and Written Opinion for International Application No. PCT/EP2018/080765, dated Apr. 11, 2019.

Chang et al., Anti-gamma chain and anti-IL-2Rbeta mAbs in combination with donor splenocyte transfusion induce H-Y skin graft acceptance in murine model. Transplant Proc. Nov. 2009;41(9):3913-5. doi: 10.1016/j.transproceed.2009.06.223.

Dutcher et al., High dose interleukin-2 (Aldesleukin)—expert consensus on best management practices-2014. J Immunother Cancer. Sep. 16, 2014;2(1):26. doi: 10.1186/s40425-014-0026-0.

Ellery et al., Activation of the interleukin 2 receptor: a possible role for tyrosine phosphatases. Cell Signal. Jun. 2000;12(6):367-73.

Hechinger et al., Therapeutic activity of multiple common gamma-chain cytokine inhibition in acute and chronic GVHD. Blood. Jan. 15, 2015;125(3):570-80. doi: 10.1182/blood-2014-06-581793. Epub Oct. 28, 2014.

Meghnem et al., Cutting Edge: Differential Fine-Tuning of IL-2- and IL-15-Dependent Functions by Targeting Their Common IL-2/15Rß/?c Receptor. J Immunol. Jun. 15, 2017;198(12):4563-4568. doi: 10.4049/jimmunol.1700046. Epub May 15, 2017.

Nakamura et al., Heterodimerization of the IL-2 receptor beta- and gamma-chain cytoplasmic domains is required for signalling. Nature. May 26, 1994;369(6478):330-3.

(Continued)

*Primary Examiner* — Maher M Haddad

(74) *Attorney, Agent, or Firm* — Wolf, Greenfield & Sacks, P.C.

(57) ABSTRACT

Antigen binding molecules capable of binding to CD122 and/or common γ chain (CD132) are disclosed herein. Also disclosed are compositions comprising such antigen binding molecules, and uses and methods using the same.

15 Claims, 83 Drawing Sheets

Specification includes a Sequence Listing.

(56) References Cited

OTHER PUBLICATIONS

Nelson et al., Cytoplasmic domains of the interleukin-2 receptor beta and gamma chains mediate the signal for T-cell proliferation. Nature. May 26, 1994;369(6478):333-6.
Rudikoff et al., Single amino acid substitution altering antigen-binding specificity. Proc Natl Acad Sci U S A. Mar. 1982;79(6):1979-83.
Spiess et al., Alternative molecular formats and therapeutic applications for bispecific antibodies. Mol Immunol. Oct. 2015;67(2 Pt A):95-106. doi: 10.1016/j.molimm.2015.01.003. Epub Jan. 27, 2015.
PCT/EP2018/080765, Apr. 11, 2019, International Search Report and Written Opinion.
Invitation to Pay Additional Fees for Application No. PCT/EP2018/080765, dated Feb. 21, 2019.
International Preliminary Report on Patentability for Application No. PCT/EP2018/080765, dated May 22, 2020.
Hamilton et al., IL-2 complex treatment can protect naive mice from bacterial and viral infection. J Immunol. Dec. 1, 2010;185(11):6584-90. doi: 10.4049/jimmunol.1001215. Epub Oct. 29, 2010.
Molloy et al., Cutting edge: IL-2 immune complexes as a therapy for persistent virus infection. J Immunol. Apr. 15, 2009;182(8):4512-5. doi: 10.4049/jimmunol.0804175.
PCT/EP2018/080765, Feb. 21, 2019, Invitation to Pay Additional Fees.
PCT/EP2018/080765, May 22, 2020, International Preliminary Report on Patentability.
Drerup et al., CD 122 selective IL 2/anti IL 2 complexes reduce regulatory T cell function and promote CD8+ T cell polyfunctionality for durable ovarian cancer immunotherapy, Cancer Res. Nov. 15, 2020;80(22):5063-5075. doi: 10.1158/0008-5472.CAN-20-0002. Epub Sep. 18, 2020.
Fuse et al., Recall responses by helpless memory CD8+ T cells are restricted by the up-regulation of PD-1. J Immunol. Apr. 1, 2009;182(7):4244-54. doi: 10.4049/jimmunol.0802041.
Tomala et al., IL-2/anti-IL-2 mAb immunocomplexes: a renascence of IL-2 in cancer immunotherapy? Oncoimmunology. Nov. 3, 2015;5(3):e1102829. doi: 10.1080/2162402X.2015.1102829. eCollection Mar. 2016.
Zhang et al., Profiling the dynamic expression of checkpoint molecules on cytokine-induced killer cells from non-small-cell lung cancer patients. Oncotarget. Jul. 12, 2016;7(28):43604-43615. doi: 10.18632/oncotarget.9871.

* cited by examiner

| | P2C4/P1A3 | P2C4_FW2/P1A3_FW2 | P2C4/P1A3 Crossmab |
|---|---|---|---|
| EC50 | 2.691 | 48.76 | 21.18 |

| | P2C4/P1A3 | P2C4_FW2/P1A3_FW2 | P2C4/P1A3 Crossmab |
|---|---|---|---|
| EC50 | 0.4164 | 1.924 | 0.7718 |

| | IL-2 | Isotype Control | P2C4/P1A3 | P2C4FW2/P1A3 | P2C4/P1A3 Crossmab | P2E6/P1A10 | P2C4/P1A10 | P1D10/P1A10 | P1E7/P1A10 | P1G11/P1A10 |
|---|---|---|---|---|---|---|---|---|---|---|
| EC50 | 0.085 | | 0.4935 | 0.9976 | 6.542 | 1.198 | 0.1486 | 0.5136 | 1.962 | 1.631 |

| | IL-2 | IL-15 | P2C4/P1A3 | P2C4/P1A10 | P2C4/P1A3 Crossmab | P2C4/P1A10 Crossmab | P2C4/P1A10 Duobody | Trastuzumab |
|---|---|---|---|---|---|---|---|---|
| EC50 | 0.01977 | 0.009593 | 0.3667 | 0.143 | 4.91 | 1.4 | 3.797 | ~ 0.7993 |

| | P2C4/P1A3 | P2C4/P1A10 | Isotype Control | IL-2 |
|---|---|---|---|---|
| EC50 | 0.7016 | 0.2118 | ~ 450.7 | 0.07268 |

| | P2C4/P1A3 | P2C4/P1A10 | Isotype | IL-2 |
|---|---|---|---|---|
| EC50 | ~ 1.49 | 0.7645 | ~ 10.16 | 3.023 |

| | P2C4/P1A3 | P2C4/P1A10 | Isotype | IL-2 |
|---|---|---|---|---|
| EC50 | ~ 5.1 | 1.357 | ~ 343.3 | 0.04443 |

| | P2C4/P1A3 | P2C4/P1A10 | Isotype | IL-2 |
|---|---|---|---|---|
| EC50 | ~ 0.2631 | 0.5313 | ~ 1473 | 0.01036 |

| | P2C4/P1A3 | P2C4/P1A10 | Isotype | IL-2 |
|---|---|---|---|---|
| EC50 | | ~ 0.6571 | 48.61 | ~ 728235356 |

| | P2C4/P1A3 | P2C4/P1A10 | Isotype | IL-2 |
|---|---|---|---|---|
| EC50 | ~ 2.04 | 0.6543 | | 1.08 |

| | P2C4/P1A3 | P2C4/P1A10 | Isotype | IL-2 |
|---|---|---|---|---|
| EC50 | | ~ 1.401 | | 0.1473 |

| | P2C4/P1A3 | P2C4/P1A10 | Isotype | IL-2 |
|---|---|---|---|---|
| EC50 | ~ 8.247 | 5.649 | ~ 149.2 | ~ 1609 |

| | P2C4/P1A3 | P2C4/P1A10 | Isotype | IL-2 |
|---|---|---|---|---|
| EC50 | 282.5 | ~ 1578 | | |

Treatment groups:
1) No VSTs
2) VSTs + Isotype (5 mg/kg per dose given every 2 weeks), total 2 doses
3) VSTs + IL-2 (1,000 IU per dose x 5 doses)
4) VSTs + P2C4/P1A3 (5 mg/kg per dose given every 2 weeks), total 2 doses
5) VSTs + P2C4/P1A10 (5 mg/kg per dose given every 2 weeks), total 2 doses Mouse deaths before endpoint:
Day 11 1x VST + P2C4/P1A3 mouse died (anaesthesia)
Day 18 1x No VST mouse euthanised
Day 22 1x No VST mouse found dead

| | IL-2 | IL-15 | Isotype | P2C4/P1A3 | P2C4/P1A10 |
|---|---|---|---|---|---|
| EC50 | 0.0446 | 0.04175 | ~ 225.9 | 4.463 | 1.521 |

| | IL-2 | IL-15 | Isotype | P2C4/P1A3 | P2C4/P1A10 |
|---|---|---|---|---|---|
| EC50 | 0.01308 | ~ 0.07182 | | 2.708 | 0.7104 |

| | IL-2 | IL-15 | Isotype | P2C4/P1A3 | P2C4/P1A10 |
|---|---|---|---|---|---|
| EC50 | 0.0153 | 0.0519 | ~ 22.08 | 1.592 | 0.8264 |

| | IL2 | Isotype | P2C4/P1A3 | P2C4/P1A10 |
|---|---|---|---|---|
| EC50 | 0.09995 | ~ 45.42 | 1.993 | 3.501 |

| | IL2 | Isotype | P2C4/P1A3 | P2C4/P1A10 |
|---|---|---|---|---|
| EC50 | 0.04946 | 30.8 | 1.892 | 4.309 |

| | IL2 | Isotype | P2C4/P1A3 | P2C4/P1A10 |
|---|---|---|---|---|
| EC50 | 0.05647 | | 2.444 | 171.7 |

| | IL2 | Isotype | P2C4/P1A3 | P2C4/P1A10 |
|---|---|---|---|---|
| EC50 | 0.01859 | | 1.709 | 5.491 |

Treatment groups:
1) No VSTs
2) VSTs + IL-2 (40,000 IU/kg per dose x 5 doses)
3) VSTs + Treg + Isotype (5 mg/kg per dose given every 2 weeks), total 2 doses
4) VSTs + Treg + IL-2 (40,000 IU/kg per dose x 5 doses)
5) VSTs + Treg + P2C4/ P1A3 (5 mg/kg per dose given every 2 weeks), total 2 doses
6) VSTs + Treg + P2C4/ P1A10 (5 mg/kg per dose given every 2 weeks), total 2 doses

SEQUENCE LISTING

```
<160> NUMBER OF SEQ ID NOS: 455

<210> SEQ ID NO 1
<211> LENGTH: 121
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120


<210> SEQ ID NO 2
<211> LENGTH: 119
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Met His Trp Val Arg Gln Ala Pro Gly Gln Ser Leu Glu Trp Met
```

```
        35                  40                  45

Gly Trp Ile Asn Thr Gly Asn Gly Asn Thr Lys Tyr Ser Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Gly Gln Leu Glu Arg Leu Tyr Phe Trp Gly Gln Gly
            100                 105                 110

Thr Leu Val Thr Val Ser Ser
        115


<210> SEQ ID NO 3
<211> LENGTH: 114
<212> TYPE: PRT
<213> ORGANISM: Artificial Sequence
<220> FEATURE:
<223> OTHER INFORMATION: Synthetic

<400> SEQUENCE: 3

His Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Asp Tyr Trp Gly Gln Gly Thr Leu Val Thr Val
            100                 105                 110

Ser Ser


<210> SEQ ID NO 4
<211> LENGTH: 117
<212> TYPE: PRT
<213> ORGANISM: Artificial Sequence
<220> FEATURE:
<223> OTHER INFORMATION: Synthetic

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Ser Ser Gly Asp Ala Phe Asp Ile Trp Gly Gln Gly Thr Met
```

```
            100                 105                 110

Val Thr Val Ser Ser
        115


<210> SEQ ID NO 5
<211> LENGTH: 121
<212> TYPE: PRT
<213> ORGANISM: Artificial Sequence
<220> FEATURE:
<223> OTHER INFORMATION: Synthetic

<400> SEQUENCE: 5

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Asn Trp Gly
            100                 105                 110

Gln Gly Thr Leu Val Thr Val Ser Ser
        115                 120


<210> SEQ ID NO 6
<211> LENGTH: 121
<212> TYPE: PRT
<213> ORGANISM: Artificial Sequence
<220> FEATURE:
<223> OTHER INFORMATION: Synthetic

<400> SEQUENCE: 6

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120


<210> SEQ ID NO 7
<211> LENGTH: 121
<212> TYPE: PRT
<213> ORGANISM: Artificial Sequence
<220> FEATURE:
```

<223> OTHER INFORMATION: Synthetic

<400> SEQUENCE: 7

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Pro Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser
115 120

<210> SEQ ID NO 8
<211> LENGTH: 121
<212> TYPE: PRT
<213> ORGANISM: Artificial Sequence
<220> FEATURE:
<223> OTHER INFORMATION: Synthetic

<400> SEQUENCE: 8

Glu Val Gln Leu Val Gln Ser Gly Ala Glu Val Lys Lys Pro Gly Ser
1 5 10 15

Thr Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser
115 120

<210> SEQ ID NO 9
<211> LENGTH: 121
<212> TYPE: PRT
<213> ORGANISM: Artificial Sequence
<220> FEATURE:
<223> OTHER INFORMATION: Synthetic

<400> SEQUENCE: 9

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met

```
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Pro Val Thr Val Ser Ser
        115                 120


<210> SEQ ID NO 10
<211> LENGTH: 121
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Asn
        115                 120


<210> SEQ ID NO 11
<211> LENGTH: 121
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Gln Ser Gly Ala Glu Val Lys Glu Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Ile Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

```
Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120


<210> SEQ ID NO 12
<211> LENGTH: 121
<212> TYPE: PRT
<213> ORGANISM: Artificial Sequence
<220> FEATURE:
<223> OTHER INFORMATION: Synthetic

<400> SEQUENCE: 12

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Asn Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120


<210> SEQ ID NO 13
<211> LENGTH: 121
<212> TYPE: PRT
<213> ORGANISM: Artificial Sequence
<220> FEATURE:
<223> OTHER INFORMATION: Synthetic

<400> SEQUENCE: 13

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Pro Gly Thr Leu Val Thr Val Ser Ser
        115                 120


<210> SEQ ID NO 14
<211> LENGTH: 121
<212> TYPE: PRT
<213> ORGANISM: Artificial Sequence
```

<220> FEATURE:
<223> OTHER INFORMATION: Synthetic

<400> SEQUENCE: 14

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Met Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120
```

<210> SEQ ID NO 15
<211> LENGTH: 121
<212> TYPE: PRT
<213> ORGANISM: Artificial Sequence
<220> FEATURE:
<223> OTHER INFORMATION: Synthetic

<400> SEQUENCE: 15

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Thr Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120
```

<210> SEQ ID NO 16
<211> LENGTH: 121
<212> TYPE: PRT
<213> ORGANISM: Artificial Sequence
<220> FEATURE:
<223> OTHER INFORMATION: Synthetic

<400> SEQUENCE: 16

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30
```

-continued

```
Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120


<210> SEQ ID NO 17
<211> LENGTH: 121
<212> TYPE: PRT
<213> ORGANISM: Artificial Sequence
<220> FEATURE:
<223> OTHER INFORMATION: Synthetic

<400> SEQUENCE: 17

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Asn Val Ser Ser
        115                 120


<210> SEQ ID NO 18
<211> LENGTH: 121
<212> TYPE: PRT
<213> ORGANISM: Artificial Sequence
<220> FEATURE:
<223> OTHER INFORMATION: Synthetic

<400> SEQUENCE: 18

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asn Tyr
            20                  25                  30

Tyr Met His Trp Val Arg Gln Ala Pro Gly Gln Gly Leu Glu Trp Ile
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Gly Glu Tyr Tyr Tyr Asp Ser Ser Gly Tyr Tyr Tyr Trp Gly
100 105 110

Gln Gly Thr Leu Val Thr Val Ser Ser
115 120

<210> SEQ ID NO 19
<211> LENGTH: 121
<212> TYPE: PRT
<213> ORGANISM: Artificial Sequence
<220> FEATURE:
<223> OTHER INFORMATION: Synthetic

<400> SEQUENCE: 19

Glu Val Gln Leu Val Gln Ser Gly Ala Glu Val Lys Lys Pro Gly Ser
1 5 10 15

Ser Val Lys Val Ser Cys Lys Ala Thr Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser
115 120

<210> SEQ ID NO 20
<211> LENGTH: 121
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Pro Val Thr Val Ser Ser
115 120

<210> SEQ ID NO 21
<211> LENGTH: 121
<212> TYPE: PRT

<213> ORGANISM: Artificial Sequence
<220> FEATURE:
<223> OTHER INFORMATION: Synthetic

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser
        115                 120

<210> SEQ ID NO 22
<211> LENGTH: 126
<212> TYPE: PRT
<213> ORGANISM: Artificial Sequence
<220> FEATURE:
<223> OTHER INFORMATION: Synthetic

<400> SEQUENCE: 22

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Tyr Ser Ser Ser Trp Tyr Tyr Tyr Tyr Tyr Gly
            100                 105                 110

Met Asp Val Trp Gly Gln Gly Thr Thr Val Thr Val Ser Ser
        115                 120                 125

<210> SEQ ID NO 23
<211> LENGTH: 120
<212> TYPE: PRT
<213> ORGANISM: Artificial Sequence
<220> FEATURE:
<223> OTHER INFORMATION: Synthetic

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Ile Ser Ser Arg
            20                  25                  30

Ser Asp His Trp Gly Trp Val Arg Gln Pro Pro Gly Lys Gly Leu Glu
35 40 45

Trp Ile Gly Ser Ile Ser Tyr Ser Gly Ser Thr Tyr Tyr Asn Pro Ser
50 55 60

Leu Lys Ser Arg Val Thr Ile Ser Val Asp Thr Ser Lys Asn Gln Leu
65 70 75 80

Ser Leu Lys Leu Ser Ser Val Thr Ala Ala Asp Thr Ala Val Tyr Tyr
85 90 95

Cys Ala Arg Glu Ser His Pro Ala Ala Ala Leu Val Gly Trp Gly Gln
100 105 110

Gly Thr Leu Val Thr Val Ser Ser
115 120

<210> SEQ ID NO 24
<211> LENGTH: 112
<212> TYPE: PRT
<213> ORGANISM: Artificial Sequence
<220> FEATURE:
<223> OTHER INFORMATION: Synthetic

<400> SEQUENCE: 24

Glu Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Thr Pro Ala Phe Trp Gly Gln Gly Thr Leu Val Thr Val Ser Ser
100 105 110

<210> SEQ ID NO 25
<211> LENGTH: 117
<212> TYPE: PRT
<213> ORGANISM: Artificial Sequence
<220> FEATURE:
<223> OTHER INFORMATION: Synthetic

<400> SEQUENCE: 25

Gln Val Gln Leu Gln Gln Trp Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Gly Gly Ser Asn Leu Asp Trp Phe Asp Pro Trp Gly Gln Gly Thr Leu 100 105 110

Val Thr Val Ser Ser
115

<210> SEQ ID NO 26
<211> LENGTH: 118
<212> TYPE: PRT
<213> ORGANISM: Artificial Sequence
<220> FEATURE:
<223> OTHER INFORMATION: Synthetic

<400> SEQUENCE: 26

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Glu Leu Ser Ser Val Thr Ala Ala Asp Thr Ala Val Tyr Tyr Cys Ala
85 90 95

Arg Ala Asp Arg Arg Phe Gly Glu Leu Arg Tyr Trp Gly Gln Gly Thr
100 105 110

Leu Val Thr Val Ser Ser
115

<210> SEQ ID NO 27
<211> LENGTH: 121
<212> TYPE: PRT
<213> ORGANISM: Artificial Sequence
<220> FEATURE:
<223> OTHER INFORMATION: Synthetic

<400> SEQUENCE: 27

Gln Val Gln Leu Val Gln Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Asp Leu His Trp Val Arg Gln Val Pro Gly Lys Gly Leu Glu Trp Val
35 40 45

Ser Leu Ile Ser Tyr Asp Gly Ser Asn Lys Tyr Tyr Ala Asp Ser Val
50 55 60

Lys Gly Arg Phe Thr Ile Ser Arg Asp Asn Ala Glu Asn Ser Leu Tyr
65 70 75 80

Leu Gln Met Asn Ser Leu Arg Ala Glu Asp Thr Ala Val Tyr Tyr Cys
85 90 95

Ala Arg Glu Pro Ile Thr Gly Thr Ser Asp Leu Phe Asp Tyr Trp Gly
100 105 110

Gln Gly Thr Leu Val Thr Val Ser Ser
115 120

<210> SEQ ID NO 28
<211> LENGTH: 117
<212> TYPE: PRT
<213> ORGANISM: Artificial Sequence
<220> FEATURE:

<223> OTHER INFORMATION: Synthetic

<400> SEQUENCE: 28

Gln Val Gln Leu Gln Glu Ser Gly Pro Gly Leu Val Lys Pro Ser Gly
1 5 10 15

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Val Arg Glu Gly Gly Leu Arg Glu Glu His Trp Gly Gln Gly Thr Leu
100 105 110

Val Thr Val Ser Ser
115

<210> SEQ ID NO 29
<211> LENGTH: 117
<212> TYPE: PRT
<213> ORGANISM: Artificial Sequence
<220> FEATURE:
<223> OTHER INFORMATION: Synthetic

<400> SEQUENCE: 29

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Thr Asp Thr Ala Met Ala Asp Tyr Trp Gly Gln Gly Thr Leu
100 105 110

Val Thr Val Ser Ser
115

<210> SEQ ID NO 30
<211> LENGTH: 120
<212> TYPE: PRT
<213> ORGANISM: Artificial Sequence
<220> FEATURE:
<223> OTHER INFORMATION: Synthetic

<400> SEQUENCE: 30

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Gly Asn
20 25 30

Ser Ala Thr Trp Asn Trp Ile Arg Gln Ser Pro Ser Arg Gly Leu Glu

```
        35                  40                  45

Trp Leu Gly Arg Thr Tyr Tyr Arg Ser Lys Trp Asn His Asp Tyr Ala
    50                  55                  60

Glu Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Ser Lys Ser Ala Phe Asp Ile Trp Gly Gln
            100                 105                 110

Gly Thr Met Val Thr Val Ser Ser
        115                 120


<210> SEQ ID NO 31
<211> LENGTH: 113
<212> TYPE: PRT
<213> ORGANISM: Artificial Sequence
<220> FEATURE:
<223> OTHER INFORMATION: Synthetic

<400> SEQUENCE: 31

Gln Leu Gln Leu Gln Glu Ser Gly Pro Gly Leu Val Lys Pro Ser Glu
1               5                   10                  15

Thr Leu Ser Leu Thr Cys Ser Val Phe Gly Val Ser Ile Thr Ser Gly
            20                  25                  30

Ser Trp Trp Ser Trp Val Arg Gln Ser Pro Gly Lys Glu Leu Glu Trp
        35                  40                  45

Ile Gly Glu Ile Tyr His Asn Gly Asn Thr Asn Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Ser Gly Phe Asp Tyr Trp Gly Gln Gly Thr Leu Val Thr Val Ser
            100                 105                 110

Ser


<210> SEQ ID NO 32
<211> LENGTH: 120
<212> TYPE: PRT
<213> ORGANISM: Artificial Sequence
<220> FEATURE:
<223> OTHER INFORMATION: Synthetic

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Ile Ser Ser Arg
            20                  25                  30

Ser Asp His Trp Gly Trp Val Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Glu Ser His Pro Ala Ala Ala Leu Val Gly Trp Gly Gln
```

```
            100                 105                 110

Gly Thr Leu Val Thr Val Ser Ser
        115                 120


<210> SEQ ID NO 33
<211> LENGTH: 126
<212> TYPE: PRT
<213> ORGANISM: Artificial Sequence
<220> FEATURE:
<223> OTHER INFORMATION: Synthetic

<400> SEQUENCE: 33

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Asp Tyr Gly Asp Ser Ser Asn Tyr Tyr Tyr Tyr Tyr
            100                 105                 110

Met Asp Val Trp Gly Lys Gly Thr Thr Val Thr Val Ser Ser
        115                 120                 125


<210> SEQ ID NO 34
<211> LENGTH: 127
<212> TYPE: PRT
<213> ORGANISM: Artificial Sequence
<220> FEATURE:
<223> OTHER INFORMATION: Synthetic

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Thr Ser Gly Asp Tyr Ser Ser Gly Trp Tyr Leu Gly Val
            100                 105                 110

Pro Phe Asp Tyr Trp Gly Gln Gly Thr Leu Val Thr Val Ser Ser
        115                 120                 125


<210> SEQ ID NO 35
<211> LENGTH: 108
<212> TYPE: PRT
<213> ORGANISM: Artificial Sequence
<220> FEATURE:
```

<223> OTHER INFORMATION: Synthetic

<400> SEQUENCE: 35

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105

<210> SEQ ID NO 36
<211> LENGTH: 107
<212> TYPE: PRT
<213> ORGANISM: Artificial Sequence
<220> FEATURE:
<223> OTHER INFORMATION: Synthetic

<400> SEQUENCE: 36

Asp Ile Gln Met Thr Gln Ser Pro Ser Thr Leu Ser Ala Ser Val Gly
1               5                   10                  15

Asp Arg Val Thr Leu Ser Cys Arg Ala Gly Gln Ala Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Asn Leu Glu Ser Gly Val Pro Ser Arg Phe Ser Gly
    50                  55                  60

Gly Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Tyr
                85                  90                  95

Thr Phe Gly Gln Gly Thr Lys Leu Glu Ile Arg
            100                 105

<210> SEQ ID NO 37
<211> LENGTH: 107
<212> TYPE: PRT
<213> ORGANISM: Artificial Sequence
<220> FEATURE:
<223> OTHER INFORMATION: Synthetic

<400> SEQUENCE: 37

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Tyr
            20                  25                  30

Leu Asn Trp Tyr Gln Leu Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro

```
65                  70                  75                  80

Glu Asp Ile Ala Thr Tyr Tyr Cys Leu Gln Leu Tyr Asp Tyr Pro Leu
                85                  90                  95

Thr Phe Gly Gly Gly Thr Lys Val Glu Ile Lys
            100                 105


<210> SEQ ID NO 38
<211> LENGTH: 110
<212> TYPE: PRT
<213> ORGANISM: Artificial Sequence
<220> FEATURE:
<223> OTHER INFORMATION: Synthetic

<400> SEQUENCE: 38

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn
            20                  25                  30

Tyr Val Gln Trp Tyr Gln Gln Arg Pro Gly Ser Ser Pro Thr Thr Val
        35                  40                  45

Ile Phe Asp Asp Asn Gln Arg Pro Thr Gly Val Pro Asp Arg Phe Ser
    50                  55                  60

Ala Ala Ile Asp Thr Ser Ser Ser Ser Ala Ser Leu Thr Ile Ser Gly
65                  70                  75                  80

Leu Thr Ala Glu Asp Glu Ala Asp Tyr Tyr Cys Gln Ser Ser His Ser
                85                  90                  95

Thr Ala Val Val Phe Gly Gly Gly Thr Lys Leu Thr Val Leu
            100                 105                 110


<210> SEQ ID NO 39
<211> LENGTH: 108
<212> TYPE: PRT
<213> ORGANISM: Artificial Sequence
<220> FEATURE:
<223> OTHER INFORMATION: Synthetic

<400> SEQUENCE: 39

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly Asp Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105


<210> SEQ ID NO 40
<211> LENGTH: 108
<212> TYPE: PRT
<213> ORGANISM: Artificial Sequence
<220> FEATURE:
<223> OTHER INFORMATION: Synthetic

<400> SEQUENCE: 40
```

-continued

```
Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Asn Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105


<210> SEQ ID NO 41
<211> LENGTH: 108
<212> TYPE: PRT
<213> ORGANISM: Artificial Sequence
<220> FEATURE:
<223> OTHER INFORMATION: Synthetic

<400> SEQUENCE: 41

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105


<210> SEQ ID NO 42
<211> LENGTH: 108
<212> TYPE: PRT
<213> ORGANISM: Artificial Sequence
<220> FEATURE:
<223> OTHER INFORMATION: Synthetic

<400> SEQUENCE: 42

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
```

```
                85                  90                  95

Asp Thr Val Val Phe Gly Gly Gly Thr Lys Leu Thr
            100                 105


<210> SEQ ID NO 43
<211> LENGTH: 108
<212> TYPE: PRT
<213> ORGANISM: Artificial Sequence
<220> FEATURE:
<223> OTHER INFORMATION: Synthetic

<400> SEQUENCE: 43

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Ile Ser Trp Tyr Gln Gln His Pro Gly Thr Ala Pro Lys Leu
        35                  40                  45

Ile Ile Tyr Asp Phe Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105


<210> SEQ ID NO 44
<211> LENGTH: 108
<212> TYPE: PRT
<213> ORGANISM: Artificial Sequence
<220> FEATURE:
<223> OTHER INFORMATION: Synthetic

<400> SEQUENCE: 44

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly His Tyr
            20                  25                  30

Asp Phe Val Ser Trp Tyr Gln Gln His Pro Gly Thr Ala Pro Lys Leu
        35                  40                  45

Ile Ile Tyr Asp Asn Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105


<210> SEQ ID NO 45
<211> LENGTH: 108
<212> TYPE: PRT
<213> ORGANISM: Artificial Sequence
<220> FEATURE:
<223> OTHER INFORMATION: Synthetic

<400> SEQUENCE: 45

Gln Ser Ala Leu Thr Gln Pro Ala Ser Val Ser Gly Ser Pro Gly Gln
1               5                   10                  15
```

Ser Ile Val Ile Ser Cys Thr Gly Thr Ser Ser Asp Ile Gly His Tyr
20 25 30

Asp Phe Val Ser Trp Tyr Gln Gln His Pro Gly Thr Ala Pro Lys Leu
35 40 45

Ile Ile Tyr Asp Ile Asn Asn Arg Pro Ser Gly Ile Ser Asn Arg Phe
50 55 60

Ser Gly Ser Lys Ser Asp Asn Met Ala Ser Leu Thr Ile Ser Gly Leu
65 70 75 80

Gln Pro Glu Asp Glu Ala Asp Tyr Tyr Cys Ser Ala Tyr Thr Ser Ser
85 90 95

Asp Thr Val Val Phe Gly Gly Gly Thr Lys Leu Thr
100 105

<210> SEQ ID NO 46
<211> LENGTH: 108
<212> TYPE: PRT
<213> ORGANISM: Artificial Sequence
<220> FEATURE:
<223> OTHER INFORMATION: Synthetic

<400> SEQUENCE: 46

Gln Ser Ala Leu Thr Gln Pro Ala Ser Val Ser Gly Ser Pro Gly Gln
1 5 10 15

Ser Ile Ala Ile Ser Cys Thr Gly Thr Ser Ser Asp Ile Gly Asp Tyr
20 25 30

Asp Phe Val Ser Trp Tyr Gln Gln His Pro Gly Thr Ala Pro Lys Leu
35 40 45

Ile Ile Tyr Asp Ile Asn Asn Arg Pro Ser Gly Ile Ser Asn Arg Phe
50 55 60

Ser Gly Ser Lys Ser Asp Asn Met Ala Ser Leu Ile Ile Ser Gly Leu
65 70 75 80

Gln Pro Glu Asp Glu Ala Asp Tyr Tyr Cys Ser Ala Tyr Thr Ser Ser
85 90 95

Asp Thr Leu Val Phe Gly Gly Gly Thr Lys Leu Thr
100 105

<210> SEQ ID NO 47
<211> LENGTH: 108
<212> TYPE: PRT
<213> ORGANISM: Artificial Sequence
<220> FEATURE:
<223> OTHER INFORMATION: Synthetic

<400> SEQUENCE: 47

Gln Ser Ala Leu Thr Gln Pro Ala Ser Val Ser Gly Ser Pro Gly Gln
1 5 10 15

Ser Ile Ala Ile Ser Cys Thr Gly Thr Ser Ser Asp Ile Gly His Tyr
20 25 30

Asp Phe Val Ser Trp Tyr Gln Gln His Pro Gly Thr Ala Pro Lys Leu
35 40 45

Ile Ile Tyr Asp Ile Asn Asn Arg Pro Ser Gly Ile Ser Asn Arg Phe
50 55 60

Ser Gly Ser Lys Ser Asp Asp Met Ala Ser Leu Thr Ile Ser Gly Leu
65 70 75 80

Gln Pro Glu Asp Glu Ala Asp Tyr Tyr Cys Ser Ala Tyr Thr Ser Ser
85 90 95

Asp Thr Val Val Phe Gly Gly Gly Thr Lys Leu Thr 100 105

<210> SEQ ID NO 48
<211> LENGTH: 108
<212> TYPE: PRT
<213> ORGANISM: Artificial Sequence
<220> FEATURE:
<223> OTHER INFORMATION: Synthetic

<400> SEQUENCE: 48

Gln Ser Ala Leu Thr Gln Pro Ala Ser Val Ser Gly Ser Pro Gly Gln
1 5 10 15

Ser Ile Ala Ile Ser Cys Thr Gly Thr Ser Ser Asp Ile Gly His Tyr
20 25 30

Asp Phe Val Ser Trp Tyr Gln Gln His Pro Gly Thr Ala Pro Lys Leu
35 40 45

Ile Ile Tyr Asp Ile Asn Asn Arg Ala Ser Gly Ile Ser Asn Arg Phe
50 55 60

Ser Gly Ser Lys Ser Asp Asn Met Ala Ser Leu Thr Ile Ser Gly Leu
65 70 75 80

Gln Pro Glu Asp Glu Ala Asp Tyr Tyr Cys Ser Ala Tyr Thr Ser Ser
85 90 95

Asp Thr Val Val Phe Gly Gly Gly Thr Lys Leu Thr
100 105

<210> SEQ ID NO 49
<211> LENGTH: 108
<212> TYPE: PRT
<213> ORGANISM: Artificial Sequence
<220> FEATURE:
<223> OTHER INFORMATION: Synthetic

<400> SEQUENCE: 49

Gln Ser Ala Leu Thr Gln Pro Ala Ser Val Ser Gly Asn Pro Gly Gln
1 5 10 15

Ser Ile Ala Ile Ser Cys Thr Gly Thr Ser Ser Asp Ile Gly His Tyr
20 25 30

Asp Phe Val Ser Trp Tyr Gln Gln His Pro Gly Thr Ala Pro Lys Leu
35 40 45

Ile Ile Tyr Asp Ile Asn Asn Arg Pro Ser Gly Ile Ser Asn Arg Phe
50 55 60

Ser Gly Ser Lys Ser Asp Asn Met Ala Ser Leu Thr Ile Ser Gly Leu
65 70 75 80

Gln Pro Glu Asp Glu Ala Asp Tyr Tyr Cys Ser Ala Tyr Thr Ser Ser
85 90 95

Asp Thr Val Val Phe Gly Gly Gly Thr Lys Leu Thr
100 105

<210> SEQ ID NO 50
<211> LENGTH: 108
<212> TYPE: PRT
<213> ORGANISM: Artificial Sequence
<220> FEATURE:
<223> OTHER INFORMATION: Synthetic

<400> SEQUENCE: 50

Gln Ser Thr Leu Thr Gln Pro Ala Ser Val Ser Gly Ser Pro Gly Gln
1 5 10 15

Ser Ile Thr Ile Ser Cys Thr Gly Thr Ser Ser Asp Ile Gly His Tyr
20 25 30

```
Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105


<210> SEQ ID NO 51
<211> LENGTH: 108
<212> TYPE: PRT
<213> ORGANISM: Artificial Sequence
<220> FEATURE:
<223> OTHER INFORMATION: Synthetic

<400> SEQUENCE: 51

Gln Ser Ala Leu Thr Gln Pro Ala Ser Val Ser Gly Ser Pro Gly Gln
1               5                   10                  15

Ser Ile Ala Ile Ser Cys Thr Gly Thr Ser Ser Asp Ile Gly Asp Tyr
            20                  25                  30

Asp Phe Val Ser Trp Tyr Gln Gln His Pro Gly Thr Ala Pro Lys Leu
        35                  40                  45

Ile Ile Tyr Asp Ile Asn Asn Arg Pro Ser Gly Ile Ser Asn Arg Phe
    50                  55                  60

Ser Gly Ser Lys Ser Asp Asn Met Ala Ser Leu Thr Ile Ser Gly Leu
65                  70                  75                  80

Gln Pro Glu Asp Glu Ala Asp Tyr Tyr Cys Ser Ala Tyr Thr Ser Ser
                85                  90                  95

Asp Thr Val Val Phe Gly Gly Gly Thr Lys Leu Thr
            100                 105


<210> SEQ ID NO 52
<211> LENGTH: 108
<212> TYPE: PRT
<213> ORGANISM: Artificial Sequence
<220> FEATURE:
<223> OTHER INFORMATION: Synthetic

<400> SEQUENCE: 52

Gln Ser Val Leu Thr Gln Pro Pro Ser Val Ser Gly Ala Pro Gly Gln
1               5                   10                  15

Arg Val Thr Ile Ser Cys Thr Gly Thr Ser Ser Asp Ile Gly His Tyr
            20                  25                  30

Asp Phe Val Ser Trp Tyr Gln Gln Leu Pro Gly Thr Ala Pro Lys Leu
        35                  40                  45

Leu Ile Tyr Asp Ile Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ala Tyr Thr Ser Ser
                85                  90                  95

Asp Thr Leu Val Phe Gly Gly Gly Thr Lys Leu Thr
            100                 105
```

<210> SEQ ID NO 53
<211> LENGTH: 112
<212> TYPE: PRT
<213> ORGANISM: Artificial Sequence
<220> FEATURE:
<223> OTHER INFORMATION: Synthetic

<400> SEQUENCE: 53

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Ser Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Leu Glu Ile Lys
            100                 105                 110
```

<210> SEQ ID NO 54
<211> LENGTH: 106
<212> TYPE: PRT
<213> ORGANISM: Artificial Sequence
<220> FEATURE:
<223> OTHER INFORMATION: Synthetic

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asp Tyr
            20                  25                  30

Leu Asn Trp Tyr Gln Gln Lys Pro Gly Lys Ala Pro Gln Ile Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Asn Leu Gln Pro
65                  70                  75                  80

Glu Asp Val Ala Thr Tyr Tyr Cys Gln Gln Tyr Glu Asp Leu Pro Ser
                85                  90                  95

Phe Gly Gly Gly Thr Lys Val Glu Ile Lys
            100                 105
```

<210> SEQ ID NO 55
<211> LENGTH: 107
<212> TYPE: PRT
<213> ORGANISM: Artificial Sequence
<220> FEATURE:
<223> OTHER INFORMATION: Synthetic

<400> SEQUENCE: 55

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Ala Leu Ile
        35                  40                  45
```

Tyr Asp Ala Ser Asn Leu Glu Thr Gly Val Pro Ser Arg Phe Ser Gly
50 55 60

Ser Gly Ser Gly Thr Asp Phe Thr Leu Thr Ile Ile Ser Leu Gln Pro
65 70 75 80

Glu Asp Phe Ala Thr Tyr Phe Cys Leu Gln Asp Tyr Ile Tyr Pro Trp
85 90 95

Thr Phe Gly Gln Gly Thr Lys Val Glu Phe Lys
100 105

<210> SEQ ID NO 56
<211> LENGTH: 111
<212> TYPE: PRT
<213> ORGANISM: Artificial Sequence
<220> FEATURE:
<223> OTHER INFORMATION: Synthetic

<400> SEQUENCE: 56

Gln Ser Val Leu Thr Gln Pro Pro Ser Val Ser Gly Ala Pro Gly Gln
1 5 10 15

Arg Val Thr Ile Ser Cys Thr Gly Gly Ser Ser Asn Val Gly Ala Gly
20 25 30

Tyr Asp Val His Trp Tyr Gln Gln Leu Pro Gly Thr Val Pro Lys Leu
35 40 45

Leu Ile Tyr Asp Asn Thr Asn Arg Pro Ser Gly Val Pro Asp Arg Phe
50 55 60

Ser Ala Ser Lys Ser Gly Thr Ser Ala Ser Leu Val Ile Thr Gly Leu
65 70 75 80

Gln Ala Glu Asp Glu Gly Asp Tyr Tyr Cys Gln Ser Tyr Asp Ser Ser
85 90 95

Leu Arg Ala Ser Val Phe Gly Gly Gly Thr Met Leu Thr Val Leu
100 105 110

<210> SEQ ID NO 57
<211> LENGTH: 111
<212> TYPE: PRT
<213> ORGANISM: Artificial Sequence
<220> FEATURE:
<223> OTHER INFORMATION: Synthetic

<400> SEQUENCE: 57

Asn Phe Met Leu Thr Gln Pro His Ser Val Ser Glu Ser Pro Gly Lys
1 5 10 15

Thr Val Thr Ile Ser Cys Thr Gly Ser Ser Gly Ser Ile Ala Ser Ser
20 25 30

Tyr Val Gln Trp Tyr Gln Gln Arg Pro Gly Ser Ala Pro Thr Thr Val
35 40 45

Ile Tyr Ala Asp Asn Gln Arg Pro Ser Gly Val Pro Asp Arg Phe Ser
50 55 60

Gly Ser Val Asp Ser Ser Ser Asn Ser Ala Ser Leu Thr Ile Ser Gly
65 70 75 80

Leu Lys Thr Glu Asp Glu Ala Asp Tyr Tyr Cys Gln Ser Phe Asp Ser
85 90 95

Ser Leu Tyr Met Ile Phe Gly Gly Gly Thr Lys Leu Thr Val Leu
100 105 110

<210> SEQ ID NO 58
<211> LENGTH: 111
<212> TYPE: PRT

<213> ORGANISM: Artificial Sequence
<220> FEATURE:
<223> OTHER INFORMATION: Synthetic

<400> SEQUENCE: 58

Gln Ser Val Leu Thr Gln Pro Pro Ser Val Ser Gly Ala Pro Gly Gln
1 5 10 15

Arg Val Thr Ile Ser Cys Thr Gly Ser Arg Ser Asn Ile Gly Ala Gly
20 25 30

Tyr Asp Val His Trp Tyr Gln His Leu Pro Gly Thr Ala Pro Lys Leu
35 40 45

Leu Ile Tyr Asp Asn Ser Asn Arg Pro Ser Gly Val Ser Asp Arg Phe
50 55 60

Ser Gly Ser Lys Ser Gly Thr Ser Ala Ser Leu Ala Ile Thr Gly Leu
65 70 75 80

Gln Ala Glu Asp Glu Ala Asp Tyr Tyr Cys Gln Ser Phe Asp Ser Ser
85 90 95

Leu Arg Gly Val Val Phe Gly Gly Gly Thr Arg Leu Thr Val Leu
100 105 110

<210> SEQ ID NO 59
<211> LENGTH: 111
<212> TYPE: PRT
<213> ORGANISM: Artificial Sequence
<220> FEATURE:
<223> OTHER INFORMATION: Synthetic

<400> SEQUENCE: 59

Ser Tyr Glu Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Thr Val Asn Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Gln
65 70 75 80

Ser Glu Asp Glu Ala Asp Tyr Tyr Cys Ala Ala Trp Asp Asp Ser Leu
85 90 95

Asn Gly Leu Trp Val Phe Gly Gly Gly Thr Lys Leu Thr Val Leu
100 105 110

<210> SEQ ID NO 60
<211> LENGTH: 112
<212> TYPE: PRT
<213> ORGANISM: Artificial Sequence
<220> FEATURE:
<223> OTHER INFORMATION: Synthetic

<400> SEQUENCE: 60

Asp Val Val Met Thr Gln Ser Pro Leu Ser Leu Pro Val Thr Pro Gly
1 5 10 15

Glu Pro Ala Ser Ile Ser Cys Arg Ser Ser Gln Arg Leu Leu His Ser
20 25 30

Asn Gly Tyr Asn Tyr Val Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

```
Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Ile Lys
            100                 105                 110
```

<210> SEQ ID NO 61
<211> LENGTH: 107
<212> TYPE: PRT
<213> ORGANISM: Artificial Sequence
<220> FEATURE:
<223> OTHER INFORMATION: Synthetic

<400> SEQUENCE: 61

```
Asp Ile Gln Met Thr Gln Ser Pro Pro Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr His Gln Lys Pro Gly Lys Ala Pro Glu Leu Leu Ile
        35                  40                  45

Tyr Asp Ala Ser Gln Leu Glu Thr Gly Val Pro Ser Arg Phe Ser Gly
    50                  55                  60

Ser Gly Ser Gly Thr Glu Phe Thr Phe Ile Ile Ser Ser Leu Gln Pro
65                  70                  75                  80

Glu Asp Thr Gly Thr Tyr Tyr Cys Gln Gln Tyr Asp Trp Leu Pro Leu
                85                  90                  95

Ser Tyr Gly Gly Gly Thr Lys Val Glu Ile Lys
            100                 105
```

<210> SEQ ID NO 62
<211> LENGTH: 111
<212> TYPE: PRT
<213> ORGANISM: Artificial Sequence
<220> FEATURE:
<223> OTHER INFORMATION: Synthetic

<400> SEQUENCE: 62

```
Asn Phe Met Leu Thr Gln Pro His Ser Val Ser Gly Ser Pro Gly Lys
1               5                   10                  15

Thr Ile Thr Ile Ser Cys Thr Arg Ser Ser Gly Asn Phe Ala Ser Thr
            20                  25                  30

Tyr Val Gln Trp Tyr Gln Gln Arg Pro Gly Ser Ser Pro Ala Ile Val
        35                  40                  45

Ile Tyr Asp Asp Asp Gln Arg Pro Ser Gly Val Pro Asp Arg Phe Ser
    50                  55                  60

Gly Ser Ile Asp Arg Ser Ser Asn Ser Ala Ser Leu Thr Ile Ser Gly
65                  70                  75                  80

Leu Glu Thr Glu Asp Glu Ala Asp Tyr Tyr Cys Gln Ser Tyr Asp Ser
                85                  90                  95

Ser Asn Phe Trp Val Phe Gly Gly Gly Thr Lys Leu Thr Val Leu
            100                 105                 110
```

<210> SEQ ID NO 63
<211> LENGTH: 106
<212> TYPE: PRT
<213> ORGANISM: Artificial Sequence
<220> FEATURE:
<223> OTHER INFORMATION: Synthetic

<400> SEQUENCE: 63

Glu Ile Val Leu Thr Gln Ser Pro Ser Ser Leu Ser Ala Ser Val Gly
1               5                   10                  15

Asp Arg Val Thr Ile Thr Cys Gln Ala Ser Gln Asp Ile Asn Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Lys Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ala Asn Leu Pro Ser
                85                  90                  95

Phe Gly Gln Gly Thr Lys Leu Glu Ile Lys
            100                 105

<210> SEQ ID NO 64
<211> LENGTH: 112
<212> TYPE: PRT
<213> ORGANISM: Artificial Sequence
<220> FEATURE:
<223> OTHER INFORMATION: Synthetic

<400> SEQUENCE: 64

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Ser Ile
65                  70                  75                  80

Ser Arg Val Glu Ala Glu Asp Val Gly Val Tyr Tyr Cys Met Gln Ala
                85                  90                  95

Leu Gln Thr Pro Pro Thr Phe Gly Gln Gly Thr Lys Val Glu Ile Lys
            100                 105                 110

<210> SEQ ID NO 65
<211> LENGTH: 107
<212> TYPE: PRT
<213> ORGANISM: Artificial Sequence
<220> FEATURE:
<223> OTHER INFORMATION: Synthetic

<400> SEQUENCE: 65

Asp Ile Gln Leu Thr Gln Ser Pro Ser Ser Leu Ser Ala Ser Val Gly
1               5                   10                  15

Asp Arg Val Thr Val Thr Cys Gln Ala Ser Gln Asp Ile Gly His Asn
            20                  25                  30

Leu Asn Trp Tyr Gln Gln Arg Pro Gly Lys Ala Pro Gln Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Gln Phe Thr Phe Thr Ile Ser Ser Leu Gln Pro
65                  70                  75                  80

Glu Asp Ile Ala Thr Tyr Tyr Cys Gln Gln Tyr Asp Phe Leu Pro Pro
85 90 95

Asp Phe Gly Pro Gly Thr Lys Val Glu Ile Lys
100 105

<210> SEQ ID NO 66
<211> LENGTH: 120
<212> TYPE: PRT
<213> ORGANISM: Artificial Sequence
<220> FEATURE:
<223> OTHER INFORMATION: Synthetic

<400> SEQUENCE: 66

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Ala Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Thr Ser Pro Gly Gly Tyr Ser Gly Gly Tyr Phe Gln His Trp Gly Gln
100 105 110

Gly Thr Leu Val Thr Val Ser Ser
115 120

<210> SEQ ID NO 67
<211> LENGTH: 120
<212> TYPE: PRT
<213> ORGANISM: Artificial Sequence
<220> FEATURE:
<223> OTHER INFORMATION: Synthetic

<400> SEQUENCE: 67

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Ser
20 25 30

Ser Tyr Tyr Trp Gly Trp Ile Arg Gln Pro Pro Gly Lys Gly Leu Glu
35 40 45

Trp Ile Gly Ser Ile Tyr Tyr Ser Gly Ser Thr Tyr Tyr Asn Pro Ser
50 55 60

Leu Lys Ser Arg Val Thr Ile Ser Val Asp Thr Ser Lys Asn Gln Phe
65 70 75 80

Ser Leu Lys Leu Ser Ser Val Thr Ala Ala Asp Thr Ala Val Tyr Tyr
85 90 95

Cys Ala Gly Asp Ile Leu Thr Gly Tyr Ala Leu Asp Tyr Trp Gly Gln
100 105 110

Gly Thr Leu Val Thr Val Ser Ser
115 120

<210> SEQ ID NO 68
<211> LENGTH: 120
<212> TYPE: PRT

<213> ORGANISM: Artificial Sequence
<220> FEATURE:
<223> OTHER INFORMATION: Synthetic

<400> SEQUENCE: 68

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Phe Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser
        115                 120
```

<210> SEQ ID NO 69
<211> LENGTH: 120
<212> TYPE: PRT
<213> ORGANISM: Artificial Sequence
<220> FEATURE:
<223> OTHER INFORMATION: Synthetic

<400> SEQUENCE: 69

```
Gln Val Gln Leu Gln Gln Trp Gly Ala Gly Met Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Phe Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser
        115                 120
```

<210> SEQ ID NO 70
<211> LENGTH: 120
<212> TYPE: PRT
<213> ORGANISM: Artificial Sequence
<220> FEATURE:
<223> OTHER INFORMATION: Synthetic

<400> SEQUENCE: 70

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30
```

```
Tyr Trp Ser Trp Val Arg Gln Ala Pro Gly Lys Gly Leu Glu Trp Val
        35                  40                  45

Ser Glu Ile Asn His Ser Gly Ser Thr Asn Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Pro Gly Gly Tyr Ser Gly Gly Tyr Phe Gln His Trp Gly Gln
            100                 105                 110

Gly Thr Leu Val Thr Val Ser Ser
        115                 120


<210> SEQ ID NO 71
<211> LENGTH: 120
<212> TYPE: PRT
<213> ORGANISM: Artificial Sequence
<220> FEATURE:
<223> OTHER INFORMATION: Synthetic

<400> SEQUENCE: 71

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Arg Ile Pro Tyr Tyr Tyr Asp Asn Pro Trp Gly Gln
            100                 105                 110

Gly Thr Leu Val Thr Val Ser Ser
        115                 120


<210> SEQ ID NO 72
<211> LENGTH: 118
<212> TYPE: PRT
<213> ORGANISM: Artificial Sequence
<220> FEATURE:
<223> OTHER INFORMATION: Synthetic

<400> SEQUENCE: 72

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

85 90 95

Ala Arg Ser Leu Tyr Tyr Ser His Phe Asp Tyr Trp Gly Gln Gly Thr
100 105 110

Leu Val Thr Val Ser Ser
115

<210> SEQ ID NO 73
<211> LENGTH: 123
<212> TYPE: PRT
<213> ORGANISM: Artificial Sequence
<220> FEATURE:
<223> OTHER INFORMATION: Synthetic

<400> SEQUENCE: 73

Glu Val Gln Leu Val Glu Thr Gly Pro Gly Leu Val Lys Pro Ser Gly
1 5 10 15

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Glu Gly Pro Leu Ser Ser Ser Gly Pro Gly Ala Phe Asp Ile
100 105 110

Trp Gly Gln Gly Thr Met Val Thr Val Ser Ser
115 120

<210> SEQ ID NO 74
<211> LENGTH: 114
<212> TYPE: PRT
<213> ORGANISM: Artificial Sequence
<220> FEATURE:
<223> OTHER INFORMATION: Synthetic

<400> SEQUENCE: 74

Gln Val Gln Leu Gln Glu Ser Gly Gly Gly Val Val Gln Pro Gly Arg
1 5 10 15

Ser Leu Arg Leu Ser Cys Ala Ala Ser Gly Phe Thr Phe Ser Asn Tyr
20 25 30

Gly Met His Trp Val Arg Gln Ala Pro Gly Lys Gly Leu Glu Trp Val
35 40 45

Ala Val Ile Ser Tyr Asp Gly Thr Asn Lys Tyr Tyr Ala Asp Ser Val
50 55 60

Lys Gly Arg Phe Thr Ile Ser Arg Asp Asn Ser Lys Asn Thr Val Tyr
65 70 75 80

Leu Gln Met Asn Ser Leu Arg Ala Glu Asp Thr Ala Val Tyr Tyr Cys
85 90 95

Ala Lys Asp Gly Phe Asp Ile Trp Gly Gln Gly Thr Met Val Thr Val
100 105 110

Ser Ser

<210> SEQ ID NO 75
<211> LENGTH: 120
<212> TYPE: PRT

<213> ORGANISM: Artificial Sequence
<220> FEATURE:
<223> OTHER INFORMATION: Synthetic

<400> SEQUENCE: 75

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Tyr Gly Asp Tyr Gly Ala Phe Asp Tyr Trp Gly Gln
            100                 105                 110

Gly Thr Leu Val Thr Val Ser Ser
        115                 120
```

<210> SEQ ID NO 76
<211> LENGTH: 117
<212> TYPE: PRT
<213> ORGANISM: Artificial Sequence
<220> FEATURE:
<223> OTHER INFORMATION: Synthetic

<400> SEQUENCE: 76

```
Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Ala Pro Pro Met Asp Val Trp Gly Lys Gly Thr Thr
            100                 105                 110

Val Thr Val Ser Ser
        115
```

<210> SEQ ID NO 77
<211> LENGTH: 121
<212> TYPE: PRT
<213> ORGANISM: Artificial Sequence
<220> FEATURE:
<223> OTHER INFORMATION: Synthetic

<400> SEQUENCE: 77

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Glu Ser Phe Ser Gly Tyr
            20                  25                  30
```

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Pro Ala Gly Ser Ser Ser Ser Gly Tyr Phe Asp Tyr Trp Gly
100 105 110

Gln Gly Thr Leu Val Thr Val Ser Ser
115 120

<210> SEQ ID NO 78
<211> LENGTH: 116
<212> TYPE: PRT
<213> ORGANISM: Artificial Sequence
<220> FEATURE:
<223> OTHER INFORMATION: Synthetic

<400> SEQUENCE: 78

Gln Val Gln Leu Gln Glu Ser Gly Pro Gly Leu Val Lys Pro Ser Gln
1 5 10 15

Thr Leu Ser Leu Thr Cys Thr Val Ser Gly Gly Ser Ile Ser Ser Gly
20 25 30

Gly Tyr Tyr Trp Thr Trp Ile Arg Gln His Pro Gly Gln Gly Leu Glu
35 40 45

Trp Ile Gly Phe Ile Ser Trp Ser Gly Thr Thr Tyr Tyr Asn Pro Ser
50 55 60

Leu Lys Asn Arg Val Thr Ile Ser Ala Asp Thr Ser Lys Asn His Phe
65 70 75 80

Ser Leu Asn Leu Thr Ser Val Thr Ala Ala Asp Thr Ala Val Tyr Tyr
85 90 95

Cys Ala Arg Gly Ser Gly Arg Leu Val Trp Gly Gln Gly Thr Leu Val
100 105 110

Thr Val Ser Ser
115

<210> SEQ ID NO 79
<211> LENGTH: 120
<212> TYPE: PRT
<213> ORGANISM: Artificial Sequence
<220> FEATURE:
<223> OTHER INFORMATION: Synthetic

<400> SEQUENCE: 79

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys

```
                85                  90                  95

Ala Arg Ala Asp Thr Ala Met Gly Asp Ala Phe Asp Ile Trp Gly Gln
            100                 105                 110

Gly Thr Met Val Thr Val Ser Ser
        115                 120


<210> SEQ ID NO 80
<211> LENGTH: 118
<212> TYPE: PRT
<213> ORGANISM: Artificial Sequence
<220> FEATURE:
<223> OTHER INFORMATION: Synthetic

<400> SEQUENCE: 80

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Gly Ile Gly Ala Phe Asp Ile Trp Gly Gln Gly Thr
            100                 105                 110

Met Val Thr Val Ser Ser
        115


<210> SEQ ID NO 81
<211> LENGTH: 121
<212> TYPE: PRT
<213> ORGANISM: Artificial Sequence
<220> FEATURE:
<223> OTHER INFORMATION: Synthetic

<400> SEQUENCE: 81

Gln Val Gln Leu Gln Gln Trp Gly Ala Gly Leu Leu Lys Pro Ser Glu
1               5                   10                  15

Thr Leu Ser Leu Thr Cys Thr Ile Tyr Gly Gly Ser Phe Ser Gly Phe
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Ile Tyr Tyr Cys Ala
                85                  90                  95

Arg Gly Pro Ala Gly Ser Thr Ser Ser Gly Tyr Phe Asp His Trp Gly
            100                 105                 110

Gln Gly Thr Leu Val Thr Val Ser Ser
        115                 120


<210> SEQ ID NO 82
<211> LENGTH: 117
```

<212> TYPE: PRT
<213> ORGANISM: Artificial Sequence
<220> FEATURE:
<223> OTHER INFORMATION: Synthetic

<400> SEQUENCE: 82

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Leu Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ser Ser Ser Tyr Tyr Met Asp Val Trp Gly Lys Gly Thr Thr
            100                 105                 110

Val Thr Val Ser Ser
        115
```

<210> SEQ ID NO 83
<211> LENGTH: 116
<212> TYPE: PRT
<213> ORGANISM: Artificial Sequence
<220> FEATURE:
<223> OTHER INFORMATION: Synthetic

<400> SEQUENCE: 83

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Ser Ala Tyr Phe Gln His Trp Gly Gln Gly Thr Leu Val
            100                 105                 110

Thr Val Ser Ser
        115
```

<210> SEQ ID NO 84
<211> LENGTH: 121
<212> TYPE: PRT
<213> ORGANISM: Artificial Sequence
<220> FEATURE:
<223> OTHER INFORMATION: Synthetic

<400> SEQUENCE: 84

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
```

```
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Glu Asp Ala Ser Lys Lys Gln Phe Ser Leu
65                  70                  75                  80

Thr Leu Thr Ser Val Thr Ala Ala Asp Thr Ala Val Tyr Tyr Cys Ala
                85                  90                  95

Arg Gly Pro Ala Gly Thr Gly Ser Ser Gly Tyr Phe Asp Tyr Trp Gly
            100                 105                 110

Gln Gly Thr Leu Val Thr Val Ser Ser
        115                 120


<210> SEQ ID NO 85
<211> LENGTH: 112
<212> TYPE: PRT
<213> ORGANISM: Artificial Sequence
<220> FEATURE:
<223> OTHER INFORMATION: Synthetic

<400> SEQUENCE: 85

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Ile Lys
            100                 105                 110


<210> SEQ ID NO 86
<211> LENGTH: 108
<212> TYPE: PRT
<213> ORGANISM: Artificial Sequence
<220> FEATURE:
<223> OTHER INFORMATION: Synthetic

<400> SEQUENCE: 86

Ser Tyr Glu Leu Thr Gln Pro Pro Ser Met Ser Val Ser Pro Gly Gln
1               5                   10                  15

Thr Ala Arg Ile Thr Cys Ser Gly Asp Ala Leu Pro Lys Gln Phe Ala
            20                  25                  30

Phe Trp Tyr Gln Gln Lys Pro Gly Gln Ala Pro Val Leu Val Ile Tyr
        35                  40                  45

Lys Asp Thr Glu Arg Pro Ser Gly Ile Pro Glu Arg Phe Ser Gly Ser
    50                  55                  60

Ser Ser Gly Thr Thr Val Thr Leu Thr Ile Thr Gly Val Gln Ala Glu
65                  70                  75                  80

Asp Glu Ala Asp Tyr Tyr Cys Gln Ser Pro Asp Ser Ser Gly Thr Val
                85                  90                  95
```

Glu Val Phe Gly Gly Gly Thr Lys Leu Thr Val Leu
100 105

<210> SEQ ID NO 87
<211> LENGTH: 112
<212> TYPE: PRT
<213> ORGANISM: Artificial Sequence
<220> FEATURE:
<223> OTHER INFORMATION: Synthetic

<400> SEQUENCE: 87

Asp Val Val Met Thr Gln Ser Pro Leu Ser Leu Pro Val Thr Pro Gly
1 5 10 15

Glu Ser Val Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Trp Thr Phe Gly Gln Gly Thr Lys Val Glu Ile Lys
100 105 110

<210> SEQ ID NO 88
<211> LENGTH: 112
<212> TYPE: PRT
<213> ORGANISM: Artificial Sequence
<220> FEATURE:
<223> OTHER INFORMATION: Synthetic

<400> SEQUENCE: 88

Asp Ile Gln Met Thr Gln Ser Pro Ser Ser Leu Ser Ala Ser Val Gly
1 5 10 15

Asp Arg Val Thr Ile Thr Cys Arg Ser Ser Gln Ser Leu Leu His Ser
20 25 30

Asn Gly Tyr Asn Tyr Leu Asp Trp Tyr Gln Gln Lys Pro Gly Lys Ala
35 40 45

Pro Lys Leu Leu Ile Tyr Leu Gly Ser Asn Arg Asp Ser Gly Val Pro
50 55 60

Ser Arg Phe Ser Gly Ser Gly Ser Gly Thr Asp Phe Thr Leu Thr Ile
65 70 75 80

Ser Ser Leu Gln Pro Glu Asp Phe Ala Thr Tyr Tyr Cys Met Gln Gly
85 90 95

Thr His Trp Pro Trp Thr Phe Gly Gln Gly Thr Lys Val Glu Ile Lys
100 105 110

<210> SEQ ID NO 89
<211> LENGTH: 112
<212> TYPE: PRT
<213> ORGANISM: Artificial Sequence
<220> FEATURE:
<223> OTHER INFORMATION: Synthetic

<400> SEQUENCE: 89

Glu Ile Val Leu Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser

```
            20                  25                  30

Asn Gly Tyr Asn Tyr Leu Asn Trp Tyr Leu Gln Lys Pro Gly Gln Ser
        35                  40                  45

Pro Gln Leu Leu Ile Tyr Leu Gly Ser Asp Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Thr Thr Phe Gly Gly Gly Thr Lys Val Glu Ile Lys
            100                 105                 110


<210> SEQ ID NO 90
<211> LENGTH: 112
<212> TYPE: PRT
<213> ORGANISM: Artificial Sequence
<220> FEATURE:
<223> OTHER INFORMATION: Synthetic

<400> SEQUENCE: 90

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Met Tyr Leu Val Ser Asn Arg Ala Ser Gly Val Pro
    50                  55                  60

Glu Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Gln Thr Pro Leu Ser Phe Gly Gln Gly Thr Lys Leu Glu Ile Lys
            100                 105                 110


<210> SEQ ID NO 91
<211> LENGTH: 107
<212> TYPE: PRT
<213> ORGANISM: Artificial Sequence
<220> FEATURE:
<223> OTHER INFORMATION: Synthetic

<400> SEQUENCE: 91

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Tyr His
            20                  25                  30

Leu Ala Trp Tyr Gln Gln Lys Pro Gly Gln Ala Pro Arg Leu Leu Ile
        35                  40                  45

Tyr Asp Thr Ser Asn Arg Ala Ser Gly Ile Pro Ala Arg Phe Ser Gly
    50                  55                  60

Ser Gly Ser Gly Thr Asp Phe Thr Leu Thr Ile Asn Ser Leu Glu Pro
65                  70                  75                  80

Glu Asp Phe Ala Val Tyr Tyr Cys Gln Gln Arg Tyr Asp Trp Pro Leu
                85                  90                  95

Thr Phe Gly Gly Gly Thr Lys Val Glu Ile Lys
            100                 105
```

<210> SEQ ID NO 92
<211> LENGTH: 107
<212> TYPE: PRT
<213> ORGANISM: Artificial Sequence
<220> FEATURE:
<223> OTHER INFORMATION: Synthetic

<400> SEQUENCE: 92

Asp Ile Gln Met Thr Gln Ser Pro Ser Phe Leu Ser Ala Ser Val Gly
1 5 10 15

Asp Arg Val Thr Ile Thr Cys Arg Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Asp Ala Ser Arg Leu Glu Asp Gly Val Pro Ser Arg Phe Ser Gly
50 55 60

Thr Gly Phe Gly Thr Asp Phe Thr Phe Thr Ile Thr Thr Leu Gln Pro
65 70 75 80

Asp Asp Ile Ala Thr Tyr Tyr Cys Gln Gln Tyr Asp Asp Leu Pro Tyr
85 90 95

Thr Phe Gly Gln Gly Thr Thr Val Asp Ile Lys
100 105

<210> SEQ ID NO 93
<211> LENGTH: 112
<212> TYPE: PRT
<213> ORGANISM: Artificial Sequence
<220> FEATURE:
<223> OTHER INFORMATION: Synthetic

<400> SEQUENCE: 93

Asp Val Val Met Thr Gln Ser Pro Val Ser Leu Pro Val Thr Leu Gly
1 5 10 15

Gln Pro Ala Ser Ile Ser Cys Lys Ser Ser Gln Ser Leu Leu Tyr Phe
20 25 30

Asn Gly Asn Thr Tyr Leu Ser Trp Phe Gln Gln Arg Pro Gly Gln Ser
35 40 45

Pro Arg Arg Leu Phe Tyr Gln Val Ser Asn Arg Asp Ser Gly Val Pro
50 55 60

Asp Arg Phe Ser Gly Ser Gly Ser Asp Thr Asp Phe Thr Leu Thr Ile
65 70 75 80

Ser Arg Val Glu Ala Glu Asp Val Gly Val Tyr Phe Cys Met Gln Gly
85 90 95

Thr Gln Trp Pro Pro Thr Phe Gly Gln Gly Thr Lys Val Glu Ile Lys
100 105 110

<210> SEQ ID NO 94
<211> LENGTH: 112
<212> TYPE: PRT
<213> ORGANISM: Artificial Sequence
<220> FEATURE:
<223> OTHER INFORMATION: Synthetic

<400> SEQUENCE: 94

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser

```
        35                  40                  45

Pro His Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Met Gln Ala
                85                  90                  95

Leu Arg Thr Pro Tyr Thr Phe Gly Gln Gly Thr Lys Leu Glu Ile Lys
            100                 105                 110


<210> SEQ ID NO 95
<211> LENGTH: 112
<212> TYPE: PRT
<213> ORGANISM: Artificial Sequence
<220> FEATURE:
<223> OTHER INFORMATION: Synthetic

<400> SEQUENCE: 95

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Gly
                85                  90                  95

Ser His Trp Pro Trp Thr Phe Gly Gln Gly Thr Lys Val Glu Ile Lys
            100                 105                 110


<210> SEQ ID NO 96
<211> LENGTH: 106
<212> TYPE: PRT
<213> ORGANISM: Artificial Sequence
<220> FEATURE:
<223> OTHER INFORMATION: Synthetic

<400> SEQUENCE: 96

Glu Thr Thr Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Ser Gly Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Leu Tyr Gly Ser Ser Leu Ala
                85                  90                  95

Phe Gly Gly Gly Thr Lys Val Glu Ile Lys
            100                 105


<210> SEQ ID NO 97
<211> LENGTH: 113
```

<212> TYPE: PRT
<213> ORGANISM: Artificial Sequence
<220> FEATURE:
<223> OTHER INFORMATION: Synthetic

<400> SEQUENCE: 97

Asp Ile Val Met Thr His Thr Pro Leu Ser Leu Pro Val Thr Pro Gly
1               5                   10                  15

Glu Pro Ala Ser Ile Ser Cys Arg Ser Ser Gln Thr Leu Phe Asp Ser
            20                  25                  30

Asp Asp Gly Lys Thr Tyr Leu Asp Trp Tyr Leu Gln Lys Pro Gly Gln
        35                  40                  45

Ser Pro Gln Leu Leu Met Tyr Thr Thr Ser Ser Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Leu Gln Phe Pro Leu Thr Phe Gly Gln Gly Thr Arg Leu Glu Phe
            100                 105                 110

Lys

<210> SEQ ID NO 98
<211> LENGTH: 112
<212> TYPE: PRT
<213> ORGANISM: Artificial Sequence
<220> FEATURE:
<223> OTHER INFORMATION: Synthetic

<400> SEQUENCE: 98

Asp Val Val Met Thr Gln Ser Pro Leu Ser Leu Pro Val Thr Pro Gly
1               5                   10                  15

Glu Pro Ala Ser Ile Ser Cys Arg Ala Thr Gln Ser Leu Leu His Gly
            20                  25                  30

Asn Gly His Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95

Leu Glu Thr Pro Val Thr Phe Gly Pro Gly Thr Lys Val Asp Ile Lys
            100                 105                 110

<210> SEQ ID NO 99
<211> LENGTH: 112
<212> TYPE: PRT
<213> ORGANISM: Artificial Sequence
<220> FEATURE:
<223> OTHER INFORMATION: Synthetic

<400> SEQUENCE: 99

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr His Trp Pro Trp Thr Phe Gly Gln Gly Thr Lys Val Glu Ile Lys
100 105 110

<210> SEQ ID NO 100
<211> LENGTH: 112
<212> TYPE: PRT
<213> ORGANISM: Artificial Sequence
<220> FEATURE:
<223> OTHER INFORMATION: Synthetic

<400> SEQUENCE: 100

Asp Val Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser
20 25 30

Asn Gly Tyr Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Leu Gln Gly
85 90 95

Thr His Trp Pro Trp Thr Phe Gly Gln Gly Thr Lys Val Glu Ile Lys
100 105 110

<210> SEQ ID NO 101
<211> LENGTH: 112
<212> TYPE: PRT
<213> ORGANISM: Artificial Sequence
<220> FEATURE:
<223> OTHER INFORMATION: Synthetic

<400> SEQUENCE: 101

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Leu His Ser
20 25 30

Asn Gly Asn Asn Tyr Leu Asp Trp Tyr Leu Gln Lys Pro Gly Gln Ser
35 40 45

Pro Gln Leu Leu Ile Tyr Leu Gly Ser Asn Arg Ala Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Ile Tyr Tyr Cys Met Gln Gly
85 90 95

Thr His Trp Pro Trp Thr Phe Gly Gln Gly Thr Lys Val Glu Ile Glu
100 105 110

<210> SEQ ID NO 102
<211> LENGTH: 112
<212> TYPE: PRT

```
<213> ORGANISM: Artificial Sequence
<220> FEATURE:
<223> OTHER INFORMATION: Synthetic

<400> SEQUENCE: 102

Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Trp Thr Phe Gly Gln Gly Thr Lys Val Glu Val Lys
            100                 105                 110


<210> SEQ ID NO 103
<211> LENGTH: 5
<212> TYPE: PRT
<213> ORGANISM: Artificial Sequence
<220> FEATURE:
<223> OTHER INFORMATION: Synthetic

<400> SEQUENCE: 103

Asn Tyr Tyr Met His
1               5


<210> SEQ ID NO 104
<211> LENGTH: 5
<212> TYPE: PRT
<213> ORGANISM: Artificial Sequence
<220> FEATURE:
<223> OTHER INFORMATION: Synthetic

<400> SEQUENCE: 104

Thr Tyr Ala Met His
1               5


<210> SEQ ID NO 105
<211> LENGTH: 5
<212> TYPE: PRT
<213> ORGANISM: Artificial Sequence
<220> FEATURE:
<223> OTHER INFORMATION: Synthetic

<400> SEQUENCE: 105

Ser Tyr Ala Met Ser
1               5


<210> SEQ ID NO 106
<211> LENGTH: 5
<212> TYPE: PRT
<213> ORGANISM: Artificial Sequence
<220> FEATURE:
<223> OTHER INFORMATION: Synthetic

<400> SEQUENCE: 106

Gly Tyr Tyr Trp Ser
1               5
```

<210> SEQ ID NO 107
<211> LENGTH: 5
<212> TYPE: PRT
<213> ORGANISM: Artificial Sequence
<220> FEATURE:
<223> OTHER INFORMATION: Synthetic

<400> SEQUENCE: 107

Asn Tyr Tyr Ile His
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic

<400> SEQUENCE: 108

Ser Tyr Ala Met His
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic

<400> SEQUENCE: 109

Ser Arg Ser Asp His Trp Gly
1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic

<400> SEQUENCE: 110

Ser Tyr Tyr Trp Ser
1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic

<400> SEQUENCE: 111

Ser Tyr Asp Leu His
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic

<400> SEQUENCE: 112

Ser Ser Asn Trp Trp Ser
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic

<400> SEQUENCE: 113

Gly Asn Ser Ala Thr Trp Asn
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic

<400> SEQUENCE: 114

Ser Gly Ser Trp Trp Ser
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic

<400> SEQUENCE: 115

Ser Tyr Gly Ile Ser
1               5

<210> SEQ ID NO 116
<211> LENGTH: 17
<212> TYPE: PRT
<213> ORGANISM: Artificial Sequence
<220> FEATURE:
<223> OTHER INFORMATION: Synthetic

<400> SEQUENCE: 116

Ala Ile Met Pro Ser Arg Gly Gly Thr Ser Tyr Pro Gln Lys Phe Gln
1               5                   10                  15

Gly

<210> SEQ ID NO 117
<211> LENGTH: 17
<212> TYPE: PRT
<213> ORGANISM: Artificial Sequence
<220> FEATURE:
<223> OTHER INFORMATION: Synthetic

<400> SEQUENCE: 117

Trp Ile Asn Thr Gly Asn Gly Asn Thr Lys Tyr Ser Gln Asn Phe Gln
1               5                   10                  15

Gly

<210> SEQ ID NO 118
<211> LENGTH: 17
<212> TYPE: PRT
<213> ORGANISM: Artificial Sequence
<220> FEATURE:
<223> OTHER INFORMATION: Synthetic

<400> SEQUENCE: 118

Ala Ile Ser Gly Ser Gly Gly Ser Thr Tyr Tyr Ala Asp Ser Val Lys 1 5 10 15

Gly

<210> SEQ ID NO 119
<211> LENGTH: 16
<212> TYPE: PRT
<213> ORGANISM: Artificial Sequence
<220> FEATURE:
<223> OTHER INFORMATION: Synthetic

<400> SEQUENCE: 119

Glu Ile Asn His Ser Gly Ser Thr Asn Tyr Asn Pro Ser Leu Lys Ser
1 5 10 15

<210> SEQ ID NO 120
<211> LENGTH: 17
<212> TYPE: PRT
<213> ORGANISM: Artificial Sequence
<220> FEATURE:
<223> OTHER INFORMATION: Synthetic

<400> SEQUENCE: 120

Val Ile Ser Tyr Asp Gly Ser Asn Lys Tyr Tyr Ala Asp Ser Val Lys
1 5 10 15

Gly

<210> SEQ ID NO 121
<211> LENGTH: 16
<212> TYPE: PRT
<213> ORGANISM: Artificial Sequence
<220> FEATURE:
<223> OTHER INFORMATION: Synthetic

<400> SEQUENCE: 121

Ser Ile Ser Tyr Ser Gly Ser Thr Tyr Tyr Asn Pro Ser Leu Lys Ser
1 5 10 15

<210> SEQ ID NO 122
<211> LENGTH: 17
<212> TYPE: PRT
<213> ORGANISM: Artificial Sequence
<220> FEATURE:
<223> OTHER INFORMATION: Synthetic

<400> SEQUENCE: 122

Ala Ile Ser Gly Ser Gly Gly Ser Thr His Tyr Ala Asp Ser Val Lys
1 5 10 15

Gly

<210> SEQ ID NO 123
<211> LENGTH: 17
<212> TYPE: PRT
<213> ORGANISM: Artificial Sequence
<220> FEATURE:
<223> OTHER INFORMATION: Synthetic

<400> SEQUENCE: 123

Leu Ile Ser Tyr Asp Gly Ser Asn Lys Tyr Tyr Ala Asp Ser Val Lys
1 5 10 15

Gly

<210> SEQ ID NO 124
<211> LENGTH: 16
<212> TYPE: PRT

<213> ORGANISM: Artificial Sequence
<220> FEATURE:
<223> OTHER INFORMATION: Synthetic

<400> SEQUENCE: 124

Glu Ile Tyr His Ser Gly Ser Thr Asn Tyr Asn Pro Ser Leu Lys Ser
1 5 10 15

<210> SEQ ID NO 125
<211> LENGTH: 18
<212> TYPE: PRT
<213> ORGANISM: Artificial Sequence
<220> FEATURE:
<223> OTHER INFORMATION: Synthetic

<400> SEQUENCE: 125

Arg Thr Tyr Tyr Arg Ser Lys Trp Asn His Asp Tyr Ala Glu Ser Val
1 5 10 15

Lys Ser

<210> SEQ ID NO 126
<211> LENGTH: 16
<212> TYPE: PRT
<213> ORGANISM: Artificial Sequence
<220> FEATURE:
<223> OTHER INFORMATION: Synthetic

<400> SEQUENCE: 126

Glu Ile Tyr His Asn Gly Asn Thr Asn Tyr Asn Pro Ser Leu Lys Ser
1 5 10 15

<210> SEQ ID NO 127
<211> LENGTH: 17
<212> TYPE: PRT
<213> ORGANISM: Artificial Sequence
<220> FEATURE:
<223> OTHER INFORMATION: Synthetic

<400> SEQUENCE: 127

Trp Ile Ser Ala Tyr Asn Gly Asn Thr Asn Tyr Ala Gln Lys Leu Gln
1 5 10 15

Gly

<210> SEQ ID NO 128
<211> LENGTH: 12
<212> TYPE: PRT
<213> ORGANISM: Artificial Sequence
<220> FEATURE:
<223> OTHER INFORMATION: Synthetic

<400> SEQUENCE: 128

Gly Glu Tyr Tyr Tyr Asp Ser Ser Gly Tyr Tyr Tyr
1 5 10

<210> SEQ ID NO 129
<211> LENGTH: 11
<212> TYPE: PRT
<213> ORGANISM: Artificial Sequence
<220> FEATURE:
<223> OTHER INFORMATION: Synthetic

<400> SEQUENCE: 129

Asp Leu Gly Gln Leu Glu Arg Leu Tyr Phe Trp
1 5 10

<210> SEQ ID NO 130
<211> LENGTH: 5
<212> TYPE: PRT
<213> ORGANISM: Artificial Sequence
<220> FEATURE:
<223> OTHER INFORMATION: Synthetic

<400> SEQUENCE: 130

Asp Leu Gly Asp Tyr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic

<400> SEQUENCE: 131

Ser Ser Ser Gly Asp Ala Phe Asp Ile
1               5

<210> SEQ ID NO 132
<211> LENGTH: 12
<212> TYPE: PRT
<213> ORGANISM: Artificial Sequence
<220> FEATURE:
<223> OTHER INFORMATION: Synthetic

<400> SEQUENCE: 132

Gly Glu Tyr Tyr Tyr Asp Ser Ser Gly Tyr Tyr Asn
1               5                   10

<210> SEQ ID NO 133
<211> LENGTH: 17
<212> TYPE: PRT
<213> ORGANISM: Artificial Sequence
<220> FEATURE:
<223> OTHER INFORMATION: Synthetic

<400> SEQUENCE: 133

Asp Leu Gly Tyr Ser Ser Ser Trp Tyr Tyr Tyr Tyr Tyr Gly Met Asp
1               5                   10                  15

Val

<210> SEQ ID NO 134
<211> LENGTH: 10
<212> TYPE: PRT
<213> ORGANISM: Artificial Sequence
<220> FEATURE:
<223> OTHER INFORMATION: Synthetic

<400> SEQUENCE: 134

Glu Ser His Pro Ala Ala Ala Leu Val Gly
1               5                   10

<210> SEQ ID NO 135
<211> LENGTH: 3
<212> TYPE: PRT
<213> ORGANISM: Artificial Sequence
<220> FEATURE:
<223> OTHER INFORMATION: Synthetic

<400> SEQUENCE: 135

Pro Ala Phe
1

<210> SEQ ID NO 136
<211> LENGTH: 9
<212> TYPE: PRT
<213> ORGANISM: Artificial Sequence
<220> FEATURE:
<223> OTHER INFORMATION: Synthetic

<400> SEQUENCE: 136

Gly Ser Asn Leu Asp Trp Phe Asp Pro
1 5

<210> SEQ ID NO 137
<211> LENGTH: 10
<212> TYPE: PRT
<213> ORGANISM: Artificial Sequence
<220> FEATURE:
<223> OTHER INFORMATION: Synthetic

<400> SEQUENCE: 137

Ala Asp Arg Arg Phe Gly Glu Leu Arg Tyr
1 5 10

<210> SEQ ID NO 138
<211> LENGTH: 12
<212> TYPE: PRT
<213> ORGANISM: Artificial Sequence
<220> FEATURE:
<223> OTHER INFORMATION: Synthetic

<400> SEQUENCE: 138

Glu Pro Ile Thr Gly Thr Ser Asp Leu Phe Asp Tyr
1 5 10

<210> SEQ ID NO 139
<211> LENGTH: 8
<212> TYPE: PRT
<213> ORGANISM: Artificial Sequence
<220> FEATURE:
<223> OTHER INFORMATION: Synthetic

<400> SEQUENCE: 139

Glu Gly Gly Leu Arg Glu Glu His
1 5

<210> SEQ ID NO 140
<211> LENGTH: 9
<212> TYPE: PRT
<213> ORGANISM: Artificial Sequence
<220> FEATURE:
<223> OTHER INFORMATION: Synthetic

<400> SEQUENCE: 140

Gly Thr Asp Thr Ala Met Ala Asp Tyr
1 5

<210> SEQ ID NO 141
<211> LENGTH: 8
<212> TYPE: PRT
<213> ORGANISM: Artificial Sequence
<220> FEATURE:
<223> OTHER INFORMATION: Synthetic

<400> SEQUENCE: 141

Asp Ser Lys Ser Ala Phe Asp Ile
1 5

<210> SEQ ID NO 142
<211> LENGTH: 6
<212> TYPE: PRT
<213> ORGANISM: Artificial Sequence
<220> FEATURE:
<223> OTHER INFORMATION: Synthetic

<400> SEQUENCE: 142

Val Ser Gly Phe Asp Tyr
1 5

<210> SEQ ID NO 143
<211> LENGTH: 17
<212> TYPE: PRT
<213> ORGANISM: Artificial Sequence
<220> FEATURE:
<223> OTHER INFORMATION: Synthetic

<400> SEQUENCE: 143

Ala Pro Asp Tyr Gly Asp Ser Ser Asn Tyr Tyr Tyr Tyr Tyr Met Asp
1 5 10 15

Val

<210> SEQ ID NO 144
<211> LENGTH: 18
<212> TYPE: PRT
<213> ORGANISM: Artificial Sequence
<220> FEATURE:
<223> OTHER INFORMATION: Synthetic

<400> SEQUENCE: 144

Asp Thr Ser Gly Asp Tyr Ser Ser Gly Trp Tyr Leu Gly Val Pro Phe
1 5 10 15

Asp Tyr

<210> SEQ ID NO 145
<211> LENGTH: 14
<212> TYPE: PRT
<213> ORGANISM: Artificial Sequence
<220> FEATURE:
<223> OTHER INFORMATION: Synthetic

<400> SEQUENCE: 145

Thr Gly Thr Ser Ser Asp Ile Gly His Tyr Asp Phe Val Ser
1 5 10

<210> SEQ ID NO 146
<211> LENGTH: 11
<212> TYPE: PRT
<213> ORGANISM: Artificial Sequence
<220> FEATURE:
<223> OTHER INFORMATION: Synthetic

<400> SEQUENCE: 146

Arg Ala Gly Gln Ala Ile Ser Ser Trp Leu Ala
1 5 10

<210> SEQ ID NO 147
<211> LENGTH: 11
<212> TYPE: PRT
<213> ORGANISM: Artificial Sequence
<220> FEATURE:
<223> OTHER INFORMATION: Synthetic

<400> SEQUENCE: 147

Gln Ala Ser Gln Asp Ile Gly Asn Tyr Leu Asn 1 5 10

<210> SEQ ID NO 148
<211> LENGTH: 13
<212> TYPE: PRT
<213> ORGANISM: Artificial Sequence
<220> FEATURE:
<223> OTHER INFORMATION: Synthetic

<400> SEQUENCE: 148

Thr Arg Ser Ser Gly Ser Ile Ala Ser Asn Tyr Val Gln
1 5 10

<210> SEQ ID NO 149
<211> LENGTH: 14
<212> TYPE: PRT
<213> ORGANISM: Artificial Sequence
<220> FEATURE:
<223> OTHER INFORMATION: Synthetic

<400> SEQUENCE: 149

Thr Gly Thr Ser Ser Asp Ile Gly Asp Tyr Asp Phe Val Ser
1 5 10

<210> SEQ ID NO 150
<211> LENGTH: 14
<212> TYPE: PRT
<213> ORGANISM: Artificial Sequence
<220> FEATURE:
<223> OTHER INFORMATION: Synthetic

<400> SEQUENCE: 150

Thr Gly Thr Ser Ser Asp Ile Gly His Tyr Asp Phe Ile Ser
1 5 10

<210> SEQ ID NO 151
<211> LENGTH: 16
<212> TYPE: PRT
<213> ORGANISM: Artificial Sequence
<220> FEATURE:
<223> OTHER INFORMATION: Synthetic

<400> SEQUENCE: 151

Arg Ser Ser Gln Ser Leu Leu His Ser Asn Gly Tyr Asn Tyr Leu Asp
1 5 10 15

<210> SEQ ID NO 152
<211> LENGTH: 11
<212> TYPE: PRT
<213> ORGANISM: Artificial Sequence
<220> FEATURE:
<223> OTHER INFORMATION: Synthetic

<400> SEQUENCE: 152

Gln Ala Ser Gln Asp Ile Ser Asp Tyr Leu Asn
1 5 10

<210> SEQ ID NO 153
<211> LENGTH: 11
<212> TYPE: PRT
<213> ORGANISM: Artificial Sequence
<220> FEATURE:
<223> OTHER INFORMATION: Synthetic

<400> SEQUENCE: 153

Arg Ala Ser Gln Ser Ile Ser Ser Tyr Leu Asn
1 5 10

<210> SEQ ID NO 154
<211> LENGTH: 14
<212> TYPE: PRT
<213> ORGANISM: Artificial Sequence
<220> FEATURE:
<223> OTHER INFORMATION: Synthetic

<400> SEQUENCE: 154

Thr Gly Gly Ser Ser Asn Val Gly Ala Gly Tyr Asp Val His
1               5                   10

<210> SEQ ID NO 155
<211> LENGTH: 13
<212> TYPE: PRT
<213> ORGANISM: Artificial Sequence
<220> FEATURE:
<223> OTHER INFORMATION: Synthetic

<400> SEQUENCE: 155

Thr Gly Ser Ser Gly Ser Ile Ala Ser Ser Tyr Val Gln
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Synthetic

<400> SEQUENCE: 156

Thr Gly Ser Arg Ser Asn Ile Gly Ala Gly Tyr Asp Val His
1               5                   10

<210> SEQ ID NO 157
<211> LENGTH: 13
<212> TYPE: PRT
<213> ORGANISM: Artificial Sequence
<220> FEATURE:
<223> OTHER INFORMATION: Synthetic

<400> SEQUENCE: 157

Ser Gly Ser Ser Ser Asn Ile Gly Ser Asn Thr Val Asn
1               5                   10

<210> SEQ ID NO 158
<211> LENGTH: 16
<212> TYPE: PRT
<213> ORGANISM: Artificial Sequence
<220> FEATURE:
<223> OTHER INFORMATION: Synthetic

<400> SEQUENCE: 158

Arg Ser Ser Gln Arg Leu Leu His Ser Asn Gly Tyr Asn Tyr Val Asp
1               5                   10                  15

<210> SEQ ID NO 159
<211> LENGTH: 11
<212> TYPE: PRT
<213> ORGANISM: Artificial Sequence
<220> FEATURE:
<223> OTHER INFORMATION: Synthetic

<400> SEQUENCE: 159

Gln Ala Ser Gln Asp Ile Asn Asn Tyr Leu Asn
1               5                   10

<210> SEQ ID NO 160
<211> LENGTH: 13
<212> TYPE: PRT
<213> ORGANISM: Artificial Sequence
<220> FEATURE:
<223> OTHER INFORMATION: Synthetic

<400> SEQUENCE: 160

Thr Arg Ser Ser Gly Asn Phe Ala Ser Thr Tyr Val Gln
1 5 10

<210> SEQ ID NO 161
<211> LENGTH: 11
<212> TYPE: PRT
<213> ORGANISM: Artificial Sequence
<220> FEATURE:
<223> OTHER INFORMATION: Synthetic

<400> SEQUENCE: 161

Gln Ala Ser Gln Asp Ile Gly His Asn Leu Asn
1 5 10

<210> SEQ ID NO 162
<211> LENGTH: 7
<212> TYPE: PRT
<213> ORGANISM: Artificial Sequence
<220> FEATURE:
<223> OTHER INFORMATION: Synthetic

<400> SEQUENCE: 162

Asp Ile Asn Asn Arg Pro Ser
1 5

<210> SEQ ID NO 163
<211> LENGTH: 7
<212> TYPE: PRT
<213> ORGANISM: Artificial Sequence
<220> FEATURE:
<223> OTHER INFORMATION: Synthetic

<400> SEQUENCE: 163

Lys Ala Ser Asn Leu Glu Ser
1 5

<210> SEQ ID NO 164
<211> LENGTH: 7
<212> TYPE: PRT
<213> ORGANISM: Artificial Sequence
<220> FEATURE:
<223> OTHER INFORMATION: Synthetic

<400> SEQUENCE: 164

Asp Ala Ser Asn Leu Glu Thr
1 5

<210> SEQ ID NO 165
<211> LENGTH: 7
<212> TYPE: PRT
<213> ORGANISM: Artificial Sequence
<220> FEATURE:
<223> OTHER INFORMATION: Synthetic

<400> SEQUENCE: 165

Asp Asp Asn Gln Arg Pro Thr
1 5

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Asp Asn Asn Asn Arg Pro Ser
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic

<400> SEQUENCE: 167

Asp Phe Asn Asn Arg Pro Ser
1               5

<210> SEQ ID NO 168
<211> LENGTH: 7
<212> TYPE: PRT
<213> ORGANISM: Artificial Sequence
<220> FEATURE:
<223> OTHER INFORMATION: Synthetic

<400> SEQUENCE: 168

Asp Ile Asn Asn Arg Ala Ser
1               5

<210> SEQ ID NO 169
<211> LENGTH: 7
<212> TYPE: PRT
<213> ORGANISM: Artificial Sequence
<220> FEATURE:
<223> OTHER INFORMATION: Synthetic

<400> SEQUENCE: 169

Leu Gly Ser Ser Arg Ala Ser
1               5

<210> SEQ ID NO 170
<211> LENGTH: 7
<212> TYPE: PRT
<213> ORGANISM: Artificial Sequence
<220> FEATURE:
<223> OTHER INFORMATION: Synthetic

<400> SEQUENCE: 170

Asp Asn Thr Asn Arg Pro Ser
1               5

<210> SEQ ID NO 171
<211> LENGTH: 7
<212> TYPE: PRT
<213> ORGANISM: Artificial Sequence
<220> FEATURE:
<223> OTHER INFORMATION: Synthetic

<400> SEQUENCE: 171

Ala Asp Asn Gln Arg Pro Ser
1               5

<210> SEQ ID NO 172

<211> LENGTH: 7
<212> TYPE: PRT
<213> ORGANISM: Artificial Sequence
<220> FEATURE:
<223> OTHER INFORMATION: Synthetic

<400> SEQUENCE: 172

Asp Asn Ser Asn Arg Pro Ser
1 5

<210> SEQ ID NO 173
<211> LENGTH: 7
<212> TYPE: PRT
<213> ORGANISM: Artificial Sequence
<220> FEATURE:
<223> OTHER INFORMATION: Synthetic

<400> SEQUENCE: 173

Ser Asn Asn Gln Arg Pro Ser
1 5

<210> SEQ ID NO 174
<211> LENGTH: 7
<212> TYPE: PRT
<213> ORGANISM: Artificial Sequence
<220> FEATURE:
<223> OTHER INFORMATION: Synthetic

<400> SEQUENCE: 174

Leu Gly Ser Asn Arg Ala Ser
1 5

<210> SEQ ID NO 175
<211> LENGTH: 7
<212> TYPE: PRT
<213> ORGANISM: Artificial Sequence
<220> FEATURE:
<223> OTHER INFORMATION: Synthetic

<400> SEQUENCE: 175

Asp Ala Ser Gln Leu Glu Thr
1 5

<210> SEQ ID NO 176
<211> LENGTH: 7
<212> TYPE: PRT
<213> ORGANISM: Artificial Sequence
<220> FEATURE:
<223> OTHER INFORMATION: Synthetic

<400> SEQUENCE: 176

Asp Asp Asp Gln Arg Pro Ser
1 5

<210> SEQ ID NO 177
<211> LENGTH: 10
<212> TYPE: PRT
<213> ORGANISM: Artificial Sequence
<220> FEATURE:
<223> OTHER INFORMATION: Synthetic

<400> SEQUENCE: 177

Ser Ala Tyr Thr Ser Ser Asp Thr Leu Val
1 5 10

<210> SEQ ID NO 178
<211> LENGTH: 9

<212> TYPE: PRT
<213> ORGANISM: Artificial Sequence
<220> FEATURE:
<223> OTHER INFORMATION: Synthetic

<400> SEQUENCE: 178

Gln Gln Tyr Gln Ser Tyr Pro Tyr Thr
1 5

<210> SEQ ID NO 179
<211> LENGTH: 9
<212> TYPE: PRT
<213> ORGANISM: Artificial Sequence
<220> FEATURE:
<223> OTHER INFORMATION: Synthetic

<400> SEQUENCE: 179

Leu Gln Leu Tyr Asp Tyr Pro Leu Thr
1 5

<210> SEQ ID NO 180
<211> LENGTH: 9
<212> TYPE: PRT
<213> ORGANISM: Artificial Sequence
<220> FEATURE:
<223> OTHER INFORMATION: Synthetic

<400> SEQUENCE: 180

Gln Ser Ser His Ser Thr Ala Val Val
1 5

<210> SEQ ID NO 181
<211> LENGTH: 10
<212> TYPE: PRT
<213> ORGANISM: Artificial Sequence
<220> FEATURE:
<223> OTHER INFORMATION: Synthetic

<400> SEQUENCE: 181

Ser Ala Tyr Thr Ser Ser Asp Thr Val Val
1 5 10

<210> SEQ ID NO 182
<211> LENGTH: 9
<212> TYPE: PRT
<213> ORGANISM: Artificial Sequence
<220> FEATURE:
<223> OTHER INFORMATION: Synthetic

<400> SEQUENCE: 182

Met Gln Ala Leu Gln Thr Pro Arg Thr
1 5

<210> SEQ ID NO 183
<211> LENGTH: 8
<212> TYPE: PRT
<213> ORGANISM: Artificial Sequence
<220> FEATURE:
<223> OTHER INFORMATION: Synthetic

<400> SEQUENCE: 183

Gln Gln Tyr Glu Asp Leu Pro Ser
1 5

<210> SEQ ID NO 184
<211> LENGTH: 9
<212> TYPE: PRT

<213> ORGANISM: Artificial Sequence
<220> FEATURE:
<223> OTHER INFORMATION: Synthetic

<400> SEQUENCE: 184

Leu Gln Asp Tyr Ile Tyr Pro Trp Thr
1 5

<210> SEQ ID NO 185
<211> LENGTH: 11
<212> TYPE: PRT
<213> ORGANISM: Artificial Sequence
<220> FEATURE:
<223> OTHER INFORMATION: Synthetic

<400> SEQUENCE: 185

Gln Ser Tyr Asp Ser Ser Leu Arg Ala Ser Val
1 5 10

<210> SEQ ID NO 186
<211> LENGTH: 10
<212> TYPE: PRT
<213> ORGANISM: Artificial Sequence
<220> FEATURE:
<223> OTHER INFORMATION: Synthetic

<400> SEQUENCE: 186

Gln Ser Phe Asp Ser Ser Leu Tyr Met Ile
1 5 10

<210> SEQ ID NO 187
<211> LENGTH: 11
<212> TYPE: PRT
<213> ORGANISM: Artificial Sequence
<220> FEATURE:
<223> OTHER INFORMATION: Synthetic

<400> SEQUENCE: 187

Gln Ser Phe Asp Ser Ser Leu Arg Gly Val Val
1 5 10

<210> SEQ ID NO 188
<211> LENGTH: 12
<212> TYPE: PRT
<213> ORGANISM: Artificial Sequence
<220> FEATURE:
<223> OTHER INFORMATION: Synthetic

<400> SEQUENCE: 188

Ala Ala Trp Asp Asp Ser Leu Asn Gly Leu Trp Val
1 5 10

<210> SEQ ID NO 189
<211> LENGTH: 9
<212> TYPE: PRT
<213> ORGANISM: Artificial Sequence
<220> FEATURE:
<223> OTHER INFORMATION: Synthetic

<400> SEQUENCE: 189

Met Gln Gly Thr His Trp Pro Trp Thr
1 5

<210> SEQ ID NO 190
<211> LENGTH: 9
<212> TYPE: PRT
<213> ORGANISM: Artificial Sequence
<220> FEATURE:
<223> OTHER INFORMATION: Synthetic

<400> SEQUENCE: 190

Gln Gln Tyr Asp Trp Leu Pro Leu Ser
1               5

<210> SEQ ID NO 191
<211> LENGTH: 10
<212> TYPE: PRT
<213> ORGANISM: Artificial Sequence
<220> FEATURE:
<223> OTHER INFORMATION: Synthetic

<400> SEQUENCE: 191

Gln Ser Tyr Asp Ser Ser Asn Phe Trp Val
1               5                   10

<210> SEQ ID NO 192
<211> LENGTH: 8
<212> TYPE: PRT
<213> ORGANISM: Artificial Sequence
<220> FEATURE:
<223> OTHER INFORMATION: Synthetic

<400> SEQUENCE: 192

Gln Gln Tyr Ala Asn Leu Pro Ser
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic

<400> SEQUENCE: 193

Met Gln Ala Leu Gln Thr Pro Pro Thr
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic

<400> SEQUENCE: 194

Gln Gln Tyr Asp Phe Leu Pro Pro Asp
1               5

<210> SEQ ID NO 195
<211> LENGTH: 7
<212> TYPE: PRT
<213> ORGANISM: Artificial Sequence
<220> FEATURE:
<223> OTHER INFORMATION: Synthetic

<400> SEQUENCE: 195

Ser Ser Ser Tyr Tyr Trp Gly
1               5

<210> SEQ ID NO 196
<211> LENGTH: 5
<212> TYPE: PRT
<213> ORGANISM: Artificial Sequence
<220> FEATURE:

<223> OTHER INFORMATION: Synthetic

<400> SEQUENCE: 196

Ser Tyr Ala Ile Ser
1 5

<210> SEQ ID NO 197
<211> LENGTH: 5
<212> TYPE: PRT
<213> ORGANISM: Artificial Sequence
<220> FEATURE:
<223> OTHER INFORMATION: Synthetic

<400> SEQUENCE: 197

Asn Tyr Gly Met His
1 5

<210> SEQ ID NO 198
<211> LENGTH: 5
<212> TYPE: PRT
<213> ORGANISM: Artificial Sequence
<220> FEATURE:
<223> OTHER INFORMATION: Synthetic

<400> SEQUENCE: 198

Ser Tyr Gly Met His
1 5

<210> SEQ ID NO 199
<211> LENGTH: 7
<212> TYPE: PRT
<213> ORGANISM: Artificial Sequence
<220> FEATURE:
<223> OTHER INFORMATION: Synthetic

<400> SEQUENCE: 199

Ser Gly Gly Tyr Tyr Trp Thr
1 5

<210> SEQ ID NO 200
<211> LENGTH: 5
<212> TYPE: PRT
<213> ORGANISM: Artificial Sequence
<220> FEATURE:
<223> OTHER INFORMATION: Synthetic

<400> SEQUENCE: 200

Gly Tyr Tyr Met His
1 5

<210> SEQ ID NO 201
<211> LENGTH: 5
<212> TYPE: PRT
<213> ORGANISM: Artificial Sequence
<220> FEATURE:
<223> OTHER INFORMATION: Synthetic

<400> SEQUENCE: 201

Gly Phe Tyr Trp Ser
1 5

<210> SEQ ID NO 202
<211> LENGTH: 15
<212> TYPE: PRT
<213> ORGANISM: Artificial Sequence
<220> FEATURE:
<223> OTHER INFORMATION: Synthetic

<400> SEQUENCE: 202

Ser Ile Tyr Tyr Ser Gly Ser Thr Tyr Tyr Asn Pro Ser Leu Lys
1 5 10 15

<210> SEQ ID NO 203
<211> LENGTH: 16
<212> TYPE: PRT
<213> ORGANISM: Artificial Sequence
<220> FEATURE:
<223> OTHER INFORMATION: Synthetic

<400> SEQUENCE: 203

Glu Ile Asn His Phe Gly Ser Thr Asn Tyr Asn Pro Ser Leu Lys Ser
1 5 10 15

<210> SEQ ID NO 204
<211> LENGTH: 17
<212> TYPE: PRT
<213> ORGANISM: Artificial Sequence
<220> FEATURE:
<223> OTHER INFORMATION: Synthetic

<400> SEQUENCE: 204

Gly Phe Asp Pro Glu Asp Gly Glu Thr Ile Tyr Ala Gln Lys Phe Gln
1 5 10 15

Gly

<210> SEQ ID NO 205

<400> SEQUENCE: 205

000

<210> SEQ ID NO 206
<211> LENGTH: 17
<212> TYPE: PRT
<213> ORGANISM: Artificial Sequence
<220> FEATURE:
<223> OTHER INFORMATION: Synthetic

<400> SEQUENCE: 206

Val Ile Ser Tyr Asp Gly Thr Asn Lys Tyr Tyr Ala Asp Ser Val Lys
1 5 10 15

Gly

<210> SEQ ID NO 207
<211> LENGTH: 17
<212> TYPE: PRT
<213> ORGANISM: Artificial Sequence
<220> FEATURE:
<223> OTHER INFORMATION: Synthetic

<400> SEQUENCE: 207

Val Ile Ser Tyr Asp Gly Gly Asn Lys Tyr Tyr Ala Asp Ser Val Lys
1 5 10 15

Gly

<210> SEQ ID NO 208
<211> LENGTH: 16
<212> TYPE: PRT
<213> ORGANISM: Artificial Sequence
<220> FEATURE:
<223> OTHER INFORMATION: Synthetic

<400> SEQUENCE: 208

Phe Ile Ser Trp Ser Gly Thr Thr Tyr Tyr Asn Pro Ser Leu Lys Asn
1 5 10 15

<210> SEQ ID NO 209
<211> LENGTH: 17
<212> TYPE: PRT
<213> ORGANISM: Artificial Sequence
<220> FEATURE:
<223> OTHER INFORMATION: Synthetic

<400> SEQUENCE: 209

Ile Ile Asn Pro Ser Gly Gly Ser Thr Ser Tyr Ala Gln Lys Phe Gln
1 5 10 15

Gly

<210> SEQ ID NO 210
<211> LENGTH: 12
<212> TYPE: PRT
<213> ORGANISM: Artificial Sequence
<220> FEATURE:
<223> OTHER INFORMATION: Synthetic

<400> SEQUENCE: 210

Ser Pro Gly Gly Tyr Ser Gly Gly Tyr Phe Gln His
1 5 10

<210> SEQ ID NO 211
<211> LENGTH: 10
<212> TYPE: PRT
<213> ORGANISM: Artificial Sequence
<220> FEATURE:
<223> OTHER INFORMATION: Synthetic

<400> SEQUENCE: 211

Asp Ile Leu Thr Gly Tyr Ala Leu Asp Tyr
1 5 10

<210> SEQ ID NO 212
<211> LENGTH: 11
<212> TYPE: PRT
<213> ORGANISM: Artificial Sequence
<220> FEATURE:
<223> OTHER INFORMATION: Synthetic

<400> SEQUENCE: 212

Asp Leu Arg Ile Pro Tyr Tyr Tyr Asp Asn Pro
1 5 10

<210> SEQ ID NO 213
<211> LENGTH: 9
<212> TYPE: PRT
<213> ORGANISM: Artificial Sequence
<220> FEATURE:
<223> OTHER INFORMATION: Synthetic

<400> SEQUENCE: 213

Ser Leu Tyr Tyr Ser His Phe Asp Tyr
1 5

<210> SEQ ID NO 214
<211> LENGTH: 14
<212> TYPE: PRT
<213> ORGANISM: Artificial Sequence
<220> FEATURE:
<223> OTHER INFORMATION: Synthetic

<400> SEQUENCE: 214

Glu Gly Pro Leu Ser Ser Ser Gly Pro Gly Ala Phe Asp Ile
1 5 10

<210> SEQ ID NO 215
<211> LENGTH: 5
<212> TYPE: PRT
<213> ORGANISM: Artificial Sequence
<220> FEATURE:
<223> OTHER INFORMATION: Synthetic

<400> SEQUENCE: 215

Asp Gly Phe Asp Ile
1 5

<210> SEQ ID NO 216
<211> LENGTH: 11
<212> TYPE: PRT
<213> ORGANISM: Artificial Sequence
<220> FEATURE:
<223> OTHER INFORMATION: Synthetic

<400> SEQUENCE: 216

Asp Val Tyr Gly Asp Tyr Gly Ala Phe Asp Tyr
1 5 10

<210> SEQ ID NO 217
<211> LENGTH: 8
<212> TYPE: PRT
<213> ORGANISM: Artificial Sequence
<220> FEATURE:
<223> OTHER INFORMATION: Synthetic

<400> SEQUENCE: 217

Ser Val Ala Pro Pro Met Asp Val
1 5

<210> SEQ ID NO 218
<211> LENGTH: 13
<212> TYPE: PRT
<213> ORGANISM: Artificial Sequence
<220> FEATURE:
<223> OTHER INFORMATION: Synthetic

<400> SEQUENCE: 218

Gly Pro Ala Gly Ser Ser Ser Ser Gly Tyr Phe Asp Tyr
1 5 10

<210> SEQ ID NO 219
<211> LENGTH: 6
<212> TYPE: PRT
<213> ORGANISM: Artificial Sequence
<220> FEATURE:
<223> OTHER INFORMATION: Synthetic

<400> SEQUENCE: 219

Gly Ser Gly Arg Leu Val
1 5

<210> SEQ ID NO 220
<211> LENGTH: 11
<212> TYPE: PRT
<213> ORGANISM: Artificial Sequence
<220> FEATURE:
<223> OTHER INFORMATION: Synthetic

<400> SEQUENCE: 220

Ala Asp Thr Ala Met Gly Asp Ala Phe Asp Ile
1 5 10

<210> SEQ ID NO 221
<211> LENGTH: 9
<212> TYPE: PRT
<213> ORGANISM: Artificial Sequence
<220> FEATURE:
<223> OTHER INFORMATION: Synthetic

<400> SEQUENCE: 221

Ser Ile Gly Ile Gly Ala Phe Asp Ile
1 5

<210> SEQ ID NO 222
<211> LENGTH: 13
<212> TYPE: PRT
<213> ORGANISM: Artificial Sequence
<220> FEATURE:
<223> OTHER INFORMATION: Synthetic

<400> SEQUENCE: 222

Gly Pro Ala Gly Ser Thr Ser Ser Gly Tyr Phe Asp His
1 5 10

<210> SEQ ID NO 223
<211> LENGTH: 9
<212> TYPE: PRT
<213> ORGANISM: Artificial Sequence
<220> FEATURE:
<223> OTHER INFORMATION: Synthetic

<400> SEQUENCE: 223

Gly Ser Ser Ser Tyr Tyr Met Asp Val
1 5

<210> SEQ ID NO 224
<211> LENGTH: 8
<212> TYPE: PRT
<213> ORGANISM: Artificial Sequence
<220> FEATURE:
<223> OTHER INFORMATION: Synthetic

<400> SEQUENCE: 224

Gly Gly Ser Ala Tyr Phe Gln His
1 5

<210> SEQ ID NO 225
<211> LENGTH: 13
<212> TYPE: PRT
<213> ORGANISM: Artificial Sequence
<220> FEATURE:
<223> OTHER INFORMATION: Synthetic

<400> SEQUENCE: 225

Gly Pro Ala Gly Thr Gly Ser Ser Gly Tyr Phe Asp Tyr
1 5 10

<210> SEQ ID NO 226
<211> LENGTH: 11
<212> TYPE: PRT
<213> ORGANISM: Artificial Sequence
<220> FEATURE:
<223> OTHER INFORMATION: Synthetic

<400> SEQUENCE: 226

Ser Gly Asp Ala Leu Pro Lys Gln Phe Ala Phe
1 5 10

<210> SEQ ID NO 227
<211> LENGTH: 16
<212> TYPE: PRT
<213> ORGANISM: Artificial Sequence
<220> FEATURE:
<223> OTHER INFORMATION: Synthetic

<400> SEQUENCE: 227

Arg Ser Ser Gln Ser Leu Leu His Ser Asn Gly Tyr Asn Tyr Leu Asn
1 5 10 15

<210> SEQ ID NO 228
<211> LENGTH: 11
<212> TYPE: PRT
<213> ORGANISM: Artificial Sequence
<220> FEATURE:
<223> OTHER INFORMATION: Synthetic

<400> SEQUENCE: 228

Arg Ala Ser Gln Ser Val Ser Tyr His Leu Ala
1 5 10

<210> SEQ ID NO 229
<211> LENGTH: 11
<212> TYPE: PRT
<213> ORGANISM: Artificial Sequence
<220> FEATURE:
<223> OTHER INFORMATION: Synthetic

<400> SEQUENCE: 229

Arg Ala Ser Gln Ser Ile Ser Ser Trp Leu Ala
1 5 10

<210> SEQ ID NO 230
<211> LENGTH: 16
<212> TYPE: PRT
<213> ORGANISM: Artificial Sequence
<220> FEATURE:
<223> OTHER INFORMATION: Synthetic

<400> SEQUENCE: 230

Lys Ser Ser Gln Ser Leu Leu Tyr Phe Asn Gly Asn Thr Tyr Leu Ser
1 5 10 15

<210> SEQ ID NO 231
<211> LENGTH: 16
<212> TYPE: PRT
<213> ORGANISM: Artificial Sequence
<220> FEATURE:
<223> OTHER INFORMATION: Synthetic

<400> SEQUENCE: 231

Arg Ser Ser Gln Ser Leu Val His Ser Asn Gly Tyr Asn Tyr Leu Asp
1 5 10 15

<210> SEQ ID NO 232
<211> LENGTH: 11
<212> TYPE: PRT
<213> ORGANISM: Artificial Sequence
<220> FEATURE:
<223> OTHER INFORMATION: Synthetic

<400> SEQUENCE: 232

Arg Ala Ser Gln Ser Val Ser Ser Asn Leu Ala
1 5 10

<210> SEQ ID NO 233
<211> LENGTH: 17
<212> TYPE: PRT
<213> ORGANISM: Artificial Sequence
<220> FEATURE:
<223> OTHER INFORMATION: Synthetic

<400> SEQUENCE: 233

Arg Ser Ser Gln Thr Leu Phe Asp Ser Asp Asp Gly Lys Thr Tyr Leu
1 5 10 15

Asp

<210> SEQ ID NO 234
<211> LENGTH: 16
<212> TYPE: PRT
<213> ORGANISM: Artificial Sequence
<220> FEATURE:
<223> OTHER INFORMATION: Synthetic

<400> SEQUENCE: 234

Arg Ala Thr Gln Ser Leu Leu His Gly Asn Gly His Asn Tyr Leu Asp
1 5 10 15

<210> SEQ ID NO 235
<211> LENGTH: 16
<212> TYPE: PRT
<213> ORGANISM: Artificial Sequence
<220> FEATURE:
<223> OTHER INFORMATION: Synthetic

<400> SEQUENCE: 235

Arg Ser Ser Gln Ser Leu Leu His Ser Asn Gly Asn Asn Tyr Leu Asp
1 5 10 15

<210> SEQ ID NO 236
<211> LENGTH: 7
<212> TYPE: PRT
<213> ORGANISM: Artificial Sequence
<220> FEATURE:
<223> OTHER INFORMATION: Synthetic

<400> SEQUENCE: 236

Leu Gly Ser Asn Arg Asp Ser
1 5

<210> SEQ ID NO 237
<211> LENGTH: 7
<212> TYPE: PRT
<213> ORGANISM: Artificial Sequence
<220> FEATURE:
<223> OTHER INFORMATION: Synthetic

<400> SEQUENCE: 237

Lys Asp Thr Glu Arg Pro Ser
1 5

<210> SEQ ID NO 238
<211> LENGTH: 7
<212> TYPE: PRT
<213> ORGANISM: Artificial Sequence
<220> FEATURE:
<223> OTHER INFORMATION: Synthetic

<400> SEQUENCE: 238

Leu Gly Ser Asp Arg Ala Ser
1               5

<210> SEQ ID NO 239
<211> LENGTH: 7
<212> TYPE: PRT
<213> ORGANISM: Artificial Sequence
<220> FEATURE:
<223> OTHER INFORMATION: Synthetic

<400> SEQUENCE: 239

Leu Val Ser Asn Arg Ala Ser
1               5

<210> SEQ ID NO 240
<211> LENGTH: 7
<212> TYPE: PRT
<213> ORGANISM: Artificial Sequence
<220> FEATURE:
<223> OTHER INFORMATION: Synthetic

<400> SEQUENCE: 240

Asp Thr Ser Asn Arg Ala Ser
1               5

<210> SEQ ID NO 241
<211> LENGTH: 7
<212> TYPE: PRT
<213> ORGANISM: Artificial Sequence
<220> FEATURE:
<223> OTHER INFORMATION: Synthetic

<400> SEQUENCE: 241

Asp Ala Ser Arg Leu Glu Asp
1               5

<210> SEQ ID NO 242
<211> LENGTH: 7
<212> TYPE: PRT
<213> ORGANISM: Artificial Sequence
<220> FEATURE:
<223> OTHER INFORMATION: Synthetic

<400> SEQUENCE: 242

Gln Val Ser Asn Arg Asp Ser
1               5

<210> SEQ ID NO 243
<211> LENGTH: 7
<212> TYPE: PRT
<213> ORGANISM: Artificial Sequence
<220> FEATURE:
<223> OTHER INFORMATION: Synthetic

<400> SEQUENCE: 243

Gly Ala Ser Ser Gly Ala Thr
1               5

<210> SEQ ID NO 244
<211> LENGTH: 7
<212> TYPE: PRT
<213> ORGANISM: Artificial Sequence
<220> FEATURE:
<223> OTHER INFORMATION: Synthetic

<400> SEQUENCE: 244

Thr Thr Ser Ser Arg Ala Ser
1 5

<210> SEQ ID NO 245
<211> LENGTH: 7
<212> TYPE: PRT
<213> ORGANISM: Artificial Sequence
<220> FEATURE:
<223> OTHER INFORMATION: Synthetic

<400> SEQUENCE: 245

Leu Ala Ser Asn Arg Ala Ser
1 5

<210> SEQ ID NO 246

<400> SEQUENCE: 246

000

<210> SEQ ID NO 247
<211> LENGTH: 11
<212> TYPE: PRT
<213> ORGANISM: Artificial Sequence
<220> FEATURE:
<223> OTHER INFORMATION: Synthetic

<400> SEQUENCE: 247

Gln Ser Pro Asp Ser Ser Gly Thr Val Glu Val
1 5 10

<210> SEQ ID NO 248
<211> LENGTH: 9
<212> TYPE: PRT
<213> ORGANISM: Artificial Sequence
<220> FEATURE:
<223> OTHER INFORMATION: Synthetic

<400> SEQUENCE: 248

Met Gln Ala Leu Gln Thr Pro Thr Thr
1 5

<210> SEQ ID NO 249
<211> LENGTH: 9
<212> TYPE: PRT
<213> ORGANISM: Artificial Sequence
<220> FEATURE:
<223> OTHER INFORMATION: Synthetic

<400> SEQUENCE: 249

Met Gln Thr Leu Gln Thr Pro Leu Ser
1 5

<210> SEQ ID NO 250
<211> LENGTH: 9
<212> TYPE: PRT
<213> ORGANISM: Artificial Sequence
<220> FEATURE:
<223> OTHER INFORMATION: Synthetic

<400> SEQUENCE: 250

Gln Gln Arg Tyr Asp Trp Pro Leu Thr
1 5

<210> SEQ ID NO 251
<211> LENGTH: 9
<212> TYPE: PRT

<213> ORGANISM: Artificial Sequence
<220> FEATURE:
<223> OTHER INFORMATION: Synthetic

<400> SEQUENCE: 251

Gln Gln Tyr Asp Asp Leu Pro Tyr Thr
1               5

<210> SEQ ID NO 252
<211> LENGTH: 9
<212> TYPE: PRT
<213> ORGANISM: Artificial Sequence
<220> FEATURE:
<223> OTHER INFORMATION: Synthetic

<400> SEQUENCE: 252

Met Gln Gly Thr Gln Trp Pro Pro Thr
1               5

<210> SEQ ID NO 253
<211> LENGTH: 9
<212> TYPE: PRT
<213> ORGANISM: Artificial Sequence
<220> FEATURE:
<223> OTHER INFORMATION: Synthetic

<400> SEQUENCE: 253

Met Gln Ala Leu Arg Thr Pro Tyr Thr
1               5

<210> SEQ ID NO 254
<211> LENGTH: 9
<212> TYPE: PRT
<213> ORGANISM: Artificial Sequence
<220> FEATURE:
<223> OTHER INFORMATION: Synthetic

<400> SEQUENCE: 254

Leu Gln Gly Ser His Trp Pro Trp Thr
1               5

<210> SEQ ID NO 255
<211> LENGTH: 8
<212> TYPE: PRT
<213> ORGANISM: Artificial Sequence
<220> FEATURE:
<223> OTHER INFORMATION: Synthetic

<400> SEQUENCE: 255

Gln Leu Tyr Gly Ser Ser Leu Ala
1               5

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Met Gln Arg Leu Gln Phe Pro Leu Thr
1               5

<210> SEQ ID NO 257
<211> LENGTH: 9
<212> TYPE: PRT
<213> ORGANISM: Artificial Sequence
<220> FEATURE:
<223> OTHER INFORMATION: Synthetic

<400> SEQUENCE: 257

Met Gln Thr Leu Glu Thr Pro Val Thr
1 5

<210> SEQ ID NO 258
<211> LENGTH: 9
<212> TYPE: PRT
<213> ORGANISM: Artificial Sequence
<220> FEATURE:
<223> OTHER INFORMATION: Synthetic

<400> SEQUENCE: 258

Leu Gln Gly Thr His Trp Pro Trp Thr
1 5

<210> SEQ ID NO 259
<211> LENGTH: 113
<212> TYPE: PRT
<213> ORGANISM: Artificial Sequence
<220> FEATURE:
<223> OTHER INFORMATION: Synthetic

<400> SEQUENCE: 259

Pro Cys Pro Ala Pro Glu Ala Ala Gly Gly Pro Ser Val Phe Leu Phe
1 5 10 15

Pro Pro Lys Pro Lys Asp Thr Leu Met Ile Ser Arg Thr Pro Glu Val
20 25 30

Thr Cys Val Val Val Asp Val Ser His Glu Asp Pro Glu Val Lys Phe
35 40 45

Asn Trp Tyr Val Asp Gly Val Glu Val His Asn Ala Lys Thr Lys Pro
50 55 60

Arg Glu Glu Gln Tyr Asn Ser Thr Tyr Arg Val Val Ser Val Leu Thr
65 70 75 80

Val Leu His Gln Asp Trp Leu Asn Gly Lys Glu Tyr Lys Cys Lys Val
85 90 95

Ser Asn Lys Ala Leu Pro Ala Pro Ile Glu Lys Thr Ile Ser Lys Ala
100 105 110

Lys

<210> SEQ ID NO 260
<211> LENGTH: 107
<212> TYPE: PRT
<213> ORGANISM: Artificial Sequence
<220> FEATURE:
<223> OTHER INFORMATION: Synthetic

<400> SEQUENCE: 260

Gly Gln Pro Arg Glu Pro Gln Val Tyr Thr Leu Pro Pro Cys Arg Asp
1 5 10 15

Glu Leu Thr Lys Asn Gln Val Ser Leu Trp Cys Leu Val Lys Gly Phe
20 25 30

Tyr Pro Ser Asp Ile Ala Val Glu Trp Glu Ser Asn Gly Gln Pro Glu
35 40 45

Asn Asn Tyr Lys Thr Thr Pro Pro Val Leu Asp Ser Asp Gly Ser Phe
50 55 60

Phe Leu Tyr Ser Lys Leu Thr Val Asp Lys Ser Arg Trp Gln Gln Gly
65 70 75 80

```
Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 261
<211> LENGTH: 113
<212> TYPE: PRT
<213> ORGANISM: Artificial Sequence
<220> FEATURE:
<223> OTHER INFORMATION: Synthetic

<400> SEQUENCE: 261

Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys


<210> SEQ ID NO 262
<211> LENGTH: 107
<212> TYPE: PRT
<213> ORGANISM: Artificial Sequence
<220> FEATURE:
<223> OTHER INFORMATION: Synthetic

<400> SEQUENCE: 262

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 263
<211> LENGTH: 113
<212> TYPE: PRT
<213> ORGANISM: Artificial Sequence
<220> FEATURE:
<223> OTHER INFORMATION: Synthetic

<400> SEQUENCE: 263
```

```
Pro Cys Pro Ala Pro Glu Ala Ala Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys


<210> SEQ ID NO 264
<211> LENGTH: 107
<212> TYPE: PRT
<213> ORGANISM: Artificial Sequence
<220> FEATURE:
<223> OTHER INFORMATION: Synthetic

<400> SEQUENCE: 264

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 265
<211> LENGTH: 480
<212> TYPE: PRT
<213> ORGANISM: Artificial Sequence
<220> FEATURE:
<223> OTHER INFORMATION: Synthetic

<400> SEQUENCE: 265

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Leu Val Phe Gly Gly Gly
225                 230                 235                 240

Thr Lys Leu Thr Val Leu Asn Ser Gly Ala Gly Thr Ala Ala Ala Thr
                245                 250                 255

His Thr Cys Pro Pro Cys Pro Ala Pro Glu Ala Ala Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
    370                 375                 380

Pro Pro Cys Arg Asp Glu Leu Thr Lys Asn Gln Val Ser Leu Trp Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480
```

<210> SEQ ID NO 266
<211> LENGTH: 241

<212> TYPE: PRT
<213> ORGANISM: Artificial Sequence
<220> FEATURE:
<223> OTHER INFORMATION: Synthetic

<400> SEQUENCE: 266

Glu Val Gln Leu Val Gln Ser Gly Thr Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Ala Met His Trp Val Arg Gln Ala Pro Gly Gln Ser Leu Glu Trp Met
        35                  40                  45

Gly Trp Ile Asn Thr Gly Asn Gly Asn Thr Lys Tyr Ser Gln Asn Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Leu Gly Gln Leu Glu Arg Leu Tyr Phe Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Thr
    130                 135                 140

Leu Ser Ala Ser Val Gly Asp Arg Val Thr Leu Ser Cys Arg Ala Gly
145                 150                 155                 160

Gln Ala Ile Ser Ser Trp Leu Ala Trp Tyr Gln Gln Lys Pro Gly Lys
                165                 170                 175

Ala Pro Lys Leu Leu Ile Tyr Lys Ala Ser Asn Leu Glu Ser Gly Val
            180                 185                 190

Pro Ser Arg Phe Ser Gly Gly Gly Ser Gly Ala Glu Phe Thr Leu Thr
        195                 200                 205

Ile Ser Ser Leu Gln Pro Asp Asp Phe Ala Thr Tyr Tyr Cys Gln Gln
    210                 215                 220

Tyr Gln Ser Tyr Pro Tyr Thr Phe Gly Gln Gly Thr Lys Leu Glu Ile
225                 230                 235                 240

Arg

<210> SEQ ID NO 267
<211> LENGTH: 236
<212> TYPE: PRT
<213> ORGANISM: Artificial Sequence
<220> FEATURE:
<223> OTHER INFORMATION: Synthetic

<400> SEQUENCE: 267

His Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Asp Leu Gly Asp Tyr Trp Gly Gln Gly Thr Leu Val Thr Val
            100                 105                 110

Ser Ser Gly Gly Gly Gly Ser Gly Gly Gly Gly Ser Gly Gly Gly Gly
        115                 120                 125

Ser Asp Ile Gln Leu Thr Gln Ser Pro Ser Ser Leu Ser Ala Ser Val
    130                 135                 140

Gly Asp Arg Val Thr Ile Thr Cys Gln Ala Ser Gln Asp Ile Gly Asn
145                 150                 155                 160

Tyr Leu Asn Trp Tyr Gln Leu Lys Pro Gly Lys Ala Pro Lys Leu Leu
                165                 170                 175

Ile Tyr Asp Ala Ser Asn Leu Glu Thr Gly Val Pro Ser Arg Phe Ser
            180                 185                 190

Gly Ser Gly Ser Gly Thr Asp Phe Thr Phe Thr Ile Ser Ser Leu Gln
        195                 200                 205

Pro Glu Asp Ile Ala Thr Tyr Tyr Cys Leu Gln Leu Tyr Asp Tyr Pro
    210                 215                 220

Leu Thr Phe Gly Gly Gly Thr Lys Val Glu Ile Lys
225                 230                 235


<210> SEQ ID NO 268
<211> LENGTH: 242
<212> TYPE: PRT
<213> ORGANISM: Artificial Sequence
<220> FEATURE:
<223> OTHER INFORMATION: Synthetic

<400> SEQUENCE: 268

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Ser Ser Gly Asp Ala Phe Asp Ile Trp Gly Gln Gly Thr Met
            100                 105                 110

Val Thr Val Ser Ser Gly Gly Gly Gly Ser Gly Gly Gly Gly Ser Gly
        115                 120                 125

Gly Gly Gly Ser Asn Phe Met Leu Thr Gln Pro His Ser Val Ser Glu
    130                 135                 140

Ser Pro Gly Lys Thr Val Thr Ile Ser Cys Thr Arg Ser Ser Gly Ser
145                 150                 155                 160

Ile Ala Ser Asn Tyr Val Gln Trp Tyr Gln Gln Arg Pro Gly Ser Ser
                165                 170                 175

Pro Thr Thr Val Ile Phe Asp Asp Asn Gln Arg Pro Thr Gly Val Pro
            180                 185                 190

Asp Arg Phe Ser Ala Ala Ile Asp Thr Ser Ser Ser Ser Ala Ser Leu
        195                 200                 205
```

Thr Ile Ser Gly Leu Thr Ala Glu Asp Glu Ala Asp Tyr Tyr Cys Gln
    210                 215                 220

Ser Ser His Ser Thr Ala Val Val Phe Gly Gly Gly Thr Lys Leu Thr
225                 230                 235                 240

Val Leu

<210> SEQ ID NO 269
<211> LENGTH: 246
<212> TYPE: PRT
<213> ORGANISM: Artificial Sequence
<220> FEATURE:
<223> OTHER INFORMATION: Synthetic

<400> SEQUENCE: 269

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly Asp Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Leu Val Phe Gly Gly Gly
225                 230                 235                 240

Thr Lys Leu Thr Val Leu
                245

<210> SEQ ID NO 270
<211> LENGTH: 246
<212> TYPE: PRT
<213> ORGANISM: Artificial Sequence
<220> FEATURE:
<223> OTHER INFORMATION: Synthetic

<400> SEQUENCE: 270

Glu Val Gln Leu Val Gln Ser Gly Ala Glu Val Lys Lys Pro Gly Ser
1               5                   10                  15

```
Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Asn Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu
                245


<210> SEQ ID NO 271
<211> LENGTH: 246
<212> TYPE: PRT
<213> ORGANISM: Artificial Sequence
<220> FEATURE:
<223> OTHER INFORMATION: Synthetic

<400> SEQUENCE: 271

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125
```

```
Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Asn Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Leu Val Phe Gly Gly Gly
225                 230                 235                 240

Thr Lys Leu Thr Val Leu
                245


<210> SEQ ID NO 272
<211> LENGTH: 246
<212> TYPE: PRT
<213> ORGANISM: Artificial Sequence
<220> FEATURE:
<223> OTHER INFORMATION: Synthetic

<400> SEQUENCE: 272

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Thr Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240
```

Thr Lys Leu Thr Val Leu
245

<210> SEQ ID NO 273
<211> LENGTH: 246
<212> TYPE: PRT
<213> ORGANISM: Artificial Sequence
<220> FEATURE:
<223> OTHER INFORMATION: Synthetic

<400> SEQUENCE: 273

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Ala Ile Ser Cys Thr Gly
145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 274
<211> LENGTH: 246
<212> TYPE: PRT
<213> ORGANISM: Artificial Sequence
<220> FEATURE:
<223> OTHER INFORMATION: Synthetic

<400> SEQUENCE: 274

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Pro Pro Gly Gln Gly Leu Glu Trp Met
35 40 45

```
Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu
                245


<210> SEQ ID NO 275
<211> LENGTH: 246
<212> TYPE: PRT
<213> ORGANISM: Artificial Sequence
<220> FEATURE:
<223> OTHER INFORMATION: Synthetic

<400> SEQUENCE: 275

Glu Val Gln Leu Val Gln Ser Gly Ala Glu Val Lys Lys Pro Gly Ser
1               5                   10                  15

Thr Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160
```

```
Thr Ser Ser Asp Ile Gly His Tyr Asp Phe Ile Ser Trp Tyr Gln Gln
                165                 170                 175

His Pro Gly Thr Ala Pro Lys Leu Ile Ile Tyr Asp Phe Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Leu Val Phe Gly Gly Gly
225                 230                 235                 240

Thr Lys Leu Thr Val Leu
                245


<210> SEQ ID NO 276
<211> LENGTH: 246
<212> TYPE: PRT
<213> ORGANISM: Artificial Sequence
<220> FEATURE:
<223> OTHER INFORMATION: Synthetic

<400> SEQUENCE: 276

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly Asp Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Leu Val Phe Gly Gly Gly
225                 230                 235                 240

Thr Lys Leu Thr Val Leu
                245


<210> SEQ ID NO 277
```

<211> LENGTH: 246
<212> TYPE: PRT
<213> ORGANISM: Artificial Sequence
<220> FEATURE:
<223> OTHER INFORMATION: Synthetic

<400> SEQUENCE: 277

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Ala Ile Ser Cys Thr Gly
145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Asn Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 278
<211> LENGTH: 253
<212> TYPE: PRT
<213> ORGANISM: Artificial Sequence
<220> FEATURE:
<223> OTHER INFORMATION: Synthetic

<400> SEQUENCE: 278

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr

```
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Val Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu Ala Ala Ala His His His His
                245                 250
```

<210> SEQ ID NO 279
<211> LENGTH: 246
<212> TYPE: PRT
<213> ORGANISM: Artificial Sequence
<220> FEATURE:
<223> OTHER INFORMATION: Synthetic

<400> SEQUENCE: 279

```
Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Asn Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
```

180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 280
<211> LENGTH: 246
<212> TYPE: PRT
<213> ORGANISM: Artificial Sequence
<220> FEATURE:
<223> OTHER INFORMATION: Synthetic

<400> SEQUENCE: 280

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Ala Ile Ser Cys Thr Gly
145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 281
<211> LENGTH: 246
<212> TYPE: PRT
<213> ORGANISM: Artificial Sequence
<220> FEATURE:
<223> OTHER INFORMATION: Synthetic

<400> SEQUENCE: 281

Glu Val Gln Leu Val Gln Ser Gly Ala Glu Val Lys Glu Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Ile Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Ala Ile Ser Cys Thr Gly
145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 282
<211> LENGTH: 246
<212> TYPE: PRT
<213> ORGANISM: Artificial Sequence
<220> FEATURE:
<223> OTHER INFORMATION: Synthetic

<400> SEQUENCE: 282

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Asn Ser Leu Arg Ser Glu Asp Thr Ala Val Tyr Tyr Cys
85 90 95

```
Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu
                245


<210> SEQ ID NO 283
<211> LENGTH: 246
<212> TYPE: PRT
<213> ORGANISM: Artificial Sequence
<220> FEATURE:
<223> OTHER INFORMATION: Synthetic

<400> SEQUENCE: 283

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly Asp Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205
```

```
Ala Ser Leu Ile Ile Ser Gly Leu Gln Pro Glu Asp Glu Ala Asp Tyr
    210                 215                 220

Tyr Cys Ser Ala Tyr Thr Ser Ser Asp Thr Leu Val Phe Gly Gly Gly
225                 230                 235                 240

Thr Lys Leu Thr Val Leu
                245


<210> SEQ ID NO 284
<211> LENGTH: 246
<212> TYPE: PRT
<213> ORGANISM: Artificial Sequence
<220> FEATURE:
<223> OTHER INFORMATION: Synthetic

<400> SEQUENCE: 284

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asp Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu
                245


<210> SEQ ID NO 285
<211> LENGTH: 246
<212> TYPE: PRT
<213> ORGANISM: Artificial Sequence
<220> FEATURE:
<223> OTHER INFORMATION: Synthetic

<400> SEQUENCE: 285

Glu Val Gln Leu Val Gln Ser Gly Ala Glu Val Lys Lys Pro Gly Ser
1               5                   10                  15
```

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Pro Gly Thr Leu Val Thr Val Ser Ser Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Ala Ile Ser Cys Thr Gly
145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 286
<211> LENGTH: 246
<212> TYPE: PRT
<213> ORGANISM: Artificial Sequence
<220> FEATURE:
<223> OTHER INFORMATION: Synthetic

<400> SEQUENCE: 286

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Ile His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser Gly Gly Gly Gly Ser Gly Gly
115 120 125

```
Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Ala Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu
                245


<210> SEQ ID NO 287
<211> LENGTH: 246
<212> TYPE: PRT
<213> ORGANISM: Artificial Sequence
<220> FEATURE:
<223> OTHER INFORMATION: Synthetic

<400> SEQUENCE: 287

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Asn Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240
```

Thr Lys Leu Thr Val Leu
245

<210> SEQ ID NO 288
<211> LENGTH: 246
<212> TYPE: PRT
<213> ORGANISM: Artificial Sequence
<220> FEATURE:
<223> OTHER INFORMATION: Synthetic

<400> SEQUENCE: 288

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Met Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gln Ser Thr Leu Thr Gln Pro Ala
130 135 140

Ser Val Ser Gly Ser Pro Gly Gln Ser Ile Thr Ile Ser Cys Thr Gly
145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 289
<211> LENGTH: 246
<212> TYPE: PRT
<213> ORGANISM: Artificial Sequence
<220> FEATURE:
<223> OTHER INFORMATION: Synthetic

<400> SEQUENCE: 289

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met

```
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Thr Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Val Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu
                245


<210> SEQ ID NO 290
<211> LENGTH: 246
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Asn Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
```

145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 291
<211> LENGTH: 246
<212> TYPE: PRT
<213> ORGANISM: Artificial Sequence
<220> FEATURE:
<223> OTHER INFORMATION: Synthetic

<400> SEQUENCE: 291

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Asn Val Ser Ser Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Ala Ile Ser Cys Thr Gly
145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 292
<211> LENGTH: 246
<212> TYPE: PRT
<213> ORGANISM: Artificial Sequence
<220> FEATURE:
<223> OTHER INFORMATION: Synthetic

<400> SEQUENCE: 292

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Ser Asn Tyr
20 25 30

Tyr Met His Trp Val Arg Gln Ala Pro Gly Gln Gly Leu Glu Trp Ile
35 40 45

Gly Ala Ile Met Pro Ser Arg Gly Gly Thr Ser Tyr Pro Gln Lys Phe
50 55 60

Gln Gly Arg Val Thr Met Thr Gly Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gln Ser Ala Leu Thr Gln Pro Ala
130 135 140

Ser Val Ser Gly Ser Pro Gly Gln Ser Ile Ala Ile Ser Cys Thr Gly
145 150 155 160

Thr Ser Ser Asp Ile Gly His Tyr Asp Phe Val Ser Trp Tyr Gln Gln
165 170 175

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 293
<211> LENGTH: 246
<212> TYPE: PRT
<213> ORGANISM: Artificial Sequence
<220> FEATURE:
<223> OTHER INFORMATION: Synthetic

<400> SEQUENCE: 293

Glu Val Gln Leu Val Gln Ser Gly Ala Glu Val Lys Lys Pro Gly Ser
1 5 10 15

Ser Val Lys Val Ser Cys Lys Ala Thr Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

```
Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly His Tyr Asp Phe Val Ser Trp Tyr Gln Gln
                165                 170                 175

His Pro Gly Thr Ala Pro Lys Leu Ile Ile Tyr Asp Ile Asn Asn Arg
            180                 185                 190

Pro Ser Gly Ile Ser Asn Arg Phe Ser Gly Ser Lys Ser Asp Asn Met
        195                 200                 205

Ala Ser Leu Thr Ile Ser Gly Leu Gln Pro Glu Asp Glu Ala Asp Tyr
    210                 215                 220

Tyr Cys Ser Ala Tyr Thr Ser Ser Asp Thr Val Val Phe Gly Gly Gly
225                 230                 235                 240

Thr Lys Leu Thr Val Leu
                245


<210> SEQ ID NO 294
<211> LENGTH: 246
<212> TYPE: PRT
<213> ORGANISM: Artificial Sequence
<220> FEATURE:
<223> OTHER INFORMATION: Synthetic

<400> SEQUENCE: 294

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asn Tyr
            20                  25                  30

Tyr Met His Trp Val Arg Gln Ala Pro Gly Gln Gly Leu Glu Trp Met
        35                  40                  45

Gly Ala Ile Met Pro Ser Arg Gly Gly Thr Ser Tyr Pro Gln Lys Phe
    50                  55                  60

Gln Gly Arg Val Thr Met Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Glu Tyr Tyr Tyr Asp Ser Ser Gly Tyr Tyr Tyr Trp Gly
            100                 105                 110

Gln Gly Thr Pro Val Thr Val Ser Ser Gly Gly Gly Gly Ser Gly Gly
        115                 120                 125

Gly Gly Ser Gly Gly Gly Gly Ser Gln Ser Ala Leu Thr Gln Pro Ala
    130                 135                 140

Ser Val Ser Gly Ser Pro Gly Gln Ser Ile Ala Ile Ser Cys Thr Gly
145                 150                 155                 160

Thr Ser Ser Asp Ile Gly Asp Tyr Asp Phe Val Ser Trp Tyr Gln Gln
                165                 170                 175
```

His Pro Gly Thr Ala Pro Lys Leu Ile Ile Tyr Asp Ile Asn Asn Arg
180 185 190

Pro Ser Gly Ile Ser Asn Arg Phe Ser Gly Ser Lys Ser Asp Asn Met
195 200 205

Ala Ser Leu Thr Ile Ser Gly Leu Gln Pro Glu Asp Glu Ala Asp Tyr
210 215 220

Tyr Cys Ser Ala Tyr Thr Ser Ser Asp Thr Val Val Phe Gly Gly Gly
225 230 235 240

Thr Lys Leu Thr Val Leu
245

<210> SEQ ID NO 295
<211> LENGTH: 246
<212> TYPE: PRT
<213> ORGANISM: Artificial Sequence
<220> FEATURE:
<223> OTHER INFORMATION: Synthetic

<400> SEQUENCE: 295

Glu Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met His Trp Val Arg Gln Ala Pro Gly Gln Gly Leu Glu Trp Met
35 40 45

Gly Ala Ile Met Pro Ser Arg Gly Gly Thr Ser Tyr Pro Gln Lys Phe
50 55 60

Gln Gly Arg Val Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Gly Glu Tyr Tyr Tyr Asp Ser Ser Gly Tyr Tyr Tyr Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Gln Ser Val Leu Thr Gln Pro Pro
130 135 140

Ser Val Ser Gly Ala Pro Gly Gln Arg Val Thr Ile Ser Cys Thr Gly
145 150 155 160

Thr Ser Ser Asp Ile Gly His Tyr Asp Phe Val Ser Trp Tyr Gln Gln
165 170 175

Leu Pro Gly Thr Ala Pro Lys Leu Leu Ile Tyr Asp Ile Asn Asn Arg
180 185 190

Pro Ser Gly Val Pro Asp Arg Phe Ser Gly Ser Lys Ser Gly Thr Ser
195 200 205

Ala Ser Leu Ala Ile Thr Gly Leu Gln Ala Glu Asp Glu Ala Asp Tyr
210 215 220

Tyr Cys Ser Ala Tyr Thr Ser Ser Asp Thr Leu Val Phe Gly Gly Gly
225 230 235 240

Thr Lys Leu Thr Val Leu
245

<210> SEQ ID NO 296
<211> LENGTH: 253
<212> TYPE: PRT
<213> ORGANISM: Artificial Sequence
<220> FEATURE:

<223> OTHER INFORMATION: Synthetic

<400> SEQUENCE: 296

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Tyr Ser Ser Ser Trp Tyr Tyr Tyr Tyr Tyr Gly
            100                 105                 110

Met Asp Val Trp Gly Gln Gly Thr Thr Val Thr Val Ser Ser Gly Gly
        115                 120                 125

Gly Gly Ser Gly Gly Gly Gly Ser Gly Gly Gly Gly Ser Asp Val Val
    130                 135                 140

Met Thr Gln Ser Pro Leu Ser Leu Pro Val Thr Pro Gly Glu Pro Ala
145                 150                 155                 160

Ser Ile Ser Cys Arg Ser Ser Gln Ser Leu Leu His Ser Asn Gly Tyr
                165                 170                 175

Asn Tyr Leu Asp Trp Tyr Leu Gln Lys Pro Gly Gln Ser Pro Gln Leu
            180                 185                 190

Leu Ile Tyr Leu Gly Ser Ser Arg Ala Ser Gly Val Pro Asp Arg Phe
        195                 200                 205

Ser Gly Ser Gly Ser Gly Thr Asp Phe Thr Leu Lys Ile Ser Arg Val
    210                 215                 220

Glu Ala Glu Asp Val Gly Val Tyr Tyr Cys Met Gln Ala Leu Gln Thr
225                 230                 235                 240

Pro Arg Thr Phe Gly Gln Gly Thr Lys Leu Glu Ile Lys
                245                 250
```

<210> SEQ ID NO 297
<211> LENGTH: 241
<212> TYPE: PRT
<213> ORGANISM: Artificial Sequence
<220> FEATURE:
<223> OTHER INFORMATION: Synthetic

<400> SEQUENCE: 297

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Val Ser Ile Ser Ser Arg
            20                  25                  30

Ser Asp His Trp Gly Trp Val Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95
```

Cys Ala Arg Glu Ser His Pro Ala Ala Ala Leu Val Gly Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Asp Ile Gln Met Thr Gln Ser Pro Ser
130 135 140

Ser Leu Ser Ala Ser Val Gly Asp Arg Val Thr Ile Thr Cys Gln Ala
145 150 155 160

Ser Gln Asp Ile Ser Asp Tyr Leu Asn Trp Tyr Gln Gln Lys Pro Gly
165 170 175

Lys Ala Pro Gln Ile Leu Ile Tyr Asp Ala Ser Asn Leu Glu Thr Gly
180 185 190

Val Pro Ser Arg Phe Ser Gly Ser Gly Ser Gly Thr Asp Phe Thr Phe
195 200 205

Thr Ile Ser Asn Leu Gln Pro Glu Asp Val Ala Thr Tyr Tyr Cys Gln
210 215 220

Gln Tyr Glu Asp Leu Pro Ser Phe Gly Gly Gly Thr Lys Val Glu Ile
225 230 235 240

Lys

<210> SEQ ID NO 298
<211> LENGTH: 234
<212> TYPE: PRT
<213> ORGANISM: Artificial Sequence
<220> FEATURE:
<223> OTHER INFORMATION: Synthetic

<400> SEQUENCE: 298

Glu Val Gln Leu Val Gln Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Thr Pro Ala Phe Trp Gly Gln Gly Thr Leu Val Thr Val Ser Ser
100 105 110

Gly Gly Gly Gly Ser Gly Gly Gly Gly Ser Gly Gly Gly Gly Ser Asp
115 120 125

Ile Gln Leu Thr Gln Ser Pro Ser Ser Leu Ser Ala Ser Val Gly Asp
130 135 140

Arg Val Thr Ile Thr Cys Arg Ala Ser Gln Ser Ile Ser Ser Tyr Leu
145 150 155 160

Asn Trp Tyr Gln Gln Lys Pro Gly Lys Ala Pro Lys Ala Leu Ile Tyr
165 170 175

Asp Ala Ser Asn Leu Glu Thr Gly Val Pro Ser Arg Phe Ser Gly Ser
180 185 190

Gly Ser Gly Thr Asp Phe Thr Leu Thr Ile Ile Ser Leu Gln Pro Glu
195 200 205

-continued

```
Asp Phe Ala Thr Tyr Phe Cys Leu Gln Asp Tyr Ile Tyr Pro Trp Thr
    210                 215                 220

Phe Gly Gln Gly Thr Lys Val Glu Phe Lys
225                 230


<210> SEQ ID NO 299
<211> LENGTH: 243
<212> TYPE: PRT
<213> ORGANISM: Artificial Sequence
<220> FEATURE:
<223> OTHER INFORMATION: Synthetic

<400> SEQUENCE: 299

Gln Val Gln Leu Gln Gln Trp Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Gly Gly Ser Asn Leu Asp Trp Phe Asp Pro Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gln Ser Val Leu Thr Gln Pro Pro Ser Val Ser Gly
    130                 135                 140

Ala Pro Gly Gln Arg Val Thr Ile Ser Cys Thr Gly Gly Ser Ser Asn
145                 150                 155                 160

Val Gly Ala Gly Tyr Asp Val His Trp Tyr Gln Gln Leu Pro Gly Thr
                165                 170                 175

Val Pro Lys Leu Leu Ile Tyr Asp Asn Thr Asn Arg Pro Ser Gly Val
            180                 185                 190

Pro Asp Arg Phe Ser Ala Ser Lys Ser Gly Thr Ser Ala Ser Leu Val
        195                 200                 205

Ile Thr Gly Leu Gln Ala Glu Asp Glu Gly Asp Tyr Tyr Cys Gln Ser
    210                 215                 220

Tyr Asp Ser Ser Leu Arg Ala Ser Val Phe Gly Gly Gly Thr Met Leu
225                 230                 235                 240

Thr Val Leu


<210> SEQ ID NO 300
<211> LENGTH: 244
<212> TYPE: PRT
<213> ORGANISM: Artificial Sequence
<220> FEATURE:
<223> OTHER INFORMATION: Synthetic

<400> SEQUENCE: 300

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30
```

```
Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Glu Leu Ser Ser Val Thr Ala Ala Asp Thr Ala Val Tyr Tyr Cys Ala
                85                  90                  95

Arg Ala Asp Arg Arg Phe Gly Glu Leu Arg Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asn Phe Met Leu Thr Gln Pro His Ser Val Ser
    130                 135                 140

Glu Ser Pro Gly Lys Thr Val Thr Ile Ser Cys Thr Gly Ser Ser Gly
145                 150                 155                 160

Ser Ile Ala Ser Ser Tyr Val Gln Trp Tyr Gln Gln Arg Pro Gly Ser
                165                 170                 175

Ala Pro Thr Thr Val Ile Tyr Ala Asp Asn Gln Arg Pro Ser Gly Val
            180                 185                 190

Pro Asp Arg Phe Ser Gly Ser Val Asp Ser Ser Ser Asn Ser Ala Ser
        195                 200                 205

Leu Thr Ile Ser Gly Leu Lys Thr Glu Asp Glu Ala Asp Tyr Tyr Cys
    210                 215                 220

Gln Ser Phe Asp Ser Ser Leu Tyr Met Ile Phe Gly Gly Gly Thr Lys
225                 230                 235                 240

Leu Thr Val Leu


<210> SEQ ID NO 301
<211> LENGTH: 247
<212> TYPE: PRT
<213> ORGANISM: Artificial Sequence
<220> FEATURE:
<223> OTHER INFORMATION: Synthetic

<400> SEQUENCE: 301

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Asp Leu His Trp Val Arg Gln Val Pro Gly Lys Gly Leu Glu Trp Val
        35                  40                  45

Ser Leu Ile Ser Tyr Asp Gly Ser Asn Lys Tyr Tyr Ala Asp Ser Val
    50                  55                  60

Lys Gly Arg Phe Thr Ile Ser Arg Asp Asn Ala Glu Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Pro Ile Thr Gly Thr Ser Asp Leu Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Gln Ser Val Leu Thr Gln Pro Pro
    130                 135                 140

Ser Val Ser Gly Ala Pro Gly Gln Arg Val Thr Ile Ser Cys Thr Gly
```

```
145                 150                 155                 160

Ser Arg Ser Asn Ile Gly Ala Gly Tyr Asp Val His Trp Tyr Gln His
                165                 170                 175

Leu Pro Gly Thr Ala Pro Lys Leu Leu Ile Tyr Asp Asn Ser Asn Arg
            180                 185                 190

Pro Ser Gly Val Ser Asp Arg Phe Ser Gly Ser Lys Ser Gly Thr Ser
        195                 200                 205

Ala Ser Leu Ala Ile Thr Gly Leu Gln Ala Glu Asp Glu Ala Asp Tyr
    210                 215                 220

Tyr Cys Gln Ser Phe Asp Ser Ser Leu Arg Gly Val Val Phe Gly Gly
225                 230                 235                 240

Gly Thr Arg Leu Thr Val Leu
                245


<210> SEQ ID NO 302
<211> LENGTH: 243
<212> TYPE: PRT
<213> ORGANISM: Artificial Sequence
<220> FEATURE:
<223> OTHER INFORMATION: Synthetic

<400> SEQUENCE: 302

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Val Arg Glu Gly Gly Leu Arg Glu Glu His Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Ser Tyr Glu Leu Thr Gln Pro Pro Ser Ala Ser Gly
    130                 135                 140

Thr Pro Gly Gln Arg Val Thr Ile Ser Cys Ser Gly Ser Ser Ser Asn
145                 150                 155                 160

Ile Gly Ser Asn Thr Val Asn Trp Tyr Gln Gln Leu Pro Gly Thr Ala
                165                 170                 175

Pro Lys Leu Leu Ile Tyr Ser Asn Asn Gln Arg Pro Ser Gly Val Pro
            180                 185                 190

Asp Arg Phe Ser Gly Ser Lys Ser Gly Thr Ser Ala Ser Leu Ala Ile
        195                 200                 205

Ser Gly Leu Gln Ser Glu Asp Glu Ala Asp Tyr Tyr Cys Ala Ala Trp
    210                 215                 220

Asp Asp Ser Leu Asn Gly Leu Trp Val Phe Gly Gly Gly Thr Lys Leu
225                 230                 235                 240

Thr Val Leu


<210> SEQ ID NO 303
```

<211> LENGTH: 244
<212> TYPE: PRT
<213> ORGANISM: Artificial Sequence
<220> FEATURE:
<223> OTHER INFORMATION: Synthetic

<400> SEQUENCE: 303

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Thr Asp Thr Ala Met Ala Asp Tyr Trp Gly Gln Gly Thr Leu
100 105 110

Val Thr Val Ser Ser Gly Gly Gly Gly Ser Gly Gly Gly Gly Ser Gly
115 120 125

Gly Gly Gly Ser Asp Val Val Met Thr Gln Ser Pro Leu Ser Leu Pro
130 135 140

Val Thr Pro Gly Glu Pro Ala Ser Ile Ser Cys Arg Ser Ser Gln Arg
145 150 155 160

Leu Leu His Ser Asn Gly Tyr Asn Tyr Val Asp Trp Tyr Leu Gln Lys
165 170 175

Pro Gly Gln Ser Pro Gln Leu Leu Ile Tyr Leu Gly Ser Asn Arg Ala
180 185 190

Ser Gly Val Pro Asp Arg Phe Ser Gly Ser Gly Ser Gly Thr Asp Phe
195 200 205

Thr Leu Lys Ile Ser Arg Val Glu Ala Glu Asp Val Gly Val Tyr Tyr
210 215 220

Cys Met Gln Gly Thr His Trp Pro Trp Thr Phe Gly Gln Gly Thr Lys
225 230 235 240

Val Glu Ile Lys

<210> SEQ ID NO 304
<211> LENGTH: 242
<212> TYPE: PRT
<213> ORGANISM: Artificial Sequence
<220> FEATURE:
<223> OTHER INFORMATION: Synthetic

<400> SEQUENCE: 304

Gln Val Gln Leu Gln Gln Ser Gly Pro Gly Leu Val Lys Pro Ser Gln
1 5 10 15

Thr Leu Ser Leu Thr Cys Ala Ile Ser Gly Asp Ser Val Ser Gly Asn
20 25 30

Ser Ala Thr Trp Asn Trp Ile Arg Gln Ser Pro Ser Arg Gly Leu Glu
35 40 45

Trp Leu Gly Arg Thr Tyr Tyr Arg Ser Lys Trp Asn His Asp Tyr Ala
50 55 60

Glu Ser Val Lys Ser Arg Ile Thr Ile Asn Pro Asp Thr Ser Lys Asn
65 70 75 80

Gln Phe Ser Leu Gln Leu Asn Ser Val Thr Pro Glu Asp Thr Ala Val
85 90 95

Tyr Tyr Cys Ala Arg Asp Ser Lys Ser Ala Phe Asp Ile Trp Gly Gln
100 105 110

Gly Thr Met Val Thr Val Ser Ser Gly Gly Gly Gly Ser Gly Gly Gly
115 120 125

Gly Ser Gly Gly Gly Gly Ser Asp Ile Gln Met Thr Gln Ser Pro Pro
130 135 140

Ser Leu Ser Ala Ser Val Gly Asp Arg Val Thr Ile Thr Cys Gln Ala
145 150 155 160

Ser Gln Asp Ile Asn Asn Tyr Leu Asn Trp Tyr His Gln Lys Pro Gly
165 170 175

Lys Ala Pro Glu Leu Leu Ile Tyr Asp Ala Ser Gln Leu Glu Thr Gly
180 185 190

Val Pro Ser Arg Phe Ser Gly Ser Gly Ser Gly Thr Glu Phe Thr Phe
195 200 205

Ile Ile Ser Ser Leu Gln Pro Glu Asp Thr Gly Thr Tyr Tyr Cys Gln
210 215 220

Gln Tyr Asp Trp Leu Pro Leu Ser Tyr Gly Gly Gly Thr Lys Val Glu
225 230 235 240

Ile Lys

<210> SEQ ID NO 305
<211> LENGTH: 239
<212> TYPE: PRT
<213> ORGANISM: Artificial Sequence
<220> FEATURE:
<223> OTHER INFORMATION: Synthetic

<400> SEQUENCE: 305

Gln Leu Gln Leu Gln Glu Ser Gly Pro Gly Leu Val Lys Pro Ser Glu
1 5 10 15

Thr Leu Ser Leu Thr Cys Ser Val Phe Gly Val Ser Ile Thr Ser Gly
20 25 30

Ser Trp Trp Ser Trp Val Arg Gln Ser Pro Gly Lys Glu Leu Glu Trp
35 40 45

Ile Gly Glu Ile Tyr His Asn Gly Asn Thr Asn Tyr Asn Pro Ser Leu
50 55 60

Lys Ser Arg Val Thr Ile Ser Val Asp Thr Ser Lys Asn Gln Phe Ser
65 70 75 80

Leu Lys Leu Ser Ser Val Thr Ala Ala Asp Thr Ala Val Tyr Tyr Cys
85 90 95

Val Ser Gly Phe Asp Tyr Trp Gly Gln Gly Thr Leu Val Thr Val Ser
100 105 110

Ser Gly Gly Gly Gly Ser Gly Gly Gly Gly Ser Gly Gly Gly Gly Ser
115 120 125

Asn Phe Met Leu Thr Gln Pro His Ser Val Ser Gly Ser Pro Gly Lys
130 135 140

Thr Ile Thr Ile Ser Cys Thr Arg Ser Ser Gly Asn Phe Ala Ser Thr
145 150 155 160

Tyr Val Gln Trp Tyr Gln Gln Arg Pro Gly Ser Ser Pro Ala Ile Val
165 170 175

Ile Tyr Asp Asp Asp Gln Arg Pro Ser Gly Val Pro Asp Arg Phe Ser
180 185 190

Gly Ser Ile Asp Arg Ser Ser Asn Ser Ala Ser Leu Thr Ile Ser Gly
195 200 205

Leu Glu Thr Glu Asp Glu Ala Asp Tyr Tyr Cys Gln Ser Tyr Asp Ser
210 215 220

Ser Asn Phe Trp Val Phe Gly Gly Gly Thr Lys Leu Thr Val Leu
225 230 235

<210> SEQ ID NO 306
<211> LENGTH: 241
<212> TYPE: PRT
<213> ORGANISM: Artificial Sequence
<220> FEATURE:
<223> OTHER INFORMATION: Synthetic

<400> SEQUENCE: 306

Gln Val Gln Leu Gln Glu Ser Gly Pro Gly Leu Val Lys Pro Ser Glu
1 5 10 15

Thr Leu Ser Leu Thr Cys Thr Val Ser Gly Val Ser Ile Ser Ser Arg
20 25 30

Ser Asp His Trp Gly Trp Val Arg Gln Pro Pro Gly Lys Gly Leu Glu
35 40 45

Trp Ile Gly Ser Ile Ser Tyr Ser Gly Ser Thr Tyr Tyr Asn Pro Ser
50 55 60

Leu Lys Ser Arg Val Thr Ile Ser Val Asp Thr Ser Lys Asn Gln Leu
65 70 75 80

Ser Leu Lys Leu Ser Ser Val Thr Ala Ala Asp Thr Ala Val Tyr Tyr
85 90 95

Cys Ala Arg Glu Ser His Pro Ala Ala Ala Leu Val Gly Trp Gly Gln
100 105 110

Gly Thr Leu Val Thr Val Ser Ser Gly Gly Gly Gly Ser Gly Gly Gly
115 120 125

Gly Ser Gly Gly Gly Gly Ser Glu Ile Val Leu Thr Gln Ser Pro Ser
130 135 140

Ser Leu Ser Ala Ser Val Gly Asp Arg Val Thr Ile Thr Cys Gln Ala
145 150 155 160

Ser Gln Asp Ile Asn Asn Tyr Leu Asn Trp Tyr Gln Gln Lys Pro Gly
165 170 175

Lys Ala Pro Lys Leu Leu Ile Tyr Asp Ala Ser Asn Leu Glu Thr Gly
180 185 190

Val Pro Ser Lys Phe Ser Gly Ser Gly Ser Gly Thr Asp Phe Thr Phe
195 200 205

Thr Ile Ser Ser Leu Gln Pro Glu Asp Ile Ala Thr Tyr Tyr Cys Gln
210 215 220

Gln Tyr Ala Asn Leu Pro Ser Phe Gly Gln Gly Thr Lys Leu Glu Ile
225 230 235 240

Lys

<210> SEQ ID NO 307
<211> LENGTH: 253
<212> TYPE: PRT
<213> ORGANISM: Artificial Sequence
<220> FEATURE:
<223> OTHER INFORMATION: Synthetic

<400> SEQUENCE: 307

Glu Val Gln Leu Val Gln Ser Gly Ala Glu Val Lys Lys Pro Gly Ser
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ala Pro Asp Tyr Gly Asp Ser Ser Asn Tyr Tyr Tyr Tyr Tyr
100 105 110

Met Asp Val Trp Gly Lys Gly Thr Thr Val Thr Val Ser Ser Gly Gly
115 120 125

Gly Gly Ser Gly Gly Gly Gly Ser Gly Gly Gly Gly Ser Glu Ile Val
130 135 140

Leu Thr Gln Ser Pro Leu Ser Leu Pro Val Thr Pro Gly Glu Pro Ala
145 150 155 160

Ser Ile Ser Cys Arg Ser Ser Gln Ser Leu Leu His Ser Asn Gly Tyr
165 170 175

Asn Tyr Leu Asp Trp Tyr Leu Gln Lys Pro Gly Gln Ser Pro Gln Leu
180 185 190

Leu Ile Tyr Leu Gly Ser Asn Arg Ala Ser Gly Val Pro Asp Arg Phe
195 200 205

Ser Gly Ser Gly Ser Gly Thr Asp Phe Thr Leu Ser Ile Ser Arg Val
210 215 220

Glu Ala Glu Asp Val Gly Val Tyr Tyr Cys Met Gln Ala Leu Gln Thr
225 230 235 240

Pro Pro Thr Phe Gly Gln Gly Thr Lys Val Glu Ile Lys
245 250

<210> SEQ ID NO 308
<211> LENGTH: 249
<212> TYPE: PRT
<213> ORGANISM: Artificial Sequence
<220> FEATURE:
<223> OTHER INFORMATION: Synthetic

<400> SEQUENCE: 308

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Thr Ser Gly Asp Tyr Ser Ser Gly Trp Tyr Leu Gly Val
100 105 110

Pro Phe Asp Tyr Trp Gly Gln Gly Thr Leu Val Thr Val Ser Ser Gly
115 120 125

```
Gly Gly Gly Ser Gly Gly Gly Gly Ser Gly Gly Gly Gly Ser Asp Ile
    130                 135                 140

Gln Leu Thr Gln Ser Pro Ser Ser Leu Ser Ala Ser Val Gly Asp Arg
145                 150                 155                 160

Val Thr Val Thr Cys Gln Ala Ser Gln Asp Ile Gly His Asn Leu Asn
                165                 170                 175

Trp Tyr Gln Gln Arg Pro Gly Lys Ala Pro Gln Leu Leu Ile Tyr Asp
            180                 185                 190

Ala Ser Asn Leu Glu Thr Gly Val Pro Ser Arg Phe Ser Gly Ser Gly
        195                 200                 205

Ser Gly Thr Gln Phe Thr Phe Thr Ile Ser Ser Leu Gln Pro Glu Asp
    210                 215                 220

Ile Ala Thr Tyr Tyr Cys Gln Gln Tyr Asp Phe Leu Pro Pro Asp Phe
225                 230                 235                 240

Gly Pro Gly Thr Lys Val Glu Ile Lys
                245


<210> SEQ ID NO 309
<211> LENGTH: 482
<212> TYPE: PRT
<213> ORGANISM: Artificial Sequence
<220> FEATURE:
<223> OTHER INFORMATION: Synthetic

<400> SEQUENCE: 309

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu His Ser Asn Gly Tyr Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Asp Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Gly Thr His Trp Pro Trp Thr Phe Gly Gln
225                 230                 235                 240
```

```
Gly Thr Lys Val Glu Ile Lys Asn Ser Gly Ala Gly Thr Ala Ala Ala
                245                 250                 255

Thr His Thr Cys Pro Pro Cys Pro Ala Pro Glu Ala Ala Gly Gly Pro
            260                 265                 270

Ser Val Phe Leu Phe Pro Pro Lys Pro Lys Asp Thr Leu Met Ile Ser
        275                 280                 285

Arg Thr Pro Glu Val Thr Cys Val Val Val Asp Val Ser His Glu Asp
    290                 295                 300

Pro Glu Val Lys Phe Asn Trp Tyr Val Asp Gly Val Glu Val His Asn
305                 310                 315                 320

Ala Lys Thr Lys Pro Arg Glu Glu Gln Tyr Asn Ser Thr Tyr Arg Val
                325                 330                 335

Val Ser Val Leu Thr Val Leu His Gln Asp Trp Leu Asn Gly Lys Glu
            340                 345                 350

Tyr Lys Cys Lys Val Ser Asn Lys Ala Leu Pro Ala Pro Ile Glu Lys
        355                 360                 365

Thr Ile Ser Lys Ala Lys Gly Gln Pro Arg Glu Pro Gln Val Cys Thr
    370                 375                 380

Leu Pro Pro Ser Arg Asp Glu Leu Thr Lys Asn Gln Val Ser Leu Ser
385                 390                 395                 400

Cys Ala Val Lys Gly Phe Tyr Pro Ser Asp Ile Ala Val Glu Trp Glu
                405                 410                 415

Ser Asn Gly Gln Pro Glu Asn Asn Tyr Lys Thr Thr Pro Pro Val Leu
            420                 425                 430

Asp Ser Asp Gly Ser Phe Phe Leu Cys Val Ser Lys Leu Thr Val Asp
        435                 440                 445

Lys Ser Arg Trp Gln Gln Gly Asn Val Phe Ser Cys Ser Val Met His
    450                 455                 460

Glu Ala Leu His Asn His Tyr Thr Gln Lys Ser Leu Ser Leu Ser Pro
465                 470                 475                 480

Gly Lys


<210> SEQ ID NO 310
<211> LENGTH: 243
<212> TYPE: PRT
<213> ORGANISM: Artificial Sequence
<220> FEATURE:
<223> OTHER INFORMATION: Synthetic

<400> SEQUENCE: 310

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Gly Asp Ile Leu Thr Gly Tyr Ala Leu Asp Tyr Trp Gly Gln
            100                 105                 110

Gly Thr Leu Val Thr Val Ser Ser Gly Gly Gly Gly Ser Gly Gly Gly
```

```
        115                 120                 125

Gly Ser Gly Gly Gly Gly Ser Ser Tyr Glu Leu Thr Gln Pro Pro Ser
    130                 135                 140

Met Ser Val Ser Pro Gly Gln Thr Ala Arg Ile Thr Cys Ser Gly Asp
145                 150                 155                 160

Ala Leu Pro Lys Gln Phe Ala Phe Trp Tyr Gln Gln Lys Pro Gly Gln
                165                 170                 175

Ala Pro Val Leu Val Ile Tyr Lys Asp Thr Glu Arg Pro Ser Gly Ile
            180                 185                 190

Pro Glu Arg Phe Ser Gly Ser Ser Ser Gly Thr Thr Val Thr Leu Thr
        195                 200                 205

Ile Thr Gly Val Gln Ala Glu Asp Glu Ala Asp Tyr Tyr Cys Gln Ser
    210                 215                 220

Pro Asp Ser Ser Gly Thr Val Glu Val Phe Gly Gly Gly Thr Lys Leu
225                 230                 235                 240

Thr Val Leu


<210> SEQ ID NO 311
<211> LENGTH: 247
<212> TYPE: PRT
<213> ORGANISM: Artificial Sequence
<220> FEATURE:
<223> OTHER INFORMATION: Synthetic

<400> SEQUENCE: 311

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Phe Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu His Ser Asn Gly Tyr Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Asp Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Gly Thr His Trp Pro Trp Thr Phe Gly Gln
225                 230                 235                 240
```

```
Gly Thr Lys Val Glu Ile Lys
                245


<210> SEQ ID NO 312
<211> LENGTH: 247
<212> TYPE: PRT
<213> ORGANISM: Artificial Sequence
<220> FEATURE:
<223> OTHER INFORMATION: Synthetic

<400> SEQUENCE: 312

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Phe Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Pro Gly Glu Ser Val Ser Ile Ser Cys Arg Ser
145                 150                 155                 160

Ser Gln Ser Leu Leu His Ser Asn Gly Tyr Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Asp Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Gly Thr His Trp Pro Trp Thr Phe Gly Gln
225                 230                 235                 240

Gly Thr Lys Val Glu Ile Lys
                245


<210> SEQ ID NO 313
<211> LENGTH: 247
<212> TYPE: PRT
<213> ORGANISM: Artificial Sequence
<220> FEATURE:
<223> OTHER INFORMATION: Synthetic

<400> SEQUENCE: 313

Gln Val Gln Leu Gln Gln Trp Gly Ala Gly Met Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
```

```
        35                  40                  45

Gly Glu Ile Asn His Phe Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu His Ser Asn Gly Tyr Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Asp Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Gly Thr His Trp Pro Trp Thr Phe Gly Gln
225                 230                 235                 240

Gly Thr Lys Val Glu Ile Lys
                245


<210> SEQ ID NO 314
<211> LENGTH: 255
<212> TYPE: PRT
<213> ORGANISM: Artificial Sequence
<220> FEATURE:
<223> OTHER INFORMATION: Synthetic

<400> SEQUENCE: 314

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Phe Gly Ser Thr Asn Tyr Asn Pro Ser Leu Lys
    50                  55                  60

Ser Arg Ala Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Thr Ser Pro Gly Gly Tyr Ser Gly Gly Tyr Phe Gln His Trp Gly Gln
            100                 105                 110

Gly Thr Leu Val Thr Val Ser Ser Gly Gly Gly Gly Ser Gly Glu Gly
        115                 120                 125

Gly Ser Gly Gly Gly Gly Ser Asp Val Val Met Thr Gln Ser Pro Leu
    130                 135                 140

Ser Leu Pro Val Thr Pro Gly Glu Pro Ala Ser Ile Ser Cys Arg Ser
```

```
145                 150                 155                 160

Ser Gln Ser Leu Leu His Ser Asn Gly Tyr Asn Tyr Leu Asp Trp Tyr
                165                 170                 175

Leu Gln Lys Pro Gly Gln Ser Pro Gln Leu Leu Ile Tyr Leu Gly Ser
            180                 185                 190

Asn Arg Asp Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Gly Thr His Trp Pro Trp Thr Phe Gly Gln
225                 230                 235                 240

Gly Thr Lys Val Glu Ile Lys Ala Ala Ala His His His His His
                245                 250                 255


<210> SEQ ID NO 315
<211> LENGTH: 247
<212> TYPE: PRT
<213> ORGANISM: Artificial Sequence
<220> FEATURE:
<223> OTHER INFORMATION: Synthetic

<400> SEQUENCE: 315

Glu Val Gln Leu Val Glu Ser Gly Gly Gly Leu Val Gln Pro Gly Gly
1               5                   10                  15

Ser Leu Arg Leu Ser Cys Ala Ala Ser Gly Gly Ser Phe Ser Gly Tyr
            20                  25                  30

Tyr Trp Ser Trp Val Arg Gln Ala Pro Gly Lys Gly Leu Glu Trp Val
        35                  40                  45

Ser Glu Ile Asn His Ser Gly Ser Thr Asn Tyr Asn Pro Ser Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Ser Pro Gly Gly Tyr Ser Gly Gly Tyr Phe Gln His Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ser
145                 150                 155                 160

Ser Gln Ser Leu Leu His Ser Asn Gly Tyr Asn Tyr Leu Asp Trp Tyr
                165                 170                 175

Gln Gln Lys Pro Gly Lys Ala Pro Lys Leu Leu Ile Tyr Leu Gly Ser
            180                 185                 190

Asn Arg Asp Ser Gly Val Pro Ser Arg Phe Ser Gly Ser Gly Ser Gly
        195                 200                 205

Thr Asp Phe Thr Leu Thr Ile Ser Ser Leu Gln Pro Glu Asp Phe Ala
    210                 215                 220

Thr Tyr Tyr Cys Met Gln Gly Thr His Trp Pro Trp Thr Phe Gly Gln
225                 230                 235                 240

Gly Thr Lys Val Glu Ile Lys
                245
```

<210> SEQ ID NO 316
<211> LENGTH: 247
<212> TYPE: PRT
<213> ORGANISM: Artificial Sequence
<220> FEATURE:
<223> OTHER INFORMATION: Synthetic

<400> SEQUENCE: 316

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Leu Arg Ile Pro Tyr Tyr Tyr Asp Asn Pro Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Glu Ile Val Leu Thr Gln Ser Pro Leu
    130                 135                 140

Ser Leu Pro Val Thr Pro Gly Glu Pro Ala Ser Ile Ser Cys Arg Ser
145                 150                 155                 160

Ser Gln Ser Leu Leu His Ser Asn Gly Tyr Asn Tyr Leu Asn Trp Tyr
                165                 170                 175

Leu Gln Lys Pro Gly Gln Ser Pro Gln Leu Leu Ile Tyr Leu Gly Ser
            180                 185                 190

Asp Arg Ala Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Met Gln Ala Leu Gln Thr Pro Thr Thr Phe Gly Gly
225                 230                 235                 240

Gly Thr Lys Val Glu Ile Lys
                245
```

<210> SEQ ID NO 317
<211> LENGTH: 245
<212> TYPE: PRT
<213> ORGANISM: Artificial Sequence
<220> FEATURE:
<223> OTHER INFORMATION: Synthetic

<400> SEQUENCE: 317

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60
```

-continued

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Tyr Tyr Ser His Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Met Thr Gln Ser Pro Leu Ser Leu
    130                 135                 140

Pro Val Thr Pro Gly Glu Pro Ala Ser Ile Ser Cys Arg Ser Ser Gln
145                 150                 155                 160

Ser Leu Leu His Ser Asn Gly Tyr Asn Tyr Leu Asp Trp Tyr Leu Gln
                165                 170                 175

Lys Pro Gly Gln Ser Pro Gln Leu Leu Met Tyr Leu Val Ser Asn Arg
            180                 185                 190

Ala Ser Gly Val Pro Glu Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Met Gln Thr Leu Gln Thr Pro Leu Ser Phe Gly Gln Gly Thr
225                 230                 235                 240

Lys Leu Glu Ile Lys
                245


<210> SEQ ID NO 318
<211> LENGTH: 245
<212> TYPE: PRT
<213> ORGANISM: Artificial Sequence
<220> FEATURE:
<223> OTHER INFORMATION: Synthetic

<400> SEQUENCE: 318

Glu Val Gln Leu Val Glu Thr Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Pro Leu Ser Ser Ser Gly Pro Gly Ala Phe Asp Ile
            100                 105                 110

Trp Gly Gln Gly Thr Met Val Thr Val Ser Ser Gly Gly Gly Gly Ser
        115                 120                 125

Gly Gly Gly Gly Ser Gly Gly Gly Gly Ser Glu Ile Val Leu Thr Gln
    130                 135                 140

Ser Pro Ala Thr Leu Ser Leu Ser Pro Gly Glu Arg Ala Thr Leu Ser
145                 150                 155                 160

Cys Arg Ala Ser Gln Ser Val Ser Tyr His Leu Ala Trp Tyr Gln Gln
                165                 170                 175
```

-continued

```
Lys Pro Gly Gln Ala Pro Arg Leu Leu Ile Tyr Asp Thr Ser Asn Arg
            180                 185                 190

Ala Ser Gly Ile Pro Ala Arg Phe Ser Gly Ser Gly Ser Gly Thr Asp
        195                 200                 205

Phe Thr Leu Thr Ile Asn Ser Leu Glu Pro Glu Asp Phe Ala Val Tyr
    210                 215                 220

Tyr Cys Gln Gln Arg Tyr Asp Trp Pro Leu Thr Phe Gly Gly Gly Thr
225                 230                 235                 240

Lys Val Glu Ile Lys
                245


<210> SEQ ID NO 319
<211> LENGTH: 236
<212> TYPE: PRT
<213> ORGANISM: Artificial Sequence
<220> FEATURE:
<223> OTHER INFORMATION: Synthetic

<400> SEQUENCE: 319

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Ser Tyr Asp Gly Thr Asn Lys Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Gly Phe Asp Ile Trp Gly Gln Gly Thr Met Val Thr Val
            100                 105                 110

Ser Ser Gly Gly Gly Gly Ser Gly Gly Gly Gly Ser Gly Gly Gly Gly
        115                 120                 125

Ser Asp Ile Gln Met Thr Gln Ser Pro Ser Phe Leu Ser Ala Ser Val
    130                 135                 140

Gly Asp Arg Val Thr Ile Thr Cys Arg Ala Ser Gln Ser Ile Ser Ser
145                 150                 155                 160

Trp Leu Ala Trp Tyr Gln Gln Lys Pro Gly Lys Ala Pro Lys Leu Leu
                165                 170                 175

Ile Tyr Asp Ala Ser Arg Leu Glu Asp Gly Val Pro Ser Arg Phe Ser
            180                 185                 190

Gly Thr Gly Phe Gly Thr Asp Phe Thr Phe Thr Ile Thr Thr Leu Gln
        195                 200                 205

Pro Asp Asp Ile Ala Thr Tyr Tyr Cys Gln Gln Tyr Asp Asp Leu Pro
    210                 215                 220

Tyr Thr Phe Gly Gln Gly Thr Thr Val Asp Ile Lys
225                 230                 235


<210> SEQ ID NO 320
<211> LENGTH: 247
<212> TYPE: PRT
<213> ORGANISM: Artificial Sequence
<220> FEATURE:
<223> OTHER INFORMATION: Synthetic

<400> SEQUENCE: 320
```

```
Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Val Tyr Gly Asp Tyr Gly Ala Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Asp Val Val Met Thr Gln Ser Pro Val
    130                 135                 140

Ser Leu Pro Val Thr Leu Gly Gln Pro Ala Ser Ile Ser Cys Lys Ser
145                 150                 155                 160

Ser Gln Ser Leu Leu Tyr Phe Asn Gly Asn Thr Tyr Leu Ser Trp Phe
                165                 170                 175

Gln Gln Arg Pro Gly Gln Ser Pro Arg Arg Leu Phe Tyr Gln Val Ser
            180                 185                 190

Asn Arg Asp Ser Gly Val Pro Asp Arg Phe Ser Gly Ser Gly Ser Asp
        195                 200                 205

Thr Asp Phe Thr Leu Thr Ile Ser Arg Val Glu Ala Glu Asp Val Gly
    210                 215                 220

Val Tyr Phe Cys Met Gln Gly Thr Gln Trp Pro Pro Thr Phe Gly Gln
225                 230                 235                 240

Gly Thr Lys Val Glu Ile Lys
                245
```

<210> SEQ ID NO 321
<211> LENGTH: 244
<212> TYPE: PRT
<213> ORGANISM: Artificial Sequence
<220> FEATURE:
<223> OTHER INFORMATION: Synthetic

<400> SEQUENCE: 321

```
Gln Leu Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Val Ala Pro Pro Met Asp Val Trp Gly Lys Gly Thr Thr
            100                 105                 110
```

```
Val Thr Val Ser Ser Gly Gly Gly Gly Ser Gly Gly Gly Gly Ser Gly
        115                 120                 125

Gly Gly Gly Ser Asp Val Val Met Thr Gln Ser Pro Leu Ser Leu Pro
    130                 135                 140

Val Thr Pro Gly Glu Pro Ala Ser Ile Ser Cys Arg Ser Ser Gln Ser
145                 150                 155                 160

Leu Leu His Ser Asn Gly Tyr Asn Tyr Leu Asp Trp Tyr Leu Gln Lys
                165                 170                 175

Pro Gly Gln Ser Pro His Leu Leu Ile Tyr Leu Gly Ser Asn Arg Ala
            180                 185                 190

Ser Gly Val Pro Asp Arg Phe Ser Gly Ser Gly Ser Gly Thr Asp Phe
        195                 200                 205

Thr Leu Lys Ile Ser Arg Val Glu Ala Glu Asp Val Gly Val Tyr Phe
    210                 215                 220

Cys Met Gln Ala Leu Arg Thr Pro Tyr Thr Phe Gly Gln Gly Thr Lys
225                 230                 235                 240

Leu Glu Ile Lys


<210> SEQ ID NO 322
<211> LENGTH: 248
<212> TYPE: PRT
<213> ORGANISM: Artificial Sequence
<220> FEATURE:
<223> OTHER INFORMATION: Synthetic

<400> SEQUENCE: 322

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Glu Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Ala Gly Ser Ser Ser Ser Gly Tyr Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Val Val Met Thr Gln Ser Pro
    130                 135                 140

Leu Ser Leu Pro Val Thr Leu Gly Gln Pro Ala Ser Ile Ser Cys Arg
145                 150                 155                 160

Ser Ser Gln Ser Leu Val His Ser Asn Gly Tyr Asn Tyr Leu Asp Trp
                165                 170                 175

Tyr Leu Gln Lys Pro Gly Gln Ser Pro Gln Leu Leu Ile Tyr Leu Gly
            180                 185                 190

Ser Asn Arg Ala Ser Gly Val Pro Asp Arg Phe Ser Gly Ser Gly Ser
        195                 200                 205

Gly Thr Asp Phe Thr Leu Lys Ile Ser Arg Val Glu Ala Glu Asp Val
    210                 215                 220
```

-continued

```
Gly Val Tyr Tyr Cys Leu Gln Gly Ser His Trp Pro Trp Thr Phe Gly
225                 230                 235                 240

Gln Gly Thr Lys Val Glu Ile Lys
                245


<210> SEQ ID NO 323
<211> LENGTH: 237
<212> TYPE: PRT
<213> ORGANISM: Artificial Sequence
<220> FEATURE:
<223> OTHER INFORMATION: Synthetic

<400> SEQUENCE: 323

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Thr Trp Ile Arg Gln His Pro Gly Gln Gly Leu Glu
        35                  40                  45

Trp Ile Gly Phe Ile Ser Trp Ser Gly Thr Thr Tyr Tyr Asn Pro Ser
    50                  55                  60

Leu Lys Asn Arg Val Thr Ile Ser Ala Asp Thr Ser Lys Asn His Phe
65                  70                  75                  80

Ser Leu Asn Leu Thr Ser Val Thr Ala Ala Asp Thr Ala Val Tyr Tyr
                85                  90                  95

Cys Ala Arg Gly Ser Gly Arg Leu Val Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Glu Thr Thr Leu Thr Gln Ser Pro Ala Thr Leu Ser Val
    130                 135                 140

Ser Pro Gly Glu Arg Ala Thr Leu Ser Cys Arg Ala Ser Gln Ser Val
145                 150                 155                 160

Ser Ser Asn Leu Ala Trp Tyr Gln Gln Lys Pro Gly Gln Ala Pro Arg
                165                 170                 175

Leu Leu Ile Tyr Gly Ala Ser Ser Gly Ala Thr Gly Ile Pro Asp Arg
            180                 185                 190

Phe Ser Gly Ser Gly Ser Gly Thr Asp Phe Thr Leu Thr Ile Ser Arg
        195                 200                 205

Leu Glu Pro Glu Asp Phe Ala Val Tyr Tyr Cys Gln Leu Tyr Gly Ser
    210                 215                 220

Ser Leu Ala Phe Gly Gly Gly Thr Lys Val Glu Ile Lys
225                 230                 235


<210> SEQ ID NO 324
<211> LENGTH: 248
<212> TYPE: PRT
<213> ORGANISM: Artificial Sequence
<220> FEATURE:
<223> OTHER INFORMATION: Synthetic

<400> SEQUENCE: 324

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

```
Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Asp Thr Ala Met Gly Asp Ala Phe Asp Ile Trp Gly Gln
            100                 105                 110

Gly Thr Met Val Thr Val Ser Ser Gly Gly Gly Gly Ser Gly Gly Gly
        115                 120                 125

Gly Ser Gly Gly Gly Gly Ser Asp Ile Val Met Thr His Thr Pro Leu
    130                 135                 140

Ser Leu Pro Val Thr Pro Gly Glu Pro Ala Ser Ile Ser Cys Arg Ser
145                 150                 155                 160

Ser Gln Thr Leu Phe Asp Ser Asp Asp Gly Lys Thr Tyr Leu Asp Trp
                165                 170                 175

Tyr Leu Gln Lys Pro Gly Gln Ser Pro Gln Leu Leu Met Tyr Thr Thr
            180                 185                 190

Ser Ser Arg Ala Ser Gly Val Pro Asp Arg Phe Ser Gly Ser Gly Ser
        195                 200                 205

Gly Thr Asp Phe Thr Leu Lys Ile Ser Arg Val Glu Ala Glu Asp Val
    210                 215                 220

Gly Val Tyr Tyr Cys Met Gln Arg Leu Gln Phe Pro Leu Thr Phe Gly
225                 230                 235                 240

Gln Gly Thr Arg Leu Glu Phe Lys
                245


<210> SEQ ID NO 325
<211> LENGTH: 245
<212> TYPE: PRT
<213> ORGANISM: Artificial Sequence
<220> FEATURE:
<223> OTHER INFORMATION: Synthetic

<400> SEQUENCE: 325

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Gly Ile Gly Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Asp Val Val Met Thr Gln Ser Pro Leu Ser Leu
    130                 135                 140

Pro Val Thr Pro Gly Glu Pro Ala Ser Ile Ser Cys Arg Ala Thr Gln
145                 150                 155                 160
```

Ser Leu Leu His Gly Asn Gly His Asn Tyr Leu Asp Trp Tyr Leu Gln
165 170 175

Lys Pro Gly Gln Ser Pro Gln Leu Leu Ile Tyr Leu Gly Ser Asn Arg
180 185 190

Ala Ser Gly Val Pro Asp Arg Phe Ser Gly Ser Gly Ser Gly Thr Asp
195 200 205

Phe Thr Leu Lys Ile Ser Arg Val Glu Ala Glu Asp Val Gly Val Tyr
210 215 220

Tyr Cys Met Gln Thr Leu Glu Thr Pro Val Thr Phe Gly Pro Gly Thr
225 230 235 240

Lys Val Asp Ile Lys
245

<210> SEQ ID NO 326
<211> LENGTH: 248
<212> TYPE: PRT
<213> ORGANISM: Artificial Sequence
<220> FEATURE:
<223> OTHER INFORMATION: Synthetic

<400> SEQUENCE: 326

Gln Val Gln Leu Gln Gln Trp Gly Ala Gly Leu Leu Lys Pro Ser Glu
1 5 10 15

Thr Leu Ser Leu Thr Cys Thr Ile Tyr Gly Gly Ser Phe Ser Gly Phe
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Ile Tyr Tyr Cys Ala
85 90 95

Arg Gly Pro Ala Gly Ser Thr Ser Ser Gly Tyr Phe Asp His Trp Gly
100 105 110

Gln Gly Thr Leu Val Thr Val Ser Ser Gly Gly Gly Gly Ser Gly Gly
115 120 125

Gly Gly Ser Gly Gly Gly Gly Ser Asp Val Val Met Thr Gln Ser Pro
130 135 140

Leu Ser Leu Pro Val Thr Pro Gly Glu Pro Ala Ser Ile Ser Cys Arg
145 150 155 160

Ser Ser Gln Ser Leu Leu His Ser Asn Gly Tyr Asn Tyr Leu Asp Trp
165 170 175

Tyr Leu Gln Lys Pro Gly Gln Ser Pro Gln Leu Leu Ile Tyr Leu Gly
180 185 190

Ser Asn Arg Ala Ser Gly Val Pro Asp Arg Phe Ser Gly Ser Gly Ser
195 200 205

Gly Thr Asp Phe Thr Leu Lys Ile Ser Arg Val Glu Ala Glu Asp Val
210 215 220

Gly Val Tyr Tyr Cys Met Gln Gly Thr His Trp Pro Trp Thr Phe Gly
225 230 235 240

Gln Gly Thr Lys Val Glu Ile Lys
245

<210> SEQ ID NO 327

<211> LENGTH: 244
<212> TYPE: PRT
<213> ORGANISM: Artificial Sequence
<220> FEATURE:
<223> OTHER INFORMATION: Synthetic

<400> SEQUENCE: 327

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Leu Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Arg Gly Ser Ser Ser Tyr Tyr Met Asp Val Trp Gly Lys Gly Thr Thr
100 105 110

Val Thr Val Ser Ser Gly Gly Gly Gly Ser Gly Gly Gly Gly Ser Gly
115 120 125

Gly Gly Gly Ser Asp Val Val Met Thr Gln Ser Pro Leu Ser Leu Pro
130 135 140

Val Thr Pro Gly Glu Pro Ala Ser Ile Ser Cys Arg Ser Ser Gln Ser
145 150 155 160

Leu Leu His Ser Asn Gly Tyr Asn Tyr Leu Asp Trp Tyr Leu Gln Lys
165 170 175

Pro Gly Gln Ser Pro Gln Leu Leu Ile Tyr Leu Gly Ser Asn Arg Ala
180 185 190

Ser Gly Val Pro Asp Arg Phe Ser Gly Ser Gly Ser Gly Thr Asp Phe
195 200 205

Thr Leu Lys Ile Ser Arg Val Glu Ala Glu Asp Val Gly Val Tyr Tyr
210 215 220

Cys Leu Gln Gly Thr His Trp Pro Trp Thr Phe Gly Gln Gly Thr Lys
225 230 235 240

Val Glu Ile Lys

<210> SEQ ID NO 328
<211> LENGTH: 243
<212> TYPE: PRT
<213> ORGANISM: Artificial Sequence
<220> FEATURE:
<223> OTHER INFORMATION: Synthetic

<400> SEQUENCE: 328

Gln Val Gln Leu Gln Gln Trp Gly Ala Gly Leu Leu Lys Pro Ser Glu
1 5 10 15

Thr Leu Ser Leu Thr Cys Ala Val Tyr Gly Gly Ser Phe Ser Gly Tyr
20 25 30

Tyr Trp Ser Trp Ile Arg Gln Pro Pro Gly Lys Gly Leu Glu Trp Ile
35 40 45

Gly Glu Ile Asn His Ser Gly Ser Thr Asn Tyr Asn Pro Ser Leu Lys
50 55 60

Ser Arg Val Thr Ile Ser Val Asp Thr Ser Lys Asn Gln Phe Ser Leu
65 70 75 80

```
Lys Leu Ser Ser Val Thr Ala Ala Asp Thr Ala Val Tyr Tyr Cys Ala
                85                  90                  95

Arg Gly Gly Ser Ala Tyr Phe Gln His Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Asp Val Val Met Thr Gln Ser Pro Leu Ser Leu Pro Val
    130                 135                 140

Thr Leu Gly Gln Pro Ala Ser Ile Ser Cys Arg Ser Ser Gln Ser Leu
145                 150                 155                 160

Leu His Ser Asn Gly Asn Asn Tyr Leu Asp Trp Tyr Leu Gln Lys Pro
                165                 170                 175

Gly Gln Ser Pro Gln Leu Leu Ile Tyr Leu Gly Ser Asn Arg Ala Ser
            180                 185                 190

Gly Val Pro Asp Arg Phe Ser Gly Ser Gly Ser Gly Thr Asp Phe Thr
        195                 200                 205

Leu Lys Ile Ser Arg Val Glu Ala Glu Asp Val Gly Ile Tyr Tyr Cys
    210                 215                 220

Met Gln Gly Thr His Trp Pro Trp Thr Phe Gly Gln Gly Thr Lys Val
225                 230                 235                 240

Glu Ile Glu


<210> SEQ ID NO 329
<211> LENGTH: 248
<212> TYPE: PRT
<213> ORGANISM: Artificial Sequence
<220> FEATURE:
<223> OTHER INFORMATION: Synthetic

<400> SEQUENCE: 329

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Glu Asp Ala Ser Lys Lys Gln Phe Ser Leu
65                  70                  75                  80

Thr Leu Thr Ser Val Thr Ala Ala Asp Thr Ala Val Tyr Tyr Cys Ala
                85                  90                  95

Arg Gly Pro Ala Gly Thr Gly Ser Ser Gly Tyr Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Glu Ile Val Leu Thr Gln Ser Pro
    130                 135                 140

Leu Ser Leu Pro Val Thr Pro Gly Glu Pro Ala Ser Ile Ser Cys Arg
145                 150                 155                 160

Ser Ser Gln Ser Leu Leu His Ser Asn Gly Tyr Asn Tyr Leu Asp Trp
                165                 170                 175

Tyr Leu Gln Lys Pro Gly Gln Ser Pro Gln Leu Leu Ile Tyr Leu Ala
            180                 185                 190
```

```
Ser Asn Arg Ala Ser Gly Val Pro Asp Arg Phe Ser Gly Ser Gly Ser
        195                 200                 205

Gly Thr Asp Phe Thr Leu Lys Ile Ser Arg Val Glu Ala Glu Asp Val
    210                 215                 220

Gly Val Tyr Tyr Cys Met Gln Gly Thr His Trp Pro Trp Thr Phe Gly
225                 230                 235                 240

Gln Gly Thr Lys Val Glu Val Lys
                245


<210> SEQ ID NO 330
<211> LENGTH: 9
<212> TYPE: PRT
<213> ORGANISM: Artificial Sequence
<220> FEATURE:
<223> OTHER INFORMATION: Synthetic

<400> SEQUENCE: 330

Asn Ser Gly Ala Gly Thr Ala Ala Ala
1               5


<210> SEQ ID NO 331
<211> LENGTH: 23
<212> TYPE: PRT
<213> ORGANISM: Artificial Sequence
<220> FEATURE:
<223> OTHER INFORMATION: Synthetic

<400> SEQUENCE: 331

Asn Ser Gly Ala Gly Thr Ser Gly Ser Gly Ala Ser Gly Glu Gly Ser
1               5                   10                  15

Gly Ser Lys Leu Ala Ala Ala
            20


<210> SEQ ID NO 332
<211> LENGTH: 8
<212> TYPE: PRT
<213> ORGANISM: Artificial Sequence
<220> FEATURE:
<223> OTHER INFORMATION: Synthetic

<400> SEQUENCE: 332

Gly Gly Gly Gly Ser Ala Ala Ala
1               5


<210> SEQ ID NO 333
<211> LENGTH: 15
<212> TYPE: PRT
<213> ORGANISM: Artificial Sequence
<220> FEATURE:
<223> OTHER INFORMATION: Synthetic

<400> SEQUENCE: 333

Gly Gly Gly Gly Ser Gly Gly Gly Gly Ser Gly Gly Gly Gly Ser
1               5                   10                  15


<210> SEQ ID NO 334
<211> LENGTH: 9
<212> TYPE: PRT
<213> ORGANISM: Artificial Sequence
<220> FEATURE:
<223> OTHER INFORMATION: Synthetic

<400> SEQUENCE: 334

Ala Ala Ala His His His His His His
1               5
```

<210> SEQ ID NO 335
<211> LENGTH: 648
<212> TYPE: DNA
<213> ORGANISM: Artificial Sequence
<220> FEATURE:
<223> OTHER INFORMATION: Synthetic

<400> SEQUENCE: 335
cagtctgccc tgactcagcc tgcctccgtg tctgggtctc ctggacagtc gatcgccatt 60
tcctgcactg gaaccagcag tgacattggt cattatgact ttgtctcctg gtaccaacag 120
cacccaggca cagcccccaa actcataatt tatgatatca ataatcggcc ctcagggatt 180
tctaatcgct tctctggctc caagtctgac aatatggcct ccctgaccat ctctgggctc 240
cagcctgagg acgaggctga ttattactgc agtgcatata caagcagcga cactctggtc 300
ttcggcggag ggaccaagtt gaccgtcctc agtcagccca aggctgcccc ctcggtcact 360
ctgttcccac cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tacctgagcc tgacgcctga gcagtggaag tcccacaaaa gctacagctg ccaggtcacg 600
catgaaggga gcaccgtgga gaagacagtg gcccctacag aatgttca 648

<210> SEQ ID NO 336
<211> LENGTH: 672
<212> TYPE: DNA
<213> ORGANISM: Artificial Sequence
<220> FEATURE:
<223> OTHER INFORMATION: Synthetic

<400> SEQUENCE: 336
gaggtccagc tggtacagtc tggggctgag gtgaagaagc ctgggtcctc agtgaaggtt 60
tcctgcaagg catctggata caccttcacc aactactata tgcactgggt gcgacaggcc 120
cctggacaag ggcttgagtg gatgggggca atcatgccta gtcgtggtgg cacaagttac 180
ccacagaagt tccagggcag agtcaccatg accggggaca cgtccacgag cacagtctac 240
atggagctga gcagcctgag atctgaggac acggccgtgt attactgtgc gagaggggag 300
tattactatg atagtagtgg ttattactac tggggccagg gcaccctggt caccgtctca 360
agcgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtccacacct tcccggctgt cctacagtcc 540
tcaggactct actccctcag cagcgtagtg accgtgccct ccagcagctt gggcacccag 600
acctacatct gcaacgtgaa tcacaagccc agcaacacca aggtggacaa gaaagttgag 660
cccaaatctt gt 672

<210> SEQ ID NO 337
<211> LENGTH: 1440
<212> TYPE: DNA
<213> ORGANISM: Artificial Sequence
<220> FEATURE:
<223> OTHER INFORMATION: Synthetic

<400> SEQUENCE: 337
gaagtgcagc tggtgcagag cggggcagaa gtgaaaaagc ctgggtcaag cgtgaaggtc 60

```
tcctgtaaag caagcggata cacattcaca aactactata tgcactgggt gcggcaggcc    120
cccggacagg gcctggagtg gatgggcgct atcatgcctt cccgaggcgg gacttcttac    180
ccacagaagt tccagggaag agtgaccatg acaggcgaca ctagcacctc cacagtctat    240
atggagctga gcagcctgag gagcgaagac actgccgtgt actattgcgc tcgcggagaa    300
tactattacg attctagtgg ctattactat tgggggcagg gaacactggt gactgtctca    360
agcggaggag gaggaagtgg cggaggaggc tccggaggag gcgggtctca gagtgcactg    420
acccagccag catcagtgag cggcagcccc ggccagtcta tcgcaattag ttgtactggg    480
acctcctctg acatcggaca ctacgatttc gtctcttggt atcagcagca ccccggcacc    540
gctcctaagc tgatcatcta cgacatcaac aatcggccca gcggcatttc caacagattt    600
tctgggagta aatcagataa tatggcctca ctgacaatta gcggcctcca gcctgaggac    660
gaagctgatt actattgctc cgcatacact agttcagata ccctggtgtt tggaggcggg    720
accaaactga cagtcctgaa cagcggcgcg ggcaccgcgg ccgcgactca cacatgccca    780
ccgtgcccag cacctgaagc cgcgggggga ccgtcagtct tcctcttccc cccaaaaccc    840
aaggacaccc tcatgatctc ccggacccct gaggtcacat gcgtggtggt ggacgtgagc    900
cacgaagacc ctgaggtcaa gttcaactgg tacgtggacg gcgtggaggt gcataatgcc    960
aagacaaagc cgcgggagga gcagtacaac agcacgtacc gtgtggtcag cgtcctcacc   1020
gtcctgcacc aggactggct gaatggcaag gagtacaagt gcaaggtctc caacaaagcc   1080
ctcccagccc ccatcgagaa aaccatctcc aaagccaaag ggcagccccg agaaccacag   1140
gtgtacaccc tgcccccatg ccgggatgag ctgaccaaga accaggtcag cctgtggtgc   1200
ctggtcaaag gcttctatcc cagcgacatc gccgtggagt gggagagcaa tgggcagccg   1260
gagaacaact acaagaccac gcctcccgtg ctggactccg acggctcctt cttcctctac   1320
agcaagctca ccgtggacaa gagcaggtgg cagcagggga acgtcttctc atgctccgtg   1380
atgcatgagg ctctgcacaa ccactacacg cagaagagcc tctccctgtc tccgggtaaa   1440
```

<210> SEQ ID NO 338
<211> LENGTH: 642
<212> TYPE: DNA
<213> ORGANISM: Artificial Sequence
<220> FEATURE:
<223> OTHER INFORMATION: Synthetic

<400> SEQUENCE: 338

```
gacatccaga tgacccagtc tccttccaca ttgtctgcat ctgtaggaga cagagtcaca     60
ctctcttgcc gggccggtca ggctattagt agttggttgg cctggtatca acagaaacca    120
ggtaaagccc caaagcttct gatctataag gcatctaatt tagaaagtgg agtcccatca    180
aggttcagcg gcggtggatc tggggcagaa ttcactctca ccatcagcag cctgcagcct    240
gatgattttg caacttatta ctgccaacag tatcagagct acccttacac ttttggccag    300
gggaccaagc tggagatcag acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 339
<211> LENGTH: 666
<212> TYPE: DNA
<213> ORGANISM: Artificial Sequence
<220> FEATURE:
<223> OTHER INFORMATION: Synthetic

<400> SEQUENCE: 339
gaggtgcagc tggtgcagtc tgggactgag gtgaagaagc ctggggcctc agtgaaggtt 60
tcctgcaagg cttctggata caccttcact acctatgcta tgcattgggt gcgccaggcc 120
cccggacaaa gccttgagtg gatgggatgg atcaacactg gcaatggtaa cacaaaatat 180
tcacagaact tccagggcag agtcaccatg accagggaca cgtccatcag cacagcctac 240
atggagctga gcaggctgag atctgacgac acggccgtgt attactgtgc gagagatctc 300
gggcaactgg aacgactcta cttctggggc cagggcaccc tggtcaccgt ctcaagcgcc 360
tccaccaagg gcccatcggt cttccccctg gcaccctcct ccaagagcac ctctgggggc 420
acagcggccc tgggctgcct ggtcaaggac tacttccccg aaccggtgac ggtgtcgtgg 480
aactcaggcg ccctgaccag cggcgtccac accttcccgg ctgtcctaca gtcctcagga 540
ctctactccc tcagcagcgt agtgaccgtg ccctccagca gcttgggcac ccagacctac 600
atctgcaacg tgaatcacaa gcccagcaac accaaggtgg acaagaaagt tgagcccaaa 660
tcttgt 666

<210> SEQ ID NO 340
<211> LENGTH: 1428
<212> TYPE: DNA
<213> ORGANISM: Artificial Sequence
<220> FEATURE:
<223> OTHER INFORMATION: Synthetic

<400> SEQUENCE: 340
gaggtgcagc tggtgcagtc tgggactgag gtgaagaagc ctggggcctc agtgaaggtt 60
tcctgcaagg cttctggata caccttcact acctatgcta tgcattgggt gcgccaggcc 120
cccggacaaa gccttgagtg gatgggatgg atcaacactg gcaatggtaa cacaaaatat 180
tcacagaact tccagggcag agtcaccatg accagggaca cgtccatcag cacagcctac 240
atggagctga gcaggctgag atctgacgac acggccgtgt attactgtgc gagagatctc 300
gggcaactgg aacgactcta cttctggggc cagggcaccc tggtcaccgt ctcaagcgga 360
ggaggaggat ctggcggagg aggcagtgga ggaggagggt cacttgacat ccagatgacc 420
cagtctcctt ccacattgtc tgcatctgta ggagacagag tcacactctc ttgccgggcc 480
ggtcaggcta ttagtagttg gttggcctgg tatcaacaga aaccaggtaa agccccaaag 540
cttctgatct ataaggcatc taatttagaa agtggagtcc catcaaggtt cagcggcggt 600
ggatctgggg cagaattcac tctcaccatc agcagcctgc agcctgatga ttttgcaact 660
tattactgcc aacagtatca gagctaccct tacacttttg gccaggggac caagctggag 720
atcagaaaca gcggcgcggg caccgcggcc gcgactcaca catgcccacc gtgcccagca 780
cctgaagccg cgggggggacc gtcagtcttc ctcttccccc caaaacccaa ggacaccctc 840
atgatctccc ggacccctga ggtcacatgc gtggtggtgg acgtgagcca cgaagaccct 900
gaggtcaagt tcaactggta cgtggacggc gtggaggtgc ataatgccaa gacaaagccg 960
cgggaggagc agtacaacag cacgtaccgt gtggtcagcg tcctcaccgt cctgcaccag 1020
gactggctga atggcaagga gtacaagtgc aaggtctcca acaaagccct cccagccccc 1080

-continued atcgagaaaa ccatctccaa agccaaaggg cagccccgag aaccacaggt gtacaccctg 1140
cccccatgcc gggatgagct gaccaagaac caggtcagcc tgtggtgcct ggtcaaaggc 1200
ttctatccca gcgacatcgc cgtggagtgg gagagcaatg ggcagccgga gaacaactac 1260
aagaccacgc ctcccgtgct ggactccgac ggctccttct tcctctacag caagctcacc 1320
gtggacaaga gcaggtggca gcaggggaac gtcttctcat gctccgtgat gcatgaggct 1380
ctgcacaacc actacacgca gaagagcctc tccctgtctc cgggtaaa 1428

<210> SEQ ID NO 341
<211> LENGTH: 642
<212> TYPE: DNA
<213> ORGANISM: Artificial Sequence
<220> FEATURE:
<223> OTHER INFORMATION: Synthetic

<400> SEQUENCE: 341
gacatccagt tgacccagtc tccatcctcc ctgtctgcat ctgtaggaga cagagtcacc 60
atcacttgcc aggcgagtca ggacattggc aactatttaa attggtatca gcttaaacca 120
gggaaagccc ctaagctcct gatctacgat gcatccaatt tggaaacagg ggtcccatca 180
aggttcagtg gaagtggatc tgggacagat tttactttca ccatcagcag cctgcagcct 240
gaagatattg caacatatta ctgtctacaa ctttatgatt accccctcac tttcggcgga 300
gggaccaagg tggagatcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 342
<211> LENGTH: 651
<212> TYPE: DNA
<213> ORGANISM: Artificial Sequence
<220> FEATURE:
<223> OTHER INFORMATION: Synthetic

<400> SEQUENCE: 342
cacgtgcagc tggtggagac tgggggaggc ttggtgcagc ctggggggtc cctgagactc 60
tcctgtgcag cctctggatt cacctttagc agctatgcca tgagctgggt ccgccaggct 120
ccagggaagg ggctggagtg ggtctcagct attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gagagatctc 300
ggggattatt ggggccaggg aaccctggtc accgtctcaa gcgcctccac caagggccca 360
tcggtcttcc ccctggcacc ctcctccaag agcacctctg ggggcacagc ggccctgggc 420
tgcctggtca aggactactt ccccgaaccg gtgacggtgt cgtggaactc aggcgccctg 480
accagcggcg tccacacctt cccggctgtc ctacagtcct caggactcta ctccctcagc 540
agcgtagtga ccgtgccctc cagcagcttg ggcacccaga cctacatctg caacgtgaat 600
cacaagccca gcaacaccaa ggtggacaag aaagttgagc ccaaatcttg t 651

<210> SEQ ID NO 343
<211> LENGTH: 1452

<212> TYPE: DNA
<213> ORGANISM: Artificial Sequence
<220> FEATURE:
<223> OTHER INFORMATION: Synthetic

<400> SEQUENCE: 343
caggtccagc tgcaggagtc cgggccaggg ctggtgaaac caagcgaaac actgagtctg 60
acatgtaccg tgagtggggg gtccattaac aatagtaact actattggtc atggatcaga 120
cagagccctg gaagaggcct ggagtggatc ggcgggatct acttcagcgg caccacatac 180
tataacccat cactgcagag ccgggtgact atctccattg acacctctaa gaatcagttc 240
agcctgaagc tgagcagcgt gaccgccgct gatacagcca tctactattg cgtccggcag 300
atgaattact atcacctggg ctctagtgtg gggttcgacc cctggggaca gggagcactg 360
gccaccgtgt caagcgtctc ctctggagga ggaggcagcg gcggaggagg ctctggagga 420
ggcgggagtg atgtggtcat gacacagagc ccagctactc tgtctgtgag tcccggcgaa 480
agggccacac tgagctgtcg cgcttcacag agcgtcagtt caaacctggc atggtaccag 540
cagaagccag gacaggcacc ttccctgctg atctatgagg cttctacacg agcaactggc 600
attcctgcta gattctccgg ctctgggagt ggaaccgact ttactctgac catcagctcc 660
ctgcagagcg aagattttgc aatctactat tgtcagcagt ataacgattg gctgtggacc 720
ttcgggcagg ggactaaagt ggagattcgg aacagcggcg cgggcaccgc ggccgcgact 780
cacacatgcc caccgtgccc agcacctgaa gccgcggggg gaccgtcagt cttcctcttc 840
cccccaaaac ccaaggacac cctcatgatc tcccggaccc ctgaggtcac atgcgtggtg 900
gtggacgtga gccacgaaga ccctgaggtc aagttcaact ggtacgtgga cggcgtggag 960
gtgcataatg ccaagacaaa gccgcgggag gagcagtaca acagcacgta ccgtgtggtc 1020
agcgtcctca ccgtcctgca ccaggactgg ctgaatggca aggagtacaa gtgcaaggtc 1080
tccaacaaag ccctcccagc ccccatcgag aaaaccatct ccaaagccaa agggcagccc 1140
cgagaaccac aggtgtacac cctgccccca tgccgggatg agctgaccaa gaaccaggtc 1200
agcctgtggt gcctggtcaa aggcttctat cccagcgaca tcgccgtgga gtgggagagc 1260
aatgggcagc cggagaacaa ctacaagacc acgcctcccg tgctggactc cgacggctcc 1320
ttcttcctct acagcaagct caccgtggac aagagcaggt ggcagcaggg gaacgtcttc 1380
tcatgctccg tgatgcatga ggctctgcac aaccactaca cgcagaagag cctctccctg 1440
tctccgggta aa 1452

<210> SEQ ID NO 344
<211> LENGTH: 648
<212> TYPE: DNA
<213> ORGANISM: Artificial Sequence
<220> FEATURE:
<223> OTHER INFORMATION: Synthetic

<400> SEQUENCE: 344
aattttatgc tgactcagcc ccactctgtg tcggagtctc cggggaagac ggtaaccatc 60
tcctgcaccc gcagcagtgg cagcattgcc agcaactatg tgcagtggta ccagcagcgc 120
ccgggcagtt cccccaccac ggtcattttt gacgacaatc aaagacccac tggtgtccct 180
gatcgcttct ctgccgccat cgacacctcc tccagttctg cctccctcac catctctgga 240
ctgacggctg aggacgaggc cgattactat tgtcagtcgt ctcatagcac cgctgtcgtc 300
tttggcggag ggaccaagct gaccgtccta agtcagccca aggctgcccc ctcggtcact 360
ctgttcccgc cctcctctga ggagcttcaa gccaacaagg ccacactggt gtgtctcata 420
agtgacttct acccgggagc cgtgacagtg gcctggaagg cagatagcag ccccgtcaag 480
gcgggagtgg agaccaccac accctccaaa caaagcaaca acaagtacgc ggccagcagc 540
tacctgagcc tgacgcctga gcagtggaag tcccacaaaa gctacagctg ccaggtcacg 600
catgaaggga gcaccgtgga gaagacagtg gcccctacag aatgttca 648

<210> SEQ ID NO 345
<211> LENGTH: 660
<212> TYPE: DNA
<213> ORGANISM: Artificial Sequence
<220> FEATURE:
<223> OTHER INFORMATION: Synthetic

<400> SEQUENCE: 345
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcgag aagctcgtcc 300
ggggatgctt ttgatatctg gggccaaggg acaatggtca ccgtctcaag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt ccacaccttc ccggctgtcc tacagtcctc aggactctac 540
tccctcagca gcgtagtgac cgtgccctcc agcagcttgg gcacccagac ctacatctgc 600
aacgtgaatc acaagcccag caacaccaag gtggacaaga aagttgagcc caaatcttgt 660

<210> SEQ ID NO 346
<211> LENGTH: 1431
<212> TYPE: DNA
<213> ORGANISM: Artificial Sequence
<220> FEATURE:
<223> OTHER INFORMATION: Synthetic

<400> SEQUENCE: 346
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcgag aagctcgtcc 300
ggggatgctt ttgatatctg gggccaaggg acaatggtca ccgtctcaag cggaggagga 360
ggatctggcg gaggaggcag tggaggagga gggtcactta attttatgct gactcagccc 420
cactctgtgt cggagtctcc ggggaagacg gtaaccatct cctgcacccg cagcagtggc 480
agcattgcca gcaactatgt gcagtggtac cagcagcgcc cgggcagttc ccccaccacg 540
gtcatttttg acgacaatca aagacccact ggtgtccctg atcgcttctc tgccgccatc 600
gacacctcct ccagttctgc ctccctcacc atctctggac tgacggctga ggacgaggcc 660
gattactatt gtcagtcgtc tcatagcacc gctgtcgtct ttggcggagg gaccaagctg 720
accgtcctaa acagcggcgc gggcaccgcg gccgcgactc acacatgccc accgtgccca 780
gcacctgaag ccgcgggggg accgtcagtc ttcctcttcc ccccaaaacc caaggacacc 840
ctcatgatct cccggacccc tgaggtcaca tgcgtggtgg tggacgtgag ccacgaagac 900
cctgaggtca agttcaactg gtacgtggac ggcgtggagg tgcataatgc caagacaaag 960
ccgcgggagg agcagtacaa cagcacgtac cgtgtggtca gcgtcctcac cgtcctgcac 1020
caggactggc tgaatggcaa ggagtacaag tgcaaggtct ccaacaaagc cctcccagcc 1080
cccatcgaga aaaccatctc caaagccaaa gggcagcccc gagaaccaca ggtgtacacc 1140
ctgcccccat gccgggatga gctgaccaag aaccaggtca gcctgtggtg cctggtcaaa 1200
ggcttctatc ccagcgacat cgccgtggag tgggagagca atgggcagcc ggagaacaac 1260
tacaagacca cgcctcccgt gctggactcc gacggctcct tcttcctcta cagcaagctc 1320
accgtggaca agagcaggtg gcagcagggg aacgtcttct catgctccgt gatgcatgag 1380
gctctgcaca accactacac gcagaagagc ctctccctgt ctccgggtaa a 1431

<210> SEQ ID NO 347
<211> LENGTH: 657
<212> TYPE: DNA
<213> ORGANISM: Artificial Sequence
<220> FEATURE:
<223> OTHER INFORMATION: Synthetic

<400> SEQUENCE: 347
gatgttgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc tagtcgggcc 180
tccggggtcc ctgacaggtt cagtggcagt ggatcaggca cagattttac actgaaaatc 240
agcagagtgg aggctgagga tgttggggtt tattactgca tgcaagctct acaaactcct 300
cgcacttttg gccaggggac caagctggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 348
<211> LENGTH: 687
<212> TYPE: DNA
<213> ORGANISM: Artificial Sequence
<220> FEATURE:
<223> OTHER INFORMATION: Synthetic

<400> SEQUENCE: 348
gaggtgcagc tggtgcagtc tggggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtc atatcatatg atggaagcaa taaatactat 180
gcagactccg tgaagggccg attcaccatc tccagagaca attccaagaa cacgctgtat 240
ctgcaaatga acagcctgag agctgaggac acggctgtgt attactgtgc gagagatctc 300
gggtatagca gcagctggta ctactactac tacggtatgg acgtctgggg ccaagggacc 360
acggtcaccg tctcaagcgc ctccaccaag ggcccatcgg tcttccccct ggcaccctcc 420
tccaagagca cctctggggg cacagcggcc ctgggctgcc tggtcaagga ctacttcccc 480

```
gaaccggtga cggtgtcgtg gaactcaggc gccctgacca gcggcgtcca caccttcccg    540

gctgtcctac agtcctcagg actctactcc ctcagcagcg tagtgaccgt gccctccagc    600

agcttgggca cccagaccta catctgcaac gtgaatcaca agcccagcaa caccaaggtg    660

gacaagaaag ttgagcccaa atcttgt                                        687
```

<210> SEQ ID NO 349
<211> LENGTH: 1461
<212> TYPE: DNA
<213> ORGANISM: Artificial Sequence
<220> FEATURE:
<223> OTHER INFORMATION: Synthetic

<400> SEQUENCE: 349

```
gaggtgcagc tggtgcagag cggggggggg gtggtgcagc ctgggaggtc actgagactg     60

agttgtgccg catccgggtt tacatttagc tcctatgcaa tgcactgggt gaggcaggcc    120

cctggcaagg ggctggagtg ggtggctgtc atcagttacg acggctcaaa caagtactat    180

gcagattctg tgaaagggcg gttcacaatt agcagagaca actccaaaaa tactctgtac    240

ctccagatga atagcctgcg agccgaagac accgccgtgt actattgcgc cagagacctg    300

ggatactcta gttcatggta ctactactac tacggcatgg acgtgtgggg acagggcacc    360

acagtgacag tcagctccgg cggaggaggc tcaggaggag gagggtccgg cggaggagga    420

tctgatgtgg tcatgaccca gtccccactg tctctgccag tgacacctgg cgagccagca    480

agcatcagct gccggagcag ccagtctctg ctgcatagta acgggtataa ttacctggac    540

tggtacttgc agaagcctgg ccagagtcct cagctgctga tctacctggg gtcaagcagg    600

gcctccggag tgcccgaccg cttcagtggg tcaggaagcg gcactgactt caccctgaag    660

atcagccggg tggaggctga agatgtgggc gtctattact gtatgcaggc actgcagaca    720

ccacggactt ttggacaggg gactaaactg gaaatcaaga acagcggcgc gggcaccgcg    780

gccgcgactc acacatgccc accgtgccca gcacctgaag ccgcgggggg accgtcagtc    840

ttcctcttcc ccccaaaacc caaggacacc ctcatgatct cccggacccc tgaggtcaca    900

tgcgtggtgg tggacgtgag ccacgaagac cctgaggtca agttcaactg gtacgtggac    960

ggcgtggagg tgcataatgc caagacaaag ccgcgggagg agcagtacaa cagcacgtac   1020

cgtgtggtca gcgtcctcac cgtcctgcac caggactggc tgaatggcaa ggagtacaag   1080

tgcaaggtct ccaacaaagc cctcccagcc cccatcgaga aaaccatctc caaagccaaa   1140

gggcagcccc gagaaccaca ggtgtacacc ctgcccccat gccgggatga gctgaccaag   1200

aaccaggtca gcctgtggtg cctggtcaaa ggcttctatc ccagcgacat cgccgtggag   1260

tgggagagca atgggcagcc ggagaacaac tacaagacca cgcctcccgt gctggactcc   1320

gacggctcct tcttcctcta cagcaagctc accgtggaca agagcaggtg gcagcagggg   1380

aacgtcttct catgctccgt gatgcatgag gctctgcaca accactacac gcagaagagc   1440

ctctccctgt ctccgggtaa a                                             1461
```

<210> SEQ ID NO 350
<211> LENGTH: 639
<212> TYPE: DNA
<213> ORGANISM: Artificial Sequence
<220> FEATURE:
<223> OTHER INFORMATION: Synthetic

<400> SEQUENCE: 350

```
gacatccaga tgacccagtc tccatcctcc ctgtctgcat ctgtaggaga cagagtcacc     60
```

atcacttgcc aggcgagtca ggacattagc gactatttaa attggtatca gcagaaacca 120
gggaaagccc ctcagatcct gatctacgat gcatccaatt tggagacagg ggtcccatca 180
agattcagtg gaagtgggtc tgggacagat tttactttca ccatcagcaa cctgcagcct 240
gaggatgttg caacatatta ctgtcaacag tatgaggatc tcccctcttt cggcggaggg 300
accaaggtgg agatcaaacg aactgtggct gcaccatctg tcttcatctt cccgccatct 360
gatgagcagt tgaaatctgg aactgcctct gttgtgtgcc tgctgaataa cttctatccc 420
agagaggcca aagtacagtg gaaggtggat aacgccctcc aatcgggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgt 639

<210> SEQ ID NO 351
<211> LENGTH: 669
<212> TYPE: DNA
<213> ORGANISM: Artificial Sequence
<220> FEATURE:
<223> OTHER INFORMATION: Synthetic

<400> SEQUENCE: 351
caggtgcagc tgcaggagtc gggcccagga ctggtgaagc cttcggagac cctgtccctc 60
acctgcactg tctctggtgt ctccatcagc agtagaagtg accactgggg ctgggtccgc 120
cagcccccag ggaaggggct ggagtggatt ggaagtatct cttatagtgg gagcacctac 180
tacaacccgt ccctcaagag ccgagtcacc atatccgtag acacctccaa gaaccaactc 240
tccctgaagc tgagctctgt gaccgccgca gacacggctg tgtattactg tgcgagagag 300
tcgcacccag cagctgcact ggttgggtgg ggccagggca ccctggtcac cgtctcaagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtc cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgt 669

<210> SEQ ID NO 352
<211> LENGTH: 1425
<212> TYPE: DNA
<213> ORGANISM: Artificial Sequence
<220> FEATURE:
<223> OTHER INFORMATION: Synthetic

<400> SEQUENCE: 352
caggtccagc tgcaggagag cggccccgga ctggtgaagc ctagcgaaac actgagcctg 60
acttgtactg tgagcggcgt gagcattagc tcccggagcg accactgggg atgggtgaga 120
cagccccctg gcaaggggct ggagtggatc ggaagtattt catacagcgg ctccacttac 180
tataacccct ctctgaaaag tagggtgact atctcagtgg acaccagcaa gaatcagctg 240
agtctgaaac tgtctagtgt gaccgccgct gatacagcag tctactattg cgcccgcgaa 300
tcccatcctg ccgccgccct ggtgggatgg ggacagggga cactggtgac tgtctcaagc 360
ggaggaggag gcagtggagg aggagggtca ggaggcgggg gaagcgacat tcagatgaca 420
cagagcccat cctctctgtc tgccagtgtg ggcgatcgag tcaccatcac atgtcaggct 480
tcccaggaca tttctgatta cctgaactgg tatcagcaga agccagggaa agctccccag 540
atcctgatct acgacgcatc caatctggag acaggcgtgc ccagccggtt cagcggaagc 600
ggctccggga ctgatttcac ttttaccatc tctaacctcc agcctgagga cgtggccacc 660
tactattgcc agcagtatga ggacctgcca tcctttggcg ggggaacaaa ggtcgagatc 720
aagaacagcg gcgcgggcac cgcggccgcg actcacacat gcccaccgtg cccagcacct 780
gaagccgcgg ggggaccgtc agtcttcctc ttccccccaa aacccaagga caccctcatg 840
atctcccgga cccctgaggt cacatgcgtg gtggtggacg tgagccacga agaccctgag 900
gtcaagttca actggtacgt ggacggcgtg gaggtgcata atgccaagac aaagccgcgg 960
gaggagcagt acaacagcac gtaccgtgtg gtcagcgtcc tcaccgtcct gcaccaggac 1020
tggctgaatg gcaaggagta caagtgcaag gtctccaaca aagccctccc agcccccatc 1080
gagaaaacca tctccaaagc caaagggcag ccccgagaac cacaggtgta caccctgccc 1140
ccatgccggg atgagctgac caagaaccag gtcagcctgt ggtgcctggt caaaggcttc 1200
tatcccagcg acatcgccgt ggagtgggag agcaatgggc agccggagaa caactacaag 1260
accacgcctc ccgtgctgga ctccgacggc tccttcttcc tctacagcaa gctcaccgtg 1320
gacaagagca ggtggcagca ggggaacgtc ttctcatgct ccgtgatgca tgaggctctg 1380
cacaaccact acacgcagaa gagcctctcc ctgtctccgg gtaaa 1425

<210> SEQ ID NO 353
<211> LENGTH: 642
<212> TYPE: DNA
<213> ORGANISM: Artificial Sequence
<220> FEATURE:
<223> OTHER INFORMATION: Synthetic

<400> SEQUENCE: 353
gacatccagt tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaaggccct gatctacgat gcatccaatt tggaaacagg ggtcccatca 180
aggttcagtg gcagtggatc tgggacagat ttcactctca ccatcatcag tctgcaacct 240
gaagattttg caacttattt ctgtctacaa gattacattt acccgtggac gttcggccaa 300
gggaccaagg tggaattcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 354
<211> LENGTH: 645
<212> TYPE: DNA
<213> ORGANISM: Artificial Sequence
<220> FEATURE:
<223> OTHER INFORMATION: Synthetic

<400> SEQUENCE: 354
gaggtgcagc tggtgcagtc tgggggaggc ttggtacagc ctggggggtc cctgagactc 60
tcctgtgcag cctctggatt cacctttagc agctatgcca tgagctgggt ccgccaggct 120

```
ccagggaagg ggctggagtg ggtctcagct attagtggta gtggtggcag cacacactac    180

gcagactccg tgaagggccg gttcaccatc tccagagaca actccaagaa cacgctgtat    240

ctgcaaatga acagcctgag agccgaggac acggccgtat attactgtgc gactccggct    300

ttctggggcc agggaaccct ggtcaccgtc tcaagcgcct ccaccaaggg cccatcggtc    360

ttccccctgg caccctcctc caagagcacc tctgggggca cagcggccct gggctgcctg    420

gtcaaggact acttccccga accggtgacg gtgtcgtgga actcaggcgc cctgaccagc    480

ggcgtccaca ccttcccggc tgtcctacag tcctcaggac tctactccct cagcagcgta    540

gtgaccgtgc cctccagcag cttgggcacc cagacctaca tctgcaacgt gaatcacaag    600

cccagcaaca ccaaggtgga caagaaagtt gagcccaaat cttgt                    645
```

```
<210> SEQ ID NO 355
<211> LENGTH: 1404
<212> TYPE: DNA
<213> ORGANISM: Artificial Sequence
<220> FEATURE:
<223> OTHER INFORMATION: Synthetic

<400> SEQUENCE: 355

gaggtgcagc tggtgcagag cgggggagga ctggtgcagc ctgggggtc actgagactg      60

agttgtgccg caagcgggtt tacatttagc tcctacgcca tgtcttgggt gcgacaggct    120

cccggaaaag gcctggagtg ggtcagcgca atcagtggat caggcgggtc tactcactac    180

gccgacagtg tgaaaggccg gttcaccatc agccgggaca acagtaagaa tactctgtac    240

ctccagatga acagcctgag agctgaagac accgccgtgt actattgcgc cacccctgct    300

ttttgggggc agggaacact ggtgactgtc tctagtggag gaggaggatc aggcggcgga    360

ggcagcggag gaggagggtc cgacatccag ctgacacagt ccccatcaag cctgagcgct    420

tccgtgggcg atagggtcac catcacatgt cgcgcatctc agagtatttc ctcttacctg    480

aactggtatc agcagaagcc cggcaaggca cctaaggccc tgatctacga cgccagcaat    540

ctggagaccg gcgtgccttc ccggttctca ggcagcgggt ccggaacaga ttttactctg    600

accatcatca gcctccagcc agaggacttc gctacctatt tttgcctcca ggattacatc    660

taccccctgga ccttcggcca ggggacaaaa gtggagttca agaacagcgg cgcgggcacc    720

gcggccgcga ctcacacatg cccaccgtgc ccagcacctg aagccgcggg gggaccgtca    780

gtcttcctct tcccccaaa acccaaggac accctcatga tctcccggac ccctgaggtc    840

acatgcgtgg tggtggacgt gagccacgaa gaccctgagg tcaagttcaa ctggtacgtg    900

gacggcgtgg aggtgcataa tgccaagaca aagccgcggg aggagcagta caacagcacg    960

taccgtgtgg tcagcgtcct caccgtcctg caccaggact ggctgaatgg caaggagtac   1020

aagtgcaagg tctccaacaa agccctccca gcccccatcg agaaaaccat ctccaaagcc   1080

aaagggcagc cccgagaacc acaggtgtac accctgcccc catgccggga tgagctgacc   1140

aagaaccagg tcagcctgtg gtgcctggtc aaaggcttct atcccagcga catcgccgtg   1200

gagtgggaga gcaatgggca gccggagaac aactacaaga ccacgcctcc cgtgctggac   1260

tccgacggct ccttcttcct ctacagcaag ctcaccgtgg acaagagcag gtggcagcag   1320

gggaacgtct tctcatgctc cgtgatgcat gaggctctgc acaaccacta cacgcagaag   1380

agcctctccc tgtctccggg taaa                                          1404

<210> SEQ ID NO 356
```

<211> LENGTH: 651
<212> TYPE: DNA
<213> ORGANISM: Artificial Sequence
<220> FEATURE:
<223> OTHER INFORMATION: Synthetic

<400> SEQUENCE: 356
cagtctgtgt tgacgcagcc gccctcagtg tctggggccc cagggcagag ggtcaccatc 60
tcctgcactg gggcagctc caacgtcggg gcaggttatg atgtacactg gtaccagcag 120
cttccaggaa cagtccccaa actcctcatc tatgataaca ccaatcggcc ctcaggtgtc 180
cctgaccggt tctctgcctc caagtctggc acctcagcct ctctggtcat cactgggctc 240
caggctgagg atgagggtga ctattactgc cagtcgtatg acagtagtct gcgtgcttcg 300
gtattcggcg gagggaccat gttgaccgtc ctaagtcagc ccaaggctgc cccctcggtc 360
actctgttcc cgccctcctc tgaggagctt caagccaaca aggccacact ggtgtgtctc 420
ataagtgact tctacccggg agccgtgaca gtggcctgga aggcagatag cagccccgtc 480
aaggcgggag tggagaccac cacaccctcc aaacaaagca acaacaagta cgcggccagc 540
agctatctga gcctgacgcc tgagcagtgg aagtcccaca aaagctacag ctgccaggtc 600
acgcatgaag ggagcaccgt ggagaagaca gtggccccta cagaatgttc a 651

<210> SEQ ID NO 357
<211> LENGTH: 660
<212> TYPE: DNA
<213> ORGANISM: Artificial Sequence
<220> FEATURE:
<223> OTHER INFORMATION: Synthetic

<400> SEQUENCE: 357
caggtgcagc tacagcagtg gggcccagga ctggtgaagc cttcggagac cctgtccctc 60
acctgcactg tctctggtgg ctccatcagt agttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcggg aggctctaat 300
ttggactggt tcgacccctg gggccaggga accctggtca ccgtctcaag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt ccacaccttc ccggctgtcc tacagtcctc aggactctac 540
tccctcagca gcgtagtgac cgtgccctcc agcagcttgg gcacccagac ctacatctgc 600
aacgtgaatc acaagcccag caacaccaag gtggacaaga aagttgagcc caaatcttgt 660

<210> SEQ ID NO 358
<211> LENGTH: 1431
<212> TYPE: DNA
<213> ORGANISM: Artificial Sequence
<220> FEATURE:
<223> OTHER INFORMATION: Synthetic

<400> SEQUENCE: 358
caggtccagc tgcagcagtg gggccagga ctggtgaagc catccgaaac tctgtctctg 60
acttgtaccg tgagcggcgg gagcatcagc tcctactatt ggagctggat caggcagccc 120
cctgggaagg gactggagtg gatcggcgaa attaaccaca gcgggtccac taactacaat 180
ccttccctga aatctcgcgt gactattagt gtggacacct caaagaatca gttctccctg 240
aaactgtcta gtgtgacagc cgctgatacc gccgtgtact attgcgccgg cgggtctaac 300
ctggactggt ttgatccctg gggacagggg accctggtga cagtctcaag cggaggagga 360
ggaagcggcg gaggaggctc cggaggagga gggtctcaga gtgtgctgac acagccacca 420
tcagtcagcg gggcccccgg acagcgagtg accatctcct gtacaggagg ctcctctaat 480
gtgggagccg gctacgacgt ccattggtat cagcagctgc ctggcaccgt gccaaagctg 540
ctgatctacg acaacacaaa tcggcccagc ggggtgcctg atagattctc cgcttctaaa 600
agtggcacat cagccagcct ggtcatcact ggactccagg ccgaggacga aggcgattac 660
tattgccagt cttatgatag ttcactgaga gctagtgtgt ttgggggagg cactatgctg 720
accgtcctga acagcggcgc gggcaccgcg gccgcgactc acacatgccc accgtgccca 780
gcacctgaag ccgcgggggg accgtcagtc ttcctcttcc ccccaaaacc caaggacacc 840
ctcatgatct cccggacccc tgaggtcaca tgcgtggtgg tggacgtgag ccacgaagac 900
cctgaggtca agttcaactg gtacgtggac ggcgtggagg tgcataatgc caagacaaag 960
ccgcgggagg agcagtacaa cagcacgtac cgtgtggtca gcgtcctcac cgtcctgcac 1020
caggactggc tgaatggcaa ggagtacaag tgcaaggtct ccaacaaagc cctcccagcc 1080
cccatcgaga aaaccatctc caaagccaaa gggcagcccc gagaaccaca ggtgtacacc 1140
ctgcccccat gccgggatga gctgaccaag aaccaggtca gcctgtggtg cctggtcaaa 1200
ggcttctatc ccagcgacat cgccgtggag tgggagagca atgggcagcc ggagaacaac 1260
tacaagacca cgcctcccgt gctggactcc gacggctcct tcttcctcta cagcaagctc 1320
accgtggaca agagcaggtg gcagcagggg aacgtcttct catgctccgt gatgcatgag 1380
gctctgcaca accactacac gcagaagagc ctctccctgt ctccgggtaa a 1431

<210> SEQ ID NO 359
<211> LENGTH: 651
<212> TYPE: DNA
<213> ORGANISM: Artificial Sequence
<220> FEATURE:
<223> OTHER INFORMATION: Synthetic

<400> SEQUENCE: 359
aattttatgc tgactcagcc ccactctgtg tcggagtctc cggggaagac ggtaaccatc 60
tcctgcaccg gcagcagtgg cagcattgcc agcagctatg tgcagtggta ccagcagcgc 120
ccgggcagtg cccccaccac tgtgatctat gcggataacc aaagaccctc tggggtccct 180
gatcggttct ctggctccgt cgacagctcc tccaactctg cctccctcac catctctgga 240
ctgaagactg aggacgaggc tgactactac tgtcagtctt ttgacagcag cctctatatg 300
atttttggcg gagggaccaa gctgaccgtc ctaggtcagc ccaaggctgc cccctcggtc 360
actctgttcc cgccctcctc tgaggagctt caagccaaca aggccacact ggtgtgtctc 420
ataagtgact tctacccggg agccgtgaca gtggcctgga aggcagatag cagccccgtc 480
aaggcgggag tggagaccac cacaccctcc aaacaaagca acaacaagta cgcggccagc 540
agctatctga gcctgacgcc tgagcagtgg aagtcccaca gaagctacag ctgccaggtc 600
acgcatgaag ggagcaccgt ggagaagaca gtggcccctg cagaatgctc t 651

<210> SEQ ID NO 360
<211> LENGTH: 663
<212> TYPE: DNA
<213> ORGANISM: Artificial Sequence
<220> FEATURE:

<223> OTHER INFORMATION: Synthetic

<400> SEQUENCE: 360
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
gagctgagct ctgtgaccgc cgcggacacg gctgtgtatt actgtgcgag agcggatcgt 300
cggttcgggg agttacgcta ctggggccag ggaaccctgg tcaccgtctc aagcgcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtccacacc ttcccggctg tcctacagtc ctcaggactc 540
tactccctca gcagcgtagt gaccgtgccc tccagcagct tgggcaccca gacctacatc 600
tgcaacgtga atcacaagcc cagcaacacc aaggtggaca agaaagttga gcccaaatct 660
tgt 663

<210> SEQ ID NO 361
<211> LENGTH: 1434
<212> TYPE: DNA
<213> ORGANISM: Artificial Sequence
<220> FEATURE:
<223> OTHER INFORMATION: Synthetic

<400> SEQUENCE: 361
caggtccagc tgcagcagtg gggagccgga ctgctgaagc caagtgagac tctgagcctg 60
acatgcgccg tgtatggggg aagtttttcc ggctactatt ggtcttggat cagacagccc 120
cctggcaagg ggctggagtg gatcggcgaa attaaccaca gtgggtcaac caactacaat 180
ccctctctga agagtcgcgt gacaatttca gtggacacta gcaaaaatca gttcagcctg 240
gagctgagca gcgtgactgc cgctgacacc gccgtctact attgcgcacg agccgatcgg 300
agatttggcg aactgcggta ttggggacag ggcacactgg tgactgtctc tagtggagga 360
ggaggcagtg gaggaggagg gtcaggaggc gggggatcta acttcatgct gactcagccc 420
catagcgtgt ccgagtctcc tgggaaaact gtcaccatca gttgtacagg gtcaagcgga 480
tctattgcct cctcttacgt gcagtggtat cagcagaggc caggctccgc tcccaccaca 540
gtgatctacg cagacaacca gaggcctagc ggagtgccag accgctttag tggctcagtc 600
gatagttcaa gcaatagcgc ctccctgacc atctccggcc tgaagacaga ggacgaagct 660
gattactatt gccagagctt cgattcctct ctgtatatga tttttggcgg gggaaccaaa 720
ctgacagtgc tgaacagcgg cgcgggcacc gcggccgcga ctcacacatg cccaccgtgc 780
ccagcacctg aagccgcggg gggaccgtca gtcttcctct tccccccaaa acccaaggac 840
accctcatga tctcccggac ccctgaggtc acatgcgtgg tggtggacgt gagccacgaa 900
gaccctgagg tcaagttcaa ctggtacgtg gacggcgtgg aggtgcataa tgccaagaca 960
aagccgcggg aggagcagta caacagcacg taccgtgtgg tcagcgtcct caccgtcctg 1020
caccaggact ggctgaatgg caaggagtac aagtgcaagg tctccaacaa agccctccca 1080
gcccccatcg agaaaaccat ctccaaagcc aaagggcagc cccgagaacc acaggtgtac 1140
accctgcccc catgccggga tgagctgacc aagaaccagg tcagcctgtg gtgcctggtc 1200
aaaggcttct atcccagcga catcgccgtg gagtgggaga gcaatgggca gccggagaac 1260
aactacaaga ccacgcctcc cgtgctggac tccgacggct ccttcttcct ctacagcaag 1320
ctcaccgtgg acaagagcag gtggcagcag gggaacgtct tctcatgctc cgtgatgcat 1380
gaggctctgc acaaccacta cacgcagaag agcctctccc tgtctccggg taaa 1434

<210> SEQ ID NO 362
<211> LENGTH: 651
<212> TYPE: DNA
<213> ORGANISM: Artificial Sequence
<220> FEATURE:
<223> OTHER INFORMATION: Synthetic

<400> SEQUENCE: 362
cagtctgtgt tgacgcagcc gccctcagtg tctggggccc cagggcagag ggtcaccatc 60
tcctgcactg ggagccgctc caacatcggg gcaggttatg atgtacactg gtatcagcat 120
cttccaggga cagcccccaa actcctcatc tatgataaca gcaatcgacc ctcaggtgtc 180
tctgaccgat tctctggctc caagtctggc acctcagcct ccctggccat cactgggctc 240
caggctgagg atgaggctga ttattactgc cagtcctttg acagcagcct gaggggtgtg 300
gtgttcggcg gagggaccag gctgaccgtc ctaagtcagc ccaaggctgc cccctcggtc 360
actctgttcc cgccctcctc tgaggagctc caagccaaca aggccacact agtgtgtctg 420
atcagtgact tctacccggg agctgtgaca gtggcctgga aggcagatgg cagccccgtc 480
aaggcgggag tggagaccac cacaccctcc aaacaaagca acaacaagta cgcggccagc 540
agctacctga gcctgacgcc tgagcagtgg aagtcccaca aaagctacag ctgccaggtc 600
acgcatgaag ggagcaccgt ggagaagaca gtggccccta cagaatgttc a 651

<210> SEQ ID NO 363
<211> LENGTH: 672
<212> TYPE: DNA
<213> ORGANISM: Artificial Sequence
<220> FEATURE:
<223> OTHER INFORMATION: Synthetic

<400> SEQUENCE: 363
caggtccagc tggtgcagtc tgggggaggc ctggtcaagc ctgggggtc cctgagactc 60 tcctgtgcag cctctggatt caccttcagt agttatgact tacactgggt ccgccaggtt 120
ccaggcaagg ggctggagtg ggtgtcactt atatcatatg atggaagtaa taaatactat 180
gcagactccg tgaagggccg attcaccatc tccagagaca acgccgagaa ctcactgtat 240
ctgcaaatga acagcctgag agctgaggac acggctgtct attactgtgc gagagagcct 300
ataactggaa cttctgacct ctttgactac tggggccagg gaaccctggt caccgtctca 360
agcgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtccacacct tcccggctgt cctacagtcc 540
tcaggactct actccctcag cagcgtagtg accgtgccct ccagcagctt gggcacccag 600
acctacatct gcaacgtgaa tcacaagccc agcaacacca aggtggacaa gaaagttgag 660
cccaaatctt gt 672

<210> SEQ ID NO 364
<211> LENGTH: 1443
<212> TYPE: DNA
<213> ORGANISM: Artificial Sequence
<220> FEATURE:

<223> OTHER INFORMATION: Synthetic

<400> SEQUENCE: 364
caggtgcagc tggtgcagag cgggggagga ctggtcaagc ctggagggtc actgagactg 60
tcatgtgccg caagcggatt cactttcagc tcctacgacc tgcactgggt gaggcaggtc 120
cccggcaagg ggctggagtg ggtgtctctg atcagttatg acgggagtaa caagtactat 180
gccgattcag tcaaaggacg gttcacaatt tccagagaca acgctgaaaa ttctctgtac 240
ctccagatga atagtctgcg cgcagaggat actgccgtgt actattgcgc cagagagcct 300
atcaccggca caagcgacct gtttgattat tggggacagg gcactctggt gaccgtctct 360
agtggcggag gaggctccgg aggaggaggg tctggaggag gaggcagcca gtctgtgctg 420
acccagccac ctagtgtctc aggcgcccct gggcagcgag tgaccatctc ctgtacaggc 480
agccggtcca acattggggc aggatacgac gtccactggt atcagcatct gccaggcaca 540
gcccccaagc tgctgatcta cgacaactct aataggccat caggggtgag cgatcgcttc 600
tctggaagta aatcaggcac tagcgcctcc ctggctatta ccggcctcca ggctgaggac 660
gaagcagatt actattgcca gtccttcgat tcaagcctga gaggcgtggt ctttggcggg 720
ggaacaaggc tgactgtgct gaacagcggc gcgggcaccg cggccgcgac tcacacatgc 780
ccaccgtgcc cagcacctga agccgcgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtaca ccctgccccc atgccgggat gagctgacca agaaccaggt cagcctgtgg 1200
tgcctggtca aaggcttcta tcccagcgac atcgccgtgg agtgggagag caatgggcag 1260
ccggagaaca actacaagac cacgcctccc gtgctggact ccgacggctc cttcttcctc 1320
tacagcaagc tcaccgtgga caagagcagg tggcagcagg ggaacgtctt ctcatgctcc 1380
gtgatgcatg aggctctgca caaccactac acgcagaaga gcctctccct gtctccgggt 1440
aaa 1443

<210> SEQ ID NO 365
<211> LENGTH: 651
<212> TYPE: DNA
<213> ORGANISM: Artificial Sequence
<220> FEATURE:
<223> OTHER INFORMATION: Synthetic

<400> SEQUENCE: 365
tcctatgagc tgactcagcc accctcagcg tctgggaccc ccgggcagag ggtcaccatc 60
tcttgttctg gaagcagctc caacatcgga agtaatactg taaactggta ccagcagctc 120
ccaggaacgg cccccaaact cctcatctat agtaataatc agcggccctc aggggtccct 180
gaccgattct ctggctccaa gtctggcacc tcagcctccc tggccatcag tgggctccag 240
tctgaggatg aggctgatta ttactgtgca gcatgggatg acagcctgaa tggtctttgg 300
gtgttcggcg gagggaccaa gctgaccgtc ctaggtcagc ccaaggctgc cccctcggtc 360
actctgttcc caccctcctc tgaggagctt caagccaaca aggccacact ggtgtgtctc 420
ataagtgact tctacccggg agccgtgaca gtggcctgga aggcagatag cagccccgtc 480
aaggcgggag tggagaccac caaaccctcc aaacagagca acaacaagta cgcggccagc 540
agctacctga gcctgacgcc cgagcagtgg aagtcccaca gaagctacag ctgccaggtc 600
acgcatgaag ggagcaccgt ggagaagaca gtggccccta cagaatgttc a 651

<210> SEQ ID NO 366
<211> LENGTH: 660
<212> TYPE: DNA
<213> ORGANISM: Artificial Sequence
<220> FEATURE:
<223> OTHER INFORMATION: Synthetic

<400> SEQUENCE: 366
caggtgcagc tgcaggagtc gggcccagga ctggtgaagc cttcggggac cctgtccctc 60
acctgcgctg tctctggtgg ctccatcagc agtagtaact ggtggagttg ggtccgccag 120
cccccaggga aggggctgga gtggattggg gaaatctatc atagtgggag caccaactac 180
aacccgtccc tcaagagtcg agtcaccata tcagtagaca agtccaagaa ccagttctcc 240
ctgaagctga gctctgtgac cgccgcggac acggccgtgt attactgtgt cagagaaggg 300
ggcttacggg aagagcactg gggccagggc accctggtca ccgtctcaag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt ccacaccttc ccggctgtcc tacagtcctc aggactctac 540
tccctcagca gcgtagtgac cgtgccctcc agcagcttgg gcacccagac ctacatctgc 600
aacgtgaatc acaagcccag caacaccaag gtggacaaga aagttgagcc caaatcttgt 660

<210> SEQ ID NO 367
<211> LENGTH: 1452
<212> TYPE: DNA
<213> ORGANISM: Artificial Sequence
<220> FEATURE:
<223> OTHER INFORMATION: Synthetic

<400> SEQUENCE: 367
caggtccagc tgcaggagtc cgggccaggg ctggtgaaac caagcgaaac actgagtctg 60
acatgtaccg tgagtggggg gtccattaac aatagtaact actattggtc atggatcaga 120
cagagccctg gaagaggcct ggagtggatc ggcgggatct acttcagcgg caccacatac 180
tataacccat cactgcagag ccgggtgact atctccattg acacctctaa gaatcagttc 240
agcctgaagc tgagcagcgt gaccgccgct gatacagcca tctactattg cgtccggcag 300
atgaattact atcacctggg ctctagtgtg gggttcgacc cctggggaca gggagcactg 360
gccaccgtgt caagcgtctc ctctggagga ggaggcagcg gcggaggagg ctctggagga 420
ggcgggagtg atgtggtcat gacacagagc ccagctactc tgtctgtgag tcccggcgaa 480
agggccacac tgagctgtcg cgcttcacag agcgtcagtt caaacctggc atggtaccag 540
cagaagccag gacaggcacc ttccctgctg atctatgagg cttctacacg agcaactggc 600
attcctgcta gattctccgg ctctgggagt ggaaccgact ttactctgac catcagctcc 660
ctgcagagcg aagattttgc aatctactat tgtcagcagt ataacgattg gctgtggacc 720
ttcgggcagg ggactaaagt ggagattcgg aacagcggcg cgggcaccgc ggccgcgact 780
cacacatgcc caccgtgccc agcacctgaa gccgcggggg gaccgtcagt cttcctcttc 840 ccccaaaac ccaaggacac cctcatgatc tcccggaccc ctgaggtcac atgcgtggtg 900
gtggacgtga gccacgaaga ccctgaggtc aagttcaact ggtacgtgga cggcgtggag 960
gtgcataatg ccaagacaaa gccgcgggag gagcagtaca acagcacgta ccgtgtggtc 1020
agcgtcctca ccgtcctgca ccaggactgg ctgaatggca aggagtacaa gtgcaaggtc 1080
tccaacaaag ccctcccagc ccccatcgag aaaaccatct ccaaagccaa agggcagccc 1140
cgagaaccac aggtgtacac cctgccccca tgccgggatg agctgaccaa gaaccaggtc 1200
agcctgtggt gcctggtcaa aggcttctat cccagcgaca tcgccgtgga gtgggagagc 1260
aatgggcagc cggagaacaa ctacaagacc acgcctcccg tgctggactc cgacggctcc 1320
ttcttcctct acagcaagct caccgtggac aagagcaggt ggcagcaggg gaacgtcttc 1380
tcatgctccg tgatgcatga ggctctgcac aaccactaca cgcagaagag cctctccctg 1440
tctccgggta aa 1452

<210> SEQ ID NO 368
<211> LENGTH: 657
<212> TYPE: DNA
<213> ORGANISM: Artificial Sequence
<220> FEATURE:
<223> OTHER INFORMATION: Synthetic

<400> SEQUENCE: 368
gatgttgtga tgactcagtc tccactctcc ctgcccgtca cccctggaga gccggcctcc 60
atctcctgca ggtctagtca gaggctcctg catagtaatg gatacaacta tgtggattgg 120
tacctgcaga aaccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaaggtac acactggccg 300
tggacgttcg gccaagggac caaggtggaa atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 369
<211> LENGTH: 660
<212> TYPE: DNA
<213> ORGANISM: Artificial Sequence
<220> FEATURE:
<223> OTHER INFORMATION: Synthetic

<400> SEQUENCE: 369
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcgag aggcacggat 300
acagctatgg ctgactactg gggccaggga accctggtca ccgtctcaag cgcctccacc 360
aagggcccat cggtcttccc cctggcaccc tcctccaaga gcacctctgg gggcacagcg 420
gccctgggct gcctggtcaa ggactacttc cccgaaccgg tgacggtgtc gtggaactca 480
ggcgccctga ccagcggcgt ccacaccttc ccggctgtcc tacagtcctc aggactctac 540
tccctcagca gcgtagtgac cgtgccctcc agcagcttgg gcacccagac ctacatctgc 600
aacgtgaatc acaagcccag caacaccaag gtggacaaga aagttgagcc caaatcttgt 660

<210> SEQ ID NO 370
<211> LENGTH: 1452
<212> TYPE: DNA
<213> ORGANISM: Artificial Sequence
<220> FEATURE:
<223> OTHER INFORMATION: Synthetic

<400> SEQUENCE: 370
caggtccagc tgcaggagtc cgggccaggg ctggtgaaac caagcgaaac actgagtctg 60
acatgtaccg tgagtggggg gtccattaac aatagtaact actattggtc atggatcaga 120
cagagccctg gaagaggcct ggagtggatc ggcgggatct acttcagcgg caccacatac 180
tataacccat cactgcagag ccgggtgact atctccattg acacctctaa gaatcagttc 240
agcctgaagc tgagcagcgt gaccgccgct gatacagcca tctactattg cgtccggcag 300
atgaattact atcacctggg ctctagtgtg gggttcgacc cctggggaca gggagcactg 360
gccaccgtgt caagcgtctc ctctggagga ggaggcagcg gcggaggagg ctctggagga 420
ggcgggagtg atgtggtcat gacacagagc ccagctactc tgtctgtgag tcccggcgaa 480
agggccacac tgagctgtcg cgcttcacag agcgtcagtt caaacctggc atggtaccag 540
cagaagccag gacaggcacc ttccctgctg atctatgagg cttctacacg agcaactggc 600
attcctgcta gattctccgg ctctgggagt ggaaccgact ttactctgac catcagctcc 660
ctgcagagcg aagattttgc aatctactat tgtcagcagt ataacgattg gctgtggacc 720
ttcgggcagg ggactaaagt ggagattcgg aacagcggcg cgggcaccgc ggccgcgact 780
cacacatgcc caccgtgccc agcacctgaa gccgcggggg gaccgtcagt cttcctcttc 840
cccccaaaac ccaaggacac cctcatgatc tcccggaccc ctgaggtcac atgcgtggtg 900
gtggacgtga gccacgaaga ccctgaggtc aagttcaact ggtacgtgga cggcgtggag 960
gtgcataatg ccaagacaaa gccgcgggag gagcagtaca acagcacgta ccgtgtggtc 1020
agcgtcctca ccgtcctgca ccaggactgg ctgaatggca aggagtacaa gtgcaaggtc 1080
tccaacaaag ccctcccagc ccccatcgag aaaaccatct ccaaagccaa agggcagccc 1140
cgagaaccac aggtgtacac cctgccccca tgccgggatg agctgaccaa gaaccaggtc 1200
agcctgtggt gcctggtcaa aggcttctat cccagcgaca tcgccgtgga gtgggagagc 1260
aatgggcagc cggagaacaa ctacaagacc acgcctcccg tgctggactc cgacggctcc 1320
ttcttcctct acagcaagct caccgtggac aagagcaggt ggcagcaggg gaacgtcttc 1380
tcatgctccg tgatgcatga ggctctgcac aaccactaca cgcagaagag cctctccctg 1440
tctccgggta aa 1452

<210> SEQ ID NO 371
<211> LENGTH: 642
<212> TYPE: DNA
<213> ORGANISM: Artificial Sequence
<220> FEATURE:
<223> OTHER INFORMATION: Synthetic

<400> SEQUENCE: 371
gacatccaga tgacccagtc tccaccctcc ctgtccgcat ctgtaggaga cagagtcacc 60
atcacttgtc aggcgagtca ggacattaac aactatttga attggtatca ccaaaaacca 120
gggaaggccc ctgagctcct gatctacgat gcatctcagt tggaaacagg ggtcccatca 180
aggttcagtg gaagtggatc tgggacagag tttactttca tcatcagcag cctgcagcct 240
gaagataccg gtacatatta ctgtcaacaa tatgattggc tccccctttc ttacggcgga 300
gggaccaagg ttgagatcaa acgaactgtg gctgcaccat ctgtcttcat cttcccgcca 360
tctgatgagc agttgaaatc tggaactgcc tctgttgtgt gcctgctgaa taacttctat 420
cccagggagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 372
<211> LENGTH: 669
<212> TYPE: DNA
<213> ORGANISM: Artificial Sequence
<220> FEATURE:
<223> OTHER INFORMATION: Synthetic

<400> SEQUENCE: 372
caggtacagc tgcagcagtc aggtccagga ctggtgaagc cctcgcagac cctctcactc 60
acctgtgcca tctccgggga cagtgtctct ggcaacagtg ctacttggaa ctggatcagg 120
cagtccccat cgcgaggcct tgagtggctg ggaaggacat attacaggtc caagtggaat 180
catgattatg cagaatctgt gaaaagtcga ataaccatca acccagacac atccaagaac 240
cagttctccc tgcagctgaa ctctgtgact cccgaggaca cggctgtcta ttactgtgca 300
agagactcca agtctgcttt tgatatctgg ggccaaggga caatggtcac cgtctcaagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtc cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgt 669

<210> SEQ ID NO 373
<211> LENGTH: 1410
<212> TYPE: DNA
<213> ORGANISM: Artificial Sequence
<220> FEATURE:
<223> OTHER INFORMATION: Synthetic

<400> SEQUENCE: 373
catgtgcagc tggtggagac tggaggggga ctggtgcagc ctggggggtc actgagactg 60
agttgtgccg cttctgggtt cactttcagc tcctacgcaa tgagctgggt gcggcaggcc 120
cccggaaaag gcctggagtg ggtctccgcc atcagtggat caggcgggag cacctactat 180
gctgactccg tgaaaggccg gttcactatt agcagagata actccaagaa taccctgtac 240
ctccagatga actccctgag ggccgaagac acagctgtct actattgcgc tcgcgacctg 300
ggcgattatt gggggcaggg aacactggtg actgtctcta gtggaggagg aggatctgga 360
ggaggaggca gtggaggagg cgggtcagac atccagctga ctcagtctcc ttcaagcctg 420
agcgcatcca tgggggaccg agtcaccatc acatgtcagg ccagccagga tattggcaac 480
tacctgaatt ggtatcagct gaagcccggc aaggctccta agctgctgat ctacgacgca 540

```
tctaatctgg agacaggcgt gccaagtaga ttctctggca gtgggtcagg aactgatttc    600

accttcacca tcagcagcct ccagccagag gacattgcca catactattg cctccagctg    660

tacgattatc ccctgacctt tggaggcggg acaaaagtgg aaatcaagaa cagcggcgcg    720

ggcaccgcgg ccgcgactca cacatgccca ccgtgcccag cacctgaagc cgcgggggga    780

ccgtcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cgcgggagga gcagtacaac    960

agcacgtacc gtgtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccacag gtgtacaccc tgcccccatg ccgggatgag   1140

ctgaccaaga accaggtcag cctgtggtgc ctggtcaaag gcttctatcc cagcgacatc   1200

gccgtggagt gggagagcaa tgggcagccg gagaacaact acaagaccac gcctcccgtg   1260

ctggactccg acggctcctt cttcctctac agcaagctca ccgtggacaa gagcaggtgg   1320

cagcagggga acgtcttctc atgctccgtg atgcatgagg ctctgcacaa ccactacacg   1380

cagaagagcc tctccctgtc tccgggtaaa                                    1410
```

<210> SEQ ID NO 374
<211> LENGTH: 651
<212> TYPE: DNA
<213> ORGANISM: Artificial Sequence
<220> FEATURE:
<223> OTHER INFORMATION: Synthetic

<400> SEQUENCE: 374

```
aattttatgc tgactcagcc ccactctgtg tcggggtctc cggggaagac gataaccatc     60

tcctgcaccc gcagcagtgg caactttgcc agcacctatg tgcagtggta ccaacagcgc    120

ccgggcagtt cccccgccat tgtgatctat gacgatgatc aacgaccctc tggtgtccct    180

gaccgcttct ctggctccat cgacaggtcc tccaactctg cctccctcac catctctgga    240

ctggagactg aggacgaggc tgactactat tgtcagtctt atgatagcag caatttttgg    300

gtgttcggcg gagggaccaa actgaccgtc ctaggtcagc ccaaggctgc cccctcggtc    360

actctgttcc caccctcctc tgaggagctt caagccaaca aggccacact ggtgtgtctc    420

ataagtgact tctacccggg agccgtgaca gtggcctgga aggcagatag cagccccgtc    480

aaggcgggag tggagaccac cacaccctcc aaacaaagca acaacaagta cgcggccagc    540

agctacctga gcctgacgcc tgagcagtgg aagtcccaca aaagctacag ctgccaggtc    600

acgcatgaag ggagcaccgt ggagaagaca gtggccccta cagaatgttc a             651
```

<210> SEQ ID NO 375
<211> LENGTH: 648
<212> TYPE: DNA
<213> ORGANISM: Artificial Sequence
<220> FEATURE:
<223> OTHER INFORMATION: Synthetic

<400> SEQUENCE: 375

```
cagctgcagc tgcaggagtc gggcccagga ctggtgaagc cttcggagac cctgtccctc     60

acctgcagtg tctttggtgt ctccatcacc agtggtagtt ggtggagttg ggtccgccag    120

tccccaggga aggagctgga gtggataggc gaaatctatc ataatgggaa caccaactac    180
```

```
aacccgtccc tcaagagtcg agtcaccata tcggttgaca cgtccaagaa ccagttctcc    240

ctgaaactga gctctgtgac cgccgcagac acggctgtct attactgtgt ctccggattt    300

gactactggg gccagggaac cctggtcacc gtctcaagcg cctccaccaa gggcccatcg    360

gtcttccccc tggcaccctc ctccaagagc acctctgggg gcacagcggc cctgggctgc    420

ctggtcaagg actacttccc cgaaccggtg acggtgtcgt ggaactcagg cgccctgacc    480

agcggcgtcc acaccttccc ggctgtccta cagtcctcag gactctactc cctcagcagc    540

gtagtgaccg tgccctccag cagcttgggc acccagacct acatctgcaa cgtgaatcac    600

aagcccagca acaccaaggt ggacaagaaa gttgagccca aatcttgt                 648
```

```
<210> SEQ ID NO 376
<211> LENGTH: 1419
<212> TYPE: DNA
<213> ORGANISM: Artificial Sequence
<220> FEATURE:
<223> OTHER INFORMATION: Synthetic

<400> SEQUENCE: 376

cagctgcagc tgcaggagag cggccccgga ctggtgaagc ctagcgaaac cctgagcctg     60

acttgttctg tctttggagt gagcatcact tctggaagtt ggtggagctg ggtgagacag    120

tcccccggca aggagctgga atggatcggg gaaatctacc acaacggaaa tacaaactat    180

aatccttccc tgaaatctcg ggtgactatc agtgtcgata cctcaaagaa ccagttcagc    240

ctgaagctga gcagcgtgac cgccgctgat acagccgtgt actattgcgt cagcggcttt    300

gactactggg gccaggggac tctggtgacc gtctctagtg gaggaggagg ctctggagga    360

ggagggagtg gaggaggagg cagcaacttc atgctgaccc agcctcattc agtgagcggc    420

agccccggca agaccatcac aatttcttgt acccgctcaa gcgggaattt tgctagcaca    480

tacgtgcagt ggtatcagca gcgacccggc tcctctcctg caatcgtgat ctacgacgat    540

gaccagcgac caagcggcgt ccccgataga ttctctggga gtatcgacag gagttcaaac    600

tcagcaagcc tgacaattag cggcctggag actgaagatg aggccgacta ctattgccag    660

tcctatgaca gctccaattt ctgggtgttt ggcgggggaa caaaactgac tgtcctgaac    720

agcggcgcgg gcaccgcggc cgcgactcac acatgcccac cgtgcccagc acctgaagcc    780

gcgggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatgc   1140

cgggatgagc tgaccaagaa ccaggtcagc ctgtggtgcc tggtcaaagg cttctatccc   1200

agcgacatcg ccgtggagtg ggagagcaat gggcagccgg agaacaacta caagaccacg   1260

cctcccgtgc tggactccga cggctccttc ttcctctaca gcaagctcac cgtggacaag   1320

agcaggtggc agcaggggaa cgtcttctca tgctccgtga tgcatgaggc tctgcacaac   1380

cactacacgc agaagagcct ctccctgtct ccgggtaaa                          1419
```

```
<210> SEQ ID NO 377
<211> LENGTH: 639
<212> TYPE: DNA
<213> ORGANISM: Artificial Sequence
```

<220> FEATURE:
<223> OTHER INFORMATION: Synthetic

<400> SEQUENCE: 377
gaaattgtgt tgacgcagtc tccatcctcc ctgtctgcat ctgtaggaga cagagtcacc 60
atcacttgcc aggcgagtca ggacattaat aattatttaa attggtatca gcagaaacca 120
gggaaagccc ctaagctcct gatctacgat gcatccaatt tggaaacagg ggtcccatca 180
aagttcagtg gaagtggatc tgggacagat tttactttca ccatcagcag cctgcagcct 240
gaagatattg caacatatta ctgtcaacag tatgccaatc tcccctcttt tggccagggg 300
accaagctgg agatcaaacg aactgtggct gcaccatctg tcttcatctt cccgccatct 360
gatgagcagt tgaaatctgg aactgcctct gttgtgtgcc tgctgaataa cttctatccc 420
agagaggcca aagtacagtg gaaggtggat aacgccctcc aatcgggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgt 639

<210> SEQ ID NO 378
<211> LENGTH: 669
<212> TYPE: DNA
<213> ORGANISM: Artificial Sequence
<220> FEATURE:
<223> OTHER INFORMATION: Synthetic

<400> SEQUENCE: 378
caggtgcagc tgcaggagtc cggcccagga ctggtgaagc cttcggagac cctgtctctc 60
acctgcactg tctctggtgt ctccatcagc agtagaagtg accactgggg ctgggtccgc 120
cagcccccag ggaaggggct ggagtggatt ggaagtatct cttatagtgg gagcacctac 180
tacaacccgt ccctcaagag ccgagtcacc atatccgtag acacctccaa gaaccaactc 240
tccctgaagc tgagctctgt gaccgccgca gacacggctg tgtattactg tgcgagagag 300
tcgcacccag cagctgcact ggttgggtgg ggccagggca ccctggtcac cgtctcaagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtc cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgt 669

<210> SEQ ID NO 379
<211> LENGTH: 1425
<212> TYPE: DNA
<213> ORGANISM: Artificial Sequence
<220> FEATURE:
<223> OTHER INFORMATION: Synthetic

<400> SEQUENCE: 379
caggtgcagc tgcaggaaag cggacccgga ctggtgaagc ctagcgagac tctgagcctg 60
acttgtaccg tgagcggcgt gagcattagc tcccggagcg accactgggg atgggtgaga 120
cagccccctg gcaaagggct ggagtggatc gggagcattt cctactctgg aagtacttac 180
tataacccct cactgaagag cagggtgact atctccgtgg acacctctaa aaatcagctg 240

```
tctctgaagc tgtctagtgt gaccgccgct gatacagcag tctactattg cgcccgcgag    300
tcccatcctg ccgccgccct ggtgggatgg ggacagggga cactggtgac tgtctcaagc    360
ggaggaggag gcagtggagg aggagggtca ggaggcgggg gaagcgaaat cgtcctgaca    420
cagagtccat cctctctgtc agccagcgtg ggcgaccgag tcaccatcac atgtcaggcc    480
tcccaggata ttaacaatta cctgaactgg tatcagcaga agccaggcaa agctcccaag    540
ctgctgatct acgatgcatc caatctggaa acaggggtgc cctctaaatt ctccggatct    600
ggcagtggga ctgacttcac cttcaccatc agcagcctcc agcctgagga tattgccacc    660
tactattgcc agcagtatgc taacctgccc agcttcggac agggcacaaa actggaaatt    720
aagaacagcg gcgcgggcac cgcggccgcg actcacacat gcccaccgtg cccagcacct    780
gaagccgcgg ggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caaagggcag ccccgagaac cacaggtgta caccctgccc   1140
ccatgccggg atgagctgac caagaaccag gtcagcctgt ggtgcctggt caaaggcttc   1200
tatcccagcg acatcgccgt ggagtgggag agcaatgggc agccggagaa caactacaag   1260
accacgcctc ccgtgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtctccgg gtaaa                   1425
```

<210> SEQ ID NO 380
<211> LENGTH: 657
<212> TYPE: DNA
<213> ORGANISM: Artificial Sequence
<220> FEATURE:
<223> OTHER INFORMATION: Synthetic

<400> SEQUENCE: 380

```
gaaattgtgc tgactcagtc tccactctcc ctgcccgtca cccctggaga gccggcctcc     60
atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgagcatc    240
agcagagtgg aggctgagga tgttggggtt tattactgca tgcaagctct acaaactcct    300
ccgacgttcg gccaagggac caaggtggaa atcaaacgaa ctgtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt       657
```

<210> SEQ ID NO 381
<211> LENGTH: 687
<212> TYPE: DNA
<213> ORGANISM: Artificial Sequence
<220> FEATURE:
<223> OTHER INFORMATION: Synthetic

<400> SEQUENCE: 381
gaggtccagc tggtacagtc tggggctgag gtgaagaagc ctgggtcctc ggtgaaggtc 60
tcctgcaagg cttctggtta cacctttacc agctatggta tcagctgggt gcgacaggcc 120
cctggacaag ggcttgagtg gatgggatgg atcagcgctt acaatggtaa cacaaactat 180
gcacagaagc tccagggcag agtcaccatg accacagaca catccacgag cacagcctac 240
atggagctga gcagcctgag atctgaggac acggccgtgt attactgtgc gagagcccct 300
gactacggtg actcctccaa ctactactac tactacatgg acgtctgggg caaagggacc 360
acggtcaccg tctcaagcgc ctccaccaag ggcccatcgg tcttccccct ggcaccctcc 420
tccaagagca cctctggggg cacagcggcc ctgggctgcc tggtcaagga ctacttcccc 480
gaaccggtga cggtgtcgtg gaactcaggc gccctgacca gcggcgtcca caccttcccg 540
gctgtcctac agtcctcagg actctactcc ctcagcagcg tagtgaccgt gccctccagc 600
agcttgggca cccagaccta catctgcaac gtgaatcaca agcccagcaa caccaaggtg 660
gacaagaaag ttgagcccaa atcttgt 687

<210> SEQ ID NO 382
<211> LENGTH: 1461
<212> TYPE: DNA
<213> ORGANISM: Artificial Sequence
<220> FEATURE:
<223> OTHER INFORMATION: Synthetic

<400> SEQUENCE: 382
gaagtgcagc tggtgcagag cggggcagag gtgaaaaaac ctgggtcatc cgtcaaagtc 60
tcctgtaagg caagcggcta cacatttact tcatacggca tcagctgggt gcgacaggcc 120
cctggccagg ggctggagtg gatgggatgg attagcgcat ataacggcaa tacaaactac 180
gcccagaagc tccaggggag agtgactatg accacagaca caagtacttc aaccgcctat 240
atggagctga gcagcctgag gtccgaagat accgctgtgt actattgcgc ccgcgctcct 300
gactacggcg attctagtaa ctactactac tactacatgg acgtctgggg aaaaggcact 360
accgtgacag tctcaagcgg cggaggaggc tccggaggag gagggtctgg aggaggagga 420
agcgagatcg tgctgactca gtctccactg agtctgccag tcacccccgg cgaacctgca 480
agcatttcct gtcggtcctc tcagtccctg ctgcactcta atgggtataa ctacctggac 540
tggtacttgc agaagccagg acagtctccc cagctgctga tctacctggg cagtaaccga 600
gctagcgggg tgcctgacag attctctggg agtggatcag gcacagattt tactctgagc 660
atcagccggg tggaggctga agatgtgggc gtctattact gcatgcaggc cctccagacc 720 cccccctacat tcgggcaggg aaccaaggtg gaaatcaaaa acagcggcgc gggcaccgcg 780
gccgcgactc acacatgccc accgtgccca gcacctgaag ccgcgggggg accgtcagtc 840
ttcctcttcc ccccaaaacc caaggacacc ctcatgatct cccggacccc tgaggtcaca 900
tgcgtggtgg tggacgtgag ccacgaagac cctgaggtca agttcaactg gtacgtggac 960
ggcgtggagg tgcataatgc caagacaaag ccgcgggagg agcagtacaa cagcacgtac 1020
cgtgtggtca gcgtcctcac cgtcctgcac caggactggc tgaatggcaa ggagtacaag 1080
tgcaaggtct ccaacaaagc cctcccagcc cccatcgaga aaaccatctc caaagccaaa 1140
gggcagcccc gagaaccaca ggtgtacacc ctgcccccat gccgggatga gctgaccaag 1200
aaccaggtca gcctgtggtg cctggtcaaa ggcttctatc ccagcgacat cgccgtggag 1260

-continued

```
tgggagagca atgggcagcc ggagaacaac tacaagacca cgcctcccgt gctggactcc   1320

gacggctcct tcttcctcta cagcaagctc accgtggaca agagcaggtg gcagcagggg   1380

aacgtcttct catgctccgt gatgcatgag gctctgcaca accactacac gcagaagagc   1440

ctctccctgt ctccgggtaa a                                              1461
```

<210> SEQ ID NO 383
<211> LENGTH: 642
<212> TYPE: DNA
<213> ORGANISM: Artificial Sequence
<220> FEATURE:
<223> OTHER INFORMATION: Synthetic

<400> SEQUENCE: 383

```
gacatccagt tgacccagtc tccatcctcc ctgtctgcat ctgtaggaga cagagtcacc     60

gtcacttgcc aggcgagcca ggacattggc cacaatttaa attggtatca gcagagacct    120

gggaaagccc ctcagctcct gatctacgat gcatccaatt tggaaacagg ggtcccatca    180

aggttcagtg gaagtggatc tgggacacaa tttactttca ccatcagcag tctgcagcct    240

gaagatattg caacatatta ctgtcaacaa tatgattttc tccctcctga cttcggccca    300

gggaccaaag tggagatcaa acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                      642
```

<210> SEQ ID NO 384
<211> LENGTH: 690
<212> TYPE: DNA
<213> ORGANISM: Artificial Sequence
<220> FEATURE:
<223> OTHER INFORMATION: Synthetic

<400> SEQUENCE: 384

```
caggtccagc tggtgcagtc tggagctgag gtgaagaagc ctggggcctc agtgaaggtc     60

tcctgcaagg cttctggtta cacctttacc agctatggta tcagctgggt gcgacaggcc    120

cctggacaag ggcttgagtg gatgggatgg atcagcgctt acaatggtaa cacaaactat    180

gcacagaagc tccagggcag agtcaccatg accacagaca catccacgag cacagcctac    240

atggagctga ggagcctgag atctgacgac acggccgtgt attactgtgc gagagatacc    300

tccggggact atagcagtgg ctggtaccta ggagttcctt ttgactactg gggccagggc    360

accctggtca ccgtctcaag cgcctccacc aagggcccat cggtcttccc cctggcaccc    420

tcctccaaga gcacctctgg gggcacagcg gccctgggct gcctggtcaa ggactacttc    480

cccgaaccgg tgacggtgtc gtggaactca ggcgccctga ccagcggcgt ccacaccttc    540

ccggctgtcc tacagtcctc aggactctac tccctcagca gcgtagtgac cgtgccctcc    600

agcagcttgg gcacccagac ctacatctgc aacgtgaatc acaagcccag caacaccaag    660

gtggacaaga aagttgagcc caaatcttgt                                    690
```

<210> SEQ ID NO 385
<211> LENGTH: 1449
<212> TYPE: DNA
<213> ORGANISM: Artificial Sequence
<220> FEATURE:
<223> OTHER INFORMATION: Synthetic

<400> SEQUENCE: 385
caggtgcagc tggtccagag cggagccgag gtgaagaagc ccggagcatc agtgaaagtc 60
agttgtaaag caagcggata cacatttaca tcttacggca tcagttgggt gcgacaggca 120
ccaggccagg ggctggagtg gatgggatgg atttctgcat acaacggcaa tacaaactat 180
gcccagaagc tccaggggag agtcactatg accacagaca ctagtacctc aacagcttac 240
atggaactgc ggagcctgag atccgacgat actgccgtgt actattgcgc tcgggacacc 300
agcggcgatt acagctccgg ctggtatctg ggggtcccct tcgactattg ggacagggc 360 accctggtga cagtctctag tggcgggga ggctcaggag gaggagggag cggaggagga 420
ggcagcgaca tccagctgac ccagagccct tcaagcctga gcgcatccgt gggcgacagg 480
gtgactgtca cctgccaggc ttcccaggac atcgggcaca atctgaactg gtatcagcag 540
cgcccaggaa aagctcccca gctgctgatc tacgacgcat ctaatctgga gaccggcgtg 600
cccagtcggt tttctgggag tggatcaggc acacagttca ccttcaccat cagcagcctc 660
cagcctgagg atattgccac ttactattgt cagcagtatg acttcctgcc ccctgatttt 720
gggccaggaa ccaaggtgga gatcaagaac agcggcgcgg gcaccgcggc cgcgactcac 780
acatgcccac cgtgcccagc acctgaagcc gcgggggac cgtcagtctt cctcttcccc 840
ccaaaaccca aggacaccct catgatctcc cggacccctg aggtcacatg cgtggtggtg 900
gacgtgagcc acgaagaccc tgaggtcaag ttcaactggt acgtggacgg cgtggaggtg 960
cataatgcca agacaaagcc gcgggaggag cagtacaaca gcacgtaccg tgtggtcagc 1020
gtcctcaccg tcctgcacca ggactggctg aatggcaagg agtacaagtg caaggtctcc 1080
aacaaagccc tcccagcccc catcgagaaa accatctcca aagccaaagg gcagccccga 1140
gaaccacagg tgtacaccct gcccccatgc cgggatgagc tgaccaagaa ccaggtcagc 1200
ctgtggtgcc tggtcaaagg cttctatccc agcgacatcg ccgtggagtg ggagagcaat 1260
gggcagccgg agaacaacta caagaccacg cctcccgtgc tggactccga cggctccttc 1320
ttcctctaca gcaagctcac cgtggacaag agcaggtggc agcaggggaa cgtcttctca 1380
tgctccgtga tgcatgaggc tctgcacaac cactacacgc agaagagcct ctccctgtct 1440
ccgggtaaa 1449

<210> SEQ ID NO 386
<211> LENGTH: 657
<212> TYPE: DNA
<213> ORGANISM: Artificial Sequence
<220> FEATURE:
<223> OTHER INFORMATION: Synthetic

<400> SEQUENCE: 386
gatgttgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttgggttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggccg 300
tggacgttcg gccaagggac caaggtggaa atcaaacgaa ctgtggctgc accatctgtc 360
ttcatcttcc cgccatctga tgagcagttg aaatctggaa ctgcctctgt tgtgtgcctg 420

```
ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

<210> SEQ ID NO 387
<211> LENGTH: 669
<212> TYPE: DNA
<213> ORGANISM: Artificial Sequence
<220> FEATURE:
<223> OTHER INFORMATION: Synthetic

<400> SEQUENCE: 387

```
caggtgcagc tacagcagtg ggcgcagga ctgttgaagc cttcggagac cctgtccctc      60

acctgcgctg tctatggtgg gtccttcagt ggttactact ggagctggat ccgccagccc    120

ccagggaagg ggctggagtg gattggggaa atcaatcata gtggaagcac caactacaac    180

ccgtccctca agagtcgagc caccatatca gtagacacgt ccaagaacca gttctccctg    240

aagctgagct ctgtgaccgc cgcggacacg gctgtgtatt actgtgcgac cagcccggga    300

ggctattccg gggatactt ccagcactgg ggccagggaa ccctggtcac cgtctcaagc     360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtc cacaccttcc cggctgtcct acagtcctca    540

ggactctact ccctcagcag cgtagtgacc gtgccctcca gcagcttggg cacccagacc    600

tacatctgca acgtgaatca caagcccagc aacaccaagg tggacaagaa agttgagccc    660

aaatcttgt                                                            669
```

<210> SEQ ID NO 388
<211> LENGTH: 1443
<212> TYPE: DNA
<213> ORGANISM: Artificial Sequence
<220> FEATURE:
<223> OTHER INFORMATION: Synthetic

<400> SEQUENCE: 388

```
caggtccagc tgcagcagtg gggagccggc ctgctgaaac catctgaaac tctgagcctg     60

acttgcgctg tctacggggg gtccttcagt ggctactatt ggtcatggat caggcagccc    120

cctgggaagg gactggagtg gatcggggaa attaaccact ccggatctac aaactacaat    180

cccagtctga aatcacgcgc caccatttct gtggacacca gtaagaatca gttcagcctg    240

aagctgagca gcgtgacagc cgctgatacc gccgtgtact attgcgcaac cagccctggc    300

ggatactccg gaggctattt tcagcattgg ggccagggga ccctggtgac agtctctagt    360

gggggaggag ggtctggagg aggaggaagt ggaggaggag gctccgacgt ggtcatgact    420

cagagcccac tgtccctgcc agtgaccccc ggcgagcctg ctagtatctc atgtcgatca    480

agccagtcac tgctgcacag caacgggtac aattatctgg attggtactt gcagaagcca    540

ggccagtctc cccagctgct gatctatctg ggctccaacc gggactctgg ggtgcctgat    600

agattcagcg gcagcggctc tgggactgac tttaccctga aaatttccag agtcgaggca    660

gaagatgtgg gagtctacta ttgcatgcag ggcactcatt ggccctggac cttcggacag    720

ggcacaaagg tggagatcaa gaacagcggc gcgggcaccg cggccgcgac tcacacatgc    780

ccaccgtgcc cagcacctga actcctgggg ggaccgtcag tcttcctctt ccccccaaaa    840
```

```
cccaaggaca ccctcatgat ctcccggacc cctgaggtca catgcgtggt ggtggacgtg    900

agccacgaag accctgaggt caagttcaac tggtacgtgg acggcgtgga ggtgcataat    960

gccaagacaa agccgcggga ggagcagtac aacagcacgt accgtgtggt cagcgtcctc   1020

accgtcctgc accaggactg gctgaatggc aaggagtaca agtgcaaggt ctccaacaaa   1080

gccctcccag cccccatcga gaaaaccatc tccaaagcca aagggcagcc ccgagaacca   1140

caggtgtgca ccctgccccc atcccgggat gagctgacca agaaccaggt cagcctgtcc   1200

tgcgccgtca aaggcttcta tcccagcgac atcgccgtgg agtgggagag caatgggcag   1260

ccggagaaca actacaagac cacgcctccc gtgctggact ccgacggctc cttcttcctc   1320

gtgagcaagc tcaccgtgga caagagcagg tggcagcagg ggaacgtctt ctcatgctcc   1380

gtgatgcatg aggctctgca caaccactac acgcagaaga gcctctccct gtctccgggt   1440

aaa                                                                 1443
```

<210> SEQ ID NO 389
<211> LENGTH: 639
<212> TYPE: DNA
<213> ORGANISM: Artificial Sequence
<220> FEATURE:
<223> OTHER INFORMATION: Synthetic

<400> SEQUENCE: 389

```
tcctatgagc tgactcagcc accctcgatg tcagtgtccc caggacagac ggccaggatc     60

acctgctctg gagatgcatt gccaaaacaa tttgcttttt ggtaccagca gaagccaggc    120

caggcccctg tgttggtgat ttataaagac actgagaggc cctcagggat ccctgagcga    180

ttctctggct ccagctcagg gacaacagtc acgttgacca tcactggagt ccaggcagaa    240

gatgaggctg actattactg tcaatctcca gacagcagtg gtaccgtcga agtgttcggc    300

ggagggacca agctgaccgt cctaggtcag cccaaggctg ccccctcggt cactctgttc    360

ccgccctcct ctgaggagct tcaagccaac aaggccacac tggtgtgtct cataagtgac    420

ttctacccgg gagccgtgac agtggcctgg aaggcagata gcagccccgt caaggcggga    480

gtggagacca ccacaccctc caaacaaagc aacaacaagt acgcggccag cagctacctg    540

agcctgacgc ctgagcagtg gaagtcccac agaagctaca gctgccaggt cacgcatgaa    600

gggagcaccg tggagaagac agtggcccct gcagaatgt                           639
```

<210> SEQ ID NO 390
<211> LENGTH: 669
<212> TYPE: DNA
<213> ORGANISM: Artificial Sequence
<220> FEATURE:
<223> OTHER INFORMATION: Synthetic

<400> SEQUENCE: 390

```
caggtgcagc tgcaggagtc gggcccagga ctggtgaagc cttcggagac cctgtccctc     60

acctgcactg tctctggtgg ctccatcagc agtagtagtt actactgggg ctggatccgc    120

cagcccccag ggaaggggct ggagtggatt gggagtatct attatagtgg gagcacctac    180

tacaacccgt ccctcaagag tcgagtcacc atatccgtag acacgtccaa gaaccagttc    240

tccctgaagc tgagctctgt gaccgccgca gacacggctg tgtattactg tgcgggcgat    300

attttgactg gttatgccct tgactactgg ggccagggaa ccctggtcac cgtctcaagc    360

gcctccacca agggcccatc ggtcttcccc ctggcaccct cctccaagag cacctctggg    420
```

```
ggcacagcgg ccctgggctg cctggtcaag gactacttcc ccgaaccggt gacggtgtcg    480

tggaactcag gcgccctgac cagcggcgtc cacaccttcc cggctgtcct acagtcctca    540

ggactctact ccctcagcag cgtagtgacc gtgccctcca gcagcttggg cacccagacc    600

tacatctgca acgtgaatca caagcccagc aacaccaagg tggacaagaa agttgagccc    660

aaatcttgt                                                            669
```

<210> SEQ ID NO 391
<211> LENGTH: 1431
<212> TYPE: DNA
<213> ORGANISM: Artificial Sequence
<220> FEATURE:
<223> OTHER INFORMATION: Synthetic

<400> SEQUENCE: 391

```
caggtgcagc tgcaggaaag cggacccgga ctggtgaagc catctgaaac actgagcctg     60

acttgtaccg tgagcggcgg aagcatcagc tcctctagtt actattgggg atggatcagg    120

cagccccctg gcaaggggct ggagtggatc ggcagcatct actatagcgg ctccacatac    180

tataacccta gcctgaaatc ccgcgtgaca atctctgtgg acactagtaa gaatcagttc    240

tctctgaaac tgtcaagcgt gaccgccgct gatacagctg tctactattg cgcaggcgac    300

attctgaccg ggtacgccct ggattattgg ggacagggca ctctggtgac cgtctcctct    360

ggaggaggag gctcaggagg aggagggtcc ggaggcgggg gaagttcata cgaactgaca    420

cagccaccct ctatgagtgt gtcaccaggg cagactgcac gaatcacctg tagcggagac    480

gccctgccca agcagttcgc tttttggtat cagcagaaac ctggccaggc tccagtgctg    540

gtcatctata aggatactga gcggccctct gggattcctg aaagattcag tggcagcagc    600

agcggaacca cagtgactct gaccattaca ggcgtgcagg cagaggacga agccgattac    660

tattgccagt cccccgacag ttcaggcacc gtggaggtct ttggcggggg aacaaaactg    720

actgtgctga acagcggcgc gggcaccgcg gccgcgactc acacatgccc accgtgccca    780

gcacctgaac tcctgggggg accgtcagtc ttcctcttcc ccccaaaacc caaggacacc    840

ctcatgatct cccggacccc tgaggtcaca tgcgtggtgg tggacgtgag ccacgaagac    900

cctgaggtca agttcaactg gtacgtggac ggcgtggagg tgcataatgc caagacaaag    960

ccgcgggagg agcagtacaa cagcacgtac cgtgtggtca gcgtcctcac cgtcctgcac   1020

caggactggc tgaatggcaa ggagtacaag tgcaaggtct ccaacaaagc cctcccagcc   1080

cccatcgaga aaaccatctc caaagccaaa gggcagcccc gagaaccaca ggtgtgcacc   1140

ctgcccccat cccgggatga gctgaccaag aaccaggtca gcctgtcctg cgccgtcaaa   1200

ggcttctatc ccagcgacat cgccgtggag tgggagagca atgggcagcc ggagaacaac   1260

tacaagacca cgcctcccgt gctggactcc gacggctcct tcttcctcgt gagcaagctc   1320

accgtggaca agagcaggtg gcagcagggg aacgtcttct catgctccgt gatgcatgag   1380

gctctgcaca accactacac gcagaagagc ctctccctgt ctccgggtaa a            1431
```

<210> SEQ ID NO 392
<211> LENGTH: 657
<212> TYPE: DNA
<213> ORGANISM: Artificial Sequence
<220> FEATURE:
<223> OTHER INFORMATION: Synthetic

<400> SEQUENCE: 392

```
gaaattgtgc tgactcagtc tccactctcc ctgcccgtta cccctggaga gccggcctcc     60
```

atctcctgca ggtctagtca gagcctcctg catagtaatg gatacaacta tttgaattgg 120
tacctacaga agccagggca gtctccacaa ctcctgatct atttgggttc tgatcgggcc 180
tccggggtcc ctgacaggtt cagtggcagt ggatcaggca cagattttac actgaaaatc 240
agcagagtgg aggctgagga tgttggggtt tattactgca tgcaagctct acaaaccccc 300
accactttcg gcggagggac caaggtggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 393
<211> LENGTH: 669
<212> TYPE: DNA
<213> ORGANISM: Artificial Sequence
<220> FEATURE:
<223> OTHER INFORMATION: Synthetic

<400> SEQUENCE: 393
caggtacagc tgcagcagtc aggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggaggt tttgatcctg aagatggtga aacaatctac 180
gcacagaagt tccagggcag agtcaccatg accgaggaca catctacaga cacagcctac 240
atggagctga gcagcctgag atctgaggac acggccgtgt attactgtgc aacagatctg 300
agaattccgt attactatga taacccctgg ggccagggca ccctggtcac cgtctcaagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtc cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgt 669

<210> SEQ ID NO 394
<211> LENGTH: 1443
<212> TYPE: DNA
<213> ORGANISM: Artificial Sequence
<220> FEATURE:
<223> OTHER INFORMATION: Synthetic

<400> SEQUENCE: 394
caggtccagc tgcagcagag cggagccgag gtcaagaagc cagggagtag cgtcaaagtc 60
agttgtaaag catcaggagg aacattcagc tcctatgcaa tctcttgggt gcgacaggcc 120
cctggacagg gcctggagtg gatgggagga ttcgacccag aggatggaga aaccatctac 180
gcccagaagt ttcagggcag agtgactatg accgaagaca catctactga taccgcttac 240
atggagctgt ctagtctgag gagtgaagac actgccgtct actattgcgc taccgacctg 300
cgcatcccat actattacga taatccctgg gggcagggaa cactggtgac tgtctcaagc 360
ggaggcgggg gatcaggcgg aggaggcagc ggaggaggag ggtccgagat cgtgctgaca 420
cagagtccac tgtcactgcc agtcacccct ggcgaaccag ccagtatttc atgtcggtcc 480
tctcagagcc tgctgcactc caacgggtat aattacctga actggtactt gcagaagcct 540
ggccagagcc ctcagctgct gatctacctg ggctctgacc gagcaagtgg ggtgcccgat 600
agattcagcg gctccgggtc tggaaccgac tttaccctga agatcagccg ggtggaggct 660
gaagatgtgg gcgtctatta ctgcatgcag gccctccaga cacctaccac attcggaggc 720
gggactaagg tggagatcaa gaacagcggc gcgggcaccg cggccgcgac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtgca ccctgccccc atcccgggat gagctgacca agaaccaggt cagcctgtcc 1200
tgcgccgtca aaggcttcta tcccagcgac atcgccgtgg agtgggagag caatgggcag 1260
ccggagaaca actacaagac cacgcctccc gtgctggact ccgacggctc cttcttcctc 1320
gtgagcaagc tcaccgtgga caagagcagg tggcagcagg ggaacgtctt ctcatgctcc 1380
gtgatgcatg aggctctgca caaccactac acgcagaaga gcctctccct gtctccgggt 1440
aaa 1443

<210> SEQ ID NO 395
<211> LENGTH: 657
<212> TYPE: DNA
<213> ORGANISM: Artificial Sequence
<220> FEATURE:
<223> OTHER INFORMATION: Synthetic

<400> SEQUENCE: 395
gaaattgtga tgacgcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatgt atttggtttc taatcgggcc 180
tccggggtcc ctgagaggtt cagtggcagt ggatcaggca cagattttac actgaaaatc 240
agcagagtgg aggctgagga tgttggggtt tattactgca tgcaaactct acaaactcct 300
ctcagttttg gccaggggac caagctggag atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 396
<211> LENGTH: 663
<212> TYPE: DNA
<213> ORGANISM: Artificial Sequence
<220> FEATURE:
<223> OTHER INFORMATION: Synthetic

<400> SEQUENCE: 396
caggtccagc tggtacagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agccgaggac acggctgtgt attactgtgc gagaagtctt 300
tactacagcc actttgacta ctggggccag ggaaccctgg tcaccgtctc aagcgcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtccacacc ttcccggctg tcctacagtc ctcaggactc 540
tactccctca gcagcgtagt gaccgtgccc tccagcagct tgggcaccca gacctacatc 600
tgcaacgtga atcacaagcc cagcaacacc aaggtggaca agaaagttga gcccaaatct 660
tgt 663

<210> SEQ ID NO 397
<211> LENGTH: 1437
<212> TYPE: DNA
<213> ORGANISM: Artificial Sequence
<220> FEATURE:
<223> OTHER INFORMATION: Synthetic

<400> SEQUENCE: 397
caggtgcagc tggtccagag cggaggaggc gtcgtccagc ccggaaggtc actgagactg 60
tcttgtgccg catcaggatt cacttttagc tcctacgcaa tgcactgggt gaggcaggcc 120
cctggcaagg ggctggagtg ggtggctgtc atcagttatg acggctcaaa caagtactat 180
gcagatagcg tgaaagggcg gttcaccatt agcagagaca actccaaaaa tacactgtac 240
ctccagatga acagcctgcg agccgaagac acagctgtgt actattgcgc ccggtctctg 300
tactatagtc actttgatta ctggggacag ggcaccctgg tgacagtctc tagtggcggg 360
ggaggcagtg gaggaggagg gagcggagga ggaggcagcg agatcgtgat gactcagtcc 420
ccactgtctc tgccagtcac ccctggcgaa ccagcatcca tttcttgtag atcaagccag 480
tcactgctgc atagcaacgg atacaattat ctggattggt acttgcagaa gcctggccag 540
tctcctcagc tgctgatgta tctggtgtcc aacagggcct ctggggtccc agagcgcttc 600
agtgggtcag gaagcggcac tgactttacc ctgaaaatct ctcgcgtgga ggctgaagat 660
gtgggcgtct actattgcat gcagacactc cagactcccc tgagcttcgg gcagggaacc 720
aagctggaga tcaagaacag cggcgcgggc accgcggccg cgactcacac atgcccaccg 780
tgcccagcac ctgaactcct ggggggaccg tcagtcttcc tcttcccccc aaaacccaag 840
gacaccctca tgatctcccg gacccctgag gtcacatgcg tggtggtgga cgtgagccac 900
gaagaccctg aggtcaagtt caactggtac gtggacggcg tggaggtgca taatgccaag 960
acaaagccgc gggaggagca gtacaacagc acgtaccgtg tggtcagcgt cctcaccgtc 1020
ctgcaccagg actggctgaa tggcaaggag tacaagtgca aggtctccaa caaagccctc 1080
ccagccccca tcgagaaaac catctccaaa gccaaagggc agccccgaga accacaggtg 1140
tgcaccctgc ccccatcccg ggatgagctg accaagaacc aggtcagcct gtcctgcgcc 1200
gtcaaaggct tctatcccag cgacatcgcc gtggagtggg agagcaatgg gcagccggag 1260
aacaactaca agaccacgcc tcccgtgctg gactccgacg gctccttctt cctcgtgagc 1320
aagctcaccg tggacaagag caggtggcag caggggaacg tcttctcatg ctccgtgatg 1380
catgaggctc tgcacaacca ctacacgcag aagagcctct ccctgtctcc gggtaaa 1437

<210> SEQ ID NO 398
<211> LENGTH: 642
<212> TYPE: DNA
<213> ORGANISM: Artificial Sequence
<220> FEATURE:
<223> OTHER INFORMATION: Synthetic

<400> SEQUENCE: 398
gaaattgtgc tgactcagtc tccagccacc ctgtctttgt ctccagggga acgagccacc 60
ctctcctgca gggccagtca gagtgttagt taccacttag cctggtacca acaaaaacct 120
ggccaggctc ccaggctcct catctatgat acatccaaca gggcctctgg catccccgcc 180
aggttcagtg gcagtgggtc tgggacagac ttcactctca ccatcaacag cctagagcct 240
gaagattttg cagtttatta ctgtcagcag cgttacgact ggcctctcac tttcggcgga 300
gggaccaagg tggagatcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 399
<211> LENGTH: 678
<212> TYPE: DNA
<213> ORGANISM: Artificial Sequence
<220> FEATURE:
<223> OTHER INFORMATION: Synthetic

<400> SEQUENCE: 399
gaggtgcagc tggtggagac tggcccagga ctggtgaagc cttcggggac cctgtccctc 60
acctgcgctg tctctggtgg ctccatcagc agtagtaact ggtggagttg ggtccgccag 120
cccccaggga aggggctgga gtggattggg gaaatctatc atagtgggag caccaactac 180
aacccgtccc tcaagagtcg agtcaccata tcagtagaca agtccaagaa ccagttctcc 240
ctgaagctga gctctgtgac cgccgcggac acggccgtgt attactgtgc gagagaaggg 300
cccctaagca gcagcggacc gggtgctttt gatatctggg gccaagggac aatggtcacc 360
gtctcaagcg cctccaccaa gggcccatcg gtcttccccc tggcaccctc ctccaagagc 420
acctctgggg gcacagcggc cctgggctgc ctggtcaagg actacttccc cgaaccggtg 480
acggtgtcgt ggaactcagg cgccctgacc agcggcgtcc acaccttccc ggctgtccta 540
cagtcctcag gactctactc cctcagcagc gtagtgaccg tgccctccag cagcttgggc 600
acccagacct acatctgcaa cgtgaatcac aagcccagca acaccaaggt ggacaagaaa 660
gttgagccca aatcttgt 678

<210> SEQ ID NO 400
<211> LENGTH: 1410
<212> TYPE: DNA
<213> ORGANISM: Artificial Sequence
<220> FEATURE:
<223> OTHER INFORMATION: Synthetic

<400> SEQUENCE: 400
caggtccagc tgcaggaatc aggagggggg gtcgtccagc cagggaggtc actgagactg 60
tcttgcgccg cttcagggtt cacttttagc aactacggaa tgcactgggt gcggcaggct 120
cccggcaaag ggctggagtg ggtggcagtc atctcttatg acggcacaaa caagtactat 180
gcagatagtg tcaaggggcg gttcaccatc agccgggaca acagtaaaaa tacagtgtac 240
ctccagatga acagcctgcg ggccgaagat actgctgtct actattgcgc caaggacggg 300
tttgacatct ggggacaggg cactatggtg accgtcagct ccggcggggg aggctcagga 360
ggaggaggga gcggaggagg aggcagcgac attcagatga cccagtcacc tagcttcctg 420
tccgcttctg tgggcgatag ggtcacaatc acttgtcgcg ccagtcagtc aatttctagt 480
tggctggctt ggtatcagca gaagcccgga aaagcaccta agctgctgat ctatgacgcc 540
tcccgactgg aggatggcgt gccaagcaga ttctccggga caggatttgg cactgacttc 600
acctttacaa tcaccacact ccagccagac gatattgcca cttactattg ccagcagtac 660
gacgatctgc cctatacctt tgggcaggga actaccgtgg atattaagaa cagcggcgcg 720
ggcaccgcgg ccgcgactca cacatgccca ccgtgcccag cacctgaact cctgggggga 780
ccgtcagtct tcctcttccc cccaaaaccc aaggacaccc tcatgatctc ccggacccct 840
gaggtcacat gcgtggtggt ggacgtgagc cacgaagacc ctgaggtcaa gttcaactgg 900
tacgtggacg gcgtggaggt gcataatgcc aagacaaagc cgcgggagga gcagtacaac 960
agcacgtacc gtgtggtcag cgtcctcacc gtcctgcacc aggactggct gaatggcaag 1020
gagtacaagt gcaaggtctc caacaaagcc ctcccagccc ccatcgagaa aaccatctcc 1080
aaagccaaag ggcagccccg agaaccacag gtgtgcaccc tgcccccatc ccgggatgag 1140
ctgaccaaga accaggtcag cctgtcctgc gccgtcaaag gcttctatcc cagcgacatc 1200
gccgtggagt gggagagcaa tgggcagccg gagaacaact acaagaccac gcctcccgtg 1260
ctggactccg acggctcctt cttcctcgtg agcaagctca ccgtggacaa gagcaggtgg 1320
cagcagggga acgtcttctc atgctccgtg atgcatgagg ctctgcacaa ccactacacg 1380
cagaagagcc tctccctgtc tccgggtaaa 1410

<210> SEQ ID NO 401
<211> LENGTH: 642
<212> TYPE: DNA
<213> ORGANISM: Artificial Sequence
<220> FEATURE:
<223> OTHER INFORMATION: Synthetic

<400> SEQUENCE: 401
gacatccaga tgacccagtc tccttccttc ctgtctgcat ctgtaggaga cagagtcacc 60
atcacttgcc gggccagtca gagtattagt agctggttgg cctggtatca gcagaaacca 120
gggaaagccc ctaaactcct gatctacgat gcatcccgtt tggaggacgg ggtcccatca 180
agattcagtg gaactggatt tgggacagat tttactttca ccattaccac cctgcagcct 240
gacgatattg cgacatatta ttgtcagcaa tacgatgatc tcccgtacac ttttggccag 300
gggaccacgg tggacatcaa acgaactgtg gctgcaccat ctgtcttcat cttcccgcca 360
tctgatgagc agttgaaatc tggaactgcc tctgttgtgt gcctgctgaa taacttctat 420
cccagagagg ccaaagtaca gtggaaggtg gataacgccc tccaatcggg taactcccag 480
gagagtgtca cagagcagga cagcaaggac agcacctaca gcctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 402
<211> LENGTH: 651
<212> TYPE: DNA
<213> ORGANISM: Artificial Sequence
<220> FEATURE:
<223> OTHER INFORMATION: Synthetic

<400> SEQUENCE: 402
caggtgcagc tgcaggagtc cgggggaggc gtggtccagc ctgggaggtc cctgagactc 60
tcctgtgcag cctctggatt caccttcagt aactatggca tgcactgggt ccgccaggct 120
ccaggcaaag ggctggagtg ggtggcagtt atatcatatg atggaactaa taaatactat 180
gcagactccg tgaagggccg attcaccatc tccagagaca attccaagaa cacggtgtat 240
ctgcaaatga acagcctgag agctgaggac acggctgtgt attactgtgc gaaagatggt 300
tttgatattt ggggccaagg gacaatggtc accgtctcaa gcgcctccac caagggccca 360
tcggtcttcc ccctggcacc ctcctccaag agcacctctg ggggcacagc ggccctgggc 420
tgcctggtca aggactactt ccccgaaccg gtgacggtgt cgtggaactc aggcgccctg 480
accagcggcg tccacacctt cccggctgtc ctacagtcct caggactcta ctccctcagc 540
agcgtagtga ccgtgccctc cagcagcttg ggcacccaga cctacatctg caacgtgaat 600
cacaagccca gcaacaccaa ggtggacaag aaagttgagc ccaaatcttg t 651

<210> SEQ ID NO 403
<211> LENGTH: 1437
<212> TYPE: DNA
<213> ORGANISM: Artificial Sequence
<220> FEATURE:
<223> OTHER INFORMATION: Synthetic

<400> SEQUENCE: 403
gaagtgcagc tggtggaaac tggacctgga ctggtgaagc caagcgggac tctgagcctg 60
acctgtgccg tgagcggggg aagtatcagc tcctctaact ggtggtcctg ggtgcgacag 120
ccccctggca aggggctgga gtggatcggc gaaatctacc acagcgggtc cacaaactat 180
aatcctagcc tgaagagccg ggtgactatc tctgtggaca agagtaaaaa tcagttcagc 240
ctgaaactga gttcagtgac agccgctgat accgccgtgt actattgcgc cagggaggga 300
cctctgagca gcagcggacc aggcgctttt gacatctggg ggcagggaac tatggtgacc 360
gtcagttcag gcggaggagg ctccggagga ggagggtctg gaggcggggg aagtgagatt 420
gtgctgaccc agtcccccgc cacactgtct ctgagtcctg gcgaacgggc caccctgtct 480
tgtagagctt cacagagcgt gtcctaccat ctggcatggt atcagcagaa accaggccag 540
gcccccagac tgctgatcta cgacacctca aacagggcta gcggcattcc cgcacgcttc 600
tctggcagtg ggtcaggaac agattttacc ctgacaatca atagcctgga gccagaagac 660
ttcgccgtgt actattgcca gcagcgctat gattggcccc tgacttttgg cgggggaacc 720
aaggtcgaga tcaagaacag cggcgcgggc accgcggccg cgactcacac atgcccaccg 780
tgcccagcac ctgaactcct ggggggaccg tcagtcttcc tcttcccccc aaaacccaag 840
gacaccctca tgatctcccg gacccctgag gtcacatgcg tggtggtgga cgtgagccac 900
gaagaccctg aggtcaagtt caactggtac gtggacggcg tggaggtgca taatgccaag 960
acaaagccgc gggaggagca gtacaacagc acgtaccgtg tggtcagcgt cctcaccgtc 1020
ctgcaccagg actggctgaa tggcaaggag tacaagtgca aggtctccaa caaagccctc 1080
ccagccccca tcgagaaaac catctccaaa gccaaagggc agccccgaga accacaggtg 1140
tgcaccctgc ccccatcccg ggatgagctg accaagaacc aggtcagcct gtcctgcgcc 1200
gtcaaaggct tctatcccag cgacatcgcc gtggagtggg agagcaatgg gcagccggag 1260
aacaactaca agaccacgcc tcccgtgctg gactccgacg gctccttctt cctcgtgagc 1320
aagctcaccg tggacaagag caggtggcag caggggaacg tcttctcatg ctccgtgatg 1380
catgaggctc tgcacaacca ctacacgcag aagagcctct ccctgtctcc gggtaaa 1437

<210> SEQ ID NO 404
<211> LENGTH: 657
<212> TYPE: DNA
<213> ORGANISM: Artificial Sequence
<220> FEATURE:
<223> OTHER INFORMATION: Synthetic

<400> SEQUENCE: 404
gatgttgtga tgactcagtc tccagtctcc ctgcccgtca cccttggaca gccggcctcc 60
atctcctgca agtctagtca aagcctcctt tactttaatg gaaacaccta cttgagctgg 120
tttcagcaga ggccaggcca atctccacgg cgcctatttt atcaggtttc taaccgggac 180
tctggggtcc cagacagatt cagcggcagt gggtcagaca ctgatttcac tctgaccatt 240
agcagggtgg aggctgaaga tgttggagtt tatttctgca tgcaaggaac acagtggcct 300
ccgacgttcg gccaagggac caaggtggaa atcaaacgaa ctgtggctgc accatctgtc 360
ttcatcttcc cgccatctga tgagcagctg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 405
<211> LENGTH: 669
<212> TYPE: DNA
<213> ORGANISM: Artificial Sequence
<220> FEATURE:
<223> OTHER INFORMATION: Synthetic

<400> SEQUENCE: 405
gaggtccagc tggtgcagtc tggggggaggc gtggtccagc ctgggaggtc cctgagactc 60
tcctgtgcag cctctggatt caccttcagt agctatggca tgcactgggt ccgccaggct 120
ccaggcaagg ggctggagtg ggtggcagtt atatcatatg atggaagtaa taaatactat 180
gcagactccg tgaagggccg attcaccatc tccagagaca attccaagaa cacgctgtat 240
ctgcaaatga acagcctgag agccgaggac acggccgtgt attactgtgc gagagatgtc 300
tacggtgact acggggcctt tgactactgg ggccagggaa ccctggtcac cgtctcaagc 360
gcctccacca agggcccatc ggtcttcccc ctggcaccct cctccaagag cacctctggg 420
ggcacagcgg ccctgggctg cctggtcaag gactacttcc ccgaaccggt gacggtgtcg 480
tggaactcag gcgccctgac cagcggcgtc cacaccttcc cggctgtcct acagtcctca 540
ggactctact ccctcagcag cgtagtgacc gtgccctcca gcagcttggg cacccagacc 600
tacatctgca acgtgaatca caagcccagc aacaccaagg tggacaagaa agttgagccc 660
aaatcttgt 669

<210> SEQ ID NO 406

<211> LENGTH: 1443
<212> TYPE: DNA
<213> ORGANISM: Artificial Sequence
<220> FEATURE:
<223> OTHER INFORMATION: Synthetic

<400> SEQUENCE: 406
gaggtccagc tggtccagag cggcggaggg gtcgtccagc ccggaagaag cctgagactg 60
tcctgtgcag caagtgggtt tacattcagc tcctacggca tgcactgggt gaggcaggca 120
cccggcaagg ggctggagtg ggtggccgtc atcagttatg acggctcaaa caagtactat 180
gccgatagcg tgaaagggag gttcacaatt agccgcgaca actccaaaaa tactctgtac 240
ctccagatga acagcctgag agccgaagat acagctgtgt actattgcgc tagggacgtc 300
tacggagatt atggcgcatt tgactattgg ggacagggca ctctggtgac cgtctctagt 360
ggaggaggag gctcaggagg aggagggagc ggcggaggag gcagcgatgt ggtcatgacc 420
cagtccccag tgtctctgcc agtcacactg ggacagccag catccatctc ttgtaagtca 480
agccagtctc tgctgtactt caacggaaat acttatctgt cttggtttca gcagcgccct 540
ggccagagtc cacggagact gttctaccag gtgtctaacc gagacagtgg cgtccctgat 600
cggttcagtg ggtcaggaag cgacaccgat tttaccctga caatcagccg agtggaggct 660
gaagacgtgg gggtctattt ctgcatgcag ggaacacagt ggccccctac ttttggccag 720
gggaccaagg tggagatcaa gaacagcggc gcgggcaccg cggccgcgac tcacacatgc 780
ccaccgtgcc cagcacctga actcctgggg ggaccgtcag tcttcctctt ccccccaaaa 840
cccaaggaca ccctcatgat ctcccggacc cctgaggtca catgcgtggt ggtggacgtg 900
agccacgaag accctgaggt caagttcaac tggtacgtgg acggcgtgga ggtgcataat 960
gccaagacaa agccgcggga ggagcagtac aacagcacgt accgtgtggt cagcgtcctc 1020
accgtcctgc accaggactg gctgaatggc aaggagtaca agtgcaaggt ctccaacaaa 1080
gccctcccag cccccatcga gaaaaccatc tccaaagcca aagggcagcc ccgagaacca 1140
caggtgtgca ccctgccccc atcccgggat gagctgacca agaaccaggt cagcctgtcc 1200
tgcgccgtca aaggcttcta tcccagcgac atcgccgtgg agtgggagag caatgggcag 1260
ccggagaaca actacaagac cacgcctccc gtgctggact ccgacggctc cttcttcctc 1320
gtgagcaagc tcaccgtgga caagagcagg tggcagcagg ggaacgtctt ctcatgctcc 1380
gtgatgcatg aggctctgca caaccactac acgcagaaga gcctctccct gtctccgggt 1440
aaa 1443

<210> SEQ ID NO 407
<211> LENGTH: 657
<212> TYPE: DNA
<213> ORGANISM: Artificial Sequence
<220> FEATURE:
<223> OTHER INFORMATION: Synthetic

<400> SEQUENCE: 407
gatgttgtga tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacac ctcctgatct acttgggttc taatcgggcc 180
tccggggtcc ctgacaggtt cagtggcagt ggatcaggca cagattttac actgaaaatt 240
agcagagtgg aggctgagga tgttggggtt tatttctgca tgcaagctct acgaactccg 300
tacacttttg gccaggggac caagctggag atcaaacgaa ctgtggctgc accatctgtc 360

```
ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

<210> SEQ ID NO 408
<211> LENGTH: 660
<212> TYPE: DNA
<213> ORGANISM: Artificial Sequence
<220> FEATURE:
<223> OTHER INFORMATION: Synthetic

<400> SEQUENCE: 408

```
cagctgcagc tgcaggagtc gggggaggc gtggtccagc ctgggaggtc cctgagactc     60

tcctgtgcag cctctggatt caccttcagt agctatgcta tgcactgggt ccgccaggct    120

ccaggcaagg ggctggagtg ggtggcagtt atatcatatg atggaggtaa taaatactac    180

gcagactccg tgaagggccg attcaccatc tccagagaca attccaagaa cacgctgtat    240

ctgcaaatga acagcctgag agctgaggac acggctgtgt attactgtgc gaaatcagtg    300

gcgcctccca tggacgtctg gggcaaaggg accacggtca ccgtctcaag cgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt ccacaccttc ccggctgtcc tacagtcctc aggactctac    540

tccctcagca gcgtagtgac cgtgccctcc agcagcttgg gcacccagac ctacatctgc    600

aacgtgaatc acaagcccag caacaccaag gtggacaaga aagttgagcc caaatcttgt    660
```

<210> SEQ ID NO 409
<211> LENGTH: 1434
<212> TYPE: DNA
<213> ORGANISM: Artificial Sequence
<220> FEATURE:
<223> OTHER INFORMATION: Synthetic

<400> SEQUENCE: 409

```
cagctgcagc tgcaggaatc cgggggaggc gtcgtccagc caggaaggtc actgagactg     60

agttgtgccg caagcgggtt cactttcagc tcctacgcta tgcactgggt gagacaggca    120

cccggaaagg gcctggagtg ggtggcagtc atctcttatg acggcgggaa caagtactat    180

gccgatagtg tgaaaggccg gttcaccatt agtagagaca actcaaaaaa tacactgtac    240

ctccagatga atagcctgcg cgccgaagac acagctgtgt actattgcgc aaagtccgtg    300

gcccccccta tggatgtctg gggaaagga accacagtga ctgtctctag tggaggagga    360

ggatcaggcg gcggaggcag cggaggagga gggtccgacg tggtcatgac tcagtcccct    420

ctgtctctgc cagtgacccc cggcgagcct gcttccatct cttgtaggtc aagccagagc    480

ctgctgcact ccaacgggta caattatctg gattggtact tgcagaagcc aggccagtct    540

ccccatctgc tgatctatct gggatctaac agggccagtg gcgtgcctga ccgcttcagt    600

ggctcaggga gcggaactga ttttaccctg aaaattagcc gagtcgaggc cgaagatgtg    660

ggcgtctact tctgcatgca ggctctgcgg acaccatata cttttggcca ggggaccaag    720

ctggagatca agaacagcgg cgcgggcacc gcggccgcga ctcacacatg cccaccgtgc    780
```

-continued ccagcacctg aactcctggg gggaccgtca gtcttcctct tcccccaaa acccaaggac 840 accctcatga tctcccggac ccctgaggtc acatgcgtgg tggtggacgt gagccacgaa 900
gaccctgagg tcaagttcaa ctggtacgtg gacggcgtgg aggtgcataa tgccaagaca 960
aagccgcggg aggagcagta caacagcacg taccgtgtgg tcagcgtcct caccgtcctg 1020
caccaggact ggctgaatgg caaggagtac aagtgcaagg tctccaacaa agccctccca 1080
gcccccatcg agaaaaccat ctccaaagcc aaagggcagc cccgagaacc acaggtgtgc 1140
accctgcccc catcccggga tgagctgacc aagaaccagg tcagcctgtc ctgcgccgtc 1200
aaaggcttct atcccagcga catcgccgtg gagtgggaga gcaatgggca gccggagaac 1260
aactacaaga ccacgcctcc cgtgctggac tccgacggct ccttcttcct cgtgagcaag 1320
ctcaccgtgg acaagagcag gtggcagcag gggaacgtct tctcatgctc cgtgatgcat 1380
gaggctctgc acaaccacta cacgcagaag agcctctccc tgtctccggg taaa 1434

<210> SEQ ID NO 410
<211> LENGTH: 657
<212> TYPE: DNA
<213> ORGANISM: Artificial Sequence
<220> FEATURE:
<223> OTHER INFORMATION: Synthetic

<400> SEQUENCE: 410
gatgttgtga tgactcagtc tccactctcc ctgcccgtca cccttggaca gccggcctcc 60
atctcctgca ggtctagtca gagcctcgtc catagtaatg gatacaacta tttggactgg 120
tacctgcaga agccagggca gtctccacag ctcctgatct atttgggttc taatcgggcc 180
tccggggtcc ctgacaggtt cagtggcagt ggatcgggca cagattttac actgaaaatc 240
agcagagtgg aggctgagga tgttggggtt tattactgcc tgcaaggttc acactggcct 300
tggacgttcg gccaagggac caaggtggaa atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 411
<211> LENGTH: 672
<212> TYPE: DNA
<213> ORGANISM: Artificial Sequence
<220> FEATURE:
<223> OTHER INFORMATION: Synthetic

<400> SEQUENCE: 411
caggtgcagc tacagcagtg gggcgcagga ctgttgaagc cttcggagac cctgtccctc 60
acctgcgctg tctatggtga gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcgag aggccccgcg 300
ggtagcagct cgtccggcta ctttgactac tggggccagg gaaccctggt caccgtctca 360
agcgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtccacacct tcccggctgt cctacagtcc 540
tcaggactct actccctcag cagcgtagtg accgtgccct ccagcagctt gggcacccag 600
acctacatct gcaacgtgaa tcacaagccc agcaacacca aggtggacaa gaaagttgag 660
cccaaatctt gt 672

<210> SEQ ID NO 412
<211> LENGTH: 1446
<212> TYPE: DNA
<213> ORGANISM: Artificial Sequence
<220> FEATURE:
<223> OTHER INFORMATION: Synthetic

<400> SEQUENCE: 412
caggtccagc tgcagcagtg gggcgccgga ctgctgaaac cctctgaaac tctgagcctg 60
acttgtgccg tctatgggga atccttctct ggctactatt ggagttggat caggcagccc 120
cctggcaagg ggctggagtg gatcggagaa attaaccaca gcggctccac caactacaat 180
ccatctctga aaagtcgcgt gaccatttcc gtggacacat ctaagaatca gttcagcctg 240
aagctgagca gcgtgacagc cgctgatact gccgtctact attgcgcacg gggccccgcc 300
gggtctagtt caagcggata ctttgactat tggggacagg gcaccctggt gacagtctcc 360
tctggcggag gaggctccgg aggaggaggg tctggaggag gaggaagcga tgtggtcatg 420
acacagtcac cactgagcct gccagtgact ctgggacagc ctgcttctat cagttgtcga 480
agttcacaga gtctggtcca ctcaaacgga tacaattatc tggactggta cttgcagaag 540
cctggccaga gcccacagct gctgatctat ctggggagca accgagcttc cggagtgccc 600
gacagattct cagggagcgg cagcggcact gattttaccc tgaaaattag cagagtggag 660
gcagaagatg tgggcgtcta ctattgcctc caggggtccc attggccttg gactttcggg 720
cagggaacca aggtggagat caagaacagc ggcgcgggca ccgcggccgc gactcacaca 780
tgcccaccgt gcccagcacc tgaactcctg gggggaccgt cagtcttcct cttcccccca 840
aaacccaagg acaccctcat gatctcccgg acccctgagg tcacatgcgt ggtggtggac 900
gtgagccacg aagaccctga ggtcaagttc aactggtacg tggacggcgt ggaggtgcat 960
aatgccaaga caaagccgcg ggaggagcag tacaacagca cgtaccgtgt ggtcagcgtc 1020
ctcaccgtcc tgcaccagga ctggctgaat ggcaaggagt acaagtgcaa ggtctccaac 1080
aaagccctcc cagcccccat cgagaaaacc atctccaaag ccaaagggca gccccgagaa 1140
ccacaggtgt gcaccctgcc cccatcccgg gatgagctga ccaagaacca ggtcagcctg 1200
tcctgcgccg tcaaaggctt ctatcccagc gacatcgccg tggagtggga gagcaatggg 1260
cagccggaga acaactacaa gaccacgcct cccgtgctgg actccgacgg ctccttcttc 1320
ctcgtgagca agctcaccgt ggacaagagc aggtggcagc aggggaacgt cttctcatgc 1380
tccgtgatgc atgaggctct gcacaaccac tacacgcaga agagcctctc cctgtctccg 1440
ggtaaa 1446

<210> SEQ ID NO 413
<211> LENGTH: 639
<212> TYPE: DNA
<213> ORGANISM: Artificial Sequence
<220> FEATURE:
<223> OTHER INFORMATION: Synthetic

<400> SEQUENCE: 413
gaaacgacac tcacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccagcg ggccactgg catcccagac 180 aggttcagtg gcagtgggtc tgggacagac ttcactctca ccatcagcag actggagcct 240
gaagattttg cagtgtatta ctgtcagctg tatggtagct cactcgcttt cggcggaggg 300
accaaggtgg agatcaaacg aactgtggct gcaccatctg tcttcatctt cccgccatct 360
gatgagcagt tgaaatctgg aactgcctct gttgtgtgcc tgctgaataa cttctatccc 420
agagaggcca aagtacagtg gaaggtggat aacgccctcc aatcgggtaa ctcccaggag 480
agtgtcacag agcaggacag caaggacagc acctacagcc tcagcagcac cctgacgctg 540
agcaaagcag actacgagaa acacaaagtc tacgcctgcg aagtcaccca tcagggcctg 600
agctcgcccg tcacaaagag cttcaacagg ggagagtgt 639

<210> SEQ ID NO 414
<211> LENGTH: 687
<212> TYPE: DNA
<213> ORGANISM: Artificial Sequence
<220> FEATURE:
<223> OTHER INFORMATION: Synthetic

<400> SEQUENCE: 414
gaggtccagc tggtgcagtc tggggctgag gtgaagaagc ctgggtcctc ggtgaaggtc 60
tcctgcaagg cttctggagg caccttcagc agctatgcta tcagctgggt gcgacaggcc 120
cctggacaag ggcttgagtg gatgggatgg atcagcgctt acaatggtga cacaagctac 180
gcacagaagt tccagggcag agtcaccatt accagggaca catccgcgag cacagcctac 240
atggagctga gcagcctgag atctgaagac acggctgtgt attactgtgc gagagattgg 300
ggatattgta gtggtggtag ctgctacctg aactggttcg acccctgggg ccagggaacc 360
ctggtcaccg tctcaagcgc ctccaccaag ggcccatcgg tcttccccct ggcaccctcc 420
tccaagagca cctctggggg cacagcggcc ctgggctgcc tggtcaagga ctacttcccc 480
gaaccggtga cggtgtcgtg gaactcaggc gccctgacca gcggcgtcca caccttcccg 540
gctgtcctac agtcctcagg actctactcc ctcagcagcg tagtgaccgt gccctccagc 600
agcttgggca cccagaccta catctgcaac gtgaatcaca agcccagcaa caccaaggtg 660
gacaagaaag ttgagcccaa atcttgt 687

<210> SEQ ID NO 415
<211> LENGTH: 1412
<212> TYPE: DNA
<213> ORGANISM: Artificial Sequence
<220> FEATURE:
<223> OTHER INFORMATION: Synthetic

<400> SEQUENCE: 415
aggtccagct gcaggaaagc gggccaggac tggtcaaacc ctcacagaca ctgtctctga 60
cttgtaccgt ctccgggggc tcaatcagct ccggcgggta ctattggaca tggatcagac 120
agcaccctgg acagggcctg gagtggatcg ggttcattag ctggtccgga accacatact 180
ataacccaag cctgaagaat agggtgacaa tttcagccga cactagcaaa aaccattttt 240
ccctgaatct gacctctgtg acagccgctg atactgctgt ctactattgc gcacgggggt 300
ccggaagact ggtgtgggga caggggactc tggtgaccgt ctctagtgga ggaggaggaa 360
gtggcggagg aggcagcgga ggaggagggt ccgagactac cctgacccag tctccagcta 420
cactgtctgt gagtcccggc gaaagggcaa ccctgagctg tcgcgcttca cagagcgtct 480
caagcaacct ggcatggtat cagcagaagc ctggccaggc ccctcgactg ctgatctatg 540
gggcatcctc tggagccact ggcattcccg accggttctc cggatctggc agtgggaccg 600
attttacact gaccatcagc cggctggagc ctgaagactt cgctgtgtac tattgccagc 660
tgtacggcag ttcactggca tttggaggcg ggacaaaggt cgagatcaag aacagcggcg 720
cgggcaccgc ggccgcgact cacacatgcc caccgtgccc agcacctgaa ctcctggggg 780
gaccgtcagt cttcctcttc cccccaaaac ccaaggacac cctcatgatc tcccggaccc 840
ctgaggtcac atgcgtggtg gtggacgtga gccacgaaga ccctgaggtc aagttcaact 900
ggtacgtgga cggcgtggag gtgcataatg ccaagacaaa gccgcgggag gagcagtaca 960
acagcacgta ccgtgtggtc agcgtcctca ccgtcctgca ccaggactgg ctgaatggca 1020
aggagtacaa gtgcaaggtc tccaacaaag ccctcccagc ccccatcgag aaaaccatct 1080
ccaaagccaa agggcagccc cgagaaccac aggtgtgcac cctgccccca tcccgggatg 1140
agctgaccaa gaaccaggtc agcctgtcct gcgccgtcaa aggcttctat cccagcgaca 1200
tcgccgtgga gtgggagagc aatgggcagc cggagaacaa ctacaagacc acgcctcccg 1260
tgctggactc cgacggctcc ttcttcctcg tgagcaagct caccgtggac aagagcaggt 1320
ggcagcaggg gaacgtcttc tcatgctccg tgatgcatga ggctctgcac aaccactaca 1380
cgcagaagag cctctccctg tctccgggta aa 1412

<210> SEQ ID NO 416
<211> LENGTH: 660
<212> TYPE: DNA
<213> ORGANISM: Artificial Sequence
<220> FEATURE:
<223> OTHER INFORMATION: Synthetic

<400> SEQUENCE: 416
gatattgtga tgacccacac tccactctcc ctgcccgtca cccctggaga gccggcctcc 60
atctcctgca ggtctagtca gaccctcttc gatagcgatg atggaaagac ctatttggac 120
tggtacctgc agaagccagg gcagtctcca caactcctga tgtataccac ttcctctcgg 180
gcctctggag tcccagacag gttcagtggc agtgggtcag gcactgattt cacactgaaa 240
atcagcaggg tggaggctga ggatgttgga gtttattact gcatgcagcg tttacagttt 300
cccctcacct tcggccaagg gacacgactg gagttcaaac gaactgtggc tgcaccatct 360
gtcttcatct tcccgccatc tgatgagcag ttgaaatctg gaactgcctc tgttgtgtgc 420
ctgctgaata acttctatcc cagagaggcc aaagtacagt ggaaggtgga taacgccctc 480
caatcgggta actcccagga gagtgtcaca gagcaggaca gcaaggacag cacctacagc 540
ctcagcagca ccctgacgct gagcaaagca gactacgaga aacacaaagt ctacgcctgc 600
gaagtcaccc atcagggcct gagctcgccc gtcacaaaga gcttcaacag gggagagtgt 660

<210> SEQ ID NO 417
<211> LENGTH: 669
<212> TYPE: DNA
<213> ORGANISM: Artificial Sequence
<220> FEATURE:
<223> OTHER INFORMATION: Synthetic

<400> SEQUENCE: 417
gaggtccagc tggtgcagtc tggggctgag gtgaagaagc ctggggcctc agtgaaggtc 60

```
tcctgcaagg cttctggata caccttcacc ggctactata tgcactgggt gcgacaggcc    120

cctggacaag ggcttgagtg gatgggaata atcaacccta gtggtggtag cacaagctac    180

gcacagaagt tccagggcag agtcaccatg accagggaca cgtccacgag cacagtctac    240

atggagctga gcagcctgag atctgaggac acggccgtgt attactgtgc gagagccgat    300

acagctatgg gtgatgcttt tgatatctgg ggccaaggga caatggtcac cgtctcaagc    360

gcctccacca agggcccatc ggtcttcccc ctggcaccct cctccaagag cacctctggg    420

ggcacagcgg ccctgggctg cctggtcaag gactacttcc ccgaaccggt gacggtgtcg    480

tggaactcag gcgccctgac cagcggcgtc cacaccttcc cggctgtcct acagtcctca    540

ggactctact ccctcagcag cgtagtgacc gtgccctcca gcagcttggg cacccagacc    600

tacatctgca acgtgaatca caagcccagc aacaccaagg tggacaagaa agttgagccc    660

aaatcttgt                                                            669
```

```
<210> SEQ ID NO 418
<211> LENGTH: 1446
<212> TYPE: DNA
<213> ORGANISM: Artificial Sequence
<220> FEATURE:
<223> OTHER INFORMATION: Synthetic

<400> SEQUENCE: 418

gaagtccagc tggtccagtc aggagccgag gtcaagaagc caggggcaag cgtcaaagtc     60

tcatgcaaag caagtgggta cacatttaca ggctactata tgcactgggt gaggcaggct    120

ccaggacagg gcctggagtg gatggggatc attaacccca gcggcgggag tacctcatac    180

gcacagaagt tccagggacg ggtgactatg accagagaca caagcacttc caccgtctat    240

atggagctga gcagcctgcg atccgaagac actgccgtgt actattgcgc cagagccgat    300

accgcaatgg gcgacgcctt tgacatctgg gggcagggca caatggtgac agtctctagt    360

ggaggaggag gatctggagg aggaggcagt ggaggaggcg ggtcagacat cgtgatgaca    420

catactccac tgtctctgcc agtcacccct ggcgagccag cctctattag ttgtcgctca    480

agccagaccc tgttcgacag tgacgatgga aagacatacc tggattggta cttgcagaaa    540

cctggccaga gccctcagct gctgatgtac accacatcct ctagggcctc cggcgtgcct    600

gaccgcttct caggcagcgg gtccggaact gattttaccc tgaagatcag ccgggtggag    660

gctgaagacg tgggggtcta ctattgcatg cagagactcc agttcccact gacatttggc    720

caggggactc ggctggagtt caagaacagc ggcgcgggca ccgcggccgc gactcacaca    780

tgcccaccgt gcccagcacc tgaactcctg gggggaccgt cagtcttcct cttcccccca    840

aaacccaagg acaccctcat gatctcccgg acccctgagg tcacatgcgt ggtggtggac    900

gtgagccacg aagaccctga ggtcaagttc aactggtacg tggacggcgt ggaggtgcat    960

aatgccaaga caaagccgcg ggaggagcag tacaacagca cgtaccgtgt ggtcagcgtc   1020

ctcaccgtcc tgcaccagga ctggctgaat ggcaaggagt acaagtgcaa ggtctccaac   1080

aaagccctcc cagcccccat cgagaaaacc atctccaaag ccaaagggca gccccgagaa   1140

ccacaggtgt gcaccctgcc cccatcccgg gatgagctga ccaagaacca ggtcagcctg   1200

tcctgcgccg tcaaaggctt ctatcccagc gacatcgccg tggagtggga gagcaatggg   1260

cagccggaga acaactacaa gaccacgcct cccgtgctgg actccgacgg ctccttcttc   1320

ctcgtgagca agctcaccgt ggacaagagc aggtggcagc aggggaacgt cttctcatgc   1380

tccgtgatgc atgaggctct gcacaaccac tacacgcaga agagcctctc cctgtctccg   1440
```

ggtaa 1446

<210> SEQ ID NO 419
<211> LENGTH: 657
<212> TYPE: DNA
<213> ORGANISM: Artificial Sequence
<220> FEATURE:
<223> OTHER INFORMATION: Synthetic

<400> SEQUENCE: 419
gatgttgtga tgactcagtc tccactctcc ctgcccgtca cccctggaga gccggcctcc 60
atctcctgca gggcaactca gagcctcctg catggaaatg gacacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagagtgg aggctgagga tgttggggtt tattactgca tgcaaactct ggaaactcct 300
gtcactttcg gccctgggac caaagtggat atcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccaggagag tgtcacagag caggacagca aggacagcac ctacagcctc 540
agcagcaccc tgacgctgag caaagcagac tacgagaaac acaaactcta cgcctgcgaa 600
gtcacccatc agggcctgag ctcgcccgtc acaaagagct tcaacagggg agagtgt 657

<210> SEQ ID NO 420
<211> LENGTH: 663
<212> TYPE: DNA
<213> ORGANISM: Artificial Sequence
<220> FEATURE:
<223> OTHER INFORMATION: Synthetic

<400> SEQUENCE: 420
gaggtccagc tggtgcagtc tgggggaggc gtggtccagc ctgggaggtc cctgagactc 60
tcctgtgcag cctctggatt caccttcagt agctatgcta tgcactgggt ccgccaggct 120
ccaggcaagg ggctggagtg ggtggcagtt atatcatatg atggaagcaa taaatactac 180
gcagactccg tgaagggccg attcaccatc tccagagaca attccaagaa cacgctgtat 240
ctgcaaatga acagcctgag agctgaggac acggctgtgt attactgtgc gaggtctatc 300
ggtatcggtg cttttgatat ctggggccaa gggacaatgg tcaccgtctc aagcgcctcc 360
accaagggcc catcggtctt ccccctggca ccctcctcca agagcacctc tgggggcaca 420
gcggccctgg gctgcctggt caaggactac ttccccgaac cggtgacggt gtcgtggaac 480
tcaggcgccc tgaccagcgg cgtccacacc ttcccggctg tcctacagtc ctcaggactc 540
tactccctca gcagcgtagt gaccgtgccc tccagcagct tgggcaccca gacctacatc 600
tgcaacgtga atcacaagcc cagcaacacc aaggtggaca agaaagttga gcccaaatct 660
tgt 663

<210> SEQ ID NO 421
<211> LENGTH: 1437
<212> TYPE: DNA
<213> ORGANISM: Artificial Sequence
<220> FEATURE:
<223> OTHER INFORMATION: Synthetic

<400> SEQUENCE: 421

```
gaggtccagc tggtccagag cggggggggg gtcgtgcagc ctgggagaag cctgagactg     60

tcctgtgccg caagcgggtt tacttttagc tcctacgcta tgcactgggt gaggcaggca    120

cccggcaagg ggctggagtg ggtggcagtc atctcctatg acggctctaa caagtactat    180

gccgatagcg tgaaagggcg gttcacaatt agtagagaca actcaaagaa cactctgtac    240

ctccagatga atagcctgcg agccgaagac actgctgtgt actattgcgc ccggtccatc    300

ggaattggcg cttttgacat ctgggggcag ggcacaatgg tgacagtctc tagtggagga    360

ggaggctctg gaggaggagg gagtggagga ggaggatcag acgtggtcat gacccagtca    420

cctctgagcc tgccagtgac acctggcgag ccagcatcaa ttagctgtag agccacccag    480

tctctgctgc acggcaacgg gcataattac ctggattggt acttgcagaa gcctggccag    540

agtcctcagc tgctgatcta tctggggagc aacagggctt ccggagtgcc agaccgcttc    600

tccggatctg gcagtgggac tgattttacc ctgaaaattt cccgcgtcga ggcagaagac    660

gtgggagtct actattgcat gcagacactg gaaactccag tgaccttcgg acccggcaca    720

aaggtggaca tcaagaacag cggcgcgggc accgcggccg cgactcacac atgcccaccg    780

tgcccagcac ctgaactcct ggggggaccg tcagtcttcc tcttcccccc aaaacccaag    840

gacaccctca tgatctcccg gacccctgag gtcacatgcg tggtggtgga cgtgagccac    900

gaagaccctg aggtcaagtt caactggtac gtggacggcg tggaggtgca taatgccaag    960

acaaagccgc gggaggagca gtacaacagc acgtaccgtg tggtcagcgt cctcaccgtc   1020

ctgcaccagg actggctgaa tggcaaggag tacaagtgca aggtctccaa caaagccctc   1080

ccagccccca tcgagaaaac catctccaaa gccaaagggc agccccgaga accacaggtg   1140

tgcaccctgc ccccatcccg ggatgagctg accaagaacc aggtcagcct gtcctgcgcc   1200

gtcaaaggct tctatcccag cgacatcgcc gtggagtggg agagcaatgg gcagccggag   1260

aacaactaca agaccacgcc tcccgtgctg gactccgacg gctccttctt cctcgtgagc   1320

aagctcaccg tggacaagag caggtggcag caggggaacg tcttctcatg ctccgtgatg   1380

catgaggctc tgcacaacca ctacacgcag aagagcctct ccctgtctcc gggtaaa      1437
```

<210> SEQ ID NO 422
<211> LENGTH: 657
<212> TYPE: DNA
<213> ORGANISM: Artificial Sequence
<220> FEATURE:
<223> OTHER INFORMATION: Synthetic

<400> SEQUENCE: 422

```
gatgttgtga tgactcagtc tccactctcc ctgcccgtca cccctggaga gccggcctcc     60

atctcctgca ggtctagtca gagcctcctg catagtaatg gatacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagggtgg aggctgagga tgttggggtt tattactgca tgcaaggtac acactggccc    300

tggacgttcg gccaagggac caaggtggaa atcaaacgaa ctgtggctgc accatctgtc    360

ttcatcttcc cgccatctga tgagcagttg aaatctggaa ctgcctctgt tgtgtgcctg    420

ctgaataatt tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaactcta cgcctgcgaa    600

gtcacccatc agggcctgag ctcgcccgtc acaaagagct tcaacagggg agagtgt       657
```

<210> SEQ ID NO 423
<211> LENGTH: 672
<212> TYPE: DNA
<213> ORGANISM: Artificial Sequence
<220> FEATURE:
<223> OTHER INFORMATION: Synthetic

<400> SEQUENCE: 423
caggtgcagc tacagcagtg gggcgcagga ctgttgaagc cttcggagac cctgtccctc 60
acctgcacta tctatggtgg gtccttcagt ggtttctact ggagctggat ccgccagccc 120
ccagggaagg gactggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctatatatt actgtgcgag aggccccgcg 300
ggatccacct cgtccggcta ctttgaccac tggggccagg gaaccctggt caccgtctca 360
agcgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtccacacct tcccggctgt cctacagtcc 540
tcaggactct actccctcag cagcgtagtg accgtgccct ccagcagctt gggcacccag 600
acctacatct gcaacgtgaa tcacaagccc agcaacacca aggtggacaa gaaagttgag 660
cccaaatctt gt 672

<210> SEQ ID NO 424
<211> LENGTH: 1446
<212> TYPE: DNA
<213> ORGANISM: Artificial Sequence
<220> FEATURE:
<223> OTHER INFORMATION: Synthetic

<400> SEQUENCE: 424
caggtccagc tgcagcagtg gggagccgga ctgctgaaac cctctgagac tctgagcctg 60
acttgcacaa tctacggggg atcattcagc ggcttctact ggtcctggat caggcagccc 120
cctggcaagg ggctggagtg gatcggagaa attaaccaca gtggctcaac aaactataat 180
cccagcctga aatcccgcgt gaccatctca gtggacacaa gcaagaatca gttcagcctg 240
aagctgagca gcgtgacagc cgctgatact gccatctact attgcgcacg gggccctgcc 300
gggtccacct ctagtgggta ctttgaccat tggggacagg gcaccctggt gacagtctca 360
agcggaggag gaggctctgg aggaggaggg agtggaggcg gggggcagcga tgtggtcatg 420 actcagtctc cactgagtct gccagtgacc cccggcgagc ctgctagcat ctcctgtcga 480
tcctctcagt ccctgctgca ctctaacgga tacaattatc tggactggta cttgcagaag 540
ccaggccaga gcccccagct gctgatctat ctggggagta accgggcttc aggagtgcct 600
gacagattct ctgggagtgg atcaggcact gattttaccc tgaaaattag cagagtcgag 660
gcagaagatg tgggcgtcta ctattgcatg caggggactc attggccctg gacctttggg 720
cagggaacaa aggtggagat caagaacagc ggcgcgggca ccgcggccgc gactcacaca 780
tgcccaccgt gcccagcacc tgaactcctg gggggaccgt cagtcttcct cttcccccca 840
aaacccaagg acaccctcat gatctcccgg acccctgagg tcacatgcgt ggtggtggac 900
gtgagccacg aagaccctga ggtcaagttc aactggtacg tggacggcgt ggaggtgcat 960
aatgccaaga caaagccgcg ggaggagcag tacaacagca cgtaccgtgt ggtcagcgtc 1020

```
ctcaccgtcc tgcaccagga ctggctgaat ggcaaggagt acaagtgcaa ggtctccaac   1080

aaagccctcc cagcccccat cgagaaaacc atctccaaag ccaaagggca gccccgagaa   1140

ccacaggtgt gcaccctgcc cccatcccgg gatgagctga ccaagaacca ggtcagcctg   1200

tcctgcgccg tcaaaggctt ctatcccagc gacatcgccg tggagtggga gagcaatggg   1260

cagccggaga acaactacaa gaccacgcct cccgtgctgg actccgacgg ctccttcttc   1320

ctcgtgagca agctcaccgt ggacaagagc aggtggcagc aggggaacgt cttctcatgc   1380

tccgtgatgc atgaggctct gcacaaccac tacacgcaga agagcctctc cctgtctccg   1440

ggtaaa                                                              1446
```

<210> SEQ ID NO 425
<211> LENGTH: 657
<212> TYPE: DNA
<213> ORGANISM: Artificial Sequence
<220> FEATURE:
<223> OTHER INFORMATION: Synthetic

<400> SEQUENCE: 425

```
gatgttgtga tgactcagtc tccactctcc ctgcccgtca cccctggaga gccggcctcc     60

atctcctgca ggtctagtca gagcctcctg catagtaatg gatacaacta tttggattgg    120

tacctgcaga agccagggca gtctccacag ctcctgatct atttgggttc taatcgggcc    180

tccggggtcc ctgacaggtt cagtggcagt ggatcaggca cagattttac actgaaaatc    240

agcagggtgg aggctgagga tgttggggtt tattactgcc tgcaaggtac acattggccg    300

tggacgttcg gccaggggac caaggtggaa atcaaacgaa ctgtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

<210> SEQ ID NO 426
<211> LENGTH: 660
<212> TYPE: DNA
<213> ORGANISM: Artificial Sequence
<220> FEATURE:
<223> OTHER INFORMATION: Synthetic

<400> SEQUENCE: 426

```
caggtgcagc tacagcagtg gggcgcagga ctgttgaagc cttcggagac cctgtccctc     60

acctgcgctg tctatggtgg gtccctcagt ggttactact ggagctggat ccgccagccc    120

ccagggaagg ggctggagtg gattggggaa atcaatcata gtggaagcac caactacaac    180

ccatccctca agagtcgagt caccatatca gtagacacgt ccaagaacca gttctccctg    240

aagctgagct ctgtgaccgc cgcggacacg gctgtgtatt actgtgcgag aggcagcagc    300

tcctactaca tggacgtctg gggcaaaggg accacggtca ccgtctcaag cgcctccacc    360

aagggcccat cggtcttccc cctggcaccc tcctccaaga gcacctctgg gggcacagcg    420

gccctgggct gcctggtcaa ggactacttc cccgaaccgg tgacggtgtc gtggaactca    480

ggcgccctga ccagcggcgt ccacaccttc ccggctgtcc tacagtcctc aggactctac    540

tccctcagca gcgtagtgac cgtgccctcc agcagcttgg gcacccagac ctacatctgc    600

aacgtgaatc acaagcccag caacaccaag gtggacaaga aagttgagcc caaatcttgt    660
```

<210> SEQ ID NO 427
<211> LENGTH: 1434
<212> TYPE: DNA
<213> ORGANISM: Artificial Sequence
<220> FEATURE:
<223> OTHER INFORMATION: Synthetic

<400> SEQUENCE: 427
caggtccagc tgcagcagtg gggagccgga ctgctgaaac caagcgagac tctgagcctg 60
acttgtgccg tgtatggggg aagcctgtcc ggctactatt ggtcttggat caggcagccc 120
cctggcaagg ggctggagtg gatcggcgaa attaaccact cagggagcac aaactacaat 180
ccctccctga aatctcgcgt gaccattagc gtggacacat ccaagaatca gttcagcctg 240
aagctgagca gcgtgacagc cgctgacacc gccgtgtact attgcgccag aggcagcagc 300
agctactata tggatgtgtg gggaaagggc accacagtga ccgtcagctc cggaggagga 360
ggcagtggag gaggagggtc cggaggcggg ggatctgacg tggtcatgac tcagagtcct 420
ctgtcactgc ctgtgacccc cggcgagcct gcatccatct cttgtcgatc tagtcagtct 480
ctgctgcaca gtaacggcta caattatctg gattggtact tgcagaagcc agggcagtcc 540
ccccagctgc tgatctatct gggatcaaac cgggctagcg gcgtgcctga cagattcagt 600
gggtcaggaa gcggcactga ttttaccctg aaaattagca gagtcgaggc agaagatgtg 660
ggggtctact attgcctcca gggaactcat tggccctgga cctttgggca gggaacaaag 720
gtggagatca agaacagcgg cgcgggcacc gcggccgcga ctcacacatg cccaccgtgc 780
ccagcacctg aactcctggg gggaccgtca gtcttcctct tcccccaaa acccaaggac 840 accctcatga tctcccggac ccctgaggtc acatgcgtgg tggtggacgt gagccacgaa 900
gaccctgagg tcaagttcaa ctggtacgtg gacggcgtgg aggtgcataa tgccaagaca 960
aagccgcggg aggagcagta caacagcacg taccgtgtgg tcagcgtcct caccgtcctg 1020
caccaggact ggctgaatgg caaggagtac aagtgcaagg tctccaacaa agccctccca 1080
gcccccatcg agaaaaccat ctccaaagcc aaagggcagc cccgagaacc acaggtgtgc 1140
accctgcccc catcccggga tgagctgacc aagaaccagg tcagcctgtc ctgcgccgtc 1200
aaaggcttct atcccagcga catcgccgtg gagtgggaga gcaatgggca gccggagaac 1260
aactacaaga ccacgcctcc cgtgctggac tccgacggct ccttcttcct cgtgagcaag 1320
ctcaccgtgg acaagagcag gtggcagcag gggaacgtct tctcatgctc cgtgatgcat 1380
gaggctctgc acaaccacta cacgcagaag agcctctccc tgtctccggg taaa 1434

<210> SEQ ID NO 428
<211> LENGTH: 657
<212> TYPE: DNA
<213> ORGANISM: Artificial Sequence
<220> FEATURE:
<223> OTHER INFORMATION: Synthetic

<400> SEQUENCE: 428
gatgttgtga tgactcagtc tccactctcc ctgcccgtca cccttggtca gccggcctcc 60
atctcctgca ggtctagtca gagcctcctg cacagtaatg gaaacaacta tttggattgg 120
tacctgcaga agccagggca gtctccacag ctcctgatct atttgggttc taatcgggcc 180
tccggggtcc ctgacaggtt cagtggcagt ggatcaggca cagattttac actgaaaatc 240
agcagggtgg aggctgagga tgttgggatt tattactgca tgcaagggac acactggcct 300
tggacgttcg gccaagggac caaggtggaa atcgaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggatag cgccctccaa 480
tcgggtaact cccaggagag tgtcacagag caggacagca aggacagcac ctacagcctc 540
agcagcaccc tgacgctgag caaagcagac tacgagaaac acaaactcta cgcctgcgaa 600
gtcacccatc agggcctgag ctcgcccgtc acaaagagct tcaacagggg agagtgt 657

<210> SEQ ID NO 429
<211> LENGTH: 657
<212> TYPE: DNA
<213> ORGANISM: Artificial Sequence
<220> FEATURE:
<223> OTHER INFORMATION: Synthetic

<400> SEQUENCE: 429
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gtagacacgt ccaagaacca gttctccctg 240
aagctgagct ctgtgaccgc cgcggacacg gctgtgtatt actgtgcgag aggcggtagc 300
gcgtacttcc agcactgggg ccagggaacc ctggtcaccg tctcaagcgc ctccaccaag 360
ggcccatcgg tcttcccct ggcaccctcc tccaagagca cctctggggg cacagcggcc 420
ctgggctgcc tggtcaagga ctacttcccc gaaccggtga cggtgtcgtg gaactcaggc 480
gccctgacca gcggcgtcca caccttcccg gctgtcctac agtcctcagg actctactcc 540
ctcagcagcg tagtgaccgt gccctccagc agcttgggca cccagaccta catctgcaac 600
gtgaatcaca agcccagcaa caccaaggtg gacaagaaag ttgagcccaa atcttgt 657

<210> SEQ ID NO 430
<211> LENGTH: 1431
<212> TYPE: DNA
<213> ORGANISM: Artificial Sequence
<220> FEATURE:
<223> OTHER INFORMATION: Synthetic

<400> SEQUENCE: 430
caggtccagc tgcagcagtg gggggccggg ctgctgaaac cttccgaaac tctgtctctg 60
acttgtgccg tgtatggggg gtcctttagt ggctactatt ggtcatggat caggcagccc 120
cctggaaagg gcctggagtg gatcggagaa attaaccact ccggctctac aaactacaat 180
ccaagtctga aatcacgcgt gaccatttct gtggacacca gtaagaatca gttcagcctg 240
aagctgagca gcgtgacagc cgctgatacc gccgtgtact attgcgcccg aggcgggtct 300
gcttattttc agcattgggg gcagggaacc ctggtgacag tctctagtgg aggaggaggc 360
agcggcggag gaggctctgg aggaggaggg agtgacgtgg tcatgactca gagcccactg 420
tccctgccag tgaccctggg acagccagct agtatctcat gtagatcaag ccagtcactg 480
ctgcacagca acggcaacaa ttacctggat tggtacttgc agaagcctgg ccagagccca 540
cagctgctga tctacctggg gtccaatcgg gcatctggag tgcccgacag attcagcggc 600
tccgggtctg gaactgattt taccctgaag atcagccggg tggaggccga agacgtcggc 660
atctactatt gcatgcaggg gactcattgg ccttggacct tcggccaggg gacaaaagtg 720
gagatcgaaa acagcggcgc gggcaccgcg gccgcgactc acacatgccc accgtgccca 780
gcacctgaac tcctgggggg accgtcagtc ttcctcttcc ccccaaaacc caaggacacc 840
ctcatgatct cccggacccc tgaggtcaca tgcgtggtgg tggacgtgag ccacgaagac 900
cctgaggtca agttcaactg gtacgtggac ggcgtggagg tgcataatgc caagacaaag 960
ccgcgggagg agcagtacaa cagcacgtac cgtgtggtca gcgtcctcac cgtcctgcac 1020
caggactggc tgaatggcaa ggagtacaag tgcaaggtct ccaacaaagc cctcccagcc 1080
cccatcgaga aaaccatctc caaagccaaa gggcagcccc gagaaccaca ggtgtgcacc 1140
ctgcccccat cccgggatga gctgaccaag aaccaggtca gcctgtcctg cgccgtcaaa 1200
ggcttctatc ccagcgacat cgccgtggag tgggagagca atgggcagcc ggagaacaac 1260
tacaagacca cgcctcccgt gctggactcc gacggctcct tcttcctcgt gagcaagctc 1320
accgtggaca agagcaggtg gcagcagggg aacgtcttct catgctccgt gatgcatgag 1380
gctctgcaca accactacac gcagaagagc ctctccctgt ctccgggtaa a 1431

<210> SEQ ID NO 431
<211> LENGTH: 657
<212> TYPE: DNA
<213> ORGANISM: Artificial Sequence
<220> FEATURE:
<223> OTHER INFORMATION: Synthetic

<400> SEQUENCE: 431
gaaattgtgc tgactcagtc tccactctcc ctgcccgtca cccctggaga gccggcctcc 60
atctcctgca ggtctagtca gagcctcctg catagtaatg gatacaacta tttggattgg 120
tacctgcaga agccagggca gtctccacag ctcctgatct atttggcttc taatcgggcc 180
tccggggtcc cagacagatt cagcggcagt gggtcaggca ctgatttcac actgaaaatc 240
agcagggtgg aggctgagga tgttggggtt tattactgca tgcaaggtac acactggccg 300
tggacgttcg gccaagggac caaggtggaa gtcaaacgaa ctgtggctgc accatctgtc 360
ttcatcttcc cgccatctga tgagcagttg aaatctggaa ctgcctctgt tgtgtgcctg 420
ctgaataact tctatcccag agaggccaaa gtacagtgga aggtggataa cgccctccaa 480
tcgggtaact cccgggagag tgtcacagag caggacagca aggacagcac ctacagcctc 540
agcagcaccc tgacgctgag caaagcagac tacgagaaac acaaagtcta cgcctgcgaa 600
gtcacccatc agggcctgag ctcgcccgtc acaaagagct tcaacagggg agagtgt 657

<210> SEQ ID NO 432
<211> LENGTH: 672
<212> TYPE: DNA
<213> ORGANISM: Artificial Sequence
<220> FEATURE:
<223> OTHER INFORMATION: Synthetic

<400> SEQUENCE: 432
caggtgcagc tacagcagtg gggcgcagga ctgttgaagc cttcggagac cctgtccctc 60
acctgcgctg tctatggtgg gtccttcagt ggttactact ggagctggat ccgccagccc 120
ccagggaagg ggctggagtg gattggggaa atcaatcata gtggaagcac caactacaac 180
ccgtccctca agagtcgagt caccatatca gaagacgcgt ccaagaagca gttctccctg 240
acgctgacct ctgtgaccgc cgcggacacg gctgtctatt actgtgcgag aggccccgcg 300
ggtaccggct cgtccggcta ctttgactac tggggccagg gaaccctggt caccgtctca 360
agcgcctcca ccaagggccc atcggtcttc cccctggcac cctcctccaa gagcacctct 420
gggggcacag cggccctggg ctgcctggtc aaggactact tccccgaacc ggtgacggtg 480
tcgtggaact caggcgccct gaccagcggc gtccacacct tcccggctgt cctacagtcc 540
tcaggactct actccctcag cagcgtagtg accgtgccct ccagcagctt gggcacccag 600
acctacatct gcaacgtgaa tcacaagccc agcaacacca aggtggacaa gaaagttgag 660
cccaaatctt gt 672

<210> SEQ ID NO 433
<211> LENGTH: 1446
<212> TYPE: DNA
<213> ORGANISM: Artificial Sequence
<220> FEATURE:
<223> OTHER INFORMATION: Synthetic

<400> SEQUENCE: 433
caggtccagc tgcagcagtg gggagccgga ctgctgaagc ctagcgaaac tctgagcctg 60
acttgtgctg tctacggagg atcatttagt ggctactatt ggtcatggat caggcagccc 120
cctggcaagg ggctggagtg gatcggagaa attaaccact ccggctctac aaactacaat 180
cccagtctga aatcacgcgt gactatttct gaggacgcca gtaagaaaca gttctccctg 240
accctgacat ctgtgaccgc cgctgataca gctgtctact attgcgcacg gggccctgcc 300
ggaacaggca gctccggata ctttgactat tgggggcagg gaactctggt gaccgtctct 360
agtggcggag gaggcagtgg aggaggaggg tccggaggag gaggatctga gatcgtgctg 420
actcagagcc cactgtccct gccagtcacc cccggcgaac ctgccagtat ttcatgtcga 480
tcaagccagt cactgctgca cagcaacgga tacaattatc tggactggta cttgcagaag 540
ccaggccaga gcccccagct gctgatctat ctggcttcca atcgggcatc tggcgtgcct 600
gacagattca gcggctccgg gtctggaaca gattttactc tgaaaatttc cagagtggag 660
gccgaagatg tgggggtcta ctattgcatg cagggaactc attggccctg gaccttcggc 720
caggggacaa aggtggaagt caaaaacagc ggcgcgggca ccgcggccgc gactcacaca 780
tgcccaccgt gcccagcacc tgaactcctg gggggaccgt cagtcttcct cttcccccca 840
aaacccaagg acaccctcat gatctcccgg acccctgagg tcacatgcgt ggtggtggac 900
gtgagccacg aagaccctga ggtcaagttc aactggtacg tggacggcgt ggaggtgcat 960
aatgccaaga caaagccgcg ggaggagcag tacaacagca cgtaccgtgt ggtcagcgtc 1020
ctcaccgtcc tgcaccagga ctggctgaat ggcaaggagt acaagtgcaa ggtctccaac 1080
aaagccctcc cagcccccat cgagaaaacc atctccaaag ccaaagggca gccccgagaa 1140
ccacaggtgt gcaccctgcc cccatcccgg gatgagctga ccaagaacca ggtcagcctg 1200
tcctgcgccg tcaaaggctt ctatcccagc gacatcgccg tggagtggga gagcaatggg 1260
cagccggaga acaactacaa gaccacgcct cccgtgctgg actccgacgg ctccttcttc 1320
ctcgtgagca agctcaccgt ggacaagagc aggtggcagc aggggaacgt cttctcatgc 1380
tccgtgatgc atgaggctct gcacaaccac tacacgcaga agagcctctc cctgtctccg 1440
ggtaaa 1446

<210> SEQ ID NO 434
<211> LENGTH: 551
<212> TYPE: PRT
<213> ORGANISM: Homo sapiens

<400> SEQUENCE: 434

Met Ala Ala Pro Ala Leu Ser Trp Arg Leu Pro Leu Leu Ile Leu Leu

-continued

```
1               5                   10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

Ile Pro Trp Leu Gly His Leu Leu Val Gly Leu Ser Gly Ala Phe Gly
                245                 250                 255

Phe Ile Ile Leu Val Tyr Leu Leu Ile Asn Cys Arg Asn Thr Gly Pro
            260                 265                 270

Trp Leu Lys Lys Val Leu Lys Cys Asn Thr Pro Asp Pro Ser Lys Phe
        275                 280                 285

Phe Ser Gln Leu Ser Ser Glu His Gly Gly Asp Val Gln Lys Trp Leu
    290                 295                 300

Ser Ser Pro Phe Pro Ser Ser Ser Phe Ser Pro Gly Gly Leu Ala Pro
305                 310                 315                 320

Glu Ile Ser Pro Leu Glu Val Leu Glu Arg Asp Lys Val Thr Gln Leu
                325                 330                 335

Leu Leu Gln Gln Asp Lys Val Pro Glu Pro Ala Ser Leu Ser Ser Asn
            340                 345                 350

His Ser Leu Thr Ser Cys Phe Thr Asn Gln Gly Tyr Phe Phe Phe His
        355                 360                 365

Leu Pro Asp Ala Leu Glu Ile Glu Ala Cys Gln Val Tyr Phe Thr Tyr
    370                 375                 380

Asp Pro Tyr Ser Glu Glu Asp Pro Asp Glu Gly Val Ala Gly Ala Pro
385                 390                 395                 400

Thr Gly Ser Ser Pro Gln Pro Leu Gln Pro Leu Ser Gly Glu Asp Asp
                405                 410                 415

Ala Tyr Cys Thr Phe Pro Ser Arg Asp Asp Leu Leu Leu Phe Ser Pro
            420                 425                 430
```

Ser Leu Leu Gly Gly Pro Ser Pro Pro Ser Thr Ala Pro Gly Gly Ser
435 440 445

Gly Ala Gly Glu Glu Arg Met Pro Pro Ser Leu Gln Glu Arg Val Pro
450 455 460

Arg Asp Trp Asp Pro Gln Pro Leu Gly Pro Pro Thr Pro Gly Val Pro
465 470 475 480

Asp Leu Val Asp Phe Gln Pro Pro Pro Glu Leu Val Leu Arg Glu Ala
485 490 495

Gly Glu Glu Val Pro Asp Ala Gly Pro Arg Glu Gly Val Ser Phe Pro
500 505 510

Trp Ser Arg Pro Pro Gly Gln Gly Glu Phe Arg Ala Leu Asn Ala Arg
515 520 525

Leu Pro Leu Asn Thr Asp Ala Tyr Leu Ser Leu Gln Glu Leu Gln Gly
530 535 540

Gln Asp Pro Thr His Leu Val
545 550

<210> SEQ ID NO 435
<211> LENGTH: 525
<212> TYPE: PRT
<213> ORGANISM: Homo sapiens

<400> SEQUENCE: 435

Ala Val Asn Gly Thr Ser Gln Phe Thr Cys Phe Tyr Asn Ser Arg Ala
1 5 10 15

Asn Ile Ser Cys Val Trp Ser Gln Asp Gly Ala Leu Gln Asp Thr Ser
20 25 30

Cys Gln Val His Ala Trp Pro Asp Arg Arg Arg Trp Asn Gln Thr Cys
35 40 45

Glu Leu Leu Pro Val Ser Gln Ala Ser Trp Ala Cys Asn Leu Ile Leu
50 55 60

Gly Ala Pro Asp Ser Gln Lys Leu Thr Thr Val Asp Ile Val Thr Leu
65 70 75 80

Arg Val Leu Cys Arg Glu Gly Val Arg Trp Arg Val Met Ala Ile Gln
85 90 95

Asp Phe Lys Pro Phe Glu Asn Leu Arg Leu Met Ala Pro Ile Ser Leu
100 105 110

Gln Val Val His Val Glu Thr His Arg Cys Asn Ile Ser Trp Glu Ile
115 120 125

Ser Gln Ala Ser His Tyr Phe Glu Arg His Leu Glu Phe Glu Ala Arg
130 135 140

Thr Leu Ser Pro Gly His Thr Trp Glu Glu Ala Pro Leu Leu Thr Leu
145 150 155 160

Lys Gln Lys Gln Glu Trp Ile Cys Leu Glu Thr Leu Thr Pro Asp Thr
165 170 175

Gln Tyr Glu Phe Gln Val Arg Val Lys Pro Leu Gln Gly Glu Phe Thr
180 185 190

Thr Trp Ser Pro Trp Ser Gln Pro Leu Ala Phe Arg Thr Lys Pro Ala
195 200 205

Ala Leu Gly Lys Asp Thr Ile Pro Trp Leu Gly His Leu Leu Val Gly
210 215 220

Leu Ser Gly Ala Phe Gly Phe Ile Ile Leu Val Tyr Leu Leu Ile Asn
225 230 235 240

Cys Arg Asn Thr Gly Pro Trp Leu Lys Lys Val Leu Lys Cys Asn Thr

```
                245                 250                 255

Pro Asp Pro Ser Lys Phe Phe Ser Gln Leu Ser Ser Glu His Gly Gly
            260                 265                 270

Asp Val Gln Lys Trp Leu Ser Ser Pro Phe Pro Ser Ser Ser Phe Ser
        275                 280                 285

Pro Gly Gly Leu Ala Pro Glu Ile Ser Pro Leu Glu Val Leu Glu Arg
    290                 295                 300

Asp Lys Val Thr Gln Leu Leu Leu Gln Gln Asp Lys Val Pro Glu Pro
305                 310                 315                 320

Ala Ser Leu Ser Ser Asn His Ser Leu Thr Ser Cys Phe Thr Asn Gln
                325                 330                 335

Gly Tyr Phe Phe Phe His Leu Pro Asp Ala Leu Glu Ile Glu Ala Cys
            340                 345                 350

Gln Val Tyr Phe Thr Tyr Asp Pro Tyr Ser Glu Glu Asp Pro Asp Glu
        355                 360                 365

Gly Val Ala Gly Ala Pro Thr Gly Ser Ser Pro Gln Pro Leu Gln Pro
    370                 375                 380

Leu Ser Gly Glu Asp Asp Ala Tyr Cys Thr Phe Pro Ser Arg Asp Asp
385                 390                 395                 400

Leu Leu Leu Phe Ser Pro Ser Leu Leu Gly Gly Pro Ser Pro Pro Ser
                405                 410                 415

Thr Ala Pro Gly Gly Ser Gly Ala Gly Glu Glu Arg Met Pro Pro Ser
            420                 425                 430

Leu Gln Glu Arg Val Pro Arg Asp Trp Asp Pro Gln Pro Leu Gly Pro
        435                 440                 445

Pro Thr Pro Gly Val Pro Asp Leu Val Asp Phe Gln Pro Pro Pro Glu
    450                 455                 460

Leu Val Leu Arg Glu Ala Gly Glu Glu Val Pro Asp Ala Gly Pro Arg
465                 470                 475                 480

Glu Gly Val Ser Phe Pro Trp Ser Arg Pro Pro Gly Gln Gly Glu Phe
                485                 490                 495

Arg Ala Leu Asn Ala Arg Leu Pro Leu Asn Thr Asp Ala Tyr Leu Ser
            500                 505                 510

Leu Gln Glu Leu Gln Gly Gln Asp Pro Thr His Leu Val
        515                 520                 525


<210> SEQ ID NO 436
<211> LENGTH: 214
<212> TYPE: PRT
<213> ORGANISM: Homo sapiens

<400> SEQUENCE: 436

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95
```

```
Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr
    210


<210> SEQ ID NO 437
<211> LENGTH: 369
<212> TYPE: PRT
<213> ORGANISM: Homo sapiens

<400> SEQUENCE: 437

Met Leu Lys Pro Ser Leu Pro Phe Thr Ser Leu Leu Phe Leu Gln Leu
1               5                   10                  15

Pro Leu Leu Gly Val Gly Leu Asn Thr Thr Ile Leu Thr Pro Asn Gly
            20                  25                  30

Asn Glu Asp Thr Thr Ala Asp Phe Phe Leu Thr Thr Met Pro Thr Asp
        35                  40                  45

Ser Leu Ser Val Ser Thr Leu Pro Leu Pro Glu Val Gln Cys Phe Val
    50                  55                  60

Phe Asn Val Glu Tyr Met Asn Cys Thr Trp Asn Ser Ser Ser Glu Pro
65                  70                  75                  80

Gln Pro Thr Asn Leu Thr Leu His Tyr Trp Tyr Lys Asn Ser Asp Asn
                85                  90                  95

Asp Lys Val Gln Lys Cys Ser His Tyr Leu Phe Ser Glu Glu Ile Thr
            100                 105                 110

Ser Gly Cys Gln Leu Gln Lys Lys Glu Ile His Leu Tyr Gln Thr Phe
        115                 120                 125

Val Val Gln Leu Gln Asp Pro Arg Glu Pro Arg Arg Gln Ala Thr Gln
    130                 135                 140

Met Leu Lys Leu Gln Asn Leu Val Ile Pro Trp Ala Pro Glu Asn Leu
145                 150                 155                 160

Thr Leu His Lys Leu Ser Glu Ser Gln Leu Glu Leu Asn Trp Asn Asn
                165                 170                 175

Arg Phe Leu Asn His Cys Leu Glu His Leu Val Gln Tyr Arg Thr Asp
            180                 185                 190

Trp Asp His Ser Trp Thr Glu Gln Ser Val Asp Tyr Arg His Lys Phe
        195                 200                 205

Ser Leu Pro Ser Val Asp Gly Gln Lys Arg Tyr Thr Phe Arg Val Arg
    210                 215                 220

Ser Arg Phe Asn Pro Leu Cys Gly Ser Ala Gln His Trp Ser Glu Trp
225                 230                 235                 240

Ser His Pro Ile His Trp Gly Ser Asn Thr Ser Lys Glu Asn Pro Phe
                245                 250                 255
```

Leu Phe Ala Leu Glu Ala Val Val Ile Ser Val Gly Ser Met Gly Leu
260 265 270

Ile Ile Ser Leu Leu Cys Val Tyr Phe Trp Leu Glu Arg Thr Met Pro
275 280 285

Arg Ile Pro Thr Leu Lys Asn Leu Glu Asp Leu Val Thr Glu Tyr His
290 295 300

Gly Asn Phe Ser Ala Trp Ser Gly Val Ser Lys Gly Leu Ala Glu Ser
305 310 315 320

Leu Gln Pro Asp Tyr Ser Glu Arg Leu Cys Leu Val Ser Glu Ile Pro
325 330 335

Pro Lys Gly Gly Ala Leu Gly Glu Gly Pro Gly Ala Ser Pro Cys Asn
340 345 350

Gln His Ser Pro Tyr Trp Ala Pro Pro Cys Tyr Thr Leu Lys Pro Glu
355 360 365

Thr

<210> SEQ ID NO 438
<211> LENGTH: 347
<212> TYPE: PRT
<213> ORGANISM: Homo sapiens

<400> SEQUENCE: 438

Leu Asn Thr Thr Ile Leu Thr Pro Asn Gly Asn Glu Asp Thr Thr Ala
1 5 10 15

Asp Phe Phe Leu Thr Thr Met Pro Thr Asp Ser Leu Ser Val Ser Thr
20 25 30

Leu Pro Leu Pro Glu Val Gln Cys Phe Val Phe Asn Val Glu Tyr Met
35 40 45

Asn Cys Thr Trp Asn Ser Ser Ser Glu Pro Gln Pro Thr Asn Leu Thr
50 55 60

Leu His Tyr Trp Tyr Lys Asn Ser Asp Asn Asp Lys Val Gln Lys Cys
65 70 75 80

Ser His Tyr Leu Phe Ser Glu Glu Ile Thr Ser Gly Cys Gln Leu Gln
85 90 95

Lys Lys Glu Ile His Leu Tyr Gln Thr Phe Val Val Gln Leu Gln Asp
100 105 110

Pro Arg Glu Pro Arg Arg Gln Ala Thr Gln Met Leu Lys Leu Gln Asn
115 120 125

Leu Val Ile Pro Trp Ala Pro Glu Asn Leu Thr Leu His Lys Leu Ser
130 135 140

Glu Ser Gln Leu Glu Leu Asn Trp Asn Asn Arg Phe Leu Asn His Cys
145 150 155 160

Leu Glu His Leu Val Gln Tyr Arg Thr Asp Trp Asp His Ser Trp Thr
165 170 175

Glu Gln Ser Val Asp Tyr Arg His Lys Phe Ser Leu Pro Ser Val Asp
180 185 190

Gly Gln Lys Arg Tyr Thr Phe Arg Val Arg Ser Arg Phe Asn Pro Leu
195 200 205

Cys Gly Ser Ala Gln His Trp Ser Glu Trp Ser His Pro Ile His Trp
210 215 220

Gly Ser Asn Thr Ser Lys Glu Asn Pro Phe Leu Phe Ala Leu Glu Ala
225 230 235 240

Val Val Ile Ser Val Gly Ser Met Gly Leu Ile Ile Ser Leu Leu Cys
245 250 255

```
Val Tyr Phe Trp Leu Glu Arg Thr Met Pro Arg Ile Pro Thr Leu Lys
            260                 265                 270

Asn Leu Glu Asp Leu Val Thr Glu Tyr His Gly Asn Phe Ser Ala Trp
        275                 280                 285

Ser Gly Val Ser Lys Gly Leu Ala Glu Ser Leu Gln Pro Asp Tyr Ser
    290                 295                 300

Glu Arg Leu Cys Leu Val Ser Glu Ile Pro Pro Lys Gly Gly Ala Leu
305                 310                 315                 320

Gly Glu Gly Pro Gly Ala Ser Pro Cys Asn Gln His Ser Pro Tyr Trp
                325                 330                 335

Ala Pro Pro Cys Tyr Thr Leu Lys Pro Glu Thr
            340                 345


<210> SEQ ID NO 439
<211> LENGTH: 240
<212> TYPE: PRT
<213> ORGANISM: Homo sapiens

<400> SEQUENCE: 439

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240


<210> SEQ ID NO 440
<211> LENGTH: 330
<212> TYPE: PRT
<213> ORGANISM: Homo sapiens

<400> SEQUENCE: 440
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 441
<211> LENGTH: 98
<212> TYPE: PRT
<213> ORGANISM: Artificial Sequence
<220> FEATURE:
<223> OTHER INFORMATION: Synthetic

<400> SEQUENCE: 441

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val

<210> SEQ ID NO 442
<211> LENGTH: 12
<212> TYPE: PRT
<213> ORGANISM: Artificial Sequence
<220> FEATURE:
<223> OTHER INFORMATION: Synthetic

<400> SEQUENCE: 442

Glu Pro Lys Ser Cys Asp Lys Thr His Thr Cys Pro
1 5 10

<210> SEQ ID NO 443
<211> LENGTH: 113
<212> TYPE: PRT
<213> ORGANISM: Artificial Sequence
<220> FEATURE:
<223> OTHER INFORMATION: Synthetic

<400> SEQUENCE: 443

Pro Cys Pro Ala Pro Glu Leu Leu Gly Gly Pro Ser Val Phe Leu Phe
1 5 10 15

Pro Pro Lys Pro Lys Asp Thr Leu Met Ile Ser Arg Thr Pro Glu Val
20 25 30

Thr Cys Val Val Val Asp Val Ser His Glu Asp Pro Glu Val Lys Phe
35 40 45

Asn Trp Tyr Val Asp Gly Val Glu Val His Asn Ala Lys Thr Lys Pro
50 55 60

Arg Glu Glu Gln Tyr Asn Ser Thr Tyr Arg Val Val Ser Val Leu Thr
65 70 75 80

Val Leu His Gln Asp Trp Leu Asn Gly Lys Glu Tyr Lys Cys Lys Val
85 90 95

Ser Asn Lys Ala Leu Pro Ala Pro Ile Glu Lys Thr Ile Ser Lys Ala
100 105 110

Lys

<210> SEQ ID NO 444
<211> LENGTH: 107
<212> TYPE: PRT
<213> ORGANISM: Artificial Sequence
<220> FEATURE:
<223> OTHER INFORMATION: Synthetic

<400> SEQUENCE: 444

Gly Gln Pro Arg Glu Pro Gln Val Tyr Thr Leu Pro Pro Ser Arg Asp
1 5 10 15

Glu Leu Thr Lys Asn Gln Val Ser Leu Thr Cys Leu Val Lys Gly Phe
20 25 30

Tyr Pro Ser Asp Ile Ala Val Glu Trp Glu Ser Asn Gly Gln Pro Glu
35 40 45

```
Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 445
<211> LENGTH: 107
<212> TYPE: PRT
<213> ORGANISM: Artificial Sequence
<220> FEATURE:
<223> OTHER INFORMATION: Synthetic

<400> SEQUENCE: 445

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 446
<211> LENGTH: 220
<212> TYPE: PRT
<213> ORGANISM: Artificial Sequence
<220> FEATURE:
<223> OTHER INFORMATION: Synthetic

<400> SEQUENCE: 446

Pro Cys Pro Ala Pro Glu Leu Leu Gly Gly Pro Ser Val Phe Leu Phe
1               5                   10                  15

Pro Pro Lys Pro Lys Asp Thr Leu Met Ile Ser Arg Thr Pro Glu Val
            20                  25                  30

Thr Cys Val Val Val Asp Val Ser His Glu Asp Pro Glu Val Lys Phe
        35                  40                  45

Asn Trp Tyr Val Asp Gly Val Glu Val His Asn Ala Lys Thr Lys Pro
    50                  55                  60

Arg Glu Glu Gln Tyr Asn Ser Thr Tyr Arg Val Val Ser Val Leu Thr
65                  70                  75                  80

Val Leu His Gln Asp Trp Leu Asn Gly Lys Glu Tyr Lys Cys Lys Val
                85                  90                  95

Ser Asn Lys Ala Leu Pro Ala Pro Ile Glu Lys Thr Ile Ser Lys Ala
            100                 105                 110

Lys Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
```

```
130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175

Phe Phe Leu Tyr Ser Lys Leu Thr Val Asp Lys Ser Arg Trp Gln Gln
            180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220


<210> SEQ ID NO 447
<211> LENGTH: 107
<212> TYPE: PRT
<213> ORGANISM: Artificial Sequence
<220> FEATURE:
<223> OTHER INFORMATION: Synthetic

<400> SEQUENCE: 447

Gly Gln Pro Arg Glu Pro Gln Val Tyr Thr Leu Pro Pro Cys Arg Asp
1               5                   10                  15

Glu Leu Thr Lys Asn Gln Val Ser Leu Trp Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105


<210> SEQ ID NO 448
<211> LENGTH: 107
<212> TYPE: PRT
<213> ORGANISM: Artificial Sequence
<220> FEATURE:
<223> OTHER INFORMATION: Synthetic

<400> SEQUENCE: 448

Gly Gln Pro Arg Glu Pro Gln Val Cys Thr Leu Pro Pro Ser Arg Asp
1               5                   10                  15

Glu Leu Thr Lys Asn Gln Val Ser Leu Ser Cys Ala Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Val Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105
```

<210> SEQ ID NO 449
<211> LENGTH: 220
<212> TYPE: PRT
<213> ORGANISM: Artificial Sequence
<220> FEATURE:
<223> OTHER INFORMATION: Synthetic

<400> SEQUENCE: 449

Pro Cys Pro Ala Pro Glu Leu Leu Gly Gly Pro Ser Val Phe Leu Phe
1 5 10 15

Pro Pro Lys Pro Lys Asp Thr Leu Met Ile Ser Arg Thr Pro Glu Val
20 25 30

Thr Cys Val Val Val Asp Val Ser His Glu Asp Pro Glu Val Lys Phe
35 40 45

Asn Trp Tyr Val Asp Gly Val Glu Val His Asn Ala Lys Thr Lys Pro
50 55 60

Arg Glu Glu Gln Tyr Asn Ser Thr Tyr Arg Val Val Ser Val Leu Thr
65 70 75 80

Val Leu His Gln Asp Trp Leu Asn Gly Lys Glu Tyr Lys Cys Lys Val
85 90 95

Ser Asn Lys Ala Leu Pro Ala Pro Ile Glu Lys Thr Ile Ser Lys Ala
100 105 110

Lys Gly Gln Pro Arg Glu Pro Gln Val Tyr Thr Leu Pro Pro Cys Arg
115 120 125

Asp Glu Leu Thr Lys Asn Gln Val Ser Leu Trp Cys Leu Val Lys Gly
130 135 140

Phe Tyr Pro Ser Asp Ile Ala Val Glu Trp Glu Ser Asn Gly Gln Pro
145 150 155 160

Glu Asn Asn Tyr Lys Thr Thr Pro Pro Val Leu Asp Ser Asp Gly Ser
165 170 175

Phe Phe Leu Tyr Ser Lys Leu Thr Val Asp Lys Ser Arg Trp Gln Gln
180 185 190

Gly Asn Val Phe Ser Cys Ser Val Met His Glu Ala Leu His Asn His
195 200 205

Tyr Thr Gln Lys Ser Leu Ser Leu Ser Pro Gly Lys
210 215 220

<210> SEQ ID NO 450
<211> LENGTH: 220
<212> TYPE: PRT
<213> ORGANISM: Artificial Sequence
<220> FEATURE:
<223> OTHER INFORMATION: Synthetic

<400> SEQUENCE: 450

Pro Cys Pro Ala Pro Glu Leu Leu Gly Gly Pro Ser Val Phe Leu Phe
1 5 10 15

Pro Pro Lys Pro Lys Asp Thr Leu Met Ile Ser Arg Thr Pro Glu Val
20 25 30

Thr Cys Val Val Val Asp Val Ser His Glu Asp Pro Glu Val Lys Phe
35 40 45

Asn Trp Tyr Val Asp Gly Val Glu Val His Asn Ala Lys Thr Lys Pro
50 55 60

Arg Glu Glu Gln Tyr Asn Ser Thr Tyr Arg Val Val Ser Val Leu Thr
65 70 75 80

Val Leu His Gln Asp Trp Leu Asn Gly Lys Glu Tyr Lys Cys Lys Val
85 90 95

Ser Asn Lys Ala Leu Pro Ala Pro Ile Glu Lys Thr Ile Ser Lys Ala
100 105 110

Lys Gly Gln Pro Arg Glu Pro Gln Val Cys Thr Leu Pro Pro Ser Arg
115 120 125

Asp Glu Leu Thr Lys Asn Gln Val Ser Leu Ser Cys Ala Val Lys Gly
130 135 140

Phe Tyr Pro Ser Asp Ile Ala Val Glu Trp Glu Ser Asn Gly Gln Pro
145 150 155 160

Glu Asn Asn Tyr Lys Thr Thr Pro Pro Val Leu Asp Ser Asp Gly Ser
165 170 175

Phe Phe Leu Val Ser Lys Leu Thr Val Asp Lys Ser Arg Trp Gln Gln
180 185 190

Gly Asn Val Phe Ser Cys Ser Val Met His Glu Ala Leu His Asn His
195 200 205

Tyr Thr Gln Lys Ser Leu Ser Leu Ser Pro Gly Lys
210 215 220

<210> SEQ ID NO 451
<211> LENGTH: 113
<212> TYPE: PRT
<213> ORGANISM: Artificial Sequence
<220> FEATURE:
<223> OTHER INFORMATION: Synthetic

<400> SEQUENCE: 451

Pro Cys Pro Ala Pro Glu Ala Ala Gly Gly Pro Ser Val Phe Leu Phe
1 5 10 15

Pro Pro Lys Pro Lys Asp Thr Leu Met Ile Ser Arg Thr Pro Glu Val
20 25 30

Thr Cys Val Val Val Asp Val Ser His Glu Asp Pro Glu Val Lys Phe
35 40 45

Asn Trp Tyr Val Asp Gly Val Glu Val His Asn Ala Lys Thr Lys Pro
50 55 60

Arg Glu Glu Gln Tyr Asn Ser Thr Tyr Arg Val Val Ser Val Leu Thr
65 70 75 80

Val Leu His Gln Asp Trp Leu Asn Gly Lys Glu Tyr Lys Cys Lys Val
85 90 95

Ser Asn Lys Ala Leu Pro Ala Pro Ile Glu Lys Thr Ile Ser Lys Ala
100 105 110

Lys

<210> SEQ ID NO 452
<211> LENGTH: 220
<212> TYPE: PRT
<213> ORGANISM: Artificial Sequence
<220> FEATURE:
<223> OTHER INFORMATION: Synthetic

<400> SEQUENCE: 452

Pro Cys Pro Ala Pro Glu Ala Ala Gly Gly Pro Ser Val Phe Leu Phe
1 5 10 15

Pro Pro Lys Pro Lys Asp Thr Leu Met Ile Ser Arg Thr Pro Glu Val
20 25 30

Thr Cys Val Val Val Asp Val Ser His Glu Asp Pro Glu Val Lys Phe
35 40 45

Asn Trp Tyr Val Asp Gly Val Glu Val His Asn Ala Lys Thr Lys Pro
50 55 60

Arg Glu Glu Gln Tyr Asn Ser Thr Tyr Arg Val Val Ser Val Leu Thr
65 70 75 80

Val Leu His Gln Asp Trp Leu Asn Gly Lys Glu Tyr Lys Cys Lys Val
85 90 95

Ser Asn Lys Ala Leu Pro Ala Pro Ile Glu Lys Thr Ile Ser Lys Ala
100 105 110

Lys Gly Gln Pro Arg Glu Pro Gln Val Tyr Thr Leu Pro Pro Cys Arg
115 120 125

Asp Glu Leu Thr Lys Asn Gln Val Ser Leu Trp Cys Leu Val Lys Gly
130 135 140

Phe Tyr Pro Ser Asp Ile Ala Val Glu Trp Glu Ser Asn Gly Gln Pro
145 150 155 160

Glu Asn Asn Tyr Lys Thr Thr Pro Pro Val Leu Asp Ser Asp Gly Ser
165 170 175

Phe Phe Leu Tyr Ser Lys Leu Thr Val Asp Lys Ser Arg Trp Gln Gln
180 185 190

Gly Asn Val Phe Ser Cys Ser Val Met His Glu Ala Leu His Asn His
195 200 205

Tyr Thr Gln Lys Ser Leu Ser Leu Ser Pro Gly Lys
210 215 220

<210> SEQ ID NO 453
<211> LENGTH: 220
<212> TYPE: PRT
<213> ORGANISM: Artificial Sequence
<220> FEATURE:
<223> OTHER INFORMATION: Synthetic

<400> SEQUENCE: 453

Pro Cys Pro Ala Pro Glu Ala Ala Gly Gly Pro Ser Val Phe Leu Phe
1 5 10 15

Pro Pro Lys Pro Lys Asp Thr Leu Met Ile Ser Arg Thr Pro Glu Val
20 25 30

Thr Cys Val Val Val Asp Val Ser His Glu Asp Pro Glu Val Lys Phe
35 40 45

Asn Trp Tyr Val Asp Gly Val Glu Val His Asn Ala Lys Thr Lys Pro
50 55 60

Arg Glu Glu Gln Tyr Asn Ser Thr Tyr Arg Val Val Ser Val Leu Thr
65 70 75 80

Val Leu His Gln Asp Trp Leu Asn Gly Lys Glu Tyr Lys Cys Lys Val
85 90 95

Ser Asn Lys Ala Leu Pro Ala Pro Ile Glu Lys Thr Ile Ser Lys Ala
100 105 110

Lys Gly Gln Pro Arg Glu Pro Gln Val Cys Thr Leu Pro Pro Ser Arg
115 120 125

Asp Glu Leu Thr Lys Asn Gln Val Ser Leu Ser Cys Ala Val Lys Gly
130 135 140

Phe Tyr Pro Ser Asp Ile Ala Val Glu Trp Glu Ser Asn Gly Gln Pro
145 150 155 160

Glu Asn Asn Tyr Lys Thr Thr Pro Pro Val Leu Asp Ser Asp Gly Ser
165 170 175

Phe Phe Leu Val Ser Lys Leu Thr Val Asp Lys Ser Arg Trp Gln Gln
180 185 190

Gly Asn Val Phe Ser Cys Ser Val Met His Glu Ala Leu His Asn His
195 200 205

-continued

```
Tyr Thr Gln Lys Ser Leu Ser Leu Ser Pro Gly Lys
    210                 215                 220


<210> SEQ ID NO 454
<211> LENGTH: 20
<212> TYPE: PRT
<213> ORGANISM: Artificial Sequence
<220> FEATURE:
<223> OTHER INFORMATION: Synthetic

<400> SEQUENCE: 454

Gly Gly Gly Gly Ser Gly Gly Gly Gly Ser Gly Gly Gly Gly Ser Gly
1               5                   10                  15

Gly Gly Gly Ser
            20


<210> SEQ ID NO 455
<211> LENGTH: 5
<212> TYPE: PRT
<213> ORGANISM: Artificial Sequence
<220> FEATURE:
<223> OTHER INFORMATION: Synthetic; Linker 6

<400> SEQUENCE: 455

Gly Gly Gly Gly Ser
1               5
```

IL2RBETA/COMMON GAMMA CHAIN ANTIBODIES

RELATED APPLICATIONS

This Application is a national stage filing under 35 U.S.C. 371 of International Patent Application Serial No, PCT/EP2018/080765, filed Nov. 9, 2018, which claims priority to Singapore Application No. SG10201709269S, filed Nov. 10, 2017, U.S. Provisional Application No. 62/652,501, filed Apr. 4, 2018, and U.S. Provisional Application No. 62/735,347 filed Sep. 24, 2018, the contents and elements of which are herein incorporated by reference for all purposes.

REFERENCE TO A SEQUENCE LISTING SUBMITTED AS A TEXT FILE VIA EFS-WEB

This Application contains a Sequence Listing which has been submitted in ASCII format via EFS-Web and is hereby incorporated by reference in its entirety. Said ASCII copy, created on Nov. 6, 2020, is named T082470017US00-SUBSEQ-AWWW and is 457 kilobytes in size.

FIELD OF THE INVENTION

The present invention relates to the fields of molecular biology and methods of medical treatment and prophylaxis. In particular, the present invention relates to antigen-binding molecules capable of binding to interleukin 2 receptorβ (IL-2Rβ; CD122) and common γ chain (ye; CD132).

BACKGROUND TO THE INVENTION

IL-2 is an essential cytokine that plays a central role in maintaining T cell homeostasis and mediating proper immune responses. Its high potency as an immune stimulator has led to clinical uses to treat a range of conditions, including cancers and AIDS; it is also widely used as an adjuvant for vaccination to stimulate activation and proliferation of various effector cells. However, the high dose of IL-2 that is required for effective treatment of certain diseases is highly toxic. Major adverse effects of such therapy include vascular leak syndrome (VLS), which results in accumulation of the intravascular fluid in organs such as lung and liver with subsequent pulmonary edema and liver damage. There is no treatment for VLS except withdrawing therapy.

IL-2 exerts its pleiotropic functions by binding to different combinations of receptor components expressed on different cell types: the alpha chain (IL-2Ra, also known as CD25), the beta chain (IL-2R□, or CD122), and the common cytokine receptor gamma chain (IL-2Ry, ye, or CD132). Isolated IL-2Ra has been termed the "low affinity" IL-2 receptor (binding affinity Ko~10 nM) and is not involved in signal transduction. A complex of IL-2R□ and ye binds IL-2 with intermediate affinity (Ko~1 nM), although IL-2Rβ alone has very low affinity (Ko~100 nM) and ye alone has virtually no detectable binding affinity for IL-2. A complex with all three subunits, IL-2Ra, IL-2Rβ, and ye, binds IL-2 with high affinity (Ko~10 pM).

Heterodimerization of IL-2Rβ and ye is necessary and sufficient for effective signal transduction through the interaction of their cytoplasmic domains and subsequent kinase activation of multiple signaling pathways; IL-2Ra plays no role in signal transduction.

High-affinity a-β-yc IL-2Rs are typically found on CD4+ T regulatory cells (Tregs) as well as recently-activated T cells. Intermediate-affinity β-ye IL-2Rs are present at a low level on naïve CDS+ cells, but are prominent on antigen-experienced (memory) and memory-phenotype (MP) CDS+ T cells as well as natural killer (NK) cells. Both MPCD8+ T cells and NK cells express very high levels of IL-2Rβ and readily respond to IL-2.

Previous studies have indicated that VLS is caused by the release of proinflammatory cytokines from IL-2-activated NK cells. However, a recent study suggested that IL-2-induced pulmonary edema may result from direct binding of IL-2 to lung endothelial cells, which express functional high affinity α-β-γc IL-2Rs. This was evidenced by the observation that interaction of IL-2 with lung endothelial cells was abrogated by blocking anti-IL-2Rα monoclonal antibody (mAb), in IL-2Rα-deficient host mice, or by the use of an IL-2/anti-IL-2 mAb (IL-2/mAb) complex in which the antibody prevents IL-2/IL-2Rα interaction, thus preventing VLS.

SUMMARY OF THE INVENTION

The present invention relates to antigen-binding molecules, that bind to CD122 (i.e. IL-2Rβ) and/or common γ chain (γc; CD132).

In one aspect, the present invention provides an antigen-binding molecule, optionally isolated, which is capable of binding to CD122 and CD132.

In some embodiments the antigen-binding molecule comprises:

(a) an antigen-binding molecule which is capable of binding to CD122, comprising:
  - a heavy chain variable (VH) region incorporating the following CDRs:
    - HC-CDR1 having the amino acid sequence of one of SEQ ID NOs:105, 106, or 108 to 115
    - HC-CDR2 having the amino acid sequence of one of SEQ ID NOs:119 to 127
    - HC-CDR3 having the amino acid sequence of one of SEQ ID NOs:133 to 144, and
  - a light chain variable (VL) region incorporating the following CDRs:
    - LC-CDR1 having the amino acid sequence of one of SEQ ID NOs:151 to 161
    - LC-CDR2 having the amino acid sequence of one of SEQ ID NOs:164, or 169 to 176
    - LC-CDR3 having the amino acid sequence of one of SEQ ID NOs:182 to 194;
  - or a variant thereof in which one or two or three amino acids in one or more of HC-CDR1, HC-CDR2, HC-CDR3, LC-CDR1, LC-CDR2 or LC-CDR3 are substituted with another amino acid; and (b) an antigen-binding molecule which is capable of binding to CD132, comprising:
  - a VH region incorporating the following CDRs:
    - HC-CDR1 having the amino acid sequence of one of SEQ ID NOs:106, 108, 112, or 195 to 201
    - HC-CDR2 having the amino acid sequence of one of SEQ ID NOs:119, 120, 124, or 202 to 209
    - HC-CDR3 having the amino acid sequence of one of SEQ ID NOs:210 to 225, and
  - a VL region incorporating the following CDRs;
    - LC-CDR1 having the amino acid sequence of one of SEQ ID NOs:151, or 226 to 235
    - LC-CDR2 having the amino acid sequence of one of SEQ ID NOs:174, or 236 to 245
    - LC-CDR3 having the amino acid sequence of one of SEQ ID NOs:189, or 247 to 258;

or a variant thereof in which one or two or three amino acids in one or more of HC-CDR1 HC-CDR2, HC-CDR3, LC-CDR1, LC-CDR2 or LC-CDR3 are substituted with another amino acid.

In some embodiments the antigen-binding molecule which is capable of binding to CD122 comprises:

(P1E7) a VH region incorporating the following CDRs:
HC-CDR1 having the amino acid sequence of SEQ ID NO:108
HC-CDR2 having the amino acid sequence of SEQ ID NO:120
HC-CDR3 having the amino acid sequence of SEQ ID NO:133; and
a VL region incorporating the following CDRs:
LC-CDR1 having the amino acid sequence of SEQ ID NO:151
LC-CDR2 having the amino acid sequence of SEQ ID NO:169
LC-CDR3 having the amino acid sequence of SEQ ID NO:182; or (P1B10) a VH region incorporating the following CDRs:
HC-CDR1 having the amino acid sequence of SEQ ID NO:109
HC-CDR2 having the amino acid sequence of SEQ ID NO:121
HC-CDR3 having the amino acid sequence of SEQ ID NO:134; and
VL region incorporating the following CDRs:
LC-CDR1 having the amino acid sequence of SEQ ID NO:152
LC-CDR2 having the amino acid sequence of SEQ ID NO:164
LC-CDR3 having the amino acid sequence of SEQ ID NO:183; or (P1F3) a VH region incorporating the following CDRs:
HC-CDR1 having the amino acid sequence of SEQ ID NO:105
HC-CDR2 having the amino acid sequence of SEQ ID NO:122
HC-CDR3 having the amino acid sequence of SEQ ID NO:135; and
a VL region incorporating the following CDRs:
LC-CDR1 having the amino acid sequence of SEQ ID NO:153
LC-CDR2 having the amino acid sequence of SEQ ID NO:164
LC-CDR3 having the amino acid sequence of SEQ ID NO:184; or (P1 D10) a VH region incorporating the following CDRs:
HC-CDR1 having the amino acid sequence of SEQ ID NO:110
HC-CDR2 having the amino acid sequence of SEQ ID NO:119
HC-CDR3 having the amino acid sequence of SEQ ID NO:136; and
a VL region incorporating the following CDRs:
LC-CDR1 having the amino acid sequence of SEQ ID NO:154
LC-CDR2 having the amino acid sequence of SEQ ID NO:170
LC-CDR3 having the amino acid sequence of SEQ ID NO:185; or (P1E1) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:137; and
a VL region incorporating the following CDRs:
LC-CDR1 having the amino acid sequence of SEQ ID NO:155
LC-CDR2 having the amino acid sequence of SEQ ID NO:171
LC-CDR3 having the amino acid sequence of SEQ ID NO:186; or (P2B11) a VH region incorporating the following CDRs:
HC-CDR1 having the amino acid sequence of SEQ ID NO:111
HC-CDR2 having the amino acid sequence of SEQ ID NO:123
HC-CDR3 having the amino acid sequence of SEQ ID NO:138; and
a VL region incorporating the following CDRs:
LC-CDR1 having the amino acid sequence of SEQ ID NO:156
LC-CDR2 having the amino acid sequence of SEQ ID NO:172
LC-CDR3 having the amino acid sequence of SEQ ID NO:187; or (P2C9) a VH region incorporating the following CDRs:
HC-CDR1 having the amino acid sequence of SEQ ID NO:112
HC-CDR2 having the amino acid sequence of SEQ ID NO:124
HC-CDR3 having the amino acid sequence of SEQ ID NO:139; and
a VL region incorporating the following CDRs:
LC-CDR1 having the amino acid sequence of SEQ ID NO:157
LC-CDR2 having the amino acid sequence of SEQ ID NO:173
LC-CDR3 having the amino acid sequence of SEQ ID NO:188; or (P2C10) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:140; and
a VL region incorporating the following CDRs:
LC-CDR1 having the amino acid sequence of SEQ ID NO:158
LC-CDR2 having the amino acid sequence of SEQ ID NO:174
LC-CDR3 having the amino acid sequence of SEQ ID NO:189; or (P2C11) a VH region incorporating the following CDRs:
HC-CDR1 having the amino acid sequence of SEQ ID NO:113
HC-CDR2 having the amino acid sequence of SEQ ID NO:125
HC-CDR3 having the amino acid sequence of SEQ ID NO:141; and
a VL region incorporating the following CDRs:
LC-CDR1 having the amino acid sequence of SEQ ID NO:159
LC-CDR2 having the amino acid sequence of SEQ ID NO:175
LC-CDR3 having the amino acid sequence of SEQ ID NO:190; or (P2E6) a VH region incorporating the following CDRs:
HC-CDR1 having the amino acid sequence of SEQ ID NO:114
HC-CDR2 having the amino acid sequence of SEQ ID NO:126
HC-CDR3 having the amino acid sequence of SEQ ID NO:142; and
a VL region incorporating the following CDRs:
LC-CDR1 having the amino acid sequence of SEQ ID NO:160
LC-CDR2 having the amino acid sequence of SEQ ID NO:176
LC-CDR3 having the amino acid sequence of SEQ ID NO:191; or
(P2E11) a VH region incorporating the following CDRs:
HC-CDR1 having the amino acid sequence of SEQ ID NO:109
HC-CDR2 having the amino acid sequence of SEQ ID NO:121
HC-CDR3 having the amino acid sequence of SEQ ID NO:134; and
a VL region incorporating the following CDRs:
LC-CDR1 having the amino acid sequence of SEQ ID NO:159
LC-CDR2 having the amino acid sequence of SEQ ID NO:164
LC-CDR3 having the amino acid sequence of SEQ ID NO:192; or
(P2F9) a VH region incorporating the following CDRs;
HC-CDR1 having the amino acid sequence of SEQ ID NO:115
HC-CDR2 having the amino acid sequence of SEQ ID NO:127
HC-CDR3 having the amino acid sequence of SEQ ID NO:143; and
a VL region incorporating the following CDRs:
LC-CDR1 having the amino acid sequence of SEQ ID NO:151
LC-CDR2 having the amino acid sequence of SEQ ID NO:174
LC-CDR3 having the amino acid sequence of SEQ ID NO:193; or
(P2F10) a VH region incorporating the following CDRs:
HC-CDR1 having the amino acid sequence of SEQ ID NO:115
HC-CDR2 having the amino acid sequence of SEQ ID NO:127
HC-CDR3 having the amino acid sequence of SEQ ID NO:144; and
a VL region incorporating the following CDRs:
LC-CDR1 having the amino acid sequence of SEQ ID NO:161
LC-CDR2 having the amino acid sequence of SEQ ID NO:164
LC-CDR3 having the amino acid sequence of SEQ ID NO:194.

In some embodiments the antigen-binding molecule which is capable of binding to CD122 comprises:

a VH region comprising an amino acid sequence having at least 85% sequence identity to one of SEQ ID NOs:22 to 34; and
a VL region comprising an amino acid sequence having at least 85% sequence identity to one of SEQ ID NOs:53 to 65.

In some embodiments the antigen-binding molecule which is capable of binding to CD122 comprises:

(P1E7) a VH region comprising an amino acid sequence having at least 85% sequence identity to SEQ ID NO:22; and
a VL region comprising an amino acid sequence having at least 85% sequence identity to SEQ ID NO:53; or
(P1B10) a VH region comprising an amino acid sequence having at least 85% sequence identity to SEQ ID NO:23; and
a VL region comprising an amino acid sequence having at least 85% sequence identity to SEQ ID NO:54; or
(P1F3) a VH region comprising an amino acid sequence having at least 85% sequence identity to SEQ ID NO:24; and
a VL region comprising an amino acid sequence having at least 85% sequence identity to SEQ ID NO:55; or
(P10) a VH region comprising an amino acid sequence having at least 85% sequence identity to SEQ ID NO:25; and
a VL region comprising an amino acid sequence having at least 85% sequence identity to SEQ ID NO:56; or
(P1E1) a VH region comprising an amino acid sequence having at least 85% sequence identity to SEQ ID NO:26; and
a VL region comprising an amino acid sequence having at least 85% sequence identity to SEQ ID NO:57; or
(P2B11) a VH region comprising an amino acid sequence having at least 85% sequence identity to SEQ ID NO:27; and
a VL region comprising an amino acid sequence having at least 85% sequence identity to SEQ ID NO:58; or
(P2C9) a VH region comprising an amino acid sequence having at least 85% sequence identity to SEQ ID NO:28; and
a VL region comprising an amino acid sequence having at least 85% sequence identity to SEQ ID NO:59; or
(P2C10) a VH region comprising an amino acid sequence having at least 85% sequence identity to SEQ ID NO:29; and
a VL region comprising an amino acid sequence having at least 85% sequence identity to SEQ ID NO:60; or
(P2C11) a VH region comprising an amino acid sequence having at least 85% sequence identity to SEQ ID NO:30; and
a VL region comprising an amino acid sequence having at least 85% sequence identity to SEQ ID NO:61; or
(P2E6) a VH region comprising an amino acid sequence having at least 85% sequence identity to SEQ ID NO:31; and
a VL region comprising an amino acid sequence having at least 85% sequence identity to SEQ ID NO:62; or
(P2E11) a VH region comprising an amino acid sequence having at least 85% sequence identity to SEQ ID NO:32; and
a VL region comprising an amino acid sequence having at least 85% sequence identity to SEQ ID NO:63; or
(P2F9) a VH region comprising an amino acid sequence having at least 85% sequence identity to SEQ ID NO:33; and
a VL region comprising an amino acid sequence having at least 85% sequence identity to SEQ ID NO:64; or
(P2F10) a VH region comprising an amino acid sequence having at least 85% sequence identity to SEQ ID NO:34; and
a VL region comprising an amino acid sequence having at least 85% sequence identity to SEQ ID NO:65.

In some embodiments the antigen-binding molecule which is capable of binding to CD132 comprises:

(P1A3) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:210; and
a VL region incorporating the following CDRs:
LC-CDR1 having the amino acid sequence of SEQ ID NO:151
LC-CDR2 having the amino acid sequence of SEQ ID NO:236
LC-CDR3 having the amino acid sequence of SEQ ID NO:189; or
(P2B9) a VH region incorporating the following CDRs:
HC-CDR1 having the amino acid sequence of SEQ ID NO:195
HC-CDR2 having the amino acid sequence of SEQ ID NO:202
HC-CDR3 having the amino acid sequence of SEQ ID NO:211; and
a VL region incorporating the following CDRs:
LC-CDR1 having the amino acid sequence of SEQ ID NO:226
LC-CDR2 having the amino acid sequence of SEQ ID NO:237
LC-CDR3 having the amino acid sequence of SEQ ID NO:247; or
(P1A3_B3) a VH region incorporating the following CDRs:
HC-CDR1 having the amino acid sequence of SEQ ID NO:106
HC-CDR2 having the amino acid sequence of SEQ ID NO:203
HC-CDR3 having the amino acid sequence of SEQ ID NO:210; and
a VL region incorporating the following CDRs:
LC-CDR1 having the amino acid sequence of SEQ ID NO:151
LC-CDR2 having the amino acid sequence of SEQ ID NO:236
LC-CDR3 having the amino acid sequence of SEQ ID NO:189; or
(P1A3_B4) a VH region incorporating the following CDRs:
HC-CDR1 having the amino acid sequence of SEQ ID NO:108
HC-CDR2 having the amino acid sequence of SEQ ID NO:203
HC-CDR3 having the amino acid sequence of SEQ ID NO:210; and
a VL region incorporating the following CDRs:
LC-CDR1 having the amino acid sequence of SEQ ID NO:151
LC-CDR2 having the amino acid sequence of SEQ ID NO:236
LC-CDR3 having the amino acid sequence of SEQ ID NO:189; or
(P1A3_E9) a VH region incorporating the following CDRs:
HC-CDR1 having the amino acid sequence of SEQ ID NO:106
HC-CDR2 having the amino acid sequence of SEQ ID NO:203
HC-CDR3 having the amino acid sequence of SEQ ID NO:210; and
a VL region incorporating the following CDRs:
LC-CDR1 having the amino acid sequence of SEQ ID NO:151
LC-CDR2 having the amino acid sequence of SEQ ID NO:236
LC-CDR3 having the amino acid sequence of SEQ ID NO:189; or
(P1A3_E8) a VH region incorporating the following CDRs:
HC-CDR1 having the amino acid sequence of SEQ ID NO:106
HC-CDR2 having the amino acid sequence of SEQ ID NO:203
HC-CDR3 having the amino acid sequence of SEQ ID NO:210; and
a VL region incorporating the following CDRs:
LC-CDR1 having the amino acid sequence of SEQ ID NO:151
LC-CDR2 having the amino acid sequence of SEQ ID NO:236
LC-CDR3 having the amino acid sequence of SEQ ID NO:189; or
(P1A3_FW2) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:210; and
a VL region incorporating the following CDRs:
LC-CDR1 having the amino acid sequence of SEQ ID NO:151
LC-CDR2 having the amino acid sequence of SEQ ID NO:236
LC-CDR3 having the amino acid sequence of SEQ ID NO:189; or
(P1A10) a VH region incorporating the following CDRs:
HC-CDR1 having the amino acid sequence of SEQ ID NO:196
HC-CDR2 having the amino acid sequence of SEQ ID NO:204
HC-CDR3 having the amino acid sequence of SEQ ID NO:212; and
a VL region incorporating the following CDRs:
LC-CDR1 having the amino acid sequence of SEQ ID NO:227
LC-CDR2 having the amino acid sequence of SEQ ID NO:238
LC-CDR3 having the amino acid sequence of SEQ ID NO:248; or
(P1B6) a VH region incorporating the following CDRs:
HC-CDR1 having the amino acid sequence of SEQ ID NO:108
HC-CDR2 having the amino acid sequence of SEQ ID NO:120
HC-CDR3 having the amino acid sequence of SEQ ID NO:213; and
a VL region incorporating the following CDRs:
LC-CDR1 having the amino acid sequence of SEQ ID NO:151
LC-CDR2 having the amino acid sequence of SEQ ID NO:239
LC-CDR3 having the amino acid sequence of SEQ ID NO:249; or
(P1C10) a VH region incorporating the following CDRs:
HC-CDR1 having the amino acid sequence of SEQ ID NO:112

HC-CDR2 having the amino acid sequence of SEQ ID NO:124

HC-CDR3 having the amino acid sequence of SEQ ID NO:214; and a VL region incorporating the following CDRs:

LC-CDR1 having the amino acid sequence of SEQ ID NO:228

LC-CDR2 having the amino acid sequence of SEQ ID NO:240

LC-CDR3 having the amino acid sequence of SEQ ID NO:250; or (P1D7) a VH region incorporating the following CDRs:

HC-CDR1 having the amino acid sequence of SEQ ID NO:197

HC-CDR2 having the amino acid sequence of SEQ ID NO:206

HC-CDR3 having the amino acid sequence of SEQ ID NO:215; and a VL region incorporating the following CDRs:

LC-CDR1 having the amino acid sequence of SEQ ID NO:229

LC-CDR2 having the amino acid sequence of SEQ ID NO:241

LC-CDR3 having the amino acid sequence of SEQ ID NO:251; or (P1E8) a VH region incorporating the following CDRs:

HC-CDR1 having the amino acid sequence of SEQ ID NO:198

HC-CDR2 having the amino acid sequence of SEQ ID NO:120

HC-CDR3 having the amino acid sequence of SEQ ID NO:216; and a VL region incorporating the following CDRs:

LC-CDR1 having the amino acid sequence of SEQ ID NO:230

LC-CDR2 having the amino acid sequence of SEQ ID NO:242

LC-CDR3 having the amino acid sequence of SEQ ID NO:252; or (P2B2) VH region incorporating the following CDRs:

HC-CDR1 having the amino acid sequence of SEQ ID NO:108

HC-CDR2 having the amino acid sequence of SEQ ID NO:207

HC-CDR3 having the amino acid sequence of SEQ ID NO:217; and a VL region incorporating the following CDRs:

LC-CDR1 having the amino acid sequence of SEQ ID NO:151

LC-CDR2 having the amino acid sequence of SEQ ID NO:174

LC-CDR3 having the amino acid sequence of SEQ ID NO:253; or (P2B7) a VH region incorporating the following CDRs:

HC-CDR1 having the amino acid sequence of SEQ ID NO:106

HC-CDR2 having the amino acid sequence of SEQ ID NO:119

HC-CDR3 having the amino acid sequence of SEQ ID NO:218; and a VL region incorporating the following CDRs:

LC-CDR1 having the amino acid sequence of SEQ ID NO:231

LC-CDR2 having the amino acid sequence of SEQ ID NO:174

LC-CDR3 having the amino acid sequence of SEQ ID NO:254; or (P2D11) a VH region incorporating the following CDRs:

HC-CDR1 having the amino acid sequence of SEQ ID NO:199

HC-CDR2 having the amino acid sequence of SEQ ID NO:208

HC-CDR3 having the amino acid sequence of SEQ ID NO:219; and a VL region incorporating the following CDRs:

LC-CDR1 having the amino acid sequence of SEQ ID NO:232

LC-CDR2 having the amino acid sequence of SEQ ID NO:243

LC-CDR3 having the amino acid sequence of SEQ ID NO:255; or (P2F10) a VH region incorporating the following CDRs:

HC-CDR1 having the amino acid sequence of SEQ ID NO:200

HC-CDR2 having the amino acid sequence of SEQ ID NO:209

HC-CDR3 having the amino acid sequence of SEQ ID NO:220; and a VL region incorporating the following CDRs:

LC-CDR1 having the amino acid sequence of SEQ ID NO:233

LC-CDR2 having the amino acid sequence of SEQ ID NO:244

LC-CDR3 having the amino acid sequence of SEQ ID NO:256; or (P2H4) a VH region incorporating the following CDRs:

HC-CDR1 having the amino acid sequence of SEQ ID NO:108

HC-CDR2 having the amino acid sequence of SEQ ID NO:120

HC-CDR3 having the amino acid sequence of SEQ ID NO:221; and a VL region incorporating the following CDRs:

LC-CDR1 having the amino acid sequence of SEQ ID NO:234

LC-CDR2 having the amino acid sequence of SEQ ID NO:174

LC-CDR3 having the amino acid sequence of SEQ ID NO:257; or (P2D3) a VH region incorporating the following CDRs:

HC-CDR1 having the amino acid sequence of SEQ ID NO:201

HC-CDR2 having the amino acid sequence of SEQ ID NO:119

HC-CDR3 having the amino acid sequence of SEQ ID NO:222; and a VL region incorporating the following CDRs:

LC-CDR1 having the amino acid sequence of SEQ ID NO:151

LC-CDR2 having the amino acid sequence of SEQ ID NO:174

LC-CDR3 having the amino acid sequence of SEQ ID NO:189; or (P1G4) a VH region incorporating the following CDRs:

HC-CDR1 having the amino acid sequence of SEQ ID NO:106

HC-CDR2 having the amino acid sequence of SEQ ID NO:119

HC-CDR3 having the amino acid sequence of SEQ ID NO:223; and

VL region incorporating the following CDRs:

LC-CDR1 having the amino acid sequence of SEQ ID NO:151

LC-CDR2 having the amino acid sequence of SEQ ID NO:174
LC-CDR3 having the amino acid sequence of SEQ ID NO:258; or
(P1B12) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:224; and
a VL region incorporating the following CDRs:
LC-CDR1 having the amino acid sequence of SEQ ID NO:235
LC-CDR2 having the amino acid sequence of SEQ ID NO:174
LC-CDR3 having the amino acid sequence of SEQ ID NO:189; or
(P1C7) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:225; and
a VL region incorporating the following CDRs:
LC-CDR1 having the amino acid sequence of SEQ ID NO:151
LC-CDR2 having the amino acid sequence of SEQ ID NO:245
LC-CDR3 having the amino acid sequence of SEQ ID NO:189.

In some embodiments the antigen-binding molecule which is capable of binding to CD132 comprises:
a VH region comprising an amino acid sequence having at least 85% sequence identity to one of SEQ ID NOs:66 to 84; and
a VL region comprising an amino acid sequence having at least 85% sequence identity to one of SEQ ID NOs:85 to 102.

In some embodiments the antigen-binding molecule which is capable of binding to CD132 comprises:
(P1A3) a VH region comprising an amino acid sequence having at least 85% sequence identity to SEQ ID NO:66; and
a VL region comprising an amino acid sequence having at least 85% sequence identity to SEQ ID NO:85; or
(P2B9) a VH region comprising an amino acid sequence having at least 85% sequence identity to SEQ ID NO:67; and
a VL region comprising an amino acid sequence having at least 85% sequence identity to SEQ ID NO:86; or
(P1A3_B3) a VH region comprising an amino acid sequence having at least 85% sequence identity to SEQ ID NO:68; and
a VL region comprising an amino acid sequence having at least 85% sequence identity to SEQ ID NO:85; or
(P1A3_B4) a VH region comprising an amino acid sequence having at least 85% sequence identity to SEQ ID NO:68; and
a VL region comprising an amino acid sequence having at least 85% sequence identity to SEQ ID NO:87; or
(P1A3_E9) a VH region comprising an amino acid sequence having at least 85% sequence identity to SEQ ID NO:68; and
a VL region comprising an amino acid sequence having at least 85% sequence identity to SEQ ID NO:85; or
(P1A3_E8) a VH region comprising an amino acid sequence having at least 85% sequence identity to SEQ ID NO:69; and
a VL region comprising an amino acid sequence having at least 85% sequence identity to SEQ ID NO:85; or
(P1A3_FW2) a VH region comprising an amino acid sequence having at least 85% sequence identity to SEQ ID NO:70; and
a VL region comprising an amino acid sequence having at least 85% sequence identity to SEQ ID NO:88; or
(P1A10) a VH region comprising an amino acid sequence having at least 85% sequence identity to SEQ ID NO:71; and
a VL region comprising an amino acid sequence having at least 85% sequence identity to SEQ ID NO:89; or
(P1B6) a VH region comprising an amino acid sequence having at least 85% sequence identity to SEQ ID NO:72; and
a VL region comprising an amino acid sequence having at least 85% sequence identity to SEQ ID NO:90; or
(P1C10) a VH region comprising an amino acid sequence having at least 85% sequence identity to SEQ ID NO:73; and
a VL region comprising an amino acid sequence having at least 85% sequence identity to SEQ ID NO:91; or
(P1D7) a VH region comprising an amino acid sequence having at least 85% sequence identity to SEQ ID NO:74; and
a VL region comprising an amino acid sequence having at least 85% sequence identity to SEQ ID NO:92; or
(P1E8) a VH region comprising an amino acid sequence having at least 85% sequence identity to SEQ ID NO:75; and
a VL region comprising an amino acid sequence having at least 85% sequence identity to SEQ ID NO:93; or
(P2B2) a VH region comprising an amino acid sequence having at least 85% sequence identity to SEQ ID NO:76; and
a VL region comprising an amino acid sequence having at least 85% sequence identity to SEQ ID NO:94; or
(P2B7) a VH region comprising an amino acid sequence having at least 85% sequence identity to SEQ ID NO:77; and
a VL region comprising an amino acid sequence having at least 85% sequence identity to SEQ ID NO:95; or
(P2D11) a VH region comprising an amino acid sequence having at least 85% sequence identity to SEQ ID NO:78; and
a VL region comprising an amino acid sequence having at least 85% sequence identity to SEQ ID NO:96; or
(P2F10) a VH region comprising an amino acid sequence having at least 85% sequence identity to SEQ ID NO:79; and
a VL region comprising an amino acid sequence having at least 85% sequence identity to SEQ ID NO:97; or
(P2H4) a VH region comprising an amino acid sequence having at least 85% sequence identity to SEQ ID NO:80; and
a VL region comprising an amino acid sequence having at least 85% sequence identity to SEQ ID NO:98; or
(P2D3) a VH region comprising an amino acid sequence having at least 85% sequence identity to SEQ ID NO:81; and
a VL region comprising an amino acid sequence having at least 85% sequence identity to SEQ ID NO:99; or (P1G4) a VH region comprising an amino acid sequence having at least 85% sequence identity to SEQ ID NO:82; and a VL region comprising an amino acid sequence having at least 85% sequence identity to SEQ ID NO:100; or (P1B12) a VH region comprising an amino acid sequence having at least 85% sequence identity to SEQ ID NO:83; and a VL region comprising an amino acid sequence having at least 85% sequence identity to SEQ ID NO:101; or (P1C7) a VH region comprising an amino acid sequence having at least 85% sequence identity to SEQ ID NO:84; and a VL region comprising an amino acid sequence having at least 85% sequence identity to SEQ ID NO:102.

In some embodiments the antigen-binding molecule comprises:

(a) an antigen-binding molecule which is capable of binding to CD122, comprising:

a heavy chain variable (VH) region incorporating the following CDRs:

HC-CDR1 having the amino acid sequence of one of SEQ ID NOs:103 to 115

HC-CDR2 having the amino acid sequence of one of SEQ ID NOs:116 to 127

HC-CDR3 having the amino acid sequence of one of SEQ ID NOs:128 to 144; and a light chain variable (VL) region incorporating the following CDRs:

LC-CDR1 having the amino acid sequence of one of SEQ ID NOs:145 to 161

LC-CDR2 having the amino acid sequence of one of SEQ ID NOs:162 to 176

LC-CDR3 having the amino acid sequence of one of SEQ ID NOs:177 to 194;

or a variant thereof in which one or two or three amino acids in one or more of HC-CDR1, HC-CDR2, HC-CDR3, LC-CDR2 or LC-CDR3 are substituted with another amino acid.

(b) an antigen-binding molecule which is capable of binding to CD132, comprising:

a VH region incorporating the following CDRs:

HC-CDR1 having the amino acid sequence of one of SEQ ID NOs:106, 108, 112, or 196 to 201

HC-CDR2 having the amino acid sequence of one of SEQ ID NOs:119, 120, 124, or 204 to 209

HC-CDR3 having the amino acid sequence of one of SEQ ID NOs:212 to 225; and a VL region incorporating the following CDRs:

LC-CDR1 having the amino acid sequence of one of SEQ ID NOs:151, or 227 to 235

LC-CDR2 having the amino acid sequence of one of SEQ ID NOs:174, or 238 to 245

LC-CDR3 having the amino acid sequence of one of SEQ ID NOs:189, or 248 to 258;

or a variant thereof in which one or two or three amino acids in one or more of HC-CDR1 HC-CDR2, HC-CDR3, LC-CDR1, LC-CDR2 or LC-CDR3 are substituted with another amino acid.

In some embodiments the antigen-binding molecule which is capable of binding to CD122 comprises:

(P2C4) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRS:

LC-CDR1 having the amino acid sequence of SEQ ID NO:145

LC-CDR2 having the amino acid sequence of SEQ ID NO:162

LC-CDR3 having the amino acid sequence of SEQ ID NO:177; or (P2C4_A4) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and

VL region incorporating the following CDRs:

LC-CDR1 having the amino acid sequence of SEQ ID NO:149

LC-CDR2 having the amino acid sequence of SEQ ID NO:162

LC-CDR3 having the amino acid sequence of SEQ ID NO:177; or (P2C4_B1) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:166

LC-CDR3 having the amino acid sequence of SEQ ID NO:177; or (P2C4_B5) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_C4) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:165

LC-CDR3 having the amino acid sequence of SEQ ID NO:181; or (P2C4_C7) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:123; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_D10) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_E6) a VH region incorporating the following CDRs:

HC-CDR1 having the amino acid sequence of SEQ ID NO:103

HC-CDR2 having the amino acid sequence of SEQ ID NO:115

HC-CDR3 having the amino acid sequence of SEQ ID NO:128; and a VL region incorporating the following CDRs:

LC-CDR1 having the amino acid sequence of SEQ ID NO:149

LC-CDR2 having the amino acid sequence of SEQ ID NO:162

LC-CDR3 having the amino acid sequence of SEQ ID NO:177; or (P2C4_E7) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_F8) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2H7) a VH region incorporating the following CDRs:

HC-CDR1 having the amino acid sequence of SEQ ID NO:104

HC-CDR2 having the amino acid sequence of SEQ ID NO:117

HC-CDR3 having the amino acid sequence of SEQ ID NO:129; and a VL region incorporating the following CDRs:

LC-CDR1 having the amino acid sequence of SEQ ID NO:146

LC-CDR2 having the amino acid sequence of SEQ ID NO:163

LC-CDR3 having the amino acid sequence of SEQ ID NO:178; or (P2D12) a VH region incorporating the following CDRs:

HC-CDR1 having the amino acid sequence of SEQ ID NO:105

HC-CDR2 having the amino acid sequence of SEQ ID NO:118

HC-CDR3 having the amino acid sequence of SEQ ID NO:130; and a VL region incorporating the following CDRs:

LC-CDR1 having the amino acid sequence of SEQ ID NO:147

LC-CDR2 having the amino acid sequence of SEQ ID NO:164

LC-CDR3 having the amino acid sequence of SEQ ID NO:179; or (P1G11) a VH region incorporating the following CDRs:

HC-CDR1 having the amino acid sequence of SEQ ID NO:106

HC-CDR2 having the amino acid sequence of SEQ ID NO:119

HC-CDR3 having the amino acid sequence of SEQ ID NO:131; and a VL region incorporating the following CDRs:

LC-CDR1 having the amino acid sequence of SEQ ID NO:148

LC-CDR2 having the amino acid sequence of SEQ ID NO:165

LC-CDR3 having the amino acid sequence of SEQ ID NO:180; or (P2C4_A9) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:132; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:177; or (P2C4_B6) a VH region incorporating the following CDRs:

HC-CDR1 having the amino acid sequence of SEQ ID NO:107

HC-CDR2 having the amino acid sequence of SEQ ID NO:116

HC-CDR3 having the amino acid sequence of SEQ ID NO:128; and

VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_E9) a VH region incorporating the following CDRs:

HC-CDR1 having the amino acid sequence of SEQ ID NO:107

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:168

LC-CDR3 having the amino acid sequence of SEQ ID NO:181; or (P2C4_B8) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_B12) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:150

LC-CDR2 having the amino acid sequence of SEQ ID NO:167

LC-CDR3 having the amino acid sequence of SEQ ID NO:177; or (P2C4_C1) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:149

LC-CDR2 having the amino acid sequence of SEQ ID NO:162

LC-CDR3 having the amino acid sequence of SEQ ID NO:177; or (P2C4_C12) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and

VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_E2) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_E3) a VH region incorporating the following CDRs:

HC-CDR1 having the amino acid sequence of SEQ ID NO:107

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:181; or (P2C4_E8) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and

VL region incorporating the following CDRs:

LC-CDR1 having the amino acid sequence of SEQ ID NO:145

LC-CDR2 having the amino acid sequence of SEQ ID NO:162
LC-CDR3 having the amino acid sequence of SEQ ID NO:181; or (P2C4_F11) a VH region incorporating the following CDRs:
HC-CDR1 having the amino acid sequence of SEQ ID NO:103
HC-CDR2 having the amino acid sequence of SEQ ID NO:116
HC-CDR3 having the amino acid sequence of SEQ ID NO:128; and
a VL region incorporating the following CDRs:
LC-CDR1 having the amino acid sequence of SEQ ID NO:145
LC-CDR2 having the amino acid sequence of SEQ ID NO:162
LC-CDR3 having the amino acid sequence of SEQ ID NO:181; or (P2C4_G2) a VH region incorporating the following CDRs:
HC-CDR1 having the amino acid sequence of SEQ ID NO:103
HC-CDR2 having the amino acid sequence of SEQ ID NO:116
HC-CDR3 having the amino acid sequence of SEQ ID NO:128; and
a VL region incorporating the following CDRs:
LC-CDR1 having the amino acid sequence of SEQ ID NO:145
LC-CDR2 having the amino acid sequence of SEQ ID NO:162
LC-CDR3 having the amino acid sequence of SEQ ID NO:181; or (P2C4_G11) a VH region incorporating the following CDRs:
HC-CDR1 having the amino acid sequence of SEQ ID NO:103
HC-CDR2 having the amino acid sequence of SEQ ID NO:116
HC-CDR3 having the amino acid sequence of SEQ ID NO:128; and
a VL region incorporating the following CDRs:
LC-CDR1 having the amino acid sequence of SEQ ID NO:145
LC-CDR2 having the amino acid sequence of SEQ ID NO:162
LC-CDR3 having the amino acid sequence of SEQ ID NO:181; or (P2C4_H1) a VH region incorporating the following CDRs:
HC-CDR1 having the amino acid sequence of SEQ ID NO:103
HC-CDR2 having the amino acid sequence of SEQ ID NO:116
HC-CDR3 having the amino acid sequence of SEQ ID NO:123; and
a VL region incorporating the following CDRs:
LC-CDR1 having the amino acid sequence of SEQ ID NO:145
LC-CDR2 having the amino acid sequence of SEQ ID NO:162
LC-CDR3 having the amino acid sequence of SEQ ID NO:181; or (P2C4_H2) a VH region incorporating the following CDRs:
HC-CDR1 having the amino acid sequence of SEQ ID NO:103
HC-CDR2 having the amino acid sequence of SEQ ID NO:116
HC-CDR3 having the amino acid sequence of SEQ ID NO:128; and
a VL region incorporating the following CDRs:
LC-CDR1 having the amino acid sequence of SEQ ID NO:145
LC-CDR2 having the amino acid sequence of SEQ ID NO:162
LC-CDR3 having the amino acid sequence of SEQ ID NO:181; or (P2C4_H3) a VH region incorporating the following CDRs:
HC-CDR1 having the amino acid sequence of SEQ ID NO:103
HC-CDR2 having the amino acid sequence of SEQ ID NO:116
HC-CDR3 having the amino acid sequence of SEQ ID NO:128; and
a VL region incorporating the following CDRs:
LC-CDR1 having the amino acid sequence of SEQ ID NO:145
LC-CDR2 having the amino acid sequence of SEQ ID NO:162
LC-CDR3 having the amino acid sequence of SEQ ID NO:181; or (P2C4_C1D10) a VH region incorporating the following CDRs:
HC-CDR1 having the amino acid sequence of SEQ ID NO:103
HC-CDR2 having the amino acid sequence of SEQ ID NO:116
HC-CDR3 having the amino acid sequence of SEQ ID NO:128; and
a VL region incorporating the following CDRs:
LC-CDR1 having the amino acid sequence of SEQ ID NO:149
LC-CDR2 having the amino acid sequence of SEQ ID NO:162
LC-CDR3 having the amino acid sequence of SEQ ID NO:181; or (P2C4_FW2) a VH region incorporating the following CDRs:
HC-CDR1 having the amino acid sequence of SEQ ID NO:103
HC-CDR2 having the amino acid sequence of SEQ ID NO:116
HC-CDR3 having the amino acid sequence of SEQ ID NO:128; and
a VL region incorporating the following CDRs:
LC-CDR1 having the amino acid sequence of SEQ ID NO:145
LC-CDR2 having the amino acid sequence of SEQ ID NO:162
LC-CDR3 having the amino acid sequence of SEQ ID NO:177; or (P1E7) a VH region incorporating the following CDRs:
HC-CDR1 having the amino acid sequence of SEQ ID NO:108
HC-CDR2 having the amino acid sequence of SEQ ID NO:120
HC-CDR3 having the amino acid sequence of SEQ ID NO:133; and a VL region incorporating the following CDRs:
LC-CDR1 having the amino acid sequence of SEQ ID NO:151
LC-CDR2 having the amino acid sequence of SEQ ID NO:169
LC-CDR3 having the amino acid sequence of SEQ ID NO:182; or
(P1B10) a VH region incorporating the following CDRs;
HC-CDR1 having the amino acid sequence of SEQ ID NO:109
HC-CDR2 having the amino acid sequence of SEQ ID NO:121
HC-CDR3 having the amino acid sequence of SEQ ID NO:134; and
a VL region incorporating the following CDRs:
LC-CDR1 having the amino acid sequence of SEQ ID NO:152
LC-CDR2 having the amino acid sequence of SEQ ID NO:164
LC-CDR3 having the amino acid sequence of SEQ ID NO:133; or
(P1F3) a VH region incorporating the following CDRs:
HC-CDR1 having the amino acid sequence of SEQ ID NO:105
HC-CDR2 having the amino acid sequence of SEQ ID NO:122
HC-CDR3 having the amino acid sequence of SEQ ID NO:135; and
a VL region incorporating the following CDRs:
LC-CDR1 having the amino acid sequence of SEQ ID NO:153
LC-CDR2 having the amino acid sequence of SEQ ID NO:164
LC-CDR3 having the amino acid sequence of SEQ ID NO:184; or
(P1D10) a VH region incorporating the following CDRs:
HC-CDR1 having the amino acid sequence of SEQ ID NO:110
HC-CDR2 having the amino acid sequence of SEQ ID NO:119
HC-CDR3 having the amino acid sequence of SEQ ID NO:136; and
a VL region incorporating the following CDRs:
LC-CDR1 having the amino acid sequence of SEQ ID NO:154
LC-CDR2 having the amino acid sequence of SEQ ID NO:170
LC-CDR3 having the amino acid sequence of SEQ ID NO:135; or
(P1E1) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:137; and
VL region incorporating the following CDRs:
LC-CDR1 having the amino acid sequence of SEQ ID NO:155
LC-CDR2 having the amino acid sequence of SEQ ID NO:171
LC-CDR3 having the amino acid sequence of SEQ ID NO:186; or
(P2B11) a VH region incorporating the following CDRs:
HC-CDR1 having the amino acid sequence of SEQ ID NO:111
HC-CDR2 having the amino acid sequence of SEQ ID NO:123
HC-CDR3 having the amino acid sequence of SEQ ID NO:138; and
a VL region incorporating the following CDRs:
LC-CDR1 having the amino acid sequence of SEQ ID NO:155
LC-CDR2 having the amino acid sequence of SEQ ID NO:172
LC-CDR3 having the amino acid sequence of SEQ ID NO:187; or
(P2C9) a VH region incorporating the following CDRs:
HC-CDR1 having the amino acid sequence of SEQ ID NO:112
HC-CDR2 having the amino acid sequence of SEQ ID NO:124
HC-CDR3 having the amino acid sequence of SEQ ID NO:139; and
a VL region incorporating the following CDRs:
LC-CDR1 having the amino acid sequence of SEQ ID NO:157
LC-CDR2 having the amino acid sequence of SEQ ID NO:173
LC-CDR3 having the amino acid sequence of SEQ ID NO:188; or
(P2C10) a VH region incorporating the fallowing CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:140; and
a VL region incorporating the following CDRs:
LC-CDR1 having the amino acid sequence of SEQ ID NO:158
LC-CDR2 having the amino acid sequence of SEQ ID NO:174
LC-CDR3 having the amino acid sequence of SEQ ID NO:189; or
(P2C11) a VH region incorporating the following CDRs:
HC-CDR1 having the amino acid sequence of SEQ ID NO:113
HC-CDR2 having the amino acid sequence of SEQ ID NO:125
HC-CDR3 having the amino acid sequence of SEQ ID NO:141; and
a VL region incorporating the following CDRs:
LC-CDR1 having the amino acid sequence of SEQ ID NO:159
LC-CDR2 having the amino acid sequence of SEQ ID NO:175
LC-CDR3 having the amino acid sequence of SEQ ID NO:190; or
(P2E6) a VH region incorporating the following CDRs:
HC-CDR1 having the amino acid sequence of SEQ ID NO:114
HC-CDR2 having the amino acid sequence of SEQ ID NO:126
HC-CDR3 having the amino acid sequence of SEQ ID NO:142; and
a VL region incorporating the following CDRs:
LC-CDR1 having the amino acid sequence of SEQ ID NO:160
LC-CDR2 having the amino acid sequence of SEQ ID NO:176
LC-CDR3 having the amino acid sequence of SEQ ID NO:191; or (P2E11) a VH region incorporating the following CDRs:
HC-CDR1 having the amino acid sequence of SEQ ID NO:109
HC-CDR2 having the amino acid sequence of SEQ ID NO:121
HC-CDR3 having the amino acid sequence of SEQ ID NO:134; and
a VL region incorporating the following CDRs:
LC-CDR1 having the amino acid sequence of SEQ ID NO:159
LC-CDR2 having the amino acid sequence of SEQ ID NO:164
LC-CDR3 having the amino acid sequence of SEQ ID NO:192; or
(P2F9) a VH region incorporating the following CDRs:
HC-CDR1 having the amino acid sequence of SEQ ID NO:115
HC-CDR2 having the amino acid sequence of SEQ ID NO:127
HC-CDR3 having the amino acid sequence of SEQ ID NO:143; and
a VL region incorporating the following CDRs:
LC-CDR1 having the amino acid sequence of SEQ ID NO:151
LC-CDR2 having the amino acid sequence of SEQ ID NO:174
LC-CDR3 having the amino acid sequence of SEQ ID NO:193; or
(P2F10) a VH region incorporating the following CDRs:
HC-CDR1 having the amino acid sequence of SEQ ID NO:115
HC-CDR2 having the amino acid sequence of SEQ ID NO:127
HC-CDR3 having the amino acid sequence of SEQ ID NO:144; and
a VL region incorporating the following CDRs:
LC-CDR1 having the amino acid sequence of SEQ ID NO:161
LC-CDR2 having the amino acid sequence of SEQ ID NO:164
LC-CDR3 having the amino acid sequence of SEQ ID NO:194.

In some embodiments the antigen-binding molecule which is capable of binding to CD122 comprises:
a VH region comprising an amino acid sequence having at least 85% sequence identity to one of SEQ ID NOs:1 to 34; and
a VL region comprising an amino acid sequence having at least 85% sequence identity to one of SEQ ID NOs:35 to 65.

In some embodiments the antigen-binding molecule which is capable of binding to CD122 comprises:
(P2C4) a VH region comprising an amino acid sequence having at least 85% sequence identity to SEQ ID NO:1; and
a VL region comprising an amino acid sequence having at least 85% sequence identity to SEQ ID NO:35; or
(P2C4_A4) a VH region comprising an amino acid sequence having at least 85% sequence identity to SEQ ID NO:1; and
a VL region comprising an amino acid sequence having at least 85% sequence identity to SEQ ID NO:39; or
(P2C4_B1) a VH region comprising an amino acid sequence having at least 85% sequence identity to SEQ ID NO:1; and
a VL region comprising an amino acid sequence having at least 85% sequence identity to SEQ ID NO:40; or
(P2C4_B5) a VH region comprising an amino acid sequence having at least 85% sequence identity to SEQ ID NO:1; and
a VL region comprising an amino acid sequence having at least 85% sequence identity to SEQ ID NO:41; or
(P2C4_C4) a VH region comprising an amino acid sequence having at least 85% sequence identity to SEQ ID NO:1; and
a VL region comprising an amino acid sequence having at least 85% sequence identity to SEQ ID NO:44; or
(P2C4_C7) a VH region comprising an amino acid sequence having at least 85% sequence identity to SEQ ID NO:1; and
a VL region comprising an amino acid sequence having at least 85% sequence identity to SEQ ID NO:45; or
(P2C4_D10) a VH region comprising an amino acid sequence having at least 85% sequence identity to SEQ ID NO:1; and
a VL region comprising an amino acid sequence having at least 85% sequence identity to SEQ ID NO:42; or
(P2C4_E6) a VH region comprising an amino acid sequence having at least 85% sequence identity to SEQ ID NO:1; and
a VL region comprising an amino acid sequence having at least 85% sequence identity to SEQ ID NO:46; or
(P2C4_E7) a VH region comprising an amino acid sequence having at least 85% sequence identity to SEQ ID NO:1; and
a VL region comprising an amino acid sequence having at least 85% sequence identity to SEQ ID NO:47; or
(P2C4_F8) a VH region comprising an amino acid sequence having at least 85% sequence identity to SEQ ID NO:1; and
a VL region comprising an amino acid sequence having at least 85% sequence identity to SEQ ID NO:49; or
(P2H7) a VH region comprising an amino acid sequence having at least 85% sequence identity to SEQ ID NO:2; and
a VL region comprising an amino acid sequence having at least 85% sequence identity to SEQ ID NO:36; or
(P2D12) a VH region comprising an amino acid sequence having at least 85% sequence identity to SEQ ID NO:3; and
a VL region comprising an amino acid sequence having at least 85% sequence identity to SEQ ID NO:37; or
(P1G11) a VH region comprising an amino acid sequence having at least 85% sequence identity to SEQ ID NO:4; and
a VL region comprising an amino acid sequence having at least 85% sequence identity to SEQ ID NO:38; or
(P2C4_A9) a VH region comprising an amino acid sequence having at least 85% sequence identity to SEQ ID NO:5; and
a VL region comprising an amino acid sequence having at least 85% sequence identity to SEQ ID NO:35; or
(P2C4_B6) a VH region comprising an amino acid sequence having at least 85% sequence identity to SEQ ID NO:6; and
a VL region comprising an amino acid sequence having at least 85% sequence identity to SEQ ID NO:42; or
(P2C4_E9) a VH region comprising an amino acid sequence having at least 85% sequence identity to SEQ ID NO:6; and
a VL region comprising an amino acid sequence having at least 85% sequence identity to SEQ ID NO:48; or (P2C4_B8) a VH region comprising an amino acid sequence having at least 85% sequence identity to SEQ ID NO:7; and a VL region comprising an amino acid sequence having at least 85% sequence identity to SEQ ID NO:42; or (P2C4_B12) a VH region comprising an amino acid sequence having at least 85% sequence identity to SEQ ID NO:8 and a VL region comprising an amino acid sequence having at least 85% sequence identity to SEQ ID NO:43; or (P2C4_C1) a VH region comprising an amino acid sequence having at least 85% sequence identity to SEQ ID NO:9; and a VL region comprising an amino acid sequence having at least 85% sequence identity to SEQ ID NO:39; or (P2C4_C12) a VH region comprising an amino acid sequence having at least 85% sequence identity to SEQ ID NO:10; and a VL region comprising an amino acid sequence having at least 85% sequence identity to SEQ ID NO:42; or (P2C4_E2) a VH region comprising an amino acid sequence having at least 85% sequence identity to SEQ ID NO:11; and a VL region comprising an amino acid sequence having at least 85% sequence identity to SEQ ID NO:42; or (P2C4_E3) a VH region comprising an amino acid sequence having at least 85% sequence identity to SEQ ID NO:12; and a VL region comprising an amino acid sequence having at least 85% sequence identity to SEQ ID NO:42; or (P2C4_E8) a VH region comprising an amino acid sequence having at least 85% sequence identity to SEQ ID NO:13; and a VL region comprising an amino acid sequence having at least 85% sequence identity to SEQ ID NO:42; or (P2C4_F11) a VH region comprising an amino acid sequence having at least 85% sequence identity to SEQ ID NO:14; and a VL region comprising an amino acid sequence having at least 85% sequence identity to SEQ ID NO:50; or (P2C4_G2) a VH region comprising an amino acid sequence having at least 85% sequence identity to SEQ ID NO:15; and a VL region comprising an amino acid sequence having at least 85% sequence identity to SEQ ID NO:42; or (P2C4_G11) a VH region comprising an amino acid sequence having at least 85% sequence identity to SEQ ID NO:16; and a VL region comprising an amino acid sequence having at least 85% sequence identity to SEQ ID NO:42; or (P2C4_H1) a VH region comprising an amino acid sequence having at least 85% sequence identity to SEQ ID NO:17; and a VL region comprising an amino acid sequence having at least 85% sequence identity to SEQ ID NO:42; or (P2C4_H2) a VH region comprising an amino acid sequence having at least 85% sequence identity to SEQ ID NO:18; and a VL region comprising an amino acid sequence having at least 85% sequence identity to SEQ ID NO:42; or (P2C4_H3) a VH region comprising an amino acid sequence having at least 85% sequence identity to SEQ ID NO:19; and a VL region comprising an amino acid sequence having at least 85% sequence identity to SEQ ID NO:42; or (P2C4_C1D10) a VH region comprising an amino acid sequence having at least 85% sequence identity to SEQ ID NO:20; and a VL region comprising an amino acid sequence having at least 85% sequence identity to SEQ ID NO:51; or (P2C4_FW2) a VH region comprising an amino acid sequence having at least 85% sequence identity to SEQ ID NO:21; and a VL region comprising an amino acid sequence having at least 85% sequence identity to SEQ ID NO:52; or (P1E7) a VH region comprising an amino acid sequence having at least 85% sequence identity to SEQ ID NO:22; and a VL region comprising an amino acid sequence having at least 85% sequence identity to SEQ ID NO:53; or (P1B10) a VH region comprising an amino acid sequence having at least 85% sequence identity to SEQ ID NO:23; and a VL region comprising an amino acid sequence having at least 85% sequence identity to SEQ ID NO:54; or (P1F3) a VH region comprising an amino acid sequence having at least 85% sequence identity to SEQ ID NO:24; and a VL region comprising an amino acid sequence having at least 85% sequence identity to SEQ ID NO:55; or (P1D10) a VH region comprising an amino acid sequence having at least 85% sequence identity to SEQ ID NO:25; and a VL region comprising an amino acid sequence having at least 85% sequence identity to SEQ ID NO:56; or (P1E1) a VH region comprising an amino acid sequence having at least 85% sequence identity to SEQ ID NO:26; and a VL region comprising an amino acid sequence having at least 85% sequence identity to SEQ ID NO:57; or (P2B11) a VH region comprising an amino acid sequence having at least 85% sequence identity to SEQ ID NO:27; and a VL region comprising an amino acid sequence having at least 85% sequence identity to SEQ ID NO:58; or (P2C9) a VH region comprising an amino acid sequence having at least 85% sequence identity to SEQ ID NO:28; and a VL region comprising an amino acid sequence having at least 85% sequence identity to SEQ ID NO:59; or (P2C10) a VH region comprising an amino acid sequence having at least 85% sequence identity to SEQ ID NO:29; and a VL region comprising an amino acid sequence having at least 85% sequence identity to SEQ ID NO:60; or (P2C11) a VH region comprising an amino acid sequence having at least 85% sequence identity to SEQ ID NO:30; and a VL region comprising an amino acid sequence having at least 85% sequence identity to SEQ ID NO:61; or (P2E6) a VH region comprising an amino acid sequence having at least 85% sequence identity to SEQ ID NO:31; and a VL region comprising an amino acid sequence having at least 85% sequence identity to SEQ ID NO:62; or (P2E11) a VH region comprising an amino acid sequence having at least 85% sequence identity to SEQ ID NO:32; and a VL region comprising an amino acid sequence having at least 85% sequence identity to SEQ ID NO:63; or (P2F9) a VH region comprising an amino acid sequence having at least 85% sequence identity to SEQ ID NO:33; and a VL region comprising an amino acid sequence having at least 85% sequence identity to SEQ ID NO:64; or (P2F10) a VH region comprising an amino acid sequence having at least 85% sequence identity to SEQ ID NO:34; and a VL region comprising an amino acid sequence having at least 85% sequence identity to SEQ ID NO:65.

In some embodiments the antigen-binding molecule which is capable of binding to CD132 comprises:

(P1A10) a VH region incorporating the following CDRs:

HC-CDR1 having the amino acid sequence of SEQ ID NO:196

HC-CDR2 having the amino acid sequence of SEQ ID NO:204

HC-CDR3 having the amino acid sequence of SEQ ID NO:212; and a VL region incorporating the following CDRs:

LC-CDR1 having the amino acid sequence of SEQ ID NO:227

LC-CDR2 having the amino acid sequence of SEQ ID NO:238

LC-CDR3 having the amino acid sequence of SEQ ID NO:248; or (P1B6) a VH region incorporating the following CDRs:

HC-CDR1 having the amino acid sequence of SEQ ID NO:108

HC-CDR2 having the amino acid sequence of SEQ ID NO:120

HC-CDR3 having the amino acid sequence of SEQ ID NO:213; and a VL region incorporating the following CDRs:

LC-CDR1 having the amino acid sequence of SEQ ID NO:151

LC-CDR2 having the amino acid sequence of SEQ ID NO:239

LC-CDR3 having the amino acid sequence of SEQ ID NO:249; or (P1C10) a VH region incorporating the following CDRs:

HC-CDR1 having the amino acid sequence of SEQ ID NO:112

HC-CDR2 having the amino acid sequence of SEQ ID NO:124

HC-CDR3 having the amino acid sequence of SEQ ID NO:214; and a VL region incorporating the following CDRs:

LC-CDR1 having the amino acid sequence of SEQ ID NO:228

LC-CDR2 having the amino acid sequence of SEQ ID NO:240

LC-CDR3 having the amino acid sequence of SEQ ID NO:250; or (P1D7) a VH region incorporating the following CDRs:

HC-CDR1 having the amino acid sequence of SEQ ID NO:197

HC-CDR2 having the amino acid sequence of SEQ ID NO:206

HC-CDR3 having the amino acid sequence of SEQ ID NO:215; and a VL region incorporating the following CDRs:

LC-CDR1 having the amino acid sequence of SEQ ID NO:229

LC-CDR2 having the amino acid sequence of SEQ ID NO:241

LC-CDR3 having the amino acid sequence of SEQ ID NO:251; or (P1E8) a VH region incorporating the following CDRs:

HC-CDR1 having the amino acid sequence of SEQ ID NO:198

HC-CDR2 having the amino acid sequence of SEQ ID NO:120

HC-CDR3 having the amino acid sequence of SEQ ID NO:216; and a VL region incorporating the following CDRs:

LC-CDR1 having the amino acid sequence of SEQ ID NO:230

LC-CDR2 having the amino acid sequence of SEQ ID NO:242

LC-CDR3 having the amino acid sequence of SEQ ID NO:252; or (P2B2) a VH region incorporating the following CDRs:

HC-CDR1 having the amino acid sequence of SEQ ID NO:108

HC-CDR2 having the amino acid sequence of SEQ ID NO:207

HC-CDR3 having the amino acid sequence of SEQ ID NO:217; and a VL region incorporating the following CDRs:

LC-CDR1 having the amino acid sequence of SEQ ID NO:151

LC-CDR2 having the amino acid sequence of SEQ ID NO:174

LC-CDR3 having the amino acid sequence of SEQ ID NO:253; or (P2B7) a VH region incorporating the following CDRs:

HC-CDR1 having the amino acid sequence of SEQ ID NO:106

HC-CDR2 having the amino acid sequence of SEQ ID NO:119

HC-CDR3 having the amino acid sequence of SEQ ID NO:218; and a VL region incorporating the following CDRs:

LC-CDR1 having the amino acid sequence of SEQ ID NO:231

LC-CDR2 having the amino acid sequence of SEQ ID NO:174

LC-CDR3 having the amino acid sequence of SEQ ID NO:254; or (P2D11) a VH region incorporating the following CDRs:

HC-CDR1 having the amino acid sequence of SEQ ID NO:199

HC-CDR2 having the amino acid sequence of SEQ ID NO:208

HC-CDR3 having the amino acid sequence of SEQ ID NO:219; and a VL region incorporating the following CDRs:

LC-CDR1 having the amino acid sequence of SEQ ID NO:232

LC-CDR2 having the amino acid sequence of SEQ ID NO:243

LC-CDR3 having the amino acid sequence of SEQ ID NO:255; or (P2F10) a VH region incorporating the following CDRs:

HC-CDR1 having the amino acid sequence of SEQ ID NO:200

HC-CDR2 having the amino acid sequence of SEQ ID NO:209

HC-CDR3 having the amino acid sequence of SEQ ID NO:220; and a VL region incorporating the following CDRs:
LC-CDR1 having the amino acid sequence of SEQ ID NO:233
LC-CDR2 having the amino acid sequence of SEQ ID NO:244
LC-CDR3 having the amino acid sequence of SEQ ID NO:256; or
(P2H4) a VH region incorporating the following CDRs:
HC-CDR1 having the amino acid sequence of SEQ ID NO:108
HC-CDR2 having the amino acid sequence of SEQ ID NO:120
HC-CDR3 having the amino acid sequence of SEQ ID NO:221; and
a VL region incorporating the following CDRs:
LC-CDR1 having the amino acid sequence of SEQ ID NO:234
LC-CDR2 having the amino acid sequence of SEQ ID NO:174
LC-CDR3 having the amino acid sequence of SEQ ID NO:257; or
(P2D3) a VH region incorporating the following CDRs:
HC-CDR1 having the amino acid sequence of SEQ ID NO:201
HC-CDR2 having the amino acid sequence of SEQ ID NO:119
HC-CDR3 having the amino acid sequence of SEQ ID NO:222; and
a VL region incorporating the following CDRs:
LC-CDR1 having the amino acid sequence of SEQ ID NO:151
LC-CDR2 having the amino acid sequence of SEQ ID NO:174
LC-CDR3 having the amino acid sequence of SEQ ID NO:189; or
(P1G4) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:223; and
a VL region incorporating the following CDRs:
LC-CDR1 having the amino acid sequence of SEQ ID NO:151
LC-CDR2 having the amino acid sequence of SEQ ID NO:174
LC-CDR3 having the amino acid sequence of SEQ ID NO:258; or
(P1B12) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:224; and
a VL region incorporating the following CDRs:
LC-CDR1 having the amino acid sequence of SEQ ID NO:235
LC-CDR2 having the amino acid sequence of SEQ ID NO:174
LC-CDR3 having the amino acid sequence of SEQ ID NO:189; or
(P1C7) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:225; and
a VL region incorporating the following CDRs:
LC-CDR1 having the amino acid sequence of SEQ ID NO:151
LC-CDR2 having the amino acid sequence of SEQ ID NO:245
LC-CDR3 having the amino acid sequence of SEQ ID NO:189.

In some embodiments the antigen-binding molecule which is capable of binding to CD132 comprises:
a VH region comprising an amino acid sequence having at least 85% sequence identity to one of SEQ ID NOs:71 to 84; and
a VL region comprising an amino acid sequence having at least 85% sequence identity to one of SEQ ID NOs:89 to 102.

In some embodiments the antigen-binding molecule, which is capable of binding to CD132 comprises:
(P1A10) a VH region comprising an amino acid sequence having at least 85% sequence identity to SEQ ID NO:71; and
a VL region comprising an amino acid sequence having at least 85% sequence identity to SEQ ID NO:89; or
(P1B5) a VH region comprising an amino acid sequence having at least 85% sequence identity to SEQ ID NO:72; and
a VL region comprising an amino acid sequence having at least 85% sequence identity to SEQ ID NO:90; or
(P1C10) a VH region comprising an amino acid sequence having at least 85% sequence identity to SEQ ID NO:73; and
a VL region comprising an amino acid sequence having at least 85% sequence identity to SEQ ID NO:91; or
(P1D7) a VH region comprising an amino acid sequence having at least 85% sequence identity to SEQ ID NO:74; and
a VL region comprising an amino acid sequence having at least 85% sequence identity to SEQ ID NO:92; or
(P1E8) a VH region comprising an amino acid sequence having at least 85% sequence identity to SEQ ID NO:75; and
a VL region comprising an amino acid sequence having at least 85% sequence identity to SEQ ID NO:93; or
(P2B2) a VH region comprising an amino acid sequence having at least 85% sequence identity to SEQ ID NO:76; and
a VL region comprising an amino acid sequence having at least 85% sequence identity to SEQ ID NO:94; or
(P2B7) a VH region comprising an amino acid sequence having at least 85% sequence identity to SEQ ID NO:77; and
a VL region comprising an amino acid sequence having at least 85% sequence identity to SEQ ID NO:95; or
(P2D11) a VH region comprising an amino acid sequence having at least 85% sequence identity to SEQ ID NO:78; and
a VL region comprising an amino acid sequence having at least 85% sequence identity to SEQ ID NO:96; or
(P2F10) a VH region comprising an amino acid sequence having at least 85% sequence identity to SEQ ID NO:79; and
a VL region comprising an amino acid sequence having at least 85% sequence identity to SEQ ID NO:97; or
(P2H4) a VH region comprising an amino acid sequence having at least 85% sequence identity to SEQ ID NO:80; and a VL region comprising an amino acid sequence having at least 85% sequence identity to SEQ ID NO:98; or (P2D3) a VH region comprising an amino acid sequence having at least 85% sequence identity to SEQ ID NO:81; and a VL region comprising an amino acid sequence having at least 85% sequence identity to SEQ ID NO:99; or (P1G4) a VH region comprising an amino acid sequence having at least 85% sequence identity to SEQ ID NO:82; and a VL region comprising an amino acid sequence having at least 85% sequence identity to SEQ ID NO:100; or (P1B12) a VH region comprising an amino acid sequence having at least 85% sequence identity to SEQ ID NO:83; and a VL region comprising an amino acid sequence having at least 85% sequence identity to SEQ ID NO:101; or (P1C7) a VH region comprising an amino acid sequence having at least 85% sequence identity to SEQ ID NO:84; and a VL region comprising an amino acid sequence having at least 85% sequence identity to SEQ ID NO:102.

The present invention also provides an antigen-binding molecule, optionally isolated, which is capable of binding to CD122, comprising:

a heavy chain variable (VH) region incorporating the following CDRs:

HC-CDR1 having the amino acid sequence of one of SEQ ID NOs:105, 106, or 108 to 115

HC-CDR2 having the amino acid sequence of one of SEQ ID NOs:119 to 127

HC-CDR3 having the amino acid sequence of one of SEQ ID NOs:133 to 144; and a light chain variable (VL) region incorporating the following CDRs:

LC-CDR1 having the amino acid sequence of one of SEQ ID NOs:151 to 161

LC-CDR2 having the amino acid sequence of one of SEQ ID NOs:164, or 169 to 176

LC-CDR3 having the amino acid sequence of one of SEQ ID NOs:182 to 194;

or a variant thereof in which one or two or three amino acids in one or more of HC-CDR1, HC-CDR2, HC-CDR3, LC-CDR1, LC-CDR2 or LC-CDR3 are substituted with another amino acid.

In some embodiments the antigen-binding molecule comprises:

(P1E7) a VH region incorporating the following CDRs:

HC-CDR1 having the amino acid sequence of SEQ ID NO:108

HC-CDR2 having the amino acid sequence of SEQ ID NO:120

HC-CDR3 having the amino acid sequence of SEQ ID NO:133; and a VL region incorporating the following CDRs:

LC-CDR1 having the amino acid sequence of SEQ ID NO:151

LC-CDR2 having the amino acid sequence of SEQ ID NO:169

LC-CDR3 having the amino acid sequence of SEQ ID NO:182; or (P1B10) a VH region incorporating the following CDRs:

HC-CDR1 having the amino acid sequence of SEQ ID NO:109

HC-CDR2 having the amino acid sequence of SEQ ID NO:121

HC-CDR3 having the amino acid sequence of SEQ ID NO:134; and a VL region incorporating the following CDRs:

LC-CDR1 having the amino acid sequence of SEQ ID NO:152

LC-CDR2 having the amino acid sequence of SEQ ID NO:164

LC-CDR3 having the amino acid sequence of SEQ ID NO:183; or (P1F3) a VH region incorporating the following CDRs;

HC-CDR1 having the amino acid sequence of SEQ ID NO:105

HC-CDR2 having the amino acid sequence of SEQ ID NO:122

HC-CDR3 having the amino acid sequence of SEQ ID NO:135; and a VL region incorporating the following CDRs:

LC-CDR1 having the amino acid sequence of SEQ ID NO:153

LC-CDR2 having the amino acid sequence of SEQ ID NO:164

LC-CDR3 having the amino acid sequence of SEQ ID NO:184; or (P1D10) a VH region incorporating the following CDRs:

HC-CDR1 having the amino acid sequence of SEQ ID NO:110

HC-CDR2 having the amino acid sequence of SEQ ID NO:119

HC-CDR3 having the amino acid sequence of SEQ ID NO:136; and

VL region incorporating the following CDRs:

LC-CDR1 having the amino acid sequence of SEQ ID NO:154

LC-CDR2 having the amino acid sequence of SEQ ID NO:170

LC-CDR3 having the amino acid sequence of SEQ ID NO:185; or (P1E1) a VH region incorporating the following CDRs:

HC-CDR1 having the amino acid sequence of SEQ ID NO:106

HC-CDR2 having the amino acid sequence of SEQ ID NO:119

HC-CDR3 having the amino acid sequence of SEQ ID NO:137; and a VL region incorporating the following CDRs:

LC-CDR1 having the amino acid sequence of SEQ ID NO:155

LC-CDR2 having the amino acid sequence of SEQ ID NO:171

LC-CDR3 having the amino acid sequence of SEQ ID NO:186; or (P2B11) a VH region incorporating the following CDRs:

HC-CDR1 having the amino acid sequence of SEQ ID NO:111

HC-CDR2 having the amino acid sequence of SEQ ID NO:123

HC-CDR3 having the amino acid sequence of SEQ ID NO:138; and a VL region incorporating the following CDRs:

LC-CDR1 having the amino acid sequence of SEQ ID NO:156

LC-CDR2 having the amino acid sequence of SEQ ID NO:172

LC-CDR3 having the amino acid sequence of SEQ ID NO:187; or (P2C9) a VH region incorporating the following CDRs:
HC-CDR1 having the amino acid sequence of SEQ ID NO:112
HC-CDR2 having the amino acid sequence of SEQ ID NO:124
HC-CDR3 having the amino acid sequence of SEQ ID NO:139; and
a VL region incorporating the following CDRs:
LC-CDR1 having the amino acid sequence of SEQ ID NO:157
LC-CDR2 having the amino acid sequence of SEQ ID NO:173
LC-CDR3 having the amino acid sequence of SEQ ID NO:188; or
(P2C10) a VH region incorporating the following CDRs:
HC-CDR1 having the amino acid sequence of SEQ ID NO:106
HC-CDR2 having the amino acid sequence of SEQ ID NO:119
HC-CDR3 having the amino acid sequence of SEQ ID NO:140; and
a VL region incorporating the following CDRs:
LC-CDR1 having the amino acid sequence of SEQ ID NO:158
LC-CDR2 having the amino acid sequence of SEQ ID NO:174
LC-CDR3 having the amino acid sequence of SEQ ID NO:189; or
(P2C11) a VH region incorporating the following CDRs:
HC-CDR1 having the amino acid sequence of SEQ ID NO:113
HC-CDR2 having the amino acid sequence of SEQ ID NO:125
HC-CDR3 having the amino acid sequence of SEQ ID NO:141; and
a VL region incorporating the following CDRs:
LC-CDR1 having the amino acid sequence of SEQ ID NO:159
LC-CDR2 having the amino acid sequence of SEQ ID NO:175
LC-CDR3 having the amino acid sequence of SEQ ID NO:190; or
(P2E6) a VH region incorporating the following CDRs:
HC-CDR1 having the amino acid sequence of SEQ ID NO:114
HC-CDR2 having the amino acid sequence of SEQ ID NO:126
HC-CDR3 having the amino acid sequence of SEQ ID NO:142; and
a VL region incorporating the following CDRs:
LC-CDR1 having the amino acid sequence of SEQ ID NO:160
LC-CDR2 having the amino acid sequence of SEQ ID NO:176
LC-CDR3 having the amino acid sequence of SEQ ID NO:191; or
(P2E11) a VH region incorporating the following CDRs:
HC-CDR1 having the amino acid sequence of SEQ ID NO:109
HC-CDR2 having the amino acid sequence of SEQ ID NO:121
HC-CDR3 having the amino acid sequence of SEQ ID NO:134; and
a VL region incorporating the following CDRs:
LC-CDR1 having the amino acid sequence of SEQ ID NO:159
LC-CDR2 having the amino acid sequence of SEQ ID NO:164
LC-CDR3 having the amino acid sequence of SEQ ID NO:192; or
(P2F9) a VH region incorporating the following CDRs:
HC-CDR1 having the amino acid sequence of SEQ ID NO:115
HC-CDR2 having the amino acid sequence of SEQ ID NO:127
HC-CDR3 having the amino acid sequence of SEQ ID NO:143; and
a VL region incorporating the following CDRs:
LC-CDR1 having the amino acid sequence of SEQ ID NO:151
LC-CDR2 having the amino acid sequence of SEQ ID NO:174
LC-CDR3 having the amino acid sequence of SEQ ID NO:193; or
(P2F10) a VH region incorporating the following CDRs:
HC-CDR1 having the amino acid sequence of SEQ ID NO:115
HC-CDR2 having the amino acid sequence of SEQ ID NO:127
HC-CDR3 having the amino acid sequence of SEQ ID NO:144; and
a VL region incorporating the following CDRs:
LC-CDR1 having the amino acid sequence of SEQ ID NO:161
LC-CDR2 having the amino acid sequence of SEQ ID NO:164
LC-CDR3 having the amino acid sequence of SEQ ID NO:194.

In some embodiments the antigen-binding molecule comprises;
a VH region comprising an amino acid sequence having at least 85% sequence identity to one of SEQ ID NOs:22 to 34; and
a VL region comprising an amino acid sequence having at east 85% sequence identity to one of SEQ ID NOs:53 to 65.

In some embodiments the antigen-binding molecule comprises:
(P1E7) a VH region comprising an amino acid sequence having at least 85% sequence identity to SEQ ID NO:22; and
a VL region comprising an amino acid sequence having at least 85% sequence identity to SEQ ID NO:53; or
(P1B10) a VH region comprising an amino acid sequence having at least 85% sequence identity to SEQ ID NO:23; and
a VL region comprising an amino acid sequence having at least 85% sequence identity to SEQ ID NO:54; or
(P1F3) a VH region comprising an amino acid sequence having at least 85% sequence identity to SEQ ID NO:24; and
a VL region comprising an amino acid sequence having at least 85% sequence identity to SEQ ID NO:55; or
(P1D10) a VH region comprising an amino acid sequence having at least 85% sequence identity to SEQ ID NO:25; and
a VL region comprising an amino acid sequence having at least 85% sequence identity to SEQ ID NO:56; or
(P1E1) a VH region comprising an amino acid sequence having at least 85% sequence identity to SEQ ID NO:26; and
a VL region comprising an amino acid sequence having at least 85% sequence identity to SEQ ID NO:57; or (P2B11) a VH region comprising an amino acid sequence having at least 85% sequence identity to SEQ ID NO:27; and a VL region comprising an amino acid sequence having at least 85% sequence identity to SEQ ID NO:58; or (P2C9) a VH region comprising an amino acid sequence having at least 85% sequence identity to SEQ ID NO:28; and a VL region comprising an amino acid sequence having at least 85% sequence identity to SEQ ID NO:59; or (P2C10) a VH region comprising an amino acid sequence having at least 85% sequence identity to SEQ ID NO:29; and a VL region comprising an amino acid sequence having at least 85% sequence identity to SEQ ID NO:60; or (P2C11) a VH region comprising an amino acid sequence having at least 85% sequence identity to SEQ ID NO:30; and a VL region comprising an amino acid sequence having at least 85% sequence identity to SEQ ID NO:61; or (P2E6) a VH region comprising an amino acid sequence having at least 85% sequence identity to SEQ ID NO:31; and a VL region comprising an amino acid sequence having at least 85% sequence identity to SEQ ID NO:62; or (P2E11) a VH region comprising an amino acid sequence having at least 85% sequence identity to SEQ ID NO:32; and a VL region comprising an amino acid sequence having at least 85% sequence identity to SEQ ID NO:63; or (P2F9) a VH region comprising an amino acid sequence having at least 85% sequence identity to SEQ ID NO:33; and a VL region comprising an amino acid sequence having at least 85% sequence identity to SEQ ID NO:64; or (F2F10) a VH region comprising an amino acid sequence having at least 85% sequence identity to SEQ ID NO:34; and a VL region comprising an amino acid sequence having at least 85% sequence identity to SEQ ID NO:65.

The present invention also provides an antigen-binding molecule, optionally isolated, which is capable of binding to CD132, comprising:

a heavy chain variable (VH) region incorporating the following CDRs:

HC-CDR1 having the amino acid sequence of one of SEQ ID NOs:106, 108, 112, or 196 to 201

HC-CDR2 having the amino acid sequence of one of SEQ ID NOs:119, 120, 124, or 204 to 209

HC-CDR3 having the amino acid sequence of one of SEQ ID NOs:212 to 225; and a light chain variable (VL) region incorporating the following CDRs:

LC-CDR1 having the amino acid sequence of one of SEQ ID NOs:151, or 227 to 235

LC-CDR2 having the amino acid sequence of one of SEQ ID NOs:174, or 238 to 245

LC-CDR3 having the amino acid sequence of one of SEQ ID NOs:189, or 248 to 258;

or a variant thereof in which one or two or three amino acids in one or more of HC-CDR1, HC-CDR2, HC-CDR3, LC-CDR1, LC-CDR2 or LC-CDR3 are substituted with another amino acid.

In some embodiments the antigen-binding molecule comprises:

(P1A10) a VH region incorporating the following CDRs:

HC-CDR1 having the amino acid sequence of SEQ ID NO:196

HC-CDR2 having the amino acid sequence of SEQ ID NO:204

HC-CDR3 having the amino acid sequence of SEQ ID NO:212; and a VL region incorporating the following CDRs:

LC-CDR1 having the amino acid sequence of SEQ ID NO:227

LC-CDR2 having the amino acid sequence of SEQ ID NO:238

LC-CDR3 having the amino acid sequence of SEQ ID NO:248; or (P1B6) a VH region incorporating the following CDRs:

HC-CDR1 having the amino acid sequence of SEQ ID NO:108

HC-CDR2 having the amino acid sequence of SEQ ID NO:120

HC-CDR3 having the amino acid sequence of SEQ ID NO:213; and a VL region incorporating the following CDRs:

LC-CDR1 having the amino acid sequence of SEQ ID NO:151

LC-CDR2 having the amino acid sequence of SEQ ID NO:239

LC-CDR3 having the amino acid sequence of SEQ ID NO:249; or (P1C10) a VH region incorporating the following CDRs:

HC-CDR1 having the amino acid sequence of SEQ ID NO:112

HC-CDR2 having the amino acid sequence of SEQ ID NO:124

HC-CDR3 having the amino acid sequence of SEQ ID NO:214; and a VL region incorporating the following CDRs:

LC-CDR1 having the amino acid sequence of SEQ ID NO:228

LC-CDR2 having the amino acid sequence of SEQ ID NO:240

LC-CDR3 having the amino acid sequence of SEQ ID NO:250; or (P1D7) a VH region incorporating the following CDRs;

HC-CDR1 having the amino acid sequence of SEQ ID NO:197

HC-CDR2 having the amino acid sequence of SEQ ID NO:206

HC-CDR3 having the amino acid sequence of SEQ ID NO:215; and a VL region incorporating the following CDRs:

LC-CDR1 having the amino acid sequence of SEQ ID NO:229

LC-CDR2 having the amino acid sequence of SEQ ID NO:241

LC-CDR3 having the amino acid sequence of SEQ ID NO:251; or (P1E8) a VH region incorporating the following CDRs:

HC-CDR1 having the amino acid sequence of SEQ ID NO:198

HC-CDR2 having the amino acid sequence of SEQ ID NO:120

HC-CDR3 having the amino acid sequence of SEQ ID NO:216; and a VL region incorporating the following CDRs:

LC-CDR1 having the amino acid sequence of SEQ ID NO:230

LC-CDR2 having the amino acid sequence of SEQ ID NO:242

LC-CDR3 having the amino acid sequence of SEQ ID NO:252; or (P2B2) a VH region incorporating the following CDRs:

HC-CDR1 having the amino acid sequence of SEQ ID NO:108

HC-CDR2 having the amino acid sequence of SEQ ID NO:207

HC-CDR3 having the amino acid sequence of SEQ ID NO:217; and a VL region incorporating the following CDRs:

LC-CDR1 having the amino acid sequence of SEQ ID NO:151

LC-CDR2 having the amino acid sequence of SEQ ID NO:174

LC-CDR3 having the amino acid sequence of SEQ ID NO:253; or (P2B7) a VH region incorporating the following CDRs:

HC-CDR1 having the amino acid sequence of SEQ ID NO:106

HC-CDR2 having the amino acid sequence of SEQ ID NO:119

HC-CDR3 having the amino acid sequence of SEQ ID NO:218; and a VL region incorporating the following CDRs:

LC-CDR1 having the amino acid sequence of SEQ ID NO:231

LC-CDR2 having the amino acid sequence of SEQ ID NO:174

LC-CDR3 having the amino acid sequence of SEQ ID NO:254; or (P2D11) a VH region incorporating the following CDRs:

HC-CDR1 having the amino acid sequence of SEQ ID NO:199

HC-CDR2 having the amino acid sequence of SEQ ID NO:208

HC-CDR3 having the amino acid sequence of SEQ ID NO:219; and a VL region incorporating the following CDRs:

LC-CDR1 having the amino acid sequence of SEQ ID NO:232

LC-CDR2 having the amino acid sequence of SEQ ID NO:243

LC-CDR3 having the amino acid sequence of SEQ ID NO:255; or (P2F10) a VH region incorporating the following CDRs:

HC-CDR1 having the amino acid sequence of SEQ ID NO:200

HC-CDR2 having the amino acid sequence of SEQ ID NO:209

HC-CDR3 having the amino acid sequence of SEQ ID NO:220; and a VL region incorporating the following CDRs:

LC-CDR1 having the amino acid sequence of SEQ ID NO:233

LC-CDR2 having the amino acid sequence of SEQ ID NO:244

LC-CDR3 having the amino acid sequence of SEQ ID NO:256; or (P2H4) a VH region incorporating the following CDRs:

HC-CDR1 having the amino acid sequence of SEQ ID NO:108

HC-CDR2 having the amino acid sequence of SEQ ID NO:120

HC-CDR3 having the amino acid sequence of SEQ ID NO:221; and a VL region incorporating the following CDRs:

LC-CDR1 having the amino acid sequence of SEQ ID NO:234

LC-CDR2 having the amino acid sequence of SEQ ID NO:174

LC-CDR3 having the amino acid sequence of SEQ ID NO:257; or (P2D3) a VH region incorporating the following CDRs:

HC-CDR1 having the amino acid sequence of SEQ ID NO:201

HC-CDR2 having the amino acid sequence of SEQ ID NO:119

HC-CDR3 having the amino acid sequence of SEQ ID NO:222; and a VL region incorporating the following CDRs:

LC-CDR1 having the amino acid sequence of SEQ ID NO:151

LC-CDR2 having the amino acid sequence of SEQ ID NO:174

LC-CDR3 having the amino acid sequence of SEQ ID NO:189; or (P1G4) a VH region incorporating the following CDRs:

HC-CDR1 having the amino acid sequence of SEQ ID NO:106

HC-CDR2 having the amino acid sequence of SEQ ID NO:119

HC-CDR3 having the amino acid sequence of SEQ ID NO:223; and a VL region incorporating the following CDRs:

LC-CDR1 having the amino acid sequence of SEQ ID NO:151

LC-CDR2 having the amino acid sequence of SEQ ID NO:174

LC-CDR3 having the amino acid sequence of SEQ ID NO:258; or (P1B12) a VH region incorporating the following CDRs;

HC-CDR1 having the amino acid sequence of SEQ ID NO:106

HC-CDR2 having the amino acid sequence of SEQ ID NO:119

HC-CDR3 having the amino acid sequence of SEQ ID NO:224; and a VL region incorporating the following CDRs:

LC-CDR1 having the amino acid sequence of SEQ ID NO:235

LC-CDR2 having the amino acid sequence of SEQ ID NO:174

LC-CDR3 having the amino acid sequence of SEQ ID NO:189; or (P1C7) a VH region incorporating the following CDRs:

HC-CDR1 having the amino acid sequence of SEQ ID NO:106

HC-CDR2 having the amino acid sequence of SEQ ID NO:119

HC-CDR3 having the amino acid sequence of SEQ ID NO:225; and a VL region incorporating the following CDRs:

LC-CDR1 having the amino acid sequence of SEQ ID NO:151

LC-CDR2 having the amino acid sequence of SEQ ID NO:245

LC-CDR3 having the amino acid sequence of SEQ ID NO:189.

In some embodiments the antigen-binding molecule comprises:

a VH region comprising an amino acid sequence having at least 85% sequence identity to one of SEQ ID NOs:71 to 84; and a VL region comprising an amino acid sequence having at least 85% sequence identity to one of SEQ ID NOs:89 to 102.

In some embodiments the antigen-binding molecule comprises:

(P1A10) a VH region comprising an amino acid sequence having at least 85% sequence identity to SEQ ID NO:71; and a VL region comprising an amino acid sequence having at least 85% sequence identity to SEQ ID NO:89; or (P1B6) a VH region comprising an amino acid sequence having at least 85% sequence identity to SEQ ID NO:72; and a VL region comprising an amino acid sequence having at least 85% sequence identity to SEQ ID NO:90; or (P1C10) a VH region comprising an amino acid sequence having at least 85% sequence identity to SEQ ID NO:73; and a VL region comprising an amino acid sequence having at least 85% sequence identity to SEQ ID NO:91; or (P1D7) a VH region comprising an amino acid sequence having at least 85% sequence identity to SEQ ID NO:74; and a VL region comprising an amino acid sequence having at least 85% sequence identity to SEQ ID NO:92; or (P1E8) a VH region comprising an amino acid sequence having at least 85% sequence identity to SEQ ID NO:75; and a VL region comprising an amino acid sequence having at least 85% sequence identity to SEQ ID NO:93; or (P2B2) a VH region comprising an amino acid sequence having at least 85% sequence identity to SEQ ID NO:76; and a VL region comprising an amino acid sequence having at least 85% sequence identity to SEQ ID NO:94; or (P2B7) a VH region comprising an amino acid sequence having at least 85% sequence identity to SEQ ID NO:77; and a VL region comprising an amino acid sequence having at least 85% sequence identity to SEQ ID NO:95; or (P2D11) a VH region comprising an amino acid sequence having at least 85% sequence identity to SEQ ID NO:78; and a VL region comprising an amino acid sequence having at least 85% sequence identity to SEQ ID NO:96; or (P2F10) a VH region comprising an amino acid sequence having at least 85% sequence identity to SEQ ID NO:79; and a VL region comprising an amino acid sequence having at least 85% sequence identity to SEQ ID NO:97; or (P2H4) a VH region comprising an amino acid sequence having at least 85% sequence identity to SEQ ID NO:80; and a VL region comprising an amino acid sequence having at least 85% sequence identity to SEQ ID NO:98; or (P2D3) a VH region comprising an amino acid sequence having at least 85% sequence identity to SEQ ID NO:81; and a VL region comprising an amino acid sequence having at least 85% sequence identity to SEQ ID NO:99; or (P1G4) a VH region comprising an amino acid sequence having at least 85% sequence identity to SEQ ID NO:82; and a VL region comprising an amino acid sequence having at least 85% sequence identity to SEQ ID NO:100; or (P1B12) a VH region comprising an amino acid sequence having at least 85% sequence identity to SEQ ID NO:83; and a VL region comprising an amino acid sequence having at least 85% sequence identity to SEQ ID NO:101; or (P1C7) a VH region comprising an amino acid sequence having at least 85% sequence identity to SEQ ID NO:84; and a VL region comprising an amino acid sequence having at least 85% sequence identity to SEQ ID NO:102.

The present invention also provides an antigen-binding molecule, optionally isolated, which is capable of binding to CD122, comprising (i) an antigen-binding molecule according to the present invention, and (ii) an antigen-binding molecule capable of binding to common γ chain (CD132).

The present invention also provides an antigen-binding molecule, optionally isolated, which is capable of binding to common γ chain (CD132), comprising (i) an antigen-binding molecule according to the present invention, and (ii) an antigen-binding molecule capable of binding to CD122.

The present invention also provides an antigen-binding molecule, optionally isolated, which is capable of binding to CD122 and common γ chain (CD132), comprising (i) an antigen-binding molecule according to the present invention, and (ii) an antigen-binding molecule according to the present invention.

In some embodiments the antigen-binding molecule further comprises a cell membrane anchor region.

In some embodiments, the antigen binding molecule is an IL-2 receptor agonist.

In some embodiments, the antigen binding molecule is capable of reducing expression of PD-1 by T cells.

The present invention also provides a chimeric antigen receptor (CAR) comprising an antigen-binding molecule according to the present invention.

The present invention also provides an in vitro complex, optionally isolated, comprising an antigen-binding molecule or CAR according to the present invention bound to CD122 and/or CD132.

The present invention also provides a nucleic acid, optionally isolated, encoding an antigen-binding molecule according to the present invention.

The present invention also provides an expression vector comprising a nucleic acid according to the present invention.

The present invention also provides a cell comprising an antigen-binding molecule, a nucleic acid or an expression vector according to the present invention.

The present invention also provides a method for producing an antigen-binding molecule according to the present invention, the method comprising culturing a cell comprising a nucleic acid or expression vector according to the present invention under conditions suitable for expression of the antigen-binding molecule from the nucleic acid or expression vector.

The present invention also provides a composition comprising an antigen-binding molecule, nucleic acid, expression vector or cell according to the present invention.

The present invention also provides an antigen-binding molecule, nucleic acid, expression vector, cell or composition according to the present invention for use in a method of medical treatment or prophylaxis.

The present invention also provides an antigen-binding molecule, nucleic acid, expression vector, cell or composition according to the present invention for use in a method of treatment or prevention of a T cell dysfunctional disorder, a cancer or an infectious disease.

The present invention also provides the use of an antigen-binding molecule, nucleic acid, expression vector, cell or composition according to the present invention in the manufacture of a medicament for use in a method of treatment or prevention of a T cell dysfunctional disorder, a cancer or an infectious disease.

The present invention also provides a method of treating or preventing a T cell dysfunctional disorder, a cancer or an infectious disease, comprising administering to a subject a therapeutically or prophylactically effective amount of an antigen-binding molecule, nucleic acid, expression vector, cell or composition according to the present invention.

In some embodiments the cancer is selected from the group consisting of: colon cancer, colon carcinoma, colorectal cancer, nasopharyngeal carcinoma, cervical carcinoma, oropharyngeal carcinoma, gastric carcinoma, hepatocellular carcinoma; head and neck cancer, head and neck squamous cell carcinoma (HNSCC), oral cancer, laryngeal cancer; prostate cancer, lung cancer, small cell lung cancer, non-small cell lung cancer, bladder cancer, urothelial carcinoma, melanoma, advanced melanoma, renal cell carcinoma, ovarian cancer or mesothelioma.

In some embodiments the antigen binding molecule is administered in combination with a therapeutically effective amount of an agent capable of inhibiting signalling mediated by an immune checkpoint protein. In some embodiments the immune checkpoint protein is PD-1, CTLA-4, LAG-3, TIM-3, VISTA, TIGIT or BTLA.

The present invention also provides a method for generating or expanding a population of immune cells, comprising contacting immune cells in vitro, in vivo or ex vivo with an antigen-binding molecule, nucleic acid, expression vector, cell or composition.

The present invention also provides a chimeric antigen receptor (CAR) comprising an antigen-binding molecule according to the present invention.

The present invention also provides an in vitro complex, optionally isolated, comprising an antigen-binding molecule or CAR according to the present invention bound to CD122 and/or CD132.

The present invention also provides a nucleic acid, optionally isolated, encoding a CAR according to the present invention.

The present invention also provides an expression vector comprising a nucleic acid according to the present invention.

The present invention also provides a cell comprising a CAR, a nucleic acid, or an expression vector according to the present invention.

The present invention also provides a composition comprising a CAR, a nucleic acid, an expression vector or a cell according to the present invention.

The present invention also provides a CAR, a nucleic acid, an expression vector, a cell or a composition according to the present invention for use in a method of medical treatment or prophylaxis.

Description

Treatment with IL-2 is an approved immunotherapy for the treatment of cancer, and works by promoting proliferation and activity of effector immune cells such as T cells and NK cells (see e.g. Skorombolas and Frelinger, Expert Rev Clin Immunol. 2014: 10(2): 207-217).

However, there several drawbacks associated with IL-2 therapy. IL-2 has a very short half-life in serum, and so large doses and regular administration is required to achieve stimulation of T cell and NK cell proliferation/activity. This is problematic because high doses of IL-2 cause increases in levels of proinflammatory cytokines sometimes referred to as "cytokine storm", which is thought to be a result of the widespread stimulation of immune cells. The cytokine storm is in turn thought to be responsible for many of the unwanted side effects of IL-2 treatment, including vascular leak syndrome (VLS). Furthermore, IL-2 is able to act on Tregs (which express the high-affinity IL-2Rα/β/γc receptors), and so treatment with IL-2 induces expansion of this suppressor T cell subset which can downregulate effector immune cell activity.

The inventors have designed and produced agonist antibodies which selectively bind to and activate intermediate-affinity IL-2Rβ/γc receptors. The antibodies are demonstrated to mimic the effect of IL-2 on cells expressing CD122 and CD132, causing expansion of effector immune cells. Unlike IL-2, the bispecific antibodies of the present invention preferentially stimulate proliferation of effector immune cells (which express intermediate-affinity IL-2Rβ/γc receptors) over regulatory T cells (which express high levels of the high-affinity IL-2Rα/β/γc receptors). Moreover, they have an increased serum half-life as compared to IL-2, and can therefore be administered less frequently and/or at a lower dose.

IL-2Rβ (CD122) and Common Gamma Chain (γc; CD132)

Human IL-2Rβ (also known as CD122, IL15RB and P70-75) is the protein identified by UniProt P14784-1, v1 (SEQ ID NO:434). The N-terminal 26 amino acids of SEQ ID NO:434 constitute a signal peptide, and so the mature form (i.e. after processing to remove the signal peptide) of human CD122 protein has the amino acid sequence shown in SEQ ID NO:435. Amino acids 27 to 240 of SEQ ID NO:434 constitute the extracellular domain of CD122, shown in SEQ ID NO:436.

In this specification "IL-2Rβ" or "CD122" refers to CD122 from any species and includes isoforms, fragments, variants or homologues of CD122 from any species.

As used herein, a "fragment", "variant" or "homologue" of a protein may optionally be characterised as having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of the reference protein. Fragments, variants, isoforms and homologues of a reference protein may be may be characterised by ability to perform a function performed by the reference protein.

A "fragment" generally refers to a fraction of the reference protein. A "variant" generally refers to a protein having an amino acid sequence comprising one or more amino acid substitutions, insertions, deletions or other modifications relative to the amino acid sequence of the reference protein, but retaining a considerable degree of sequence identity (e.g. at least 60%) to the amino acid sequence of the reference protein. An "isoform" generally refers to a variant of the reference protein expressed by the same species as the species of the reference protein. A "homologue" generally refers to a variant of the reference protein produced by a different species as compared to the species of the reference protein. For example, human CD122 (P14784-1, v1; SEQ ID NO:434) and cynomolgus macaque CD122 (UniProt: Q38J85-1, v1) are homologues of one another.

A "fragment" of a reference protein may be of any length (by number of amino acids), although may optionally be at least 25% of the length of the reference protein (that is, the protein from which the fragment is derived) and may have a maximum length of one of 50%, 75%, 80%, 85%, 90%, 91%, 92%, 93%, 94%, 95%, 96%, 97%, 98%, or 99% of the length of the reference protein.

A fragment of CD122 may have a minimum length of one of 10, 20, 30, 40, 50, 100, 150, 200, 250 or 300 amino acids, and may have a maximum length of one of 20, 30, 40, 50, 100, 150, 200, 250, 300, 350, 400, 450 or 500 amino acids.

In some embodiments, the CD122 is mammalian CD122 (e.g. cynomolgous, human and/or rodent (e.g. rat and/or murine) CD122). Isoforms, fragments, variants or homologues of CD122 may optionally be characterised as having at least 70%, preferably one of 80%, 85%, 90%, 91%, 92%, 93%, 94%, 95%, 96%, 97%, 98%, 99% or 100% amino acid sequence identity to the amino acid sequence of immature or mature CD122 from a given species, e.g. human CD122. Isoforms, fragments, variants or homologues of CD122 may optionally be functional isoforms, fragments, variants or homologues, e.g. having a functional property/activity of the reference CD122 (e.g. full-length human CD122), as determined by analysis by a suitable assay for the functional property/activity. For example, an isoform, fragment, variant or homologue of CD122 may display one or more of: association with one or more of CD132, IL-2Rα (CD25) or IL-15Rα (CD215), or binding to IL-2 or IL-15.

In some embodiments, the CD122 has at least 70%, preferably one of 30%, 85%, 90%, 91%, 92%, 93%, 94%, 95%, 96%, 97%, 98%, 99% or 100% amino acid sequence identity to one of SEQ ID NOs:434 to 436.

Human common gamma chain (γc; also known as CD132, IL21-RG and CIDX) is the protein identified by UniProt P31785-1, v1 (SEQ ID NO:437). The N-terminal 23 amino acids of SEQ ID NO:437 constitute a signal peptide, and so the mature form (i.e. after processing to remove the signal peptide) of human CD132 protein has the amino acid sequence shown in SEQ ID NO:438. Amino acids 23 to 262 of SEQ ID NO:437 constitute the extracellular domain of CD132, shown in SEQ ID NO:439.

In this specification "γc" or "CD132" refers to CD132 from any species and includes isoforms, fragments, variants or homologues of CD132 from any species.

In some embodiments, the CD132 is mammalian CD132 (e.g. cynomolgous, human and/or rodent (e.g. rat and/or murine) CD132). Isoforms, fragments, variants or homologues of CD132 may optionally be characterised as having at least 70%, preferably one of 30%, 85%, 90%, 91%, 92%, 93%, 94%, 95%, 96%, 97%, 98%, 99% or 100% amino acid sequence identity to the amino acid sequence of immature or mature CD132 from a given species, e.g. human CD132, Isoforms, fragments, variants or homologues of CD132 may optionally be functional isoforms, fragments, variants or homologues, e.g. having a functional property/activity of the reference CD132 (e.g. full-length human CD132), as determined by analysis by a suitable assay for the functional property/activity. For example, an isoform, fragment, variant or homologue of CD132 may display one or more of: association with one or more of CD122, IL-21Rα, L-15Rα, IL-4R (CD124), IL-9R (CD129), IL-21R (CD360) or IL7R (CD127), or binding to one or more of IL-2, IL-15, IL-4, IL-9, IL-21 or IL-7.

A fragment of CD132 may have a minimum length of one of 10, 20, 30, 40, 50, 100, 150, 200, 250 or 300 amino acids, and may have a maximum length of one of 20, 30, 40, 50, 100, 150, 200, 250, 300, 350 amino acids.

In some embodiments, the CD132 has at least 70%, preferably one of 80%, 85%, 90%, 91%, 92%, 93%, 94%, 95%, 96%, 97%, 98%, 99% or 100% amino acid sequence identity to one of SEQ ID NOs:438 to 440.

IL-2 receptors and their biology is described, for example, Skrombolas and Frelinger, Expert Rev Clin Immunol. (2014)10(2) 207-217, which is hereby incorporated by reference in its entirety.

CD122 and CD132 participate in the formation of receptors for IL-2. CD122 and CD132 associate with IL-2Rα (CD25) to form the trimeric, high-affinity IL-2 receptor (sometimes designated "IL-2Rα/β/γc" or "CD25/CD122/CD132"), which binds to IL-2 with a Kd of ~10 pM. CD122 and CD132 are also capable of associating to form a functional intermediate-affinity IL-2 receptor (sometimes designated "IL-2Rβ/γc" or "CD122/CD132"), which binds to IL-2 with a Kd of ~1 nM.

The composition of the receptors, the number, and likely signalling capacity can vary with the cell type and activation stage. IL-2 receptors are expressed at relatively low levels on resting naive T cells. However, activated CD4 and CD8 T cells begin to express high levels of CD25, which allows them to bind IL-2 efficiently. CD25 is expressed at higher amounts (8-10 fold) compared to CD122 and CD132. CD25 is thought to bind IL-2 initially, effectively increasing its concentration at the cell surface and inducing a conformational change in IL-2 which then subsequently binds to the CD122 and CD132 (Liao et al., Immunity (2013) 38(1):13-25). NK cells and memory phenotype CD8 cells express high levels of CD122 and CD132 compared to naïve cells and some NK cells can also express CD25 after stimulation with IL-2.

Importantly, CD4 regulatory T cells (Tregs) constitutively express high levels of CD25. Tregs act in multiple ways to down regulate many immune responses, including anti-tumor responses (see e.g. Shevach, Immunity (2009) 30(5): 636-45).

Antigen-Binding Molecules

The present invention provides antigen-binding molecules. In aspects of the present invention the antigen-binding molecules are capable of binding to CD122. In aspects of the present invention the antigen-binding molecules are capable of binding to CD132. In aspects of the present invention the antigen-binding molecules are capable of binding to CD122 and CD132. In aspects of the present invention the antigen-binding molecules are capable of binding to CD122 and CD132, and comprise an antigen-binding molecule capable of binding to CD122 and an antigen-binding molecule capable of binding to CD132.

An "antigen-binding molecule" as used herein refers to a polypeptide or polypeptide complex which is capable of binding to a target antigen or antigens, and encompasses monoclonal antibodies, polyclonal antibodies, monospecific and multispecific antibodies (e.g., bispecific antibodies), and antibody fragments, as long as they display binding to the relevant target antigen(s).

The antigen-binding molecule of the present invention comprises a moiety or moieties capable of binding to the target antigen(s). The moiety capable of binding to a target antigen comprises an antibody heavy chain variable region (VH) and an antibody light chain variable region (VL) of an antibody capable of specific binding to the target antigen. In some embodiments, the moiety capable of binding to a target antigen comprises or consists of an aptamer capable of binding to the target antigen; e.g. a nucleic acid aptamer (reviewed, for example, in Zhou and Rossi Nat Rev Drug Discov. 2017 16(3):181-202). In some embodiments, the moiety capable of binding to a target antigen comprises or consists of a antigen-binding peptide/polypeptide, e.g. a peptide aptamer, thioredoxin, monobody, anticalin, Kunitz domain, avimer, knottin, fynomer, atrimer, DARPin, affibody, nanobody (i.e. a single-domain antibody (sdAb)) affilin, armadillo repeat protein (ArmRP), OBody or fibronectin—reviewed e.g. in Reverdatto et al., Curr Top Med Chem. 2015; 15(12): 1082-1101, which is hereby incorporated by reference in its entirety (see also e.g. Boersma et al, J Biol Chem (2011) 286:41273-85 and Emanuel et al., Mabs (2011) 3:38-48).

The antigen-binding molecules of the present invention generally comprise antigen-binding moieties comprising a VH and a VL of an antibody capable of specific binding to the target antigen. The antigen-binding moiety formed by a VH and a VL may also be referred to herein as an Fv region.

An antigen-binding molecule may be, or may comprise, an antigen-binding polypeptide, or an antigen-binding polypeptide complex. An antigen-binding molecule may comprise more than one polypeptide which together form an antigen-binding domain. The polypeptides may associate covalently or non-covalently. In some embodiments the polypeptides form part of a larger polypeptide comprising the polypeptides (e.g. in the case of scFv comprising VH and VL, or in the case of scFab comprising VH-CH1 and VL-CL).

An antigen-binding molecule may comprise or consist of one or more polypeptides. In some embodiments an antigen-binding molecule comprises 1, 2, 3, 4, 5, 6, 7, 8, 9, 10, 11 or 12 polypeptides. In some embodiments an antigen-binding molecule is a covalent or non-covalent complex of more than one polypeptide (e.g. 2, 3, 4, 6, 8, 10 or more polypeptides). For example, in some embodiments an antigen-binding molecule comprises two heavy chain polypeptides and two light chain polypeptides.

The antigen-binding molecules described herein preferably display specific binding to the relevant target (e.g. CD122 and/or CD132). As used herein, "specific binding" refers to binding which is selective for the antigen, and which can be discriminated from non-specific binding to non-target antigen. An antigen-binding molecule that specifically binds to a target molecule preferably binds the target with greater affinity, and/or with greater duration than it binds to other, non-target molecules.

An antigen-binding molecule described herein may be capable of binding to CD122 as described herein. An antigen-binding molecule described herein may be capable of binding to CD132 as described herein. An antigen-binding molecule described herein may be capable of binding to CD122 as described herein and CD132 as described herein.

The ability of a given polypeptide to bind specifically to a given molecule can be determined by analysis according to methods known in the art, such as by ELISA, Surface Plasmon Resonance (SPR; see e.g. Hearty et al., Methods Mol Biol (2012) 907:411-442), Bio-Layer Interferometry (see e.g. Lad et al., (2015) J Biomol Screen 20(4): 498-507), flow cytometry, or by a radiolabeled antigen-binding assay (RIA) enzyme-linked immunosorbent assay. Through such analysis binding to a given molecule can be measured and quantified. In some embodiments, the binding may be the response detected in a given assay.

In some embodiments, the extent of binding of the antigen-binding molecule to an non-target molecule is less than about 10% of the binding of the antibody to the target molecule as measured, e.g. by ELISA, SPR, Bio-Layer Interferometry or by RIA. Alternatively, binding specificity may be reflected in terms of binding affinity where the antigen-binding molecule binds with a dissociation constant (KD) that is at least 0.1 order of magnitude (i.e. $0.1\times10^n$, where n is an integer representing the order of magnitude) greater than the KD of the antigen-binding molecule towards a non-target molecule. This may optionally be one of at least 0.2, 0.3, 0.4, 0.5, 0.6, 0.7, 0.8, 0.9, 1.0, 1.5, or 2.0.

In certain embodiments, the antigen-binding molecule binds to the target molecule with a KD of ≤10 μM, ≤1 μM; ≤100 nM, ≤10 nM, ≤1 nM, ≤0.1 nM, ≤0.01 nM, or ≤0.001 nM as determined by analysis according to SPR, Bio-Layer Interferometry or by RIA.

In some embodiments, the antigen-binding molecule binds to the same or an overlapping epitope of the target molecule as a reference antigen-binding molecule which is capable of binding to the target molecule (i.e. CD122 or CD132). In some embodiments, the antigen-binding molecule displays competitive binding with a reference antigen-binding molecule which is capable of binding to the target molecule. Whether a given antigen-binding molecule displays such competitive binding can be determined by various methods known to the skilled person, including competition ELISA.

In some embodiments, the antigen-binding molecule comprises the complementarity-determining regions (CDRs) of an antigen-binding molecule which is capable of binding to the target molecule (i.e. CD122 or CD132). Antibodies generally comprise six CDRs; three in the light chain variable region (VL): LC-CDR1, LC-CDR2, LC-CDR3, and three in the heavy chain variable region (VH): HC-CDR1, HC-CDR2 and HC-CDR3. The six CDRs together define the paratope of the antibody, which is the part of the antibody which binds to the target molecule. There are several different conventions for defining antibody CDRs, such as those described in Kabat et al., Sequences of Proteins of Immunological interest, 5th Ed. Public Health Service, National Institutes of Health, Bethesda, Md. (1991), Chothia et al., J. Mol. Biol. 196:901-917 (1987), and VBASE2, as described in Retter et al., Nucl. Acids Res. (2005) 33 (suppl 1): D671-D674. Unless otherwise specified, CDRs of the antigen-binding molecules described herein are defined according to Kabat et al., Sequences of Proteins of Immunological interest, 5th Ed. Public Health Service, National institutes of Health, Bethesda, Md. (1991).

The antigen-binding molecule may be designed and prepared using the sequences of monoclonal antibodies (mAbs) capable of binding to CD122, and mAbs capable binding to CD132 described herein. Antigen-binding regions of antibodies, such as single chain variable fragment (scFv), Fab and $Fab_2$ fragments may also be used/provided. An 'antigen-binding region' is any fragment of an antibody which is capable of binding to the target for which the given antibody is specific.

In some embodiments, the antigen-binding molecule of the present invention is a CD122-binding molecule. In some embodiments, the antigen-binding molecule comprises or consists of a CD122-binding molecule. In some embodiments the antigen-binding molecule comprises a heavy chain variable (VH) region comprising HC-CDR1, HC-CDR2 and HC-CDR3 of a CD122-binding antibody clone described herein, or a variant thereof in which one or two or three amino acids in one or more of HC-CDR1, HC-CDR2, HC-CDR3 are substituted with another amino acid. In some embodiments the antigen-binding molecule comprises a light chain variable (VL) region comprising LC-CDR1, LC-CDR2 and LC-CDR3 of a CD122-binding antibody clone described herein, or a variant thereof in which one or two or three amino acids in one or more of LC-CDR1, LC-CDR2, LC-CDR3 are substituted with another amino acid. In some embodiments the antigen-binding molecule comprises a VH region comprising HC-CDR1, HC-CDR2 and HC-CDR3 and a VL region comprising LC-CDR1, LC-CDR2 and LC-CDR3 of a CD122-binding antibody clone described herein, or a variant thereof in which one or two or three amino acids in one or more of HC-CDR1, HC-CDR2, HC-CDR3, LC-CDR1, LC-CDR2 or LC-CDR3 are substituted with another amino acid.

In some embodiments the antigen-binding molecule comprises a VH region which comprises or consists of an amino acid sequence having at least 70%, more preferably one of at least 75%, 80%, 85%, 86%, 37%, 88%, 89%, 90%, 91%, 92%, 93%, 94%, 95%, 96%, 97%, 98%, 99%, or 100%, sequence identity to VH region of a CD122-binding antibody clone described herein. In some embodiments the antigen-binding molecule comprises a VL region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 93%, 99%, or 100%, sequence identity to VL region of a CD122-binding antibody clone described herein. In some embodiments the antigen-binding molecule comprises a VH region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to VH region of a CD122-binding antibody clone described herein and a VL region which comprises or consists of an amino acid sequence having at least 70%, more preferably one of at least 75%, 80%, 85%, 86%, 87%, 83%, 89%, 90%, 91%, 92%, 93%, 94%, 95%, 96%, 97%, 98%, 99%, or 100%, sequence identity to VL region of a CD122-binding antibody clone described herein.

In some embodiments a CD122-binding antibody clone is selected from: P2C4, P2C4_A4; P2C4_B1, P2C4_B5, P2C4_C1, P2C4_C4, P2C4_C7, P2C4_D10, P2C4_E6, P2C4_E7, P2C4_F8, P2C4_C1D10; P2C4_FW2, P2H7, P2D12, P1G11, P2C4_A9, P2C4_B6, P2C4_E9, P2C4_F8, P2C4_B12, P2C4_C12, P2C4_E2, P2C4_E3, P2C4_E8, P2C4_F11, P2C4_C2, P2C4_G11, P2C4_H1, P2C4_H2, P2C4_H3, P1E7, P1B10, P1F3, P1D10, P1E1, P2B11, P2C9, P2C10, P2C11, P2E6, P2E11, P2F9 and P2F10. In some embodiments a CD122-binding antibody clone is selected from: P1E7, P1B10, P1F3, P1D10, P1E1, P2B11, P2C9, P2C10, P2D11, P2E6, P2E11, P2F9 and P2F10. In some embodiments the CD122-binding antibody clone is P2C4, P2C4_FW2, P2E6, P1D10, P187 or P1G11. In some embodiments the CD122-binding antibody clone is P2C4 or P2C4_FW2.

In some embodiments, the antigen-binding molecule of the present invention is a CD132-binding molecule. In some embodiments, the antigen-binding molecule comprises or consists of a CD132-binding molecule. In some embodiments the antigen-binding molecule comprises a heavy chain variable (VH) region comprising HC-CDR1, HC-CDR2 and HC-CDR3 of a CD132-binding antibody clone described herein, or a variant thereof in which one or two or three amino acids in one or more of HC-CDR1, HC-CDR2, HC-CDR3 are substituted with another amino acid. In some embodiments the antigen-binding molecule comprises a light chain variable (VL) region comprising LC-CDR1, LC-CDR2 and LC-CDR3 of a CD132-binding antibody clone described herein, or a variant thereof in which one or two or three amino acids in one or more of LC-CDR1, LC-CDR2, LC-CDR3 are substituted with another amino acid. In some embodiments the antigen-binding molecule comprises a VH region comprising HC-CDR1, HC-CDR2 and HC-CDR3 and a VL region comprising LC-CDR1, LC-CDR2 and LC-CDR3 of a CD132-binding antibody clone described herein, or a variant thereof in which one or two or three amino acids in one or more of HC-CDR1, HC-CDR2, HC-CDR3, LC-CDR1, LC-CDR2 or LC-CDR3 are substituted with another amino acid.

In some embodiments the antigen-binding molecule comprises a VH region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to VH region of a CD132-binding antibody clone described herein. In some embodiments the antigen-binding molecule comprises a VL region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to VL region of a CD132-binding antibody clone described herein. In some embodiments the antigen-binding molecule comprises a VH region which comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to VH region of a CD132-binding antibody clone described herein and a VL region which comprises or consists of an amino acid sequence having at least 70%, more preferably one of at least 75%, 80%, 85%, 85%, 87%, 88%, 89%, 90%, 91%, 92%, 93%, 94%, 95%, 96%, 97%, 98%, 99%, or 100%, sequence identity to VL region of a CD132-binding antibody clone described herein.

In some embodiments a CD132-binding antibody clone is selected from: P1A3, P1A3_B3, P1A3_E8, P1A3_E9, P2B9, P1A3_B4, P1A3_FW2, P1A10, P1B6, P1C10, P1D7, P1E8, P2B2, P2B7, P2D11, P2F10, P2H4, P2D3, P1G4, P1B12 and P1C7. In some embodiments a CD132-binding antibody clone is selected from: P1A10, P1B6, P1C10, P1D7, P1E8, P2B2, P2B7, P2D11, P2F10, P2H4, P2D3, P1G4, P1B12 and P1C7. In some embodiments the CD132-binding antibody clone is P1A10. In some embodiments the CD132-binding antibody clone is P1A3 or P1A3_FW2.

In some embodiments the antigen-binding molecule of the present invention comprises:

a VH region comprising HC-CDR1 HC-CDR2 and HC-CDR3 and a VL region comprising LC-CDR1, LC-CDR2 and LC-CDR3 of a CD122-binding antibody clone, or a variant thereof in which one or two or three amino acids in one or more of HC-CD1, HC-CDR2, HC-CDR3, LC-CDR1, LC-CDR2 or LC-CDR3 are substituted with another amino acid; and a VH region comprising HC-CDR1, HC-CDR2 and HC-CDR3 and a VL region comprising LC-CDR1, LC-CDR2 and LC-CDR3 of a CD132-binding antibody clone, or a variant thereof in which one or two or three amino acids in one or more of HC-CDR1, HC-CDR2, HC-CDR3, LC-CDR1, LC-CDR2 or LC-CDR3 are substituted with another amino acid;

wherein:

the CD122-binding antibody clone is P2C4 and the CD132-binding antibody clone is P1A10; or the CD122-binding antibody clone is P2C4 and the CD132-binding antibody clone is P1A3; or the CD122-binding antibody clone is P2C4_FW2 and the CD132-binding antibody clone is P1A3; or the CD122-binding antibody clone is P2E6 and the CD132-binding antibody clone is P1A10; or the CD122-binding antibody clone is P1D10 and the CD132-binding antibody clone is P1A10; or the CD122-binding antibody clone is P1E7 and the CD132-binding antibody clone is P1A10; or the CD122-binding antibody clone is P1G11 and the CD132-binding antibody clone is P1A10.

In some embodiments the antigen-binding molecule of the present invention comprises:

a VH region having at least 70% sequence identity to the VH region of a CD122-binding antibody clone; and a VL region having at least 70% sequence identity to the VL region of the CD122-binding antibody clone; and a VH region having at least 70% sequence identity to the VH region of a CD132-binding antibody done, and a VL region having at least 70% sequence identity to the VL region of the CD132-binding antibody clone;

wherein:

the CD122-binding antibody clone is P2C4 and the CD132-binding antibody clone is P1A10; or the CD122-binding antibody clone is P2C4 and the CD132-binding antibody clone is P1A3; or the CD122-binding antibody clone is P2C4_FW2 and the CD132-binding antibody clone is P1A3; or the CD122-binding antibody clone is P2E6 and the CD132-binding antibody clone is P1A10; or the CD122-binding antibody clone is P1D10 and the CD132-binding antibody clone is P1A10; or the CD122-binding antibody clone is P1E7 and the CD132-binding antibody clone is P1A10; or the CD122-binding antibody clone is P1G11 and the CD132-binding antibody clone is P1A10.

In some embodiments the antigen-binding molecule of the present invention comprises:

(i) a CD122-binding antigen-binding molecule comprising:

(P2C4) a VH region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a VL region incorporating the following CDRs:

LC-CDR1 having the amino acid sequence of SEQ ID NO:145

LC-CDR2 having the amino acid sequence of SEQ ID NO: 162

LC-CDR3 having the amino acid sequence of SEQ ID NO:177; and (ii) a CD132-binding antigen-binding molecule comprising:

(P1A10) a VH region incorporating the following CDRs:

HC-CDR1 having the amino acid sequence of SEQ ID NO:195

HC-CDR2 having the amino acid sequence of SEQ ID NO:204

HC-CDR3 having the amino acid sequence of SEQ ID NO:212; and a VL region incorporating the following CDRs:

LC-CDR1 having the amino acid sequence of SEQ ID NO:227

LC-CDR2 having the amino acid sequence of SEQ ID NO:238

LC-CDR3 having the amino acid sequence of SEQ ID NO:248.

In some embodiments the antigen-binding molecule comprises:

(i) a CD122-binding antigen-binding molecule comprising:

(P2C4) a VH region comprising an amino acid sequence having at least 85% sequence identity to SEQ ID NO:1; and a VL region comprising an amino acid sequence having at least 85% sequence identity to SEQ ID NO:35; and (ii) a CD132-binding antigen-binding molecule comprising:

(P1A10) a VH region comprising an amino acid sequence having at least 85% sequence identity to SEQ ID NO:71; and a VL region comprising an amino acid sequence having at least 85% sequence identity to SEQ ID NO:89.

In some embodiments, the antigen-binding molecule may comprise a variant of a reference VL/VH region, e.g. comprising 1, 2, 3, 4, 5, 6, 7, 8, 9 or 10 substitutions with respect to the amino acid sequence of the reference VL/VH region(s). In some embodiments the substitution(s) are not in the CDRs. In some embodiments the substitution(s) are in the framework region(s)—i.e. the amino acid sequences of the VL/VH region(s) other than the CDRs.

In some embodiments, the substitutions are conservative substitutions, for example according to the following Table. In some embodiments, amino acids in the same block in the middle column are substituted. In some embodiments, amino acids in the same line in the rightmost column are substituted:

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some embodiments the antigen-binding molecule of the present invention does not comprise a combination of CDRs or VL/VH domains disclosed in WO 2017/021540 A1 (hereby incorporated by reference in its entirety).

In some embodiments the CD122-binding antigen-binding molecule according to the invention comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs:265 to 308. In some embodiments the CD122-binding antigen-binding molecule according to the invention comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%, or 100%, sequence identity to one of SEQ ID NOs:296 to 308.

In some embodiments the CD132-binding antigen-binding molecule according to the invention comprises or consists of an amino acid sequence having at least 70%, more preferably one of at least 75%, 80%, 85%, 86%, 87%, 88%, 89%, 90%, 91%, 92%, 93%, 94%, 95%, 96%, 97%, 98%, 99%; or 100%, sequence identity to one of SEQ ID NOs:309 to 329. In some embodiments the CD132-binding antigen-binding molecule according to the invention comprises or consist of an amino acid sequence having at least 70%, more preferably one of at least 75%; 30%, 85%, 86%, 87%, 83%, 89%, 90%; 91%, 92%; 93%, 94%, 95%, 96%, 97%, 98%, 99%, or 100%, sequence identity to one of SEQ ID NOs:316 to 329.

In some embodiments, the CD122-binding antigen-binding molecule according to the present invention lacks HC-CDR1, HC-CDR2, HC-CDR3, LC-CDR1, LC-CDR2, and LC-CDR3 of one or more of the following clones: P2C4, P2C4_A4, P2C4_B1, P2C4_B5, P2C4_C1, P2C4_C4, P2C4_C7, P2C4_D10, P2C4_E6, P2C4_E7, P2C4_F8, P2C4_C1D10, P2C4_FW2, P2H7, P2D12, P1G11, P2C4_A9, P2C4_B6, P2C4_E9, P2C4_B8, P2C4_B12, P2C4_C12, P2C4_E2, P2C4_E3, P2C4_E8, P2C4_F11, P2C4_G2, P2C4_G11, P2C4_H1, P2C4_H2 and P2C4_H3. In some embodiments the CD122-binding antigen-binding molecule according to the present invention lacks the VL domain sequence and/or the VH domain sequence of one or more of said clones. In some embodiments the CD122-binding antigen-binding molecule according to the present invention lacks the VL domain sequence and/or the VH domain sequence of one or more of said clones.

In some embodiments, the CD132-binding antigen-binding molecule according to the present invention lacks HC-CDR1, HC-CDR2, HC-CDR3, LC-CDR1, LC-CDR2, and LC-CDR3 of one or more of the following clones: P1A3, P1A3_B3, P1A3_E8, P1A3_E9, P1A3_B4, P1A3_FW2 and P2B9. In some embodiments the CD132-binding antigen-binding molecule according to the present invention lacks the VL domain sequence and/or the VH domain sequence of one or more of said clones.

Antigen-binding molecules may be produced by a process of affinity maturation in which a modified antibody is generated that has an improvement in the affinity of the antibody for antigen, compared to an unmodified parent antibody. Affinity-matured antigen-binding molecules may be produced by procedures known in the art, e.g., Marks et al., *Rio/Technology* 10:779-783 (1992); Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-159 (1995); and Hawkins et al, *J. Mol. Biol.* 226:889-896 (1992).

The VL and VH region of an antigen-binding region of an antibody together constitute the Fv region. In some embodiments; the antigen-binding molecule according to the present invention comprises; or consists of, an Fv region which binds to CD122. In some embodiments; the antigen-binding molecule comprises, or consists of, an Fv region which binds to CD132.

The VL and light chain constant (CL) region, and the VH region and heavy chain constant 1 (CH1) region of an antigen-binding region of an antibody together constitute the Fab region. In some embodiments, the antigen-binding molecule of the antigen-binding molecule described herein comprises, or consists of, a Fab region which binds to CD122. In some embodiments, the antigen-binding molecule comprises, or consists of, a Fab region which binds to CD132.

In some embodiments, the antigen-binding molecule described herein comprises, or consists of, a whole antibody which binds to CD122. In some embodiments, the antigen-binding molecule described herein comprises, or consists of, a whole antibody which binds to a CD132. As used herein, "whole antibody" refers to an antibody having a structure which is substantially similar to the structure of an immunoglobulin (Ig). Different kinds of immunoglobulins and their structures are described e.g. in Schroeder and Cavacini J Allergy Clin Immunol. (2010) 125(202): S41-S52, which is hereby incorporated by reference in its entirety.

Immunoglobulins of type G (i.e. IgG) are ~150 kDa glycoproteins comprising two heavy chains and two light chains. From N- to C-terminus, the heavy chains comprise a VH followed by a heavy chain constant region comprising three constant domains (CH1, CH2, and CH3), and similarly the light chains comprise a VL followed by a CL. Depending on the heavy chain, immunoglobulins may be classed as IgG (e.g. IgG1, IgG2, IgG3, IgG4), IgA (e.g. IgA1, IgA2), IgD, IgE, or IgM. The light chain may be kappa (κ) or lambda (λ).

In some embodiments the immunoglobulin heavy chain constant sequence is human immunoglobulin G 1 constant (IGHG1, UniProt: P01857-1, v1 SEQ ID NO:440). Positions 1 to 98 of SEQ ID NO:440 form the CH1 region (SEQ ID NO:441). Positions 99 to 110 of SEQ ID NO:440 form a hinge region between CH1 and CH2 regions (SEQ ID NO:442). Positions 111 to 223 of SEQ ID NO:440 form the CH2 region (SEQ ID NO:443). Positions 224 to 330 of SEQ ID NO:440 form the CH3 region (SEQ ID NO:444).

In some embodiments a CH1 region comprises or consists of the sequence of SEQ ID NO:441, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:441. In some embodiments a CH1-CH2 hinge region comprises or consists of the sequence of SEQ ID NO:442, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:442. In some embodiments a CH2 region comprises or consists of the sequence of SEQ ID NO:443, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:443. In some embodiments a CH3 region comprises or consists of the sequence of SEQ ID NO:444, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:444.

It will be appreciated that CH3 regions may be provided with further substitutions in accordance with modification to an Fc region of the antigen-binding molecule as described herein. In some embodiments a CH3 region comprises or consists of the sequence of SEQ ID NO:447, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:447. In some embodiments a CH3 region comprises or consists of the sequence of SEQ ID NO:448, or a sequence having at least 60%, preferably one of 70%; 75%, 80%, 85%, 90%, 91%, 92%, 93%; 94%, 95%; 96%, 97%, 98%, 99% or 100% amino acid sequence identity to the amino acid sequence of SEQ ID NO:448.

In some embodiments the antigen-binding molecule of the present invention comprises one or more regions of an immunoglobulin light chain constant sequence. In some embodiments the immunoglobulin light chain constant sequence is human immunoglobulin kappa constant (IGKC; Cκ; UniProt: P01834-1, v2; SEQ ID NO:445). In some embodiments the immunoglobulin light chain constant sequence is a human immunoglobulin lambda constant (IGLC; Cλ), e.g. IGLC1, IGLC2, IGLC3, IGLC6 or IGLC7. In some embodiments a CL region comprises or consists of the sequence of SEQ ID NO:445, or a sequence having at least 60%, preferably one of 70%, 75%, 80%, 85%, 90%, 91%, 92%, 93%, 94%, 95%, 96%, 97%, 98%, 99% or 100% amino acid sequence identity to the amino acid sequence of SEQ ID NO:445.

In some embodiments, the antigen-binding molecule described herein comprises, or consists of, an IgG (e.g. IgG1; IgG2, IgG3, IgG4), IgA (e.g. IgA1, IgA2), IgD, IgE, or IgM which binds to CD122. In some embodiments, the antigen-binding molecule described herein comprises, or consists of, an IgG (e.g. IgG1, IgG2, IgG3, IgG4), IgA (e.g. IgA1, IgA2), IgD, IgE, or IgM which binds to CD132.

The antigen-binding molecules according to the present invention may be provided in any suitable format.

Aspects of the present invention relate to multispecific antigen-binding molecules. By "multispecific" it is meant that the antigen-binding molecule displays specific binding to more than one target. In particular; the antigen-binding molecule is binding to CD122 and CD132, and so is at least bispecific. The term "bispecific" means that the antigen-binding molecule is able to bind specifically to at least two distinct antigenic determinants.

Multispecific antigen-binding molecules described herein display at least monovalent binding with respect to CD122, and also displays at least monovalent binding with respect to CD132. Binding valency refers to the number of binding sites in an antigen-binding molecule for a given antigenic determinant. For example, bispecific antigen-binding molecules in scFv-KiH-Fc, CrossMab and Duobody formats are provided herein; which are monovalent with respect to binding to CD122, and monovalent with respect to binding to CD132.

In some embodiments the antigen-binding molecule comprises one binding site for CD122, and one binding site for CD132. In some embodiments the antigen-binding molecule comprises more than one binding site (e.g. two, three) for CD122. In some embodiments the antigen-binding molecule comprises more than one binding site (e.g. two, three) for CD132. In some embodiments the antigen-binding molecule comprises more than one binding site (e.g. two, three) for CD122, and more than one binding site (e.g. two, three) for CD132.

In some embodiments the antigen-binding molecule is multivalent (e.g. bivalent, trivalent) for CD122. In some embodiments the antigen-binding molecule is multivalent (e.g. bivalent, trivalent) for CD132. In some embodiments the antigen-binding molecule is multivalent (e.g. bivalent, trivalent) for CD122, and multivalent (e.g. bivalent, trivalent) for CD132.

In some embodiments the antigen-binding molecule comprises two binding sites for CD122. In some embodiments the antigen-binding molecule comprises two binding sites for CD132. In some embodiments the antigen-binding molecule comprises two binding sites for CD122, and two binding sites for CD132.

Multispecific antigen-binding molecules according to the invention may be provided in any suitable format, such as those formats described in Kontermann MAbs 2012, 4(2): 182-197, which is hereby incorporated by reference in its entirety. For example, an antigen-binding molecule may be a bispecific antibody conjugate (e.g. an IgG2, $F(ab')_2$ or CovX-Body), a bispecific IgG or IgG-like molecule (e.g. an IgG, $scFv_4$-Ig, IgG-scFv, scFv-IgG, DVD-Ig, IgG-sVD, sVD-IgG, 2 in 1-IgG, $mAb^2$, or Tandernab common LC), an asymmetric bispecific IgG or IgG-like molecule (e.g. a kih IgG, kih IgG common LC, CrossMab, kih IgG-scFab, mAb-Fv, charge pair or SEED-body), a small bispecific antibody molecule (e.g. a Diabody (db), dsDb, DART, scDb, tandAbs, tandem scFv (taFv), tandem dAb/VHH, triple body, triple head, Fab-scFv, or $F(ab')_2$-$scFv_2$), a bispecific Fc and $C_H3$ fusion protein (e.g. a taFv-Fc, Di-diabody, scDb-$C_H3$, scFv-Fc-scFv, HCAb-VHH, scFv-kih-Fc, or scF-v-kih-$C_H3$), or a bispecific fusion protein (e.g. a $scFv_2$-albumin, scab-albumin, taFv-toxin, DNL-$Fab_3$, DNL-$Fab_4$-IgG, DNL-$Fab_4$-IgG-$cytokine_2$): See in particular Figure 2 of Kontermann MAbs 2012, 4(2): 182-19. See also Brinkmann and Kontermann, MAbs (2017) 9(2):182-212 (hereby incorporated by reference in its entirety), in particular FIG. 2.

The skilled person is able to design and prepare bispecific antigen-binding molecules. Methods for producing bispecific antigen-binding molecules include chemically cross-linking of antigen-binding molecules or antibody fragments, e.g. with reducible disulphide or non-reducible thioether bonds, for example as described in Segal and Bast, 2001. Production of Bispecific Antigen-binding molecules. Current Protocols in Immunology, 14:IV:2.13:2.13.1-2.13.15, which is hereby incorporated by reference in its entirety. For example, N-succinimidyl-3-(-2-pyridyldithio)-propionate (SPDP) can be used to chemically crosslink e.g. Fab fragments via hinge region SH— groups, to create disulfide-linked bispecific $F(ab)_2$ heterodimers.

Other methods for producing bispecific antigen-binding molecules include fusing antibody-producing hybridomas e.g. with polyethylene glycol, to produce a quadroma cell capable of secreting bispecific, antibody, for example as described in D. M. and Bast, B. J. 2001. Production of Bispecific Antigen-binding molecules. Current Protocols in Immunology. 14:IV:2.13:2.13.1-2.13.18.

Bispecific antigen-binding molecules according to the present invention can also be produced recombinantly, by expression from e.g. a nucleic acid construct encoding polypeptides for the antigen-binding molecules, for example as described in Antibody Engineering: Methods and Protocols, Second Edition (Humana Press, 2012), at Chapter 40: Production of Bispecific Antigen-binding molecules: Diabodies and Tandem scFv (Hornig and Färber-Schwarz), or French, How to make bispecific antigen-binding molecules, Methods Mol. Med. 2000; 40:333-339, the entire contents of both of which are hereby incorporated by reference.

For example, a DNA construct encoding the light and heavy chain variable domains for the two antigen-binding fragments (i.e. the light and heavy chain variable domains for the antigen-binding fragment capable of binding CD122 or CD132, and the light and heavy chain variable domains for the antigen-binding fragment capable of binding to another target protein), and including sequences encoding a suitable linker or dimerization domain between the antigen-binding fragments can be prepared by molecular cloning techniques. Recombinant bispecific antibody can thereafter be produced by expression (e.g. in vitro) of the construct in a suitable host cell (e.g. a mammalian host cell), and expressed recombinant bispecific antibody can then optionally be purified.

In some embodiments, the antigen-binding molecule comprises an Fv fragment, scFv or Fab fragment specific for CD122 and an Fv, scFv or Fab fragment specific for CD132.

In some embodiments, the antigen-binding molecule according to the present invention comprises:

- a CD122-binding region comprising:
  - a polypeptide comprising a VH, a CH2 domain and a CH3 domain
  - a polypeptide comprising a VL and a CL domain; and
- a CD132-binding region comprising:
  - a polypeptide comprising a VH, a CH2 domain and a CH3 domain
  - a polypeptide comprising a VL and a CL domain.

In some embodiments, the antigen-binding molecule according to the present invention comprises:

a CD122-binding region comprising:

a polypeptide comprising a VH, a CH1 domain, a CH2 domain and a CH3 domain a polypeptide comprising a VL and CL domain; and a CD132-binding region comprising:

a polypeptide comprising a VH, a CH1 domain, a CH2 domain and a CH3 domain a polypeptide comprising a VL and CL domain.

In some embodiments, the antigen-binding molecule according to the present invention comprises:

a CD122-binding region comprising:

a polypeptide comprising a VL, a VH, a CH2 domain and a CH3 domain; and a CD132-binding region comprising:

a polypeptide comprising a VL, VH, a CH2 domain and a CH3 domain.

In some embodiments, the antigen-binding molecule according to the present invention comprises:

a CD122-binding region comprising:

a polypeptide comprising a VH, a VL, a CH2 domain and a CH3 domain; and a CD132-binding region comprising:

a polypeptide comprising a VH, VL, a CH2 domain and a CH3 domain.

In some embodiments, the antigen-binding molecule according to the present invention comprises:

a CD122-binding region comprising:

a polypeptide comprising a VL, a VH, a CH1 domain, a CH2 domain and a CH3 domain; and a CD132-binding region comprising:

a polypeptide comprising a VL, VH, a CH1 domain, a CH2 domain and a CH3 domain.

In some embodiments, the antigen-binding molecule according to the present invention comprises:

a CD122-binding region comprising:

a polypeptide comprising a VH, a VL, a CH1 domain, a CH2 domain and a CH3 domain; and a CD132-binding region comprising:

a polypeptide comprising a VH, VL, a CH1 domain, a CH2 domain and a CH3 domain.

The variable of the heavy and light chains or the constant regions of the heavy (i.e. CH1) and light chain (CL) regions of a Fab fragment of an antigen-binding molecule according to the invention may be exchanged (i.e. Fab light chain=VL-CH1; Fab heavy chain=VH-CL). Fab fragments formed by association of polypeptides comprising such structure are referred to as “cross-Fab” or “crossover Fab” fragments. In some embodiments, the antigen-binding molecule comprises or consists of, a cross-Fab region which binds to CD122. In some embodiments, the antigen-binding molecule comprises, or consists of, a cross-Fab region which binds to CD132.

In some embodiments, the antigen-binding molecule comprises a cross-Fab fragment specific for CD122 and/or a cross-Fab fragment specific for CD132.

In some embodiments, the antigen-binding molecule according to the present invention comprises:

a CD122-binding region comprising:

a polypeptide comprising a VH, a CL domain, a CH2 domain and a CH3 domain a polypeptide comprising a VL and a CH1 domain; and a CD132-binding region comprising:

a polypeptide comprising a VH, a CL domain, a CH2 domain and a CH3 domain a polypeptide comprising a VL and a CH1 domain.

In some embodiments the antigen-binding molecules of the present invention comprise an Fc region.

In IgG IgA and IgD isotypes Fc regions are composed of CH2 and CH3 regions from one polypeptide, and CH2 and CH3 regions from another polypeptide. The CH2 and CH3 regions from the two polypeptides together form the Fc region. In IgM and IgE isotypes the Fc regions contain three constant domains (CH2, CH3 and CH4), and CH2 to CH4 from the two polypeptides together form the Fc region, Fc regions provide for interaction with Fc receptors and other molecules of the immune system to bring about functional effects. IgG Fc-mediated effector functions are reviewed e.g. in Jefferis et al., Immunol Rev 1998 163:59-76 (hereby incorporated by reference in its entirety), and are brought about through Fc-mediated recruitment and activation of immune cells (e.g. macrophages, dendritic cells, NK cells and T cells) through interaction between the Fc region and Fc receptors expressed by the immune cells, recruitment of complement pathway components through binding of the Fc region to complement protein C1q, and consequent activation of the complement cascade.

In some embodiments, the antigen-binding molecule comprises a polypeptide comprising an amino acid sequence having at least 70%, preferably one of 80%, 85%, 90%, 91%, 92%, 93%. 94%, 95%, 96%, 97%, 98%, 99% or 100% amino acid sequence identity to SEQ ID NO:444. In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:446. In some embodiments the antigen-binding molecule comprises more than one polypeptide (e.g. 2 polypeptides), each comprising a an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:444. In some embodiments the antigen-binding molecule comprises more than one polypeptide (e.g. 2 polypeptides), each comprising a an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:446.

In some embodiments the antigen-binding molecule of the present invention comprises an Fc region comprising modification to reduce antibody effector function. Fc-mediated effector functions include Fc receptor binding, antibody-dependent cellular cytotoxicity (ADCC), antibody-dependent cell-mediated phagocytosis (ADCP), complement-dependent cytotoxicity (CDC), formation of the membrane attack complex (MAC), cell degranulation, cytokine and/or chemokine production, and antigen processing and presentation.

Modifications to antibody Fc regions that influence Fc-mediated functions are known in the art, such as those described e.g. in Wang et al., Protein Cell (2018) 9(1):63-73, which is hereby incorporated by reference in its entirety. In particular, exemplary Fc region modifications known to influence antibody effector function are summarised in Table 1 of Wang et al., Protein Cell (2018) 9(1):63-73.

The combination of substitutions “L234A/L235A” and corresponding substitutions (such as e.g. F234A/L235A in human IgG4) are known to disrupt binding of Fc to Fcγ receptors and inhibit ADCC, ADCP, and also to reduce C1q binding and thus CDC (Schlothauer et al., Protein Engineering, Design and Selection (2016), 29(10):457-466, hereby incorporated by reference in entirety).

In some embodiments the antigen-binding molecule of the present invention comprises an Fc region comprising modification corresponding to the combination of substitutions L234A/L235A.

In some embodiments, the antigen-binding molecule of the present invention comprises an Fc region comprising modification in one or more of the CH2 and CH3 regions promoting association of the Fc region. Recombinant co-expression of constituent polypeptides of an antigen-binding molecule and subsequent association leads to several possible combinations. To improve the yield of bispecific antigen-binding molecules of the invention in recombinant production, it is advantageous to introduce in the Fc regions modification(s) promoting association of the desired combination of polypeptides. Suitable modifications are described e.g. in Ha et al., Front. Immnol (2016) 7:394, which is hereby incorporated by reference in its entirety.

In some embodiments the antigen antigen-binding molecule of the present invention comprises an Fc region comprising paired substitutions in the CH3 regions of the Fc region according to one of the following formats, as shown in Table 1 of Ha et al., Front, Immnol (2016) 7:394: KiH, $KiH_{s-s}$, HA-TF, ZW1, 7.8.60, DD-KK, EW-RVT, EW-$RVT_{s-s}$, SEED or A107.

In some embodiments, the bispecific antigen-binding molecule of the present invention is provided with an Fc region comprising the "knob-into-hole" or "KiH" modification, e.g. as described e.g. in U.S. Pat. No. 7,695,936 and Carter, J Immunol Meth 248, 7-15 (2001). In such embodiments, one of the CH3 regions of the Fc region comprises a "knob" modification, and the other CH3 region comprises a "hole" modification. The "knob" and "hole" modifications are positioned within the respective CH3 regions so that the "knob" can be positioned in the "hole" in order to promote heterodimerisation (and inhibit homodimerisation) of the polypeptides and/or stabilise heterodimers. Knobs are constructed by substituting amino acids having small chains with those having larger side chains (e.g. tyrosine or tryptophan). Holes are created by substituting amino acids having large side chains with those having smaller side chains (e.g. alanine or threonine).

In some embodiments, one of the CH3 regions of the Fc region of the antigen-binding molecule of the present invention comprises the substitution (numbering of positions/substitutions in the Fc region herein is according to the EU numbering system as described in Kabat et al., Sequences of Proteins of Immunological Interest, 5th Ed. Public Health Service, National Institutes of Health, Bethesda, Md., 1991) T366W, and the other CH3 region of the Fc region comprises the substitution Y407V. In some embodiments, one of the CH3 regions of the Fc region of the antigen-binding molecule comprises the substitution T366W, and the other CH3 region of the Fc region comprises the substitutions T366S and L368A. In some embodiments, one of the CH3 regions of the Fc region of the antigen-binding molecule comprises the substitution T356W, and the other CH3 region of the Fc region comprises the substitutions Y407V, T356S and L368A.

In some embodiments, one of the CH3 regions comprises the substitution S354C, and the other CH3 region of the Fc region comprises the substitution Y349C. Introduction of these cysteine residues results in formation of a disulfide bridge between the two CH3 regions of the Fc region, further stabilizing the heterodimer (Carter (2001), J Immunol Methods 248, 7-15).

In some embodiments, the Fc region comprises the "$KiH_{s-s}$" modification. In some embodiments one of the CH3 regions comprises the substitutions T366W and S354C, and the other CH3 region of the Fc region comprises the substitutions T366S, L368A, Y407V and Y349C.

In some embodiments, one of the CH3 regions comprises the substitutions K392D and K409D, and the other CH3 region of the Fc region comprises the substitutions E356K and D399K. "DDKK" knob-into-hole technology is described e.g. in WO 2014/131694 A1, and promotes assembly of the heavy chains providing the complementary amino acid residues.

In some embodiments, the antigen-binding molecule of the present invention comprises an Fc region modified as described in Labrijn et al., Proc Natl Acad Sci USA. (2013) 110(13):5145-50, referred to as 'Duobody' format. In some embodiments one of the CH3 regions comprises the substitution K409R, and the other CH3 region of the Fc region comprises the substitution K405L.

In some embodiments, the antigen-binding molecule of the present invention comprises an Fc region modified as described in Strop et al., J Mol Biol. (2012) 420(3):204-19, so-called 'EEE-RRR' format. In some embodiments one of the CH3 regions comprises the substitutions D221E, P228E and L368E, and the other CH3 region of the Fc region comprises the substitutions D221R, P228R and K409R.

In some embodiments, the antigen-binding molecule comprises an Fc region comprising the "EW-RVT" modification described in Choi et al., Mol Cancer Ther (2013) 12(12):2748-59. In some embodiments one of the CH3 regions comprises the substitutions K360E and K409W, and the other CH3 region of the Fc region comprises the substitutions Q347R, D399V and F405T.

In some embodiments, the antigen-binding molecule of the present invention comprises an Fc region comprising the "SEED" modification as described in Davis et al., Protein Eng Des Sel (2010) 23(4):195-202, in which β-strand segments of human IgG1 CH3 and IgA CH3 are exchanged.

In some embodiments, one of the CH3 regions comprises the substitutions S364H and F405A, and the other CH3 region of the Fc region comprises the substitutions Y349T and T394F (see e.g. Moore et al., MAbs (2011) 3(6):546-57).

In some embodiments, one of the CH3 regions comprises the substitutions T350V, L351Y, F405A and Y407V, and the other CH3 region of the Fc region comprises the substitutions T350V, T366L, K392L and T394W (see e.g. Von Kreudenstein et al., MAbs (2013) 5(5):646-54).

In some embodiments, one of the CH3 regions comprises the substitutions K360D, D399M and Y407A, and the other CH3 region of the Fc region comprises the substitutions E345R, Q347R, T366V and K409V (see e.g. Leaver-Fay et al., Structure (2016) 24(4):641-51).

In some embodiments, one of the CH3 regions comprises the substitutions K370E and K409W, and the other CH3 region of the Fc region comprises the substitutions E357N, D399V and F405T (see e.g. Choi et al., PLoS One (2015) 10(12):e0145349).

In particular embodiments, the antigen-binding molecule comprises a KiH Fc region. In particular embodiments, the antigen-binding molecule comprises a $KiH_{s-s}$ Fc region.

In some embodiments the antigen-binding molecule comprises a polypeptide comprising a CH3 region comprising W at the position corresponding to position 366. In some embodiments the antigen-binding molecule comprises a polypeptide comprising a CH3 region comprising W at the position corresponding to position 360 and C at the position corresponding to position 354.

In some embodiments the antigen-binding molecule comprises a polypeptide comprising a CH3 region comprising S at the position corresponding to position 366, and A at the position corresponding to position 368. In some embodiments the antigen-binding molecule comprises a polypeptide comprising a CH3 region comprising S at the position corresponding to position 366, A at the position corresponding to position 368, and Y at the position corresponding to position 407. In some embodiments the antigen-binding molecule comprises a polypeptide comprising a CH3 region comprising S at the position corresponding to position 366, A at the position corresponding to position 368, Y at the position corresponding to position 407, and C at the position corresponding to position 349.

In some embodiments the antigen-binding molecule comprises: (a) a polypeptide comprising a CH3 region comprising W at the position corresponding to position 366, and C at the position corresponding to position 354; and (b) a polypeptide comprising a CH3 region comprising S at the position corresponding to position 366, A at the position corresponding to position 368, Y at the position corresponding to position 407, and C at the position corresponding to position 349.

In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:259. In some embodiments, the antigen-binding molecule comprises a polypeptide comprising an amino acid sequence having at least 70%, preferably one of 80%, 85%, 90%, 91%, 92%, 93%, 94%, 95%, 90%, 97%, 98%, 99% or 100% amino acid sequence identity to SEQ ID NO:451.

In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:447. In some embodiments, the antigen-binding molecule comprises a polypeptide comprising an amino acid sequence having at least 70%, preferably one of 80%, 85%, 90%, 91%, 92%, 93%, 94%, 95%, 90%, 97%, 98%, 99% or 100% amino acid sequence identity to SEQ ID NO:448: In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:447, and a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:448.

In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:449. In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 93%, 99% or 100% amino acid sequence identity to SEQ ID NO:450. In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:449, and a polypeptide comprising an amino acid sequence having at least 70%, preferably one of 80%. 85%, 90%, 91%, 92%, 93%, 94%, 95%, 96%, 97%, 98%, 99% or 100% amino acid sequence identity to SEQ ID NO:450.

In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:452. In some embodiments, the antigen-binding molecule comprises a polypeptide comprising an amino acid sequence having at least 70%, preferably one of 80%, 85%, 90%, 91%, 92%, 93%, 94%, 95%, 96%. 97%, 98%, 99% or 100% amino acid sequence identity to SEQ ID NO:453. In some embodiments, the antigen-binding molecule comprises a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:452, and a polypeptide comprising an amino acid sequence having at least 70%, preferably one of 80%, 85%, 90%, 91%, 92%, 93%, 94%, 95%, 96%, 97%, 98%, 99% or 100% amino acid sequence identity to SEQ ID NO:453.

The present invention also provides polypeptide constituents of the antigen-binding molecules described herein. The polypeptides may be provided in isolated or substantially purified form.

The antigen-binding molecule of the present invention may be, or may comprise, a complex of polypeptides.

In the present specification where a polypeptide comprises more than one domain or region, it will be appreciated that the plural domains/regions can be present in the same polypeptide chain. That is, the polypeptide may comprise more than one domain or region in a fusion polypeptide comprising the domains/regions.

In some embodiments a polypeptide according to the present invention comprises, or consists of, a VH as described herein. In some embodiments a polypeptide according to the present invention comprises, or consists of, a VL as described herein.

In some embodiments, the polypeptide additionally comprises one or more antibody heavy chain constant regions (CH). In some embodiments, the polypeptide additionally comprises one or more antibody light chain constant regions (CL). In some embodiments, the polypeptide comprises a CH1, CH2 region and/or a CH3 region of an immunoglobulin (Ig).

In some embodiments the polypeptide comprises one or more regions of an Immunoglobulin heavy chain constant sequence. In some embodiments the polypeptide comprises a CH1 region as described herein. In some embodiments the polypeptide comprises a CH1-CH2 hinge region as described herein. In some embodiments the polypeptide comprises a CH2 region as described herein. In some embodiments the polypeptide comprises a CH3 region as described herein.

In some embodiments the polypeptide comprises a CH3 region comprising any one of the following amino acid substitutions/combinations of amino acid substitutions (shown e.g. in Table 1 of Ha et al., Front. Immnol (2016) 7:394, incorporated by reference hereinabove): T366 W; T366 S, L368A and Y407V; T366W and S354C; T366S, L368A, Y407V and Y349C; S364H and F405A; Y349T and T394F; T350V, L351Y, F405A and Y407V; T350V, T366L, K392L and T394W; K360D, D399M and Y407A; E345R, Q347R, T366V and K409V; K409D and K392D; D399K and E356K; K360E and K409W; Q347R, D399V and F405T; K360E, K409W and Y349C; Q347R, D399V, F405T and S354C; K370E and K409W; and E357N, D399V and F405T.

In some embodiments the CH2 and/or CH3 regions of the polypeptide comprise one or more amino acid substitutions for promoting association of the polypeptide with another polypeptide comprising a CH2 and/or CH3 region.

In some embodiments the polypeptide comprises one or more regions of an immunoglobulin light chain constant sequence. In some embodiments the polypeptide comprises a CL region as described herein.

Also provided by the present invention are antigen-binding molecules comprising a polypeptide according to the present invention.

In some embodiments the antigen-binding molecules and polypeptides of the present invention comprise one or more linker sequences between amino acid sequences. A linker sequence may be provided at one or both ends of one or more of a VH, VL, CH1-CH2 hinge region, CH2 region and a CH3 region of the antigen-binding molecule/polypeptide.

Linker sequences are known to the skilled person, and are described, for example in Chen et al., Adv Drug Deliv Rev (2013) 65(10): 1357-1369, which is hereby incorporated by reference in its entirety. In some embodiments, a linker sequence may be a flexible linker sequence. Flexible linker sequences allow for relative movement of the amino acid sequences which are linked by the linker sequence. Flexible linkers are known to the skilled person, and several are identified in Chen et al., Adv Drug Deliv Rev (2013) 65(10): 1357-1369. Flexible linker sequences often comprise high proportions of glycine and/or serine residues.

In some embodiments, the linker sequence comprises at least one glycine residue and/or at least one serine residue. In some embodiments the linker sequence consists of glycine and serine residues. In some embodiments, the linker sequence has a length of 1-2, 1-3, 1-4, 1-5, 1-10, 1-15, 1-20, 1-30, 1-40 or 1-50 amino acids. In some embodiments a linker sequence comprises, or consists of, one or more copies (e.g. 2, 3 or 4 copies) of the amino acid sequence of SEQ ID NO:330, 331, 332, 333, 454 or 455.

The antigen-binding molecules and polypeptides of the present invention may additionally comprise further amino acids or sequences of amino acids. For example, the antigen-binding molecules and polypeptides may comprise amino acid sequence(s) to facilitate expression, folding, trafficking, processing, purification or detection of the antigen-binding molecule/polypeptide. For example, the antigen-binding molecule/polypeptide may comprise a sequence encoding a His, (e.g. 6×His). Myc, GST, MBP, FLAG, HA, E, or Biotin tag, optionally at the N- or C-terminus of the antigen-binding molecule/polypeptide. In some embodiments the antigen-binding molecule/polypeptide comprises a detectable moiety, e.g. a fluorescent, luminescent, immuno-detectable, radio, chemical, nucleic acid or enzymatic label.

The antigen-binding molecules and polypeptides of the present invention may additionally comprise a signal peptide (also known as a leader sequence or signal sequence). Signal peptides normally consist of a sequence of 5-30 hydrophobic amino acids, which form a single alpha helix. Secreted proteins and proteins expressed at the cell surface often comprise signal peptides.

The signal peptide may be present at the N-terminus of the antigen-binding molecule/polypeptide, and may be present in the newly synthesised antigen-binding molecule/polypeptide. The signal peptide provides for efficient trafficking and secretion of the antigen-binding molecule/polypeptide. Signal peptides are often removed by cleavage, and thus are not comprised in the mature antigen-binding molecule/polypeptide secreted from the cell expressing the antigen-binding molecule/polypeptide.

Signal peptides are known for many proteins, and are recorded in databases such as GenBank, UniProt, Swiss-Prot, TrEMBL, Protein Information Resource, Protein Data Bank, Ensembl, and InterPro, and/or can be identified/predicted e.g. using amino acid sequence analysis tools such as SignalP (Petersen et al., 2011 Nature Methods 8: 785-786) or Signal-BLAST (Frank and Sippl, 2008 Bioinformatics 24: 2172-2176).

Functional Properties of the Antigen-Binding Molecules

The antigen-binding molecule described herein may be characterised by reference to certain functional properties. In some embodiments, the antigen-binding molecule described herein may possess one or more of the following properties:

binds to CD122;
binds to CD132;
binds to CD122-expressing cells;
binds to CD132-expressing cells;
stimulates signalling by a polypeptide complex comprising CD122 and CD132;
stimulates proliferation of cells expressing CD122 and CD132;
preferentially stimulates proliferation of effector T cells and/or NK cells over regulatory T cells;
reduces expression of one or more immune checkpoint proteins (e.g. FD-1);
enhances anticancer activity of cancer antigen-specific immune cells, e.g. in vivo;
improved thermostability, e.g. as compared to an antigen-binding molecule described in WO 2017/021540 A1.

In some embodiments, the extent of binding of an antigen-binding molecule to an non-target is less than about 10% of the binding of the antibody to the target as measured, e.g., by ELISA, SPR, Bio-Layer Interferometry (BLI), MicroScale Thermophoresis (MST), or by a radioimmunoassay (RIA). Alternatively, the binding specificity may be reflected in terms of binding affinity, where the antigen-binding molecule described herein binds to CD122 and/or CD132 with an affinity that is at least 0.1 order of magnitude greater than the affinity towards a non-target molecule. In some embodiments, the antigen-binding molecule described herein binds to CD122 and/or CD132 with an affinity that is one of at least 0.2, 0.3, 0.4, 0.5, 0.6, 0.7, 0.8, 0.9, 1.0, 1.5, or 2.0 orders of magnitude greater than the affinity towards another, non-target molecule.

Binding affinity of an antigen-binding molecule for its target is often described in terms of its dissociation constant ($K_D$). Binding affinity can be measured by methods known in the art, such as by ELISA, Surface Plasmon Resonance (SPR; see e.g. Hearty et al., Methods Mol Biol (2012) 907:411-442; or Rich et al., Anal Biochem. 2008 Feb. 1; 373(1):112-20), Bio-Layer Interferometry (see e.g. Lad et al., (2015) J Biomol Screen 20(4): 498-507; or Concepcion et al., Comb Chem High Throughput Screen. 2009 September; 12(8):791-800), MicroScale Thermophoresis (MST) analysis (see e.g. Jerabek-Willemsen et al., Assay Drug Dev Technol. 2011 August; 9(4): 342-353), or by a radiolabelled antigen-binding assay (RIA).

In some embodiments, the antigen-binding molecule described herein binds to CD122 with a $K_D$ of 10 μM or less, preferably one of ≤5 μM, ≤2 μM, ≤1 μM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM, ≤3 nM, ≤2 nM, ≤1 nM, ≤500 pM. In some embodiments, the antigen-binding molecule described herein binds to CD132 with a $K_D$ of 10 μM or less, preferably one of ≤5 μM, ≤2 μM, ≤1 μM, ≤500 nM, ≤100 nM, ≤75 nM, ≤50 nM, ≤40 nM, ≤30 nM, ≤20 nM, ≤15 nM, ≤12.5 nM, ≤10 nM, ≤9 nM, ≤8 nM, ≤7 nM, ≤6 nM, ≤5 nM, ≤4 nM ≤3 nM, ≤2 nM, ≤1 nM, ≤500 pM.

In some embodiments, the antigen-binding molecule described herein binds to CD122 with an affinity of binding (e.g. as determined by ELISA) of EC50=1000 ng/ml or less, preferably one of ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤100 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, or ≤2.5 ng/ml. In some embodiments, the antigen-binding molecule described herein binds to CD132 with an affinity of binding (e.g. as determined by ELISA) of EC50=1000 ng/ml or less, preferably one of ≤900 ng/ml, ≤800 ng/ml, ≤700 ng/ml, ≤600 ng/ml, ≤500 ng/ml, ≤400 ng/ml, ≤300 ng/ml, ≤200 ng/ml, ≤200 ng/ml, ≤90 ng/ml, ≤80 ng/ml, ≤70 ng/ml, ≤60 ng/ml, ≤50 ng/ml, ≤40 ng/ml, ≤30 ng/ml, ≤20 ng/ml, ≤15 ng/ml, ≤10 ng/ml, ≤7.5 ng/ml, ≤5 ng/ml, ≤2.5 ng/ml, or ≤1 ng/ml.

Affinity of binding to CD122 and/or CD132 may be analysed in vitro by ELISA assay. Suitable assays are well known in the art and can be performed by the skilled person, for example, as described in Antibody Engineering, vol. 1 ($2^{nd}$ Edn), Springer Protocols, Springer (2010), Part V, pp 657-665.

In some embodiments the binding affinity of the antigen-binding molecule of the present invention to CD122 is greater than the binding affinity of an antigen-binding molecule described in WO 2017/021540 A1. In some embodiments, the antigen-binding molecule described herein binds to CD122 with a $K_D$ which is less than 1 times, e.g. ≤0.9 times, ≤0.85 times, ≤0.8 times, ≤1.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times or ≤0.1 times the $K_D$ of binding to CD122 for an antigen-binding molecule described in WO 2017/021540 A1. In some embodiments the binding affinity of the antigen-binding molecule of the present invention to CD132 is greater than the binding affinity of an antigen-binding molecule described in WO 2017/021540 A1. In some embodiments, the antigen-binding molecule described herein binds to CD132 with a $K_D$ which is less than 1 times, e.g. ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times or ≤0.1 times the $K_D$ of binding to CD132 for an antigen-binding molecule, described in WO 2017/021540 A1.

The antigen-binding molecule described herein preferably binds to CD122 in a region of CD122 which is accessible to an antigen-binding molecule (i.e., an extracellular antigen-binding molecule) when CD122 is expressed at the cell surface (i.e. in or at the cell membrane). In some embodiments the antigen-binding molecule described herein is capable of binding to CD122 when CD122 is expressed at the cell surface. The antigen-binding molecule described herein preferably binds to CD132 in a region of CD132 which is accessible to an antigen-binding molecule (i.e., an extracellular antigen-binding molecule) when CD132 is expressed at the cell surface (i.e. in or at the cell membrane). In some embodiments the antigen-binding molecule described herein is capable of binding to CD132 when CD132 is expressed at the cell surface.

For example, the antigen-binding molecule may bind to CD122 and/or CD132-expressing cells, such as cells expressing CD122 and CD132 at the cell surface, e.g. immune cells, lymphocytes, T cells (CD4+ T cells, CD8+ T cells) or NK cells.

The ability of an antigen-binding molecule to bind to a given cell type can be analysed by contacting cells with the antigen-binding molecule, and detecting antigen-binding molecule bound to the cells, e.g. after a washing step to remove unbound antigen-binding molecule. The ability of an antigen-binding molecule, to bind to CD132-expressing cells and/or CD122-expressing cells can be analysed by methods such as flow cytometry and immunofluorescence microscopy, e.g. as described in the experimental examples of the present application.

The antigen-binding molecules of the present invention may stimulate signalling through the intermediate-affinity IL-2 receptor (i.e. the polypeptide complex comprising CD122 and CD132; and not comprising CD25). The antigen-binding molecules are preferably agonists of signalling through the intermediate-affinity IL-2 receptor.

The ability of a given antigen-binding molecule to stimulate signalling through the intermediate-affinity IL-2 receptor can be evaluated e.g. in an in vitro assay, e.g. as described in Example 4 herein. Briefly, cells expressing CD122 and CD132 at the cell surface can be contacted with the antigen-binding molecule, and activation of intracellular signalling can be determined by detecting an increase in the level of phosphorylated STAT5 (i.e. pSTAT5). pSTAT5 can be detected e.g. using antibody- or reporter-based methods as described herein.

In some embodiments the antigen-binding molecule of the present invention is capable of increasing the amount of pSTAT5 to more than 1 times, e.g. ≥1.01 times, ≥1.02 times, ≥1.03 times, ≥1.04 times, ≥1.05 times; ≥1.06 times, ≥1.07 times, ≥1.08 times; ≥1.09 times, ≥1.1 times, ≥1.2 times, ≥1.3 times; ≥1.4 times, ≥1.5 times, ≥1.6 times, ≥1.7 times, ≥1.8 times, ≥1.9 times, ≥2 times, ≥3 times, ≥4 times, ≥5 times, ≥6 times; ≥7 times, ≥8 times, ≥9 times, ≥10 times, ≥20 times, ≥30 times, ≥40 times, ≥50 times, ≥60 times, ≥70 times; ≥80 times; ≥90 times, or ≥100 times the level of pSTAT5 detected following culture in the absence of the antigen-binding molecule, or in the presence of an appropriate control antigen-binding molecule (e.g. isotype-matched control antigen-binding molecule), in a comparable assay.

In some embodiments the antigen-binding molecule of the present invention activates signalling through the intermediate-affinity IL-2 receptor to a greater extent than an antigen-binding molecule described in WO 2017/021540 A1. In some embodiments, culture of cells expressing CD122 and CD132 in the presence of an antigen-binding molecule according to the present invention increases the amount of pSTAT5 to more than 1 times, e.g. ≥1.01 times, ≥1.02 times, ≥1.03 times, ≥1.04 times; ≥1.05 times; ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times; ≥1.8 times, ≥1.9 times, ≥2 times, ≥3 times, ≥4 times, ≥5 times, ≥6 times, ≥7 times; ≥8 times, ≥9 times, or ≥10 times the level of pSTAT5 detected following culture in the presence of an antigen-binding molecule described in WO 2017/021540 A1, in a comparable assay.

In some embodiments the antigen-binding molecule of the present invention is capable of increasing proliferation of cells expressing CD122 and CD132.

Cell proliferation can be determined by analysing cell division over a period of time. Cell division can be analysed, for example, by in vitro analysis of incorporation of $^3$H-thymidine or by CFSE dilution assay, e.g. as described in Fulcher and Wong, Immunol Cell Biol (1999) 77(6): 559-564; hereby incorporated by reference in entirety. Proliferating cells may also be identified by analysis of incorporation of 5-ethynyl-2'-deoxyuridine, (EdU) by an appropriate assay, as described e.g. in Buck et al., Biotechniques. 2008 June; 44(7):927-9, and Sail and Mitchison, PNAS USA 2008 Feb. 19; 105(7): 2415-2420, both hereby incorporated by reference in their entirety, or by alamarBlue dilution assay as described in Example 3 herein (see e.g. Rampersad et al. Sensors (Basel). (2012)12(9):12347-12360).

In some embodiments the antigen-binding molecule of the present invention is capable of increasing the number or proportion of proliferating cells to more than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥0.9 times, ≥10 times, ≥20 times, ≥30 times, ≥40 times, ≥50 times, ≥60 times, ≥70 times, ≥80 times, ≥90 times, or ≥100 times the number/proportion of proliferating detected following culture in the absence of the antigen-binding molecule, or in the presence of an appropriate control antigen-binding molecule (e.g. isotype-matched control antigen-binding molecule), in a comparable assay.

In some embodiments the antigen-binding molecule of the present invention increases the number or proportion of proliferating cells to a greater extent than an antigen-binding molecule described in WO 2017/021540 A1. In some embodiments, culture of cells expressing CD122 and CD132 in the presence of an antigen-binding molecule of the present invention increases the number/proportion of proliferating cells to more than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times, or ≥10 times the number/proportion of proliferating cells detected following culture in the presence of an antigen-binding molecule described in WO 2017/021540 A1, in a comparable assay.

In some embodiments culture in the presence of an antigen-binding molecule of the present invention causes expansion of cells expressing CD122 and CD132 to a number of cells which is more than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times, ≥10 times, ≥20 times, ≥30 times, ≥40 times, ≥50 times, ≥60 times, ≥70 times, ≥80 times, ≥90 times, or ≥100 times the number of cells detected following culture in the absence of the antigen-binding molecule, or in the presence of an appropriate control antigen-binding molecule (e.g. isotype-matched control antigen-binding molecule).

In some embodiments the antigen-binding molecule of the present invention causes expansion of cells expressing CD122 and CD132 to a greater extent than an antigen-binding molecule described in WO 2017/021540 A1. In some embodiments, culture of cells expressing CD122 and CD132 in the presence of an antigen-binding molecule of the present invention causes expansion of the cells to a number of cells which is more than 1 times, e.g. ≥1.01 times, ≥1.02 times, ≥1.03 times, ≥1.04 times, ≥1.05 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times, or ≥10 times the number of cells detected following culture in the presence of an antigen-binding molecule described in WO 2017/021540 A1, in a comparable assay.

In some embodiments the antigen-binding molecule of the present invention preferentially stimulates proliferation/expansion of one or more of the following cell types over (i.e. in preference to) regulatory T cells (e.g. CD4+CD25+ FoxP3+ T cells): antigen-specific T cells virus-specific T cells), antigen-specific CD4 T cells, antigen-specific CD8 T cells, effector memory CD4 T cells, effector memory CD8 T cells, central memory CD4 T cells, central memory CD8 T cells, cytotoxic CD8+ T cells (i.e. CTLs), NK cells, antigen-specific NK cells, or cells comprising/expressing a chimeric antigen receptor (CAR) or nucleic acid encoding a CAR.

In some embodiments the antigen-binding molecule of the present invention is capable of reducing expression of one or more immune checkpoint proteins. In some embodiments the antigen-binding molecule is capable of reducing expression of one or more immune checkpoint proteins by immune cells, e.g. T cells. Immune checkpoint proteins are well known to the skilled person, and include e.g. PD-1, CTLA-4, LAG-3, TIM-3, VISTA, TIGIT and BTLA.

In some embodiments the antigen-binding molecule of the present invention is capable of reducing expression of PD-1. The ability of an antigen-binding molecule to reduce the expression of an immune checkpoint protein can be analysed by contacting a population of immune cells with the antigen-binding molecule, and subsequently analysing the cells for expression of the immune checkpoint protein, e.g. by flow cytometry. The cells may be contacted with the antigen-binding molecule in vivo, e.g. through administration of the antigen-binding molecule to a subject, or cells obtained from a subject may be contacted in vitro or ex vivo with the antigen-binding molecule.

In some embodiments the antigen-binding molecule of the present invention causes a reduction in the level expression of PD-1 by T cells to less than less than 1 times, e.g. ≤0.99 times, ≤0.95 times, ≤0.9 times, ≤0.85 times, ≤0.8 times, ≤0.75 times, ≤0.7 times, ≤0.65 times, ≤0.6 times, ≤0.55 times, ≤0.5 times, ≤0.45 times, ≤0.4 times, ≤0.35 times, ≤0.3 times, ≤0.25 times, ≤0.2 times, ≤0.15 times, ≤0.1 times, ≤0.05 times, or ≤0.01 times the level of expression by PD-1 by T cells observed in the absence of the antigen-binding molecule (or in the presence of an appropriate control antigen-binding molecule), in a given assay.

In some embodiments the antigen-binding molecule of the present invention enhances anticancer activity of cancer antigen-specific immune cells, e.g. in vivo. The ability of an antigen-binding molecule to enhance anticancer immune response can be analysed e.g. as described in Example 9 herein.

In some embodiments, the antigen-binding molecule of the present invention may display improved thermostability, e.g. as compared to an antigen-binding molecule described in WO 2017/021540 A1.

Thermostability of antigen-binding molecules can be analysed by methods well known to the skilled person, including Differential Scanning Fluorimetry and Differential Scanning calorimetry (DSC), which are described e.g. in He et al., J Pharm Sci. (2010) which is hereby incorporated by reference in its entirety.

In some embodiments, the antigen-binding molecule of the present invention may be determined in such an assay to have a $T_m1$ value which is more than 1 times, e.g. ≥1.01 times, ≥1.02 times, ≥1.03 times, ≥1.04 times, ≥1.05 times, ≥1.06 times, ≥1.07 times, ≥1.08 times, ≥1.09 times, ≥1.1 times, ≥1.2 times, ≥1.3 times, ≥1.4 times, ≥1.5 times, ≥1.6 times, ≥1.7 times, ≥1.8 times, ≥1.9 times, ≥2 times, ≥3 times, ≥4 times, ≥5 times, ≥6 times, ≥7 times, ≥8 times, ≥9 times, or ≥10 times the $T_m1$ value determined for an antigen-binding molecule described in WO 2017/021540 A1.

Membrane-Anchored Antigen-Binding Molecules

In some embodiments, the antigen-binding molecule of the present invention further comprises a cell membrane anchor region. As used herein, a 'cell membrane anchor region' is a region providing for anchoring of the antigen-binding molecule to the cell membrane of a cell expressing the antigen-binding molecule. 'Anchoring' may be reversible or irreversible.

In some embodiments the cell membrane anchor region is a transmembrane domain. A transmembrane domain refers to any three-dimensional structure formed by a sequence of amino acids which is thermodynamically stable in a biological membrane, e.g. a cell membrane.

The transmembrane domain may comprise or consist of a sequence of amino acids which forms a hydrophobic alpha helix or beta-barrel. The amino acid sequence of the transmembrane domain may be, or may be derived from, the amino acid sequence of a transmembrane domain of a protein comprising a transmembrane domain. Transmembrane domains are recorded in databases such as GenBank, UniProt, Swiss-Prot, TrEMBL, Protein Information Resource, Protein Data Bank. Ensembl, and InterPro, and/or can be identified/predicted e.g. using amino acid sequence analysis tools such as TMHMM (Krogh et al., 2001 J Mol Bid 305: 567-580).

In some embodiments, the amino acid sequence of the transmembrane domain may be, or may be derived from, the amino acid sequence of the transmembrane domain of a protein expressed at the cell surface. In some embodiments the protein expressed at the cell surface is a receptor or ligand, e.g. an immune receptor or ligand. In some embodiments the amino acid sequence of the transmembrane domain may be, or may be derived from, the amino acid sequence of the transmembrane domain of one of ICOS, ICOSL, CD86, CTLA-4, CD28, CD80, MHC class I α, MHC class II α, MHC class II β, CD3ε, CD3δ, CD3γ, CD3-ζ, TCRα TCRβ, CD4, CD8α, CD8β, CD40, CD40L, PD-1, PD-L1, PD-L2, 4-1BB, 4-1BBL, OX40, OX40L, GITR, GITRL, TIM-3, Galectin 9, LAG3, CD27, CD70, LIGHT, HVEM, TIM-4, TIM-1, ICAM1, LFA-1, LFA-3, CD2, BTLA, CD160, LILRB4, LILRB2, VTCN1, CD2, CD48, 2B4, SLAM, CD30, CD30L, DR3, TL1A, CD226, CD155, CD112 and CD276.

In some embodiments, the cell membrane anchor region may be a lipid anchor region. In some embodiments, a lipid anchor region comprises or consists of a lipid anchor (e.g. a GPI anchor). A 'lipid anchor' refers to a moiety capable of associating (e.g. covalently) with the lipid component of a biological membrane (e.g. cell membrane). Through such association, a protein having a lipid anchor attached thereto is 'anchored' in the cell membrane. A lipid anchor typically comprises a lipophilic group. Lipid anchors, lipophilic groups thereof and modification of proteins to attach lipid anchors is described for example in Resh 2013, Curr Biol. 23(10): R431R435, which is hereby incorporated by reference in its entirety. A lipid anchor may comprise or consist of an isoprenyl, myristoyl, palmitoyl, fatty acyl, diacylglycerol, steroyl, or phospholipid group, or a glycosylphosphatidyl inositol (GPI) anchor.

In some embodiments, a lipid anchor region comprises or consists of a lipid anchor signal sequence. A 'lipid anchor signal sequence' refers to an amino acid sequence directing processing of a protein to attach a lipid anchor. Following such processing the antigen-binding molecule comprises a lipid anchor.

Chimeric Antigen Receptors (CARs)

The present invention also provides a chimeric antigen receptor (CAR) comprising an antigen-binding molecule according to the present invention.

Chimeric Antigen Receptors (CARs) are recombinant receptors that provide both antigen-binding and T cell activating functions. CAR structure and engineering is reviewed, for example, in Dotti et al., Immunol Rev (2014) 257(1), hereby incorporated by reference in its entirety.

CARs comprise an antigen-binding region linked to a cell membrane anchor region and a signaling region. An optional hinge region may provide separation between the antigen-binding region and cell membrane anchor region, and may act as a flexible linker. The antigen-binding region of a CAR may be based on the antigen-binding region of an antibody which is specific for the antigen to which the CAR is targeted, or other agent capable of binding to the target. For example, the antigen-binding domain of a CAR may comprise amino acid sequences for the complementarity-determining regions (CDRs) or complete light chain and heavy chain variable region amino acid sequences of an antibody which binds specifically to the target protein. Antigen-binding domains of CARs may target antigen based on other protein:protein interaction, such as ligand:receptor binding; for example an IL-13Rα2-targeted CAR has been developed using an antigen-binding domain based on IL-13 (see e.g. Kahlon et al, 2004 Cancer Res 64(24): 9160-9156).

The antigen-binding region of the CAR of the present invention may be provided with any suitable format, e.g. scFv, Fab, etc.

The cell membrane anchor region is provided between the antigen-binding region and the signalling region of the CAR. The cell membrane anchor region provides for anchoring the CAR to the cell membrane of a cell expressing a CAR, with the antigen-binding region in the extracellular space, and signalling region inside the cell. In some embodiments, the CAR of the present invention comprises a cell membrane anchor region comprising or consisting of an amino acid sequence which comprises, consists of, or is derived from, the transmembrane region amino acid sequence for one of CD3-ζ, CD4, CD8 or CD28. As used herein, a region which is 'derived from' a reference amino acid sequence comprises an amino acid sequence having at least 60%, e.g. one of at least 65%, 70%, 75%, 80%, 85%, 90%, 91%, 92%, 93%. 94%, 95%, 96%, 97%, 98%, 99% or 100% sequence identity to the reference sequence.

The signalling region of a CAR allows for activation of the T cell. The CAR signalling regions may comprise the amino acid sequence of the intracellular domain of CD3-ζ, which provides immunoreceptor tyrosine-based activation motifs (ITAMs) for phosphorylation and activation of the CAR-expressing T cell. Signalling regions comprising sequences of other ITAM-containing proteins have also been employed in CARs, such as domains comprising the ITAM containing region of FcγRI (Haynes et al., 2001 J Immunol 166(1):182-187). CARs comprising a signalling region derived from the intracellular domain of CD3-ζ are often referred to as first generation CARs. Signalling regions of CARs may also comprise co-stimulatory sequences derived from the signalling region of co-stimulatory molecules, to facilitate activation of CAR-expressing T cells upon binding to the target protein. Suitable co-stimulatory molecules include CD28, OX40, 4-1BB, ICOS and CD27. CARs having a signalling region including additional co-stimulatory sequences are often referred to as second generation CARs.

In some cases CARs are engineered to provide for co-stimulation of different intracellular signalling pathways. For example, signalling associated with CD28 costimulation preferentially activates the phosphatidylinositol 3-kinase (P13K) pathway, whereas the 4-1BB-mediated signalling is through TNF receptor associated factor (TRAF) adaptor proteins. Signalling regions of CARs therefore sometimes contain co-stimulatory sequences derived from signalling regions of more than one co-stimulatory molecule. CARs comprising a signalling region with multiple co-stimulatory sequences are often referred to as third generation CARs. In some embodiments, the CAR of the present invention comprises one or more co-stimulatory sequences comprising or consisting of an amino acid sequence which comprises, consists of, or is derived from, the amino acid sequence of the intracellular domain of one or more of CD28, OX40, 4-1BB, ICOS and CD27.

An optional hinge region may provide separation between the antigen-binding domain and the transmembrane domain, and may act as a flexible linker. Hinge regions may be flexible domains allowing the binding moiety to orient in different directions. Hinge regions may be derived from IgG1 or the CH2CH3 region of immunoglobulin. In some embodiments, the CAR of the present invention comprises a hinge region comprising or consisting of an amino acid sequence which comprises, consists of, or is derived from, the amino acid sequence of the hinge region of IgG1 or the CH2CH3 region of immunoglobulin. CARs may be combined with costimulatory ligands, chimeric costimulatory receptors or cytokines to further enhance T cell potency, specificity and safety (Sadelain et al., The basic principles of chimeric antigen receptor (CAR) design. Cancer Discov. 2013 April; 3(4): 388-398. doi:10.1158/2159-8290.CD-12-0548, specifically incorporated herein by reference).

Also provided is a cell comprising a CAR according to the invention. The CAR according to the present invention may be used to generate CAR-expressing immune cells, e.g. CAR-T or CAR-NK cells. Engineering of CARs into immune cells may be performed during culture, in vitro, for transduction and expansion, such as happens during expansion of T cells for adoptive T cell therapy.

Nucleic Acids and Expression Vectors

The present invention provides a nucleic acid encoding an antigen-binding molecule or CAR according to the present invention. In some embodiments, the nucleic acid is purified or isolated, e.g. from other nucleic acid, or naturally-occurring biological material.

The present invention also provides a vector comprising nucleic acid encoding an antigen-binding molecule or CAR according to the present invention.

The nucleic acid and/or vector according to the present invention may be provided for introduction into a cell, e.g. a primary human immune cell. Suitable vectors include plasmids, binary vectors, DNA vectors, mRNA vectors, viral vectors (e.g. gammaretroviral vectors (e.g. murine Leukemia virus (MLV)-derived vectors), lentiviral vectors, adenovirus vectors, adeno-associated virus vectors, vaccinia virus vectors and herpesvirus vectors), transposon-based vectors, and artificial chromosomes (e.g. yeast artificial chromosomes), e.g. as described in Maus et al., Annu Rev Immunol (2014) 32:189-225 or Morgan and Boyerinas, Biomedicines 2016 4, 9, which are both hereby incorporated by reference in their entirety. In some embodiments, the viral vector may be a lentiviral, retroviral, adenoviral, or Herpes Simplex Virus vector. In some embodiments, the lentiviral vector may be pELNS, or may be derived from pELNS. In some embodiments, the vector may be a vector encoding CRISFR/Cas9.

In some embodiments, the nucleic acid according to the present invention comprises, or consists of, a nucleic acid sequence having at least 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to one of SEQ ID NOs:335 to 433, or a nucleic acid sequence encoding the same amino acid sequence as one of SEQ ID NOs:335 to 433 as a result of codon degeneracy.

Cells Comprising/Expressing the Antigen-Binding Molecules/CARs

The present invention also provides a cell comprising or expressing an antigen-binding molecule or CAR according to the present invention. Also provided is a cell comprising or expressing a nucleic acid or expression vector according to the invention.

The cell may be a eukaryotic cell, e.g. a mammalian cell. The mammal may be a human, or a non-human mammal (e.g. rabbit, guinea pig, rat, mouse or other rodent (including any animal in the order Rodentia), cat, dog, pig, sheep, goat, cattle (including cows, e.g. dairy cows, or any animal in the order Bos), horse (including any animal in the order Equidae), donkey, and non-human primate).

In some embodiments, the cell may be from, or may have been obtained from, a human subject.

The cell may be an immune cell. The cell may be a cell of hematopoietic origin, e.g. a neutrophil, eosinophil, basophil, dendritic cell, lymphocyte, or monocyte. The lymphocyte may be e.g. a T cell, B cell, NK cell, NKT cell or innate lymphoid cell (ILC), or a precursor thereof. The cell may express e.g. CD3 polypeptides (e.g. CD3γ CD3ε CD3ζ or CD3δ), TCR polypeptides (TCRα or TCRβ), CD27, CD28, CD4 or CD8. In some embodiments, the cell is a T cell. In some embodiments, the T cell is a CD3+ T cell. In some embodiments, the T cell is a CD3+, CD8+ T cell. In some embodiments, the T cell s a cytotoxic T cell (e.g. a cytotoxic T lymphocyte (CTL)).

In some embodiments, the cell is an antigen-specific T cell. In embodiments herein, an "antigen-specific" T cell is a cell which displays certain functional properties of a T cell in response to the antigen for which the T cell is specific, or a cell expressing said antigen. In some embodiments, the properties are functional properties associated with effector T cells, e.g. cytotoxic T cells. In some embodiments, an antigen-specific T cell may display one or more of the following properties: cytotoxicity, e.g. to a cell comprising/expressing antigen for which the T cell is specific; proliferation, IFNγ expression, CD107a expression, IL-2 expression, TNFα expression, perforin expression, granzyme expression, granulysin expression, and/or FAS ligand (FASL) expression, e.g. in response to antigen for which the T cell is specific or a cell comprising/expressing antigen for which the T cell is specific. In some embodiments, the antigen for which the T cell is specific may be a peptide or polypeptide of a virus, e.g. Epstein-Barr virus (EBV), influenza virus, measles virus, hepatitis B virus (HBV), hepatitis C virus (HCV), human immunodeficiency virus (HIV), lymphocytic choriomeningitis virus (LCMV), Herpes simplex virus (HSV) or human papilloma virus (HPV).

The present invention also provides a method for producing a cell comprising a nucleic acid or expression vector according to the present invention, comprising introducing a nucleic acid or expression vector according to the present invention into a cell. The present invention also provides a method for producing a cell expressing an antigen-binding molecule or CAR, according to the present invention, comprising introducing a nucleic acid or expression vector according to the present invention in a cell. In some embodiments, the methods additionally comprise culturing the cell under conditions suitable for expression of the nucleic acid or expression vector by the cell. In some embodiments, the methods are performed in vitro.

In some embodiments, introducing an isolated nucleic acid or expression vector according to the invention into a cell comprises transduction, e.g. retroviral transduction. Accordingly, in some embodiments the isolated nucleic acid or expression vector is comprised in a viral vector, or the vector is a viral vector. In some embodiments, the method comprises introducing a nucleic acid or expression vector according to the invention by electroporation, e.g. as described in Koh et al., Molecular Therapy—Nucleic Acids (2013) 2, e114, which is hereby incorporated by reference in its entirety.

The present invention also provides cells obtained or obtainable by the methods according, to the present invention.

Producing the Antigen-Binding Molecules and CARs

Antigen-binding molecules and CARs according to the invention may be prepared according to methods for the production of polypeptides known to the skilled person.

The polypeptide(s) of interest may be prepared by chemical synthesis, e.g. liquid or solid phase synthesis. For example, peptides/polypeptides can by synthesised using the methods described in, for example, Chandrudu et al., Molecules (2013), 18: 4373-4388, which is hereby incorporated by reference in its entirety. Alternatively, antigen-binding molecules and CARs according the invention may be produced by recombinant expression. Molecular biology techniques suitable for recombinant production are well known in the art, such as those set out in Green and Sambrook, Molecular Cloning: A Laboratory Manual (4th Edition), Cold Spring Harbor Press, 2012, which is hereby incorporated by reference in its entirety.

Expression may be from a nucleotide sequence. The nucleotide sequence may be contained in a vector. A “vector” as used herein is an oligonucleotide molecule (DNA or RNA) used as a vehicle to transfer foreign genetic material into a cell. The vector may be an expression vector for expression of the foreign genetic material in the cell. Such vectors may include a promoter sequence operably linked to the nucleotide sequence encoding the sequence to be expressed. A vector may also include a termination codon and expression enhancers. Any suitable vectors, promoters, enhancers and termination codons known in the art may be used to express a peptide or polypeptide from a vector according to the invention. In some embodiments, the vector may be a plasmid, MAC, virus, etc. In some embodiments, the vector may be a eukaryotic expression vector, e.g. a vector comprising the elements necessary for expression of protein from the vector in a eukaryotic cell. In some embodiments, the vector may be a mammalian expression vector, e.g. comprising a cytomegalovirus (CMV) or SV40 promoter to drive protein expression.

The term “operably linked” may include the situation where a selected nucleotide sequence and regulatory nucleotide sequence (e.g. promoter and/or enhancer) are covalently linked in such a way as to place the expression of the nucleotide sequence under the influence or control of the regulatory sequence (thereby forming an expression cassette). Thus a regulatory sequence is operably linked to the selected nucleotide sequence if the regulatory sequence is capable of effecting transcription of the nucleotide sequence. The resulting transcript may then be translated into a desired peptide or polypeptide.

In some cases the antigen-binding molecules according to the present invention are comprised of more than one polypeptide chain. In such cases, production of the antigen-binding molecules may comprise transcription and translation of more than one polypeptide chain, and subsequent association of the polypeptide chains to form the antigen-binding molecule.

For recombinant production according to the invention, any cell suitable for the expression of polypeptides may be used. The cell may be a prokaryote or eukaryote. In some embodiments the cell is a prokaryotic cell, such as a cell of archaea or bacteria. In some embodiments the bacteria may be Gram-negative bacteria such as bacteria of the family Enterobacteriaceae, for example *Escherichia coli*.

In some embodiments, the cell is a eukaryotic cell such as a yeast cell, a plant cell, insect cell or a mammalian cell, e.g. CHO, HEK, HeLa or COS cells.

In some cases the cell is not a prokaryotic cell because some prokaryotic cells do not allow for the same folding or post-translational modifications as eukaryotic cells. In addition, very high expression levels are possible in eukaryotes and proteins can be easier to purify from eukaryotes using appropriate tags. Specific plasmids may also be utilised which enhance secretion of the protein into the media.

Production may involve culture or fermentation of a eukaryotic cell modified to express the peptide or polypeptide. The culture or fermentation may be performed in a bioreactor provided with an appropriate supply of nutrients, air/oxygen and/or growth factors. Secreted proteins can be collected by partitioning culture media/fermentation broth from the cells, extracting the protein content, and separating individual proteins to isolate secreted peptide or polypeptide. Culture, fermentation and separation techniques are well known to those of skill in the art, and are described, for example, in Green and Sambrook. Molecular Cloning: A Laboratory Manual (4th Edition; incorporated by reference herein above).

Bioreactors include one or more vessels in which cells may be cultured. Culture in the bioreactor may occur continuously, with a continuous flow of reactants into, and a continuous flow of cultured cells from, the reactor. Alternatively, the culture may occur in batches. The bioreactor monitors and controls environmental conditions such as pH, oxygen, flow rates into and out of, and agitation within the vessel such that optimum conditions are provided for the cells being cultured.

Following culture of cells that express the antigen-binding molecule or CAR, the polypeptide of interest is preferably isolated. Any suitable method for separating proteins from cell culture known in the art may be used. In order to isolate the polypeptide from a culture, it may be necessary to first separate the cultured cells from media containing the polypeptide of interest. If the polypeptide of interest is secreted from the cells, the cells may be separated from the culture media that contains the secreted polypeptide of interest by centrifugation. If the polypeptide of interest collects within the cell it will be necessary to disrupt the cells prior to centrifugation, for example using sonification, rapid freeze-thaw or osmotic lysis. Centrifugation will produce a pellet containing the cultured cells, or cell debris of the cultured cells, and a supernatant containing culture medium and the polypeptide of interest.

It may then be desirable to isolate the polypeptide of interest from the supernatant or culture medium, which may contain other protein and non-protein components. A common approach to separating protein components from a supernatant or culture medium is by precipitation. Proteins of different solubilities are precipitated at different concentrations of precipitating agent such as ammonium sulfate. For example, at low concentrations of precipitating agent, water soluble proteins are extracted. Thus, by adding different increasing concentrations of precipitating agent, proteins of different solubilities may be distinguished. Dialysis may be subsequently used to remove ammonium sulfate from the separated proteins.

Other methods for distinguishing different proteins are known in the art, or example ion exchange chromatography and size chromatography. These may be used as an alternative to precipitation, or may be performed subsequently to precipitation.

Once the polypeptide of interest has been isolated from culture it may be desired or necessary to concentrate the peptide or polypeptide. A number of methods for concentrating proteins are known in the art, such as ultrafiltration or lyophilisation.

Generating/Expanding Populations of Immune Cells

Antigen-binding molecules according to the present invention also find use in methods for generating/expanding populations of immune cells. Essentially, the antigen-binding molecules according to the present invention find use in generating/expanding populations of cell types expressing CD122 and CD132 (e.g. at the cell surface).

The cells may be e.g. T cells, antigen-specific T cells (e.g. virus-specific T cells), antigen-specific CD4 T cells, antigen-specific CD8 T cells, effector memory CD4 T cells, effector memory CD8 T cells, central memory CD4 T cells, central memory CD8 T cells, cytotoxic CD8+ T cells (i.e. CTLs), NK cells or antigen-specific NK cells.

The cells may be antigen-specific immune cells, e.g. antigen-specific T cells. For example, the cells may be specific for a peptide/polypeptide of a virus, e.g. adenovirus, Epstein-Barr virus (EBV), cytomegalovirus (CMV), human papilloma virus (HPV), influenza virus, measles virus, hepatitis B virus (HBV), hepatitis C virus (HCV), human immunodeficiency virus (HIV), lymphocytic choriomeningitis virus (LCMV), or herpes simplex virus (HSV). Virus-specific immune cells may be an adenovirus-specific T cells (AdVSTs), Epstein-Barr virus-specific T cells (EBVSTs), cytomegalovirus-specific T cells (CMVSTs), human papilloma virus-specific T cells (HPVSTs), influenza virus-specific T cells, measles virus-specific T cells, hepatitis B virus-specific T cells (HBVSTs), hepatitis C virus-specific T cells (HCVSTs), human immunodeficiency virus-specific T cells (HIVSTs), lymphocytic choriomeningitis virus-specific T cells (LCMVSTs), or herpes simplex virus-specific T cells (HSVSTs).

The cells may comprise/express a chimeric antigen receptor (CAR) or nucleic acid encoding a CAR. The cells may comprise/express a TGFβ decoy receptor, or nucleic acid encoding a TGFβ decoy receptor.

The methods comprise contacting cells expressing CD122 and CD132 in the presence of an antigen-binding molecule according to the present invention. The cells expressing CD122 and CD132 are stimulated by the antigen-binding molecule to undergo cell division (i.e. proliferate), resulting in an increase in the number of cells.

In some embodiments, the methods comprise generating/expanding cells in vitro. In some embodiments, the methods comprise generating/expanding cells ex vivo. In some embodiments the methods comprise culturing cells in vitro in the presence of an antigen-binding molecule according to the present invention.

Culture of cells may be performed using suitable medium and under suitable environmental conditions (e.g. temperature, pH, humidity, atmospheric conditions, agitation etc.) for the in vitro culture of immune cells, which are well known to the person skilled in the art of cell culture. Conveniently, cultures of cells may be maintained at 37° C. in a humidified atmosphere containing 5% $CO_2$. Cultures can be performed in any vessel suitable for the volume of the culture, e.g. in wells of a cell culture plate, cell culture flasks, a bioreactor, etc. The cell cultures can be established and/or maintained at any suitable density, as can readily be determined by the skilled person. In some embodiments cells are cultured in a bioreactor. In some embodiments, cells are cultured in a bioreactor described in Somerville and Dudley, Oncoimmunology (2012) 1(8)1435-1437, which is hereby incorporated by reference in its entirety. In some embodiments cells are cultured in a GRex cell culture vessel, e.g. a GRex flask or a GRex 100 bioreactor.

In some embodiments, immune cells expressing CD122 and CD132 may be generated or expanded from within a population of immune cells. It will be appreciated that the population of immune cells comprises the immune cells expressing CD122 and CD132. The population of immune cells from which the population of immune cells expressing CD122 and CD132 are generated/expanded according to the methods of the present invention comprise at least one immune cell expressing CD122 and CD132.

In some embodiments, immune cells expressing CD122 and CD132 may be generated or expanded from within a population of PBMCs. The methods may involve expansion of T cells (e.g. antigen-specific T cells) from within a population of immune cells (e.g. PBMCs, PBLs). The immune cells (e.g. PBMCs, PBLs) used in the methods of the invention may be freshly obtained, or may be thawed from a sample of immune cells which has previously been obtained and frozen.

In embodiments of the methods disclosed herein, generation or expansion of a population of immune cells may involve culture of a population of PBMCs. In some embodiments, a population of immune cells may be generated/expanded from within a population of T cells (e.g. a population of T cells of heterogeneous type and/or specificity), which may have been obtained from a blood sample or a population of PBMCs. Culture of the population of immune cells from which the cells expressing CD122 and CD132 are generated/expanded may result in an increase of the number of cells expressing CD122 and CD132, and/or result in an increased proportion of such cells in the cell population at the end of the culture.

In some embodiments, the methods comprise treating cells to increase expression (e.g. surface expression) of CD122 and/or CD132, and expansion of cells expressing CD122 and CD132. For example, T cell activation (e.g. by stimulation using anti-CD3 (e.g. clone OKT3) and anti-CD28) induces upregulation of CD122 and CD132. Antigen-specific T cells also have upregulated expression of CD122 and CD132. In some embodiments the methods comprise contacting immune cells with antigen or cells presenting antigen.

In some embodiments, the population of cells is generated/expanded in vivo following administration of an antigen-binding molecule according to the present invention (or administration of cells expressing the antigen-binding molecule) to a subject.

Compositions and Formulations

The invention described herein also provides compositions comprising the antigen-binding molecules, nucleic acids, expression vectors and cells described herein.

The antigen-binding molecules, nucleic acids, expression vectors and cells described herein may be formulated as pharmaceutical compositions or medicaments for clinical use and may comprise a pharmaceutically acceptable carrier, diluent, excipient or adjuvant. The composition may be formulated for topical, parenteral, systemic; intracavitary, intravenous, intra-arterial, intramuscular, intrathecal, intraocular, intraconjunctival, intratumoral, subcutaneous, intradermal, intrathecal, oral or transdermal routes of administration which may include injection or infusion. Suitable formulations may comprise the antigen-binding molecule in a sterile or isotonic medium. Medicaments and pharmaceutical compositions may be formulated in fluid, including gel, form. Fluid formulations may be formulated for administration by injection or infusion (e.g. via catheter) to a selected region of the human or animal body.

In some embodiments the antigen-binding molecule, nucleic acid, expression vector, CAR, composition or cells according to the present invention are formulated for injection or infusion, e.g. into a blood vessel or tumor.

In accordance with the invention described herein methods are also provided for the production of pharmaceutically useful compositions, such methods of production may comprise one or more steps selected from: isolating an antigen-binding molecule, nucleic acid, expression vector or cells described herein; and/or mixing an antigen-binding molecule, nucleic acid, expression vector or cells described herein with a pharmaceutically acceptable carrier, adjuvant, excipient or diluent.

For example, a further aspect the invention described herein relates to a method of formulating or producing a medicament or pharmaceutical composition for use in the treatment of a cancer, the method comprising formulating a pharmaceutical composition or medicament by mixing an antigen-binding molecule, nucleic acid; expression vector or cells described herein with a pharmaceutically acceptable carrier, adjuvant, excipient or diluent.

Therapeutic and Prophylactic Applications

The antigen-binding molecules, CARs, nucleic acids, expression vectors, cells and compositions described herein find use in therapeutic and prophylactic methods.

The invention described herein provides antigen-binding molecules, nucleic acids, expression vectors, cells and compositions described herein for use in a method of medical treatment or prophylaxis. The invention described herein also provides the use of antigen-binding molecules, nucleic acids, expression vectors, cells and compositions described herein in the manufacture of medicaments for treating or preventing a disease or condition. The invention described herein also provides methods of treating or preventing a disease or condition, comprising administering to a subject a therapeutically or prophylactically effective amount of an antigen-binding molecule, nucleic acid, expression vector, cell or composition described herein.

'Treatment' may, for example, be reduction in the development or progression of a disease/condition, alleviation of the symptoms of a disease/condition or reduction in the pathology of a disease/condition. Treatment or alleviation of a disease/condition may be effective to prevent progression of the disease/condition, e.g. to prevent worsening of the condition or to slow the rate of development. In some embodiments treatment or alleviation may lead to an improvement in the disease/condition, e.g. a reduction in the symptoms of the disease/condition or reduction in some other correlate of the severity/activity of the disease/condition. Prevention of a disease/condition may refer to prevention of a worsening of the condition or prevention of the development of the disease/condition, e.g. preventing an early stage disease/condition developing to a later, chronic, stage.

The articles of the present invention find use in the treatment of any disease/condition which would benefit from an increase in the number/frequency of immune cells such as T cells (in particular effector T cells) and/or NK cells. In particular, the antigen-binding molecules and pharmaceutical compositions described herein find use to treat or prevent T cell dysfunctional disorders, cancers and infectious disease.

It will be appreciated that the therapeutic and prophylactic utility of the present invention extends to the treatment of any subject that would benefit in an increase in the number of (i.e. expansion of a population of) cells expressing CD122 and CD132 (e.g. effector T cells and/or NK cells).

T Cell Dysfunctional Disorders

A T cell dysfunctional disorder may be a disease or condition in which normal T cell function is impaired causing downregulation of the subject's immune response to pathogenic antigens, e.g. generated by infection by exogenous agents such as microorganisms, bacteria and viruses, or generated by the host in some disease states such as in some forms of cancer (e.g. in the form of tumor-associated antigens).

The T cell dysfunctional disorder may comprise T cell exhaustion or T cell anergy. T cell exhaustion comprises a state in which CD8+ T cells fail to proliferate or exert T cell effector functions such as cytotoxicity and cytokine (e.g. IFNγ) secretion in response to antigen stimulation. Exhausted T cells may also be characterised by sustained expression of one or more markers of T cell exhaustion, e.g. PD-1, CTLA-4, LAG-3, TIM-3. Thus, in some cases the antigen-binding molecules and pharmaceutical compositions described herein find use to treat or prevent T cell dysfunctional disorders, cancers and infectious disease, wherein treatment with the antigen-binding molecules and pharmaceutical compositions results in reduced expression by T cells of one or more markers of T cell exhaustion. In some cases, the treatment results in reduced expression by T cells of PD-1.

The T cell dysfunctional disorder may be manifest as an infection, or inability to mount an effective immune response against an infection. The infection may be chronic, persistent, latent or slow, and may be the result of bacterial, viral, fungal or parasitic infection. As such, treatment may be provided to patients having a bacterial, viral or fungal infection. Examples of bacterial infections include infection with *Helicobacter pylori*. Examples of viral infections include infection with HIV, hepatitis B or hepatitis C.

The T-cell dysfunctional disorder may be associated with a cancer, such as tumor immune escape. Many human tumors express tumor-associated antigens recognised by T cells and capable of inducing an immune response.

Cancer

Cancers may also be treated where there is no indication of a T-cell dysfunctional disorder, but the use of an antigen-binding molecule, cell or composition according, to the present invention stimulates proliferation and expansion of T cells (particularly effector T cells) and allows the subject to mount an effective immune response.

The cancer to be treated prevented in accordance with the invention described herein may be any unwanted cell proliferation (or any disease manifesting itself by unwanted cell proliferation), neoplasm or tumor. The cancer may be benign or malignant and may be primary or secondary (metastatic). A neoplasm or tumor may be any abnormal growth or proliferation of cells and may be located in any tissue. The cancer may be of tissues/cells derived from e.g. the adrenal gland, adrenal medulla, anus, appendix, bladder, blood, bone, bone marrow, brain, breast, cecum, central nervous system (including or excluding the brain), cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

In some embodiments, the cancer to be treated may be a cancer of a tissue selected from the group consisting of colon, rectum, nasopharynx, cervix, oropharynx, stomach, liver, head and neck, oral cavity, oesophagus, lip, mouth, tongue, tonsil, nose, throat, salivary gland, sinus, pharynx, larynx, prostate, lung, bladder, skin, kidney, ovary or mesothelium.

Tumors to be treated may be nervous or non-nervous system tumors. Nervous system tumors may originate either in the central or peripheral nervous system, e.g. glioma, medulloblastoma, meningioma, neurofibroma, ependymoma, Schwannoma, neurofibrosarcoma, astrocytoma and oligodendroglioma. Non-nervous system cancers/tumors may originate in any other non-nervous tissue, examples include melanoma, mesothelioma, lymphoma, myeloma, leukemia, Non-Hodgkin's lymphoma (NHL), Hodgkin's lymphoma, chronic myelogenous leukemia (CML), acute myeloid leukemia (AML), myelodysplastic syndrome (MDS), cutaneous T-cell lymphoma (CTCL), chronic lymphocytic leukemia (CLL), hepatoma, epidermoid carcinoma, prostate carcinoma, breast cancer, lung cancer, colon cancer, ovarian cancer, pancreatic cancer, thymic carcinoma, NSCLC, haematologic cancer and sarcoma.

In some embodiments, the cancer to be treated may be colon cancer, colon carcinoma, colorectal cancer, nasopharyngeal carcinoma, cervical carcinoma, oropharyngeal carcinoma, gastric carcinoma, hepatocellular carcinoma, head and neck cancer, head and neck squamous cell carcinoma (HNSCC), oral cancer, laryngeal cancer, prostate cancer, lung cancer, small cell lung cancer, non-small cell lung cancer, bladder cancer, urothelial carcinoma, melanoma, advanced melanoma, renal cell carcinoma, ovarian cancer or mesothelioma.

In some embodiments the cancer to be treated/prevented in accordance with the present invention is a virus-associated cancer, e.g. an EBV-associated cancer or a HPV-associated cancer. "EBV associated" and "HPV associated" cancers may be a cancers which are caused or exacerbated by infection with the respective viruses, cancers for which infection is a risk factor and/or cancers for which infection is positively associated with onset, development, progression, severity or metastasis.

EBV-associated cancers which may be treated with cells produced by methods of the disclosure include nasopharyngeal carcinoma (NPC) and gastric carcinoma (GC).

HPV-associated medical conditions that may be treated with cells produced by methods of the disclosure include at least dysplasias of the genital area(s), cervical intraepithelial neoplasia, vulvar intraepithelial neoplasia, penile intraepithelial neoplasia, anal intraepithelial neoplasia, cervical cancer, anal cancer, vulvar cancer, vaginal cancer, penile cancer, genital cancers, oral papillomas, oropharyngeal cancer.

In some embodiments, the cancer to be treated in accordance with various aspects of the present disclosure is one or more of nasopharyngeal carcinoma (NPC; e.g. Epstein-Barr Virus (EBV)-positive NPC), cervical carcinoma (CC; e.g. human Papillomavirus (HPV)-positive CC), oropharyngeal carcinoma (OPC; e.g. HPV-positive OPC), gastric carcinoma (GC; e.g. EBV-positive GC), hepatocellular carcinoma (HCC; e.g. Hepatitis B Virus (HBV)-positive HCC), lung cancer (e.g. non-small cell lung cancer (NSCLC)) and head and neck cancer (e.g. cancer originating from tissues of the lip, mouth, nose, sinuses, pharynx or larynx, e.g. head and neck squamous cell carcinoma (HNSCC)).

The treatment may be aimed at reducing the number of cells of the cancer, and/or reducing the size of a tumour, and/or inhibiting signalling mediated by an immune checkpoint protein (e.g. PD-1).

Administration of the antigen-binding molecules and compositions described herein may delay or prevent the onset of symptoms of the cancer. Administration of the antigen-binding molecules and compositions described herein may reduce the severity of symptoms of the cancer. Administration of the antigen-binding molecules and compositions described herein may delay or prevent the onset of invasion and/or metastasis. Administration of the antigen-binding molecules and compositions described herein reduce invasion and/or metastasis. Administration of the antigen-binding molecules and compositions described herein may decrease survival of cancer cells. Administration of the antigen-binding molecules and compositions described herein may increase survival of non-cancer cells and/or may increase survival of subjects.

Infection

An infection may be any infection or infectious disease, e.g. bacterial, viral, fungal, or parasitic infection. In some embodiments it may be particularly desirable to treat chronic/persistent infections, e.g. where such infections are associated with T cell dysfunction or T cell exhaustion.

It is well established that T cell exhaustion is a state of T cell dysfunction that arises during many chronic infections (including viral, bacterial and parasitic), as well as in cancer (Wherry Nature Immunology Vol. 12, No. 6, p 492-499, June 2011).

Examples of bacterial infections that may be treated include infection by *Bacillus* spp., *Bordetella pertussis, Clostridium* spp., *Corynebacterium* spp., *Vibrio chloerae, Staphylococcus* spp., *Streptococcus* spp. *Escherichia, Klebsiella, Proteus, Yersinia, Erwina, Salmonella, Listeria* sp, *Helicobacter* mycobacteria (e.g. *Mycobacterium tuberculosis*) and *Pseudomonas aeruginosa*. For example, the bacterial infection may be sepsis or tuberculosis.

Examples of viral infections that may be treated include infection by influenza virus, measles virus, hepatitis B virus (HBV), hepatitis C virus (HCV), human immunodeficiency virus (HIV), lymphocytic choriomeningitis virus (LCMV), Herpes simplex virus and human papilloma virus (HPV).

Examples of fungal infections that may be treated include infection by *Alternaria* sp, *Aspergillus* sp, *Candida* sp and *Histoplasma* sp. The fungal infection may be fungal sepsis or histoplasmosis.

Examples of parasitic infections that may be treated include infection by *Plasmodium* species (e.g. *Plasmodium falciparum, Plasmodium yoeli, Plasmodium ovale, Plasmo-*

*dium vivax*, or *Plasmodium chabaudi chabaudi*). The parasitic infection may be a disease such as malaria, leishmaniasis and toxoplasmosis.

Methods of medical treatment may also involve in vivo, ex vivo; and adoptive immunotherapies, including those using autologous and/or heterologous cells or immortalised cell lines.

Adoptive Transfer

The antigen-binding molecules of the present invention are also useful in connection with methods comprising adoptive cell transfer (ACT). In particular, the antigen-binding molecules of the present invention are useful in methods for generating/expanding populations of immune cells in vitro or ex vivo, which may then be administered to subject. Methods for generating/expanding populations of immune cells may also be performed in vivo.

The present invention provides a method of treatment or prophylaxis comprising adoptive transfer of immune cells (e.g. T Cells, effector T cells, virus-specific T cells, NK cells) produced (i.e. generated or expanded) according to the methods of the present invention. Adoptive cell transfer generally refers to a process by which immune cells are obtained from a subject, typically by drawing a blood sample from which the immune cells are isolated. The immune cells are then typically treated or altered in some way, optionally expanded, and then administered either to the same subject or to a different subject. The treatment is typically aimed at providing an immune cell population with certain desired characteristics to a subject, or increasing the frequency of immune cells with such characteristics in that subject.

The immune cells may be e.g. T cells, antigen-specific T cells (e.g. virus-specific T cells), antigen-specific CD4 T cells, antigen-specific CD8 T cells; effector memory CD4 T cells, effector memory CD8 T cells, central memory CD4 T cells, central memory CD8 T cells, cytotoxic CD8+ T cells (i.e. CTLs) NK cells or antigen-specific NK cells. The immune cells preferably express CD122 and CD132.

The cells may be antigen-specific immune cells, e.g. antigen-specific T cells. For example, the cells may be specific for a peptide/polypeptide of a virus, e.g. adenovirus, Epstein-Barr virus (EBV), cytomegalovirus (CMV), human papilloma virus (HPV), influenza virus, measles virus, hepatitis B virus (HBV), hepatitis C virus (HCV), human immunodeficiency virus (HIV), lymphocytic choriomeningitis virus (LCMV), or herpes simplex virus (HSV). Virus-specific immune cells may be an adenovirus-specific T cells (AdVSTs), Epstein-Barr virus-specific T cells (EBVSTs), cytomegalovirus-specific T cells (CMVSTs), human papilloma virus-specific T cells (HPVSTs), influenza virus-specific T cells, measles virus-specific T hepatitis B virus-specific T cells (HBVSTs), hepatitis C virus-specific T cells (HCVSTs), human immunodeficiency virus-specific T cells (HIVSTs), lymphocytic choriomeningitis virus-specific T cells (LCMVSTs), or herpes simplex virus-specific T cells (HSVSTs).

The cells may comprise/express a chimeric antigen receptor (CAR) or nucleic acid encoding a CAR. The cells may comprise/express a TGFβ decoy receptor, or nucleic acid encoding a TGFβ decoy receptor.

In some cases, the immune cells are derived from the patient that they are introduced to (autologous cell therapy). That is, cells may have been obtained from the patient, generated according to methods described herein, and then returned to the same patient. Methods disclosed herein may also be used in allogeneic cell therapy, in which cells obtained from a different individual are introduced into the patient.

Adoptive T cell transfer is described, for example, in Chia W K et al., Molecular Therapy (2014), 22(1): 132-139, Kalos and June 2013, Immunity 39(1): 49-60 and Cobbold et al., (2005) J. Exp. Med. 202: 379-386, which are hereby incorporated by reference in their entirety.

In the present invention, adoptive transfer is performed with the aim of introducing, or increasing the frequency of, immune cells in a subject.

Accordingly, the present invention provides a method of treating or preventing a disease or condition in a subject, comprising:

(a) isolating PBMCs from a subject;

(b) generating or expanding a population of immune cells by culture in the presence of an antigen-binding molecule according to the present invention, and;

(c) administering the generated/expanded population of immune cells to a subject.

In some embodiments, the subject from which the PBMCs are isolated is the subject administered with the generated/expanded cells (i.e., adoptive transfer is of autologous cells). In some embodiments, the subject from which the PBMCs are isolated is a different subject to the subject to which the generated/expanded cells are administered (i.e., adoptive transfer is of allogenic cells).

In some embodiments the method may comprise one or more of the following steps: taking a blood sample from a subject; isolating PBMCs from the blood sample; generating or expanding a population of immune cells by culture in the presence of an antigen-binding molecule according to the present invention; collecting the generated or expanded population of immune cells; mixing the generated or expanded population of immune cells with an adjuvant, diluent, or carrier; administering the generated or expanded population of immune cells or composition to a subject.

In some embodiments, the method may additionally comprise administering to a subject a therapeutically or prophylactically effective amount of an antigen-binding molecule according to the present invention.

The skilled person is able to determine appropriate reagents and procedures for adoptive transfer of immune cells generated or expanded according to the methods of the present invention for example by reference to Chia W K et al., Molecular Therapy (2014), 22(1): 132-139, Kalos and June 2013, Immunity 39(1): 49-60 and Cobbold et al., (2005) J. Exp. Med. 202: 379-386.

Administration

Administration of an antigen-binding molecule or composition according to the invention is preferably in a "therapeutically effective" or "prophylactically effective" amount, this being sufficient to show benefit to the subject. The actual amount administered, and rate and time-course of administration, will depend on the nature and severity of the disease or disorder. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins. It will be appreciated that the articles of the present invention (e.g. the antigen-binding molecules or compositions of the invention) are administered in an amount sufficient to cause an increase in the number of (i.e. cause expansion a population of) cells expressing CD122 and CD132 (e.g. effector T cells, NK cells and/or CAR-T cells).

Administration of an antigen-binding molecule encompasses administration of a cell comprising/expressing the antigen-binding molecule.

Administration may be alone or in combination with other treatments, either simultaneously or sequentially dependent upon the disease/condition to be treated/prevented. The antigen-binding molecule or composition described herein and an additional agent, e.g. a therapeutic agent, may be administered simultaneously or sequentially. In some embodiments, the methods comprise additional therapeutic or prophylactic intervention, e.g. for the treatment/prevention of a cancer. In some embodiments, the therapeutic or prophylactic intervention is selected from chemotherapy, immunotherapy, radiotherapy, surgery, vaccination and/or hormone therapy.

Simultaneous administration refers to administration of the antigen-binding molecule, nucleic acid, vector, cell or composition and therapeutic agent together, for example as a pharmaceutical composition containing both agents (combined preparation), or immediately after each other and optionally via the same route of administration, e.g. to the same artery, vein or other blood vessel. Sequential administration refers to administration of one of the antigen-binding molecule/composition or therapeutic agent followed after a given time interval by separate administration of the other agent. It is not required that the two agents are administered by the same route, although this is the case in some embodiments. The time interval may be any time interval.

In some embodiments, the antigen-binding molecule is administered in combination with a chimeric antigen receptor (CAR) or a CAR-expressing cell (e.g. a CAR-T cell). In some embodiments, the antigen-binding molecule is administered in combination with a population of immune cells, e.g. a population of immune cells generated/expanded according to the methods described herein. In some embodiments, the antigen-binding molecule is administered in a method comprising adoptive cell transfer (ACT), as described herein.

In some embodiments, the antigen-binding molecule is administered in combination with an agent capable of inhibiting signalling mediated by an immune checkpoint protein. Immune checkpoint proteins are sometimes referred to as immune checkpoint inhibitors.

Immune checkpoint proteins help keep immune responses in check and thereby protect against autoimmunity, but can also act to inhibit desirable effector immune cell activity such as killing of cancer cells by T cells, or killing of cells infected with a pathogen (particularly in instances of chronic infection). Inhibition of signalling mediated by immune checkpoint proteins is desirable in such settings as it releases effector immune cells from immune checkpoint protein-mediated inhibition, thereby promoting effector immune responses.

Agents capable of inhibiting signalling mediated by a given immune checkpoint protein include, e.g. agents capable of binding to the immune checkpoint protein or a ligand for the immune checkpoint protein and inhibiting signalling mediated by the immune checkpoint protein; agents capable of reducing gene/protein expression of the immune checkpoint protein or a ligand for the immune checkpoint protein (e.g. through inhibiting transcription of the gene(s) encoding the immune checkpoint protein/ligand, inhibiting post-transcriptional processing of RNA encoding the immune checkpoint protein/ligand, reducing stability of RNA encoding the immune checkpoint protein/ligand, promoting degradation of RNA encoding the immune checkpoint protein/ligand, inhibiting post-translational processing of the immune checkpoint protein/ligand, reducing stability the immune checkpoint protein/ligand, or promoting degradation of the immune checkpoint protein/ligand), and small molecule inhibitors.

In some embodiments the immune checkpoint protein is PD-1, CTLA-4, LAG-3, TIM-3, VISTA, TIGIT or BTLA. In some embodiments the immune checkpoint protein is selected from PD-1, CTLA-4, LAG-3 and TIM-3.

In some embodiments, the antigen-binding molecule of the present invention is administered in combination with an agent capable of inhibiting signalling mediated by PD-1. The agent capable of inhibiting signalling mediated by PD-1 may be a PD-1-targeted agent, or an agent targeted against a ligand for PD-1 such as PD-L1 or PD-L2. In some embodiments, the agent capable of inhibiting signalling mediated by PD-1 may e.g. be an antibody capable of binding to PD-1, PD-L1 or PD-L2 and inhibiting PD-1-mediated signalling. In some embodiments the agent capable of inhibiting signalling mediated by PD-1 is an antibody/fragment described in WO2016/068801 or WO2016/111645, both of which are hereby incorporated by reference in their entirety.

In some embodiments, the antigen-binding molecule of the present invention is administered in combination with an agent capable of inhibiting signalling mediated by CTLA-4. The agent capable of inhibiting signalling mediated by CTLA-4 may be a CTLA-4-targeted agent, or an agent targeted against a ligand for CTLA-4 such as CD80 or CD86. In some embodiments, the agent capable of inhibiting signalling mediated by CTLA-4 may e.g. be an antibody capable of binding to CTLA-4, CD80 or CD86 and inhibiting CTLA-4-mediated signalling. In some embodiments the agent capable of inhibiting signalling mediated by CTLA-4 is an antibody/fragment described in WO2017/194265, which is hereby incorporated by reference in its entirety.

In some embodiments, the antigen-binding molecule of the present invention is administered in combination with an agent capable of inhibiting signalling mediated by LAG-3. The agent capable of inhibiting signalling mediated by LAG-3 may be a LAG-3-targeted agent, or an agent targeted against a ligand for LAG-3 such as MHC class II. In some embodiments, the agent capable of inhibiting signalling mediated by PD-1 may e.g. be an antibody capable of binding to LAG-3 or MHC Class II and inhibiting LAG-3-mediated signalling. In some embodiments the agent capable of inhibiting signalling mediated by LAG-3 is an antibody/fragment described in WO2017/149143, which is hereby incorporated by reference in its entirety.

In some embodiments, the antigen-binding molecule of the present invention is administered in combination with an agent capable of inhibiting signalling mediated by TIM-3. The agent capable of inhibiting signalling mediated by TIM-3 may be a TIM-3-targeted agent, or an agent targeted against a ligand for TIM-3 such as Galectin 9. In some embodiments, the agent capable of inhibiting signalling mediated by TIM-3 may e.g. be an antibody capable of binding to TIM-3 or Galectin 9 and inhibiting TIM-3-mediated signalling. In some embodiments the agent capable of inhibiting signalling mediated by PD-1 is an antibody/fragment described in WO2016/068802 or WO2016/068803, both of which are hereby incorporated by reference in their entirety.

Chemotherapy and radiotherapy respectively refer to treatment of a cancer with a drug or with ionising radiation (e.g. radiotherapy using X-rays or γ-rays). The drug may be a chemical entity, e.g. small molecule pharmaceutical, antibiotic, DNA intercalator, protein inhibitor (e.g. kinase inhibitor), or a biological agent, e.g. antibody, antibody fragment, aptamer, nucleic acid (e.g. DNA, RNA), peptide, polypeptide, or protein. The drug may be formulated as a pharmaceutical composition or medicament.

The formulation may comprise one or more drugs (e.g. one or more active agents) together with one or more pharmaceutically acceptable diluents, excipients or carriers.

A treatment may involve administration of more than one drug. A drug may be administered alone or in combination with other treatments, either simultaneously or sequentially dependent upon the condition to be treated. For example, the chemotherapy may be a co-therapy involving administration of two drugs, one or more of which may be intended to treat the cancer.

The chemotherapy may be administered by one or more routes of administration, e.g. parenteral, intravenous injection, oral, subcutaneous, intradermal or intratumoral.

The chemotherapy may be administered according to a treatment regime. The treatment regime may be a pre-determined timetable, plan, scheme or schedule of chemotherapy administration which may be prepared by a physician or medical practitioner and may be tailored to suit the patient requiring treatment.

The treatment regime may indicate one or more of: the type of chemotherapy to administer to the patient; the dose of each drug or radiation; the time interval between administrations; the length of each treatment; the number and nature of any treatment holidays, if any etc. For a co-therapy a single treatment regime may be provided which indicates how each drug is to be administered.

Chemotherapeutic drugs and biologics may be selected from: alkylating agents such as cisplatin, carboplatin, mechlorethamine, cyclophosphamide, chlorambucil, ifosfamide; purine or pyrimidine anti-metabolites such as azathiopurine or mercaptopurine; alkaloids and terpenoids, such as vinca alkaloids (e.g. vincristine, vinblastine, vinorelbine, vindesine), podophyllotoxin, etoposide, teniposide, taxanes such as paclitaxel (Taxol™), docetaxel; topoisomerase inhibitors such as the type I topoisomerase inhibitors camptothecins irinotecan and topotecan, or the type II topoisomerase inhibitors amsacrine, etoposide, etoposide phosphate, teniposide; antitumor antibiotics (e.g. anthracyline antibiotics) such as dactinomycin, doxorubicin (Adriamycin™), epirubicin, bleomycin, rapamycin; antibody based agents, such as anti-PD-1 antibodies, anti-PD-L1 antibodies, anti-TIM-3 antibodies, anti-CTLA-4, anti-4-1BB, anti-GITR, anti-CD27, anti-BLTA, anti-OX43, anti-VEGF, anti-TNFα, anti-IL-2, antiGpIIb/IIIa, anti-CD-52, anti-CD20, anti-RSV, anti-HER2/neu (erbB2), anti-TNF receptor, anti-EGFR antibodies, monoclonal antibodies or antibody fragments, examples include: cetuximab, panitumumab, infliximab, basiliximab, bevacizumab (Avastin®), abciximab, daclizumab, gemtuzumab, alemtuzumab, rituximab (Mabthera®), palivizumab, trastuzumab, etanercept, adalimumab, nimotuzumab; EGFR inhibitors such as erlotinib, cetuximab and gefitinib; anti-angiogenic agents such as bevacizumab (Avastin®); cancer vaccines such as Sipuleucel-T (Provenge®).

Further chemotherapeutic drugs may be selected from: 13-cis-Retinoic Acid, 2-Chlorodeoxyaderiosine 5-Azacitidine 5-Fluorouracil, 6-Mercaptopurine, 6-Thioguanine, Abraxane, Accutane®, Actinomycin-D Adriamycin®, Adrucil®, Afinitoi®, Agrylin®, Ala-Cort®, Aldesleukin, Alemtuzumab, ALIMTA, Alitmetinoin, Alkaban-AQ®, Alkeran®, All-transretinoic Acid, Alpha Interferon, Altretamine, Amethopterin, Arnifostine, Aminoglutethimide, Anagrelide, Anandron®, Anastrozole, Arabinosylcytosine, Aranesp®, Aredia®, Arimidex®, Aromasin®, Arranon®, Arsenic Trioxide, Asparaginase, ATRA Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, Calcium Leucovorin, Campath®, Camptosar®, Camptothecin-11, Capecitabine, Carac™, Carboplatin, Carmustine, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine Cytosar-U®, Cytoxan®, Dacogen, Dactinomycin, Darbepoetin Alfa, Dasatinib, Daunomycin, Daunorubicin, Daunorubicin Hydrochloride, Daunorubicin Liposornal, DaunoXorne®, Decadron, Decitabine, Delta-Cortef®, Deltasone®, Denileukin, Diftitox, DepoCyL™, Dexamethasone, Dexarnethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™; DTIC, DTIC-Dome®, Duraione®, Eiigard™, Ellence™, Eloxatin™, Elspar®, Emcyt®, Epirubicin, Epoetin Alfa, Erbitux, Erlotinib, Erwinia L-asparaginase, Estramustine, Ethyol Etopophos®, Etoposide, Etoposide Phosphate, Eulexin®, Everolimus, Evista®, Exemestane, Faslodex®, Femara®, Filgrastim, Floxuridine, Fludara®, Fludarabine, Fluoroplex®, Fluorouracil, Fluoxymesterone, Flutamide, Folinic Acid, FUDR®, Fulvestrant, Gefitinib, Gemcitabine, Gemtuzumab ozogamicin, Gleevec™, Gliadel® Wafer, Goserelin, Granulocyte—Colony Stimulating Factor, Granulocyte Macrophage Colony Stimulating Factor, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan, Idamycin®, Idarubicin, Ifex®, IFN-alpha, Ifosfamide, IL-11, IL-2, Imatinib mesylate, imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisole®, MTC, MTX, Mustargen®, Mustine, Mutamycin®, Myleran®, Mylocel™, Mylotarg®, Navelbine®, Nelarabine, Neosar®, Neulasta™, Neumegar®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapreci®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PRO- CRIT®, Proleukin®, Prolifeprospan 20 with Carmustine Implant Purinethol®, Raloxifene, Revlimid®, Rheumatrex®, Rituxan®, Rituximab, Roferon-A® (Interferon Alfa-2a), Rubex®, Rubidomycin hydrochloride, Sandostatin® Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Ternozolomide, Ternsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositurnomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, Zometa®.

Multiple doses of the antigen-binding molecule or composition may be provided. One or more, or each, of the doses may be accompanied by simultaneous or sequential administration of another therapeutic agent.

Multiple doses may be separated by a predetermined time interval, which may be selected to be one of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, 3, 4, 5, or 6 months. By way of example, doses may be given once every 7, 14, 21 or 28 days (plus or minus 3, 2, or 1 days).

In some embodiments, the antigen-binding molecule may be conjugated to a drug moiety or a detectable moiety.

Methods of Detection

The antigen-binding molecules described herein may be used in methods that involve detection of CD122 and/or CD132, or cells expressing CD122 and/or CD132 (e.g. at the cell surface). The methods may be in vitro or in vivo methods. Such methods may involve detection of the bound complex of the antigen-binding molecule and CD122 and/or CD132, or cells expressing CD122 and/or CD132.

As such, a method is provided, the method comprising contacting a sample containing, or suspected to contain, CD122 and/or CD132 or cells expressing CD122 and/or CD132, and detecting the formation of a complex of the antigen-binding molecule and CD122 and/or CD132 or cells expressing CD122 and/or CD132.

Suitable method formats are well known in the art, including immunoassays such as sandwich assays, e.g. ELISA. The methods may involve labelling the antigen-binding molecule, or target(s), or both, with a detectable moiety, e.g. a detectable moiety as described hereinabove. In some embodiment the detectable moiety is a fluorescent label, a luminescent label, an immuno-detectable label or a radio-label. In some embodiments, the detectable moiety may be selected from: a radio-nucleotide, positron-emitting radionuclide (e.g. for positron emission tomography (PET)), MRI contrast agent or fluorescent label. Analysis in vitro or in vivo may involve analysis by positron emission tomography (PET), magnetic resonance imaging (MRI), or fluorescence imaging, e.g. by detection of appropriately labelled species.

Methods of this kind may provide the basis of methods for the diagnostic and/or prognostic evaluation of a disease or condition. Such methods may be performed in vitro on a patient sample, or following processing of a patient sample. Once the sample is collected, the patient is not required to be present for the in vitro method to be performed, and therefore the method may be one which is not practised on the human or animal body.

In some embodiments the methods may involve detecting or quantifying CD122 and/or CD132, or cells expressing CD122 and/or CD132, e.g. in a patient sample. Where the method comprises quantifying the relevant factor, the method may further comprise comparing the determined amount against a standard or reference value as part of the diagnostic or prognostic evaluation. Other diagnostic/prognostic tests may be used in conjunction with those described herein to enhance the accuracy of the diagnosis or prognosis or to confirm a result obtained by using the tests described herein.

A sample may be taken from any tissue or bodily fluid. The sample may comprise or may be derived from: a quantity of blood; a quantity of serum derived from the individual's blood which may comprise the fluid portion of the blood obtained after removal of the fibrin clot and blood cells; a tissue sample or biopsy; pleural fluid; cerebrospinal fluid (CSF); or cells isolated from said individual. In some embodiments, the sample may be obtained or derived from a tissue or tissues which are affected by the disease/condition (e.g. tissue or tissues in which symptoms of the disease manifest, or which are involved in the pathogenesis of the disease/condition).

Subjects

The subject to be treated in accordance with aspects the invention described herein may be any animal or human. The subject is preferably mammalian, more preferably human. The subject may be a non-human mammal, but is more preferably human. The subject may be male or female. The subject may be a patient. A subject may have been diagnosed with a disease or condition requiring treatment (e.g. a cancer), may be suspected of having such a disease/condition, or may be at risk of developing/contracting such a disease/condition.

In embodiments according to the present invention the subject is preferably a human subject. In some embodiments, the subject to be treated according to a therapeutic or prophylactic method of the invention herein is a subject having, or at risk of developing, a cancer. In embodiments according to the present invention, a subject may be selected for treatment according to the methods based on characterisation for certain markers of such disease/condition.

Kits

The present invention also provides a kit of parts. In some embodiments the kit may have at least one container having a predetermined quantity of an antigen-binding molecule, nucleic acid, expression vector, CAR, composition or cells described herein.

The kit may provide the antigen-binding molecule, nucleic acid, expression vector, CAR, composition or cells together with instructions for administration to a patient in order to treat a specified disease/condition.

In some embodiments, the kit may comprise materials for producing antigen-binding molecule or composition described herein.

The kit may additionally instructions for administration to a patient in order to treat a specified disease/condition. In some embodiments, the kit may comprise materials and/or instructions for producing an antigen-binding molecule, nucleic acid, expression vector, CAR, cell or composition described herein.

In some embodiments the kit may further comprise at least one container having a predetermined quantity of another therapeutic agent (e.g. anti-infective agent or chemotherapy agent). In such embodiments, the kit may also comprise a second medicament or pharmaceutical composition such that the two medicaments or pharmaceutical compositions may be administered simultaneously or separately such that they provide a combined treatment for the specific disease or condition.

Sequence Identity

Pairwise and multiple sequence alignment for the purposes of determining percent identity between two or more amino acid or nucleic acid sequences can be achieved in various ways known to a person of skill in the art, for instance, using publicly available computer software such as ClustalOmega (Söding, J. 2005, Bioinformatics 21, 951-960), T-coffee (Notredame et al. 2000, J. Mol. Biol. (2000) 302, 205-217), Kalign (Lassmann and Sonnhammer 2005, BMG Bioinformatics, 6(298)) and MAFFT (Katoh and Standley 2013, Molecular Biology and Evolution, 30(4) 772-780 software. When using such software, the default parameters, e.g. for gap penalty and extension penalty, are preferably used.

Sequences

| SEQ ID NO: | DESCRIPTION | SEQUENCE |
|---|---|---|
| 1 | Anti-CD122 heavy chain, clone P2C4, P2C4_A4 P2C4_B1, P2C4_B5, P2C4_C4, P2C4_C7, P2C4_E7, P2C4_F8 | EVQLVQSGAEVKKPGSSVKVSCKASGYTFTNYYMHWVRQAPGQGLEWMGAIMPSRG GTSYPQKFQGRVTMTGDTSTSTVYMELSSLRSEDTAVYYCARGEYYYDSSGYYYWGQ GTLVTVSS |
| 2 | Anti-CD122 heavy chain, clone P2H7 | EVQLVQSGTEVKKPGASVKVSCKASGYTFTTYAMHWVRQAPGQSLEWMGWINTGNG NTKYSQNFQGRVTMTRDTSISTAYMELSRLRSDDTAVYYCARDLGQLERLYFWGQGTL VTVSS |
| 3 | Anti-CD122 heavy chain, clone P2D12 | HVQLVETGGGLVQPGGSLRLSCAASGFTFSSYAMSWVRQAPGKGLEWVSAISGSGGS TYYADSVKGRFTISRDNSKNTLYLQMNSLRAEDTAVYYCARDLGDYWGQGTLVTVSS |
| 4 | Anti-CD122 heavy chain, clone P1G11 | QVQLQQWGAGLLKPSETLSLTCAVYGGSFSGYYWSWIRQPPGKGLEWIGEINHSGSTN YNPSLKSRVTISVDTSKNQFSLKLSSVTAADTAVYYCARSSSGDAFDIWGQGTMVTVSS |
| 5 | Anti-CD122 heavy chain, clones P2C4_A9 | EVQLVQSGAEVKKPGSSVKVSCKASGYTFTNYYMHWVRQAPGQGLEWMGAIMPSRG GTSYPQKFQGRVTMTGDTSTSTWMELSSLRSEDTAVYYCARGEYYYDSSGYYNWGQ GTLVTVSS |
| 6 | Anti-CD122 heavy chain, clones P2C4_B6, P2C4_ E9 | EVQLVQSGAEVKKPGSSVKVSCKASGYTFTNYYIHVWRQAPGQGLEWMGAIMPSRGG TSYPQKFQGRVTMTGDTSTSTVYMELSSLRSEDTAVYYCARGEYYYDSSGYYYWGQG TLVTVSS |
| 7 | Anti-CD122 heavy chain, clone P2C4_B8 | EVQLVQSGAEVKKPGSSVKVSCKASGYTFTNYYMHWVRQPPGQGLEWMGAIMPSRG GTSYPQKFQGRVTMTGDTSTSTVYMELSSLRSEDTAVYYCARGEYYYDSSGYYYWGQ GTLVTVSS |
| 8 | Anti-CD122 heavy chain, clone P2C4_B12 | EVQLVQSGAEVKKPGSTVKVSCKASGYTFTNYYMFIWVRQAPGQGLEWMGAIMPSRG GTSYPQKFQGRVTMTGDTSTSTVYMELSSLRSEDTAVYYCARGEYYYDSSGYYYWGQ GTLVTVSS |
| 9 | Anti-CD122 heavy chain, clone P2C4_C1 | EVQLVQSGAEVKKPGSSVKVSCKASGYTFTNYYMHWVRQAPGQGLEWMGAIMPSRG GTSYPQKFQGRVTMTGDTSTSTVYMELSSLRSEDTAVYYCARGEYYYDSSGYYYWGQ GTPVTVSS |
| 10 | Anti-CD122 heavy chain, clone P2C4_C12 | EVQLVQSGAEVKKPGSSVKVSCKASGYTFTNYYMFNWRQAPGQGLEWMGAIMPSRG GTSYPQKFQGRVTMTGDTSTSTVYMELSNLRSEDTAVYYCARGEYYYDSSGYYYWGQ GTLVTVSN |
| 11 | Anti-CD122 heavy chain, clone P2C4_E2 | EVQLVQSGAEVKEPGSSVKVSCKASGYTFTNYYMHWVRQAPGQGLEWMGAIMPSRG GTSYPQKFQGRVTMTGDISTSTVYMELSSLRSEDTAVYYCARGEYYYDSSGYYYWGQ GTLVTVSS |
| 12 | Anti-CD122 heavy chain, clone P2C4_E3 | EVQLVQSGAEVKKPGSSVKVSCKASGYTFTNYYIHWVRQAPGQGLEWMGAIMPSRGG TSYPQKFQGRVTMTGDTSTSTVYMELNSLRSEDTAVYYCARGEYYYDSSGYYYWGQG TLVTVSS |
| 13 | Anti-CD122 heavy chain, clone P2C4_E8 | EVQLVQSGAEVKKPGSSVKVSCKASGYTFTNYYMHWVRQAPGQGLEWMGAIMPSRG GTSYPQKFQGRVTMTGDTSTSTVYMELSSLRSEDTAVYYCARGEYYYDSSGYYYWGP GTLVTVSS |
| 14 | Anti-CD122 heavy chain, clone P2C4_F11 | EVQLVQSGAEVKKPGSSVKVSCKASGYTFTNYYMHWVRQAPGQGLEWMGAIMPSRG GTSYPQKFQGRVTMTGDTSTSTVYMELSSLRSEDTAMYYCARGEYYYDSSGYYYWGQ GTLVTVSS |
| 15 | Anti-CD122 heavy chain, clone P2C4_G2 | EVQLVQSGAEVKKPGSSVKVSCKASGYTFTNYYMHWVRQAPGQGLEWMGAIMPSRG GTSYPQKFQGRVTMTGDTSTSTVYMELSSLRTEDTAVYYCARGEYYYDSSGYYYWGQ GTLVTVSS |
| 16 | Anti-CD122 heavy chain, clone P2C4_G11 | EVQLVQSGAEVKKPGSSVKVSCKASGYTFTNYYMHWVRQAPGQGLEWMGAIMPSRG GTSYPQKFQGRVTMTGDTSTSTVYMELSNLRSEDTAVYYCARGEYYYDSSGYYYWGQ GTLVTVSS |

-continued

| SEQ ID NO: | DESCRIPTION | SEQUENCE |
|---|---|---|
| 17 | Anti-CD122 heavy chain, clone P2C4_H1 | EVQLVQSGAEVKKPGSSVKVSCKASGYTFTNYYMHWVRQAPGQGLEWMGAIMPSRG GTSYPQKFQGRVTMTGDTSTSTVYMELSSLRSEDTAVYYCARGEYYYDSSGYYYWGQ GTLVNVSS |
| 18 | Anti-CD122 heavy chain, clone P2C4_H2 | EVQLVQSGAEVKKPGSSVKVSCKASGYTFSNYYMHWVRQAPGQGLEWIGAIMPSRGG TSYPQKFQGRVTMTGDTSTSTVYMELSSLRSEDTAVYYCARGEYYYDSSGYYYWGQG TLVTVSS |
| 19 | Anti-CD122 heavy chain, clone P2C4_H3 | EVQLVQSGAEVKKPGSSVKVSCKATGYTFTNYYMHWVRQAPGQGLEWMGAIMPSRG GTSYPQKFQGRVTMTGDTSTSTVYMELSSLRSEDTAVYYCARGEYYYDSSGYYYWGQ GTLVTVSS |
| 20 | Anti-CD122 heavy chain, clone P2C4_C1D10 | EVQLVQSGAEVKKPGSSVKVSCKASGYTFTNYYMHWVRQAPGQGLEWMGAIMPSRG GTSYPQKFQGRVTMTGDTSTSTVYMELSSLRSEDTAVYYCARGEYYYDSSGYYYWGQ GTPVTVSS |
| 21 | Anti-CD122 heavy chain, clone P2C4_FW2 | EVQLVQSGAEVKKPGASVKVSCKASGYTFTNYYMHWVRQAPGQGLEWMGAIMPSRG GTSYPQKFQGRVTITADKSTSTAYMELSSLRSEDTAVYYCARGEYYYDSSGYYYWGQG TLVTVSS |
| 22 | Anti-CD122 heavy chain, clone P1E7 | EVQLVQSGGGWQPGRSLRLSCAASGFTFSSYAMHWVRQAPGKGLEWVAVISYDGSN KYYADSVKGRFTISRDNSKNTLYLQMNSLRAEDTAVYYCARDLGYSSSWYYYYYGMDV WGQGTTVTVSS |
| 23 | Anti-CD122 heavy chain, clone P1B10 | QVQLQESGPGLVKPSETLSLTCTVSGVSISSRSDHWGWVRQPPGKGLEWIGSISYSGS TYYNPSLKSRVTISVDTSKNQLSLKLSSVTAADTAVYYCARESHPAAALVGWGQGTLVT VSS |
| 24 | Anti-CD122 heavy chain, clone P1F3 | EVQLVQSGGGLVQPGGSLRLSCAASGFTFSSYAMSWVRQAPGKGLEWVSAISGSGGS THYADSVKGRFTISRDNSKNTLYLQMNSLRAEDTAVYYCATPAFWGQGTLVTVSS |
| 25 | Anti-CD122 heavy chain, clone P1D10 | QVQLQQWGPGLVKPSETLSLTCTVSGGSISSYYWSWIRQPPGKGLEWIGEINHSGSTN YNPSLKSRVTISVDTSKNQFSLKLSSVTAADTAVYYCAGGSNLDWFDPWGQGTLVTVSS |
| 26 | Anti-CD122 heavy chain, clone P1E1 | QVQLQQWGAGLLKPSETLSLTCAVYGGSFSGYYWSWIRQPPGKGLEWIGEINHSGSTN YNPSLKSRVTISVDTSKNQFSLELSSVTAADTAVYYCARADRRFGELRYWGQGTLVTVS S |
| 27 | Anti-CD122 heavy chain, clone P2B11 | QVQLVQSGGGLVKPGGSLRLSCAASGFTFSSYDLHWVRQVPGKGLEWVSLISYDGSNK YYADSVKGRFTISRDNAENSLYLQMNSLRAEDTAVYYCAREPITGTSDLFDYWGQGTLV TVSS |
| 28 | Anti-CD122 heavy chain, clone P2C9 | QVQLQESGPGLVKPSGTLSLTCAVSGGSISSSNWWSWVRQPPGKGLEWIGEIYHSGST NYNPSLKSRVTISVDKSKNQFSLKLSSVTAADTAVYYCVREGGLREEHWGQGTLVTVSS |
| 29 | Anti-CD122 heavy chain, clone P2C10 | QVQLQQWGAGLLKPSETLSLTCAVYGGSFSGYYWSWIRQPPGKGLEWIGEINHSGSTN YNPSLKSRVTISVDTSKNQFSLKLSSVTAADTAVYYCARGTDTAMADYWGQGTLVTVSS |
| 30 | Anti-CD122 heavy chain, clone P2C11 | QVQLQQSGPGLVKPSQTLSLTCAISGDSVSGNSATWNWIRQSPSRGLEWLGRTYYRSK WNHDYAESVKSRITINPDTSKNQFSLQLNSVTPEDTAVYYCARDSKSAFDIWGQGTMVT VSS |
| 31 | Anti-CD122 heavy chain, clone P2E6 | QLQLQESGPGLVKPSETLSLTCSVFGVSITSGSWWSWVRQSPGKELEWIGEIYHNGNT NYNPSLKSRVTISVDTSKNQFSLKLSSVTAADTAVYYCVSGFDYWGQGTLVTVSS |
| 32 | Anti-CD122 heavy chain, clone P2E11 | QVQLQESGPGLVKPSETLSLTCTVSGVSISSRSDHWGWVRQPPGKGLEWIGSISYSGS TYYNPSLKSRVTISVDTSKNQLSLKLSSVTAADTAVYYCARESHPAAALVGWGQGTLVT VSS |
| 33 | Anti-CD122 heavy chain, clone P2F9 | EVQLVQSGAEVKKPGSSVKVSCKASGYTFTSYGISVWRQAPGQGLEWMGWISAYNGN TNYAQKLQGRVTMTTDTSTSTAYMELSSLRSEDTAVYYCARAPDYGDSSNYYYYYMDV WGKGTTVTVSS |
| 34 | Anti-CD122 heavy chain, clone P2F10 | QVQLVQSGAEVKKPGASVKVSCKASGYTFTSYGISWVRQAPGQGLEWMGWISAYNGN TNYAQKLQGRVTMTTDTSTSTAYMELRSLRSDDTAVYYCARDTSGDYSSGWYLGVPFD YWGQGTLVTVSS |
| 35 | Anti-CD122 light chain, clone P2C4, P2C4_A9 | QSALTQPASVSGSPGQSIAISCTGTSSDIGHYDFVSWYQQHPGTAPKLIIYDINNRPSGIS NRFSGSKSDNMASLTISGLQPEDEADYYCSAYTSSDTLVFGGGTKLT |
| 36 | Anti-CD122 light chain, clone P2H7 | DIQMTQSPSTLSASVGDRVTLSCRAGQAISSWLAWYQQKPGKAPKLLIYKASNLESGVP SRFSGGGSGAEFTLTISSLQPDDFATYYCQQYQSYPYTFGQGTKLEIR |

-continued

Sequences

| SEQ ID NO: | DESCRIPTION | SEQUENCE |
|---|---|---|
| 37 | Anti-CD122 light chain, clone P2D12 | DIQLTQSPSSLSASVGDRVTITCQASQDIGNYLNWYQLKPGKAPKLLIYDASNLETGVPS RFSGSGSGTDFTFTISSLQPEDIATYYCLQLYDYPLTFGGGTKVEIK |
| 38 | Anti-CD122 light chain, clone P1G11 | NFMLTQPHSVSESPGKTVTISCTRSSGSIASNYVQWYQQRPGSSPTTVIFDDNQRPTGV PDRFSAAIDTSSSSASLTISGLTAEDEADYYCQSSHSTAWFGGGTKLTVL |
| 39 | Anti-CD122 light chain, clones, P2C4_A4, P2C4_ C1 | QSALTQPASVSGSPGQSIAISCTGTSSDIGDYDFVSWYQQHPGTAPKLIIYDINNRPSGIS NRFSGSKSDNMASLTISGLQPEDEADYYCSAYTSSDTLVFGGGTKLT |
| 40 | Anti-CD122 light chain, clones P2C4_B1 | QSALTQPASVSGSPGQSIAISCTGTSSDIGHYDFVSWYQQHPGTAPKLIIYDNNNRPSGI SNRFSGSKSDNMASLTISGLQPEDEADYYCSAYTSSDTLVFGGGTKLT |
| 41 | Anti-CD122 light chain, clones P2C4_B5 | QSALTQPASVSGSPGQSITISCTGTSSDIGHYDFVSWYQQHPGTAPKLIIYDINNRPSGIS NRFSGSKSDNMASLTISGLQPEDEADYYCSAYTSSDTWFGGGTKLT |
| 42 | Anti-CD122 light chain, clones P2C4_B6, P2C4_ B8, P2C4_C12, P2C4_D10, P2C4_E2, P2C4_E3, P2C4_E8, P2C4_G2, P2C4_G11, P2C4_H1, P2C4_H2, P2C4_H3 | QSALTQPASVSGSPGQSIAISCTGTSSDIGHYDFVSWYQQHPGTAPKLIIYDINNRPSGIS NRFSGSKSDNMASLT1SGLQPEDEADYYCSAYTSSDTWFGGGTKLT |
| 43 | Anti-CD122 light chain, clone P2C4_B12 | QSALTQPASVSGSPGQSIAISCTGTSSDIGHYDFISWYQQHPGTAPKLIIYDFNNRPSGIS NRFSGSKSDNMASLTISGLQPEDEADYYCSAYTSSDTLVFGGGTKLT |
| 44 | Anti-CD122 light chain, clone P2C4_C4 | QSALTQPASVSGSPGQSIAISCTGTSSDIGHYDFVSWYQQHPGTAPKLIIYDNNNRPSGI SNRFSGSKSDNMASLTISGLQPEDEADYYCSAYTSSDTWFGGGTKLT |
| 45 | Anti-CD122 light chain, clone P2C4_C7 | QSALTQPASVSGSPGQSIVISCTGTSSDIGHYDFVSWYQQHPGTAPKLIIYDINNRPSGIS NRFSGSKSDNMASLTISGLQPEDEADYYCSAYTSSDTWFGGGTKLT |
| 46 | Anti-CD122 light chain, clone P2C4_E6 | QSALTQPASVSGSPGQSIAISCTGTSSDIGDYDFVSWYQQHPGTAPKLIIYDINNRPSGIS NRFSGSKSDNMASLIISGLQPEDEADYYCSAYTSSDTLVFGGGTKLT |
| 47 | Anti-CD122 light chain, clone P2C4_E7 | QSALTQPASVSGSPGQSIAISCTGTSSDIGHYDFVSWYQQHPGTAPKLIIYDINNRPSGIS NRFSGSKSDDMASLTISGLQPEDEADYYCSAYTSSDTWFGGGTKLT |
| 48 | Anti-CD122 light chain, clone P2C4_E9 | QSALTQPASVSGSPGQSIAISCTGTSSDIGHYDFVSWYQQHPGTAPKLIIYDINNRASGIS NRFSGSKSDNMASLTISGLQPEDEADYYCSAYTSSDTWFGGGTKLT |
| 49 | Anti-CD122 light chain, clone P2C4_F8 | QSALTQPASVSGNPGQSIAISCTGTSSDIGHYDFVSWYQQHPGTAPKLIIYDINNRPSGIS NRFSGSKSDNMASLTISGLQPEDEADYYCSAYTSSDTWFGGGTKLT |
| 50 | Anti-CD122 light chain, clone P2C4_F11 | QSTLTQPASVSGSPGQSITISCTGTSSDIGHYDFVSWYQQHPGTAPKLIIYDINNRPSGIS NRFSGSKSDNMASLT1SGLQPEDEADYYCSAYTSSDTWFGGGTKLT |
| 51 | Anti-CD122 light chain, clone P2C4_C1D10 | QSALTQPASVSGSPGQSIAISCTGTSSDIGDYDFVSWYQQHPGTAPKLIIYDINNRPSGIS NRFSGSKSDNMASLTISGLQPEDEADYYCSAYTSSDTWFGGGTKLT |
| 52 | Anti-CD122 light chain, clone P2C4_FW2 | QSVLTQPPSVSGAPGQRVTISCTGTSSDIGHYDFVSWYQQLPGTAPKLLIYDINNRPSGV PDRFSGSKSGTSASLAITGLQAEDEADYYCSAYTSSDTLVFGGGTKLT |
| 53 | Anti-CD122 light chain, clone P1E7 | DVVMTQSPLSLPVTPGEPASISCRSSQSLLHSNGYNYLDWYLQKPGQSPQLLIYLGSSR ASGVPDRFSGSGSGTDFTLKISRVEAEDVGVYYCMQALQTPRTFGQGTKLEIK |
| 54 | Anti-CD122 light chain, clone P1B10 | DIQMTQSPSSLSASVGDRVTITCQASQDISDYLNWYQQKPGKAPQILIYDASNLETGVPS RFSGSGSGTDFTFTISNLQPEDVATYYCQQYEDLPSFGGGTKVEIK |
| 55 | Anti-CD122 light chain, clone P1F3 | DIQLTQSPSSLSASVGDRVTITCRASQSISSYLNWYQQKPGKAPKALIYDASNLETGVPS RFSGSGSGTDFTLTIISLQPEDFATYFCLQDYIYPWTFGQGTKVEFK |
| 56 | Anti-CD122 light chain, clone P1D10 | QSVLTQPPSVSGAPGQRVTISCTGGSSNVGAGYDVHWYQQLPGTVPKLLIYDNTNRPS GVPDRFSASKSGTSA3LVITGLQAEDEGDYYCQSYDSSLRASVFGGGTMLTVL |
| 57 | Anti-CD122 light chain, clone P1E1 | NFMLTQPHSVSESPGKTVTISCTGSSGSIASSYVQWYQQRPGSAPTTVIYADNQRPSGV PDRFSGSVDSSSNSASLTISGLKTEDEADYYCQSFDSSLYMIFGGGTKLTVL |
| 58 | Anti-CD122 light chain, clone P2B11 | QSVLTQPPSVSGAPGQRVTISCTGSRSNIGAGYDVHWYQHLPGTAPKLLIYDNSNRPSG VSDRFSGSKSGTSASLAITGLQAEDEADYYCQSFDSSLRGWFGGGTRLTVL |
| 59 | Anti-CD122 light chain, clone P2C9 | SYELTQPPSASGTPGQRVTISCSGSSSNIGSNTVNWYQQLPGTAPKLLIYSNNQRPSGV PDRFSGSKSGTSASLAISGLQSEDEADYYCAAWDDSLNGLWVFGGGTKLTVL |

-continued

Sequences

| SEQ ID NO: | DESCRIPTION | SEQUENCE |
|---|---|---|
| 60 | Anti-CD122 light chain, clone P2C10 | DVVMTQSPLSLPVTPGEPASISCRSSQRLLHSNGYNYVDWYLQKPGQSPQLLIYLGSNRASGVPDRFSGSGSGTDFTLKISRVEAEDVGVYYCMQGTHWPWTFGQGTKVEIK |
| 61 | Anti-CD122 light chain, clone P2C11 | DIQMTQSPPSLSASVGDRVTITCQASQDINNYLNWYHQKPGKAPELLIYDASQLETGVPSRFSGSGSGTEFTFIISSLQPEDTGTYYCQQYDWLPLSYGGGTKVEIK |
| 62 | Anti-CD122 light chain, clone P2E6 | NFMLTQPHSVSGSPGKTITISCTRSSGNFASTYVQWYQQRPGSSPAIVIYDDDQRPSGVPDRFSGSIDRSSNSASLTISGLETEDEADYYCQSYDSSNFWVFGGGTKLTVL |
| 63 | Anti-CD122 light chain, clone P2E11 | EIVLTQSPSSLSASVGDRVTITCQASQDINNYLNWYQQKPGKAPKLLIYDASNLETGVPSKFSGSGSGTDFTFTISSLQPEDIATYYCQQYANLPSFGQGTKLEIK |
| 64 | Anti-CD122 light chain, clone P2F9 | EIVLTQSPLSLPVTPGEPASISCRSSQSLLHSNGYNYLDWYLQKPGQSPQLLIYLGSNRASGVPDRFSGSGSGTDFTLSISRVEAEDVGVYYCMQALQTPPTFGQGTKVEIK |
| 65 | Anti-CD122 light chain, clone P2F10 | DIQLTQSPSSLSASVGDRVTVTCQASQDIGHNLNWYQQRPGKAPQLLIYDASNLETGVPSRFSGSGSGTQFTFTISSLQPEDIATYYCQQYDFLPPDFGPGTKVEIK |
| 66 | Anti-CD132 heavy chain, clone P1A3 | QVQLQQWGAGLLKPSETLSLTCAVYGGSFSGYYWSWIRQPPGKGLEWIGEINHSGSTNYNPSLKSRATISVDTSKNQFSLKLSSVTAADTAWYCATSPGGYSGGYFQHWGQGTLVTVSS |
| 67 | Anti-CD132 heavy chain, clone P2B9 | QVQLQESGPGLVKPSETLSLTCTVSGGSISSSSYYWGWIRQPPGKGLEWIGSIYYSGSTYYNPSLKSRVTISVDTSKNQFSLKLSSVTAADTAVYYCAGDILTGYALDYWGQGTLVTVSS |
| 68 | Anti-CD132 heavy chain, clones P1A3_B3, P1A3_B4, P1A3_E9 | QVQLQQWGAGLLKPSETLSLTCAVYGGSFSGYYWSWIRQPPGKGLEWIGEINHFGSTNYNPSLKSRATISVDTSKNQFSLKLSSVTAADTAWYCATSPGGYSGGYFQHWGQGTLVTVSS |
| 69 | Anti-CD132 heavy chain, clone P1A3_E8 | QVQLQQWGAGMLKPSETLSLTCAVYGGSFSGYYWSWIRQPPGKGLEWIGEINHFGSTNYNPSLKSRATISVDTSKNQFSLKLSSVTAADTAVYYCATSPGGYSGGYFQHWGQGTLVTVSS |
| 70 | Anti-CD132 heavy chain, clone P1A3_FW2 | EVQLVESGGGLVQPGGSLRLSCAASGGSFSGYYWSWVRQAPGKGLEWVSEINHSGSTNYNPSLKSRFTISRDNSKNTLYLQMNSLRAEDTAVYYCARSPGGYSGGYFQHWGQGTLVTVSS |
| 71 | Anti-CD132 heavy chain, clone P1A10 | QVQLQQSGAEVKKPGSSVKVSCKASGGTFSSYAISWVRQAPGQGLEWMGGFDPEDGETIYAQKFQGRVTMTEDTSTDTAYMELSSLRSEDTAVYYCATDLRIPYYYDNPWGQGTLVTVSS |
| 72 | Anti-CD132 heavy chain, clone P1B6 | QVQLVQSGGGWQPGRSLRLSCAASGFTFSSYAMHWVRQAPGKGLEWVAVISYDGSNKYYADSVKGRFTISRDNSKNTLYLQMNSLRAEDTAVYYCARSLYYSHFDYWGQGTLVTVSS |
| 73 | Anti-CD132 heavy chain, clone P1C10 | EVQLVETGPGLVKPSGTLSLTCAVSGGSISSSNWWSWVRQPPGKGLEWIGEIYHSGSTNYNPSLKSRVTISVDKSKNQFSLKLSSVTAADTAVYYCAREGPLSSSGPGAFDIWGQGTMVTVSS |
| 74 | Anti-CD132 heavy chain, clone P1D7 | QVQLQESGGGWQPGRSLRLSCAASGFTFSNYGMHVWRQAPGKGLEWVAVISYDGTNKYYADSVKGRFTISRDNSKNTVYLQMNSLRAEDTAVYYCAKDGFDIWGQGTMVTVSS |
| 75 | Anti-CD132 heavy chain, clone P1E8 | EVQLVQSGGGWQPGRSLRLSCAASGFTFSSYGMHWVRQAPGKGLEWVAVISYDGSNKYYADSVKGRFTISRDNSKNTLYLQMNSLRAEDTAVYYCARDVYGDYGAFDYWGQGTLVTVSS |
| 76 | Anti-CD132 heavy chain, clone P1B2 | QLQLQESGGGWQPGRSLRLSCAASGFTFSSYAMHWVRQAPGKGLEWVAVISYDGGNKYYADSVKGRFTISRDNSKNTLYLQMNSLRAEDTAVYYCAKSVAPPMDVWGKGTTVTVSS |
| 77 | Anti-CD132 heavy chain, clone P2B7 | QVQLQQWGAGLLKPSETLSLTCAVYGESFSGYYWSWIRQPPGKGLEWIGEINHSGSTNYNPSLKSRVTISVDTSKNQFSLKLSSVTAADTAVYYCARGPAGSSSSGYFDYWGQGTLVTVSS |
| 78 | Anti-CD132 heavy chain, clone P2D11 | QVQLQESGPGLVKPSQTLSLTCTVSGGSISSGGYYWTWIRQHPGQGLEWIGFISWSGTTYYNPSLKNRVTISADTSKNHFSLNLTSVTAADTAVYYCARGSGRLVWGQGTLVTVSS |
| 79 | Anti-CD132 heavy chain, clone P2F10 | EVQLVQSGAEVKKPGASVKVSCKASGYTFTGYYMHWVRQAPGQGLEWMGIINPSGGSTSYAQKFQGRVTMTRDTSTSTVYMELSSLRSEDTAVYYCARADTAMGDAFDIWGQGTMVTVSS |

-continued

Sequences

| SEQ ID NO: | DESCRIPTION | SEQUENCE |
|---|---|---|
| 80 | Anti-CD132 heavy chain, clone P2H4 | EVQLVQSGGGWQPGRSLRLSCAASGFTFSSYAMHWVRQAPGKGLEWVAVISYDGSN KYYADSVKGRFTISRDNSKNTLYLQMNSLRAEDTAVYYCARSIGIGAFDIWGQGTMVTV SS |
| 81 | Anti-CD132 heavy chain, clone P2D3 | QVQLQQWGAGLLKPSETLSLTCTIYGGSFSGFYWSWIRQPPGKGLEWIGEINHSGSTNY NPSLKSRVTISVDTSKNQFSLKLSSVTAADTAIYYCARGPAGSTSSGYFDHWGQGTLVT VSS |
| 82 | Anti-CD132 heavy chain, clone P1G4 | QVQLQQWGAGLLKPSETLSLTCAVYGGSLSGYYWSWIRQPPGKGLEWIGEINHSGSTN YNPSLKSRVTISVDTSKNQFSLKLSSVTAADTAVYYCARGSSSYYMDVWGKGTTVTVSS |
| 83 | Anti-CD132 heavy chain, clone P1B12 | QVQLQQWGAGLLKPSETLSLTCAVYGGSFSGYYWSWIRQPPGKGLEWIGEINHSGSTN YNPSLKSRVTISVDTSKNQFSLKLSSVTAADTAVYYCARGGSAYFQHWGQGTLVTVSS |
| 84 | Anti-CD132 heavy chain, clone P1C7 | QVQLQQWGAGLLKPSETLSLTCAVYGGSFSGYYWSWIRQPPGKGLEWIGEINHSGSTN YNPSLKSRVTISEDASKKQFSLTLTSVTAADTAVYYCARGPAGTGSSGYFDYWGQGTLV TVSS |
| 85 | Anti-CD132 light chain, clones P1A3, P1A3_B3, P1A3_E8, P1A3_E9 | DVVMTQSPLSLPVTPGEPASISCRSSQSLLHSNGYNYLDWYLQKPGQSPQLLIYLGSNR DSGVPDRFSGSGSGTDFTLKISRVEAEDVGVYYCMQGTHWPWTFGQGTKVEIK |
| 86 | Anti-CD132 light chain, clone P2B9 | SYELTQPPSMSVSPGQTARITCSGDALPKQFAFWYQQKPGQAPVLVIYKDTERPSGIPE RFSGSSSGTTVTLTITGVQAEDEADYYCQSPDSSGTVEVFGGGTKLTVL |
| 87 | Anti-CD132 light chain, clone P1A3_B4 | DVVMTQSPLSLPVTPGESVSISCRSSQSLLHSNGYNYLDWYLQKPGQSPQLLIYLGSNR PSGVPPRFSGSGSGTPFTLKISRVEAEDVGVYYCMQGTHWPWTFGQGTKVEIK |
| 88 | Anti-CD132 light chain, clone P1A3_FW2 | PIQMTQSPSSLSASVGPRVTITCRSSQSLLHSNGYNYLDWYQQKPGKAPKLLIYLGSNR PSGVPSRFSGSGSGTDFTLTISSLQPEDFATYYCMQGTHWPWTFGQGTKVEIK |
| 89 | Anti-CD132 light chain, clone P1A10 | EIVLTQSPLSLPVTPGEPASISCRSSQSLLHSNGYNYLNWYLQKPGQSPQLLIYLGSDRA SGVPDRFSGSGSGTDFTLKISRVEAEDVGVYYCMQALQTPTTFGGGTKVEIK |
| 90 | Anti-CD132 light chain, clone P1B6 | EIVMTQSPLSLPVTPGEPASISCRSSQSLLHSNGYNYLDWYLQKPGQSPQLLMYLVSNR ASGVPERFSGSGSGTDFTLKISRVEAEDVGVYYCMQTLQTPLSFGQGTKLEIK |
| 91 | Anti-CD132 light chain, clone P1C10 | EIVLTQSPATLSLSPGERATLSCRASQSVSYHLAWYQQKPGQAPRLLIYDTSNRASGIPA RFSGSGSGTDFTLTINSLEPEDFAVYYCQQRYDWPLTFGGGTKVEIK |
| 92 | Anti-CD132 light chain, clone P1D7 | DIQMTQSPSFLSASVGDRVTITCRASQSISSWLAWYQQKPGKAPKLLIYDASRLEDGVPS RFSGTGFGTPFTFTITTLQPPPIATYYCQQYPPLPYTFGQGTTVDIK |
| 93 | Anti-CD132 light chain, clone P1E8 | DVVMTQSPVSLPVTLGQPASISCKSSQSLLYFNGNTYLSWFQQRPGQSPRRLFYQVSN RDSGVPDRFSGSGSDTDFTLTISRVEAEDVGVYFCMQGTQWPPTFGQGTKVEIK |
| 94 | Anti-CD132 light chain, clone P2B2 | DVVMTQSPLSLPVTPGEPASISCRSSQSLLHSNGVNYLDWYLQKPGQSPHLLIYLGSNR ASGVPDRFSGSGSGTDFTLKISRVEAEDVGVYFCMQALRTPYTFGQGTKLEIK |
| 95 | Anti-CD132 light chain, clone P2B7 | DVVMTQSPLSLPVTLGQPASISCRSSQSLVHSNGYNYLDWYLQKPGQSPQLLIYLGSNR ASGVPDRFSGSGSGTDFTLKISRVEAEDVGVYYCLQGSHWPWTFGQGTKVEIK |
| 96 | Anti-CD132 light chain, clone P2D11 | ETTLTQSPATLSVSPGERATLSCRASQSVSSNLAWYQQKPGQAPRLLIYGASSGATGIP DRFSGSGSGTDFTLTISRLEPEDFAVYYCQLYGSSLAFGGGTKVEIK |
| 97 | Anti-CD132 light chain, clone P2F10 | DIVMTHTPLSLPVTPGEPASISCRSSQTLFDSDDGKTYLDWYLQKPGQSPQLLMYTTSS RASGVPDRFSGSGSGTDFTLKISRVEAEDVGVYYCMQRLQFPLTFGQGTRLEFK |
| 98 | Anti-CD132 light chain, clone P2H4 | DVVMTQSPLSLPVTPGEPASISCRATQSLLHGNGHNYLDWYLQKPGQSPQLLIYLGSNR ASGVPDRFSGSGSGTDFTLKISRVEAEDVGVYYCMQTLETPVTFGPGTKVDIK |
| 99 | Anti-CD132 light chain, clone P2D3 | DVVMTQSPLSLPVTPGEPASISCRSSQSLLHSNGYNYLDWYLQKPGQSPQLLIYLGSNR ASGVPDRFSGSGSGTDFTLKISRVEAEDVGVYYCMQGTHWPWTFGQGTKVEIK |
| 100 | Anti-CD132 light chain, clone P1G4 | DVVMTQSPLSLPVTPGEPASISCRSSQSLLHSNGYNYLDWYLQKPGQSPQLLIYLGSNR ASGVPDRFSGSGSGTDFTLKISRVEAEDVGVYYCLQGTHWPWTFGQGTKVEIK |
| 101 | Anti-CD132 light chain, clone P1B12 | DVVMTQSPLSLPVTLGQPASISCRSSQSLLHSNGNNYLDWYLQKPGQSPQLLIYLGSNR ASGVPDRFSGSGSGTDFTLKISRVEAEDVGIYYCMQGTHWPWTFGQGTKVEIE |
| 102 | Anti-CD132 light chain, clone P1C7 | EIVLTQSPLSLPVTPGEPASISCRSSQSLLHSNGYNYLDWYLQKPGQSPQLLIYLASNRA SGVPDRFSGSGSGTDFTLKISRVEAEDVGVYYCMQGTHWPWTFGQGTKVEVK |

-continued

| Sequences | | |
|---|---|---|
| SEQ ID NO: | DESCRIPTION | SEQUENCE |
| 103 | HC-CDR1 Anti-CD122 clones P2C4, P2C4_A4, P2C4_C4, P2C4_C7, P2C4_D10, P2C4_E6, P2C4_E7, P2C4_F8, P2C4_A9, P2C4_B8, P2C4_B12, P2C4_C1, P2C4_C12, P2C4_E2, P2C4_E8, P2C4_F11, P2C4_G2, P2C4_G11, P2C4_H1, P2C4_H2, P2C4_H3, P2C4_C1D10, P2C4_FW2 | NYYMH |
| 104 | HC-CDR1 Anti-CD122 clone P2H7 | TYAMH |
| 105 | HC-CDR1 Anti-CD122 clones P2D12, P1F3 | SYAMS |
| 106 | HC-CDR1 Anti-CD122 clones P1G11, P1E1, P2C10; HC-CDR1 Anti-CD132 clones P1A3, P1A3_B3, P1A3_B4, P1A3_E9 P1A3_E8, P1A3_FW2, P2B7, P1G4, P1B12, P1C7 | GYYWS |
| 107 | HC-CDR1 Anti-CD122 clones P2C4_B6, P2C4_ E9, P2C4_E3 | NYYIH |
| 108 | HC-CDR1 Anti-CD122 clone P1E7; HC-CDR1 Anti-CD132 clones P1B6, P2V2, P2H4 | SYAMH |
| 109 | HC-CDR1 Anti-CD122 clones P1B10, P2E11 | SRSDHWG |
| 110 | HC-CDR1 Anti-CD122 clone P1D10 | SYYWS |
| 111 | HC-CDR1 Anti-CD122 clone P2B11 | SYDLH |
| 112 | HC-CDR1 Anti-CD122 clone P2C9; HC-CDR1 Anti-CD132 clone P1C10 | SSNWWS |
| 113 | HC-CDR1 Anti-CD122 clone P2C11 | GNSATWN |
| 114 | HC-CDR1 Anti-CD122 clone P2E6 | SGSWWS |
| 115 | HC-CDR1 Anti-CD122 clones P2F9, P2F10 | SYGIS |
| 116 | HC-CDR2 Anti-CD122 clones P2C4, P2C4_A4, P2C4_B1, P2C4_B5, P2C4_C4, P2C4_C7, P2C4_D10, P2C4_E6, P2C4_E7, P2C4_F8, P2C4_A9, P2C4_B6, P2C4_E9, P2C4_B8, P2C4_B12, P2C4_C1, P2C4_C12, P2C4_E2, P2C4_E3, P2C4_E8, P2C4_F11, P2C4_G2, P2C4_G11, P2C4_H1, | AIMPSRGGTSYPQKFQG |

-continued

| Sequences | | |
|---|---|---|
| SEQ ID NO: | DESCRIPTION | SEQUENCE |
| | P2C4_H2, P2C4_H3, P2C4_C1D10, P2C4_FW2 | |
| 117 | HC-CDR2 Anti-CD122 clone P2H7 | WINTGNGNTKYSQNFQG |
| 118 | HC-CDR2 Anti-CD122 clone P2D12 | AISGSGGSTYYADSVKG |
| 119 | HC-CDR2 Anti-CD122 clones P1G11, P1D10, P1E1, P2C10; HC-CDR2 Anti-CD132 clones P1A3, P1A3_FW2, P2B7, P2D3, P1G4, P1B12, P1C7 | EINHSGSTNYNPSLKS |
| 120 | HC-CDR2 Anti-CD122 clone P1E7; HC-CDR2 Anti-CD132 clones P1B6; P1E8, P2H4 | VISYDGSNKYYADSVKG |
| 121 | HC-CDR2 Anti-CD122 clones P1B10, P2E11 | SISYSGSTYYNPSLKS |
| 122 | HC-CDR2 Anti-CD122 clone P1F3 | AISGSGGSTHYADSVKG |
| 123 | HC-CDR2 Anti-CD122 clone P2B11 | LISYDGSNKYYADSVKG |
| 124 | HC-CDR2 Anti-CD122 clone P2C9; HC-CDR2 Anti-CD132 clone P1C10 | EIYHSGSTNYNPSLIKS |
| 125 | HC-CDR2 Anti-CD122 clone P2C11 | RTYYRSKWNHDYAESVKS |
| 126 | HC-CDR2 Anti-CD122 clone P2E6 | EIYHNGNTNYNPSLKS |
| 127 | HC-CDR2 Anti-CD122 clones P2F9, P2F10 | WISAYNGNTNYAQKLQG |
| 128 | HC-CDR3 Anti-CD122 clones P2C4, P2C4_A4, P2C4_C4, P2C4_C7, P2C4_D10, P2C4_F8, P2C4_E7, P2C4_C7, P2C4_B6, P2C4_E9, P2C4_B8, P2C4_B12, P2C4_C1, P2C4_C12, P2C4_E2, P2C4_E3, P2C4_E8, P2C4_F11, P2C4_G2, P2C4_G11, P2C4_H1, P2C4_H2, P2C4_H3, P2C4_C1D10, P2C4_FW2 | GEYYYDSSGYYY |
| 129 | HC-CDR3 Anti-CD122 clone P2H7 | DLGQLERLYFW |
| 130 | HC-CDR3 Anti-CD122 clone P2D12 | DLGDY |
| 131 | HC-CDR3 Anti-CD122 clone P1G11 | SSSGDAFDI |
| 132 | HC-CDR3 Anti-CD122 clone P2C4_A9 | GEYYYDSSGYYN |
| 133 | HC-CDR3 Anti-CD122 clone P1E7 | DLGYSSSWYYYYYGNADV |

-continued

Sequences

| SEQ ID NO: | DESCRIPTION | SEQUENCE |
|---|---|---|
| 134 | HC-CDR3 Anti-CD122 clones P1B10, P2E11 | ESHPAAALVG |
| 135 | HC-CDR3 Anti-CD122 clone P1F3 | PAF |
| 136 | HC-CDR3 Anti-CD122 clone P1D10 | GSNLDWFDP |
| 137 | HC-CDR3 Anti-CD122 clone P1E1 | ADRRFGELRY |
| 138 | HC-CDR3 Anti-CD122 clone P2B11 | EPITGTSDLFDY |
| 139 | HC-CDR3 Anti-CD122 clone P2C9 | EGGLREEH |
| 140 | HC-CDR3 Anti-CD122 clone P2C10 | GTDTAMADY |
| 141 | HC-CDR3 Anti-CD122 clone P2C11 | DSKSAFDI |
| 142 | HC-CDR3 Anti-CD122 clone P2E6 | VSGFDY |
| 143 | HC-CDR3 Anti-CD122 clone P2F9 | APDYGDSSNYYYYYMDV |
| 144 | HC-CDR3 Anti-CD122 clone P2F10 | DTSGDYSSGWYLGVPFDY |
| 145 | LC-CDR1 Anti-CD122 clones P2C4, P2C4_A9, P2C4_B1, P2C4_B5, P2C4_B6, P2C4_B8, P2C4_C12, P2C4_D10, P2C4_E2, P2C4_E3, P2C4_E8,P2C4_G2, P2C4_G11, P2C4_H1, P2C4_H2, P2C4_H3, P2C4_C4, P2C4_C7, P2C4_E7, P2C4_E9, P2C4_F8, P2C4_F11, P2C4_FW2 | TGTSSDIGHYDFVS |
| 146 | LC-CDR1 Anti-CD122 clone P2H7 | RAGQAISSWLA |
| 147 | LC-CDR1 Anti-CD122 clone P2D12 | QASQDIGNYLN |
| 148 | LC-CDR1 Anti-CD122 clone P1G11 | TRSSGSIASNYVQ |
| 149 | LC-CDR1 Anti-CD122 clones P2C4_A4, P2C4_ C1, P2C4_E6, P2C4_C1D10 | TGTSSDIGDYDEVS |
| 150 | LC-CDR1 Anti-CD122 clone P2C4_B12 | TGTSSDIGHYDFIS |
| 151 | LC-CDR1 Anti-CD122 clones P1E7, P2F9; LC-CDR1 Anti-CD132 clones P1A3, P1A3_B3, P1A3_E8, P1A3_E9, P1A3_B4, P1A3_FW2, P1B2, P2D3, P1G4, P1C7 | RSSQSLLHSNGYNYLD |
| 152 | LC-CDR1 Anti-CD122 clone P1B10 | QASQDISDYLN |

-continued

Sequences

| SEQ ID NO: | DESCRIPTION | SEQUENCE |
|---|---|---|
| 153 | LC-CDR1 Anti-CD122 clone P1F3 | RASQSISSYLN |
| 154 | LC-CDR1 Anti-CD122 clone P1D10 | TGGSSNVGAGYDVH |
| 155 | LC-CDR1 Anti-CD122 clone P1E1 | TGSSGSIASSYVQ |
| 156 | LC-CDR1 Anti-CD122 clone P2B11 | TGSRSNIGAGYDVH |
| 157 | LC-CDR1 Anti-CD122 clone P2C9 | SGSSSNIGSNTVN |
| 158 | LC-CDR1 Anti-CD122 clone P2C10 | RSSQRLLHSNGYNYVD |
| 159 | LC-CDR1 Anti-CD122 clones P2C11, P2E11 | QASQDINNYLN |
| 160 | LC-CDR1 Anti-CD122 clone P2E6 | TRSSGNFASTYVQ |
| 161 | LC-CDR1 Anti-CD122 clone P2F10 | QASQDIGHNLN |
| 162 | LC-CDR2 Anti-CD122 clones P2C4, PC4_A9, P2C4_A4, P2C4_C1, P2C4_B5, P2C4_B6, P2C4_B8, P2C4_C12, P2C4_D10, P2C4_E2, P2C4_E3, P2C4_E8, P2C4_G2, P2C4_G11, P2C4_H1, P2C4_H2, P2C4_H3, P2C4_C7, P2C4_E6, P2C4_E7, P2C4_F8, P2C4_F11, P2C4_C1D10, P2C4_FW2 | DINNRPS |
| 163 | LC-CDR2 Anti-CD122 clone P2H7 | KASNLES |
| 164 | LC-CDR2 Anti-CD122 clones P2D12, P1B10, P1F3, P2E11, P2F10 | DASNLET |
| 165 | LC-CDR2 Anti-CD122 clone P1G11 | DDNQRPT |
| 166 | LC-CDR2 Anti-CD122 clones P2C4_B1, P2C4_C4 | DNNNRPS |
| 167 | LC-CDR2 Anti-CD122 clone P2C4_B12 | DFNNRPS |
| 168 | LC-CDR2 Anti-CD122 clone P2C4_E9 | DINNRAS |
| 169 | LC-CDR2 Anti-CD122 clone P1E7 | LGSSRAS |
| 170 | LC-CDR2 Anti-CD122 clone P1D10 | DNTNRPS |
| 171 | LC-CDR2 Anti-CD122 clone P1E1 | ADNQRPS |
| 172 | LC-CDR2 Anti-CD122 clone P2B11 | DNSNRPS |

-continued

| Sequences | | |
|---|---|---|
| SEQ ID NO: | DESCRIPTION | SEQUENCE |
| 173 | LC-CDR2 Anti-CD122 clone P2C9 | SNNQRPS |
| 174 | LC-CDR2 Anti-CD122 clones P2C10, P2F9; LC-CDR2 Anti-IL-CD132 clones P2B2, P2B7, P2H4, P2D3, P1G4, P1B12 | LGSNRAS |
| 175 | LC-CDR2 Anti-CD122 clone P2C11 | DASQLET |
| 176 | LC-CDR2 Anti-CD122 clone P2E6 | DDDQRPS |
| 177 | LC-CDR3 Anti-CD122 clones P2C4, P2C4_A9, P2C4_A4, P2C4_C1, P2C4_B1, P2C4_E6, P2C4_FW2 | SAYTSSDTLV |
| 178 | LC-CDR3 Anti-CD122 clones P2H7 | QQYQSYPYT |
| 179 | LC-CDR3 Anti-CD122 clones P2D12 | LQLYDYPLT |
| 180 | LC-CDR3 Anti-CD122 clones P1G11 | QSSHSTAW |
| 181 | LC-CDR3 Anti-CD122 clones P2C4_B5, P2C4_B6 P2C4_B8, P2C4_C12, P2C4_D10, P2C4_E2, P2C4_E3, P2C4_E8, P2C4_G2, P2C4_G11, P2C4_H1, P2C4_H2, P2C4_H3, P2C4_C4, P2C4_C7, P2C4_E7, P2C4_E9, P2C4_F8, P2C4_F11, P2C4_C1D10 | SAYTSSIDTVV |
| 182 | LC-CDR3 Anti-CD122 clone P1E7 | MQALQTPRT |
| 183 | LC-CDR3 Anti-CD122 clone P1B10 | QQYEDLPS |
| 184 | LC-CDR3 Anti-CD122 clone P1F3 | LQDYIYPWT |
| 185 | LC-CDR3 Anti-CD122 clone P1D10 | QSYDSSLRASV |
| 186 | LC-CDR3 Anti-CD122 clone P1E1 | QSFDSSLYMI |
| 187 | LC-CDR3 Anti-CD122 clone P2B11 | QSFDSSLRGVV |
| 188 | LC-CDR3 Anti-CD122 clone P2C9 | AAWDDSLNGLWV |
| 189 | LC-CDR3 Anti-CD122 clone P2C10; LC-CDR3 Anti-CD132 clones P1A3, P1A3_B3, P1A3_E8, P1A3_E9, P1A3_B4, P1A3_FW2, P2D3, P1B12, P1C7 | MQGTHWPWT |
| 190 | LC-CDR3 Anti-CD122 clone P2C11 | QQYDWLPLS |

-continued

| Sequences | | |
|---|---|---|
| SEQ ID NO: | DESCRIPTION | SEQUENCE |
| 191 | LC-CDR3 Anti-CD122 clone P2E6 | QSYDSSNFWV |
| 192 | LC-CDR3 Anti-CD122 clone P2E11 | QQYANLPS |
| 193 | LC-CDR3 Anti-CD122 clone P2F9 | MQALQTPPT |
| 194 | LC-CDR3 Anti-CD122 clone P2F10 | QQYDFLPPD |
| 195 | HC-CDR1 Anti-CD132 clone P2B9 | SSSYYWG |
| 196 | HC-CDR1 Anti-CD132 clone P1A10 | SYAIS |
| 197 | HC-CDR1 Anti-CD132 clone P1D7 | NYGMH |
| 198 | HC-CDR1 Anti-CD132 clone P1E8 | SYGMH |
| 199 | HC-CDR1 Anti-CD132 clone P2D11 | SGGYYWT |
| 200 | HC-CDR1 Anti-CD132 clone P2F10 | GYYMH |
| 201 | HC-CDR1 Anti-CD132 clone P2D3 | GFYWS |
| 202 | HC-CDR2 Anti-CD132 clone P2B9 | SIYYSGSTYYNPSLK |
| 203 | HC-CDR2 Anti-CD132 clones P1A3_B3, P1A3_B4, P1A3_E9, P1A3_E8 | EINHFGSTNYNPSLKS |
| 204 | HC-CDR2 Anti-CD132 clone P1A10 | GFDPEDGETIYAQKFQG |
| 206 | HC-CDR2 Anti-CD132 clone P1D7 | VISYDGTNKYYADSVKG |
| 207 | HC-CDR2 Anti-CD132 clone P2B2 | VISYDGGNKYYADSVNG |
| 208 | HC-CDR2 Anti-CD132 clone P2D11 | FISWSGTTYYNPSLKN |
| 209 | HC-CDR2 Anti-CD132 clone P2F10 | IINPSGGSTSYACKFQG |
| 210 | HC-CDR3 Anti-CD132 clones P1A3, P1A3_B3, P1A3_B4, P1A3_E9, P1A3_E8, P1A3_FW2 | SPGGYSGGYFQH |
| 211 | HC-CDR3 Anti-CD132 clone P2B9 | DILTGYALDY |
| 212 | HC-CDR3 Anti-CD132 clone P1A10 | DLRIPYYYDNP |
| 213 | HC-CDR3 Anti-CD132 clone P1B6 | SLYYSHFDY |
| 214 | HC-CDR3 Anti-CD132 clone P1C10 | EGPLSSSGPGAFDI |
| 215 | HC-CDR3 Anti-CD132 clone P1D7 | DGFDI |

-continued

Sequences

| SEQ ID NO: | DESCRIPTION | SEQUENCE |
|---|---|---|
| 216 | HC-CDR3 Anti-CD132 clone P1E8 | DVYGDYGAFDY |
| 217 | HC-CDR3 Anti-CD132 clone P2B2 | SVAPPMDV |
| 218 | HC-CDR3 Anti-CD132 clone P2B7 | GPAGSSSSGYFDY |
| 219 | HC-CDR3 Anti-CD132 clone P2D11 | GSGRLV |
| 220 | HC-CDR3 Anti-CD132 clone P2F10 | ADTAMGDAFDI |
| 221 | HC-CDR3 Anti-CD132 clone P2H4 | SIGIGAFDI |
| 222 | HC-CDR3 Anti-CD132 clone P2D3 | GPAGSTSSGYFDH |
| 223 | HC-CDR3 Anti-CD132 clone P1G4 | GSSSYYMDV |
| 224 | HC-CDR3 Anti-CD132 clone P1B12 | GGSAYFQH |
| 225 | HC-CDR3 Anti-CD132 clone P1C7 | GPAGTGSSGYFDY |
| 226 | LC-CDR1 Anti-CD132 clone P2B9 | SGDALPKQFAF |
| 227 | LC-CDR1 Anti-CD132 clone P1A10 | RSSQSLLHSNGYNYLN |
| 228 | LC-CDR1 Anti-CD132 clone P1C10 | RASQSVSYHLA |
| 229 | LC-CDR1 Anti-CD132 clone P1D7 | RASQSISSWLA |
| 230 | LC-CDR1 Anti-CD132 clone P1E8 | KSSQSLLYFNGNTYLS |
| 231 | LC-CDR1 Anti-CD132 clone P2B7 | RSSQSLVHSNGYNYLD |
| 233 | LC-CDR1 Anti-CD132 clone P2D11 | RASQSVSSNLA |
| 233 | LC-CDR1 Anti-CD132 clone P2F10 | RSSQTLFDSDDGKTYLD |
| 234 | LC-CDR1 Anti-CD132 clone P2H4 | RATQSLLHGNGHNYLD |
| 235 | LC-CDR1 Anti-CD132 clone P1B12 | RSSQSLLHSNGNNYLD |
| 236 | LC-CDR2 Anti-CD132 clones P1A3, P1A3_B3, P1A3_E8, P1A3_E9, P1A3_B4, P1A3_FW2 | LGSNRDS |
| 237 | LC-CDR2 Anti-CD132 clone P2B9 | KDTERPS |
| 238 | LC-CDR2 Anti-CD132 clone P1A10 | LGSDRAS |
| 239 | LC-CDR2 Anti-CD132 clone P1B6 | LVSNRAS |

-continued

Sequences

| SEQ ID NO: | DESCRIPTION | SEQUENCE |
|---|---|---|
| 240 | LC-CDR2 Anti-CD132 clone P1C10 | DTSNRAS |
| 241 | LC-CDR2 Anti-CD132 clone P1D7 | DASRLED |
| 242 | LC-CDR2 Anti-CD132 clone P1E8 | QVSNRDS |
| 243 | LC-CDR2 Anti-CD132 clone P2D11 | GASSGAT |
| 244 | LC-CDR2 Anti-CD132 clone P2F10 | TTSSRAS |
| 245 | LC-CDR2 Anti-CD132 clone P1C7 | LANRAS |
| 247 | LC-CDR3 Anti-CD132 clone P2B9 | QSPDSSGTVEV |
| 248 | LC-CDR3 Anti-CD132 clone P1A10 | MQALQTPTT |
| 249 | LC-CDR3 Anti-CD132 clone P1B6 | MQTLQTPLS |
| 250 | LC-CDR3 Anti-CD132 clone P1C10 | QQRYDWPLT |
| 251 | LC-CDR3 Anti-CD132 clone P1D7 | QQYDDLPYT |
| 252 | LC-CDR3 Anti-CD132 clone P1E8 | MQGTQWPPT |
| 253 | LC-CDR3 Anti-CD132 clone P2B2 | MQALRTPYT |
| 254 | LC-CDR3 Anti-CD132 clone P2B7 | LQGWSHWPWT |
| 255 | LC-CDR3 Anti-CD132 clone P2D11 | QLYGSSLA |
| 256 | LC-CDR3 Anti-CD132 clone P2F10 | MQRLQFPLT |
| 257 | LC-CDR3 Anti-CD132 clone P2H4 | MQTLETPVT |
| 258 | LC-CDR3 Anti-CD132 clone P1G4 | LQGTHWPWT |
| 259 | CH2 domain P2C4 | PCPAPEAAGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAK |
| 260 | CH3 domain P2C4 | GQPREPQVYTLPPCRDELTKNQVSLWCLVKGFYPSDIAVEWESNGQPENNYKTTPPVL DSDGSFFLYSKLTVDKSRWQQGNVFSCSVMHEALHNHYTQKSLSLSPGK |
| 261 | CH2 domain P1A3 | PCPAPEAAGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAK |
| 262 | CH3 domain P1A3 | GQPREPQVCTLPPSRDELTKNQVSLSCAVKGFYPSDIAVEWESNGQPENNYKTTPPVL DSDGSFFLVSKLTVDKSRWQQGNVFSCSVMHEALHNHYTQKSLSLSPG |
| 263 | CH2 domain P1A10 | PCPAPEAAGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAK |
| 264 | CH3 domain P1A10 | GQPREPQVCTLPPSRDELTKNQVSLSCAVKGFYPSDIAVEWESNGQPENNYKTTPPVL DSDGSFFLVSKLTVDKSRWQQGNVFSCSVMHEALHNHYTQKSLSLSPGK |

-continued

Sequences

| SEQ ID NO: | DESCRIPTION | SEQUENCE |
|---|---|---|
| 265 | Anti-CD122 clone P2C4 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTLVFGGGTKLTVLNSGAGTAAATHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDELTKNQVSLWCLVKGFYPSDIAVEWESNGQPENNYKTTPPVLDSDGSFFLYSKLTVDKSRWQQGNVFSCSVMHEALHNHYTQKSLSLSPGK |
| 266 | Anti-CD122 clone P2H7 | EVQLVQSGTEVKKPGASVKVSCKASGYTFTTYAMHWVRQAPGQSLEWMGWINTGNGNTKYSQNFQGRVTMTRDTSISTAYMELSRLRSDDTAVYYCARDLGQLERLYFWGQGTLVTVSSGGGGSGGGGSGGGGSDIQMTQSPSTLSASVGDRVTLSCRAGQAISSWLAWYQQKPGKAPKLLIYKASNLESGVPSRFSGGGSGAEFTLTISSLQPDDFATYYCQQYQSYPYTFGQGTKLEIR |
| 267 | Anti-CD122 clone P2D12 | HVQLVETGGGLVQPGGSLRLSCAASGFTFSSYAMSWVRQAPGKGLEWVSAISGSGGSTYYADSVKGRFTISRDNSKNTLYLQMNSLRAEDTAVYYCARDLGDYWGQGTLVTVSSGGGGSGGGGSGGGGSDIQLTQSPSSLSASVGDRVTITCQASQDIGNYLNWYQLKPGKAPKLLIYDASNLETGVPSRFSGSGSGTDFTFTISSLQPEDIATYYCLQLYDYPLTFGGGTKVEIK |
| 268 | Anti-CD122 clone P1G11 | QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARSSSGDAFDIWGQGTMVTVSSGGGGSGGGGSGGGGSNFMLTQPHSVSESPGKTVTISCTRSSGSIASNYVQWYQQRPGSSPTTVIFDDNQRPTGVPDRFSAAIDTSSSSASLTISGLTAEDEADYYCQSSHSTAVVFGGGTKLTVL |
| 269 | Anti-CD122 clone P2C4_A4 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGDYDFVSWYQQHPGTAPKLIIYDINNRPSGISNRFSGSKSDNMASLTISGLQPEDEADYYCSAYTSSDTLVFGGGTKLTVL |
| 270 | Anti-CD122 clone P2C4_A9 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYNWGQGTLVTVSSGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |
| 271 | Anti-CD122 clone P2C4_B1 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDNNNRPSGISNRFSGSKSDNMASLTISGLQPEDEADYYCSAYTSSDTLVFGGGTKLTVL |
| 272 | Anti-CD122 clone P2C4_B5 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSITISCTGTSSDIGHYDFVSWYQQHPGTAPKLIIYDINNRPSGISNRFSGSKSDNMASLTISGLQPEDEADYYCSAYTSSDTVVFGGGTKLTVL |
| 273 | Anti-CD122 clone P2C4_B6 | EVQLVQSGAEVKKPGSSVKVSCKASGYTFTNYYIHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |
| 274 | Anti-CD122 clone P2C4_B8 | EVQLVQSGAEVKKPGSSVKVSCKASGYTFTNYYMHWVRQPPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |
| 275 | Anti-CD122 clone P2C4_B12 | EVQLVQSGAEVKKPGSTVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFISWYQQHPGTAPKLIIYDFNNRPSGISNRFSGSKSDNMASLTISGLQPEDEADYYCSAYTSSDTLVFGGGTKLTVL |

-continued

| Sequences | | |
|---|---|---|
| SEQ ID NO: | DESCRIPTION | SEQUENCE |
| 276 | Anti-CD122 clone P2C4_C1 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTPVTVSSGGGGSGGGGSGGGGSQSALTQPASVSGSPGQSIAISCTGTSSDIGDYDFVSWYQQHPGTAPKLIIYDINNRPSGISNRFSGSKSDNMASLTISGLQPEDEADYYCSAYTSSDTLVFGGGTKLTVL |
| 277 | Anti-CD122 clone P2C4_C4 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDNNNRPSGISNRFSGSKSDNMASLTISGLQPEDEADYYCSAYTSSDTVVFGGGTKLTVL |
| 278 | Anti-CD122 clone P2C4_C7 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIVISCTGTSSDIGHYDFVSWYQQHPGTAPKLIIYDINNRPSGISNRFSGSKSDNMASLTISGLQPEDEADYYCSAYTSSDTVVFGGGTKLTVLAAAHHHH |
| 279 | Anti-CD122 clone P2C4_C12 | EVQLVQSGAEVKKPGSSVKVSCKASGYTFTNYYMHWVRQAPGQGLEWMGAIMPSRGGTSYPQKFQGRVTMTGDTSTSTVYMELSNLRSEDTAVYYCARGEYYYDSSGYYYWGQGTLVTVSNGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |
| 280 | Anti-CD122 clone P2C4_D10 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |
| 281 | Anti-CD122 clone P2C4_E2 | EVQLVQSGAEVKEPGSSVKVSCKASGYTFTNYYMHWVRQAPGQGLEWMGAIMPSRGGTSYPQKFQGRVTMTGDISTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |
| 282 | Anti-CD122 clone P2C4_E3 | EVQLVQSGAEVKKPGSSVKVSCKASGYTFTNYYIHWVRQAPGQGLEWMGAIMPSRGGTSYPQKFQGRVTMTGDTSTSTVYMELNSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |
| 283 | Anti-CD122 clone P2C4_E6 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGDYDFVSWYQQHPGTAPKLIIYDINNRPSGISNRFSGSKSDNMASLIISGLQPEDEADYYCSAYTSSDTLVFGGGTKLTVL |
| 284 | Anti-CD122 clone P2C4_E7 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDINNRPSGISNRFSGSKSDDMASLTISGLQPEDEADYYCSAYTSSDTVVFGGGTKLTVL |
| 285 | Anti-CD122 clone P2C4_E8 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGPGTLVTVSSGGGGSGGGGSGGGGSQSALTQPASVSGSPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |
| 286 | Anti-CD122 clone P2C4_E9 | EVQLVQSGAEVKKPGSSVKVSCKASGYTFTNYYIHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGSPGQSIAISCTGTSSDIGHYDFVSWYQQHPGTAPKLIIYDINNRASGISNRFSGSKSDNMASLTISGLQPEDEADYYCSAYTSSDTVVFGGGTKLTVL |
| 287 | Anti-CD122 clone P2C4_F8 | EVQLVQSGAEVKKPGSSVKVSCKASGYTFTNYYMHWVRQAPGQGLEWMGAIMPSRGGTSYPQKFQGRVTMTGDTSTSTVYMELSSLRSEDTAVYYCARGEYYYDSSGYYYWGQGTLVTVSSGGGGSGGGGSGGGGSQSALTQPASVSGNPGQSIAISCTGTSSDIGHYDFVSWYQQHPGTAPKLIIYDINNRPSGISNRFSGSKSDNMASLTISGLQPEDEADYYCSAYTSSDTVVFGGGTKLTVL |

-continued

Sequences

| SEQ ID NO: | DESCRIPTION | SEQUENCE |
|---|---|---|
| 288 | Anti-CD122 clone P2C4_F11 | EVQLVQSGAEVKKPGSSVKVSCKASGYTFTNYYMHWVRQAPGQGLEWMGAIMPSRG GTSYPQKFQGRVTMTGDTSTSTVYMELSSLRSEDTAMYYCARGEYYYDSSGYYYWGQ GTLVTVSSGGGGSGGGGSGGGGSQSTLTQPASVSGSPGQSITISCTGTSSDIGHYDFV SWYQQHPGTAPKLIIYDINNRPSGISNRFSGSKSDNMASLTISGLQPEDEADYYCSAYTS SDTVVFGGGTKLTVL |
| 289 | Anti-CD122 clone P2C4_G2 | EVQLVQSGAEVKKPGSSVKVSCKASGYTFTNYYMHWVRQAPGQGLEWMGAIMPSRG GTSYPQKFQGRVTMTGDTSTSTVYMELSSLRTEDTAVYYCARGEYYYDSSGYYYWGQ GTLVTVSSGGGGSGGGGSGGVGSQSALTQPASVSGSPGQSIAISCTGTSSDIGHYDFV SWYQQHPGTAPKLIIYDINNRPSGISNRFSGSKSDNMASLTISGLQPEDEADYYCSAYTS SDTVVFGGGTKLTVL |
| 290 | Anti-CD122 clone P2C4_G11 | EVQLVQSGAEVKKPGSSVKVSCKASGYTFTNYYMHWVRQAPGQGLEWMGAIMPSRG GTSYPQKFQGRVTMTGDTSTSTVYMELSNLRSEDTAVYYCARGEYYYDSSGYYYWGQ GTLVTVSSGGGGSGGGGSGGGGSQSALTQPASVSGSPGQSIAISCTGTSSDIGHYDFV SWYQQHPGTAPKLIIYDINNRPSGISNRFSGSKSDNMASLTISGLQPEDEADYYCSAYTS SDTVVFGGGTKLTVL |
| 291 | Anti-CD122 clone P2C4_H1 | EVQLVQSGAEVKKPGSSVKVSCKASGYTFTNYYMHWVRQAPGQGLEWMGAIMPSRG GTSYPQKFQGRVTMTGDTSTSTVYMELSSLRSEDTAVYYCARGEYYYDSSGYYYWGQ GTLVNVSSGGGGSGGGGSGGGGSQSALTQPASVSGSPGQSIAISCTGTSSDIGHYDFV SWYQQHPGTAPKLIIYDINNRPSGISNRFSGSKSDNMASLTISGLQPEDEADYYCSAYTS SDTVVFGGGTKLTVL |
| 292 | Anti-CD122 clone P2C4_H2 | EVQLVQSGAEVKKPGSSVKVSCKASGYTFSNYYMHWVRQAPGQGLEWIGAIMPSRGG TSYPQKFQGRVTMTGDTSTSTVYMELSSLRSEDTAVYYCARGEYYYDSSGYYYWGQG TLVTVSSGGGGSGGGGSGGGGSQSALTQPASVSGSPGQSIAISCTGTSSDIGHYDFVS WYQQHPGTAPKLIIYDINNRPSGISNRFSGSKSDNMASLTISGLQPEDEADYYCSAYTSS DTVVFGGGTKLTVL |
| 293 | Anti-CD122 clone P2C4_H3 | EVQLVQSGAEVKKPGSSVKVSCKATGYTFTNYYMHWVRQAPGQGLEWMGAIMPSRG GTSYPQKFQGRVTMTGDTSTSTVYMELSSLRSEDTAVYYCARGEYYYDSSGYYYWGQ GTLVTVSSGGGGSGGGGSGGGGSQSALTQPASVSGSPGQSIAISCTGTSSDIGHYDFV SWYQQHPGTAPKLIIYDINNRPSGISNRFSGSKSDNMASLTISGLQPEDEADYYCSAYTS SDTVVFGGGTKLTVL |
| 294 | Anti-CD122 clone P2C4_C1D10 | EVQLVQSGAEVKKPGSSVKVSCKASGYTFTNYYMHWVRQAPGQGLEWMGAIMPSR GTSYPQKFQGRVTMTGDTSTSTVYMELSSLRSEDTAVYYCARGEYYYDSSGYYYWGQ GTPVTVSSGGGGSGGGGSGGGGSQSALTQPASVSGSPGQSIAISCTGTSSDIGDYDFV SWYQQHPGTAPKLIIYDINNRPSGISNRFSGSKSDNMASLTISGLQPEDEADYYCSAYTS SDTVVFGGGTKLTVL |
| 295 | Anti-CD122 clone P2C4_FW2 | EVQLVQSGAEVKKPGASVKVSCKASGYTFTNYYMHWVRQAPGQGLEWMGAIMPSRG GTSYPQKFQGRVTITADKSTSTAYMELSSLRSEDTAVYYCARGEYYYDSSGYYYWGQG TLVTVSSGGGGSGGGGSGGGGSQSVLTQPPSVSGAPGQRVTISCTGTSSDIGHYDFVS WYQQLPGTAPKLLIYDINNRPSGVPDRFSGSKSGTSASLAITGLQAEDEADYYCSAYTSS DTLVFGGGTKLTVL |
| 296 | Anti-CD122 clone P1E7 | EVQLVQSGGGWQPGRSLRLSCAASGFTFSSYAMHWVRQAPGKGLEWVAVISYDGSN KYYADSVKGRFTISRDNSKNTLYLQMNSLRAEDTAVYYCARDLGYSSSWYYYYYGMDV WGQGTTVTVSSGGGGSGGGGSGGGGSDWMTQSPLSLPVTPGEPASISCRSSQSLLH SNGYNYLDWYLQKPGQSPQLLIYLGSSRASGVPDRFSGSGSGTDFTLKISRVEAEDVGV YYCMQALQTPRTFGQGTKLEIK |
| 297 | Anti-CD122 clone P1B10 | QVQLQESGPGLVKPSETLSLTCTVSGVSISSRSDHWGWVRQPPGKGLEWIGSISYSGS TYYNPSLKSRVTISVDTSKNQLSLKLSSVTAADTAVYYCARESHPAAALVGWGQGTLVT VSSGGGGSGGGGSGGGGSDIQMTQSPSSLSASVGDRVTITCQASQDISDYLNWYQQK PGKAPQILIYDASNLETGVPSRFSGSGSGTDFTFTISNLQPEDVATYYCQQYEDLPSFGG GTKVEIK |
| 298 | Anti-CD122 clone P1F3 | EVQLVQSGGGLVQPGGSLRLSCAASGFTFSSYAMSWVRQAPGKGLEWVSAISGSGGS THYADSVKGRFTISRDNSKNTLYLQMNSLRAEDTAVYYCATPAFWGQGTLVTVSSGGG GSGGGGSGGGGSDIQLTQSPSSLSASVGDRVTITCRASQSISSYLNWYQQKPGKAPKA LIYDASNLETGVPSRFSGSGSGTDFTLTIISLQPEDFATYFCLQDYIYPWTFGQGTKVEFK |
| 299 | Anti-CD122 clone P1D10 | QVQLQQWGPGLVKPSETLSLTCTVSGGSISSYYWSWIRQPPGKGLEWIGEINHSGSTN YNPSLKSRVTISVDTSKNQFSLKLSSVTAADTAVYYCAGGSNLDWFDPWGQGTLVTVSS GGGGSGGGGSGGGGSQSVLTQPPSVSGAPGQRVTISCTGGSSNVGAGYDVHWYQQL PGTVPKLLIYDNTNRPSGVPDRFSASKSGTSASLVITGLQAEDEGDYYCQSYDSSLRAS VFGGGTMLTVL |
| 300 | Anti-CD122 clone P1E1 | QVQLQQWGAGLLKPSETLSLTCAVYGGSFSGYYWSWIRQPPGKGLEWIGEINHSGSTN YNPSLKSRVTISVDTSKNQFSLELSSVTAADTAVYYCARADRRFGELRYWGQGTLVTVS |

-continued

Sequences

| SEQ ID NO: | DESCRIPTION | SEQUENCE |
|---|---|---|
| | | SGGGGSGGGGSGGGGSNFMLTQPHSVSESPGKTVTISCTGSSGSIASSYVQWYQQRP GSAPTTVIYADNQRPSGVPDRFSGSVDSSSNSASLTISGLKTEDEADYYCQSFDSSLYMI FGGGTKLTVL |
| 301 | Anti-CD122 clone P2B11 | QVQLVQSGGGLVKPGGSLRLSCAASGFTFSSYDLHWVRQVPGKGLEWVSLISYDGSNK YYADSVKGRFTISRDNAENSLYLQMNSLRAEDTAVYYCAREPITGTSDLFDYWGQGTLV TVSSGGGGSGGGGSGGGGSQSVLTQPPSVSGAPGQRVTISCTGSRSNIGAGYDVHWY QHLPGTAPKLLIYDNSNRPSGVSDRFSGSKSGTSASLAITGLQAEDEADYYCQSFDSSL RGVVFGGGTRLTVL |
| 302 | Anti-CD122 clone P2C9 | QVQLQESGPGLVKPSGTLSLTCAVSGGSISSSNWWSWVRQPPGKGLEWIGEIYHSGST NYNPSLKSRVTISVDKSKNQFSLKLSSVTAADTAVYYCVREGGLREEHWGQGTLVTVSS GGGGSGGGGSGGGGSSYELTQPPSASGTPGQRVTISCSGSSSNIGSNTVNWYQQLPG TAPKLLIYSNNQRPSGVPDRFSGSKSGTSASLAISGLQSEDEADYYCAAWDDSLNGLWV FGGGTKLTVL |
| 303 | Anti-CD122 clone P2C10 | QVQLQQWGAGLLKPSETLSLTCAVYGGSFSGYYWSWIRQPPGKGLEWIGEINHSGSTN YNPSLKSRVTISVDTSKNQFSLKLSSVTAADTAVYYCARGTDTAMADYWGQGTLVTVSS GGGGSGGGGSGGGGSDVVMTQSPLSLPVTPGEPASISCRSSQRLLHSNGYNYVDWYL QKPGQSPQLLIYLGSNRASGVPDRFSGSGSGTDFTLKISRVEAEDVGVYYCMQGTHWP WTFGQGTKVEIK |
| 304 | Anti-CD122 clone P2C11 | QVQLQQSGPGLVKPSQTLSLTCAISGDSVSGNSATWNWIRQSPSRGLEWLGRTYYRSK WNHDYAESVKSRITINPDTSKNQFSLQLNSVTPEDTAVYYCARDSKSAFDIWGQGTMVT VSSGGGGSGGGGSGGGGSDIQMTQSPPSLSASVGDRVTITCQASQDINNYLNWYHQK PGKAPELLIYDASQLETGVPSRFSGSGSGTEFTFIISSLQPEDTGTYYCQQYDWLPLSYG GGTKVEIK |
| 305 | Anti-CD122 clone P2E6 | QLQLQESGPGLVKPSETLSLTCSVFGVSITSGSWWSWVRQSPGKELEWIGEIYHNGNT NYNPSLKSRVTISVDTSKNQFSLKLSSVTAADTAVYYCVSGFDYWGQGTLVTVSSGGG GSGGGGSGGGGSNFMLTQPHSVSGSPGKTITISCTRSSGNFASTYVQWYQQRPGSSP AIVIYDDDQRPSGVPDRFSGSIDRSSNSASLTISGLETEDEADYYCQSYDSSNFWVFGG GTKLTVL |
| 306 | Anti-CD122 clone P2E11 | QVQLQESGPGLVKPSETLSLTCTVSGVSISSRSDHWGWVRQPPGKGLEWIGSISYSGS TYYNPSLKSRVTISVDTSKNQLSLKLSSVTAADTAVYYCARESHPAAALVGWGQGTLVT VSSGGGGSGGGGSGGGGSEIVLTQSPSSLSASVGDRVTITCQASQDINNYLNWYQQKP GKAPKLLIYDASNLETGVPSKFSGSGSGTDFTFTISSLQPEDIATYYCQQYANLPSFGQG TKLEIK |
| 307 | Anti-CD122 clone P2F9 | EVQLVQSGAEVKKPGSSVKVSCKASGYTFTSYGISWVRQAPGQGLEWMGWISAYNGN TNYAQKLQGRVTMTTDTSTSTAYMELSSLRSEDTAVYYCARAPDYGDSSNYYYYMDV WGKGTTVTVSSGGGGSGGGGSGGGGSEIVLTQSPLSLPVTPGEPASISCRSSQSLLHS NGYNYLDWYLQKPGQSPQLLIYLGSNRASGVPDRFSGSGSGTDFTLSISRVEAEDVGVY YCMQALQTPPTFGQGTKVEIK |
| 308 | Anti-CD122 clone P2F10 | QVQLVQSGAEVKKPGASVKVSCKASGYTFTSYGISWVRQAPGQGLEWMGWISAYNGN TNYAQKLQGRVTMTTDTSTSTAYMELRSLRSDDTAVYYCARDTSGDYSSGWYLGVPFD YWGQGTLVTVSSGGGGSGGGGSGGGGSDIQLTQSPSSLSASVGDRVTVTCQASQDIG HNLNWYQQRPGKAPQLLIYDASNLETGVPSRFSGSGSGTQFTFTISSLQPEDIATYYCQ QYDFLPPDFGPGTKVEIK |
| 309 | Anti-CD132 clone P1A3 | QVQLQQWGAGLLKPSETLSLTCAVYGGSFSGYYWSWIRQPPGKGLEWIGEINHSGSTN YNPSLKSRATISVDTSKNQFSLKLSSVTAADTAVYYCATSPGGYSGGYFQHWGQGTLVT VSSGGGGSGGGGSGGGGSDWMTQSPLSLPVTPGEPASISCRSSQSLLHSNGYNYLD WYLQKPGQSPQLLIYLGSNRDSGVPDRFSGSGSGTDFTLKISRVEAEDVGVYYCMQGT HWPWTFGQGTKVEIKNSGAGTAAATHTCPPCPAPEAAGGPSVFLFPPKPKDTLMISRTP EVTCVVVDVSHEDPEVKFNWYVDGVEVHNAKTKPREEQYNSTYRVVSVLTVLHQDWLN GKEYKCKVSNKALPAPIEKTISKAKGQPREPQVCTLPPSRDELTKNQVSLSCAVKGFYPS DIAVEWESNGQPENNYKTTPPVLDSDGSFFLCVSKLTVDKSRWQQGNVFSCSVMHEAL HNHYTQKSLSLSPGK |
| 310 | Anti-CD132 clone P2B9 | QVQLQESGPGLVKPSETLSLTCTVSGGSISSSSYVWGWIRQPPGKGLEWIGSIYYSGST YYNPSLKSRVTISVDTSKNQFSLKLSSVTAADTAVYYCAGDILTGYALDYWGQGTLVTVS SGGGGSGGGGSGGGGSSYELTQPPSMSVSPGQTARITCSGDALPKQFAFWYQQKPG QAPVLVIYKDTERPSGIPERFSGSSSGTTVTLTITGVQAEDEADYYCQSPDSSGTVEVFG GGTKLTVL |
| 311 | Anti-CD132 clone P1A3_B3 | QVQLQQWGAGLLKPSETLSLTCAVYGGSFSGYYWSWIRQPPGKGLEWIGEINHFGSTN YNPSLKSRATISVDTSKNQFSLKLSSVTAADTAVYYCATSPGGYSGGYFQHWGQGTLVT VSSGGGGSGGGGSGGGGSDVVMTQSPLSLPVTPGEPASISCRSSQSLLHSNGYNYLD WYLQKPGQSPQLLIYLGSNRDSGVPDRFSGSGSGTDFTLKISRVEAEDVGVYYCMQGT HWPWTFGQGTKVEIK |

-continued

| SEQ ID NO: | DESCRIPTION | SEQUENCE |
|---|---|---|
| 312 | Anti-CD132 clone P1A3_B4 | QVQLQQWGAGLLKPSETLSLTCAVYGGSFSGYYWSWIRQPPGKGLEWIGEINHFGSTN YNPSLKSRATISVDTSKNQFSLKLSSVTAADTAVYYCATSPGGYSGGYFQHWGQGTLVT VSSGGGGSGGGGSGGGGSDWMTQSPLSLPVTPGESVSISCRSSQSLLHSNGYNYLD WYLQKPGQSPQLLIYLGSNRDSGVPDRFSGSGSGTDFTLKISRVEAEDVGVYYCMQGT HWPWTFGQGTKVEIK |
| 313 | Anti-CD132 clone P1A3_E8 | QVQLQQWGAGMLKPSETLSLTCAVYGGSFSGYYWSWIRQPPGKGLEWIGEINHFGST NYNPSLKSRATISVDTSKNQFSLKLSSVTAADTAVYYCATSPGGYSGGYFQHWGQGTL VTVSSGGGGSGGGGSGGGGSDWMTQSPLSLPVTPGEPASISCRSSQSLLHSNGYNY LDWYLQKPGQSPQLLIYLGSNRDSGVPDRFSGSGSGTDFTLKISRVEAEDVGVYYCMQ GTHWPWTFGQGTKVEIK |
| 314 | Anti-CD132 clone P1A3_E9 | QVQLQQWGAGLLKPSETLSLTCAVYGGSFSGYYWSWIRQPPGKGLEWIGEINHFGSTN YNPSLKSRATISVDTSKNQFSLKLSSVTAADTAVYYCATSPGGYSGGYFQHWGQGTLVT VSSGGGGSGEGGSGGGGSDWMTQSPLSLPVTPGEPASISCRSSQSLLHSNGYNYLD WYLQKPGQSPQLLIYLGSNRDSGVPDRFSGSGSGTDFTLKISRVEAEDVGVYYCMQGT HWPWTFGQGTKVEIKAAAHHHHH |
| 315 | Anti-CD132 clone P1A3_FW2 | EVQLVESGGGLVQPGGSLRLSCAASGGSFSGYYWSWVRQAPGKGLEWVSEINHSGST NYNPSLKSRFTISRDNSKNTLYLQMNSLRAEDTAVYYCARSPGGYSGGYFQHWGQGTL VTVSSGGGGSGGGGSGGGGSDIQMTQSPSSLSASVGDRVTITCRSSQSLLHSNGYNYL DWYQQKPGKAPKLLIYLGSNRDSGVPSRFSGSGSGTDFTLTISSLQPEDFATYYCMQGT HWPWTFGQGTKVEIK |
| 316 | Anti-CD132 clone P1A10 | QVQLQQSGAEVKKPGSSVKVSCKASGGTFSSYAISWVRQAPGQGLEWMGGFDPEDG ETIYAQKFQGRVTMTEDTSTDTAYMELSSLRSEDTAVYYCATDLRIPYYYDNPWGQGTL VTVSSGGGGSGGGGSGGGGSEIVLTQSPLSLPVTPGEPASISCRSSQSLLHSNGYNYL NWYLQKPGQSPQLLIYLGSDRASGVPDRFSGSGSGTDFTLKISRVEAEDVGVYYCMQA LQTPTTFGGGTKVEIK |
| 317 | Anti-CD132 clone P1B6 | QVQLVQSGGGWQPGRSLRLSCAASGFTFSSYAMHWVRQAPGKGLEWVAVISYDGSN KYYADSVKGRFTISRDNSKNTLYLQMNSLRAEDTAVYYCARSLYYSHFDYWGQGTLVTV SSGGGGSGGGGSGGGGSEIVMTQSPLSLPVTPGEPASISCRSSQSLLHSNGYNYLDW YLQKPGQSPQLLMYLVSNRASGVPERFSGSGSGTDFTLKISRVEAEDVGVYYCMQTLQ TPLSFGQGTKLEIK |
| 318 | Anti-CD132 clone P1C10 | EVQLVETGPGLVKPSGTLSLTCAVSGGSISSSNWWSWVRQPPGKGLEWIGEIYHSGST NYNPSLKSRVTISVDKSKNQFSLKLSSVTAADTAVYYCAREGPLSSSGPGAFDIWGQGT MVTVSSGGGGSGGGGSGGGGSEIVLTQSPATLSLSPGERATLSCRASQSVSYHLAWY QQKPGQAPRLLIYDTSNRASGIPARFSGSGSGTDFTLTINSLEPEDFAVYYCQQRYDWP LTFGGGTKVEIK |
| 319 | Anti-CD132 clone P1D7 | QVQLQESGGGWQPGRSLRLSCAASGFTFSNYGMHWVRQAPGKGLEWVAVISYDGTN KYYADSVKGRFTISRDNSKNTVYLQMNSLRAEDTAVYYCAKDGFDIWGQGTMVTVSSG GGGSGGGGSGGGGSDIQMTQSPSFLSASVGDRVTITCRASQSISSWLAWYQQKPGKA PKLLIYDASRLEDGVPSRFSGTGFGTDFTFTITTLQPDDIATYYCQQYDDLPYTFGQGTT VDIK |
| 320 | Anti-CD132 clone P1E8 | EVQLVQSGGGWQPGRSLRLSCAASGFTFSSYGMHWVRQAPGKGLEWVAVISYDGSN KYYADSVKGRFTISRDNSKNTLYLQMNSLRAEDTAVYYCARDVYGDYGAFDYWGQGTL VTVSSGGGGSGGGGSGGGGSDWMTQSPVSLPVTLGQPASISCKSSQSLLYFNGNTYL SWFQQRPGQSPRRLFYQVSNRDSGVPDRFSGSGSDTDFTLTISRVEAEDVGVYFCMQ GTQWPPTFGQGTKVEIK |
| 321 | Anti-CD132 clone P2B2 | QLQLQESGGGWQPGRSLRLSCAASGFTFSSYAMHWVRQAPGKGLEWVAVISYDGGN KYYADSVKGRFTISRDNSKNTLYLQMNSLRAEDTAVYYCAKSVAPPMDVWGKGTTVTV SSGGGGSGGGGSGGGGSDWMTQSPLSLPVTPGEPASISCRSSQSLLHSNGYNYLDW YLQKPGQSPHLLIYLGSNRASGVPDRFSGSGSGTDFTLKISRVEAEDVGVYFCMQALRT PYTFGQGTKLEIK |
| 322 | Anti-CD132 clone P2B7 | QVQLQQWGAGLLKPSETLSLTCAVYGESFSGYYWSWIRQPPGKGLEWIGEINHSGSTN YNPSLKSRVTISVDTSKNQFSLKLSSVTAADTAVYYCARGPAGSSSSGYFDYWGQGTLV TVSSGGGGSGGGGSGGGGSDWMTQSPLSLPVTLGQPASISCRSSQSLVHSNGYNYL DWYLQKPGQSPQLLIYLGSNRASGVPDRFSGSGSGTDFTLKISRVEAEDVGVYYCLQG SHWPWTFGQGTKVEIK |
| 323 | Anti-CD132 clone P2D11 | QVQLQESGPGLVKPSQTLSLTCTVSGGSISSGGYYWTWIRQHPGQGLEWIGFISWSGT TYYNPSLKNRVTISADTSKNHFSLNLTSVTAADTAVYYCARGSGRLVWGQGTLVTVSSG GGGSGGGGSGGGGSETTLTQSPATLSVSPGERATLSCRASQSVSSNLAWYQQKPGQ APRLLIYGASSGATGIPDRFSGSGSGTDFTLTISRLEPEDFAVYYCQLYGSSLAFGGGTK VEIK |
| 324 | Anti-CD132 clone P2F10 | EVQLVQSGAEVKKPGASVKVSCKASGYTFTGYYMHWVRQAPGQGLEWMGIINPSGGS TSYAQKFQGRVTMTRDTSTSTVYMELSSLRSEDTAVYYCARADTAMGDAFDIWGQGTM |

-continued

Sequences

| SEQ ID NO: | DESCRIPTION | SEQUENCE |
|---|---|---|
| | | VTVSSGGGGSGGGGSGGGGSDIVMTHTPLSLPVTPGEPASISCRSSQTLFDSDDGKTYLDWYLQKPGQSPQLLMYTTSSRASGVPDRFSGSGSGTDFTLKISRVEAEDVGVYYCMQRLQFPLTFGQGTRLEFK |
| 325 | Anti-CD132 clone P2H4 | EVQLVQSGGGWQPGRSLRLSCAASGFTFSSYAMHWVRQAPGKGLEWVAVISYDGSNKYYADSVKGRFTISRDNSKNTLYLQMNSLRAEDTAVYYCARSIGIGAFDIWGQGTMVTVSSGGGGSGGGGSGGGGSDVVMTQSPLSLPVTPGEPASISCRATQSLLHGNGHNYLDWYLQKPGQSPQLLIYLGSNRASGVPDRFSGSGSGTDFTLKISRVEAEDVGVYYCMQTLETPVTFGPGTKVDIK |
| 326 | Anti-CD132 clone P2H4 | QVQLQQWGAGLLKPSETLSLTCTIYGGSFSGFYWSWIRQPPGKGLEWIGEINHSGSTNYNPSLKSRVTISVDTSKNQFSLKLSSVTAADTAIYYCARGPAGSTSSGYFDHWGQGTLVTVSSGGGGSGGGGSGGGGSDWMTQSPLSLPVTPGEPASISCRSSQSLLHSNGYNYLDWYLQKPGQSPQLLIYLGSNRASGVPDRFSGSGSGTDFTLKISRVEAEDVGVYYCMQGTHWPWTFGQGTKVEIK |
| 327 | Anti-CD132 clone P1G4 | QVQLQQWGAGLLKPSETLSLTCAVYGGSLSGYYWSWIRQPPGKGLEWIGEINHSGSTNYNPSLKSRVTISVDTSKNQFSLKLSSVTAADTAVYYCARGSSSYYMDVWGKGTTVTVSSGGGGSGGGGSGGGGSDVVMTQSPLSLPVTPGEPASISCRSSQSLLHSNGYNYLDWYLQKPGQSPQLLIYLGSNRASGVPDRFSGSGSGTDFTLKISRVEAEDVGVYYCLQGTHWPWTFGQGTKVEIK |
| 328 | Anti-CD132 clone P1B12 | QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGGSAYFQHWGQGTLVTVSSGGGGSGGGGSGGGGSDWMTQSPLSLPVTLGQPASISCRSSQSLLHSNGNNYLDWYLQKPGQSPQLLIYLGSNRASGVPDRFSGSGSGTDFTLKISRVEAEDVGIYYCMQGTHWPWTFGQGTKVEIE |
| 329 | Anti-CD132 clone P1C7 | QVQLQQWGAGLLKPSETLSLTCAVYGGSFSGYYWSWIRQPPGKGLEWIGEINHSGSTNYNPSLKSRVTISEDASKKQFSLTLTSVTAADTAVYYCARGPAGTGSSGYFDYWGQGTLVTVSSGGGGSGGGGSGGGGSEIVLTQSPLSLPVTPGEPASISCRSSQSLLHSNGYNYLDWYLQKPGQSPQLLIYLASNRASGVPDRFSGSGSGTDFTLKISRVEAEDVGVYYCMQGTHWPWTFGQGTKVEVK |
| 330 | Linker 1 | NSGAGTAAA |
| 331 | Linker 2 | NSGAGTSGSGASGEGSGSKLAAA |
| 332 | Linker 3 | GGGGSAAA |
| 333 | Linker 4 | GGGGSGGGGSGGGGS |
| 334 | Tag | AAAHHHHHH |
| 335 | Anti-CD122 P2C4 Fab LC (VL, joint CL) | CAGTCTGCCCTGACTCAGCCTGCCTCCGTGTCTGGGTCTCCTGGACAGTCGATCGCCATTTCCTGCACTGGAACCAGCAGTGACATTGGTCATTATGACTTTGTCTCCTGGTACCAACAGCACCCAGGCACAGCCCCCAAACTCATAATTTATGATATCAATAATCGGCCCTCAGGGATTTCTAATCGCTTCTCTGGCTCCAAGTCTGACAATATGGCCTCCCTGACCATCTCTGGGCTCCAGCCTGAGGACGAGGCTGATTATTACTGCAGTGCATATACAAGCAGCGACACTCTGGTCTTCGGCGGAGGGACCAAGTTGACCGTCCTCAGTCAGCCCAAGGCTGCCCCCTCGGTCACTCTGTTCCCACCCTCCTCTGAGGAGCTTCAAGCCAACAAGGCCACACTGGTGTGTCTCATAAGTGACTTCTACCCGGGAGCCGTGACAGTGGCCTGGAAGGCAGATAGCAGCCCCGTCAAGGCGGGAGTGGAGACCACCACACCCTCCAAACAAAGCAACAACAAGTACGCGGCCAGCAGCTACCTGAGCCTGACGCCTGAGCAGTGGAAGTCCCACAAAAGCTACAGCTGCCAGGTCACGCATGAAGGGAGCACCGTGGAGAAGACAGTGGCCCCTACAGAATGTTCA |
| 336 | Anti-CD122 P2C4 Fab HC (VH, joint CH1) | GAGGTCCAGCTGGTACAGTCTGGGGCTGAGGTGAAGAAGCCTGGGTCCTCAGTGAAGGTTTCCTGCAAGGCATCTGGATACACCTTCACCAACTACTATATGCACTGGGTGCGACAGGCCCCTGGACAAGGGCTTGAGTGGATGGGGGCAATCATGCCTAGTCGTGGTGGCACAAGTTACCCACAGAAGTTCCAGGGCAGAGTCACCATGACCGGGGACACGTCCACGAGCACAGTCTACATGGAGCTGAGCAGCCTGAGATCTGAGGACACGGCCGTGTATTACTGTGCGAGAGGGGAGTATTACTATGATAGTAGTGGTTATTACTACTGGGGCCAGGGCACCCTGGTCACCGTCTCAAGCGCCTCCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTCCACACCTTCCCGGCTGTCCTACAGTCCTCAGGACTCTACTCCCTCAGCAGCGTAGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGT |
| 337 | Anti-CD122 P2C4 scFv and Fc witn knob modifcation | GAAGTGCAGCTGGTGCAGAGCGGGGCAGAAGTGAAAAAGCCTGGGTCAAGCGTGAAGGTCTCCTGTAAAGCAAGCGGATACACATTCACAAACTACTATATGCACTGGGTGCGGCAGGCCCCCGGACAGGGCCTGGAGTGGATGGGCGCTATCATGCCTTCCCGAGG |

-continued

| Sequences | | |
|---|---|---|
| SEQ ID NO: | DESCRIPTION | SEQUENCE |
| | | CGGGACTTCTTACCCACAGAAGTTCCAGGGAAGAGTGACCATGACAGGCGACACTA<br>GCACCTCCACAGTCTATATGGAGCTGAGCAGCCTGAGGAGCGAAGACACTGCCGTG<br>TACTATTGCGCTCGCGGACTAATACTATTACGATTCTAGTGGCTATTACTATTGGGGG<br>CAGGGAACACTGGTGACTGTCTCAAGCGGAGGAGGAGGAAGAGGCGGAGGAGGCT<br>CCGGAGGAGGCGGGTCTCAGAGTGCACTGACCCAGCCAGCATCAGTGAGCGGCAG<br>CCCCGGCCAGTCTATCGCAATTAGTTGTACTGGGACCTCCTCTGACATCGGACACTA<br>CGATTTCGTCTCTTGGTATCAGCAGCACCCCGGCACCGCTCCTAAGCTGATCATCTA<br>CGACATCAACAATCGGCCCAGCGGCATTTCCAACAGATTTTCTGGGAGTAAATCAGA<br>TAATATGGCCTCACTGACAATTAGCCGGCCTCCAGCCTGAGGACGAAGCTGATTACTA<br>TTGCTCCGCATACACTAGTTCAGATACCCTGGTGTTTGGAGGCGGGACCAAACTGAC<br>AGTCCTGAACAGCGGCGCGGGCACCGCGGCCGCGACTCACACATGCCCACCGTGC<br>CCAGCACCTGAAGCCGCCGGGGGCGGACCGTCACGTCTTCCTCTTCCCCCCAAAACCCAA<br>GGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCAT<br>AATGCCAAGACAAAGCCGCGGGAGGAGCAGTACAACAGCACGTACCGTGTGGTCA<br>GCGTCCTCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGCCAAAGG<br>GCAGCCCCGAGAACCACAGGTGTACACCCTGCCCCCATGCCGGGATGAGCTGACC<br>AAGAACCAGGTCAGCCTGTGGTGCCTGGTCAAAGGCTTCTATCCCAGCGACATCGC<br>CGTGGAGTGGGAGAGCAATGGGCAGCCGGAGAACAACTACAAGACCACGCCTCCC<br>GTGCTGGACTCCGACGGCTCCTTCTTCCTCTACAGCAAGCTCACCGTGGACAAGAG<br>CAGGTGGCAGCAGGGGAACGTCTTCTCATGCTCCGTGATGCATGAGGCTCTGCACA<br>ACCACTACACGCAGAAGAGGCTCTCCCTGTCTCCGGGTAAA |
| 338 | Anti-CD122 P2H7 Fab LC (VL, joint CL) | GACATCCAGATGACCCAGTCTCCTTCCACATTGTCTGCATCTGTAGGAGACAGAGTC<br>ACACTCTCTTGCCGGGCCGGTCAGGCTATTAGTAGTTGGTTGGCCTGGTATCAACA<br>GAAACCAGGTAAAGCCCCAAAGCTTCTGATCTATAAGGCATCTAATTTAGAAAGTGG<br>AGTCCCATCAAGGTTCAGCGGCGGTGGATCTGGGGCAGAATTCACTCTCACCATCA<br>GCAGCCTGCAGCCTGATGATTTTGCAACTTATTACTGCCAACAGTATCAGAGCTACC<br>CTTACACTTTTGGCCAGGGGACCAAGCTGGAGATCAGACGAACTGTGGCTGCACCA<br>TCTGTCTTCATCTTCCCGCCATCTGATGAGCAGTTGAAATCTGGAACTGCCTCTGTT<br>GTGTGCCTGCTGAATAACTTCTATCCCAGAGAGGCCAAAGTACAGTGGAAGGTGGA<br>TAACGCCCTCCAATCGGGTAACTCCCAGGAGAGTGTCACAGAGCAGGACAGCAAGG<br>ACAGCACCTACAGCCTCAGCAGCACCCTGACGCTGAGCAAAGCAGACTACGAGAAA<br>CACAAAGTCTACGCCTGCGAAGTCACCCATCAGGGCCTGAGCTCGCCCGICACAAA<br>GAGCTTCAACAGGGGAGAGTGT |
| 339 | Anti-CD122 P2H7 Fab HC (VH, joint CH1) | GAGGTGCAGCTGGTGCAGTCTGGGACTGAGGTGAAGAAGCCTGGGGCCTCAGTGA<br>AGGTTTCCTGCAAGGCTTCTGGATACACCTTCACTACCTATGCTATGCATTGGGTGC<br>GCCAGGCCCCCGGACAAAGCCTTGAGTGGATGGGATGGATCAACACTGGCAATGGT<br>AACACAAAATATTCACAGAACTTCCAGGGCAGAGTCACCATGACCAGGGACACGTCC<br>ATCAGCACAGCCTACATGGAGCTGAGCAGGCTGAGATCTGACGACACGGCCGTGTA<br>TTACTGTGCGAGAGATCTCGGGCAACTGGAACGACTCTACTTCTGGGGCCAGGGCA<br>CCCTGGTCACCGTCTCAAGCGCCTCCACCAAGGGCCCATCGGTCTTCCCCCTGGCA<br>CCCTCCTCCAAGAGCACCTCTGGGGGCACAGCGGCCCTGGGCTGCCTGGTCAAGG<br>ACTACTTCCCCGAACCGGTGACGGTGTCGTGGAACTCAGGCGCCCTGACCAGCGG<br>CGTCCACACCTTCCCGGCTGTCCTACAGTCCTCAGGACTCTACTCCCTCAGCAGCG<br>TAGTGACCGTGCCCTCCAGCAGCTTGGGCACCCAGACCTACATCTGCAACGTGAAT<br>CACAAGCCCAGCAACACCAAGGTGGACAAGAAAGTTGAGCCCAAATCTTGT |
| 340 | Anti-CD122 P2H7 scFv and Fc with knob modification | GAGGTGCAGCTGGTGCAGTCTGGGACTGAGGTGAAGAAGCCTGGGGCCTCAGTGA<br>AGGTTTCCTGCAAGGCTTCTGGATACACCTTCACTACCTATGCTATGCATTGGGTGC<br>GCCAGGCCCCCGGACAAAGCCTTGAGTGGATGGGATGGATCAACACTGGCAATGGT<br>AACACAAAATATTCACAGAACTTCCAGGGCAGAGTCACCATGACCAGGGACACGTCC<br>ATCAGCACAGCCTACATGGAGCTGAGCAGGCTGAGATCTGACGACACGGCCGTGTA<br>TTACTGTGCGAGAGATCTCGGGCAACTGGAACGACTCTACTTCTGGGGCCAGGGCA<br>CCCTGGTCACCGTCTCAAGCGGAGGAGGAGGATCTGGCGGAGGAGGCAGTGGAGG<br>AGGAGGGTCACTTGACATCCAGATGACCCAGTCTCCTTCCACATTGTCTGCATCTGT<br>AGGAGACAGAGTCACACTCTCTTGCCGGGCCGGTCAGGCTATTAGTAGTTGGTTGG<br>CCTGGTATCAACAGAAACCAGGTAAAGCCCCAAAGCTTCTGATCTATAAGGCATCTA<br>ATTTAGAAAGTGGAGTCCCATCAAGGTTCAGCGGCGGTGGATCTGGGGCAGAATTC<br>ACTCTCACCATCAGCAGCCTGCAGCCTGATGATTTTGCAACTTATTACTGCCAACAG<br>TATCAGAGCTACCCTTACACTTTTGGCCAGGGGACCAAGCTGGAGATCAGAAACAG<br>CGGCGCGGGCACCGCGGCCGCGACTCACACATGCCCACCGTGCCCAGCACCTGAA<br>GCCGCGGGGGGACCGTCAGTCTTCCTCTTCCCCCCAAAACCCAAGGACACCCTCAT<br>GATCTCCCGGACCCCTGAGGTCACATGCGTGGTGGTGGACGTGAGCCACGAAGAC<br>CCTGAGGTCAAGTTCAACTGGTACGTGGACGGCGTGGAGGTGCATAATGCCAAGAC<br>AAAGCCGCGGGAGGAGCAGTACAACAGCACGTACCGTGTGGTCAGCGTCCTCACC<br>GTCCTGCACCAGGACTGGCTGAATGGCAAGGAGTACAAGTGCAAGGTCTCCAACAA<br>AGCCCTCCCAGCCCCCATCGAGAAAACCATCTCCAAAGCCAAAGGGCAGCCCCGAG<br>AACCACAGGTGTACACCCTGCCCCCATGCCGGGATGAGCTGACCAAGAACCAGGTC<br>AGCCTGTGGTGCCTGGTCAAAGGCTTCTATCCCAGCGACATCGCCGTGGAGTGGGA<br>GAGCAATGGGCAGCCGGAGAACAACTACAAGACCACGCCTCCCGTGCTGGACTCC<br>GACGGCTCCTTCTTCCTCTACAGCAAGCTCACCGTGGACAAGAGCAGGTGGCAGCA |

-continued

Sequences

| SEQ ID NO: | DESCRIPTION | SEQUENCE |
|---|---|---|
| | | GGGGAACGTCTTCTCATGCTCCGTGATGCATGAGGCTCTGCACAACCACTACACGC AGAAGAGCCTCTCCCTGTCTCCGGGTAAA |
| 341 | Anti-CD122 P2D12 Fab LC (VL, joint CL) | GACATCCAGTTGACCCAGTCTCCATCCTCCCTGTCTGCATCTGTAGGAGACAGAGTC ACCATCACTTGCCAGGCGAGTCAGGACATTGGCAACTATTTAAATTGGTATCAGCTT AAACCAGGGAAAGCCCCTAAGCTCCTGATCTACGATGCATCCAATTTGGAAACAGGG GTCCCATCAAGGTTCAGTGGAAGTGGATCTGGGACAGATTTTACTTTCACCATCAGC AGCCTGCAGCCTGAAGATATTGCAACATATTACTGTCTACAACTTTATGATTACCCCC TCACTTTCGGCGGAGGGACCAAGGTGGAGATCAAACGAACTGTGGCTGCACCATCT GTCTTCATCTTCCCGCCATCTGATGAGCAGTTGAAATCTGGAACTGCCTCTGTTGTG TGCCTGCTGAATAACTTCTATCCCAGAGAGGCCAAAGTACAGTGGAAGGTGGATAAC GCCCTCCAATCGGGTAACTCCCAGGAGAGTGTCACAGAGCAGGACAGCAAGGACA GCACCTACAGCCTCAGCAGCACCCTGACGCTGAGCAAAGCAGACTACGAGAAACAC AAAGTCTACGCCTGCGAAGTCACCCATCAGGGCCTGAGCTCGCCCGTCACAAAGAG CTTCAACAGGGGAGAGTGT |
| 342 | Anti-CD122 P2D12 Fab HC (VH, joint CH1) | CACGTGCAGCTGGTGGAGACTGGGGGAGGCTTGGTGCAGCCTGGGGGGTCCCTGA GACTCTCCTGTGCAGCTCTGGATTCACCTTTAGCAGCTATGCCATGAGCTGGGTCC GCCAGGCTCCAGGGAAGGGGCTGGAGTGGGTCTCAGCTATTAGTGGTAGTGGTGG TAGCACATACTACGCAGACTCCGTGAAGGGCCGGTTCACCATCTCCAGAGACAATTC CAAGAACACGCTGTATGTGCAAATGAACAGCCTGAGAGCCGAGGACACGGCCGTAT ATTACTGTGCGAGAGATCTCGGGGATTATTGGGGCCAGGGAACCCTGGTCACCGTC TCAAGCGCCTCCACCAAGGGCCCATCGGTCTTCCCCCTGGCACCCTCCTCCAAGAG CACCTGTGGGGGCACAGCGGCCCTGGGCTGCCTGGTCAAGGACTACTTCCCCGAA CCGGTGACGGTGTCGTGGAACTCAGGCGCCCTGACCAGCGGCGTCCACACCTTCC CGGCTGTCCTACAGTCCTCAGGACTCTACTCCCTCAGCAGCGTAGTGACCGTGCCC TCCAGCAGCTTGGGCACCCAGACCTACATCTGCAACGTGAATCACAAGCCCAGCAA CACCAAGGTGGACAAGAAAGTTGAGCCCAAATCTTGT |
| 343 | Anti-CD122 P2D12 scFv and Fc with knob modification | CAGGTCCAGCTGCAGGAGTCCGGGCCAGGGCTGGTGAAACCAAGCGAAACACTGA GTCTGACATGTACCGTGAGTGGGGGGTCCATTAACAATAGTAACTACTATTGGTCAT GGATGAGACAGAGCCCTGGAAGAGGCCTGGAGTGGATCGGCGGGATCTACTTCAG CGGCACCACATACTATAACCCATCACTGCAGAGCCGGGTGACTATCTCCATTGACAC CTCTAAGAATCAGTTCAGCCTGAAGCTGAGCAGCGTGACCGCCGCTGATACAGCCA TCTACTATTGCGTCCGGCAGATGAATTACTATCACCTGGGCTCTAGTGTGGGGTTCG ACCCCTGGGGACAGGGAGCACTGGCCACCGTGTCAAGCGTCTCCTCTGGAGGAGG AGGCAGCGGCGGAGGAGGCTCTGGAGGAGGCGGGAGTGATGTGGTCATGACAGA GAGCCCAGCTACTCTGTCTGTGAGTCCCGGCGAAAGGGCCACACTGAGCTGTCGC GCTTCACAGAGCGTCAGTTCAAACCTGGCATGGTACCAGCAGAAGCCAGGACAGGC ACCTTCCGTGCTGATCTATGAGGCTTCTACACGAGGAACTGGCATTCCTGGTTAGATT CTCCGGCTCTGGGAGTGGAACCGACTTTACTCTGACCATCAGCTCCCTGCAGAGCG AAGATTGCAATCTACTATTGTCAGCAGTATAACGATTGGCTGTGGACCTTCGGGC AGGGGACTAAAGTGGAGATTCGGAACAGCGGCGCGGGCACCGCGGCCGCGACTCA CACATGCCCACCGTGCCCAGCACCTGAAGCCGCGGGGGGACCGTCAGTCTTCCTC TTCCCCCCAAAACCCAAGGACACCCTCATGATCTCCCGGACCCCTGAGGTCACATG CGTGGTGGTGGACGTGAGCCACGAAGACCCTGAGGTCAAGTTCAACTGGTACGTGG ACGGCGTGGAGGTGCATAATGCCAAGACAAAGCCGCGGGAGGAGCAGTACAACAG CACGTACCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAGAAAACC ATCTCCAAAGCCAAAGGGCAGCCCCGAGAACCACAGGTGTACACCCTGCCCCCATG CCGGGATGAGCTGACCAAGAACCAGGTCAGCCTGTGGTGCCTGGTCAAAGGCTTCT ATCCCAGCGACATCGCCGTGGAGTGGGAGAGCAATGGGCAGCCGGAGAACAACTA CAAGACCACGCCTCCCGTGCTGGACTCCGACGGCTCCTTCTTCCTCTACAGCAAGC TCACCGTGGACAAGAGCAGGTGGCAGCAGGGGAACGTCTTCTCATGCTCCGTGATG CATGAGGCTCTGCACAACCACTACACGCAGAAGAGCCTCTCCCTGTCTCCGGGTAA A |
| 344 | P1G11 Fab LC (VL, joint CL) | AATTTTATGCTGACTCAGCCCCACTCTGTGTCGGAGTCTCCGGGGAAGACGGTAAC CATCTCCTGCACCCGCAGCAGTGGCAGCATTGCCAGCAACTATGTGCAGTGGTACC AGCAGCGCCCGGGCAGTTCCCCCACCACGGTCATTTTTGACGACAATCAAAGACCC ACTGGTGTCCCTGATCGCTTGTCTGCCGCCATCGACACCTCCTCCAGTTCTGCCTCC CTCACCATCTCTGGACTGACGGCTGAGGACGAGGCCGATTACTATTGTCAGTCGTCT CATAGCACCGCTGTCGTCTTTGGCGGAGGGACCAAGCTGACCGTCCTAAGTCAGCC CAAGGCTGCCCCCTCGGTCACTCTGTTCCCGCCCTCCTCTGAGGAGGTTCAAGCCA ACAAGGCCACACTGGTGTGTCTCATAAGTGACTTCTACCCGGGAGCCGTGACAGTG GCCTGGAAGGCAGATAGCAGCCCCGTCAAGGCGGGAGTGGAGACCACCACACCCT CCAAACAAAGCAACAACAAGTACGCGGCCAGCAGCTACCTGAGCCTGACGCCTGAG CAGTGGAAGTCCCACAAAAGCTACAGCTGCCAGGTCACGCATGAAGGGAGCACCGT GGAGAAGACAGTGGCCCCTACAGAATGTTCA |
| 345 | Anti-CD122 P1G11 Fab HC (VH, joint CH1) | CAGGTGCAGCTACAGCAGTGGGGCGCAGGACTGTTGAAGCCTTCGGAGACCCTGT CCGTCACCTGCGCTGTCTATGGTGGGTCCTTCAGTGGTTACTACTGGAGCTGGATC CGCCAGCCCCCAGGGAAGGGGCTGGAGTGGATTGGGGAAATCAATCATAGTGGAA GCACCAACTACAACCCGTCCCTCAAGAGTCGAGTCACCATATCAGTAGACACGTCCA |

-continued

Sequences

| SEQ ID NO: | DESCRIPTION | SEQUENCE |
|---|---|---|
| | | AGAACCAGTTGTCCCTGAAGCTGAGCTCTGTGACCGCCGCGGACACGGCTGTGTAT TACTGTGCGAGAAGCTCGTCCGGGGATGCTTTTGATATCTGGGGCCAAGGGACAAT GGTCACCGTCTCAAGCGCCTCCACCAAGGGCCCATCGGTCTTCCCCCTGGCACCCT CCTCCAAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCGGCGTC CACACCTTCCCGGCTGTCCTACAGTCCTCAGGACTCTACTCCCTCAGCAGCGTAGT GACCGTGCCCTCCAGCAGCTTGGGCACCCAGACCTACATCTGCAACGTGAATCACA AGCCCAGCAACACCAAGGTGGACAAGAAAGTTGAGCCCAAATCTTGT |
| 346 | Anti-CD122 P1G11 scFv and Fc with knob modification | CAGGTGCAGCTACAGCAGTGGGGCGCAGGACTGTTGAAGCCTTCGGAGACCCTGT CCCTCACCTGCGCTGTCTATGGTGGGTCCTTCAGTGGTTAGTACTGGAGCTGGATC CGCCAGCCCCCAGGGAAGGGGCTGGAGTGGATTGGGGAAATCAATCATAGTGGAA GCACCAACTACAACCCGTCCCTCAAGAGTCGAGTCACCATATCAGTAGACACGTCCA AGAACCAGTTCTCCCTGAAGCTGAGCTCTGTGACCGCCGCGGACACGGCTGTGTAT TACTGTGCGAGAAGCTCGTCCGGGGATGCTTTTGATATCTGGGGCCAAGGGACAAT GGTCACCGTCTCAAGCGGAGGAGGAGGATCTGGCGGAGGAGGCAGTGGAGGAGG AGGGTCACTTAATTTTATGCTGACTCAGCCCCACTCTGTGTCGGAGTCTCCGGGGAA GACGGTAACCATCTCCTGCACCCGCAGCAGTGGCAGCATTGCCAGCAACTATGTGC AGTGGTACCAGCAGCGCCCGGGCAGTTCCCCCACCACGGTCATTTTTGACGACAAT CAAAGACCCACTGGTGTCCCTGATCGCTTCTCTGCCGCCATCGACACCTCCTCCAGT TCTGCCTCCCTCACCATCTCTGGACTGACGGCTGAGGACGAGGCCGATTACTATTGT CAGTCGTCTCATAGCACCGCTGTCGTCTTTGGCGGAGGGACCAAGCTGACCGTCCT AAACAGCGGCGCGGGCACCGCGGCCGCGACTCACACATGCCCACCGTGCCCAGCA CCTGAAGCCGCGGGGGGACCGTCAGTCTTCCTCTTCCCCCCAAAACCCAAGGACAC CCTCATGATCTCCCGGACCCCTGAGGTCACATGCGTGGTGGTGGACGTGAGCCACG AAGACCCTGAGGTCAAGTTCAACTGGTACGTGGACGGCGTGGAGGTGCATAATGCC AAGACAAAGCCGCGGGAGGAGCAGTACAACAGCACGTACCGTGTGGTCAGCGTCC TCACCGTCCTGCACCAGGACTGGCTGAATGGCAAGGAGTACAAGTGCAAGGTCTCC AACAAAGCCCTCCCAGCCCCCATCGAGAAAACCATCTCCAAAGCCAAAGGGCAGCC CCGAGAACCACAGGTGTACACCCTGCCCCCATGCCGGGATGAGCTGACCAAGAACC AGGTCAGCCTGTGGTGCCTGGTCAAAGGCTTCTATCCCAGCGACATCGCCGTGGAG TGGGAGAGCAATGGGCAGCCGGAGAACAACTACAAGACCACGCCTCCCGTGCTGG ACTCCGACGGCTCCTTCTTCCTCTACAGCAAGCTCACCGTGGACAAGAGCAGGTGG CAGCAGGGGCGTCTTCTCATGCTCCGTGATGCATGAGGCTCTGCACAACCACTA CACGCAGAAGAGCCTCTCCCTGTCTCCGGGTAAA |
| 347 | Anti-CD122 P1E7 Fab LC (V/L, joint CL) | GATGTTGTGATGACTCAGTCTCCACTCTCCCTGCCCGTCACCCCTGGAGAGCCGGC CTCCATCTCCTGCAGGTCTAGTCAGAGCCTCCTGCATAGTAATGGATACAACTATTT GGATTGGTACCTGCAGAAGCCAGGGCAGTCTCCACAGCTCCTGATCTATTTGGGTT CTAGTCGGGCCTCCGGGGTCCCTGACAGGTTCAGTGGCAGTGGATCAGGCACAGA TTTTACACTGAAAATCAGCAGAGTGGAGGCTGAGGATGTTGGGGTTTATTACTGCAT GCAAGCTCTACAAACTCCTCGCACTTTTGGCCAGGGGACCAAGCTGGAGATCAAAC GAACTGTGGCTGCACCATCTGTCTTCATCTTCCCGCCATCTGATGAGCAGTTGAAAT CTGGAACTGCCTCTGTTGTGTGCCTGCTGAATAACTTCTATCCCAGAGAGGCCAAAG TACAGTGGAAGGTGGATAACGCCCTCCAATCGGGTAACTCCCAGGAGAGTGTCACA GAGCAGGACAGCAAGGACAGCACCTACAGCCTCAGCAGCACCCTGACGCTGAGCA AAGCAGACTACGAGAAACACAAAGTCTACGCCTGCGAAGTCACCCATCAGGGCCTG AGCTCGCCCGTCACAAAGAGCTTCAACAGGGGAGAGTGT |
| 348 | Anti-CD122 P1E7 Fab HC (VH, joint CH1) | GAGGTGCAGCTGGTGCAGTCTGGGGGAGGCGTGGTCCAGCCTGGGAGGTCCCTGA GACTCTCCTGTGCAGCCTCTGGATTCACCTTCAGTAGCTATGCTATGCACTGGGTCC GCCAGGCTCCAGGCAAGGGGCTGGAGTGGGTGGCAGTCATATCATATGATGGAAG CAATAAATACTATGCAGACTCCGTGAAGGGCCGATTCACCATCTCCAGAGACAATTC CAAGAACACGCTGTATCTGCAAATGAACAGCCTGAGAGCTGAGGACACGGCTGTGT ATTACTGTGCGAGAGATCTCGGGTATAGCAGCAGCTGGTACTACTACTACTACGGTA TGGACGTCTGGGGCCAAGGGACCACGGTCACCGTCTCAAGCGCCTCCACCAAGGG CCCATCGGTCTTCCCCCTGGCACCCTCCTCCAAGAGCACCTCTGGGGGCACAGCG GCCCTGGGCTGCCTGGTCAAGGACTACTTCCCCGAACCGGTGACGGTGTCGTGGA ACTCAGGCGCCCTGACCAGCGGCGTCCACACCTTCCCGGCTGTCCTACAGTCCTCA GGACTCTACTCCCTCAGCAGCGTAGTGACCGTGCCCTCCAGCAGCTTGGGCACCCA GACCTACATCTGCAACGTGAATCACAAGCCCAGCAACACCAAGGTGGACAAGAAAG TTGAGCCCAAATCTTGT |
| 349 | Anti-CD122 P1E7 scFv and Fc with knob modification | GAGGTGCAGCTGGTGCAGAGCGGGGGGGGGGTGGTGCAGCCTGGGAGGTCACTG AGACTGAGTTGTGCCGCATCCGGGTTTACATTTAGCTCCTATGCAATGCACTGGGTG AGGCAGGCCCCTGGCAAGGGGCTGGAGTGGGTGGCTGTCATCAGTTACGACGGCT CAAACAAGTACTATGCAGATTCTGTGAAAGGGCGGTTCACAATTAGCAGAGACAACT CCAAAAATACTCTGTACCTCCAGATGAATAGCCTGCGAGCCGAAGACACCGCCGTG TACTATTGCGCCAGAGACCTGGGATACTCTAGTTCATGGTACTACTACTACTACGGC ATGGACGTGTGGGGACAGGGCACCACAGTGACAGTCAGCTCCGGCGGAGGAGGCT CAGGAGGAGGAGGGTCCGGCGGAGGAGGATCTGATGTGGTCATGACCCAGTCCCC ACTGTCTCTGCCAGTGACACCTGGCGAGCCAGCAAGCATCAGCTGCCGGAGCAGC CAGTCTCTGCTGCATAGTAACGGGTATAATTACCTGGACTGGTACTTGCAGAAGCCT GGCCAGAGTCCTCAGCTGCTGATCTACCTGGGGTCAAGCAGGGCCTCCGGAGTGC |

-continued

Sequences

| SEQ ID NO: | DESCRIPTION | SEQUENCE |
|---|---|---|
| | | CCGACCGCTTCAGTGGGTCAGGAAGCGGCACTGACTTCACCCTGAAGATCAGCCGG<br>GTGGAGGCTGAAGATGTGGGCGTCTATTACTGTATGCAGGCACTGCAGACACCACG<br>GACTTTTGGACAGGGGACTAAACTGGAAATCAAGAACAGCGGCGCGGGCACCGCG<br>GCCGCGACTCACACATGCCCACCGTGCCCAGCACCTGAAGCCGCGGGGGGACCGT<br>CAGTCTTCCTCTTCCCCCCAAAACCCAAGGACACCCTCATGATGTCCCGGACCCGTG<br>AGGTCACATGCGTGGTGGTGGACGTGAGCCACGAAGACCCTGAGGTCAAGTTCAAC<br>TGGTACGTGGACGGCGTGGAGGTGCATAATGCCAAGACAAAGCCGCGGGAGGAGC<br>AGTACAACAGCACGTACCGTGTGGTCAGCGTCCTCACCGTCCTGCACCAGGACTGG<br>CTGAATGGCAAGGAGTACAAGTGCAAGGTCTCCAACAAAGCCCTCCCAGCCCCCAT<br>CGAGAAAACCATCTCCAAAGCCAAAGGGCAGCCCCGAGAACCACAGGTGTACACCC<br>TGCCCCCATGCCGGGATGAGCTGACCAAGAACCAGGTCAGCCTGTGGTGCCTGGT<br>CAAAGGCTTCTATCCCAGCGACATCGCCGTGGAGTGGGAGAGCAATGGGCAGCCG<br>GAGAACAACTACAAGACCACGCCTCCCGTGCTGGACTCCGACGGCTCCTTCTTCCT<br>CTACAGCAAGCTCACCGTGGACAAGAGCAGGTGGCAGCAGGGGAACGTCTTCTCAT<br>GCTCCGTGATGCATGAGGCTCTGCACAACCACTACACGCAGAAGAGCCTCTCCCTG<br>TCTCCGGGTAAA |
| 350 | Anti-CD122 P1B10 Fab LC (VL, joint CL) | GACATCCAGATGACCCAGTCTCCATCCTCCCTGTCTGCATCTGTAGGAGACAGAGTC<br>ACCATCACTTGCCAGGCGAGTCAGGACATTAGCGACTATTTAAATTGGTATCAGCAG<br>AAACCAGGGAAAGCCCCTCAGATCCTGATCTACGATGCATCCAATTTGGAGACAGG<br>GGTCCCATCAAGATTCAGTGGAAGTGGGTCTGGGACAGATTTTACTTTCACCATCAG<br>CAACCTGCAGCCTGAGGATGTTGCAACATATTACTGTCAACAGTATGAGGATCTCCC<br>CTCTTTCGGCGGAGGGACCAAGGTGGAGATCAAACGAACTGTGGCTGCACCATCTG<br>TCTTCATCTTCCCGCCATCTGATGAGCAGTTGAAATCTGGAACTGCCTCTGTTGTGT<br>GCCTGCTGAATAACTTCTATCCCAGAGAGGCCAAAGTACAGTGGAAGGTGGATAAC<br>GCCCTCCAATCGGGTAACTCCCAGGAGAGTGTCACAGAGCAGGACAGCAAGGACA<br>GCACCTACAGCCTCAGCAGCACCCTGACGCTGAGCAAAGCAGACTACGAGAAACAC<br>AAAGTCTACGCCTGCGAAGTCACCCATCAGGGCCTGAGCTCGCCCGTCACAAAGAG<br>CTTCAACAGGGGAGAGTGT |
| 351 | Anti-CD122 P1B10 Fab HC (VH, joint CH1) | CAGGTGCAGCTGCAGGAGTCGGGCCCAGGACTGGTGAAGCCTTCGGAGACCCTGT<br>CCCTCACCTGCACTGTCTCTGGTGTCTCCATCAGCAGTAGAAGTGACCACTGGGGC<br>TGGGTCCGCCAGCCCCCAGGGAAGGGGCTGGAGTGGATTGGAAGTATCTCTTATAG<br>TGGGAGCACCTACTACAACCCGTCCCTCAAGAGCCGAGTCACCATATCCGTAGACA<br>CCTCCAAGAACCAACTCTCCCTGAAGCTGAGCTCTGTGACCGCCGCAGACACGGCT<br>GTGTATTACTGTGCGAGAGAGTCGCACCCAGCAGCTGCACTGGTTGGGTGGGGCCA<br>GGGCACCCTGGTCACCGTCTCAAGCGCCTCCACCAAGGGCCCATCGGTCTTCCCCC<br>TGGCACCCTCCTCCAAGAGCACCTCTGGGGGCACAGCGGCCCTGGGCTGCCTGGT<br>CAAGGACTACTTCCCCGAACCGGTGACGGTGTCGTGGAACTCAGGCGCCCTGACCA<br>GCGGCGTCCACACCTTCCCGGCTGTCCTACAGTCCTCAGGACTCTACTCCCTCAGC<br>AGCGTAGTGACCGTGCCCTCCAGCAGCTTGGGCACCCAGACCTACATCTGCAACGT<br>GAATCACAAGCCCAGCAACACCAAGGTGGACAAGAAAGTTGAGCCCAAATCTTGT |
| 352 | Anti-CD122 P1B10 scFv and Fc with knob modification | CAGGTCCAGCTGCAGGAGAGCGGCCCCGGACTGGTGAAGCCTAGCGAAACACTGA<br>GCCTGACTTGTACTGTGAGCGGCGTGAGCATTAGCTCCCGGAGCGACCACTGGGG<br>ATGGGTGAGACAGCCCCCTGGCAAGGGGCTGGAGTGGATCGGAAGTATTTCATACA<br>GCGGCTCCACTTACTATAACCCCTCTCTGAAAAGTAGGGTGACTATCTCAGTGGACA<br>CCAGCAAGAATCAGCTGAGTCTGAAACTGTCTAGTGTGACCGCCGCTGATACAGCA<br>GTCTACTATTGCGCCCGCGAATCCCATCCTGCCGCCGCCCTGGTGGGATGGGGACA<br>GGGGACACTGGTGACTGTCTCAAGCGGAGGAGGAGGCAGTGGAGGAGGAGGGTCA<br>GGAGGCGGGGGAAGCGACATTCAGATGACACAGAGCCCATCCTCTCTGTCTGCCAG<br>TGTGGGCGATCGAGTCACCATCACATGTCAGGCTTCCCAGGACATTTCTGATTACCT<br>GAACTGGTATCAGCAGAAGCCAGGGAAAGCTCCCCAGATCCTGATCTACGACGCAT<br>CCAATCTGGAGACAGGCGTGCCCAGCCGGTTCAGCGGAAGCGGCTCCGGGACTGA<br>TTTCACTTTTACCATCTCTAACCTCCAGCCTGAGGACGTGGCCACCTACTATTGCCA<br>GCAGTATGAGGACCTGCCATCCTTTGGCGGGGGAACAAAGGTCGAGATCAAGAACA<br>GCGGCGCGGGCACCGCGGCCGCGACTCACACATGCCCACCGTGCCCAGCACCTGA<br>AGCCGCGGGGGGACCGTCAGTCTTCCTCTTCCCCCCAAACCCAAGGACACCCTCA<br>TGATCTCCCGGACCCCTGAGGTCACATGCGTGGTGGTGGACGTGAGCCACGAAGA<br>CCCTGAGGTCAAGTTCAACTGGTACGTGGACGGCGTGGAGGTGCATAATGCCAAGA<br>CAAAGCCGCGGGAGGAGCAGTACAACAGCACGTACCGTGTGGTCAGCGTCCTCAC<br>CGTCCTGCACCAGGACTGGCTGAATGGCAAGGAGTACAAGTGCAAGGTCTCCAACA<br>AAGCCCTCCCAGCCCCCATCGAGAAAACCATCTCCAAAGCCAAAGGGCAGCCCCGA<br>GAACCACAGGTGTACACCCTGCCCCCATGCCGGGATGAGCTGACCAAGAACCAGGT<br>CAGCCTGTGGTGCCTGGTCAAAGGCTTCTATCCCAGCGACATCGCCGTGGAGTGGG<br>AGAGCAATGGGCAGCCGGAGAACAACTACAAGACCACGCCTCCCGTGCTGGACTCC<br>GACGGCTCCTTCTTCCTCTACAGCAAGCTCACCGTGGACAAGAGCAGGTGGCAGCA<br>GGGGAACGTCTTCTCATGCTCCGTGATGCATGAGGCTCTGCACAACCACTACACGC<br>AGAAGAGCCTCTCCCTGTCTCCGGGTAAA |
| 353 | Anti-CD122 P1F3 Fab LC (VL, joint CL) | GACATCCAGTTGACCCAGTCTCCATCCTCCCTGTCTGCATCTGTAGGAGACAGAGTC<br>ACCATCACTTGCCGGGCAAGTCAGAGCATTAGCAGCTATTTAAATTGGTATCAGCAG<br>AAACCAGGGAAAGCCCCTAAGGCCCTGATCTACGATGCATCCAATTTGGAAACAGG<br>GGTCCCATCAAGGTTCAGTGGCAGTGGATCTGGGACAGATTTCACTCTCACCATCAT |

-continued

| SEQ ID NO: | DESCRIPTION | SEQUENCE |
|---|---|---|
| | | CAGTCTGCAACCTGAAGATTTTGCAACTTATTTCTGTCTACAAGATTACATTTACCCG TGGACGTTCGGCCAAGGGACCAAGGTGGAATTCAAACGAACTGTGGCTGCACCATC TGTCTTCATCTTCCCGCCATCTGATGAGCAGTTGAAATCTGGAACTGCCTCTGTTGT GTGCCTGCTGAATAACTTCTATCCCAGAGAGGCCAAAGTACAGTGGAAGGTGGATAA CGCCCTCCAATCGGGTAACTCCCAGGAGAGTGTCACAGAGCAGGACAGCAAGGACA GCACCTACAGCCTCAGCAGCACCCTGACGCTGAGCAAAGCAGACTACGAGAAACAC AAAGTCTACGCCTGCGAAGTCACCCATCAGGGCCTGAGCTCGCCCGTCACAAAGAG CTTCAACAGGGGAGAGTGT |
| 354 | Anti-CD122 P1F3 Fab HC (VH, joint CH1) | GAGGTGCAGCTGGTGCAGTCTGGGGGAGGCTTGGTACAGCCTGGGGGGTCCCTGA GACTCTCCTGTGCAGCCTCTGGATTCACCTTTAGCAGCTATGCCATGAGCTGGGTCC GCCAGGCTCCAGGGAAGGGGCTGGAGTGGGTCTCAGCTATTAGTGGTAGTGGTGG CAGCACACACTACGCAGACTCCGTGAAGGGCCGGTTCACCATCTCCAGAGACAACT CCAAGAACACGCTGTATCTGCAAATGAACAGCCTGAGAGCCGAGGACACGGCCGTA TATTACTGTGCGACTCCGGCTTTCTGGGGCCAGGGAACCCTGGTCACCGTCTCAAG CGCCTCCACCAAGGGCCCATCGGTCTTCCCCCTGGCACCCTCCTCCAAGAGCACCT CTGGGGGCACAGCGGCCCTGGGCTGCCTGGTCAAGGACTACTTCCCCGAACCGGT GACGGTGTCGTGGAACTCAGGCGCCCTGACCAGCGGCGTCCACACCTTCCCGGCT GTCCTACAGTCCTCAGGACTCTACTCCCTCAGCAGCGTAGTGACCGTGCCCTCCAG CAGCTTGGGCACCCAGACCTACATCTGCAACGTGAATCACAAGCCCAGCAACACCA AGGTGGACAAGAAAGTTGAGCCCAAATCTTGT |
| 355 | Anti-CD122 P1F3 scFv and Fc with knob modification | GAGGTGCAGCTGGTGCAGAGCGGGGGAGGACTGGTGCAGCCTGGGGGGTCACTG AGACTGAGTTGTGCCGCAAGCGGGTTTACATTTAGCTCCTACGCCATGTCTTGGGTG CGACAGGCTCCCGGAAAAGGCCTGGAGTGGGTCAGCGCAATCAGTGGATCAGGCG GGTCTACTCACTACGCCGACAGTGTGAAAGGCCGGTTCACCATCAGCCGGGACAAC AGTAAGAATACTCTGTACCTCCAGATGAACAGCCTGAGAGCTGAAGACACCGCCGT GTACTATTGCGCCACCCCTGCTTTTTGGGGGCAGGGAACACTGGTGACTGTCTCTA GTGGAGGAGGAGGATCAGGCGGCGGAGGCAGCGGAGGAGGAGGGTCCGACATCC AGCTGACACAGTCCCCATCAAGCCTGAGCGCTTCCGTGGGCGATAGGGTCACCATC ACATGTCGCGCATCTCAGAGTATTTCCTCTTACCTGAACTGGTATCAGCAGAAGCCC GGCAAGGCACCTAAGGCCCTGATCTACGACGCCAGCAATCTGGAGACCGGCGTGC CTTCCCGGTTCTCAGGCAGCGGGTCCGGAACAGATTTTACTCTGACCATCATCAGCC TCCAGCCAGAGGACTTCGCTACCTATTTTTGCCTCCAGGATTACATCTACCCCTGGA CCTTCGGCCAGGGGACAAAAGTGGAGTTCAAGAACAGCGGCGCGGGCACCGCGGC CGCGACTCACACATGCCCACCGTGCCCAGCACCTGAAGCCGCGGGGGGACCGTCA GTCTTCCTCTTCCCCCCAAAACCCAAGGACACCCTCATGATCTCCCGGACCCCTGAG GTCACATGCGTGGTGGTGGACGTGAGCCACGAAGACCCTGAGGTCAAGTTCAACTG GTACGTGGACGGCGTGGAGGTGCATAATGCCAAGACAAAGCCGCGGGAGGAGCAG TACAACAGCACGTACCGTGTGGTCAGCGTCCTCACCGTCCTGCACCAGGACTGGCT GAATGGCAAGGAGTACAAGTGCAAGGTCTCCAACAAAGCCCTCCCAGCCCCCATCG AGAAAACCATCTCCAAAGCCAAAGGGCAGCCCCGAGAACCACAGGTGTACACCCTG CCCCCATGCCGGGATGAGCTGACCAAGAACCAGGTCAGCCTGTGGTGCCTGGTCAA AGGCTTCTATCCCAGCGACATCGCCGTGGAGTGGGAGAGCAATGGGCAGCCGGAG AACAACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCATGCTC CGTGATGCATGAGGCTCTGCACAACCACTACACGCAGAAGAGCCTCTCCCTGTCTC CGGGTAAA |
| 356 | Anti-CD122 P1D10 Fab LC (VL, joint CL) | CAGTCTGTGTTGACGCAGCCGCCCTCAGTGTCTGGGGCCCCAGGGCAGAGGGTCA CCATCTCCTGCACTGGGGGCAGCTCCAACGTCGGGGCAGGTTATGATGTACACTGG TACCAGCAGCTTCCAGGAACAGTCCCCAAACTCCTCATCTATGATAACACCAATCGG CCCTCAGGTGTCCCTGACCGGTTCTCTGCCTCCAAGTCTGGCACCTCAGCCTCTCT GGTCATCACTGGGCTCCAGGCTGAGGATGAGGGTGACTATTACTGCCAGTCGTATG ACAGTAGTCTGCGTGCTTCGGTATTCGGCGGAGGGACCATGTTGACCGTCCTAAGT CAGCCCAAGGCTGCCCCCTCGGTCACTCTGTTCCCGCCCTCCTCTGAGGAGCTTCA AGCCAACAAGGCCACACTGGTGTGTCTCATAAGTGACTTCTACCCGGGAGCCGTGA CAGTGGCCTGGAAGGCAGATAGCAGCCCCGTCAAGGCGGGAGTGGAGACCACCAC ACCCTCCAAACAAAGCAACAACAAGTACGCGGCCAGCAGCTATCTGAGCCTGACGC CTGAGCAGTGGAAGTCCCACAAAAGCTACAGCTGCCAGGTCACGCATGAAGGGAGC ACCGTGGAGAAGACAGTGGCCCCTACAGAATGTTCA |
| 357 | Anti-CD122 P1D10 Fab HC (VH, joint CH1) | CAGGTGCAGCTACAGCAGTGGGGCCCAGGACTGGTGAAGCCTTCGGAGACCCTGT CCCTCACCTGCACTGTCTCTGGTGGCTCCATCAGTAGTTACTACTGGAGCTGGATCC GCCAGCCCCCAGGGAAGGGGCTGGAGTGGATTGGGGAAATCAATCATAGTGGAAG CACCAACTACAACCCGTCCCTCAAGAGTCGAGTCACCATATCAGTAGACACGTCCAA GAACCAGTTCTCCCTGAAGCTGAGCTCTGTGACCGCCGCGGACACGGCTGTGTATT ACTGTGCGGGAGGCTCTAATTTGGACTGGTTCGACCCCTGGGGCCAGGGAACCCTG GTCACCGTCTCAAGCGCCTCCACCAAGGGCCCATCGGTCTTCCCCCTGGCACCCTC CTCCAAGAGCACCTCTGGGGGCACAGCGGCCCTGGGCTGCCTGGTCAAGGACTAC TTCCCCGAACCGGTGACGGTGTCGTGGAACTCAGGCGCCCTGACCAGCGGCGTCC ACACCTTCCCGGCTGTCCTACAGTCCTCAGGACTCTACTCCCTCAGCAGCGTAGTGA CCGTGCCCTCCAGCAGCTTGGGCACCCAGACCTACATCTGCAACGTGAATCACAAG CCCAGCAACACCAAGGTGGACAAGAAAGTTGAGCCCAAATCTTGT |

-continued

Sequences

| SEQ ID NO: | DESCRIPTION | SEQUENCE |
|---|---|---|
| 358 | Anti-CD122 P1D10 scFv and Fc with knob modification | CAGGTCCAGCTGCAGCAGTGGGGGCCAGGACTGGTGAAGCCATCCGAAACTCTGT CTCTGACTTGTACCGTGAGCGGCGGGAGCATCAGCTCCTACTATTGGAGCTGGATC AGGCAGCCCCCTGGGAAGGGACTGGAGTGGATCGGCGAAATTAACCACAGCGGGT CCACTAACTACAATCCTTCCCTGAAATCTCGCGTGACTATTAGTGTGGACACCTCAAA GAATCAGTTCTCCCTGAAACTGTCTAGTGTGACAGCCGCTGATACCGCCGTGTACTA TTGCGCCGGCGGGTCTAACCTGGACTCTGGTTTGATCCCTGGGGACAGGGGACCCTG GTGACAGTGTCAAGCGGAGGAGGAGGAAGCGGCGGAGGAGGCTCCGGAGGAGGA GGGTCTCAGAGTGTGCTGACACAGCCACCATCAGTCAGCGGGGCCCCCGGACAGC GAGTGACCATCTCCTGTACAGGAGGCTCCTCTAATGTGGGAGCCGGCTACGACGTC CATTGGTATCAGCAGCTGCCTGGCACCGTGCCAAAGCTGCTGATCTACGACAACAC AAATCGGCCCAGCGGGGTGCCTGATAGATTCTCCGCTTCTAAAAGTGGCACATCAG CCAGCCTGGTCATCACTGGACTCCAGGCCGAGGACGAAGGCGATTACTATTGCCAG TCTTATGATAGTTCACTGAGAGCTAGTGTGTTTGGGGGAGGCACTATGCTGACCGTC CTGAACAGCGGCGCGGGCACCGCGGCCGCGACTCACACATGCCCACCGTGCCCAG CACCTGAAGCCGCGGGGGGACCGTCAGTCTTCCTCTTCCCCCCAAAACCCAAGGAC ACCCTCATGATCTCCCGGACCCCTGAGGTCACATGCGTGGTGGTGGACGTGAGCCA CGAAGACCCTGAGGTCAAGTTCAACTGGTACGTGGACGGCGTGGAGGTGCATAATG CCAAGACAAAGCCGCGGGAGGAGCAGTACAACAGCACGTACCGTGTGGTCAGCGT CCTCACCGTCCTGCACCAGGACTGGCTGAATGGCAAGGAGTACAAGTGCAAGGTCT CCAACAAAGCCCTGCCAGCCCCCATCGAGAAAACCATCTCCAAAGCCAAAGGGCAG CCCCGAGAACCACAGGTGTACACCCTGCCCCCATGCCGGGATGAGGTGACCAAGAA CCAGGTCAGCCTGTGGTGCCTGGTCAAAGGCTTCTATCCCAGCGACATCGCCGTGG AGTGGGAGAGCAATGGGCAGCCGGAGAACAACTACAAGACCACGCCTGCCGTGCT GGACTCCGACGGCTCCTTCTTCCTGTACAGCAAGCTCACCGTGGACAAGAGCAGGT GGCAGCAGGGGAACGTCTTCTCATGCTCCGTGATGCATGAGGCTCTGCACAACCAC TACACGCAGAAGAGCCTCTCCCTGTCTCCGGGTAAA |
| 359 | Anti-CD122 P1E1 Fab LC (VL, joint CL) | AATTTTATGCTGACTCAGGCCCACTCTGTGTCGGAGTCTCCGGGGAAGACGGTAAC CATCTCCTGCACCGGCAGCAGTGGCAGCATTGCCAGCAGCTATGTGCAGTGGTACC AGCAGCGCCCGGGCAGTGCCCCCACCACTGTGATCTATGCGGATAACCAAAGACCC TCTGGGGTCCCTGATCGGTTCTCTGGCTCCGTCGACAGCTCCTCCAACTCTGCCTC CCTCACCATCTCTGGACTGAAGACTGAGGACGAGGCTGACTACTACTGTCAGTCTTT TGACAGCAGCCTCTATATGATTTTTGGCGGAGGGACCAAGGGACCGTCCTAGGTC AGCCCAAGGCTGCCCCCTCGGTCACTCTGTTCCCGCCCTCCTCTGAGGAGCTTCAA GCCAACAAGGCCACACTGGTGTGTCTCATAAGTGACTTCTACCCGGGAGCCGTGAC AGTGGCCTGGAAGGCAGATAGCAGCCCCGTCAAGGCGGGAGTGGAGACCACCACA CCCTCCAAACAAAGCAACAACAAGTACGCGGCCAGCAGCTATCTGAGCCTGACGCC TGAGCAGTGGAAGTCCCACAGAAGCTACAGCTGCCAGGTCACGCATGAAGGGAGCA CCGTGGAGAAGACAGTGGCCCCTGCAGAATGCTCT |
| 360 | Anti-CD122 P1E1 Fab HC (VH, joint CH1) | CAGGTGCAGCTACAGCAGTGGGGCGCAGGACTGTTGAAGCCTTCGGAGACCCTGT CCCTCACCTGCGCTGTCTATGGTGGGTCCTTCAGTGGTTACTACTGGAGCTGGATC CGCCAGCCCCCAGGGAAGGGGCTGGAGTGGATTGGGGAAATCAATCATAGTGGAA GCACCAACTACAACCCGTCCCTCAAGAGTCGAGTCACCATATCAGTAGACACGTCCA AGAACCAGTTCTCCCTGGAGCTGAGCTCTGTGACCGCCGCGGACACGGCTGTGTAT TACTGTGCGAGAGCGGATCGTCGGTTCGGGGAGTTACGCTACTGGGGCCAGGGAA CCCTGGTCACCGTCTCAAGCGCCTCCACCAAGGGCCCATCGGTCTTCCCCCTGGCA CCCTCCTCCAAGAGCACCTCTGGGGGCACAGCGGCCCTGGGCTGCCTGGTCAAGG ACTACTTCCCCGAACCGGTGACGGTGTCGTGGAACTCAGGCGCCCTGACCAGCGG CGTCCACACCTTCCCGGCTGTCCTACAGTCCTCAGGACTCTACTCCCTCAGCAGCG TAGTGACCGTGCCCTCCAGCAGCTTGGGCACCCAGACCTACATCTGCAACGTGAAT CACAAGCCCAGCAACACCAAGGTGGACAAGAAAGTTGAGCCCAAATCTTGT |
| 361 | Anti-CD122 P1E1 scFv and Fc with knob modification | CAGGTCCAGCTGCAGCAGTGGGGAGCCGGACTGCTGAAGCCAAGTGAGACTCTGA GCCTGACATGCGCCGTGTATGGGGGAAGTTTTTCCGGCTACTATTGGTCTTGGATCA GACAGCCCCCTGGCAAGGGGCTGGAGTGGATCGGCGAAATTAACCACAGTGGGTC AACCAACTACAATCCCTCTCTGAAGAGTCGCGTGACAATTTCAGTGGACACTAGCAA AAATCAGTTCAGCCTGGAGCTGAGCAGCGTGACTGCCGCTGACACCGCCGTCTACT ATTGCGCACGAGCCGATCGGAGATTTGGCGAACTGCGGTATTGGGGACAGGGCAC ACTGGTGACTGTCTCTAGTGGAGGAGGAGGCAGTGGAGGAGGAGGGTCAGGAGGC GGGGGATCTAACTTCATGCTGACTCAGCCCCATAGCGTGTCCGAGTCTCCTGGGAA AACTGTCACCATCAGTTGTACAGGGTCAAGCGGATCTATTGCCTCCTCTTACGTGCA GTGGTATCAGCAGAGGCCAGGCTCCGCTCCCACCACAGTGATCTACGCAGACAACC AGAGGCCTAGCGGAGTGCCAGACCGCTTTAGTGGCTCAGTCGATAGTTCAAGCAAT AGCGCCTCCCTGACCATCTCCGGCCTGAAGACAGAGGACGAAGCTGATTACTATTG CCAGAGCTTCGATTCCTCTCTGTATATGATTTTTGGCGGGGGAACCAAACTGACAGT GCTGAACAGCGGCGCGGGCACCGCGGCCGCGACTCACACATGCCCACCGTGCCCA GCACCTGAAGCCGGGGGGGGACCGTCAGTCTTCCTCTTCCCCCCAAAACCCAAGGA CACCCTCATGATCTCCCGGACCCCTGAGGTCACATGCGTGGTGGTGGACGTGAGCC ACGAAGACCCTGAGGTCAAGTTCAACTGGTACGTGGACGGCGTGGAGGTGCATAAT GCCAAGACAAAGCCGCGGGAGGAGCAGTACAACAGCACGTACCGTGTGGTCAGCG TCCTCACCGTCCTGCACCAGGACTGGCTGAATGGCAAGGAGTACAAGTGCAAGGTC TCCAACAAAGCCCTCCCAGCCCCCATCGAGAAAACCATCTCCAAAGCCAAAGGGCA |

-continued

| SEQ ID NO: | DESCRIPTION | SEQUENCE |
|---|---|---|
| | | GCCCCGAGAACCACAGGTGTACACCCTGCCCCCATGCCGGGATGAGCTGACCAAG AACCAGGTCAGCCTGTGGTGCCTGGTCAAAGGCTTCTATCCCAGCGACATCGCCGT GGAGTGGGAGAGCAATGGGCAGCCGGAGAACAACTACAAGACCACGCCTCCCGTG CTGGACTCCGACGGCTCGTTGTTCCTCTACAGCAAGCTCACCGTGGACAAGAGCAG GTGGCAGCAGGGGAACGTCTTCTCATGCTCCGTGATGCATGAGGCTCTGCACAACC ACTACACGCAGAAGAGCCTCTCCCTGTCTCCGGGTAAA |
| 362 | Anti-CD122 P2B11 Fab LC (VL, joint CL) | CAGTCTGTGTTGACGCAGCCGCCCTCAGTGTCTGGGGCCCCAGGGCAGAGGGTCA CCATCTCCTGCACTGGGAGCCGCTCCAACATCGGGGCAGGTTATGATGTACACTGG TATCAGCATCTTCCAGGGACAGCCCCCAAACTCCTCATCTATGATAACAGCAATCGA CCCTCAGGTGTCTCTGACCGATTCTCTGGCTCCAAGTCTGGCACCTCAGCCTCCCT GGCCATCACTGGGCTCCAGGCTGAGGATGAGGCTGATTATTACTGCCAGTCCTTTG ACAGCAGCCTGAGGGGTGTGGTGTTCGGCGGAGGGACCAGGCTGACCGTCCTAAG TCAGCCCAAGGCTGCCCCCTCGGTCACTCTGTTCCCGCCCTCCTCTGAGGAGCTCC AAGCCAACAAGGCCACACTAGTGTGTCTGATCAGTGACTTCTACCCGGGAGCTGTG ACAGTGGCCTGGAAGGCAGATGGCAGCCCCGTCAAGGCGGGAGTGGAGACCACCA CACCCTCCAAACAAAGCAACAACAAGTACGCGGCCAGCAGCTACCTGAGCCTGACG CCTGAGCAGTGGAAGTCCCACAAAAGCTACAGCTGCCAGGTCACGCATGAAGGGAG CACCGTGGAGAAGACAGTGGCCCCTACAGAATGTTCA |
| 363 | Anti-CD122 P2B11 Fab HC (VH, joint CH1) | CAGGTCCAGCTGGTGCAGTCTGGGGGAGGCCTGGTCAAGCCTGGGGGGTCCCTGA GACTCTCCTGTGCAGCCTCTGGATTCACCTTCAGTAGTTATGACTTACACTGGGTCC GCCAGGTTCCAGGCAAGGGGCTGGAGTGGGTGTCACTTATATCATATGATGGAAGT AATAAATACTATGCAGACTGCGTGAAGGGCCGATTCACCATCTCCAGAGACAACGCC GAGAACTCACTGTATCTGCAAATGAACAGCCTGAGAGCTGAGGACACGGCTGTCTAT TACTGTGCGAGAGAGCCTATAACTGGAACTTCTGACCTCTTTGACTACTGGGGCCAG GGAACCCTGGTCACCGTCTCAAGCGCCTCCACCAAGGGCCCATCGGTCTTCCCCCT GGCACCCTCCTCCAAGAGCACCTCTGGGGGCACAGCGGCCCTGGGCTGCCTGGTG AAGGACTACTTCCCCGAACCGGTGACGGTGTCGTGGAACTCAGGCGCCCTGACCAG CGGCGTCCACACCTTCCCGGCTGTCCTACAGTCCTCAGGACTCTACTCCCTCAGCA GCGTAGTGACCGTGCCCTCCAGCAGCTTGGGCACCCAGACCTACATCTGCAACGTG AATCACAAGCCCAGCAACACCAAGGTGGACAAGAAAGTTGAGCCCAAATCTTGT |
| 364 | Anti-CD122 P2B11 scFv and Fc with knob modification | CAGGTGCAGCTGGTGCAGAGCGGGGGAGGACTGGTCAAGCCTGGAGGGTCACTGA GACTGTCATGTGCCGCAAGCGGATTCACTTTCAGCTCCTACGACCTGCACTGGGTG AGGCAGGTCCCCGGCAAGGGGCTGGAGTGGGTGTCTCTGATCAGTTATGACGGGA GTAACAAGTACTATGCCGATTCAGTCAAAGGACGGTTCACAATTTCCAGAGACAACG CTGAAAATTCTCTGTACCTCCAGATGAATAGTCTGCGCGCAGAGGATACTGCCGTGT ACTATTGCGCCAGAGAGCCTATCACCGGCACAAGCGACCTGTTTGATTATTGGGGA CAGGGCACTCTGGTGACCGTCTCTAGTGGCGGAGGAGGCTCCGGAGGAGGAGGGT CTGGAGGAGGAGGCAGCCAGTCTGTGCTGACCCAGCCACCTAGTGTCTCAGGCGC CCCTGGGCAGCGAGTGACCATCTCCTGTACAGGCAGCCGGTCCAACATTGGGGCA GGATACGACGTCCACTGGTATCAGCATCTGCCAGGCACAGCCCCCAAGCTGCTGAT CTACGACAACTCTAATAGGCCATCAGGGGTGAGCGATCGCTTCTCTGGAAGTAAATC AGGCACTAGCGCCTCCCTGGCTATTACCGGCCTCCAGGCTGAGGACGAAGCAGATT ACTATTGCCAGTCCTTCGATTCAAGCCTGAGAGGCGTGGTCTTTGGCGGGGGAACA AGGCTGACTGTGCTGAACAGCGGCGCGGGCACCGCGGCCGCGACTCACACATGCC CACCGTGCCCAGCACCTGAAGCCGCGGGGGGACCGTCAGTCTTCCTCTTCCCCCC AAAACCCAAGGACACCCTCATGATCTCCCGGACCCCTGAGGTCACATGCGTGGTGG TGGACGTGAGCCACGAAGACCCTGAGGTCAAGTTCAACTGGTACGTGGACGGCGTG GAGGTGCATAATGCCAAGACAAAGCCGCGGGAGGAGCAGTACAACAGCACGTACC GTGTGGTCAGCGTCCTCACCGTCCTGCACCAGGACTGGCTGAATGGCAAGGAGTAC AAGTGCAAGGTCTCCAACAAAGCCCTCCCAGCCCCCATCGAGAAAACCATCTCCAAAA GCCAAAGGGCAGCCCCGAGAACCACAGGTGTACACCCTGCCCCCATGCCGGGATG AGCTGACCAAGAACCAGGTCAGCCTGTGGTGCCTGGTCAAAGGCTTCTATCCCAGC GACATCGCCGTGGAGTGGGAGAGCAATGGGCAGCCGGAGAACAACTACAAGACCA CGCCTCCCGTGCTGGACTCCGACGGCTCCTTCTTCCTCTACAGCAAGCTCACCGTG GACAAGAGCAGGTGGCAGCAGGGGAACGTCTTCTCATGCTCCGTGATGCATGAGGC TCTGCACAACCACTACACGCAGAAGAGCCTCTCCCTGTCTCCGGGTAAA |
| 365 | Anti-CD122 P2C9 Fab LC (VL, joint CL) | TCCTATGAGCTGACTCAGCCACCCTCAGCGTCTGGGACCCCCGGGCAGAGGGTCA CCATCTCTTGTTCTGGAAGCAGCTCCAACATCGGAAGTAATACTGTAAACTGGTACC AGCAGCTCCCAGGAACGGCCCCCAAACTCCTCATCTATAGTAATAATCAGCGGCCCT CAGGGGTGGCCTGACCGATTCTCTGGCTCCAAGTCTGGCACCTCAGCCTCCCTGGCC ATCAGTGGGCTCCAGTCTGAGGATGAGGCTGATTATTACTGTGCAGCATGGGATGA CAGCCTGAATGGTCTTTTGGGTGTTCGGCGGAGGGACCAAGCTGACCGTCCTAGGTC AGCCCAAGGCTGCCCCCTCGGTCACTCTGTTCCCACCCTCCTCTGAGGAGCTTCAA GCCAACAAGGCCACACTGGTGTGTCTCATAAGTGACTTCTACCCGGGAGCCGTGAC AGTGGCCTGGAAGGCAGATAGCAGCCCCGTCAAGGCGGGAGTGGAGACCACCAAA CCCTCCAAACAGAGCAACAACAAGTACGCGGCCAGCAGCTACCTGAGCCTGACGCC CGAGCAGTGGAAGTCCCACAGAAGCTACAGGTGCCAGGTCACGCATGAAGGGAGC ACCGTGGAGAAGACAGTGGCCCCTACAGAATGTTCA |

-continued

Sequences

| SEQ ID NO: | DESCRIPTION | SEQUENCE |
|---|---|---|
| 366 | Anti-CD122 P2C9 Fab HC (VH, joint CH1) | CAGGTGCAGCTGCAGGAGTCGGGCCCAGGACTGGTGAAGCCTTCGGGGACCCTGT CCCTCACCTGCGCTGTCTCTGGTGGCTCCATCAGCAGTAGTAACTGGTGGAGTTGG GTCCGCCAGCCCCCAGGGAAGGGGCTGGAGTGGATTGGGGAAATCTATCATAGTG GGAGCACCAACTACAACCCGTCCCTCAAGAGTCGAGTCACCATATCAGTAGACAAGT CCAAGAACCAGTTCTCCCTGAAGCTGAGCTCTGTGACCGCCGCGGACACGGCCGTG TATTACTGTGTCAGAGAAGGGGGCTTACGGGAAGAGCAGTGGGGCCAGGGCACCC TGGTCACCGTCTCAAGCGCCTCCACCAAGGGCCCATCGGTCTTCCCCCTGGCACCC TCCTCCAAGAGCACCTCTGGGGGCACAGCGGCCCTGGGCTGCGTGGTCAAGGACT ACTTCCCCGAACCGGTGACGGTGTCGTGGAACTCAGGCGCCCTGACCAGCGGCGT CCACACCTTCCCGGCTGTCCTACAGTCCTCAGGACTCTACTCCCTCAGCAGCGTAGT GACCGTGCCCTCCAGCAGCTTGGGCACCCAGACCTACATCTGCAACGTGAATCACA AGCCCAGCAACACCAAGGTGGACAAGAAAGTTGAGCCCAAATCTTGT |
| 367 | Anti-CD122 P2C9 scFv and Fc with knob modification | CAGGTCCAGCTGCAGGAGTCCGGGCCAGGGCTGGTGAAACCAAGCGAAACACTGA GTCTGACATGTACCGTGAGTGGGGGGTCCATTAACAATAGTAACTACTATTGGTCAT GGATCAGACAGAGCCCTGGAAGAGGCCTGGAGTGGATCGGCGGGATCTACTTCAG CGGCACCACATACTATAACCCATCACTGCAGAGCCGGGTGACTATCTCCATTGACAC CTCTAAGAATCAGTTCAGCCTGAAGCTGAGCAGCGTGACCGCCGCTGATACAGCCA TCTACTATTGCGTCCGGCAGATGAATTACTATCACCTGGGCTCTAGTGTGGGGTTCG ACCCCTGGGGACAGGGAGCACTGGCCACCGTGTCAAGCGTCTCCTCTGGAGGAGG AGGCAGCGGCGGAGGAGGCTCTGGAGGAGGCGGGAGTGATGTGGTCATGACACA GAGCCCAGCTACTCTGTCTGTGAGTCCCGGCGAAAGGGCCACACTGAGCTGTCGC GCTTCACAGAGCGTCAGTTCAAACCTGGCATGGTACCAGCAGAAGCCAGGACAGGC ACCTTCCCTGCTGATCTATGAGGCTTCTACACGAGCAACTGGCATTCCTGCTAGATT CTCCGGCTCTGGGAGTGGAACCGACTTTACTCTGACCATCAGCTCCCTGCAGAGCG AAGATTTTGCAATCTACTATTGTCAGCAGTATAACGATTGGCTGTGGACCTTCGGGC AGGGGACTAAAGTGGAGATTCGGAACAGGGGCGCGGGCACCGCGGCCGCGACTCA CACATGCCCACCGTGCCCAGCACCTGAAGCCGCGGGGGGACCGTCAGTCTTCCTC TTCCCCCCAAAACCCAAGGACACCCTCATGATCTCCCGGACCCCTGAGGTCACATG CGTGGTGGTGGACGTGAGCCACGAAGACCCTGAGGTCAAGTTCAACTGGTACGTGG ACGGCGTGGAGGTGCATAATGCCAAGACAAAGCCGCGGGAGGAGCAGTACAACAG CACGTACCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAGAAAACC ATCTCCAAAGCCAAAGGGCAGCCCCGAGAACCACAGGTGTACACCCTGCCCCCATG CCGGGATGAGCTGACCAAGAACCAGGTCAGCCTGTGGTGCCTGGTCAAAGGCTTCT ATCCCAGCGACATCGCCGTGGAGTGGGAGAGCAATGGGCAGCCGGAGAACAACTA CAAGACCACGCCTCCCGTGCTGGACTCCGACGGCTCCTTCTTCCTCTACAGCAAGC TCACCGTGGACAAGAGCAGGTGGCAGCAGGGGAACGTCTTCTCATGCTCCGTGATG CATGAGGCTCTGCACAACCACTACACGCAGAAGAGCCTCTCCCTGTCTCCGGGTAA A |
| 368 | Anti-CD122 P2C10 Fab LC (VL, joint CL) | GATGTTGTGATGACTCAGTCTCCACTCTCCCTGCCCGTCACCCCTGGAGAGCCGGC CTCCATCTCCTGCAGGTCTAGTCAGAGGCTCCTGCATAGTAATGGATACAACTATGT GGATTGGTACCTGCAGAAACCAGGGCAGTCTCCACAGCTCCTGATCTATTTGGGTTC TAATCGGGCCTCCGGGGTCCCTGACAGGTTCAGTGGCAGTGGATCAGGCACAGATT TTACACTGAAAATCAGCAGAGTGGAGGCTGAGGATGTTGGGGTTTATTACTGCATGC AAGGTACACACTGGCCGTGGACGTTCGGCCAAGGGACCAAGGTGGAAATCAAACGA ACTGTGGCTGCACCATCTGTCTTCATCTTCCCGCCATCTGATGAGCAGTTGAAATCT GGAACTGCCTCTGTTGTGTGCCTGCTGAATAACTTCTATCCCAGAGAGGCCAAAGTA CAGTGGAAGGTGGATAACGCCCTCCAATCGGGTAACTCCCAGGAGAGTGTCACAGA GCAGGACAGCAAGGACAGCACCTACAGCCTCAGCAGCACCCTGACGCTGAGCAAA GGAGACTACGAGAAACACAAAGTCTACGCCTGCGAAGTCACCCATCAGGGCCTGAG CTCGCCCGTCACAAAGAGCTTCAACAGGGGAGAGTGT |
| 369 | Anti-CD122 P2C10 Fab HC (VH, joint CH1) | CAGGTGCAGCTACAGCAGTGGGGCGCAGGACTGTTGAAGCCTTCGGAGACCCTGT CCCTCACCTGCGCTGTCTATGGTGGGTCCTTCAGTGGTTACTACTGGAGCTGGATC CGCCAGCCCCCAGGGAAGGGGCTGGAGTGGATTGGGGAAATCAATCATAGTGGAA GCACCAACTACAACCCGTCCCTCAAGAGTCGAGTCACCATATCAGTAGACACGTCCA AGAACCAGTTCTCCCTGAAGCTGAGCTCTGTGACCGCCGCGGACACGGCTGTGTAT TACTGTGCGAGAGGCACGGATACAGCTATGGCTGACTACTGGGGCCAGGGAACCCT GGTCACCGTCTCAAGCGCCTCCACCAAGGGCCCATCGGTCTTCCCCCTGGCACCCT CCTCCAAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCGGCGTC CACACCTTCCCGGCTGTCCTACAGTCCTCAGGACTCTACTCCCTCAGCAGCGTAGT GACCGTGCCCTCCAGCAGCTTGGGCACCCAGACCTACATCTGCAACGTGAATCACA AGCCCAGCAACACCAAGGTGGACAAGAAAGTTGAGCCCAAATCTTGT |
| 370 | Anti-CD122 P2C10 scFv and Fc with knob modification | CAGGTCCAGCTGCAGGAGTCCGGGCCAGGGCTGGTGAAACCAAGCGAAACACTGA GTCTGACATGTACCGTGAGTGGGGGGTCCATTAACAATAGTAACTACTATTGGTCAT GGATCAGACAGAGCCCTGGAAGAGGCCTGGAGTGGATCGGCGGGATCTACTTCAG CGGCACCACATACTATAACCCATCACTGCAGAGCCGGGTGACTATCTCCATTGACAC CTCTAAGAATCAGTTCAGCCTGAAGCTGAGCAGCGTGACCGCCGCTGATACAGCCA TCTACTATTGCGTCCGGCAGATGAATTACTATCACCTGGGCTCTAGTGTGGGGTTCG |

-continued

Sequences

| SEQ ID NO: | DESCRIPTION | SEQUENCE |
|---|---|---|
| | | ACCCCTGGGGACAGGGAGCACTGGCCACCGTGTCAAGCGTCTCCTCTGGAGGAGG AGGCAGCGGCGGAGGAGGCTCTGGAGGAGGCGGGAGTGATGTGGTCATGACACA GAGCCCAGCTACTCTGTCTGTGAGTCCCGGCGAAAGGGCCACACTGAGCTGTCGC GCTTCACAGAGCGTCAGTTCAAACCTGGCATGGTACCAGCAGAAGCCAGGACAGGC ACCTTCCCTGCTGATCTATGAGGCTTCTACACGAGCAACTGGCATTCCTGCTAGATT CTCCGGCTCTGGGAGTGGAACCGACTTTACTGTGACCATCAGCTCCCTGCAGAGCG AAGATTTTGCAATCTACTATTGTCAGCAGTATAACGATTGGCTGTGGACCTTCGGGC AGGGGACTAAAGTGGAGATTCGGAACAGCGGCGCGGGCACCGCGGCCGCGACTCA CACATGCCCACCGTGCCCAGCACCTGAAGCCGCGGGGGGACCGTCAGTCTTCCTC TTCCCCCCAAAACCCAAGGACACCCTCATGATCTCCCGGACCCCTGAGGTCACATG CGTGGTGGTGGACGTGAGCCACGAAGACCCTGAGGTCAAGTTCAACTGGTACGTGG ACGGCGTGGAGGTGCATAATGCCAAGACAAAGCCGCGGGAGGAGCAGTACAACAG CACGTACCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAGAAAACC ATCTCCAAAGCCAAAGGGCAGCCCCGAGAACCACAGGTGTACACCGTGCCCCCATG CCGGGATGAGCTGACCAAGAACCAGGTCAGCCTGTGGTGCCTGGTCAAAGGCTTCT ATCCCAGCGACATCGCCGTGGAGTGGGAGAGCAATGGGCAGCCGGAGAACAACTA CAAGACCACGCCTCCCGTGCTGGACTCCGACGGCTCCTTCTTCCTCTACAGCAAGC TCACCGTGGACAAGAGCAGGTGGCAGCAGGGGAACGTCTTCTCATGCTCCGTGATG CATGAGGCTCTGCACAACCACTACACGCAGAAGAGCCTCTCCCTGTCTCCGGGTAA A |
| 371 | Anti-CD122 P2C11 Fab LC (VL, joint CL) | GACATCCAGATGACCCAGTCTCCACCCTCCCTGTCCGCATCTGTAGGAGACAGAGT CACCATCACTTGTCAGGCGAGTCAGGACATTAACAACTATTTGAATTGGTATCACCAA AAACCAGGGAAGGCCCCTGAGCTCCTGATCTACGATGCATCTCAGTTGGAAACAGG GGTCCCATCAAGGTTCAGTGGAAGTGGATCTGGGACAGAGTTTACTTTCATCATCAG CAGCCTGCAGCCTGAAGATACCGGTACATATTACTGTCAACAATATGATTGGCTCCC CCTTTCTTACGGCGGAGGGACCAAGGTTGAGATCAAACGAACTGTGGCTGCACCAT CTGTCTTCATCTTCCCGCCATCTGATGAGCAGTTGAAATCTGGAACTGCCTCTGTTG TGTGCCTGCTGAATAACTTCTATCCCAGGGAGGCCAAAGTACAGTGGAAGGTGGAT AACGCCCTCCAATCGGGTAACTCCCAGGAGAGTGTCACAGAGCAGGACAGCAAGGA CAGCACCTACAGCCTCAGCAGCACCCTGACGCTGAGCAAAGCAGACTACGAGAAAC ACAAAGTCTACGCCTGCGAAGTCACCCATCAGGGCCTGAGCTCGCCCGTCACAAAG AGCTTCAACAGGGGAGAGTGT |
| 372 | Anti-CD122 P2C11 Fab HC (VH, joint CH1) | CAGGTACAGCTGCAGCAGTCAGGTCCAGGACTGGTGAAGCCCTCGCAGACCCTCTC ACTCACCTGTGCCATCTCCGGGGACAGTGTCTCTGGCAACAGTGCTACTTGGAACT GGATCAGGCAGTCCCCATCGCGAGGCCTTGAGTGGCTGGGAAGGACATATTACAGG TCCAAGTGGAATCATGATTATGCAGAATCTGTGAAAAGTCGAATAACCATCAACCCA GACACATCCAAGAACCAGTTCTCCCTGCAGCTGAACTCTGTGACTCCCGAGGACAC GGCTGTCTATTACTGTGCAAGAGACTCCAAGTCTGCTTTTGATATCTGGGGCCAAGG GACAATGGTCACCGTCTCAAGCGCCTCCACCAAGGGCCCATCGGTCTTCCCCCTGG CACCCTCCTCCAAGAGCACCTCTGGGGGCACAGCGGCCCTGGGCTGCCTGGTCAA GGACTACTTCCCCGAACCGGTGACGGTGTCGTGGAACTCAGGCGCCCTGACCAGC GGCGTCCACACCTTCCCGGCTGTCCTACAGTCCTCAGGACTCTACTCCCTCAGCAG CGTAGTGACCGTGCCCTCCAGCAGCTTGGGCACCCAGACCTACATCTGCAACGTGA ATCACAAGCCCAGCAACACCAAGGTGGACAAGAAAGTTGAGCCCAAATCTTGT |
| 373 | Anti-CD122 P2C11 scFv and Fc with knob modification | CATGTGCAGCTGGTGGAGACTGGAGGGGGACTGGTGCAGCCTGGGGGGTCACTGA GACTGAGTTGTGCCGCTTCTGGGTTCACTTTCAGCTCCTACGCAATGAGCTGGGTG CGGCAGGCCCCCGGAAAAGGCCTGGAGTGGGTCTCCGCCATCAGTGGATCAGGCG GGAGCACCTACTATGCTGACTCCGTGAAAGGCCGGTTCACTATTAGCAGAGATAACT CCAAGAATACCCTGTACCTCCAGATGAACTCCCTGAGGGCCGAAGACACAGCTGTC TACTATTGCGCTCGCGACCTGGGCGATTATTGGGGGCAGGGAACACTGGTGACTGT CTCTAGTGGAGGAGGAGGATCTGGAGGAGGAGGCAGTGGAGGAGGCGGGTCAGA CATCCAGCTGACTCAGTCTCCTTCAAGCCTGAGCGCATCCATGGGGGACCGAGTCA CCATCACATGTCAGGCCAGCCAGGATATTGGCAACTACCTGAATTGGTATCAGCTGA AGCCCGGCAAGGCTCCTAAGCTGCTGATCTACGACGCATCTAATCTGGAGACAGGC GTGCCAAGTAGATTCTCTGGCAGTGGGTCAGGAACTGATTTCACCTTCACCATCAGC AGCCTCCAGCCAGAGGACATTGCCACATACTATTGCCTCCAGCTGTACGATTATCCC CTGACCTTTGGAGGCGGGACAAAAGTGGAAATCAAGAACAGCGGCGCGGGCACCG CGGCCGCGACTCACACATGCCCACCGTGCCCAGCACCTGAAGCCGCGGGGGGACC GTCAGTCTTCCTCTTCCCCCCAAAACCCAAGGACACCCTCATGATCTCCCGGACCCC TGAGGTCACATGCGTGGTGGTGGACGTGAGCCACGAAGACCCTGAGGTCAAGTTCA ACTGGTACGTGGACGGCGTGGAGGTGCATAATGCCAAGACAAAGCCGCGGGAGGA GCAGTACAACAGCACGTACCGTGTGGTCAGCGTCCTCACCGTCCTGCACCAGGACT GGCTGAATGGCAAGGAGTACAAGTGCAAGGTCTCCAACAAAGCCCTCCCAGCCCCC ATCGAGAAAACCATCTCCAAAGCCAAAGGGCAGCCCCGAGAACCACAGGTGTACAC CCTGCCCCCATGCCGGGATGAGCTGACCAAGAACCAGGTCAGCCTGTGGTGCCTG GTCAAAGGCTTCTATCCCAGCGACATCGCCGTGGAGTGGGAGAGCAATGGGCAGC CGGAGAACAACTACAAGACCACGCCTCCCGTGCTGGACTCCGACGGCTCCTTCTTC CTCTACAGCAAGCTCACCGTGGACAAGAGCAGGTGGCAGCAGGGGAACGTCTTCTC ATGCTCCGTGATGCATGAGGCTCTGCACAACCACTACACGCAGAAGAGCCTCTCCC TGTCTCCGGGTAAA |

-continued

Sequences

| SEQ ID NO: | DESCRIPTION | SEQUENCE |
|---|---|---|
| 374 | Anti-CD122 P2E6 Fab LC (VL, joint CL) | AATTTTATGCTGACTCAGCCCCACTCTGTGTCGGGGTCTCCGGGGAAGACGATAAC CATCTCCTGCACCCGCAGCAGTGGCAACTTTGCCAGCACCTATGTGCAGTGGTACC AACAGCGCCCGGGCAGTTCCCCCGCCATTGTGATCTATGACGATGATCAACGACCC TCTGGTGTCCCTGACCGCTTCTCTGGCTCCATCGACAGGTCCTCCAACTCTGCCTCC CTCACCATCTCTGGACTGGAGACTGAGGACGAGGCTGACTACTATTGTCAGTCTTAT GATAGCAGCAATTTTTGGGTGTTCGGCGGAGGGACCAAACTGACCGTCCTAGGTCA GCCCAAGGCTGCCCCCTCGGTCACTCTGTTCCCACCCTCCTCTGAGGAGCTTCAAG CCAACAAGGCCACACTGGTGTGTCTCATAAGTGACTTCTACCCGGGAGCCGTGACA GTGGCCTGGAAGGCAGATAGCAGCCCCGTCAAGGCGGGAGTGGAGACCACCACAC CCTCCAAACAAAGCAACAACAAGTACGCGGCCAGCAGCTACCTGAGCCTGACGCCT GAGCAGTGGAAGTCCCACAAAAGCTACAGCTGCCAGGTCACGCATAAGGGAGCAC CGTGGAGAAGACAGTGGCCCCTACAGAATGTTCA |
| 375 | Anti-CD122 P2E6 Fab HC (VH, joint CH1) | CAGCTGCAGCTGCAGGAGTCGGGCCCAGGACTGGTGAAGCCTTCGGAGACCCTGT CCCTCACCTGCAGTGTCTTTGGTGTCTCCATCACCAGTGGTAGTTGGTGGAGTTGG GTCCGCCAGTCCCCAGGGAAGGAGCTGGAGTGGATAGGCGAAATCTATCATAATGG GAACACCAACTACAACCCGTCCCTCAAGAGTCGAGTCACCATATCGGTTGACACGTC CAAGAACCAGTTCTCCCTGAAACTGAGCTCTGTGACCGCCGCAGACACGGCTGTCT ATTACTGTGTCTCCGGATTTGACTACTGGGGCCAGGGAACCCTGGTCACCGTCTCAA GCGCCTCCACCAAGGGCCCATCGGTCTTCCCCCTGGCACCCTCCTCCAAGAGCACC TCTGGGGGCACAGCGGCCCTGGGCTGCCTGGTCAAGGACTACTTCCCCGAACCGG TGACGGTGTCGTGGAACTCAGGCGCCCTGACCAGCGGCGTCCACACCTTCCCGGC TGTCCTACAGTCCTCAGGACTCTACTCCCTCAGCAGCGTAGTGACCGTGCCCTCCA GCAGCTTGGGCACCCAGACCTACATCTGCAACGTGAATCACAAGCCCAGCAACACC AAGGTGGACAAGAAAGTTGAGCCCAAATCTTGT |
| 376 | Anti-CD122 P2E6 scFv and Fc with knob modification | GCCTGACTTGTTCTGTCTTTGGAGTGAGCATCACTTCTGGAAGTTGGTGGAGCTGGG TGAGACAGTCCCCCGGCAAGGAGCTTGGAATGGATCGGGGAAATCTACCACAACGGA AATACAAACTATAATCCTTCCCTGAAATCTCGGGTGACTATCAGTGTCGATACCTCAA AGAACCAGTTCAGCCTGAAGCTGAGCAGCGTGACCGCCGCTGATACAGCCGTGTAC TATTGCGTCAGCGGCTTTGACTACTGGGGCCAGGGGACTCTGGTGACCGTCTCTAG TGGAGGAGGAGGCTCTGGAGGAGGAGGGAGTGGAGGAGGAGGCAGCAACTTCATG CTGACCCAGCCTCATTCAGTGAGCGGCAGCCCCGGCAAGACCATCACAATTTCTTG TACCCGCTCAAGCGGGAATTTTGCTAGCACATACGTGCAGTGGTATCAGCAGCGAC CCGGCTCCTCTCCTGCAATCGTGATCTACGACGATGACCAGCGACCAAGCGGCGTC CCCGATAGATTCTCTGGGAGTATCGACAGGAGTTCAAACTCAGCAAGCCTGACAATT AGCGGCCTGGAGACTGAAGATGAGGCCGACTACTATTGCCAGTCCTATGACAGCTC CAATTTCTGGGTGTTTGGCGGGGGAACAAAACTGACTGTCCTGAACAGCGGCGCGG GCACCGCGGCCGCGACTCACACATGCCCACCGTGCCCAGCACCTGAAGCCGCGGG GGGACCGTCAGTCTTCCTCTTCCCCCCAAAACCCAAGGACACCCTCATGATCTCCC GGACCCCTGAGGTCACATGCGTGGTGGTGGACGTGAGCCACGAAGACCCTGAGGT CAAGTTCAACTGGTACGTGGACGGCGTGGAGGTGCATAATGCCAAGACAAAGCCGC GGGAGGAGCAGTACAACAGCACGTACCGTGTGGTCAGCGTCCTCACCGTCCTGCAC CAGGACTGGCTGAATGGCAAGGAGTACAAGTGCAAGGTCTCCAACAAAGCCCTCCC AGCCCCCATCGAGAAAACCATCTCCAAAGCCAAAGGGCAGCCCCGAGAACCACAGG TGTACACCCTGCCCCCATGCCGGGATGAGCTGACCAAGAACCAGGTCAGCCTGTGG TGCCTGGTCAAAGGCTTCTATCCCAGCGACATCGCCGTGGAGTGGGAGAGCAATGG GCAGCCGGAGAACAACTACAAGACCACGCCTCCCGTGCTGGACTCCGACGGCTCCT TCTTCCTCTACAGCAAGCTCACCGTGGACAAGAGCAGGTGGCAGCAGGGGAACGTC TTCTCATGCTCCGTGATGCATGAGGCTCTGCACAACCACTACACGCAGAAGAGCCTC TCCCTGTCTCCGGGTAAA |
| 377 | Anti-CD122 P2E11 Fab LC (VL, joint CL) | GAAATTGTGTTGACGCAGTCTCCATCCTCCCTGTCTGCATCTGTAGGAGACAGAGTC ACCATCACTTGCCAGGCGAGTCAGGACATTAATAATTATTTAAATTGGTATCAGCAGA AACCAGGGAAAGCCCCTAAGCTCCTGATCTACGATGCATCCAATTTGGAAACAGGG GTCCCATCAAAGTTCAGTGGAAGTGGATCTGGGACAGATTTTACTTTCACCATCAGC AGCCTGCAGCCTGAAGATATTGCAACATATTACTGTCAACAGTATGCCAATCTCCCC TCTTTTGGCCAGGGGACCAAGCTGGAGATCAAACGAACTGTGGCTGCACCATCTGT CTTCATCTTCCCGCCATCTGATGAGCAGTTGAAATCTGGAACTGCCTCTGTTGTGTG CCTGCTGAATAACTTCTATCCCAGAGAGGCCAAAGTACAGTGGAAGGTGGATAACG CCCTCCAATCGGGTAACTCCCAGGAGAGTGTCACAGAGCAGGACAGCAAGGACAGC ACCTACAGCCTCAGCAGCACCCTGACGCTGAGCAAAGCAGACTACGAGAAACACAA AGTCTACGCCTGCGAAGTCACCCATCAGGGCCTGAGCTCGCCCGTCACAAAGAGCT TCAACAGGGGAGAGTGT |
| 378 | Anti-CD122 P2E11 Fab HC (VH, joint CH1) | CAGGTGCAGCTGCAGGAGTCCGGCCCAGGACTGGTGAAGCCTTCGGAGACCCTGT CTCTCACCTGCACTGTCTCTGGTGTCTCCATCAGCAGTAGAAGTGACCACTGGGGCT GGGTCCGCCAGCCCCCAGGGAAGGGGCTGGAGTGGATTGGAAGTATCTCTTATAGT GGGAGCACCTACTACAACCCGTCCCTCAAGAGCCGAGTCACCATATCCGTAGACAC CTCCAAGAACCAACTCTCCCTGAAGCTGAGCTCTGTGACCGCCGCAGACACGGCTG TGTATTACTGTGCGAGAGACTTCGCACCCAGCAGCTGCACTGGTTGGGTGGGGCCAG GGCACCCTGGTCACCGTCTCAAGCGCCTCCACCAAGGGCCCATCGGTCTTCCCCCT GGCACCCTCCTCCAAGAGCACCTCTGGGGGCACAGCGGCCCTGGGCTGCCTGGTC |

-continued

| SEQ ID NO: | DESCRIPTION | SEQUENCE |
|---|---|---|
| | | AAGGACTACTTCCCCGAACCGGTGACGGTGTCGTGGAACTCAGGCGCCCTGACCAG CGGCGTCCACACCTTCCCGGCTGTCCTACAGTCCTCAGGACTCTACTCCCTCAGCA GCGTAGTGACCGTGCCCTCCAGCAGCTTGGGCACCCAGACCTACATCTGCAACGTG AATCACAAGCCCAGCAACACCAAGGTGGACAAGAAACTTGAGCCCAAATCTTGT |
| 379 | Anti-CD122 P2E11 scFv and Fc with knob modification | CAGGTGCAGCTGCAGGAAAGCGGACCCGGACTGGTGAAGCCTAGCGAGACTCTGA GCCTGACTTGTACCGTGAGCGGCGTGAGCATTAGCTCCCGGAGCGACCACTGGGG ATGGGTGAGACAGCCCCCTGGCAAAGGGCTGGAGTGGATCGGGAGCATTTCCTACT CTGGAAGTACTTACTATAACCCCTCACTGAAGAGCAGGGTGACTATCTCCGTGGACA CCTCTAAAAATCAGCTGTCTCTGAAGCTGTCTAGTGTGACCGCCGCTGATACAGCAG TCTACTATTGCGCCCGCGAGTCCCATCCTGCCGCCGCCCTGGTGGGATGGGGACA GGGGACACTGGTGACTGTCTCAAGCGGAGGAGGAGGCAGTGGAGGAGGAGGGTCA GGAGGCGGGGGAAGCGAAATCGTCCTGACACAGAGTCCATCCTCTCTGTCAGCCAG CGTGGCGCGACCGAGTCACCATCACATGTCAGGCCTCCCAGGATATTAACAATTACCT GAACTGGTATCAGCAGAAGCCAGGCAAAGCTCCCAAGCTGCTGATCTACGATGCAT CCAATCTGGAAACAGGGGTGCCCTCTAAATTCTCCGGATCTGGCAGTGGGACTGAC TTCACCTTCACCATCAGCAGCCTCCAGCCTGAGGATATTGCCACCTACTATTGCCAG CAGTATGCTAACCTGCCCAGCTTCGGACAGGGCACAAAACTGGAAATTAAGAACAG CGGCGCGGGCACCGCGGCCGCGACTCACACATGCCCACCGTGCCCAGCACCTGAA GCCGCGGGGGGACCGTCAGTCTTCCTCTTCCCCCCAAAACCCAAGGACACCCTCAT GATCTCCCGGACCCCTGAGGTCACATGCGTGGTGGTGGACGTGAGCCACGAAGAC CCTGAGGTCAAGTTCAACTGGTACGTGGACGGCGTGGAGGTGCATAATGCCAAGAC AAAGCCGCGGGAGGAGCAGTACAACAGCACGTACCGTGTGGTCAGCGTCCTCACC GTCCTGCACCAGGACTGGCTGAATGGCAAGGAGTACAAGTGCAAGGTCTCCAACAA AGCCCTCCCAGCCCCCATCGAGAAAACCATCTCCAAAGCCAAAGGGCAGCCCCGAG AACCACAGGTGTACACCCTGCCCCCATGCCGGGATGAGCTGACCAAGAACCAGGTC AGCCTGTGGTGCCTGGTCAAAGGCTTCTATCCCAGCGACATCGCCGTGGAGTGGGA GAGCAATGGGCAGCCGGAGAACAACTACAAGACCACGCCTCCCGTGCTGGACTCC GACGGCTCCTTCTTCCTCTACAGCAAGCTCACCGTGGACAAGAGCAGGTGGCAGCA GGGGAACGTCTTCTCATGCTCCGTGATGCATGAGGCTCTGCACAACCACTACACGC AGAAGAGCCTCTCCCTGTCTCCGGGTAAA |
| 380 | Anti-CD122 P2F9 Fab LC (VL, joint CL) | GAAATTGTGCTGACTCAGTCTCCACTCTCCCTGCCCGTCACCCCTGGAGAGCCGGC CTCCATCTCCTGCAGGTCTAGTCAGAGCCTCCTGCATAGTAATGGATACAACTATTT GGATTGGTACCTGCAGAAGCCAGGGCAGTCTCCACAGCTCCTGATCTATTTGGGTT CTAATCGGGCCTCCGGGGTCCCTGACAGGTTCAGTGGCAGTGGATCAGGCACAGAT TTTACACTGAGCATCAGCAGAGTGGAGGCTGAGGATGTTGGGGTTTATTACTGCATG CAAGCTCTACAAACTCCTCCGACGTTCGGCCAAGGGACCAAGGTGGAAATCAAACG AACTGTGGCTGCACCATCTGTCTTCATCTTCCCGCCATCTGATGAGCAGTTGAAATC TGGAACTGCCTCTGTTGTGTGCCTGCTGAATAACTTCTATCCCAGAGAGGCCAAAGT ACAGTGGAAGGTGGATAACGCCCTCCAATCGGGTAACTCCCAGGAGAGTGTCACAG AGCAGGACAGCAAGGACAGCACCTACAGCCTCAGCAGCACCCTGACGCTGAGCAAA GCAGACTACGAGAAACACAAAGTCTACGCCTGCGAAGTCACCCATCAGGGCCTGAG CTCGCCCGTCACAAAGAGCTTCAACAGGGGAGAGTGT |
| 381 | Anti-CD122 P2F9 Fab HC (VH, joint CH1) | GAGGTCCAGCTGGTACAGTCTGGGGCTGAGGTGAAGAAGCCTGGGTCCTCGGTGA AGGTCTCCTGCAAGGCTTCTGGTTACACCTTTACCAGCTATGGTATCAGCTGGGTGC GACAGGCCCCTGGACAAGGGCTTGAGTGGATGGGATGGATCAGCGCTTACAATGGT AACACAAACTATGCACAGAAGCTCCAGGGCAGAGTCACCATGACCACAGACACATC CACGAGCACAGCCTACATGGAGCTGAGCAGCCTGAGATCTGAGGACACGGCCGTG TATTACTGTGCGAGAGCCCCTGACTACGGTGACTCCTCCAACTACTACTACTACTAC ATGGACGTCTGGGGCAAAGGGACCACGGTCACCGTCTCAAGCGCCTCCACCAAGG GCCCATCGGTCTTCCCCCTGGCACCCTCCTCCAAGAGCACCTCTGGGGGCACAGC GGCCCTGGGCTGCCTGGTCAAGGACTACTTCCCCGAACCGGTGACGGTGTCGTGG AACTCAGGCGCCCTGACCAGCGGCGTCCACACCTTCCCGGCTGTCCTACAGTCCTC AGGACTCTACTCCCTCAGCAGCGTAGTGACCGTGCCCTCCAGCAGCTTGGGCACCC AGACCTACATCTGCAACGTGAATCACAAGCCCAGCAACACCAAGGTGGACAAGAAA GTTGAGCCCAAATCTTGT |
| 382 | Anti-CD122 P2F9 scFv and Fc with knob modification | GAAGTGCAGCTGGTGCAGAGCGGGGCAGAGGTGAAAAAACCTGGGTCATCCGTCA AAGTCTCCTGTAAGGCAAGCGGCTACACATTTACTTCATACGGCATCAGCTGGGTGC GACAGGCCCCTGGCCAGGGGCTGGAGTGGATGGGATGGATTAGCGCATATAACGG CAATACAAACTACGCCCAGAAGCTCCAGGGGAGAGTGACTATGACCACAGACACAA GTACTTCAACCGCCTATATGGAGCTGAGCAGCCTGAGGTCCGAAGATACCGCTGTG TACTATTGCGCCCGCGCTCCTGACTACGGCGATTCTAGTAACTACTACTACTACTAC ATGGACGTCTGGGGAAAAGGCACTACCGTGACAGTCTCAAGCGGCGGAGGAGGCT CCGGAGGAGGAGGGTCTGGAGGAGGAGGAAGCGAGATCGTGCTGACTCAGTCTCC ACTGAGTCTGCCAGTCACCCCCGGCGAACCTGCAAGCATTTCCTGTCGGTCCTCTC AGTCCCTGCTGCACTCTAATGGGTATAACTACCTGGACTGGTACTTGCAGAAGCCAG GACAGTCTCCCCAGCTGCTGATCTACCTGGGCAGTAACCGAGCTAGCGGGGTGCCT GACAGATTCTCTGGGAGTGGATCAGGCACAGATTTTACTCTGAGCATCAGCCGGGT GGAGGCTGAAGATGTGGGCGTCTATTACTGCATGCAGGCCCTCCAGACCCCCCCTA CATTCGGGCAGGGAACCAAGGTGGAAATCAAAAACAGCGGCGCGGGCACCGCGGC CGCGACTCACACATGCCCACCGTGCCCAGCACCTGAAGCCGCGGGGGGACCGTCA |

-continued

Sequences

| SEQ ID NO: | DESCRIPTION | SEQUENCE |
|---|---|---|
| | | GTCTTCCTCTTCCCCCCAAAACCCAAGGACACCCTCATGATCTCCCGGACCCCTGAG GTCACATGCGTGGTGGTGGACGTGAGCCACGAAGACCCTGAGGTCAAGTTCAACTG GTACGTGGACGGCGTGGAGGTGCATAATGCCAAGACAAAGCCGCGGGAGGAGCAG TACAACAGCACGTACCGTGTGGTCAGCGTCCTCACCCGTCCTGCACCAGGACTGGCT GAATGGCAAGGAGTACAAGTGCAAGGTCTCCAACAAAGCCCTCCCAGCCCCCATCG AGAAAACCATCTCCAAAGCCAAAGGGCAGCCCCGAGAACCACAGGTGTACACCCTG CCCCCATGCCGGGATGAGCTGACCAAGAACCAGGTCAGCCTGTGGTGCCTGGTCAA AGGCTTCTATCCCAGCGACATCGCCGTGGAGTGGGAGAGCAATGGGCAGCCGGAG AACAACTACAAGACCACGCCTCCCGTGCTGGACTCCGACGGCTCCTTCTTCCTCTAC AGCAAGCTCACCGTGGACAAGAGCAGGTGGCAGCAGGGGAACGTCTTCTCATGCTC CGTGATGCATGAGGCTCTGCACAACCACTACACGCAGAAGAGCCTCTCCCTGTCTC CCCGTAAA |
| 383 | Anti-CD122 P2F10 Fab LC (VL, joint CL) | GACATCCAGTTGACCCAGTCTCCATCCTCCCTGTCTGCATCTGTAGGAGACAGAGTC ACCGTCACTTGCCAGGCGAGCCAGGACATTGGCCACAATTTAAATTGGTATCAGCAG AGACCTGGGAAAGCCCCTCAGCTCCTGATCTACGATGCATCCAATTTGGAAACAGG GGTCCCATCAAGGTTCAGTGGAAGTGGATCTGGGACACAATTTACTTTCACCATCAG CAGTCTGCAGCCTGAAGATATTGCAACATATTACTGTCAACAATATGATTTTCTCCCT CCTGACTTCGGCCCAGGGACCAAAGTGGAGATCAAACGAACTGTGGCTGCACCATC TGTCTTCATCTTCCCGCCATCTGATGAGCAGTTGAAATCTGGAACTGCCTCTGTTGT GTGCCTGCTGAATAACTTCTATCCCAGAGAGGCCAAAGTACAGTGGAAGGTGGATAA CGCCCTCCAATCGGGTAACTCCCAGGAGAGTGTCACAGAGCAGGACAGCAAGGACA GCACCTACAGCCTCAGCAGCACCCTGACGCTGAGCAAAGCAGACTACGAGAAACAC AAAGTCTACGCCTGCGAAGTCACCCATCAGGGCCTGAGCTCGCCCGTCACAAAGAG CTTCAACAGGGGAGAGTGT |
| 384 | Anti-CD122 P2F10 Fab HC (VH, joint CH1) | CAGGTCCAGCTGGTGCAGTCTGGAGCTGAGGTGAAGAAGCCTGGGGCCTCAGTGA AGGTCTCCTGCAAGGCTTCTGGTTACACCTTTACCAGCTATGGTATCAGCTGGGTGC GACAGGCCCCTGGACAAGGGCTTGAGTGGATGGGATGGATCAGCGCTTACAATGGT AACACAAACTATGCACAGAAGCTCCAGGGCAGAGTCACCATGACCACAGACACATC CACGAGCACAGCCTACATGGAGCTGAGGAGCCTGAGATCTGACGACACGGCCGTG TATTACTGTGCGAGAGATACCTCCGGGGACTATAGCAGTGGCTGGTACCTAGGAGT TCCTTTTGACTACTGGGGCCAGGGCACCCTGGTCACCGTGTCAAGCGCCTCCACCA AGGGCCCATCGGTCTTCCCCCTGGCACCCTOCTCCAAGAGCACCTCTGGGGGCACA GCGGCCCTGGGCTGCCTGGTCAAGGACTACTTCCCCGAACCGGTGACGGTGTCGT GGAACTCAGGCGCCCTGACCAGCGGCGTCCACACCTTCCCGGCTGTCCTACAGTCC TCAGGACTCTACTCCCTCAGCAGCGTAGTGACCGTGCCCTCCAGCAGCTTGGGCAC CCAGACCTACATCTGCAACGTGAATCACAAGCCCAGCAACACCAAGGTGGACAAGA AAGTTGAGCCCAAATCTTGT |
| 385 | Anti-CD122 P2F10 scFv and Fc with knob modification | CAGGTGCAGCTGGTCCAGAGCGGAGCCGAGGTGAAGAAGCCCGGAGCATCAGTGA AAGTCAGTTGTAAAGCAAGCGGATACACATTTACATCTTACGGCATCAGTTGGGTGC GACAGGCACCAGGCCAGGGGCTGGAGTGGATGGGATGGATTTCTGCATACAACGG CAATACAAACTATGCCCAGAAGCTCCAGGGGAGAGTCACTATGACCACAGACACTA GTACCTCAACAGCTTACATGGAACTGCGGAGCCTGAGATCCGACGATACTGCCGTG TACTATTGCGCTCGGGACACCAGCGGCGATTACAGCTCCGGCTGGTATCTGGGGGT CCCCTTCGACTATTGGGGACAGGGCACCCTGGTGACAGTCTCTAGTGGCGGGGGA GGCTCAGGAGGAGGAGGGAGCGGAGGAGGAGGCAGCGACATCCAGCTGACCCAG AGCCCTTCAAGCCTGAGCGCATCCGTGGGCGACAGGGTGACTGTCACCTGCCAGG CTTCCCAGGACATCGGGCACAATCTGAACTGGTATCAGCAGCGCCCAGGAAAAGCT CCCCAGCTGCTGATCTACGACGCATCTAATCTGGAGACCGGCGTGCCCAGTCGGTT TTCTGGGAGTGGATCAGGCACACAGTTCACCTTCACCATCAGCAGCCTCCAGCCTG AGGATATTGCCACTTACTATTGTCAGCAGTATGACTTCCTGCCCCCTGATTTTGGGC CAGGAACCAAGGTGGAGATCAAGAACAGCGGCGCGGGCACCGCGGCCGCGACTCA CACATGCCCACCGTGCCCAGCACCTGAAGCCGCGGGGGGACCGTCAGTCTTCCTC TTCCCCCCAAAACCCAAGGACACCCTCATGATCTCCCGGACCCCTGAGGTCACATG CGTGGTGGTGGACGTGAGCCACGAAGACCCTGAGGTCAAGTTCAACTGGTACGTGG ACGGCGTGGAGGTGCATAATGCCAAGACAAAGCCGCGGGAGGAGCAGTACAACAG CACGTACCGTGTGGTCAGCGTCCTCACCGTCCTGCACCAGGACTGGCTGAATGGCA AGGAGTACAAGTGCAAGGTCTCCAACAAAGCCCTCCCAGCCCCCATCGAGAAAACC ATCTCCAAAGCCAAAGGGCAGCCCCGAGAACCACAGGTGTACACCCTGCCCCCATG CCGGGATGAGCTGACCAAGAACCAGGTCAGCGTGTGGTGCCTGGTCAAAGGCTTCT ATCCCAGCGACATCGCCGTGGAGTGGGAGAGCAATGGGCAGCCGGAGAACAACTA CAAGACCACGCCTCCCGTGCTGGACTCCGACGGCTCCTTCTTCCTCTACAGCAAGC TCACCGTGGACAAGAGCAGGTGGCAGCAGGGGAACGTCTTCTCATGCTCCGTGATG CATGAGGCTCTGCACAACCACTACACGCAGAAGAGCCTCTCCCTGTCTCCGGGTAA A |
| 386 | Anti-CD132 P1A3 Fab LC (VL, joint CL) | GATGTTGTGATGACTCAGTCTCCACTCTCCCTGCCCGTCACCCCTGGAGAGCCGGC CTCCATCTCCTGCAGGTCTAGTCAGAGCCTCCTGCATAGTAATGGATACAACTATTT GGATTGGTACCTGCAGAAGCCAGGGCAGTCTCCACAGCTCCTGATCTATTTGGGTT CTAACCGGGACTCTGGGGTCCCAGACAGATTCAGCGGCAGTGGGTCAGGCACTGAT TTCACACTGAAAATCAGCAGGGTGGAGGCTGAGGATGTTGGGGTTTATTACTGCATG CAAGGTACACACTGGCCGTGGACGTTCGGCCAAGGGACCAAGGTGGAAATCAAACG |

-continued

| Sequences | | |
|---|---|---|
| SEQ ID NO: | DESCRIPTION | SEQUENCE |
| | | AACTGTGGCTGCACCATCTGTCTTCATCTTCCCGCCATCTGATGAGCAGTTGAAATC TGGAACTGCCTCTGTTGTGTGCCTGCTGAATAACTTCTATCCCAGAGAGGCCAAAGT ACAGTGGAAGGTGGATAACGCCCTCCAATCGGGTAACTCCCAGGAGAGTGTCACAG AGCAGGACAGCAAGGACAGCACCTACAGCCTCAGCAGCACCCTGACGCTGAGCAAA GCAGACTACGAGAAACACAAAGTCTACGCCTGCGAAGTCACCCATCAGGGCCTGAG CTCGCCCGTCACAAAGAGCTTCAACAGGGGAGAGTGT |
| 387 | Anti-CD132 P1A3 Fab HC (VH, joint CH1) | CAGGTGCAGCTACAGCAGTGGGGCGCAGGACTGTTGAAGGCTTCGGAGACCCTGT CCCTCACCTGCGCTGTCTATGGTGGGTCCTTCAGTGGTTACTACTGGAGCTGGATC CGCCAGCCCCCAGGGAAGGGGCTGGAGTGGATTGGGGAAATCAATCATAGTGGAA GCACCAACTACAACCCGTCCCTCAAGAGTCGAGCCACCATATCAGTAGACACGTCC AAGAACCAGTTCTCCCTGAAGCTGAGCTCTGTGACCGCCGCGGACACGGCTGTGTA TTACTGTGCGACCAGCCCGGGAGGCTATTCCGGGGGATACTTCCAGCACTGGGGC CAGGGAACCCTGGTCACCGTCTCAAGCGCCTCCACCAAGGGCCCATCGGTCTTCCC CCTGGCACCCTCCTCCAAGAGCACCTCTGGGGGCACAGCGGCCCTGGGCTGCCTG GTCAAGGACTACTTCCCCGAACCGGTGACGGTGTCGTGGAACTCAGGCGCCCTGAC CAGCGGCGTCCACACCTTCCGGGCTGTGCTACAGTGCTCAGGACTCTACTCCCTCA GCAGCGTAGTGACCGTGCCCTCCAGCAGCTTGGGCACCCAGACCTACATCTGCAAC GTGAATCACAAGCCCAGCAACACCAAGGTGGACAAGAAAGTTGAGCCCAAATCTTGT |
| 388 | Anti-CD132 P1A3 scFv and Fc with hole modification | CAGGTCCAGCTGCAGCAGTGGGGAGCCGGCCTGCTGAAACCATCTGAAACTCTGAG CCTGACTTGCGCTGTCTACGGGGGGTCCTTCAGTGGCTACTATTGGTCATGGATCA GGCAGCCCCCTGGGAAGGGACTGGAGTGGATCGGGGAAATTAACCACTCCGGATC TACAAACTACAATCCCAGTCTGAAATCACGCGCCACCATTTCTGTGGACACCAGTAA GAATCAGTTCAGCCTGAAGCTGAGCAGCGTGACAGCCGCTGATACCGCCGTGTACT ATTGCGCAACCAGCCCTGGCGGATACTCCGGAGGCTATTTTCAGCATTGGGGCCAG GGGACCCTGGTGACAGTGTCTAGTGGGGGAGGAGGGTCTGGAGGAGGAGGAAGTG GAGGAGGAGGCTCCGACGTGGTCATGACTCAGAGCCCACTGTCCCTGCCAGTGAC CCCCGGCGAGCCTGCTAGTATCTCATGTCGATCAAGCCAGTCACTGCTGCACAGCA ACGGGTACAATTATCTGGATTGGTACTTGCAGAAGCCAGGCCAGTCTCCCCAGCTG CTGATCTATCTGGGCTCCAACCGGGACTCTGGGGTGCCTGATAGATTCAGCGGCAG CGGCTCTGGGACTGACTTTACCCTGAAAATTTCCAGAGTCGAGGCAGAAGATGTGG GAGTGTACTATTGCATGCAGGGCACTCATTGGCCCTGGACCTTCGGACAGGGCACA AAGGTGGAGATCAAGAACAGCGGCGCGGGCACCGCGGCCGCGACTCACACATGCC CACCGTGCCCAGCACCTGAACTCCTGGGGGGACCGTCAGTCTTCCTCTTCCCCCCA AAACCCAAGGACACCCTCATGATCTGCCGGACCCCTGAGGTCACATGCGTGGTGGT GGACGTGAGCCACGAAGACCCTGAGGTCAAGTTCAACTGGTACGTGGACGGCGTG GAGGTGCATAATGCCAAGACAAAGCCGCGGGAGGAGCAGTACAACAGCACGTACC GTGTGGTCAGCGTGCTCACCGTGCTGCACCAGGACTGGCTGAATGGCAAGGAGTAC AAGTGCAAGGTCTCCAACAAAGCCCTCCCAGCCCCCATCGAGAAAACCATCTCCAAA GCCAAAGGGCAGCCCCGAGAACCACAGGTGTGCACCCTGCCCCCATCCCGGGATG AGCTGACCAAGAACCAGGTCAGCCTGTCCTGCGCCGTCAAAGGCTTCTATCCCAGC GACATCGCCGTGGAGTGGGAGAGCAATGGGCAGCCGGAGAACAACTACAAGACCA CGCCTCCCGTGCTGGACTCCGACGGCTCCTTCTTCCTCGTGAGCAAGCTCACCGTG GACAAGAGCAGGTGGCAGCAGGGGAACGTCTTCTCATGCTCCGTGATGCATGAGGC TCTGCACAACCACTACACGCAGAAGAGCCTCTCCCTGTCTCCGGGTAAA |
| 389 | Anti-CD132 P2B9 Fab LC (VL, joint CL) | TCCTATGAGCTGACTCAGCCACCCTCGATGTCAGTGTCCCCAGGACAGACGGCCAG GATCACCTGCTCTGGAGATGCATTGCCAAAACAATTTGCTTTTTGGTACCAGCAGAA GCCAGGCCAGGCCCCTGTGTTGGTGATTTATAAAGACACTGAGAGGCCCTCAGGGA TCCCTGAGCGATTCTCTGGCTCCAGCTCAGGGACAACAGTCACGTTGACCATCACT GGAGTCCAGGCAGAAGATGAGGCTGACTATTACTGTCAATCTCCAGACAGCAGTGG TACCGTCGAAGTGTTCGGCGGAGGGACCAAGCTGACCGTCCTAGGTCAGCCCAAG GCTGCCGCCTCGGTCACTCTGTTCCCGCCCTCCTCTGAGGAGCTTCAAGCCAACAA GGCCACACTGGTGTGTGTCATAAGTGACTTCTACCCGGGAGCCGTGACAGTGGCCT GGAAGGCAGATAGCAGCCCCGTCAAGGCGGGAGTGGAGACCACCACACCCTCCAA ACAAAGCAACAACAAGTACGCGGCCAGCAGCTACCTGAGCCTGACGCCTGAGCAGT GGAAGTCCCACAGAAGCTACAGCTGCCAGGTCACGCATGAAGGGAGCACCGTGGA GAAGACAGTGGCCCCTGCAGAATGT |
| 390 | Anti-CD132 P2B9 Fab HC (VH, joint CL) | CAGGTGCAGCTGCAGGAGTCGGGCCCAGGACTGGTGAAGCCTTCGGAGACCCTGT CCCTCACCTGCACTGTCTCTGGTGGCTCCATCAGCAGTAGTAGTTACTACTGGGGCT GGATCCGCCAGCCGCCAGGGAAGGGGCTGGAGTGGATTGGGAGTATCTATTATAGT GGGAGCACCTACTACAACCCGTCCCTCAAGAGTCGAGTCACCATATCCGTAGACAC GTCCAAGAACCAGTTCTCCCTGAAGCTGAGCTCTGTGACCGCCGCAGACACGGCTG TGTATTACTGTGCGGGCGATATTTTGACTGGTTATGCCCTTGACTACTGGGGCCAGG GAACCCTGGTCACCGTGTCAAGCGCCTCCACCAAGGGCCCATCGGTGTTCCCCCTG GCACCCTCCTCCAAGAGCACCTCTGGGGGCACAGCGGCCCTGGGCTGCCTGGTCA AGGACTACTTCCCCGAACCGGTGACGGTGTCGTGGAACTCAGGCGCCCTGACCAG CGGCGTCCACACCTTCCCGGCTGTCCTACAGTCCTCAGGACTCTACTCCCTCAGCA GCGTAGTGACCGTGCCCTCCAGCAGCTTGGGCACCCAGACCTACATCTGCAACGTG AATCACAAGCCCAGCAACACCAAGGTGGACAAGAAAGTTGAGCCCAAATCTTGT |

-continued

Sequences

| SEQ ID NO: | DESCRIPTION | SEQUENCE |
|---|---|---|
| 391 | Anti-CD132 P2B9 scFv and Fc with hole modification | CAGGTGCAGCTGCAGGAAAGCGGACCCGGACTGGTGAAGCCATCTGAAACACTGA<br>GCCTGACTTGTACCGTGAGCGGCGGAAGCATCAGCTCCTCTAGTTACTATTGGGGA<br>TGGATCAGGCAGCCCGCTGGCAAGGGGCTGGAGTGGATCGGCAGCATCTACTATA<br>GCGGCTCCACATACTATAACCCTAGCCTGAAATCCCGCGTGACAATCTCTGTGGACA<br>CTAGTAAGAATCAGTTCTCTCTGAAACTGTCAAGCGTGACCGCCGCTGATACAGCTG<br>TCTACTATTGCGCAGGCGACATTCTGACCGGGTACGCCCTGGATTATTGGGGACAG<br>GAGGCGGGGGAAGTTCATACGAACTGACACAGCCACCCTCTATGAGTGTGTCACCA<br>GGGCAGACTGCACGAATCACCTGTAGCGGAGACGCCCTGCCCAAGCAGTTCGCTTT<br>TTGGTATCAGCAGAAACCTGGCCAGGCTCCAGTGCTGGTCATCTATAAGGATACTGA<br>GCGGCCCTCTGGGATTCCTGAAAGATTCAGTGGCAGCAGCAGCGGAACCACAGTGA<br>CTCTGACCATTACAGGCGTGCAGGCAGAGGACGAAGCCGATTACTATTGCCAGTCC<br>CCCGACAGTTCAGGCACCGTGGAGGTCTTTGGCGGGGGAACAAAACTGACTGTGCT<br>GAACAGCGGCGCGGGCACCGCGGCCGCGACTCACACATGCCCACCGTGCCCAGCA<br>CCTGAACTCCTGGGGGGACCGTCAGTCTTCCTCTTCCCCCCAAAACCCAAGGACAC<br>CCTCATGATCTCCGGGACCCCTGAGGTCACATGCGTGGTGGTGGACGTGAGCCACG<br>AAGACCTCGAGGTCAAGTTCAACTGGTACGTGGACTGGCGTGGAGGTGCTATAATGCC<br>AAGACAAAGCCGCGGGAGGAGCAGTACAACAGCACGTACCGTGTGGTCAGCGTCC<br>TCACCGTCCTGCACCAGGACTGGCTGAATGGCAAGGAGTACAAGTGCAAGGTCTCC<br>AACAAAGCCCTCCCAGCCCCCATCGAGAAAACCATCTCCTAAAGCCAAAGGGCAGCC<br>CCGAGAACCACAGGTGTGCACCCTGCCCCCATCCCGGGATGAGCTGACCAAGAAC<br>CAGGTCAGCCTGTCCTGCGCCGTCAAAGGCTTCTATCCCAGCGACATCGCCGTGGA<br>GTGGGAGAGCAATGGGCAGCCGGAGAACAACTACAAGACCACGCCTCCCGTGCTG<br>GACTCCGACGGCTCCTTCTTCCTCGTGAGCAAGCTCACCGTGGACAAGAGCAGGTG<br>GCTAGCAGGGGAACGTCTTCTCATGCTCCGTGATGCATGAGGCTCTGCACAACCACT<br>ACACGCAGAAGAGCCTCTCCCTGTCTCCGGGTAAA |
| 392 | Anti-CD132 P1A10 Fab LC (VL, joint CL) | GAAATTGTGCTGACTCAGTCTCCTACTCTCCCTGCTCCGTTACCCGTGGAGAGCCGGC<br>CTCCATCTCCTGCAGGTCTAGTCAGAGCCTCCTGCATAGTAATGGATACAACTATTT<br>GAATTGGTACCTACAGAAGCCAGGGCAGTCTCCACAACTCCTGATCTATTTGGGTTC<br>TGATCGGGCCTCCGGGGTCCCTGACAGGTTCAGTGGCAGTGGATCAGGCACAGATT<br>TTACACTGAAAATCAGCAGAGTGGAGGCTGAGGATGTTGGGGTTTATTACTGCATGC<br>AAGCTCTACAAACCCCCACCACTTTCGGCGGAGGGACCAAGGTGGAGATCAAACGA<br>ACTGTGGCTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGCCAAAGTA<br>CAGTGGAAGGTGGATAACGCCCTCCAATCGGGTAACTCCCAGGAGAGTGTCACAGA<br>GCAGGACAGCAAGGACAGCACCTACAGCCTCAGCAGCACCCTGACGCTGAGCAAA<br>GCAGACTACGAGAAACACAAAGTCTACGCCTGCGAAGTCACCCATCAGGGCCTGAG<br>CTCGCCCGTCACAAAGAGCTTCAACAGGGGAGAGTGT |
| 393 | Anti-CD132 P1A10 Fab HC (VH, joint CH1) | CAGGTACAGCTGCAGCAGTCAGGGGCTGAGGTGAAGAAGCCTGGGTCCTCGGTGA<br>AGGTCTCCTGCAAGGCTTCTGGAGGCACCTTCAGCAGCTATGCTATCAGCTGGGTG<br>CGACAGGCCCCTGGACAAGGGCTTGAGTGGATGGGAGGTTTTGATCCTGAAGATGG<br>TGAAACAATCTACGCACAGAAGTTCCAGGGCAGAGTCACCATGACCGAGGACACAT<br>CTACAGACACAGCCTACATGGAGCTGAGCAGCCTGAGATCTGAGGACACGGCCGTG<br>TATTACTGTGCAACAGATCTGAGAATTCCGTATTACTATGATAACCCCTGGGGCCAG<br>GGCACCCTGGTCACCGTCTCAAGCGCCTCCACCAAGGGCCCATCGGTCTTCCCCCT<br>GGCACCCTCCTCCAAGAGCACCTCTGGGGGCACAGCGGCCCTGGGCTGCCTGGTC<br>AAGGACTACTTCCCCGAACCGGTGACGGTGTCGTGGAACTCAGGCGCCCTGACCAG<br>CGGCGTCCACACCTTCCGGGCTGTCCTACAGTCCTCAGGACTCTACTCCCTCAGCA<br>GCGTAGTGACCGTGCCCTCCAGCAGCTTGGGCACCCAGACCTACATCTGCAACGTG<br>AATCACAAGCCCAGCAACACCAAGGTGGACAAGAAAGTTGAGCCCAAATCTTGT |
| 394 | Anti-CD132 P1A10 scFv and Fc with hole modification | CAGGTCCAGCTGCAGCAGAGCGGAGCCGAGGTCAAGAAGCCAGGGAGTAGCGTCA<br>AAGTCAGTTGTAAAGCATCAGGAGGAACATTCAGCTCCTATGCAATCTCTTGGGTGC<br>GACAGGCCCCTGGACAGGGCCTGGAGTGGATGGGAGGATTCGACCCAGAGGATGG<br>AGAAACCATCTACGCCCAGAAGTTTCAGGGCAGAGTGACTATGACCGAAGACACAT<br>CTACTGATACCGCTTACATGGAGCTGTCTAGTCTGAGGAGTGAAGACACTGCCGTCT<br>ACTATTGCGCTACCGACCTGCGCATCCCATACTATTACGATAATCCCTGGGGGCAGG<br>GAACACTGGTGACTGTCTCAAGCGGAGGCGGGGGATCAGGCGGAGGAGGCAGCG<br>GAGGAGGAGGGTCCGAGATCGTGCTGACACAGAGTCCACTGTCACTGCCAGTCACC<br>CCTGGCGAACCAGCCAGTATTTCATGTCGGTCCTCTCAGAGCCTGCTGCACTCCAA<br>CGGGTATAATTACCTGAACTGGTACTTGCAGAAGCCTGGCCAGAGCCCTCAGCTGC<br>TGATCTACCTGGGCTCTGACCGAGCAAGTGGGGTGCCCGATAGATTCAGCGGCTCC<br>GGGTCTGGAACCGACTTTACCCTGAAGATCAGCCGGGTGGAGGCTGAAGATGTGG<br>GCGTCTATTACTGCATGCAGGCCCTCCAGACACCTACCACATTCGGAGGCGGGACT<br>AAGGTGGAGATCAAGAACAGCGGCGCGGGCACCGCGGCCGCGACTCACACATGCC<br>CACCGTGCCCAGCACCTGAACTCCTGGGGGGACCGTCAGTCTTCCTCTTCCCCCCA<br>AAACCCAAGGACACCCTCATGATCTCCCGGACCGCTGAGGTCACATGCGTGGTGGT<br>GGACGTGAGCCACGAAGACCCTGAGGTCAAGTTCAACTGGTACGTGGACGGCGTG<br>GAGGTGCATAATGCCAAGACAAAGCCGCGGGAGGAGCAGTACAACAGCACGTACC<br>GTGTGGTCAGCGTCCTCACCGTCCTGCACCAGGACTGGCTGAATGGCAAGGAGTAC<br>AAGTGCAAGGTCTCCAACAAAGCCCTCCCAGCCGCCATCGAGAAAACCATCTCCAAA<br>GCCAAAGGGCAGCCCCGAGAACCACAGGTGTGCACCGTGCCCCCATCCCGGGATG |

-continued

Sequences

| SEQ ID NO: | DESCRIPTION | SEQUENCE |
|---|---|---|
| | | AGCTGACCAAGAACCAGGTCAGCCTGTCCTGCGCCGTCAAAGGCTTCTATCCCAGC GACATCGCCGTGGAGTGGGAGAGCAATGGGCAGCCGGAGAACAACTACAAGACCA CGCCTCCCGTGCTGGACTCCGACGGCTCCTTCTTCCTCGTGAGCAAGCTCACCGTG GACAAGAGCAGGTGGCAGCAGGGGAACGTCTTCTCATGCTCCGTGATGCATGAGGC TCTGCACAACCACTACACGCAGAAGAGCCTCTCCCTGTCTCCGGGTAAA |
| 395 | Anti-CD132 P1B6 Fab LC (VL, joint CL) | GAAATTGTGATGACGCAGTCTCCACTCTCCCTGCCCGTCACCCCTGGAGAGCCGGC CTCCATCTCCTGCAGGTCTAGTCAGAGCCTCCTGCATAGTAATGGATACAACTATTT GGATTGGTACCTGCAGAAGCCAGGGCAGTCTCCACAGCTCCTGATGTATTTGGTTTC TAATCGGGCCTCCGGGGTCCCTGAGAGGTTCAGTGGCAGTGGATCAGGCACAGATT TTACACTGAAAATCAGCAGAGTGGAGGCTGAGGATGTTGGGGTTTATTACTGCATGC AAACTCTACAAACTCCTCTCAGTTTTGGCCAGGGGACCAAGCTGGAGATCAAACGAA CTGTGGCTGCACCATCTGTCTTCATCTTCCCGCCATCTGATGAGCAGTTGAAATCTG GAACTGCCTCTGTTGTGTGCCTGCTGAATAACTTCTATCCCAGAGAGGCCAAAGTAC AGTGGAAGGTGGATAACGCCCTCCAATCGGGTAACTCCCAGGAGAGTGTCACAGAG CAGGACAGCAAGGACAGCACCTACAGCCTCAGCAGCACCCTGACGCTGAGCAAAG CAGACTACGAGAAACACAAAGTCTACGCCTGCGAAGTCACCCATCAGGGCCTGAGC TCGCCCGTCACAAAGAGCTTCAACAGGGGAGAGTGT |
| 396 | Anti-CD132 P1B6 Fab HC (VH, joint CH1) | CAGGTCCAGCTGGTACAGTCTGGGGGAGGCGTGGTCCAGCCTGGGAGGTCCCTGA GACTCTCCTGTGCAGCCTCTGGATTCACCTTCAGTAGCTATGCTATGCACTGGGTCC GCCAGGCTCCAGGCAAGGGGCTGGAGTGGGTGGCAGTTATATCATATGATGGAAGC AATAAATACTACGCAGACTCCGTGAAGGGCCGATTCACCATCTCCAGAGACAATTCC AAGAACACGCTGTATCTGCAAATGAACAGCCTGAGAGCCGAGGACACGGCTGTGTA TTACTGTGCGAGAAGTCTTTACTACAGCCACTTTGACTACTGGGGCCAGGGAACCCT GGTCACCGTCTCAAGCGCCTCCACCAAGGGCCCATCGGTCTTCCCCCTGGCACCCT CCTCCAAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCGGCGTC CACACCTTCCCGGCTGTCCTACAGTCCTCAGGACTCTACTCCCTCAGCAGCGTAGT GACCGTGCCCTCCAGCAGCTTGGGCACCCAGACCTACATCTGCAACGTGAATCACA AGCCCAGCAACACCAAGGTGGACAAGAAAGTTGAGCCCAAATCTTGT |
| 397 | Anti-CD132 P1B6 scFv and Fc with hole modification | CAGGTGCAGCTGGTCCAGAGCGGAGGAGGCGTCGTCCAGCCCGGAAGGTCACTGA GACTGTCTTGTGCCGCATCAGGATTCACTTTTAGCTCCTACGCAATGCACTGGGTGA GGCAGGCCCCTGGCAAGGGGCTGGAGTGGGTGGCTGTCATCAGTTATGACGGCTC AAACAAGTACTATGCAGATAGCGTGAAAGGGCGGTTCACCATTAGCAGAGACAACTC CAAAAATACACTGTACCTCCAGATGAACAGCCTGCGAGCCGAAGACACAGCTGTGTA CTATTGCGCCCGGTCTCTGTACTATAGTCACTTTGATTACTGGGGACAGGGCACCCT GGTGACAGTCTCTAGTGGCGGGGGAGGCAGTGGAGGAGGAGGGAGCGGAGGAGG AGGCAGCGAGATCGTGATGACTCAGTCCCCACTGTCTCTGCCAGTCACCCCTGGCG AACCAGCATCCATTTCTTGTAGATCAAGCCAGTCACTGCTGCATAGCAACGGATACA ATTATCTGGATTGGTACTTGCAGAAGCCTGGCCAGTCTCCTCAGCTGCTGATGTATC TGGTGTCCAACAGGGCCTCTGGGGTCCCAGAGCGCTTCAGTGGGTCAGGAAGCGG CACTGACTTTACCCTGAAAATCTCTCGCGTGGAGGCTGAAGATGTGGGCGTCTACTA TTGCATGCAGACACTCCAGACTCCCCTGAGCTTCGGGCAGGGAACCAAGCTGGAGA TCAAGAACAGCGGCGCGGGCACCGCGGCCGCGACTCACACATGCCCACCGTGCCC AGCACCTGAACTCCTGGGGGGACCGTCAGTCTTCCTCTTCCCCCCAAAACCCAAGG ACACCCTCATGATCTCCCGGACCCCTGAGGTCACATGCGTGGTGGTGGACGTGAGC CACGAAGACCCTGAGGTCAAGTTCAACTGGTACGTGGACGGCGTGGAGGTGCATAA TGCCAAGACAAAGCCGCGGGAGGAGCAGTACAACAGCACGTACCGTGTGGTCAGC GTCCTCACCGTCCTGCACCAGGACTGGCTGAATGGCAAGGAGTACAAGTGCAAGGT CTCCAACAAAGCCCTCCCAGCCCCCATCGAGAAAACCATCTCCAAAGCCAAAGGGC AGCCCCGAGAACCACAGGTGTGCACCCTGCCCCCATCCCGGGATGAGCTGACCAA GAACCAGGTCAGCCTGTCCTGCGCCGTCAAAGGCTTCTATCCCAGCGACATCGCCG TGGAGTGGGAGAGCAATGGGCAGCCGGAGAACAACTACAAGACCACGCCTCCCGT GCTGGACTCCGACGGCTCCTTCTTCCTCGTGAGCAAGCTCACCGTGGACAAGAGCA GGTGGCAGCAGGGGAACGTCTTCTCATGCTCCGTGATGCATGAGGCTCTGCACAAC CACTACACGCAGAAGAGCCTCTCCCTGTCTCCGGGTAAA |
| 398 | Anti-CD132 P1C10 Fab LC (VL, joint CL) | GAAATTGTGCTGACTCAGTCTCCAGCCACCCTGTCTTTGTCTCCAGGGGAACGAGC CACCCTCTCCTGCAGGGCCAGTCAGAGTGTTAGTTACCACTTAGCCTGGTACCAACA AAAACCTGGCCAGGCTCCCAGGCTCCTCATCTATGATACATCCAACAGGGCCTCTG GCATCCCCGCCAGGTTCAGTGGCAGTGGGTCTGGGACAGACTTCACTCTCACCATC AACAGCCTAGAGCCTGAAGATTTTGCAGTTTATTACTGTCAGCAGCGTTACGACTGG CCTCTCACTTTCGGCGGAGGGACCAAGGTGGAGATCAAACGAACTGTGGCTGCACC ATCTGTCTTCATCTTCCCGCCATCTGATGAGCAGTTGAAATCTGGAACTGCCTCTGTT GTGTGCCTGCTGAATAACTTCTATCCCAGAGAGGCCAAAGTACAGTGGAAGGTGGA TAACGCCCTCCAATCGGGTAACTCCCAGGAGAGTGTCACAGAGCAGGACAGCAAGG ACAGCACCTACAGCCTCAGCAGCACCCTGACGCTGAGCAAAGCAGACTACGAGAAA CACAAAGTCTACGCCTGCGAAGTCACCCATCAGGGCCTGAGCTCGCCCGTCACAAA GAGCTTCAACAGGGGAGAGTGT |

-continued

Sequences

| SEQ ID NO: | DESCRIPTION | SEQUENCE |
|---|---|---|
| 399 | Anti-CD132 P1C10 Fab HC (VH, joint CH1) | GAGGTGCAGCTGGTGGAGACTGGCCCAGGACTGGTGAAGCCTTCGGGGACCCTGT CCCTCACCTGCGCTGTCTCTGGTGGCTCCATCAGCAGTAGTAACTGGTGGAGTTGG GTCCGCCAGCCCCCAGGGAAGGGGCTGGAGTGGATTGGGGAAATCTATCATAGTG GGAGCACCAACTACAACCCGTCCCTCAAGAGTCGAGTCACCATATCAGTAGACAAGT CCAAGAACCAGTTCTCCCTGAAGCTGAGCTCTGTGACCGCCGCGGACACGGCCGTG TATTACTGTGCGAGAGAAGGGCCCCTAAGCAGCAGCGGACCGGGTGCTTTTGATAT CTGGGGCCAAGGGACAATGGTCACCGTCTCAAGCGCCTCCACCAAGGGCCCATCG GTCTTCCCCCTGGCACCCTCCTCCAAGAGCACCTCTGGGGGCACAGCGGCCCTGG GCTGCCTGGTCAAGGACTACTTCCCCGAACCGGTGACGGTGTCGTGGAACTCAGGC GCCCTGACCAGCGGCGTCCACACCTTCCCGGCTGTCCTACAGTCCTCAGGACTCTA CTCCCTCAGCAGCGTAGTGACCGTGCCCTCCAGCAGCTTGGGCACCCAGACCTACA TCTGCAACGTGAATCACAAGCCCAGCAACACCAAGGTGGACAAGAAAGTTGAGCCC AAATCTTGT |
| 400 | Anti-CD132 P1010 scFv and Fc with hole modification | CAGGTCCAGCTGCAGGAATCAGGAGGGGGGGTCGTCCAGCCAGGGAGGTCACTGA GACTGTCTTGCGCCGCTTCAGGGTTCACTTTTAGCAACTACGGAATGCACTGGGTGC GGCAGGCTCCCGGCAAAGGGCTGGAGTGGGTGGCAGTCATCTCTTATGACGGCAC AAACAAGTACTATGCAGATAGTGTCAAGGGGCGGTTCACCATCAGCCGGGACAACA GTAAAAATACAGTGTACCTCCAGATGAACAGCCTGCGGGCCGAAGATACTGCTGTCT ACTATTGCGCCAAGGACGGGTTTGACATCTGGGGACAGGGCACTATGGTGACCGTC AGCTCCGGCGGGGGAGGCTCAGGAGGAGGAGGGAGCGGAGGAGGAGGCAGCGA CATTCAGATGACCCAGTCACCTAGCTTCCTGTCCGCTTCTGTGGGCGATAGGGTCAC AATCACTTGTCGCGCCAGTCAGTCAATTTCTAGTTGGCTGGCTTGGTATCAGCAGAA GCCCGGAAAAGCACCTAAGCTGCTGATCTATGACGCCTCCCGACTGGAGGATGGCG TGCCAAGCAGATTCTCCGGGACAGGATTTGGCACTGACTTCACCTTTACAATCACCA CACTCCAGCCAGACGATATTGCCACTTACTATTGCCAGCAGTACGACGATCTGCCCT ATACCTTTGGGCAGGGAACTACCGTGGATATTAAGAACAGCGGCGCGGGCACCGCG GCCGCGACTCACACATGCCCACCGTGCCCAGCACCTGAACTCCTGGGGGGACCGT CAGTCTTCCTCTTCCCCCCAAAACCCAAGGACACCCTCATGATCTCCCGGACCCCTG AGGTCACATGCGTGGTGGTGGACGTGAGCCACGAAGACCCTGAGGTCAAGTTCAAC TGGTACGTGGACGGCGTGGAGGTGCATAATGCCAAGACAAAGCCGCGGGAGGAGC AGTACAACAGCACGTACCGTGTGGTCAGCGTCCTCACCGTCCTGCACCAGGACTGG CTGAATGGCAAGGAGTACAAGTGCAAGGTCTCCAACAAAGCCCTCCCAGCCCCCAT CGAGAAAACCATCTCCAAAGCCAAAGGGCAGCCCCGAGAACCACAGGTGTGCACCC TGCCCCCATCCCGGGATGAGCTGACCAAGAACCAGGTCAGCCTGTCCTGCGCCGTC AAAGGCTTCTATCCCAGCGACATCGCCGTGGAGTGGGAGAGCAATGGGCAGCCGG AGAACAACTACAAGACCACGCCTCCCGTGCTGGACTCCGACGGCTCCTTCTTCCTC GTGAGCAAGCTCACCGTGGACAAGAGCAGGTGGCAGCAGGGGAACGTCTTCTCAT GCTCCGTGATGCATGAGGCTCTGCACAACCACTACACGCAGAAGAGCCTCTCCCTG TCTCCGGGTAAA |
| 401 | Anti-CD132 P1D7 Fab LC (VL, joint CL) | GACATCCAGATGACCCAGTCTCCTTCCTTCCTGTCTGCATCTGTAGGAGACAGAGTC ACCATCACTTGCCGGGCCAGTCAGAGTATTAGTAGCTGGTTGGCCTGGTATCAGCA GAAACCAGGGAAAGCCCCTAAACTCCTGATCTACGATGCATCCCGTTTGGAGGACG GGGTCCCATCAAGATTCAGTGGAACTGGATTTGGGACAGATTTTACTTTCACCATTA CCACCCTGCAGCCTGACGATATTGCGACATATTATTGTCAGCAATACGATGATCTCC CGTACACTTTTGGCCAGGGGACCACGGTGGACATCAAACGAACTGTGGCTGCACCA TCTGTCTTCATCTTCCCGCCATCTGATGAGCAGTTGAAATCTGGAACTGCCTCTGTT GTGTGCCTGCTGAATAACTTCTATCCCAGAGAGGCCAAAGTACAGTGGAAGGTGGA TAACGCCCTCCAATCGGGTAACTCCCAGGAGAGTGTCACAGAGCAGGACAGCAAGG ACAGCACCTACAGCCTCAGCAGCACCCTGACGCTGAGCAAAGCAGACTACGAGAAA CACAAAGTCTACGCCTGCGAAGTCACCCATCAGGGCCTGAGCTCGCCCGTCACAAA GAGCTTCAACAGGGGAGAGTGT |
| 402 | Anti-CD132 P1D7 Fab HC (VH, joint CH1) | CAGGTGCAGCTGCAGGAGTCCGGGGGAGGCGTGGTCCAGCCTGGGAGGTCCCTG AGACTCTCCTGTGCAGCCTCTGGATTCACCTTCAGTAACTATGGCATGCACTGGGTC CGCCAGGCTCCAGGCAAAGGGCTGGAGTGGGTGGCAGTTATATCATATGATGGAAC TAATAAATACTATGCAGACTCCGTGAAGGGCCGATTCACCATCTCCAGAGACAATTC CAAGAACACGGTGTATCTGCAAATGAACAGCCTGAGAGCTGAGGACACGGCTGTGT ATTACTGTGCGAAAGATGGTTTTGATATTTGGGGCCAAGGGACAATGGTCACCGTCT CAAGCGCCTCCACCAAGGGCCCATCGGTCTTCCCCCTGGCACCCTCCTCCAAGAGC ACCTCTGGGGGCACAGCGGCCCTGGGCTGCCTGGTCAAGGACTACTTCCCCGAAC CGGTGACGGTGTCGTGGAACTCAGGCGCCCTGACCAGCGGCGTCCACACCTTCCC GGCTGTCCTACAGTCCTCAGGACTCTACTCCCTCAGCAGCGTAGTGACCGTGCCCT CCAGCAGCTTGGGCACCCAGACCTACATCTGCAACGTGAATCACAAGCCCAGCAAC ACCAAGGTGGACAAGAAAGTTGAGCCCAAATCTTGT |
| 403 | Anti-CD132 P1D7 scFv and Fc with hole modification | GAAGTGCAGCTGGTGGAAACTGGACCTGGACTGGTGAAGCCAAGCGGGACTCTGA GCCTGACCTGTGCCGTGAGCGGGGGAAGTATCAGCTCCTCTAACTGGTGGTCCTGG GTGCGACAGCCCCCTGGCAAGGGGCTGGAGTGGATCGGCGAAATCTACCACAGCG GGTCCACAAACTATAATCCTAGCCTGAAGAGCCGGGTGACTATCTCTGTGGACAAGA GTAAAAATCAGTTCAGCCTGAAACTGAGTTCAGTGACAGCCGCTGATACCGCCGTGT ACTATTGCGCCAGGGAGGGACCTCTGAGCAGCAGCGGACCAGGCGCTTTTGACATC |

-continued

Sequences

| SEQ ID NO: | DESCRIPTION | SEQUENCE |
|---|---|---|
| | | TGGGGGCAGGGAACTATGGTGACCGTCAGTTCAGGCGGAGGAGGCTCCGGAGGAG<br>GAGGGTCTGGAGGCGGGGGAAGTGAGATTGTGCTGACCCAGTCCCCCGCCACACT<br>GTCTCTGAGTCCTGGCGAACGGGCCACCCTGTCTTGTAGAGCTTCACAGAGCGTGT<br>CCTACCATCTGGCATGGTATCAGCAGAAACCAGGCCAGGCCCCCAGACTGCTGATC<br>TACGACACCTCAAACAGGGCTAGCGGCATTCCCGCACGCTTCTCTGGCAGTGGGTC<br>AGGAACAGATTTTACCCTGACAATCAATAGCCTGGAGCCAGAAGACTTCGCCGTGTA<br>CTATTGCCAGCAGCGCTATGATTGGCCCCTGACTTTTGGCGGGGGAACCAAGGTCG<br>AGATCAAGAACAGCGGCGCGGGCACCGCGGCCGCGACTCACACATGCCCACCGTG<br>CCCAGCACCTGAACTCCTGGGGGGACCGTCAGTCTTCCTCTTCCCCCCAAAACCCA<br>AGGACACCCTCATGATCTCCCGGACCCCTGAGGTCACATGCGTGGTGGTGGACGTG<br>AGCCACGAAGACCCTGAGGTCAAGTTCAACTGGTACGTGGACGGCGTGGAGGTGC<br>ATAATGCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAGTGCAA<br>GGTCTCCAACAAAGCCCTCCCAGCCCCCATCGAGAAAACCATCTCCAAAGCCAAAG<br>GGCAGCCCCGAGAACCACAGGTGTGCACCCTGCCCCCATCCCGGGATGAGCTGAC<br>CAAGAACCAGGTCAGCCTGTCCTGCGCCGTCAAAGGCTTCTATCCCAGCGACATCG<br>CCGTGGAGTGGGAGAGCAATGGGCAGCCGGAGAACAACTACAAGACCACGCCTCC<br>CGTGCTGGACTCCGACGGCTCCTTCTTCCTCGTGAGCAAGCTCACCGTGGACAAGA<br>GCAGGTGGCAGCAGGGGAACGTCTTCTCATGCTCCGTGATGCATGAGGCTCTGCAC<br>AACCACTACACGCAGAAGAGCCTCTCCCTTCTCCGGGTAAA |
| 404 | Anti-CD132 P1E8 Fab LC (VL, joint CL) | GATGTTGTGATGACTCAGTCTCCAGTCTCCCTGCCCGTCACCCTTGGACAGCCGGC<br>CTCCATCTCCTGCAAGTCTAGTCAAAGCCTCCTTTACTTTAATGGAAACACCTACTTG<br>AGCTGGTTTCAGCAGAGGCCAGGCCAATCTCCACGGCGCCTATTTTATCAGGTTTCT<br>AACCGGGACTCTGGGGTCCCAGACAGATTCAGCGGCAGTGGGTCAGACACTGATTT<br>CACTCTGACCATTAGCAGGGTGGAGGCTGAAGATGTTGGAGTTTATTTCTGCATGCA<br>AGGAACACAGTGGCCTCCGACGTTCGGCCAAGGGACCAAGGTGGAAATCAAACGAA<br>CTGTGGCTGCACCATCTGTCTTCATCTTCCCGCCATCTGATGAGCAGCTGAAATCTG<br>GAACTGCCTCTGTTGTGTGCCTGCTGAATAACTTCTATCCCAGAGAGGCCAAAGTAC<br>AGTGGAAGGTGGATAACGCCCTCCAATCGGGTAACTCCCAGGAGAGTGTCACAGAG<br>CAGGACAGCAAGGACAGCACCTACAGCCTCAGCAGCACCCTGACGCTGAGCAAAG<br>CAGACTACGAGAAACACAAAGTCTACGCCTGCGAAGTCACCCATCAGGGCCTGAGC<br>TCGCCCGTCACAAAGAGCTTCAACAGGGGAGAGTGT |
| 405 | Anti-CD132 P1E8 Fab HC (VH, joint CH1) | GAGGTCCAGCTGGTGCAGTCTGGGGGAGGCGTGGTCCAGCCTGGGAGGTCCCTGA<br>GACTCTCCTGTGCAGCCTCTGGATTCACCTTCAGTAGCTATGGCATGCACTGGGTCC<br>GCCAGGCTCCAGGCAAGGGGCTGGAGTGGGTGGCAGTTATATCATATGATGGAAGT<br>AATAAATACTATGCAGACTCCGTGAAGGGCCGATTCACCATCTCCAGAGACAATTCC<br>AAGAACACGCTGTATCTGCAAATGAACAGCCTGAGAGCCGAGGACACGGCCGTGTA<br>TTACTGTGCGAGAGATGTCTACGGTGACTACGGGGCCTTTGACTACTGGGGCCAGG<br>GAACCCTGGTCACCGTCTCAAGCGCCTCCACCAAGGGCCCATCGGTCTTCCCCCTG<br>GCACCCTCCTCCAAGAGCACCTCTGGGGGCACAGCGGCCCTGGGCTGCCTGGTCA<br>AGGACTACTTCCCCGAACCGGTGACGGTGTCGTGGAACTCAGGCGCCCTGACCAG<br>CGGCGTCCACACCTTCCCGGCTGTCCTACAGTCCTCAGGACTCTACTCCCTCAGCA<br>GCGTAGTGACCGTGCCCTCCAGCAGCTTGGGCACCCAGACCTACATCTGCAACGTG<br>AATCACAAGCCCAGCAACACCAAGGTGGACAAGAAAGTTGAGCCCAAATCTTGT |
| 406 | Anti-CD132 P1E8 scFv and Fc with hole modification | GAGGTCCAGCTGGTCCAGAGCGGCGGAGGGGTCGTCCAGCCCGGAAGAAGCCTGA<br>GACTGTCCTGTGCAGCAAGTGGGTTTACATTCAGCTCCTACGGCATGCACTGGGTG<br>AGGCAGGCACCCGGCAAGGGGCTGGAGTGGGTGGCCGTCATCAGTTATGACGGCT<br>CAAACAAGTACTATGCCGATAGCGTGAAAGGGAGGTTCACAATTAGCCGCGACAACT<br>CCAAAAATACTCTGTACCTCCAGATGAACAGCCTGAGAGCCGAAGATACAGCTGTGT<br>ACTATTGCGCTAGGGACGTCTACGGAGATTATGGCGCATTTGACTATTGGGGACAG<br>GGCACTCTGGTGACCGTCTCTAGTGGAGGAGGAGGCTCAGGAGGAGGAGGAGCG<br>GCGGAGGAGGCAGCGATGTGGTCATGACCCAGTCCCCAGTGTCTCTGCCAGTCACA<br>CTGGGACAGCCAGCATCCATCTCTTGTAAGTCAAGCCAGTCTCTGCTGTACTTCAAC<br>GGAAATACTTATCTGTCTTGGTTTCAGCAGCGCCCTGGCCAGAGTCCACGGAGACT<br>GTTCTACCAGGTGTCTAACCGAGACAGTGGCGTCCCTGATCGGTTCAGTGGGTCAG<br>GAAGCGACACCGATTTTACCCTGACAATCAGCCGAGTGGAGGCTGAAGACGTGGGG<br>GTCTATTTCTGCATGCAGGGAACACAGTGGCCCCCTACTTTTGGCCAGGGGACCAA<br>GGTGGAGATCAAGAACAGCGGCGCGGGCACCGCGGCCGCGACTCACACATGCCCA<br>CCGTGCCCAGCACCTGAACTCCTGGGGGGACCGTCAGTCTTCCTCTTCCCCCCAAA<br>ACCCAAGGACACCCTCATGATCTCCCGGACCCCTGAGGTCACATGCGTGGTGGTGG<br>ACGTGAGCCACGAAGACCCTGAGGTCAAGTTCAACTGGTACGTGGACGGCGTGGA<br>GGTGCATAATGCCAAGACAAAGCCGCGGGAGGAGCAGTACAACAGCACGTACCGT<br>GTGGTCAGCGTCCTCACCGTCCTGCACCAGGACTGGCTGAATGGCAAGGAGTACAA<br>GTGCAAGGTCTCCAACAAAGCCCTCCCAGCCCCCATCGAGAAAACCATCTCCAAAG<br>CCAAAGGGCAGCCCCGAGAACCACAGGTGTGCACCCTGCCCCCATCCCGGGATGA<br>GCTGACCAAGAACCAGGTCAGCCTGTCCTGCGCCGTCAAAGGCTTCTATCCCAGCG<br>ACATCGCCGTGGAGTGGGAGAGCAATGGGCAGCCGGAGAACAACTACAAGACCAC<br>GCCTCCCGTGCTGGACTCCGACGGCTCCTTCTTCCTCGTGAGCAAGCTCACCGTGG<br>ACAAGAGCAGGTGGCAGCAGGGGAACGTCTTCTCATGCTCCGTGATGCATGAGGCT<br>CTGCACAACCACTACACGCAGAAGAGCCTCTCCCTGTCTCCGGGTAAA |

-continued

Sequences

| SEQ ID NO: | DESCRIPTION | SEQUENCE |
|---|---|---|
| 407 | Anti-CD132 P2B2 Fab LC (VL, joint CL) | GATGTTGTGATGACTCAGTCTCCACTCTCCCTGCCCGTCACCCCTGGAGAGCCGGC<br>CTCCATCTCCTGCAGGTCTAGTCAGAGCCTCCTGCATAGTAATGGATACAACTATTT<br>GGATTGGTACCTGCAGAAGCCAGGGCAGTCTCCACACCTCCTGATCTACTTGGGTT<br>CTAATCGGGCCTCCGGGGTCCCTGACAGGTTCAGTGGCAGTGGATCAGGCACAGAT<br>TTTACACTGAAAATTAGCAGAGTGGAGGCTGAGGATGTTGGGGTTTATTTCTGCATG<br>CAAGCTCTACGAACTCCGTACACTTTTGGCCAGGGGACCAAGCTGGAGATCAAACG<br>AACTGTGGCTGCACCATCTGTCTTCATCTTCCCGCCATCTGATGAGCAGTTGAAATC<br>TGGAACTGCCTCTGTTGTGTGCCTGCTGAATAACTTCTATCCCAGAGAGGCCAAAGT<br>ACAGTGGAAGGTGGATAACGCCCTCCAATCGGGTAACTCCCAGGAGAGTGTCACAG<br>AGCAGGACAGCAAGGACAGCACCTACAGCCTCAGCAGCACCCTGACGCTGAGCAAA<br>GCAGACTACGAGAAACACAAAGTCTACGCCTGCGAAGTCACCCATCAGGGCCTGAG<br>CTCGCCCGTCACAAAGAGCTTCAACAGGGGAGAGTGT |
| 408 | Anti-CD132 P2B2 Fab HC (VH, joint CH1) | CAGCTGCAGCTGCAGGAGTCGGGGGGAGGCGTGGTCCAGCCTGGGAGGTCCCTG<br>AGACTCTCCTGTGCAGCCTCTGGATTCACCTTCAGTAGCTATGCTATGCACTGGGTC<br>CGCCAGGCTCCAGGCAAGGGGCTGGAGTGGGTGGCAGTTATATCATATGATGGAG<br>GTAATAAATACTACGCAGACTCCGTGAAGGGCCGATTCACCATCTCCAGAGACAATT<br>CCAAGAACACGCTGTATCTGCAAATGAACAGCCTGAGAGCTGAGGACACGGCTGTG<br>TATTACTGTGCGAAATCAGTGGCGCCTCCCATGGACGTCTGGGGCAAAGGGACCAC<br>GGTCACCGTCTCAAGCGCCTCCACCAAGGGCCCATCGGTCTTCCCCCTGGCACCCT<br>CCTCCAAGAGCACCTCTGGGGGCACAGCGGCCCTGGGCTGCCTGGTCAAGGACTA<br>CTTCCCCGAACCGGTGACGGTGTCGTGGAACTCAGGCGCCCTGACCAGCGGCGTC<br>CACACCTTCCCGGCTGTCCTACAGTCCTCAGGACTCTACTCCCTCAGCAGCGTAGT<br>GACCGTGCCCTCCAGCAGCTTGGGCACCCAGACCTACATCTGCAACGTGAATCACA<br>AGCCCAGCAACACCAAGGTGGACAAGAAAGTTGAGCCCAAATCTTGT |
| 409 | Anti-CD132 P2B2 scFv and Fc with hole modification | CAGCTGCAGCTGCAGGAATCCGGGGGAGGCGTCGTCCAGCCAGGAAGGTCACTGA<br>GACTGAGTTGTGCCGCAAGCGGGTTCACTTTCAGCTCCTACGCTATGCACTGGGTG<br>AGACAGGCACCCGGAAAGGGCCTGGAGTGGGTGGCAGTCATCTCTTATGACGGCG<br>GGAACAAGTACTATGCCGATAGTGTGAAAGGCCGGTTCACCATTAGTAGAGACAACT<br>CAAAAAATACACTGTACCTCCAGATGAATAGCCTGCGCGCCGAAGACACAGCTGTGT<br>ACTATTGCGCAAAGTCCGTGGCCCCCCCTATGGATGTCTGGGGGAAAGGAACCACA<br>GTGACTGTCTCTAGTGGAGGAGGAGGATCAGGCGGCGGAGGCAGCGGAGGAGGA<br>GGGTCCGACGTGGTCATGACTCAGTCCCCTCTGTCTCTGCCAGTGACCCCCGGCGA<br>GCCTGCTTCCATCTCTTGTAGGTCAAGCCAGAGCCTGCTGCACTCCAACGGGTACA<br>ATTATCTGGATTGGTACTTGCAGAAGCCAGGCCAGTCTCCCCATCTGCTGATCTATC<br>TGGGATCTAACAGGGCCAGTGGCGTGCCTGACCGCTTCAGTGGCTCAGGGAGCGG<br>AACTGATTTTACCCTGAAAATTAGCCGAGTCGAGGCCGAAGATGTGGGCGTCTACTT<br>CTGCATGCAGGCTCTGCGGACACCATATACTTTTGGCCAGGGGACCAAGCTGGAGA<br>TCAAGAACAGCGGCGCGGGCACCGCGGCCGCGACTCACACATGCCCACCGTGCCC<br>AGCACCTGAACTCCTGGGGGGACCGTCAGTCTTCCTCTTCCCCCCAAAACCCAAGG<br>ACACCCTCATGATCTCCCGGACCCCTGAGGTCACATGCGTGGTGGTGGACGTGAGC<br>CACGAAGACCCTGAGGTCAAGTTCAACTGGTACGTGGACGGCGTGGAGGTGCATAA<br>TGCCAAGACAAAGCCGCGGGAGGAGCAGTACAACAGCACGTACCGTGTGGTCAGC<br>GTCCTCACCGTCCTGCACCAGGACTGGCTGAATGGCAAGGAGTACAAGTGCAAGGT<br>CTCCAACAAAGCCCTCCCAGCCCCCATCGAGAAAACCATCTCCAAAGCCAAAGGGC<br>AGCCCCGAGAACCACAGGTGTGCACCCTGCCCCCATCCCGGGATGAGCTGACCAA<br>GAACCAGGTCAGCCTGTCCTGCGCCGTCAAAGGCTTCTATCCCAGCGACATCGCCG<br>TGGAGTGGGAGAGCAATGGGCAGCCGGAGAACAACTACAAGACCACGCCTCCCGT<br>GCTGGACTCCGACGGCTCCTTCTTCCTCGTGAGCAAGCTCACCGTGGACAAGAGCA<br>GGTGGCAGCAGGGGAACGTCTTCTCATGCTCCGTGATGCATGAGGCTCTGCACAAC<br>CACTACACGCAGAAGAGCCTCTCCCTGTCTCCGGGTAAA |
| 410 | Anti-CD132 P2B7 Fab LC (VL, joint CL) | GATGTTGTGATGACTCAGTCTCCACTCTCCCTGCCCGTCACCCTTGGACAGCCGGC<br>CTCCATCTCCTGCAGGTCTAGTCAGAGCCTCGTCCATAGTAATGGATACAACTATTT<br>GGACTGGTACCTGCAGAAGCCAGGGCAGTCTCCACAGCTCCTGATCTATTTGGGTT<br>CTAATCGGGCCTCCGGGGTCCCTGACAGGTTCAGTGGCAGTGGATCGGGCACAGA<br>TTTTACACTGAAAATCAGCAGAGTGGAGGCTGAGGATGTTGGGGTTTATTACTGCCT<br>GCAAGGTTCACACTGGCCTTGGACGTTCGGCCAAGGGACCAAGGTGGAAATCAAAC<br>GAACTGTGGCTGCACCATCTGTCTTCATCTTCCCGCCATCTGATGAGCAGTTGAAAT<br>CTGGAACTGCCTCTGTTGTGTGCCTGCTGAATAACTTCTATCCCAGAGAGGCCAAAG<br>TACAGTGGAAGGTGGATAACGCCCTCCAATCGGGTAACTCCCAGGAGAGTGTCACA<br>GAGCAGGACAGCAAGGACAGCACCTACAGCCTCAGCAGCACCCTGACGCTGAGCA<br>AAGCAGACTACGAGAAACACAAAGTCTACGCCTGCGAAGTCACCCATCAGGGCCTG<br>AGCTCGCCCGTCACAAAGAGCTTCAACAGGGGAGAGTGT |
| 411 | Anti-CD132 P2B7 Fab HC (VH, joint CH1) | CAGGTGCAGCTACAGCAGTGGGGCGCAGGACTGTTGAAGCCTTCGGAGACCCTGT<br>CCCTCACCTGCGCTGTCTATGGTGAGTCCTTCAGTGGTTACTACTGGAGCTGGATCC<br>GCCAGCCCCCAGGGAAGGGGCTGGAGTGGATTGGGGAAATCAATCATAGTGGAAG<br>CACCAACTACAACCCGTCCCTCAAGAGTCGAGTCACCATATCAGTAGACACGTCCAA<br>GAACCAGTTCTCCCTGAAGCTGAGCTCTGTGACCGCCGCGGACACGGCTGTGTATT<br>ACTGTGCGAGAGGCCCCGCGGGTAGCAGCTCGTCCGGCTACTTTGACTACTGGGG<br>CCAGGGAACCCTGGTCACCGTCTCAAGCGCCTCCACCAAGGGCCCATCGGTCTTCC<br>CCCTGGCACCCTCCTCCAAGAGCACCTCTGGGGGCACAGCGGCCCTGGGCTGCCT |

-continued

| Sequences | | |
|---|---|---|
| SEQ ID NO: | DESCRIPTION | SEQUENCE |
| | | GGTCAAGGACTACTTCCCCGAACCGGTGACGGTGTCGTGGAACTCAGGCGCCCTGA CCAGCGGCGTCCACACCTTCCCGGCTGTCCTACAGTCCTCAGGACTCTACTCCCTC AGCAGCGTAGTGACCGTGCCCTCCAGCAGCTTGGGCACCCAGACCTACATCTGCAA CGTGAATCACAAGCCCAGCAACACCAAGGTGGACAAGAAAGTTGAGCCCAAATCTT GT |
| 412 | Anti-CD132 P2B7 scFv and Fc with hold modification | CAGGTCCAGCTGCAGCAGTGGGGCGCCGGACTGCTGAAACCCTCTGAAACTCTGA GCCTGACTTGTGCCGTCTATGGGGAATCCTTCTCTGGCTACTATTGGAGTTGGATCA GGCAGCCCCCTGGCAAGGGGCTGGAGTGGATCGGAGAAATTAACCACAGCGGCTC CACCAACTACAATCCATCTCTGAAAAGTCGCGTGACCATTTCCGTGGACACATCTAA GAATCAGTTCAGCCTGAAGCTGAGCAGCGTGACAGCCGCTGATACTGCCGTCTACT ATTGCGCACGGGGCCCCGCCGGGTCTAGTTCAAGCGGATACTTTGACTATTGGGGA CAGGGCACCCTGGTGACAGTCTCCTCTGGCGGAGGAGGCTCCGGAGGAGGAGGGT CTGGAGGAGGAGGAAGCGATGTGGTCATGACACAGTCACCACTGAGCCTGCCAGT GACTCTGGGACAGCCTGCTTCTATCAGTTGTCGAAGTTCACAGAGTCTGGTCCACTC AAACGGATACAATTATCTGGACTGGTACTTGCAGAAGCCTGGCCAGAGCCCACAGC TGCTGATCTATCTGGGGAGCAACCGAGCTTCCGGAGTGCCCGACAGATTCTCAGGG AGCGGCAGCGGCACTGATTTTACCCTGAAAATTAGCAGAGTGGAGGCAGAAGATGT GGGCGTCTACTATTGCCTCCAGGGGTCCCATTGGCCTTGGACTTTCGGGCAGGGAA CCAAGGTGGAGATCAAGAACAGCGGCGCGGGCACCGCGGCCGCGACTCACACATG CCCACCGTGCCCAGCACCTGAACTCCTGGGGGGACCGTCAGTCTTCCTCTTCCCCC CAAAACCCAAGGACACCCTCATGATCTCCCGGACCCCTGAGGTCACATGCGTGGTG GTGGACGTGAGCCACGAAGACCCTGAGGTCAAGTTCAACTGGTACGTGGACGGCGT GGAGGTGCATAATGCCAAGACAAAGCCGCGGGAGGAGCAGTACAACAGCACGTAC CGTGTGGTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCATCTCCA AAGCCAAAGGGCAGCCCCGAGAACCACAGGTGTGCACCCTGCCCCCATCCCGGGA TGAGCTGACCAAGAACCAGGTCAGCCTGTCCTGCGCCGTCAAAGGCTTCTATCCCA GCGACATCGCCGTGGAGTGGGAGAGCAATGGGCAGCCGGAGAACAACTACAAGAC CACGCCTCCCGTGCTGGACTCCGACGGCTCCTTCTTCCTCGTGAGCAAGCTCACCG TGGACAAGAGCAGGTGGCAGCAGGGGAACGTCTTCTCATGCTCCGTGATGCATGAG GCTCTGCACAACCACTACACGCAGAAGAGCCTCTCCCTGTCTCCGGGTAAA |
| 413 | Anti-CD132 P2D11 Fab LC (VL, joint CL) | GAAACGACACTCACGCAGTCTCCAGCCACCCTGTCTGTGTCTCCAGGGGAAAGAGC CACCCTCTCCTGCAGGGCCAGTCAGAGTGTTAGCAGCAACTTAGCCTGGTACCAGC AGAAACCTGGCCAGGCTCCCAGGCTCCTCATCTATGGTGCATCCAGCGGGGCCACT GGCATCCCAGACAGGTTCAGTGGCAGTGGGTCTGGGACAGACTTCACTCTCACCAT CAGCAGACTGGAGCCTGAAGATTTTGCAGTGTATTACTGTCAGCTGTATGGTAGCTC ACTCGCTTTCGGCGGAGGGACCAAGGTGGAGATCAAACGAACTGTGGCTGCACCAT CTGTCTTCATCTTCCCGCCATCTGATGAGCAGTTGAAATCTGGAACTGCCTCTGTTG TGTGCCTGCTGAATAACTTCTATCCCAGAGAGGCCAAAGTACAGTGGAAGGTGGATA ACGCCCTCCAATCGGGTAACTCCCAGGAGAGTGTCACAGAGCAGGACAGCAAGGAC AGCACCTACAGCCTCAGCAGCACCCTGACGCTGAGCAAAGCAGACTACGAGAAACA CAAAGTCTACGCCTGCGAAGTCACCCATCAGGGCCTGAGCTCGCCCGTCACAAAGA GCTTCAACAGGGGAGAGTGT |
| 414 | Anti-CD132 P2D11 Fab HC (VH, joint CH1) | GAGGTCCAGCTGGTGCAGTCTGGGGCTGAGGTGAAGAAGCCTGGGTCCTCGGTGA AGGTCTCCTGCAAGGCTTCTGGAGGCACCTTCAGCAGCTATGCTATCAGCTGGGTG CGACAGGCCCCTGGACAAGGGCTTGAGTGGATGGGATGGATCAGCGCTTACAATG GTGACACAAGCTACGCACAGAAGTTCCAGGGCAGAGTCACCATTACCAGGGACACA TCCGCGAGCACAGCCTACATGGAGCTGAGCAGCCTGAGATCTGAAGACACGGCTGT GTATTACTGTGCGAGAGATTGGGGATATTGTAGTGGTGGTAGCTGCTACCTGAACTG GTTCGACCCCTGGGGCCAGGGAACCCTGGTCACCGTCTCAAGCGCCTCCACCAAG GGCCCATCGGTCTTCCCCCTGGCACCCTCCTCCAAGAGCACCTCTGGGGGCACAG CGGCCCTGGGCTGCCTGGTCAAGGACTACTTCCCCGAACCGGTGACGGTGTCGTG GAACTCAGGCGCCCTGACCAGCGGCGTCCACACCTTCCCGGCTGTCCTACAGTCCT CAGGACTCTACTCCCTCAGCAGCGTAGTGACCGTGCCCTCCAGCAGCTTGGGCACC CAGACCTACATCTGCAACGTGAATCACAAGCCCAGCAACACCAAGGTGGACAAGAA AGTTGAGCCCAAATCTTGT |
| 415 | Anti-CD132 P2d11 scFv and Fc with hole modification | AGGTCCAGCTGCAGGAAAGCGGGCCAGGACTGGTCAAACCCTCACAGACACTGTCT CTGACTTGTACCGTCTCCGGGGGCTCAATCAGCTCCGGCGGGTACTATTGGACATG GATCAGACAGCACCCTGGACAGGGCCTGGAGTGGATCGGGTTCATTAGCTGGTCCG GAACCACATACTATAACCCAAGCCTGAAGAATAGGGTGACAATTTCAGCCGACACTA GCAAAAACCATTTTTCCCTGAATCTGACCTCTGTGACAGCCGCTGATACTGCTGTCT ACTATTGCGCACGGGGGTCCGGAAGACTGGTGTGGGGACAGGGGACTCTGGTGAC CGTCTCTAGTGGAGGAGGAGGAAGTGGCGGAGGAGGCAGCGGAGGAGGAGGGTC CGAGACTACCCTGACCCAGTCTCCAGCTACACTGTCTGTGAGTCCCGGCGAAAGGG CAACCCTGAGCTGTCGCGCTTCACAGAGCGTCTCAAGCAACCTGGCATGGTATCAG CAGAAGCCTGGCCAGGCCCCTCGACTGCTGATCTATGGGGCATCCTCTGGAGCCAC TGGCATTCCCGACCGGTTCTCCGGATCTGGCAGTGGGACCGATTTTACACTGACCA TCAGCCGGCTGGAGCCTGAAGACTTCGCTGTGTACTATTGCCAGCTGTACGGCAGT TCACTGGCATTTGGAGGCGGGACAAAGGTCGAGATCAAGAACAGCGGCGCGGGCA CCGCGGCCGCGACTCACACATGCCCACCGTGCCCAGCACCTGAACTCCTGGGGGG |

-continued

Sequences

| SEQ ID NO: | DESCRIPTION | SEQUENCE |
|---|---|---|
| | | ACCGTCAGTCTTCCTCTTCCCCCCAAAACCCAAGGACACCCTCATGATCTCCCGGAC<br>CCCTGAGGTCACATGCGTGGTGGTGGACGTGAGCCACGAAGACCCTGAGGTCAAG<br>TTCAACTGGTACGTGGACGGCGTGGAGGTGCATAATGCCAAGACAAAGCCGCGGGA<br>GGAGCAGTACAACAGCACGTACCGTGTGGTCAGCGTCCTCACCGTCCTGCACCAGG<br>ACTGGCTGAATGGCAAGGAGTACAAGTGCAAGGTCTCCAACAAAGCCCTCCCAGCC<br>CCCATCGAGAAAACCATCTCCAAAGCCAAAGGGCAGCCCCGAGAACCACAGGTGTG<br>CACCCTGCCCCCATCCCGGGATGAGCTGACCAAGAACCAGGTCAGCCTGTCCTGCG<br>CCGTCAAAGGCTTCTATCCCAGCGACATCGCCGTGGAGTGGGAGAGCAATGGGCA<br>GCCGGAGAACAACTACAAGACCACGCCTCCCGTGCTGGACTCCGACGGCTCCTTCT<br>TCCTCGTGAGCAAGCTCACCGTGGACAAGAGCAGGTGGCAGCAGGGGAACGTCTT<br>CTCATGCTCCGTGATGCATGAGGCTCTGCACAACCACTACACGCAGAAGAGCCTCT<br>CCCTGTCTCCGGGTAAA |
| 416 | Anti-CD132 P2F10 Fab LC (VL, joint CL) | GATATTGTGATGACCCACACTCCACTCTCCCTGCCCGTCACCCCTGGAGAGCCGGC<br>CTCCATCTCCTGCAGGTCTAGTCAGACCCTCTTCGATAGCGATGATGGAAAGACCTA<br>TTTGGACTGGTACCTGCAGAAGCCAGGGCAGTCTCCACAACTCCTGATGTATACCAC<br>TTCCTCTCGGGCCTCTGGAGTCCCAGACAGGTTCAGTGGCAGTGGGTCAGGCACTG<br>ATTTCACACTGAAAATCAGCAGGGTGGAGGCTGAGGATGTTGGAGTTTATTACTGCA<br>TGCAGCGTTTACAGTTTCCCCTCACCTTCGGCCAAGGGACACGACTGGAGTTCAAAC<br>GAACTGTGGCTGCACCATCTGTCTTCATCTTCCCGCCATCTGATGAGCAGTTGAAAT<br>CTGGAACTGCCTCTGTTGTGTGCCTGCTGAATAACTTCTATCCCAGAGAGGCCAAAG<br>TACAGTGGAAGGTGGATAACGCCCTCCAATCGGGTAACTCCCAGGAGAGTGTCACA<br>GAGCAGGACAGCAAGGACAGCACCTACAGCCTCAGCAGCACCCTGACGCTGAGCA<br>AAGCAGACTACGAGAAACACAAAGTCTACGCCTGCGAAGTCACCCATCAGGGCCTG<br>AGCTCGCCCGTCACAAAGAGCTTCAACAGGGGAGAGTGT |
| 417 | Anti-CD132 P2F10 Fab HC (VH, joint CH1) | GAGGTCCAGCTGGTGCAGTCTGGGGCTGAGGTGAAGAAGCCTGGGGCCTCAGTGA<br>AGGTCTCCTGCAAGGCTTCTGGATACACCTTCACCGGCTACTATATGCACTGGGTGC<br>GACAGGCCCCTGGACAAGGGCTTGAGTGGATGGGAATAATCAACCCTAGTGGTGGT<br>AGCACAAGCTACGCACAGAAGTTCCAGGGCAGAGTCACCATGACCAGGGACACGTC<br>CACGAGCACAGTCTACATGGAGCTGAGCAGCCTGAGATCTGAGGACACGGCCGTGT<br>ATTACTGTGCGAGAGCCGATACAGCTATGGGTGATGCTTTTGATATCTGGGGCCAAG<br>GGACAATGGTCACCGTCTCAAGCGCCTCCACCAAGGGCCCATCGGTCTTCCCCCTG<br>GCACCCTCCTCCAAGAGCACCTCTGGGGGCACAGCGGCCCTGGGCTGCCTGGTCA<br>AGGACTACTTCCCCGAACCGGTGACGGTGTCGTGGAACTCAGGCGCCCTGACCAG<br>CGGCGTCCACACCTTCCCGGCTGTCCTACAGTCCTCAGGACTCTACTCCCTCAGCA<br>GCGTAGTGACCGTGCCCTCCAGCAGCTTGGGCACCCAGACCTACATCTGCAACGTG<br>AATCACAAGCCCAGCAACACCAAGGTGGACAAGAAAGTTGAGCCCAAATCTTGT |
| 418 | Anti-CD132 P2F10 scFv and Fc with hole modification | GAAGTCCAGCTGGTCCAGTCAGGAGCCGAGGTCAAGAAGCCAGGGGCAAGCGTCA<br>AAGTCTCATGCAAAGCAAGTGGGTACACATTTACAGGCTACTATATGCACTGGGTGA<br>GGCAGGCTCCAGGACAGGGCCTGGAGTGGATGGGGATCATTAACCCCAGCGGCGG<br>GAGTACCTCATACGCACAGAAGTTCCAGGGACGGGTGACTATGACCAGAGACACAA<br>GCACTTCCACCGTCTATATGGAGCTGAGCAGCCTGCGATCCGAAGACACTGCCGTG<br>TACTATTGCGCCAGAGCCGATACCGCAATGGGCGACGCCTTTGACATCTGGGGGCA<br>GGGCACAATGGTGACAGTCTCTAGTGGAGGAGGAGGATCTGGAGGAGGAGGCAGT<br>GGAGGAGGCGGGTCAGACATCGTGATGACACATACTCCACTGTCTCTGCCAGTCAC<br>CCCTGGCGAGCCAGCCTCTATTAGTTGTCGCTCAAGCCAGACCCTGTTCGACAGTG<br>ACGATGGAAAGACATACCTGGATTGGTACTTGCAGAAACCTGGCCAGAGCCCTCAG<br>CTGCTGATGTACACCACATCCTCTAGGGCCTCCGGCGTGCCTGACCGCTTCTCAGG<br>CAGCGGGTCCGGAACTGATTTTACCCTGAAGATCAGCCGGGTGGAGGCTGAAGACG<br>TGGGGGTCTACTATTGCATGCAGAGACTCCAGTTCCCACTGACATTTGGCCAGGGG<br>ACTCGGCTGGAGTTCAAGAACAGCGGCGCGGGCACCGCGGCCGCGACTCACACAT<br>GCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGT<br>GGTGGACGTGAGCCACGAAGACCCTGAGGTCAAGTTCAACTGGTACGTGGACGGC<br>GTGGAGGTGCATAATGCCAAGACAAAGCCGCGGGAGGAGCAGTACAACAGCACGT<br>ACCGTGTGGTCAGCGTCCTCACCGTCCTGCACCAGGACTGGCTGAATGGCAAGGAG<br>TACAAGTGCAAGGTCTCCAACAAAGCCCTCCCAGCCCCCATCGAGAAAACCATCTCC<br>AAAGCCAAAGGGCAGCCCCGAGAACCACAGGTGTGCACCCTGCCCCCATCCCGGG<br>ATGAGCTGACCAAGAACCAGGTCAGCCTGTCCTGCGCCGTCAAAGGCTTCTATCCC<br>AGCGACATCGCCGTGGAGTGGGAGAGCAATGGGCAGCCGGAGAACAACTACAAGA<br>CCACGCCTCCCGTGCTGGACTCCGACGGCTCCTTCTTCCTCGTGAGCAAGCTCACC<br>GTGGACAAGAGCAGGTGGCAGCAGGGGAACGTCTTCTCATGCTCCGTGATGCATGA<br>GGCTCTGCACAACCACTACACGCAGAAGAGCCTCTCCCTGTCTCCGGGTAAA |
| 419 | Anti-CD132 P2H4 Fab LC (VL, joint CL) | GATGTTGTGATGACTCAGTCTCCACTCTCCCTGCCCGTCACCCCTGGAGAGCCGGC<br>CTCCATCTCCTGCAGGGCAACTCAGAGCCTCCTGCATGGAAATGGACACAACTATTT<br>GGATTGGTACCTGCAGAAGCCAGGGCAGTCTCCACAGCTCCTGATCTATTTGGGTT<br>CTAATCGGGCCTCCGGGGTCCCTGACAGGTTCAGTGGCAGTGGATCAGGCACAGAT<br>TTTACACTGAAAATCAGCAGAGTGGAGGCTGAGGATGTTGGGGTTTATTACTGCATG<br>CAAACTCTGGAAACTCCTGTCACTTTCGGCCCTGGGACCAAAGTGGATATCAAACGA<br>ACTGTGGCTGCACCATCTGTCTTCATCTTCCCGCCATCTGATGAGCAGTTGAAATCT<br>GGAACTGCCTCTGTTGTGTGCCTGCTGAATAACTTCTATCCCAGAGAGGCCAAAGTA |

-continued

| SEQ ID NO: | DESCRIPTION | SEQUENCE |
|---|---|---|
| | | CAGTGGAAGGTGGATAACGCCCTCCAATCGGGTAACTCCCAGGAGAGTGTCACAGA GCAGGACAGCAAGGACAGCACCTACAGCCTCAGCAGCACCCTGACGCTGAGCAAA GCAGACTACGAGAAACACAAACTCTACGCCTGCGAAGTCACCCATCAGGGCCTGAG CTCGCCCGTCACAAAGAGCTTCAACAGGGGAGAGTGT |
| 420 | Anti-CD132 P2H4 Fab HC (VH, joint CH1) | GAGGTCCAGCTGGTGCAGTCTGGGGGAGGCGTGGTCCAGCCTGGGAGGTCCCTGA GACTCTCCTGTGCAGCCTCTGGATTCACCTTCAGTAGCTATGCTATGCACTGGGTCC GCCAGGCTCCAGGCAAGGGGCTGGAGTGGGTGGCAGTTATATCATATGATGGAAGC AATAAATACTACGCAGACTCCGTGAAGGGCCGATTCACCATCTCCAGAGACAATTCC AAGAACACGCTGTATCTGCAAATGAACAGCCTGAGAGCTGAGGACACGGCTGTGTA TTACTGTGCGAGGTCTATCGGTATCGGTGCTTTTGATATCTGGGGCCAAGGGACAAT GGTCACCGTCTCAAGCGCCTCCACCAAGGGCCCATCGGTCTTCCCCCTGGCACCCT CCTCCAAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCGGCGTC CACACCTTCCCGGCTGTCCTACAGTCCTCAGGACTCTACTCCCTCAGCAGCGTAGT GACCGTGCCCTCCAGCAGCTTGGGCACCCAGACCTACATCTGCAACGTGAATCACA AGCCCAGCAACACCAAGGTGGACAAGAAAGTTGAGCCCAAATCTTGT |
| 421 | Anti-CD132 P2H4 scFv and Fc with hole modification | GAGGTCCAGCTGGTCCAGAGCGGGGGGGGGgTCGTGCAGCCTGGGAGAAGCCTGA GACTGTCCTGTGCCGCAAGCGGGTTTACTTTTAGCTCCTACGCTATGCACTGGGTGA GGCAGGCACCCGGCAAGGGGCTGGAGTGGGTGGCAGTCATCTCCTATGACGGCTC TAACAAGTACTATGCCGATAGCGTGAAAGGGCGGTTCACAATTAGTAGAGACAACTC AAAGAACACTCTGTACCTCCAGATGAATAGCCTGCGAGCCGAAGACACTGCTGTGTA CTATTGCGCCCGGTCCATCGGAATTGGCGCTTTTGACATCTGGGGGCAGGGCACAA TGGTGACAGTCTCTAGTGGAGGAGGAGGCTCTGGAGGAGGAGGGAGTGGAGGAGG AGGATCAGACGTGGTCATGACCCAGTCACCTCTGAGCCTGCCAGTGACACCTGGCG AGCCAGCATCAATTAGCTGTAGAGCCACCCAGTCTCTGCTGCACGGCAACGGGCAT AATTACCTGGATTGGTACTTGCAGAAGCCTGGCCAGAGTCCTCAGCTGCTGATCTAT CTGGGGAGCAACAGGGCTTCCGGAGTGCCAGACCGCTTCTCCGGATCTGGCAGTG GGACTGATTTTACCCTGAAAATTTCCCGCGTCGAGGCAGAAGACGTGGGAGTCTACT ATTGCATGCAGACACTGGAAACTCCAGTGACCTTCGGACCCGGCACAAAGGTGGAC ATCAAGAACAGCGGCGCGGGCACCGCGGCCGCGACTCACACATGCCCACCGTGCC CAGCACCTGAACTCCTGGGGGGACCGTCAGTCTTCCTCTTCCCCCCAAAACCCAAG GACACCCTCATGATCTCCCGGACCCCTGAGGTCACATGCGTGGTGGTGGACGTGAG CCACGAAGACCCTGAGGTCAAGTTCAACTGGTACGTGGACGGCGTGGAGGTGCATA ATGCCAAGACAAAGCCGCGGGAGGAGCAGTACAACAGCACGTACCGTGTGGTCAG CGTCCTCACCGTCCTGCACCAGGACTGGCTGAATGGCAAGGAGTACAAGTGCAAGG TCTCCAACAAAGCCCTCCCAGCCCCCATCGAGAAAACCATCTCCAAAGCCAAAGGG CAGCCCCGAGAACCACAGGTGTGCACCCTGCCCCCATCCCGGGATGAGCTGACCA AGAACCAGGTCAGCCTGTCCTGCGCCGTCAAAGGCTTCTATCCCAGCGACATCGCC GTGGAGTGGGAGAGCAATGGGCAGCCGGAGAACAACTACAAGACCACGCCTCCCG TGCTGGACTCCGACGGCTCCTTCTTCCTCGTGAGCAAGCTCACCGTGGACAAGAGC AGGTGGCAGCAGGGGAACGTCTTCTCATGCTCCGTGATGCATGAGGCTCTGCACAA CCACTACACGCAGAAGAGCCTCTCCCTGTCTCCGGGTAAA |
| 422 | Anti-CD132 P2O3 Fab LC (VL, joint CL) | GATGTTGTGATGACTCAGTCTCCACTCTCCCTGCCCGTCACCCCTGGAGAGCCGGC CTCCATCTCCTGCAGGTCTAGTCAGAGCCTCCTGCATAGTAATGGATACAACTATTT GGATTGGTACCTGCAGAAGCCAGGGCAGTCTCCACAGCTCCTGATCTATTTGGGTT CTAATCGGGCCTCCGGGGTCCCTGACAGGTTCAGTGGCAGTGGATCAGGCACAGAT TTTACACTGAAAATCAGCAGGGTGGAGGCTGAGGATGTTGGGGTTTATTACTGCATG CAAGGTACACACTGGCCCTGGACGTTCGGCCAAGGGACCAAGGTGGAAATCAAACG AACTGTGGCTGCACCATCTGTCTTCATCTTCCCGCCATCTGATGAGCAGTTGAAATC TGGAACTGCCTCTGTTGTGTGCCTGCTGAATAATTTCTATCCCAGAGAGGCCAAAGT ACAGTGGAAGGTGGATAACGCCCTCCAATCGGGTAACTCCCAGGAGAGTGTCACAG AGCAGGACAGCAAGGACAGCACCTACAGCCTCAGCAGCACCCTGACGCTGAGCAAA GCAGACTACGAGAAACACAAACTCTACGCCTGCGAAGTCACCCATCAGGGCCTGAG CTCGCCCGTCACAAAGAGCTTCAACAGGGGAGAGTGT |
| 423 | Anti-CD132 P2d3 Fab HC (VH, joint CH1) | CAGGTGCAGCTACAGCAGTGGGGCGCAGGACTGTTGAAGCCTTCGGAGACCCTGT CCCTCACCTGCACTATCTATGGTGGGTCCTTCAGTGGTTTCTACTGGAGCTGGATCC GCCAGCCCCCAGGGAAGGGACTGGAGTGGATTGGGGAAATCAATCATAGTGGAAG CACCAACTACAACCCGTCCCTCAAGAGTCGAGTCACCATATCAGTAGACACGTCCAA GAACCAGTTCTCCCTGAAGCTGAGCTCTGTGACCGCCGCGGACACGGCTATATATT ACTGTGCGAGAGGCCCCGCGGGATCCACCTCGTCCGGCTACTTTGACCACTGGGG CCAGGGAACCCTGGTCACCGTCTCAAGCGCCTCCACCAAGGGCCCATCGGTCTTCC CCCTGGCACCCTCCTCCAAGAGCACCTCTGGGGGCACAGCGGCCCTGGGCTGCCT GGTCAAGGACTACTTCCCCGAACCGGTGACGGTGTCGTGGAACTCAGGCGCCCTGA CCAGCGGCGTCCACACCTTCCCGGCTGTCCTACAGTCCTCAGGACTCTACTCCCTC AGCAGCGTAGTGACCGTGCCCTCCAGCAGCTTGGGCACCCAGACCTACATCTGCAA CGTGAATCACAAGCCCAGCAACACCAAGGTGGACAAGAAAGTTGAGCCCAAATCTT GT |

-continued

Sequences

| SEQ ID NO: | DESCRIPTION | SEQUENCE |
|---|---|---|
| 424 | Anti-cd132 P2d3 scFv and Fc with hole modification | CAGGTCCAGCTGCAGCAGTGGGGAGCCGGACTGCTGAAACCCTCTGAGACTCTGA GCCTGACTTGCACAATCTACGGGGGATCATTCAGCGGCTTCTACTGGTCCTGGATCA GGCAGCCCCCTGGCAAGGGGCTGGAGTGGATCGGAGAAATTAACCACAGTGGCTC AACAAACTATAATCCCAGCCTGAAATCCCGCGTGACCATCTCAGTGGACACAAGCAA GAATCAGTTCAGCCTGAAGCTGAGCAGCGTGACAGCCGCTGATACTGCCATCTACT ATTGCGCACGGGGCCCTGCCGGGTCCACCTCTAGTGGGTACTTTGACCATTGGGGA CAGGGCACCCTGGTGACAGTCTCAAGCGGAGGAGGAGGCTCTGGAGGAGGAGGGA GTGGAGGCGGGGGCAGCGATGTGGTCATGACTCAGTCTCCACTGAGTCTGCCAGT GACCCCCGGCGAGCCTGCTAGCATCTCCTGTCGATCCTCTCAGTCCCTGCTGCACT CTAACGGATACAATTATCTGGACTGGTACTTGCAGAAGCCAGGCCAGAGCCCCCAG CTGCTGATCTATCTGGGGAGTAACCGGGCTTCAGGAGTGCCTGACAGATTCTCTGG GAGTGGATCAGGCACTGATTTTACCCTGAAAATTAGCAGAGTCGAGGCAGAAGATGT GGGCGTCTACTATTGCATGCAGGGGACTCATTGGCCCTGGACCTTTGGGCAGGGAA CAAAGGTGGAGATCAAGAACAGCGGCGCGGGCACCGCGGCCGCGACTCACACATG CCCACCGTGCCCAGCACCTGAACTCCTGGGGGGACCGTCAGTCTTCCTCTTCCCCC CAAAACCCAAGGACACCCTCATGATCTCCCGGACCCCTGAGGTCACATGCGTGGTG GTGGACGTGAGCCACGAAGACCCTGAGGTCAAGTTCAACTGGTACGTGGACGGCGT GGAGGTGCATAATGCCAAGACAAAGCCGCGGGAGGAGCAGTACAACAGCACGTAC CGTGTGGTCAGCGTCCTCACCGTCCTGCACCAGGACTGGCTGAATGGCAAGGAGTA CAAGTGCAAGGTCTCCAACAAAGCCCTCCCAGCCCCCATCGAGAAAACCATCTCCA AAGCCAAAGGGCAGCCCCGAGAACCACAGGTGTGCACCCTGCCCCCATCCCGGGA TGAGCTGACCAAGAACCAGGTCAGCCTGTCCTGCGCCGTCAAAGGCTTCTATCCCA GCGACATCGCCGTGGAGTGGGAGAGCAATGGGCAGCCGGAGAACAACTACAAGAC CACGCCTCCCGTGCTGGACTCCGACGGCTCCTTCTTCCTCGTGAGCAAGCTCACCG TGGACAAGAGCAGGTGGCAGCAGGGGAACGTCTTCTCATGCTCCGTGATGCATGAG GCTCTGCACAACCACTACACGCAGAAGAGCCTCTCCCTGTCTCCGGGTAAA |
| 425 | Anti-CD132 P1G4 Fab LC (VL, joint CL) | GATGTTGTGATGACTCAGTCTCCACTCTCCCTGCCCGTCACCCCTGGAGAGCCGGC CTCCATCTCCTGCAGGTCTAGTCAGAGCCTCCTGCATAGTAATGGATACAACTATTT GGATTGGTACCTGCAGAAGCCAGGGCAGTCTCCACAGCTCCTGATCTATTTGGGTT CTAATCGGGCCTCCGGGGTCCCTGACAGGTTCAGTGGCAGTGGATCAGGCACAGAT TTTACACTGAAAATCAGCAGGGTGGAGGCTGAGGATGTTGGGGTTTATTACTGCCTG CAAGGTACACATTGGCCGTGGACGTTCGGCCAGGGGACCAAGGTGGAAATCAAACG AACTGTGGCTGCACCATCTGTCTTCATCTTCCCGCCATCTGATGAGCAGTTGAAATC TGGAACTGCCTCTGTTGTGTGCCTGCTGAATAACTTCTATCCCAGAGAGGCCAAAGT ACAGTGGAAGGTGGATAACGCCCTCCAATCGGGTAACTCCCAGGAGAGTGTCACAG AGCAGGACAGCAAGGACAGCACCTACAGCCTCAGCAGCACCCTGACGCTGAGCAAA GCAGACTACGAGAAACACAAAGTCTACGCCTGCGAAGTCACCCATCAGGGCCTGAG CTCGCCCGTCACAAAGAGCTTCAACAGGGGAGAGTGT |
| 426 | Anti-CD132 P1G4 Fab HC (VH, joint CH1) | CAGGTGCAGCTACAGCAGTGGGGCGCAGGACTGTTGAAGCCTTCGGAGACCCTGT CCCTCACCTGCGCTGTCTATGGTGGGTCCCTCAGTGGTTACTACTGGAGCTGGATC CGCCAGCCCCCAGGGAAGGGGCTGGAGTGGATTGGGGAAATCAATCATAGTGGAA GCACCAACTACAACCCATCCCTCAAGAGTCGAGTCACCATATCAGTAGACACGTCCA AGAACCAGTTCTCCCTGAAGCTGAGCTCTGTGACCGCCGCGGACACGGCTGTGTAT TACTGTGCGAGAGGCAGCAGCTCCTACTACATGGACGTCTGGGGCAAAGGGACCAC GGTCACCGTCTCAAGCGCCTCCACCAAGGGCCCATCGGTCTTCCCCCTGGCACCCT CCTCCAAGAGCACCTCTGGGGGCACAGCGGCCCTGGGCTGCCTGGTCAAGGACTA CTTCCCCGAACCGGTGACGGTGTCGTGGAACTCAGGCGCCCTGACCAGCGGCGTC CACACCTTCCCGGCTGTCCTACAGTCCTCAGGACTCTACTCCCTCAGCAGCGTAGT GACCGTGCCCTCCAGCAGCTTGGGCACCCAGACCTACATCTGCAACGTGAATCACA AGCCCAGCAACACCAAGGTGGACAAGAAAGTTGAGCCCAAATCTTGT |
| 427 | Anti-CD132 P1G4 scFv and Fc with hole modification | CAGGTCCAGCTGCAGCAGTGGGGAGCCGGACTGCTGAAACCAAGCGAGACTCTGA GCCTGACTTGTGCCGTGTATGGGGGAAGCCTGTCCGGCTACTATTGGTCTTGGATC AGGCAGCCCCCTGGCAAGGGGCTGGAGTGGATCGGCGAAATTAACCACTCAGGGA GCACAAACTACAATCCCTCCCTGAAATCTCGCGTGACCATTAGCGTGGACACATCCA AGAATCAGTTCAGCCTGAAGCTGAGCAGCGTGACAGCCGCTGACACCGCCGTGTAC TATTGCGCCAGAGGCAGCAGCAGCTACTATATGGATGTGTGGGGAAAGGGCACCAC AGTGACCGTCAGCTCCGGAGGAGGAGGCAGTGGAGGAGGAGGGTCCGGAGGCGG GGGATCTGACGTGGTCATGACTCAGAGTCCTCTGTCACTGCCTGTGACCCCCGGCG AGCCTGCATCCATCTCTTGTCGATCTAGTCAGTCTCTGCTGCACAGTAACGGCTACA ATTATCTGGATTGGTACTTGCAGAAGCCAGGGCAGTCCCCCCAGCTGCTGATCTATC TGGGATCAAACCGGGCTAGCGGCGTGCCTGACAGATTCAGTGGGTCAGGAAGCGG CACTGATTTTACCCTGAAAATTAGCAGAGTCGAGGCAGAAGATGTGGGGGTCTACTA TTGCCTCCAGGGAACTCATTGGCCCTGGACCTTTGGGCAGGGAACAAAGGTGGAGA TCAAGAACAGCGGCGCGGGCACCGCGGCCGCGACTCACACATGCCCACCGTGCCC AGCACCTGAACTCCTGGGGGGACCGTCAGTCTTCCTCTTCCCCCCAAAACCCAAGG ACACCCTCATGATCTCCCGGACCCCTGAGGTCACATGCGTGGTGGTGGACGTGAGC CACGAAGACCCTGAGGTCAAGTTCAACTGGTACGTGGACGGCGTGGAGGTGCATAA TGCCAAGACAAAGCCGCGGGAGGAGCAGTACAACAGCACGTACCGTGTGGTCAGC GTCCTCACCGTCCTGCACCAGGACTGGCTGAATGGCAAGGAGTACAAGTGCAAGGT CTCCAACAAAGCCCTCCCAGCCCCCATCGAGAAAACCATCTCCAAAGCCAAAGGGC |

-continued

Sequences

| SEQ ID NO: | DESCRIPTION | SEQUENCE |
|---|---|---|
| | | AGCCCCGAGAACCACAGGTGTGCACCCTGCCCCCATCCCGGGATGAGCTGACCAA GAACCAGGTCAGCCTGTCCTGCGCCGTCAAAGGCTTCTATCCCAGCGACATCGCCG TGGAGTGGGAGAGCAATGGGCAGCCGGAGAACAACTACAAGACCACGCCTCCCGT GCTGGACTCCGACGGCTCCTTCTTCCTCGTGAGCAAGCTCACCGTGGACAAGAGCA GGTGGCAGCAGGGGAACGTCTTCTCATGCTCCGTGATGCATGAGGCTCTGCACAAC CACTACACGCAGAAGAGCCTCTCCCTGTCTCCGGGTAAA |
| 428 | Anti-CD132 P1B12 Fab LC (VL, joint CL) | GATGTTGTGATGACTCAGTCTCCACTCTCCCTGCCCGTCACCCTTGGTCAGCCGGC CTCCATCTCCTGCAGGTCTAGTCAGAGCCTCCTGCACAGTAATGGAAACAACTATTT GGATTGGTACCTGCAGAAGCCAGGGCAGTCTCCACAGCTCCTGATCTATTTGGGTT CTAATCGGGCCTCCGGGGTCCCTGACAGGTTCAGTGGCAGTGGATCAGGCACAGAT TTTACACTGAAAATCAGCAGGGTGGAGGCTGAGGATGTTGGGATTTATTACTGCATG CAAGGGACACACTGGCCTTGGACGTTCGGCCAAGGGACCAAGGTGGAAATCGAAC GAACTGTGGCTGCACCATCTGTCTTCATCTTCCCGCCATCTGATGAGCAGTTGAAAT CTGGAACTGCCTCTGTTGTGTGCCTGCTGAATAACTTCTATCCCAGAGAGGCCAAAG TACAGTGGAAGGTGGATAGCGCCCTCCAATCGGGTAACTCCCAGGAGAGTGTCACA GAGCAGGACAGCAAGGACAGCACCTACAGCCTCAGCAGCACCCTGACGCTGAGCA AAGCAGACTACGAGAAACACAAACTCTACGCCTGCGAAGTCACCCATCAGGGCCTG AGCTCGCCCGTCACAAAGAGCTTCAACAGGGGAGAGTGT |
| 429 | Anti-CD132 P1B12 Fab HC (VH, joint CH1) | CAGGTGCAGCTACAGCAGTGGGGCGCAGGACTGTTGAAGCCTTCGGAGACCCTGT CCCTCACCTGCGCTGTCTATGGTGGGTCCTTCAGTGGTTACTACTGGAGCTGGATC CGCCAGCCCCCAGGGAAGGGGCTGGAGTGGATTGGGGAAATCAATCATAGTGGAA GCACCAACTACAACCCGTCCCTCAAGAGTCGAGTCACCATATCAGTAGACACGTCCA AGAACCAGTTCTCCCTGAAGCTGAGCTCTGTGACCGCCGCGGACACGGCTGTGTAT TACTGTGCGAGAGGCGGTAGCGCGTACTTCCAGCACTGGGGCCAGGGAACCCTGG TCACCGTCTCAAGCGCCTCCACCAAGGGCCCATCGGTCTTCCCCCTGGCACCCTCC TCCAAGAGCACCTCTGGGGGCACAGCGGCCCTGGGCTGCCTGGTCAAGGACTACT TCCCCGAACCGGTGACGGTGTCGTGGAACTCAGGCGCCCTGACCAGCGGCGTCCA CACCTTCCCGGCTGTCCTACAGTCCTCAGGACTCTACTCCCTCAGCAGCGTAGTGA CCGTGCCCTCCAGCAGCTTGGGCACCCAGACCTACATCTGCAACGTGAATCACAAG CCCAGCAACACCAAGGTGGACAAGAAAGTTGAGCCCAAATCTTGT |
| 430 | Anti-CD132 P1B12 scFv and Fc with hole modification | CAGGTCCAGCTGCAGCAGTGGGGGGCCGGGCTGCTGAAACCTTCCGAAACTCTGT CTCTGACTTGTGCCGTGTATGGGGGGTCCTTTAGTGGCTACTATTGGTCATGGATCA GGCAGCCCCCTGGAAAGGGCCTGGAGTGGATCGGAGAAATTAACCACTCCGGCTCT ACAAACTACAATCCAAGTCTGAAATCACGCGTGACCATTTCTGTGGACACCAGTAAG AATCAGTTCAGCCTGAAGCTGAGCAGCGTGACAGCCGCTGATACCGCCGTGTACTA TTGCGCCCGAGGCGGGTCTGCTTATTTTCAGCATTGGGGGCAGGGAACCCTGGTGA CAGTCTCTAGTGGAGGAGGAGGCAGCGGCGGAGGAGGCTCTGGAGGAGGAGGGA GTGACGTGGTCATGACTCAGAGCCCACTGTCCCTGCCAGTGACCCTGGGACAGCCA GCTAGTATCTCATGTAGATCAAGCCAGTCACTGCTGCACAGCAACGGCAACAATTAC CTGGATTGGTACTTGCAGAAGCCTGGCCAGAGCCCACAGCTGCTGATCTACCTGGG GTCCAATCGGGCATCTGGAGTGCCCGACAGATTCAGCGGCTCCGGGTCTGGAACTG ATTTTACCCTGAAGATCAGCCGGGTGGAGGCCGAAGACGTCGGCATCTACTATTGC ATGCAGGGGACTCATTGGCCTTGGACCTTCGGCCAGGGGACAAAAGTGGAGATCGA AAACAGCGGCGCGGGCACCGCGGCCGCGACTCACACATGCCCACCGTGCCCAGCA CCTGAACTCCTGGGGGGACCGTCAGTCTTCCTCTTCCCCCCAAAACCCAAGGACAC CCTCATGATCTCCCGGACCCCTGAGGTCACATGCGTGGTGGTGGACGTGAGCCACG AAGACCCTGAGGTCAAGTTCAACTGGTACGTGGACGGCGTGGAGGTGCATAATGCC AAGACAAAGCCGCGGGAGGAGCAGTACAACAGCACGTACCGTGTGGTCAGCGTCC TCACCGTCCTGCACCAGGACTGGCTGAATGGCAAGGAGTACAAGTGCAAGGTCTCC AACAAAGCCCTCCCAGCCCCCATCGAGAAAACCATCTCCAAAGCCAAAGGGCAGCC CCGAGAACCACAGGTGTGCACCCTGCCCCCATCCCGGGATGAGCTGACCAAGAAC CAGGTCAGCCTGTCCTGCGCCGTCAAAGGCTTCTATCCCAGCGACATCGCCGTGGA GTGGGAGAGCAATGGGCAGCCGGAGAACAACTACAAGACCACGCCTCCCGTGCTG GACTCCGACGGCTCCTTCTTCCTCGTGAGCAAGCTCACCGTGGACAAGAGCAGGTG GCAGCAGGGGAACGTCTTCTCATGCTCCGTGATGCATGAGGCTCTGCACAACCACT ACACGCAGAAGAGCCTCTCCCTGTCTCCGGGTAAA |
| 431 | Anti-CD132 P1C7 Fab LC (VL, joint CL) | GAAATTGTGCTGACTCAGTCTCCACTCTCCCTGCCCGTCACCCCTGGAGAGCCGGC CTCCATCTCCTGCAGGTCTAGTCAGAGCCTCCTGCATAGTAATGGATACAACTATTT GGATTGGTACCTGCAGAAGCCAGGGCAGTCTCCACAGCTCCTGATCTATTTGGCTTC TAATCGGGCCTCCGGGGTCCCAGACAGATTCAGCGGCAGTGGGTCAGGCACTGATT TCACACTGAAAATCAGCAGGGTGGAGGCTGAGGATGTTGGGGTTTATTACTGCATG CAAGGTACACACTGGCCGTGGACGTTCGGCCAAGGGACCAAGGTGGAAGTCAAAC GAACTGTGGCTGCACCATCTGTCTTCATCTTCCCGCCATCTGATGAGCAGTTGAAAT CTGGAACTGCCTCTGTTGTGTGCCTGCTGAATAACTTCTATCCCAGAGAGGCCAAAG TACAGTGGAAGGTGGATAACGCCCTCCAATCGGGTAACTCCCGGGAGAGTGTCACA GAGCAGGACAGCAAGGACAGCACCTACAGCCTCAGCAGCACCCTGACGCTGAGCA AAGCAGACTACGAGAAACACAAAGTCTACGCCTGCGAAGTCACCCATCAGGGCCTG AGCTCGCCCGTCACAAAGAGCTTCAACAGGGGAGAGTGT |

-continued

| SEQ ID NO: | DESCRIPTION | SEQUENCE |
|---|---|---|
| 432 | Anti-CD132 P1C7 Fab HC (VH, joint CH1) | CAGGTGCAGCTACAGCAGTGGGGCGCAGGACTGTTGAAGCCTTCGGAGACCCTGT CCCTCACCTGCGCTGTCTATGGTGGGTCCTTCAGTGGTTACTACTGGAGCTGGATC CGCCAGCCCCCAGGGAAGGGGCTGGAGTGGATTGGGGAAATCAATCATAGTGGAA GCACCAACTACAACCCGTCCCTCAAGAGTCGAGTCACCATATCAGAAGACGCGTCC AAGAAGCAGTTCTCCCTGACGCTGACCTCTGTGACCGCCGCGGACACGGCTGTCTA TTACTGTGCGAGAGGCCCCGCGGGTACCGGCTCGTCCGGCTACTTTGACTACTGGG GCCAGGGAACCCTGGTCACCGTCTCAAGCGCCTCCACCAAGGGCCCATCGGTCTTC CCCCTGGCACCCTCCTCCAAGAGCACCTCTGGGGGCACAGCGGCCCTGGGCTGCC TGGTCAAGGACTACTTCCCCGAACCGGTGACGGTGTCGTGGAACTCAGGCGCCCTG ACCAGCGGCGTCCACACCTTCCCGGCTGTCCTACAGTCCTCAGGACTCTACTCCCT CAGCAGCGTAGTGACCGTGCCCTCCAGCAGCTTGGGCACCCAGACCTACATCTGCA ACGTGAATCACAAGCCCAGCAACACCAAGGTGGACAAGAAAGTTGAGCCCAAATCTT GT |
| 433 | Anti-CD132 P1C7 scFv and Fc with hole modification | CAGGTCCAGCTGCAGCAGTGGGGAGCCGGACTGCTGAAGCCTAGCGAAACTCTGA GCCTGACTTGTGCTGTCTACGGAGGATCATTTAGTGGCTACTATTGGTCATGGATCA GGCAGCCCCCTGGCAAGGGGCTGGAGTGGATCGGAGAAATTAACCACTCCGGCTC TACAAACTACAATCCCAGTCTGAAATCACGCGTGACTATTTCTGAGGACGCCAGTAA GAAACAGTTCTCCCTGACCCTGACATCTGTGACCGCCGCTGATACAGCTGTCTACTA TTGCGCACGGGGCCCTGCCGGAACAGGCAGCTCCGGATACTTTGACTATTGGGGG CAGGGAACTCTGGTGACCGTCTCTAGTGGCGGAGGAGGCAGTGGAGGAGGAGGGT CCGGAGGAGGAGGATCTGAGATCGTGCTGACTCAGAGCCCACTGTCCCTGCCAGTC ACCCCCGGCGAACCTGCCAGTATTTCATGTCGATCAAGCCAGTCACTGCTGCACAG CAACGGATACAATTATCTGGACTGGTACTTGCAGAAGCCAGGCCAGAGCCCCCAGC TGCTGATCTATCTGGCTTCCAATCGGGCATCTGGCGTGCCTGACAGATTCAGCGGC TCCGGGTCTGGAACAGATTTTACTCTGAAAATTTCCAGAGTGGAGGCCGAAGATGTG GGGGTCTACTATTGCATGCAGGGAACTCATTGGCCCTGGACCTTCGGCCAGGGGAC AAAGGTGGAAGTCAAAAACAGCGGCGCGGGCACCGCGGCCGCGACTCACACATGC CCACCGTGCCCAGCACCTGAACTCCTGGGGGGACCGTCAGTCTTCCTCTTCCCCCC AAAACCCAAGGACACCCTCATGATCTCCCGGACCCCTGAGGTCACATGCGTGGTGG TGGACGTGAGCCACGAAGACCCTGAGGTCAAGTTCAACTGGTACGTGGACGGCGTG GAGGTGCATAATGCCAAGACAAAGCCGCGGGAGGAGCAGTACAACAGCACGTACC GTGTGGTCAGCGTCCTCACCGTCCTGCACCAGGACTGGCTGAATGGCAAGGAGTAC AAGTGCAAGGTCTCCAACAAAGCCCTCCCAGCCCCCATCGAGAAAACCATCTCCAAA GCCAAAGGGCAGCCCCGAGAACCACAGGTGTGCACCCTGCCCCCATCCCGGGATG AGCTGACCAAGAACCAGGTCAGCCTGTCCTGCGCCGTCAAAGGCTTCTATCCCAGC GACATCGCCGTGGAGTGGGAGAGCAATGGGCAGCCGGAGAACAACTACAAGACCA CGCCTCCCGTGCTGGACTCCGACGGCTCCTTCTTCCTCGTGAGCAAGCTCACCGTG GACAAGAGCAGGTGGCAGCAGGGGAACGTCTTCTCATGCTCCGTGATGCATGAGGC TCTGCACAACCACTACACGCAGAAGAGCCTCTCCCTGTCTCCGGGTAAA |
| 434 | Human CD122 (UniProt: P14784-1, v1) | MAAPALSWRLPLLILLLPLATSWASAAVNGTSQFTCFYNSRANISCVWSQDGALQDTSC QVHAWPDRRRWNQTCELLPVSQASWACNLILGAPDSQKLTTVDIVTLRVLCREGVRWR VMAIQDFKPFENLRLMAPISLQVVHVETHRCNISWEISQASHYFERHLEFEARTLSPGHT WEEAPLLTLKQKQEWICLETLTPDTQYEFQVRVKPLQGEFTTWSPWSQPLAFRTKPAAL GKDTIPWLGHLLVGLSGAFGFIILVYLLINCRNTGPWLKKVLKCNTPDPSKFFSQLSSEHG GDVQKWLSSPFPSSSFSPGGLAPEISPLEVLERDKVTQLLLQQDKVPEPASLSSNHSLT SCFTNQGYFFFHLPDALEIEACQVYFTYDPYSEEDPDEGVAGAPTGSSPQPLQPLSGED DAYCTFPSRDDLLLFSPSLLGGPSPPSTAPGGSGAGEERMPPSLQERVPRDWDPQPLG PPTPGVPDLVDFQPPPELVLREAGEEVPDAGPREGVSFPWSRPPGQGEFRALNARLPL NTDAYLSLQELQGQDPTHLV |
| 435 | Mature form Human CD122 (UniProt: P14784-1, v1 residues 27 to 525) | AVNGTSQFTCFYNSRANISCVWSQDGALQDTSCQVHAWPDRRRWNQTCELLPVSQAS WACNLILGAPDSQKLTTVDIVTLRVLCREGVRWRVMAIQDFKPFENLRLMAPISLQVVHV ETHRCNISWEISQASHYFERHLEFEARTLSPGHTWEEAPLLTLKQKQEWICLETLTPDTQ YEFQVRVKPLQGEFTTWSPWSQPLAFRTKPAALGKDTIPWLGHLLVGLSGAFGFIILVYL LINCRNTGPWLKKVLKCNTPDPSKFFSQLSSEHGGDVQKWLSSPFPSSSFSPGGLAPEI SPLEVLERDKVTQLLLQQDKVPEPASLSSNHSLTSCFTNQGYFFFHLPDALEIEACQVYF TYDPYSEEDPDEGVAGAPTGSSPQPLQPLSGEDDAYCTFPSRDDLLLFSPSLLGGPSPP STAPGGSGAGEERMPPSLQERVPRDWDPQPLGPPTPGVPDLVDFQPPPELVLREAGE EVPDAGPREGVSFPWSRPPGQGEFRALNARLPLNTDAYLSLQELQGQDPTHLV |
| 436 | Extracellular domain of Human CD122 (UniProt: P14784-1, v1 residues 27 to 240) | AVNGTSQFTCFYNSRANISCVWSQDGALQDTSCQVHAWPDRRRWNQTCELLPVSQAS WACNLILGAPDSQKLTTVDIVTLRVLCREGVRWRVMAIQDFKPFENLRLMAPISLQWHV ETHRCNISWEISQASHYFERHLEFEARTLSPGHTWEEAPLLTLKQKQEWICLETLTPDTQ YEFQVRVKPLQGEFTTWSPWSQPLAFRTKPAALGKDT |
| 437 | Human CD132 (UniProt: P31785-1, v1) | MLKPSLPFTSLLFLQLPLLGVGLNTTILTPNGNEDTTADFFLTTMPTDSLSVSTLPLPEVQ CFVFNVEYMNCTWNSSSEPQPTNLTLHYWYKNSDNDKVQKCSHYLFSEEITSGCQLQK KEIHLYQTFWQLQDPREPRRQATQMLKLQNLVIPWAPENLTLHKLSESQLELNWNNRF |

-continued

Sequences

| SEQ ID NO: | DESCRIPTION | SEQUENCE |
|---|---|---|
| | | LNHCLEHLVQYRTDWDHSWTEQSVDYRHKFSLPSVDGQKRYTFRVRSRFNPLCGSAQ HWSEWSHPIHWGSNTSKENPFLFALEAWISVGSMGLIISLLCVYFWLERTMPRIPTLKN LEDLVTEYHGNFSAWSGVSKGLAESLQPDYSERLCLVSEIPPKGGALGEGPGASPCNQ HSPYWAPPCYTLKPET |
| 438 | Mature form Human CD132 (UniProt: P31785-1, v1 residues 23 to 369) | LNTTILTPNGNEDTTADFFLTTMPTDSLSVSTLPLPEVQCFVFNVEYMNCTWNSSSEPQP TNLTLHYWYKNSDNDKVQKCSHYLFSEEITSGCQLQKKEIHLYQTFVVQLQDPREPRRQ ATQMLKLQNLVIPWAPENLTLHKLSESQLELNWNNRFLNHCLEHLVQYRTDWDHSWTE QSVDYRHKFSLPSVDGQKRYTFRVRSRFNPLCGSAQHWSEWSHPIHWGSNTSKENPF LFALEAVVISVGSMGLIISLLCVYFWLERTMPRIPTLKNLEDLVTEYHGNFSAWSGVSKGL AESLQPDYSERLCLVSEIPPKGGALGEGPGASPCNQHSPYWAPPCYTLKPET |
| 439 | Extracellular domain of Human CD132 (UniProt: P31785-1, v1 residues 23 to 262) | LNTTILTPNGNEDTTADFFLTTMPTDSLSVSTLPLPEVQCFVFNVEYMNCTWNSSSEPQP TNLTLHYWYKNSDNDKVQKCSHYLFSEEITSGCQLQKKEIHLYQTFVVQLQDPREPRRQ ATQMLKLQNLVIPWAPENLTLHKLSESQLELNWNNRFLNHCLEHLVQYRTDWDHSWTE QSVDYRHKFSLPSVDGQKRYTFRVRSRFNPLCGSAQHWSEWSHPIHWGSNTSKENPF LFALEA |
| 440 | Human IgG1 constant region (IGHG1; UniProt: P01857-1, v1) | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKVEPKSCDKTHTCPPCPAPELL GGPSVFLFPPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTV DKSRWQQGNVFSCSVMHEALHNHYTQKSLSLSPGK |
| 441 | CH1 IgG1 (positions 1-98 of P01857-1, v1) | ASTKGPSVFPLAPSSKSTSGGTAALGCLVKDYFPEPVTVSWNSGALTSGVHTFPAVLQS SGLYSLSSVVTVPSSSLGTQTYICNVNHKPSNTKVDKKV |
| 442 | Hinge IgG1 (positions 99-110 of P01857-1, v1) | EPKSCDKTHTCP |
| 443 | CH2 IgG1 (positions 111-223 of P01857-1, v1) | PCPAPELLGGPSVFLFPPKPKDTLMISRTPEVTCVVDVSHEDPEVKFNWYVDGVEVHN AKTKPREEQYNSTYRWSVLTVLHQDWLNGKEYKCKVSNKALPAPIEKTISKAK |
| 444 | CH3 IgG1 (positions 224-330 of P01857-1, v1) | GQPREPQVYTLPPSRDELTKNQVSLTCLVKGFYPSDIAVEWESNGQPENNYKTTPPVLD SDGSFFLYSKLTVDKSRWQQGNVFSCSVMHEALHNHYTQKSLSLSPGK |
| 445 | Cκ CL (IGCK: UniProt: P01834-1, v2) | RTVAAPSVFIFPPSDEQLKSGTASWCLLNNFYPREAKVQWKVDNALQSGNSQESVTEQ DSKDSTYSLSSTLTLSKADYEKHKVYACEVTHQGLSSPVTKSFNRGEC |
| 446 | CH2-CH3 IgG1 (positions 111-330 of P01057-1, v1) | PCPAPELLGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEKTISKAKGQPRE PQVYTLPPSRDELTKNQVSLTCLVKGFYPSDIAVEWESNGQPENNYKTTPPVLDSDGSF FLYSKLTVDKSRWQQGNVFSCSVMHEALHNHYTQKSLSLSPGK |
| 447 | CH3 (T366W, S354C) | GQPREPQVYTLPPCRDELTKNQVSLWCLVKGFYPSDIAVEWESNGQPENNYKTTPPVL DSDGSFFLYSKLTVDKSRWQQGNVFSCSVMHEALHNHYTQKSLSLSPGK |
| 448 | CH3 (T366S, L368A, Y407V, Y349C) | GQPREPQVCTLPPSRDELTKNQVSLSCAVKGFYPSDIAVEWESNGQPENNYKTTPPVL DSDGSFFLVSKLTVDKSRWQQGNVFSCSVMHEALHNHYTQKSLSLSPGK |
| 449 | CH2-CH3 (T366W, S354C) | PCPAPELLGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEKTISKAKGQPRE PQVYTLPPCRDELTKNQVSLWCLVKGFYPSDIAVEWESNGQPENNYKTTPPVLDSDGS FFLYSKLTVDKSRWQQGNVFSCSVMHEALHNHYTQKSLSLSPGK |
| 450 | CH2-CH3 (T356S, L368A, Y407V, Y349C) | PCPAPELLGGPSVFLFPPKPKDTLMISRTPEVTCVVVDVSHEDPEVKFNWYVDGVEVHN AKTKPREEQYNSTYRVVSVLTVLHQDWLNGKEYKCKVSNKALPAPIEKTISKAKGQPRE PQVCTLPPSRDELTKNQVSLSCAVKGFYPSDIAVEWESNGQPENNYKTTPPVLDSDGSF FLVSKLTVDKSRWQQGNVFSCSVMHEALHNHYTQKSLSLSPGK |
| 451 | CH2(LALA)-CH3 | PCPAPEAAGGPSVFLFPPKPKDTLMISRTPEVTCVVDVSHEDPEVKFNWYVDGVEVH NAKTKPREEQYNSTYRVVSVLTVLHQDWLNGKEYKCKVSNKALPAPIEKTISKAK |
| 452 | CH2(LALA)-CH3 9T366W, S345C) | PCPAPEAAGGPSVFLFPPKPKDTLMISRTPEVTCVVDVSHEDPEVKFNWYVDGVEVH NAKTKPREEQYNSTYRVVSVLTVLHQDWLNGKEYKCKVSNKALPAPIEKTISKAKGQPR EPQVYTLPPCRDELTKNQVSLWCLVKGFYPSDIAVEWESNGQPENNYKTTPPVLDSDG SFFLYSKLTVDKSRWQQGNVFSCSVMHEALHNHYTQKSLSLSPGK |

-continued

| Sequences | | |
|---|---|---|
| SEQ ID NO: | DESCRIPTION | SEQUENCE |
| 453 | CH2(LALA)-CH3 (T366S, L368A, Y407V, Y349C) | PCPAPEAAGGPSVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIEKTISKAKGQPR EPQVCTLPPSRDELTKNQVSLSCAVKGFYPSDIAVEWESNGQPENNYKTTPPVLDSDG SFFLVSKLTVDKSRWQQGNVFSCSVMHEALHNHYTQKSLSLSPGK |
| 454 | Linker 5 | GGGGSGGGGSGGGGSGGGGS |
| 454 | Linker 6 | GGGGS |

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Where a nucleic acid sequence is disclosed herein, the reverse complement thereof is also expressly contemplated.

Methods described herein may preferably performed in vitro. The term "in vitro" is intended to encompass experiments with cells in culture whereas the term "in vivo" is intended to encompass experiments with intact multi-cellular organisms.

BRIEF DESCRIPTION OF THE FIGURES

Embodiments and experiments illustrating the principles of the invention will now be discussed with reference to the accompanying figures.

EXAMPLES

In the following Examples, the inventors design, produce and characterise antibodies capable of binding to IL-2Rβ and γc.

Example 1: IL-2Rβ and γc Binding Antibodies

Anti-IL-2Rβ antibody clones and anti-γc antibody clones were isolated from a human antibody phage display library via in vitro selection.

Illustrative bispecific antibodies were constructed using IL-2Rβ-binding clone P2C4 in combination with one of the γc-binding antibody clones P1A3 or P1A10. The bispecific antibodies were designated 'P2C4/P1A3' and 'P2C4/P1A10', respectively.

The closest matching antibody germline genes for clone P2C4 are IGHV1-46*01 and IGLV2-14*01.

The closest matching antibody germline genes for clone P1A3 are IGHV4-34*01 and IGKV2-28*01.

|  | IL-2Rβ | γc |
|---|---|---|
| P2C4/P1A3 | $k_{on}$ = 2.21 × 10$^5$ M$^{-1}$s$^{-1}$  $k_{off}$ = 6.62 × 10$^{-3}$ s$^{-1}$<br>$K_D$ = 3.00 × 10$^{-8}$ M | $k_{on}$ = 5.22 × 10$^4$ M$^{-1}$s$^{-1}$  $k_{off}$ = 4.42 × 10$^{-3}$ s$^{-1}$<br>$K_D$ = 8.47 × 10$^{-8}$ M |
| P2C4/P1A10 | $k_{on}$ = 1.56 × 10$^5$ M$^{-1}$s$^{-1}$  $k_{off}$ = 4.40 × 10$^{-3}$ s$^{-1}$<br>$K_D$ = 2.82 × 10$^{-8}$ M | $k_{on}$ = 1.56 × 10$^5$ M$^{-1}$s$^{-1}$  $k_{off}$ = 9.61 × 10$^{-3}$ s$^{-1}$<br>$K_D$ = 6.18 × 10$^{-8}$ M |

The closest matching antibody germline genes for clone P1A10 are IGHV1-24*01 and IGKV2-28*01

Three bispecific antibody formats were prepared: scFv-KiH-Fc, CrossMab and Duobody formats.

The bispecific antibodies were expressed by transient transfection of HEK 293 cells, and yields were as follows:
ScFv-KiH-Fc:
  P2C4/P1A3: 4-14 mg/L; P2C4/P1A10: 28-40 mg/L
CrossMab:
  P2C4/P1A3: 14-160 mg/L; P2C4/P1A10: 63 mg/L
Duobody:
  P2C4/P1A10: (P2C4) 77 mg/L; (P1A10) 110 mg/L Except where otherwise indicated, in the following examples P2C4/P1A3 and P2C4/P1A10 were investigated in the scFv-KiH-Fc format, in which scFv comprising VH and VL domains for P2C4 are fused via a linker to Fc comprising the 'knob' modification is expressed with scFv comprising VH and VL domains for P1A3 (P2C4/P1A3) or P1A10 (P2C4/P1A10) fused via a linker to Fc comprising the 'hole' modification.

Example 2: Analysis of Binding to IL-2 Receptors 2.1 Analysis of Binding Affinity by ELISA Binding of P2C4/P1A3 to IL-2Rβ or γc was measured by ELISA analysis, using recombinant IL-2Rβ-Fc and γc-Fc coated on maxisorp plates.

Biotinylated P2C4/P1A3 was added at various concentrations. Detection of binding was performed using a colorimetric assay using HRP-conjugated streptavidin which converts TMB substrate to a blue solution. The reaction was stopped using hydrochloric acid, and absorbance was measured at 450 nm and 670 nm.

Figure 1A:
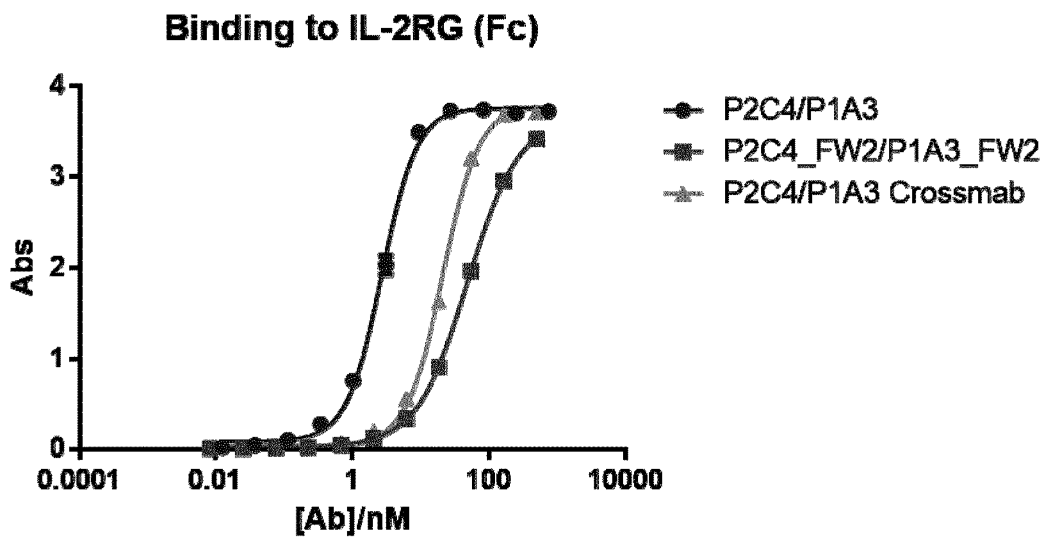
FIGS. 1A and 1B. Graphs showing binding of different formats of bispecific anti-IL2Rβ/γc antibodies to (1A) γc-Fc and (1B) IL2Rβ-Fc as determined by ELISA.
Figure 1B:
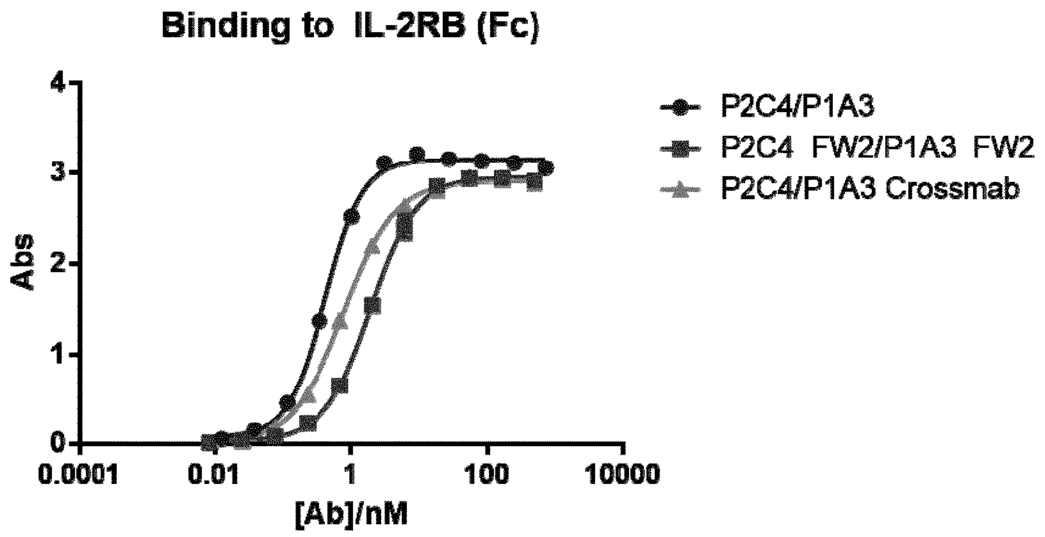

The results are shown in FIGS. 1A and 18. P2C4/P1A3 was shown to bind to both IL-2Rβ and γc. EC50s for binding were calculated and are shown in the Figures.

The bispecific antibodies analysed in this assay were:
scFv (P2C4): scFv (P1A3)—KiH-Fc—designated 'P2C4/P1A3' in the Figures.
scFv (P2C4_FW2): scFv (P1A3_FW2)—KiH-Fc—designated 'P2C4_FW2/P1A3_FW2' in the Figures.
Fab (P2C4): Fab (P1A3) in CrossMab format—designated 'P2C4/P1A3 Crossmab' in the Figures.

2.2 Analysis of Binding Affinity by Bio-Layer Interferometry

The affinity of binding of P2C4/P1A3 and P2C4/P1A10 to IL-2Rβ and γc was measured by Bio-Layer Interferometry (BLI).

P2C4/P1A3 or P2C4/P1A10 were captured on anti-human Fc biosensor tips, and 5 different concentrations of monomeric IL-2Rβ or γc were allowed to bind to the captured antibodies. Dissociation of the antigen from the immobilised antibodies was performed for 5 min. Binding affinity was calculated by fitting binding curves using the 1:1 Langmuir model.

The affinity data are summarised in the table below.

Similar binding to IL-2Rβ for P2C4/P1A3 and P2C4/P1A10 was observed (30 nM vs 28.2 nM). This was to be expected because the bispecific antibodies have the same IL-2Rβ-binding clone P2C4.

Whilst the affinity of binding to γc was similar for P2C4/P1A3 and P2C4/P1A10 (84.7 nM vs 61.8 nM), P2C4/P1A10 was found to have a faster on-rate and a faster off-rate than P2C4/P1A3.

2.3 Analysis of Binding to IL-2Rβ and γc Expressed at the Cell Surface

To determine whether P2C4/P1A3 and P2C4/P1A10 are able to bind to IL-2 receptors expressed on the surface of cells, HEK293-6E cells were transfected with plasmids encoding human IL-2Rα-GFP, or IL-2Rβ-OFP and γc-GFP.

Transfected cells were stained with P2C4/P1A3, P2C4/P1A10 or an isotype control antibody, followed by detection with a fluorochrome-conjugated secondary antibody for analysis by flow cytometry.

Normalized Median Fluorescence intensity (nMFI) was calculated in the GFP+ cell population (for cells transfected with constructs encoding IL-2Rα-GFP) or the GFP+/OFP+ cell population (for cells transfected with constructs encoding IL-2Rβ-OFP and γc-GFP) by subtracting the MFI obtained when secondary antibody only was added to the cells (negative control condition).

Figure 2A:
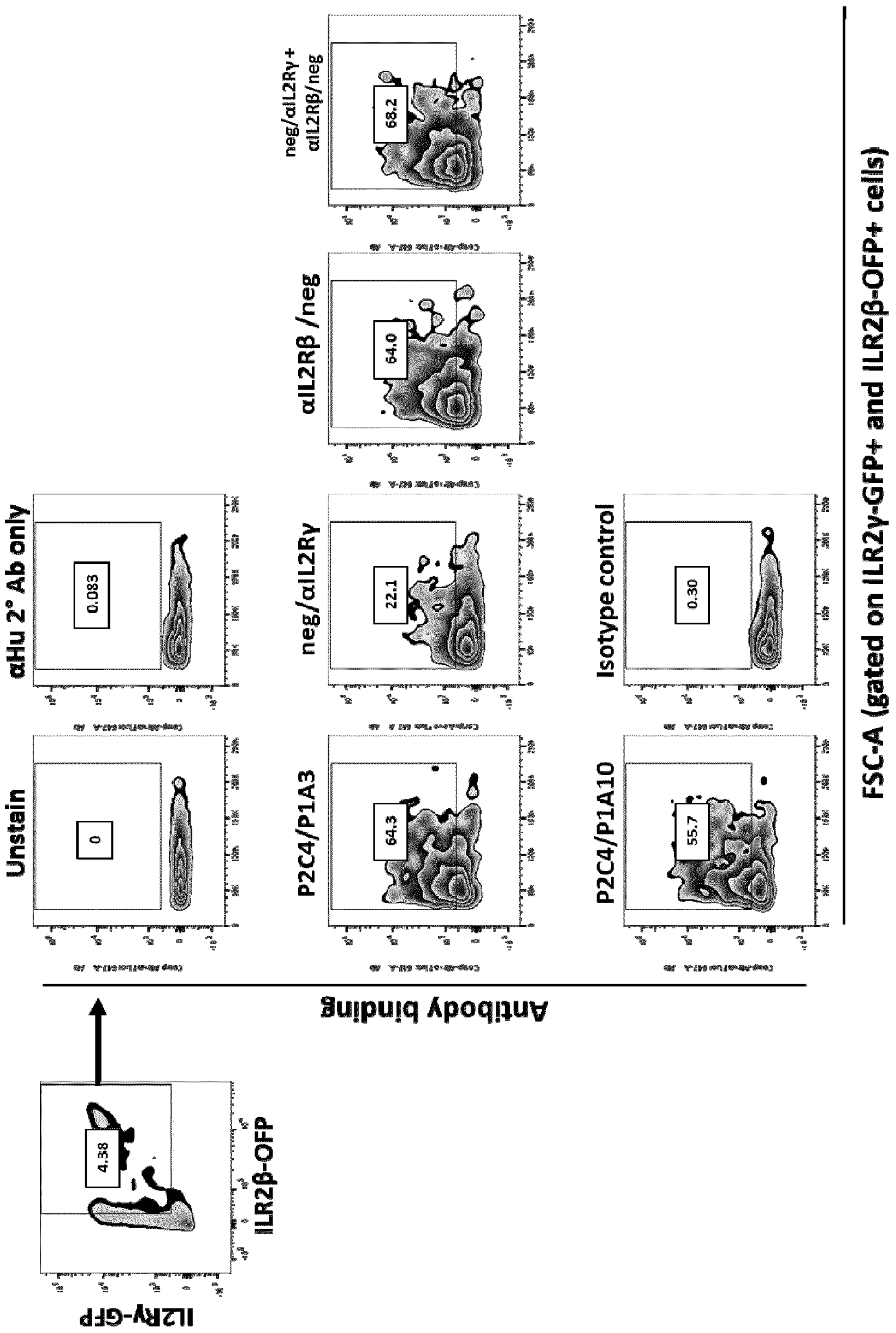
FIGS. 2A to 2C. Graphs and bar chart showing binding of bispecific and monospecific IL2Rβ- and/or γc-binding antibodies to cells expressing human IL2Rβ, γc or IL-2Rα at the cell surface, as determined by flow cytometry. (2A) Graphs showing analysis of binding of P2C4/P1A3, P2C4/P1A10, a monospecific anti-γc ('neg/αIL2Rγ'), a monospecific anti-IL-2Rβ (('αIL2Rβ/neg') to cells transfected with constructs encoding human IL-2Rβ and γc. Negative unstained, secondary antibody only and isotype control conditions are indicated. (2B) Graphs showing analysis of binding of P2C4/P1A3, P2C4/P1A10, a monospecific anti-γc ('neg/αIL2Rγ'), a monospecific anti-IL-2Rβ ('αIL2Rβ/neg') to cells transfected with construct encoding IL-2Rα. Negative unstained, secondary antibody only and isotype control conditions, and positive αIL2Rα control conditions are indicated. (2C) Bar chart summarising normalised median fluorescence intensity (nMFI) for binding of the indicated antibodies to cells transfected with constructs encoding IL-2Rβ and γc.
Figure 2B:
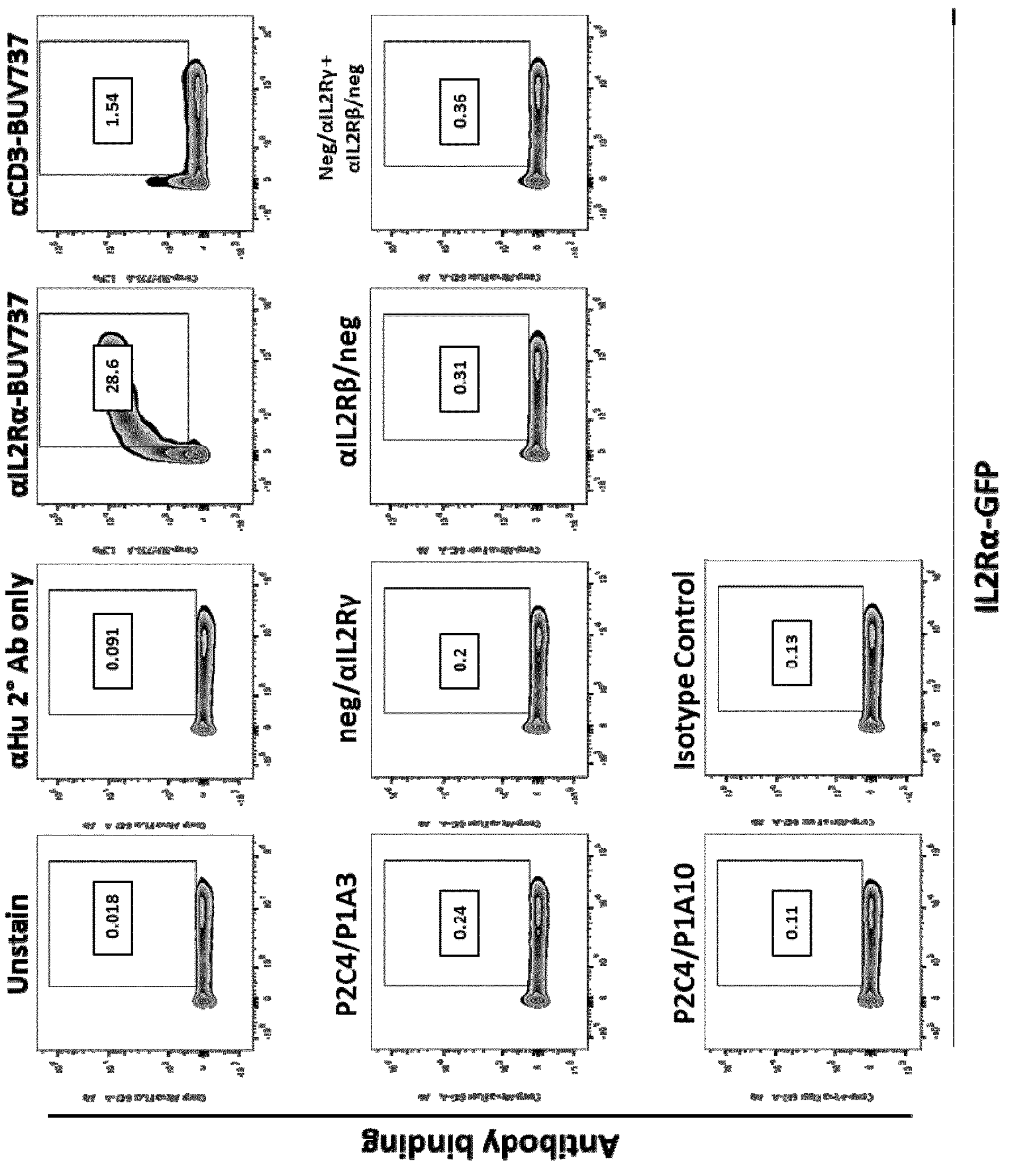
Figure 2C:
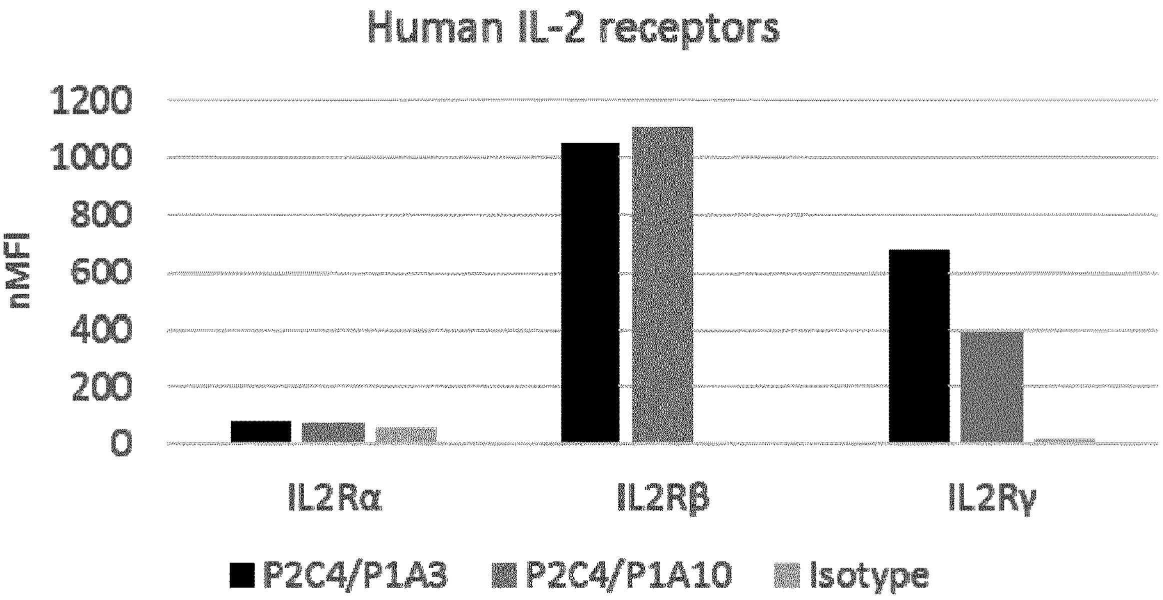

The results of the analysis are shown in FIGS. 2A to 2C. Both P2C4/P1A3 and P2C4/P1A10 showed specific binding to cells expressing human IL-2Rβ and γc, but did not bind to cells expressing IL-2Rα.

2.4 Analysis of Binding to Human T Cell Subsets

To identify the subsets of human T cells that P2C4/P1A3 and P2C4/P1A10 bind to, human peripheral blood mononuclear cells (PBMCs) were isolated and stained with P2C4/P1A3, P2C4/P1A10 or isotype control antibody, followed by detection with a fluorochrome-conjugated secondary antibody. Cells were then stained with antibodies for the T cell markers CD3, CD4, CD8, CD45RA, CCR7, Foxp3 and CD25 to enable the delineation of the following T cell subsets: Naïve (CD45RA+CCR7+), T central memory (CD45RA−CCR7+), T effector memory (CD45RA−CCR7−), T effector memory re-expressing CD45RA (TEMRA; CD45RA+CCR7−) and Treg (CD4+CD25+Foxp34).

Samples were analysed by flow cytometry. Normalized Median Fluorescence Intensity (nMFI) was calculated by subtracting the MFI of the secondary antibody control.

Figure 3A:
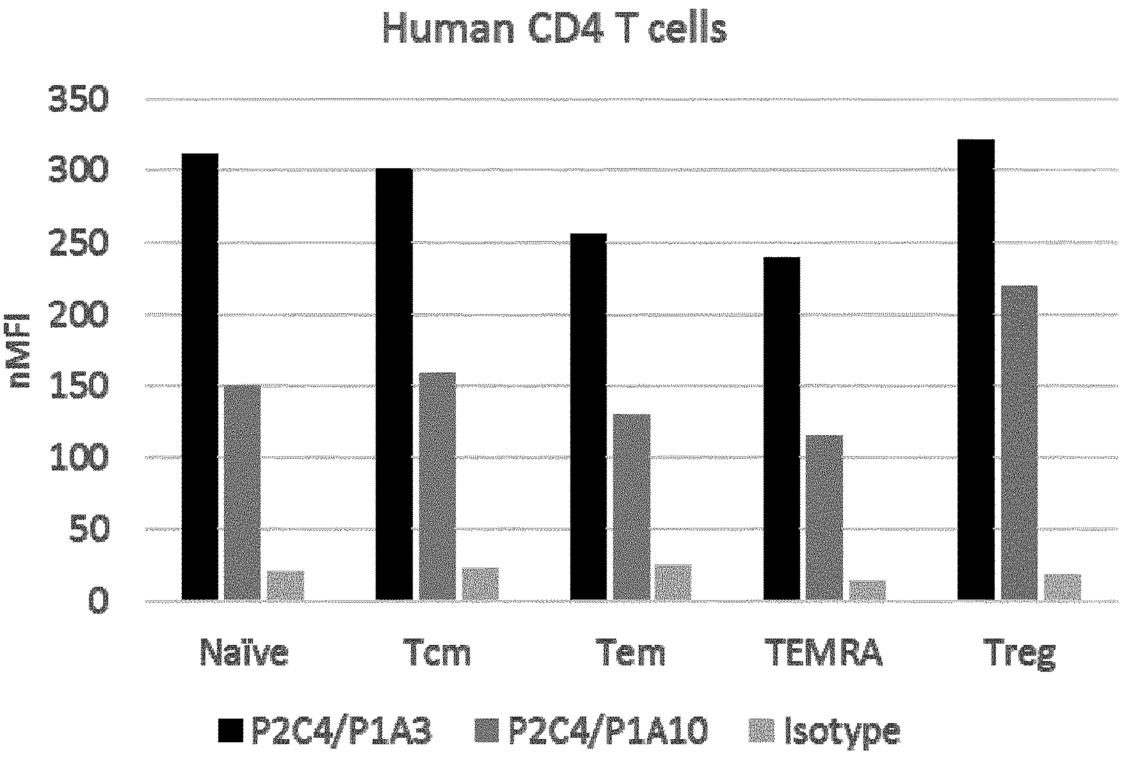
FIGS. 3A and 3B. Bar charts showing binding of bispecific IL-2Rβ- and γc-binding antibodies to primary human T cell subsets, as determined by flow cytometry. (3A and 3B) Bar chart summarising normalised MFIs for binding of the indicated antibodies to the indicated CD4+ (3A) and CD8+ (3B) human T cell subsets.
Figure 3B:
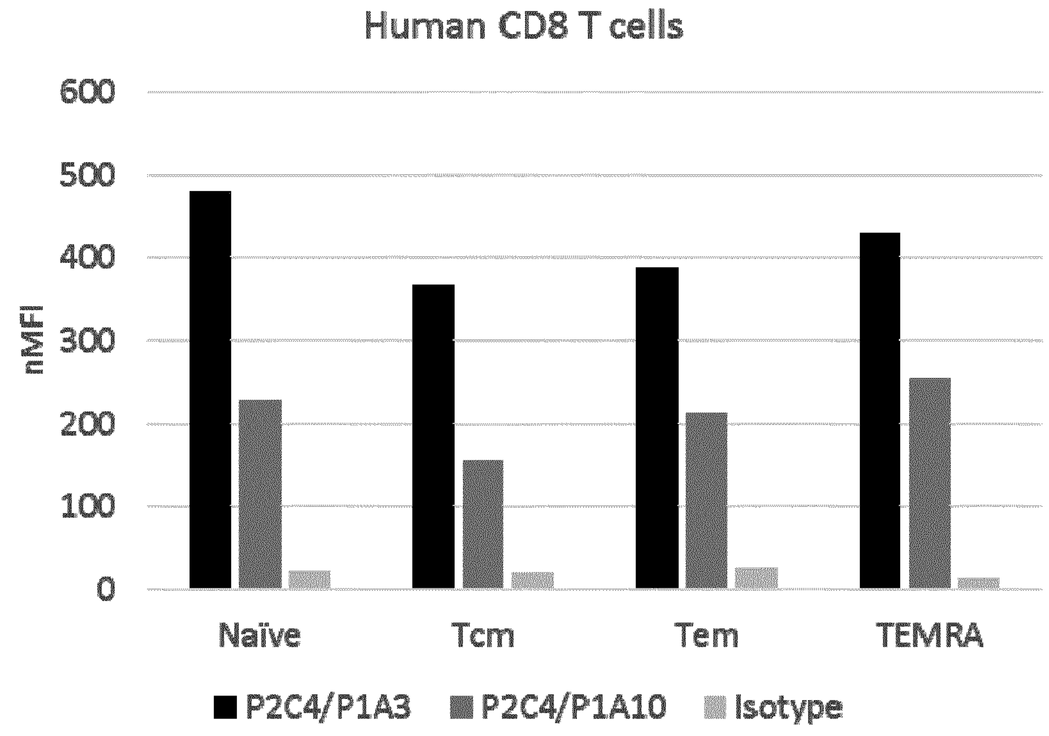

The results are shown in FIGS. 3A and 3B. P2C4/P1A3 and P2C4/P1A10 were found to bind to all of the different human T cell subsets tested. P2C4/P1A10 displayed reduced level of binding as compared to P2C4/P1A3.

2.5 Analysis of Binding to Rhesus IL-2Rβ and γc Expressed at the Cell Surface

Cross-reactivity of P2C4/P1A3 and P2C4/P1A10 for rhesus IL-2Rβ and γc was analysed essentially as described in Example 2.3 above, using HEK293-5E cells transfected with plasmids encoding rhesus IL-2Rβ-OFP and γc-GFP.

Figure 4A:
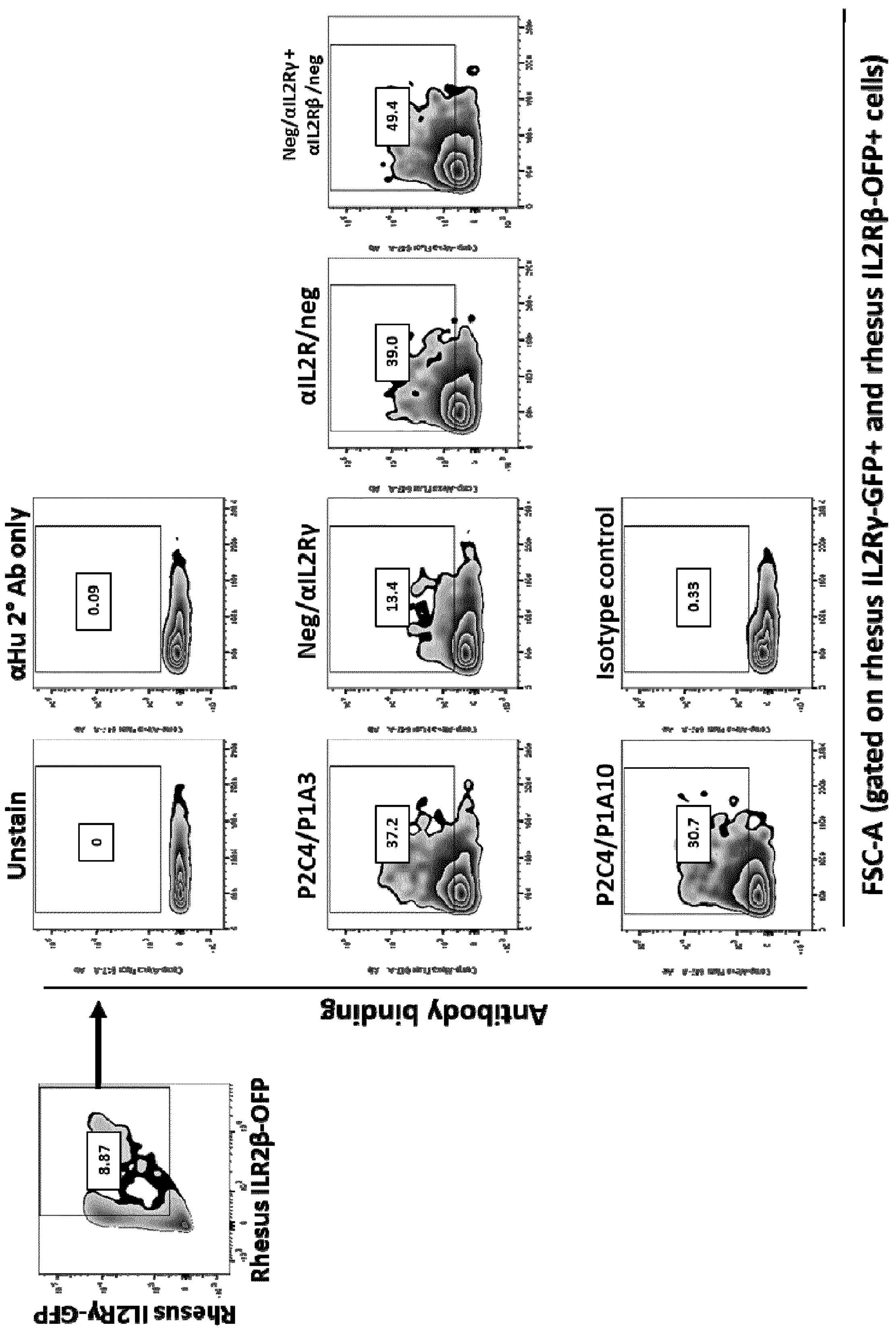
FIGS. 4A and 4B. Graphs and bar chart showing binding of bispecific and monospecific IL-2Rβ- and/or γc-binding antibodies to cells expressing rhesus IL-2Rβ and γc at the cell surface, as determined by flow cytometry. (4A) Graphs showing analysis of binding of P2C4/P1A3, P2C4/P1A10, a monospecific anti-γc ('neg/αIL2Rγ'), a monospecific anti-IL-2Rβ (('αIL2Rβ/neg') to cells transfected with constructs encoding rhesus IL-2Rβ and γc. Negative unstained, secondary antibody only and isotype control conditions are indicated. (4B) Bar chart summarising normalised MFIs for binding of the indicated antibodies to cells transfected with constructs encoding rhesus IL-2Rβ and γc.
Figure 4B:
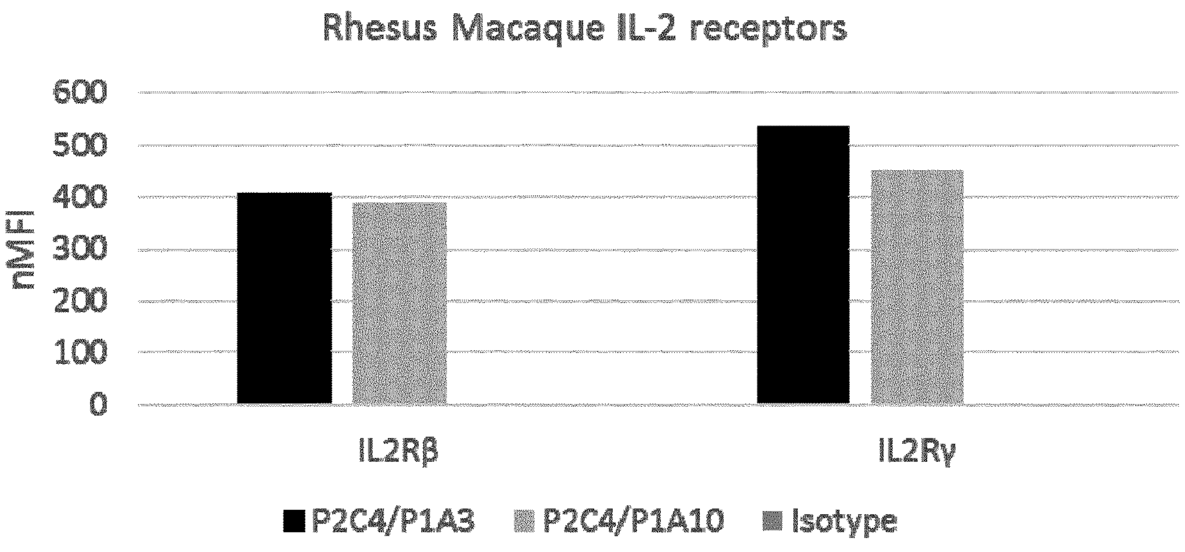

The results of the analysis are shown in FIGS. 4A and 4B. Both P2C4/P1A3 and P2C4/P1A10 showed specific binding to cells expressing rhesus IL-2Rβ and γc.

2.6 Analysis of Binding to Cynomolgus Macaque T Cells

Cynomolgus macaque PBMCs were isolated and stained with P2C4/P1A3, P2C4/P1A10 or isotype control antibody, followed by a fluorochrome-conjugated secondary antibody. Cells were then stained with T cell markers CD3, CD28 and CD95 to delineate the following T cell subsets: Naïve (CD28+CD95−), Effector (CD28-CD95+) and Memory (CD28+CD95+).

Samples were analysed by flow cytometry. Normalized Median Fluorescence Intensity (nMFI) was calculated by subtracting the MFI of the secondary antibody control.

Figure 5:
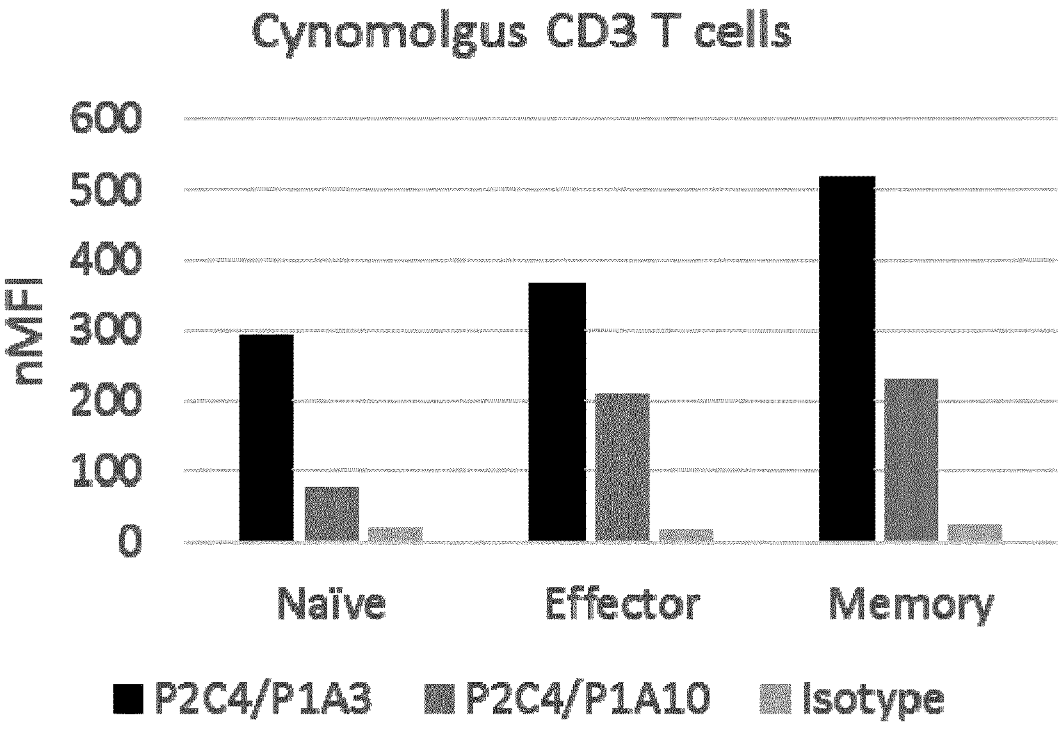
FIG. 5. Bar chart showing binding of bispecific IL-2Rβ- and γc-binding antibodies to primary cynomolgus macaque T cell subsets, as determined by flow cytometry.

The results are shown in FIG. 5. P2C4/P1A3 and P2C4/P1A10 were found to bind to naïve, effector and memory subsets of cynomolgus T cells. P2C4/P1A10 displayed reduced level of binding as compared to P2C4/P1A3.

Example 3: Analysis of Induction of Cell Proliferation by IL-2n- and γc-Binding Bispecific Antibodies 3.1 Analysis of the Effect on NK Cells To analyse the functional activity of the IL-2Rβ- and γc-binding bispecific antibodies, a stimulation assay was performed using the NK92 cell line which expresses both IL-2Rβ and γc.

Anti-IL-2Rβ antibody clones and anti-γc antibody clones identified from human antibody phage display library were paired to form various bispecific antibody combinations, based on a single chain variable fragment (scFv) linked to a IgG1 knob or hole Fc. These antibodies were then used in a NK92 cell stimulation assay.

Briefly, cells were washed and stimulated with antibodies or cytokines for 3 days. Trastuzumab was used as a negative control. To quantify cell proliferation, alamarBlue, reagent was added and fluorescence signal was measured at fluorescence excitation wavelength 544 nm and fluorescence emission wavelength 590 nm.

Figure 6A:
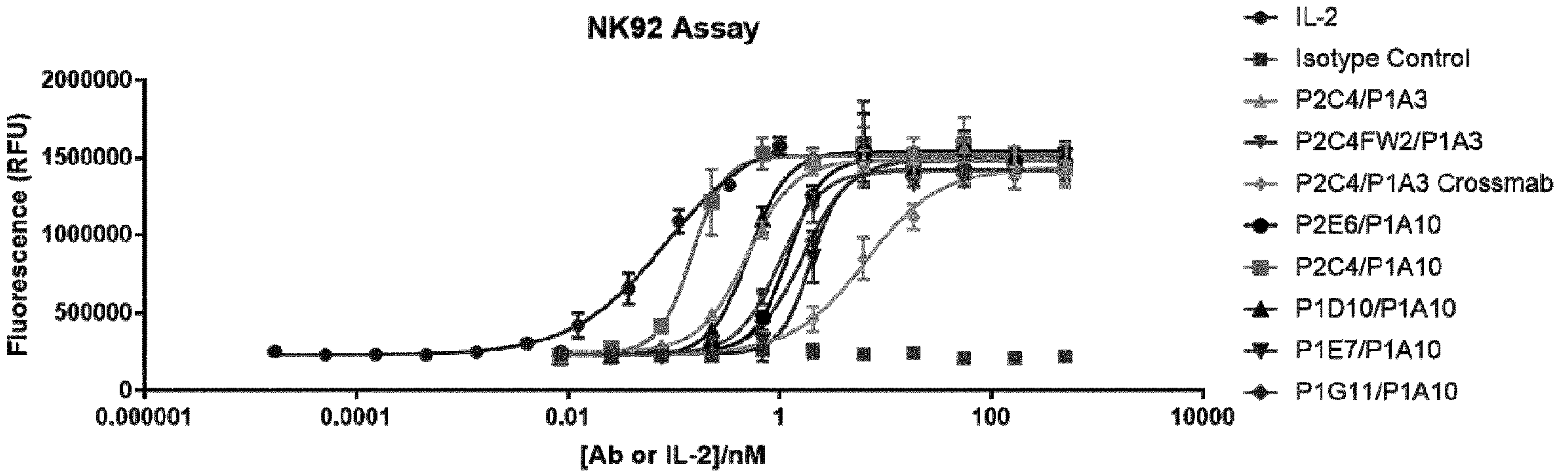
FIGS. 6A and 6B. Graphs showing analysis of proliferation of NK92 cells in response to treatment with bispecific IL-2Rβ- and γc-binding antibodies or the indicated cytokines. EC50 values for induction of NK92 cell proliferation are shown. 6A and 6B show the results from different experiments investigating different bispecific IL-2Rβ- and γc-binding antibodies.

The results are shown in FIG. 6A. Several combinations anti-IL2Rβ and anti-γc clones are capable of inducing NK92 cell proliferation.

In a separate assay, the following bispecific antibodies were analysed:

- scFv (P2C4): scFv (P1A3)—KiH-Fc—designated 'P2C4/P1A3' in the Figure.
- scFv (P2C4): scFv (P1A10)—KiH-Fc—designated 'P2C4/P1A10' in the Figure.
- Fab (P2C4): Fab (P1A3) in CrossMab format—designated 'P2C4/P1A3 Crossmab' in the Figure.
- Fab (P2C4): Fab (P1A10) in CrossMab format—designated 'P2C4/P1A10 Crossmab' in the Figure.
- Fab (P2C4): Fab (P1A10) in Duobody format—designated 'P2C4/P1A10 Duobody' in the Figure.

Figure 6B:
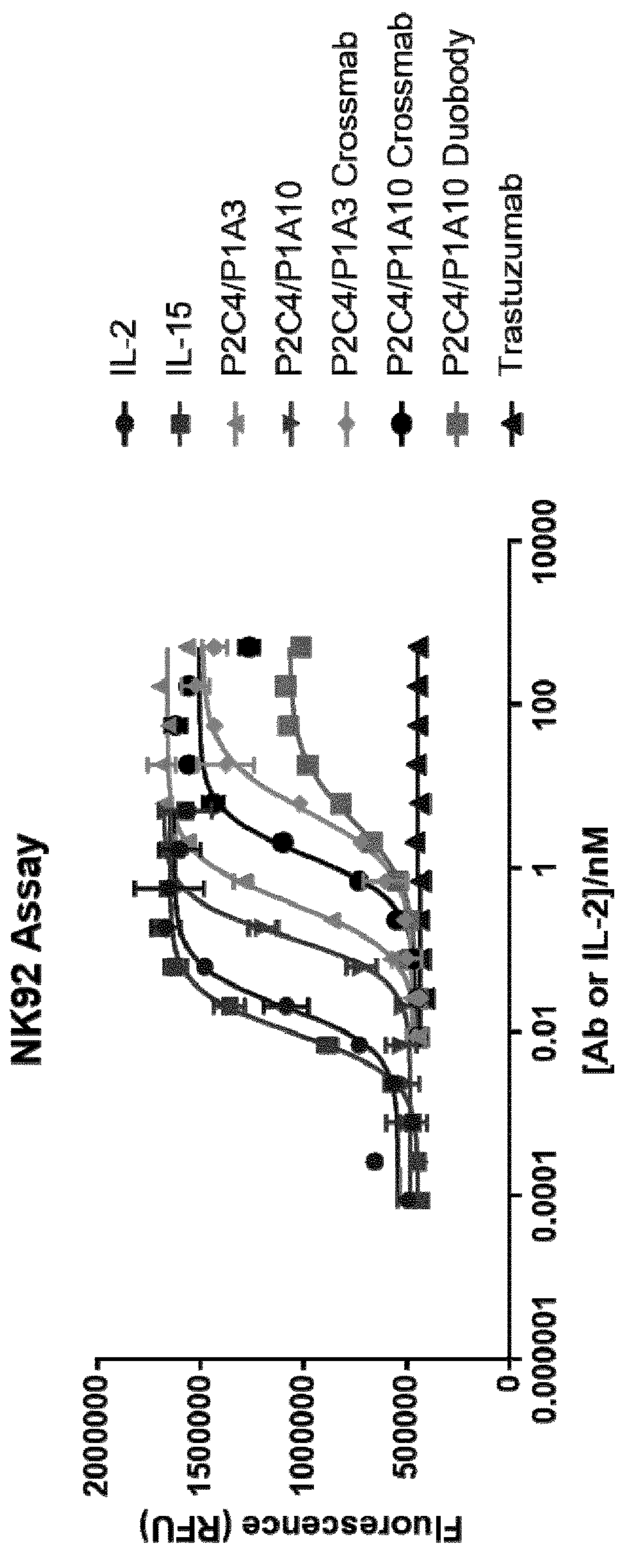

The results are shown in FIG. 6B. P2C4/P1A3 and P2C4/P1A10 induced NK92 proliferation in a dose-dependent manner, with an average EC50 of 0.43 nM and 0.16 nM respectively from four independent experiments.

3.2 Analysis of the Effect on Primary Human T Cells

To analyse the effects of P2C4/P1A3 and P2C4/P1A10 on primary human T cells, T cells were isolated from human PBMCs and pre-activated for three days with anti-CD3-coated plates (2 μg/ml) plus soluble anti-CD28 (1 μg/ml). Cells were then rested in fresh media for a day before being labelled with CellTrace Violet. Cells were seeded at 100,000 per well and treated with P2C4/P1A3, P2C4/P1A10 (200 nM, 40 nM, 8 nM and 1.6 nM), IL-2 (20 nM, 4 nM, 0.8 nM, 0.16 nM) or anti-CD3/CD28 beads. Isotype antibody and untreated cells were included as negative controls. After four days, cells were stained with T cell markers CD3, CD4, CD8, CD45RO, CCR7, Foxp3 and CD25 to delineate T cell subsets:

- CD4+ naïve T cells: CD3+CD4+FoxP3−CCR7+CD45RO−
- CD8+ naïve T cells: CD3+CD8+CCR7+CD45RO−
- CD4+ central memory T cells: CD3+CD4+FoxP3−CCR7+CD45RO+
- CD8+ central memory T cells: CD3+CD3+CCR7+CD45RO+
- CD4+ effector memory T cells: CD3+CD4+FoxP3−CCR7−CD45RO+
- CD8+ effector memory T cells: CD3+CD8+CCR7−CD45RO+
- CD4+ Tregs: CD3+CD4+CD25+FoxP3+

Counting beads were included to allow absolute cell numbers to be determined by flow cytometry.

Figure 7A:
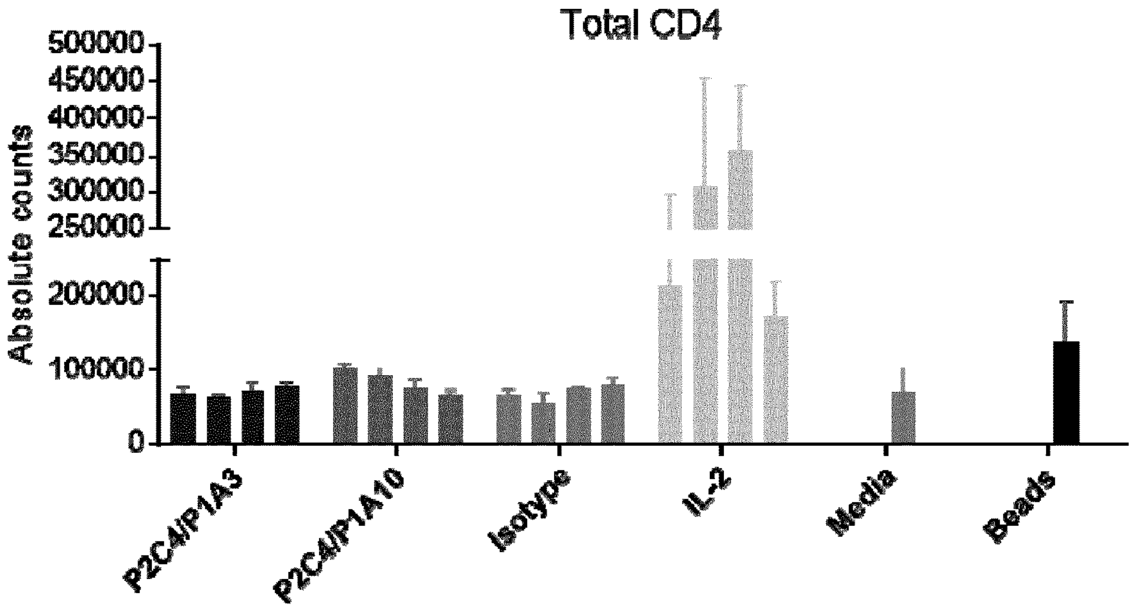
FIGS. 7A to 7L. Bar charts and graphs showing analysis of proliferation of pre-activated, primary human T cell subsets in response to treatment with bispecific IL-2Rβ- and γc-binding antibodies or IL-2. Unstimulated cells (media) and anti-CD3/CD28 bead-stimulated controls (beads) are indicated. (7A) Absolute numbers of CD4+ T cells, (7B) Absolute numbers of CD8+ T cells. (7C) Absolute numbers of Tregs. (7D) Graphs showing CD4+CD25+FoxP3+ regulatory T cell compartment following stimulation with the indicated agents. (7E) Absolute numbers of naïve CD8+ T cells, (7F) Absolute numbers of nave CD4+ T cells. (7G) Absolute numbers of central memory CD8+ T cells. (7H) Absolute numbers of central memory CD4+ T cells. (7I) Absolute numbers of effector memory CD8+ T cells. (7J) Absolute numbers of effector memory CD4+ T cells. (7K) Graphs showing dividing effector memory CD8+ T cells as determined by Cell Trace Violet staining. (7L) Percentage of CD8+ effector memory cells which are dividing.
Figure 7B:
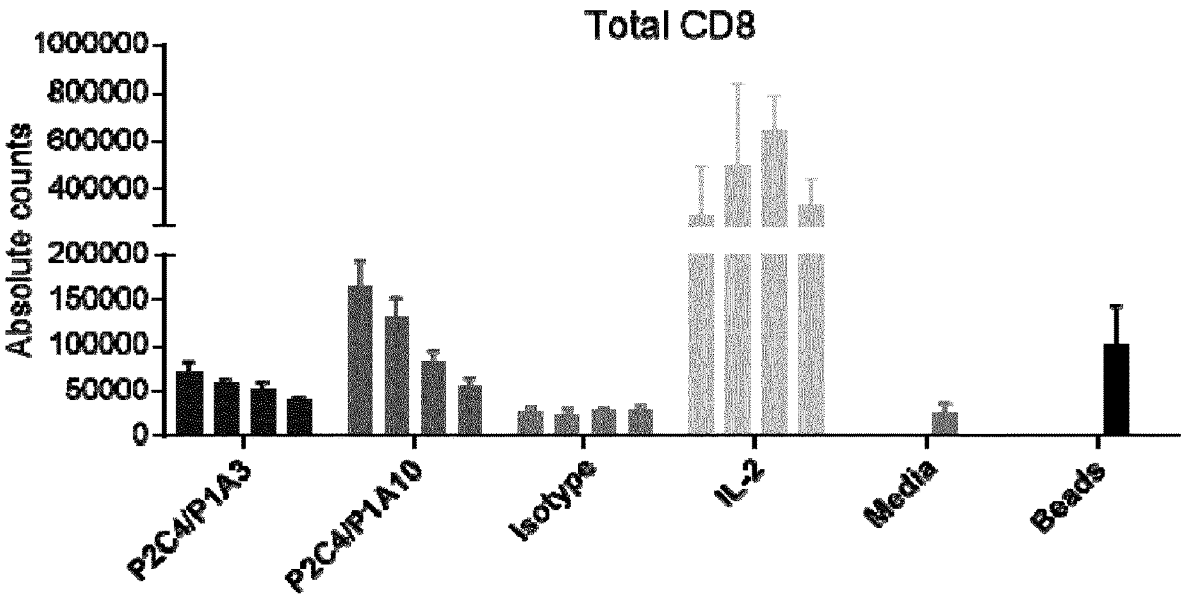
Figure 7C:
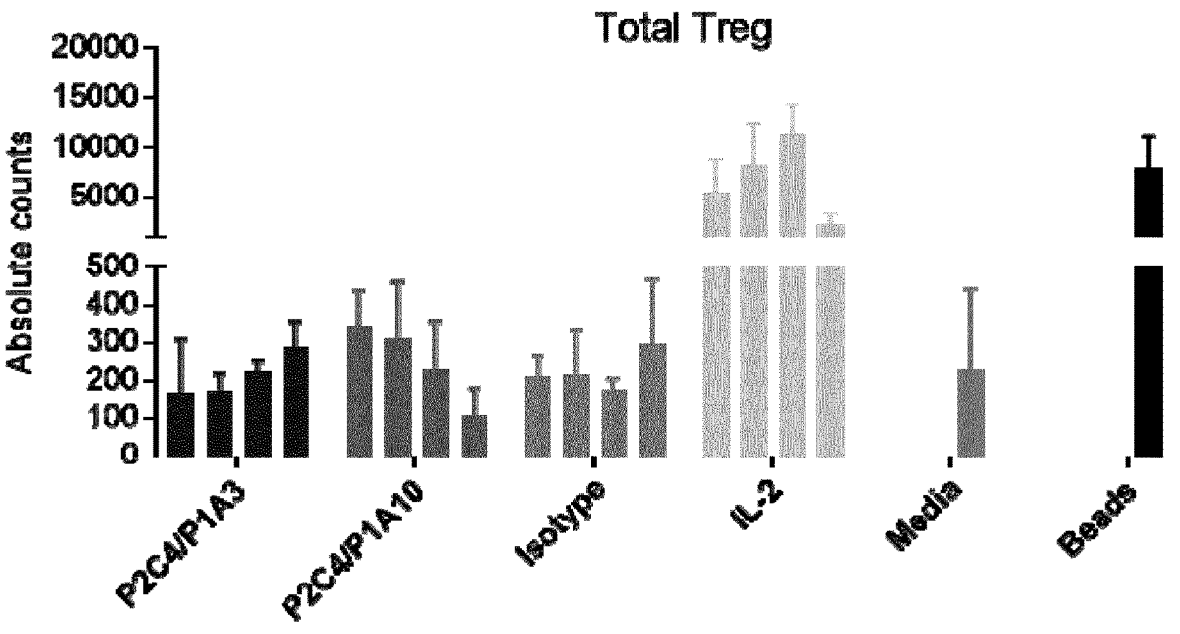
Figure 7D:
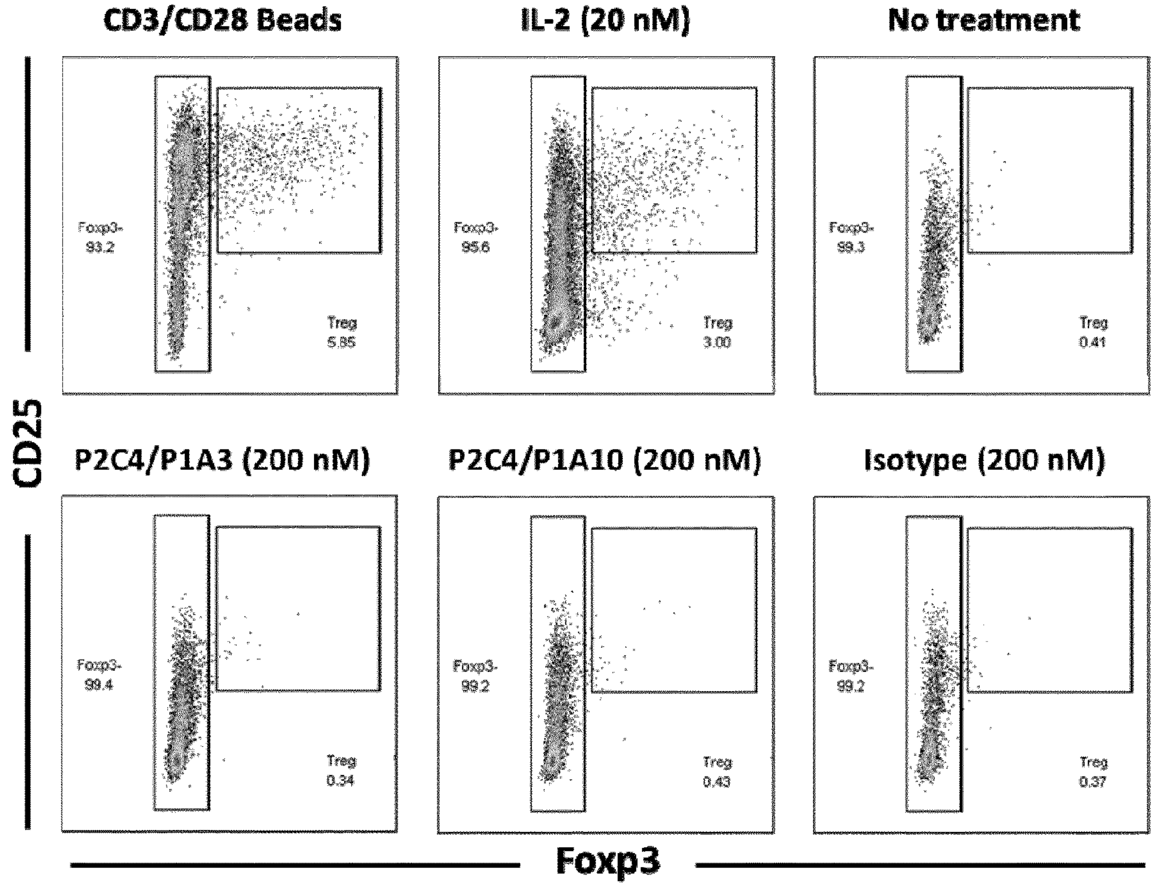
Figure 7E:
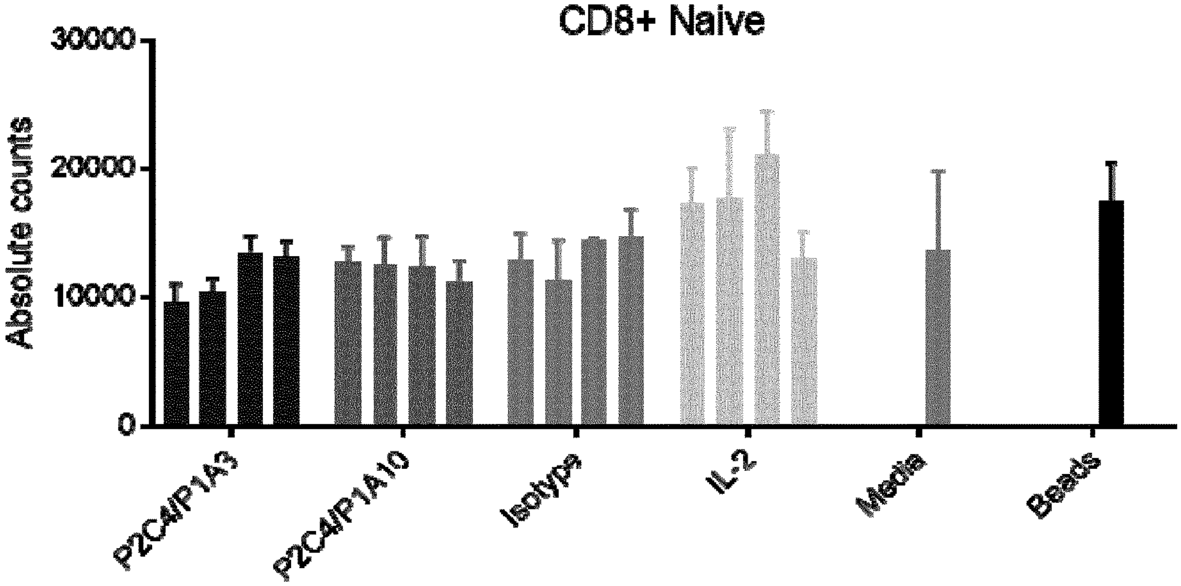
Figure 7F:
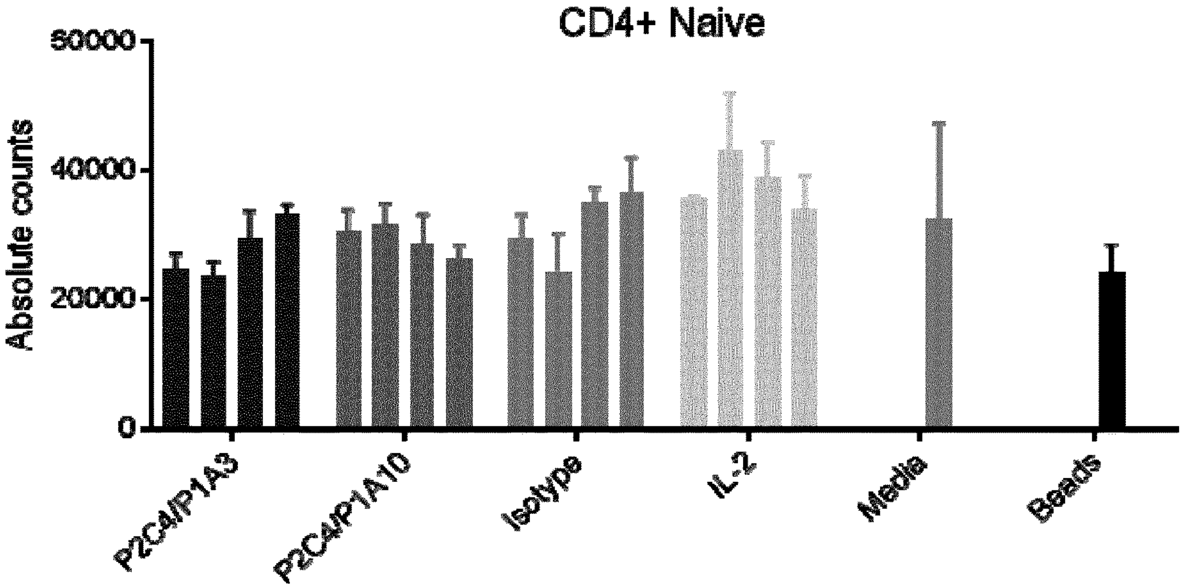
Figure 7G:
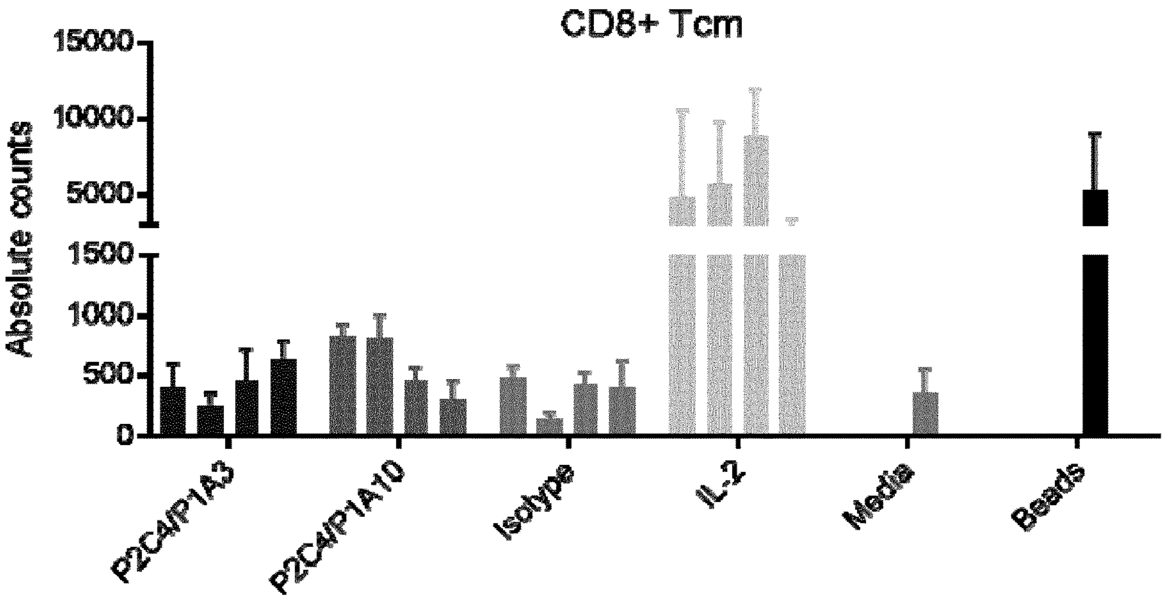
Figure 7H:
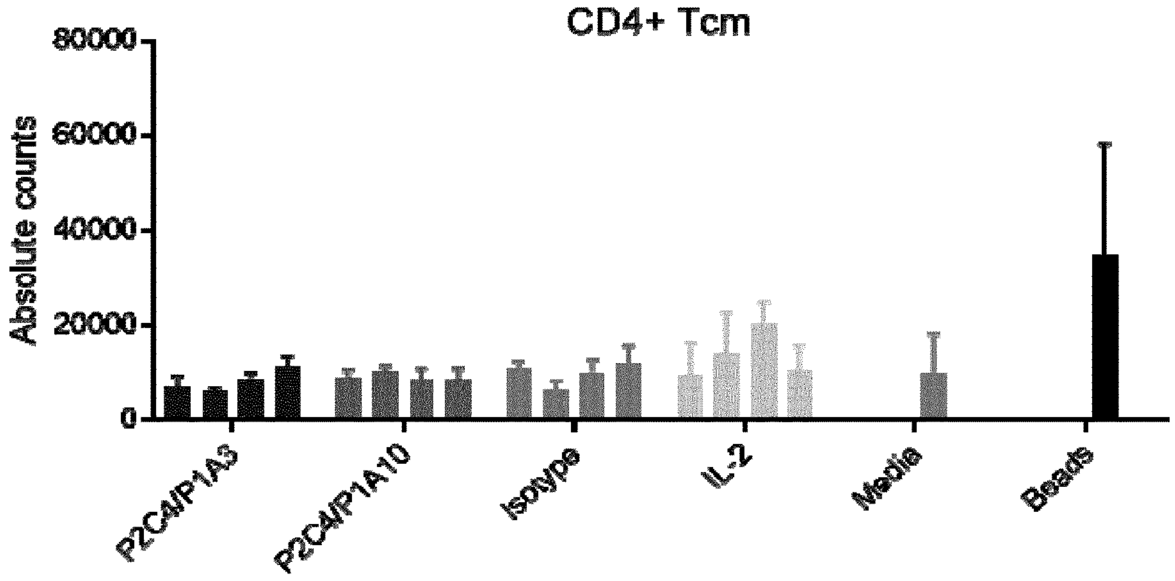

The results are shown in FIG. 7A to 7L. Treatment of pre-activated T cells with P2C4/P1A3 and P2C4/P1A10 was found to induce expansion of CD8+ T cells whilst inducing only minimal expansion of CD4+FoxP3+ regulatory T cells (Treg)—see FIGS. 7B and 7C. Absolute numbers of Tregs were ~10-fold lower following treatment with P2C4/P1A3 or P2C4/P1A10 as compared to treatment with IL-2 (FIG. 7C).

Figure 7I:
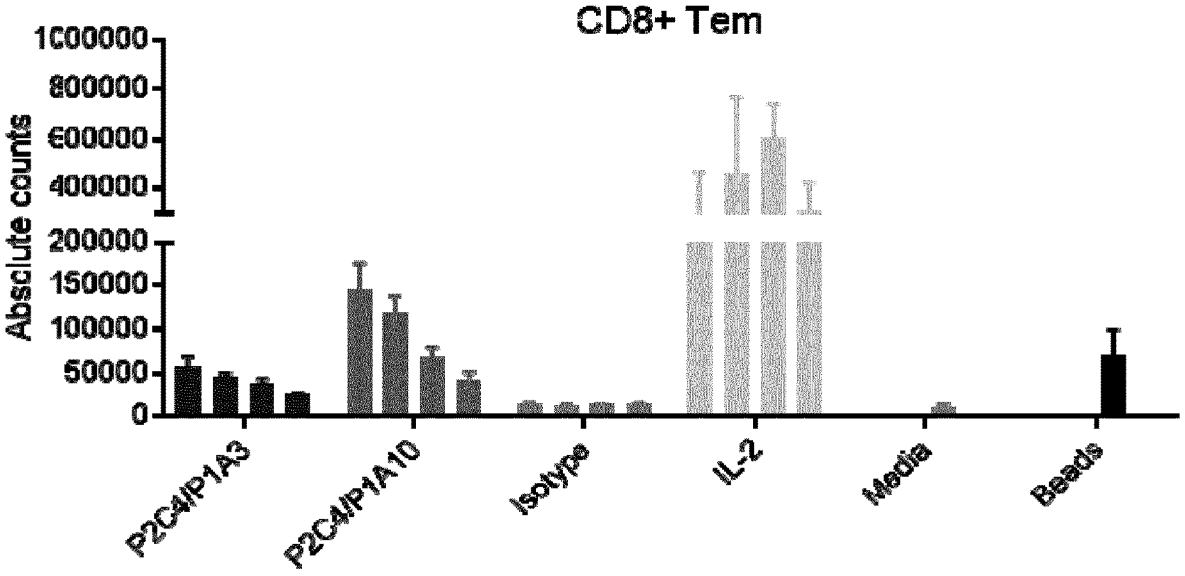
Figure 7J:
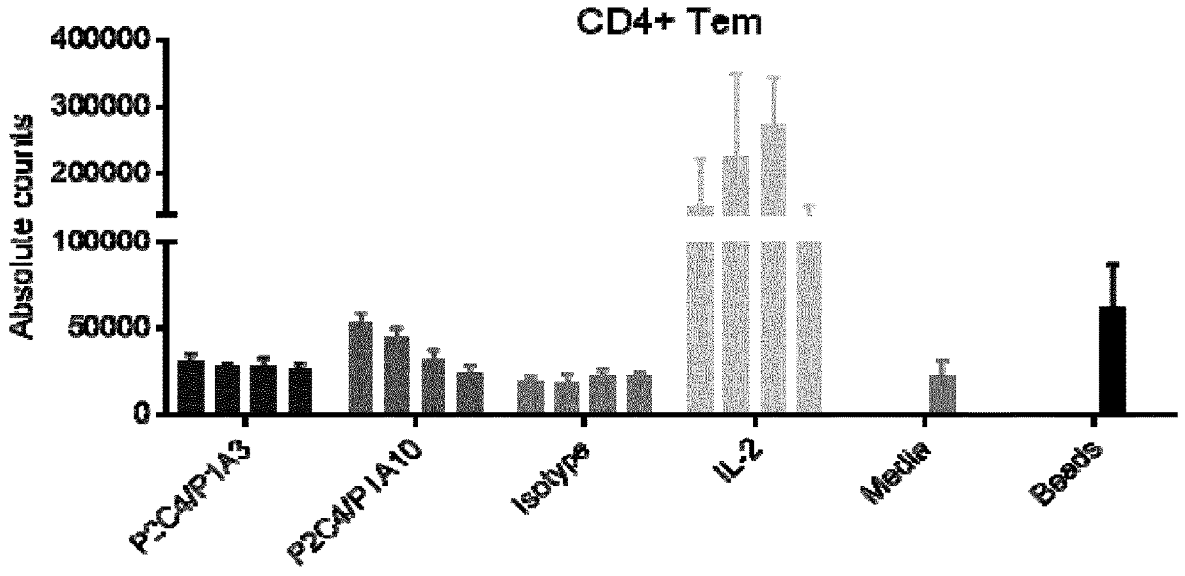
Figure 7K:
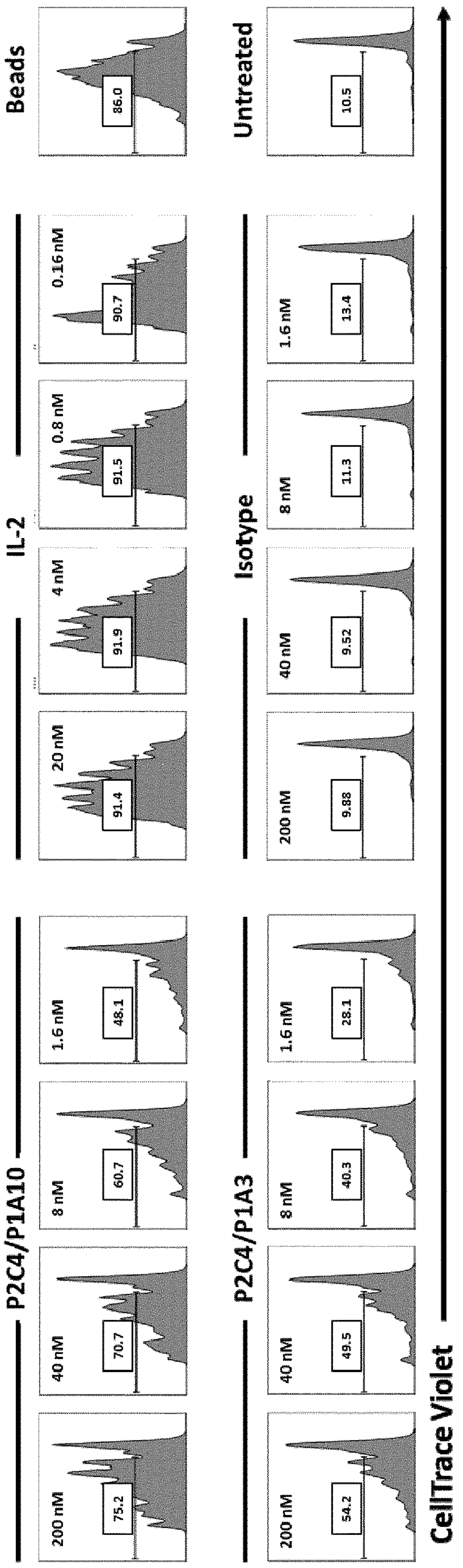
Figure 7L:
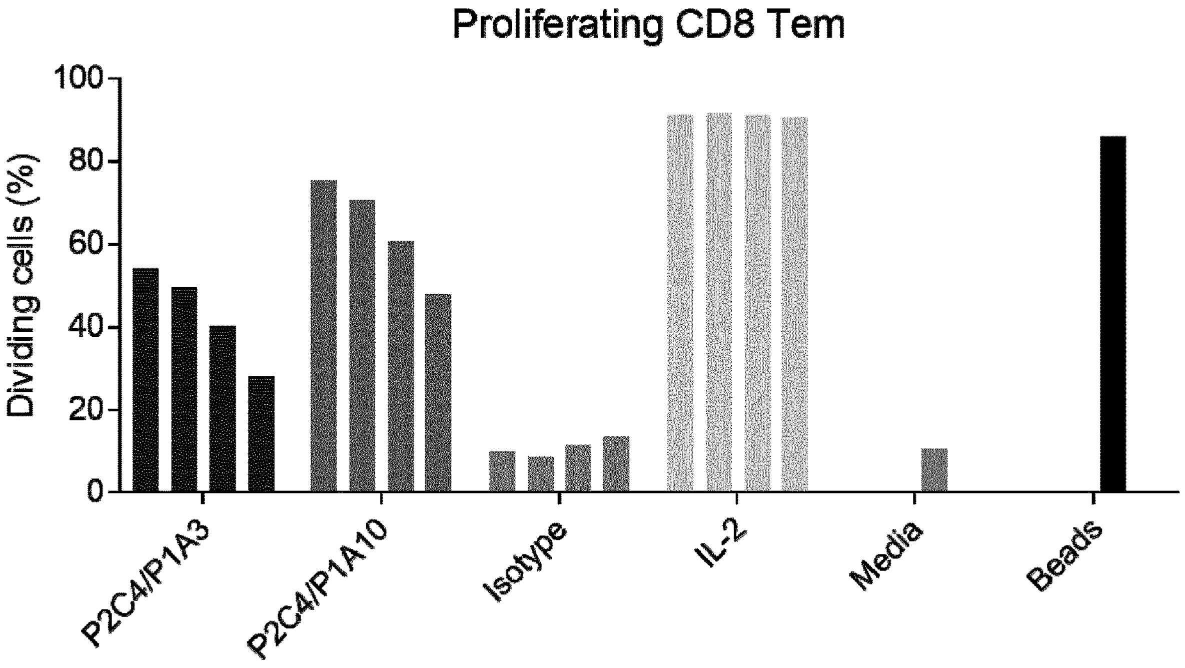

With respect to the individual T cell subsets, CD8+ T effector memory subset responded the most to stimulation with P2C4/P1A3 and P2C4/P1A10 (FIG. 7I). Proliferation of CD4+ T effector memory cells was also observed in P2C4/P1A10-treated cells. Based on CellTrace Violet staining, a high percentage of dividing CD8+ T effector memory cells were observed following P2C4/P1A3 and P2C4/P1A10 treatment (FIGS. 7K and 7L).

In a separate experiment, pre-activated T cells were stimulated with 8 different concentrations of P2C4/P1A3, P2C4/P1A10, isotype control antibody, IL-2 or IL-15. The ratio of CD8 to Treg cells was determined by dividing the absolute number of CD8 T cells with the absolute number of Tregs.

Figure 8A:
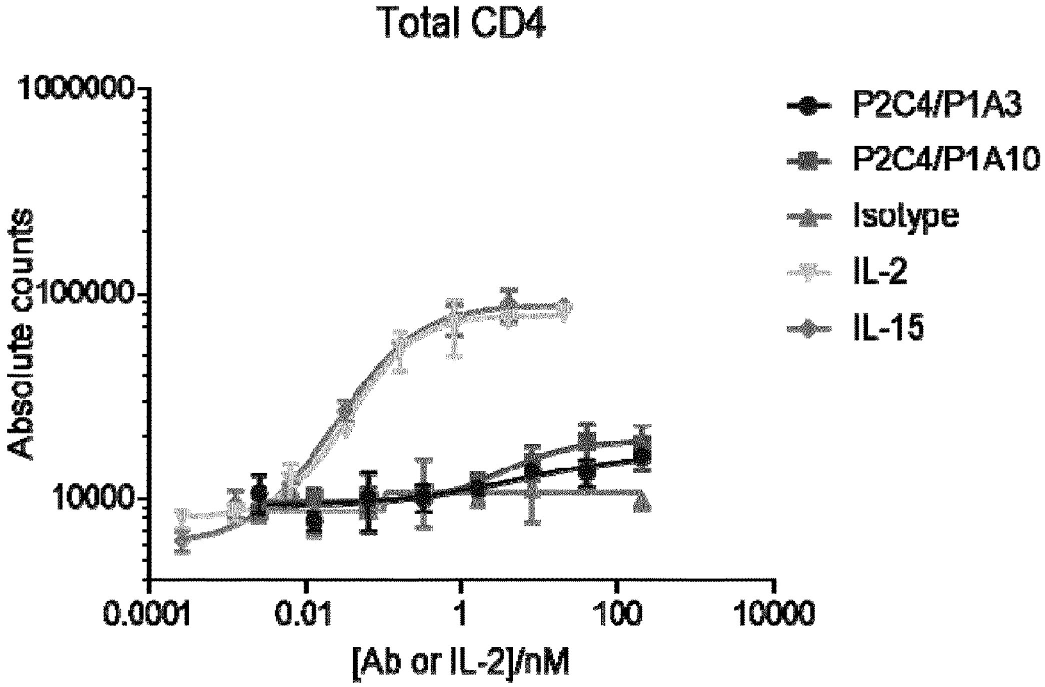
FIGS. 8A to 8H. Graphs showing analysis of proliferation of pre-activated, primary human T cell subsets in response to treatment with different amounts of bispecific IL-2Rβ- and γc-binding antibodies or the indicated cytokines. (8A) Absolute numbers of CD4+ T cells. (8B) Absolute numbers of CD8+ T (8C) Absolute numbers of Tregs, (8D) Ratio of the absolute number of CD8+ T cells to the absolute number of Tregs. (8E) Absolute numbers of effector memory CD4+ T cells. (8F) Absolute numbers of effector memory CD8+ T cells. (8G) Percentage of CD8+ effector memory cells which are dividing. Unstimulated cells (media) and anti-CD3/CD28 bead-stimulated controls (beads) are indicated. (8H) Absolute numbers of pre-expanded Tregs after treatment with bispecific IL-2Rβ- and γc-binding antibodies or the indicated cytokines.
Figure 8B:
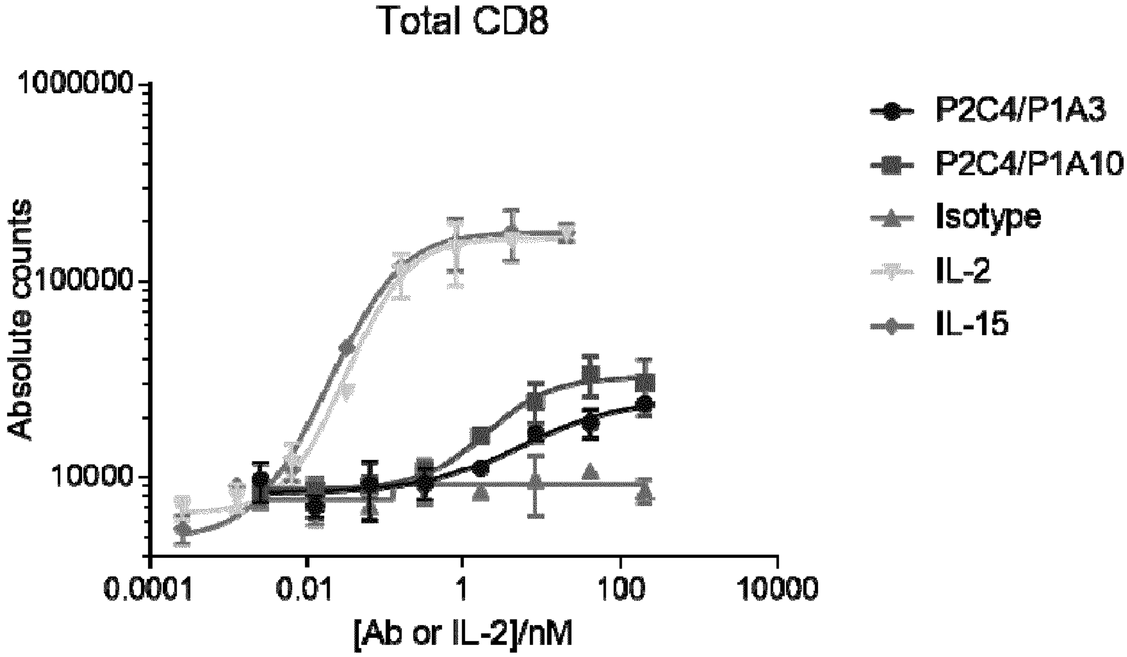
Figure 8C:
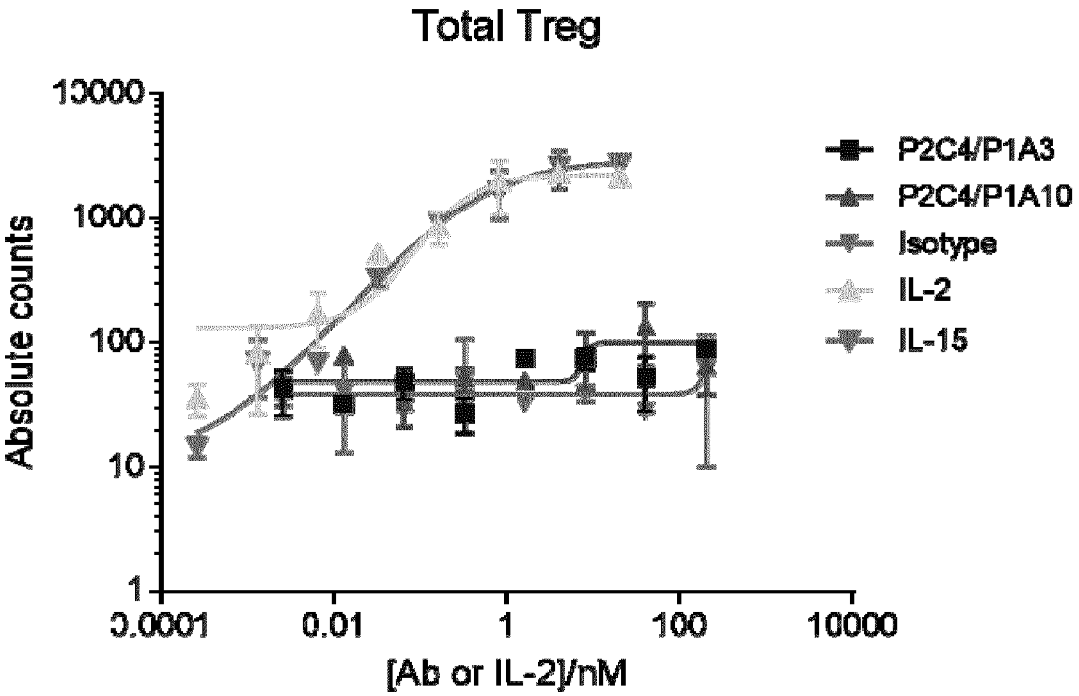
Figure 8D:
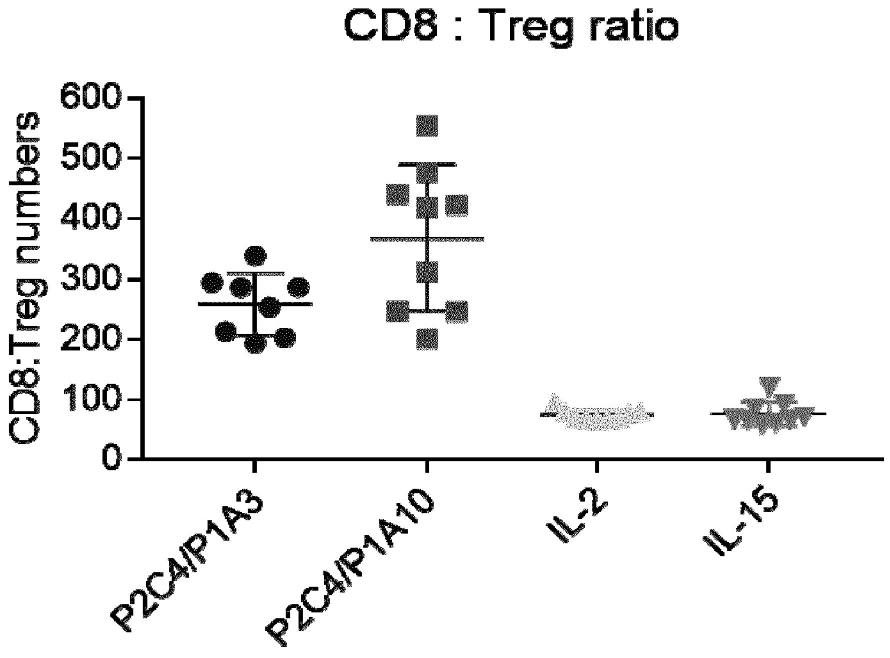
Figure 8E:
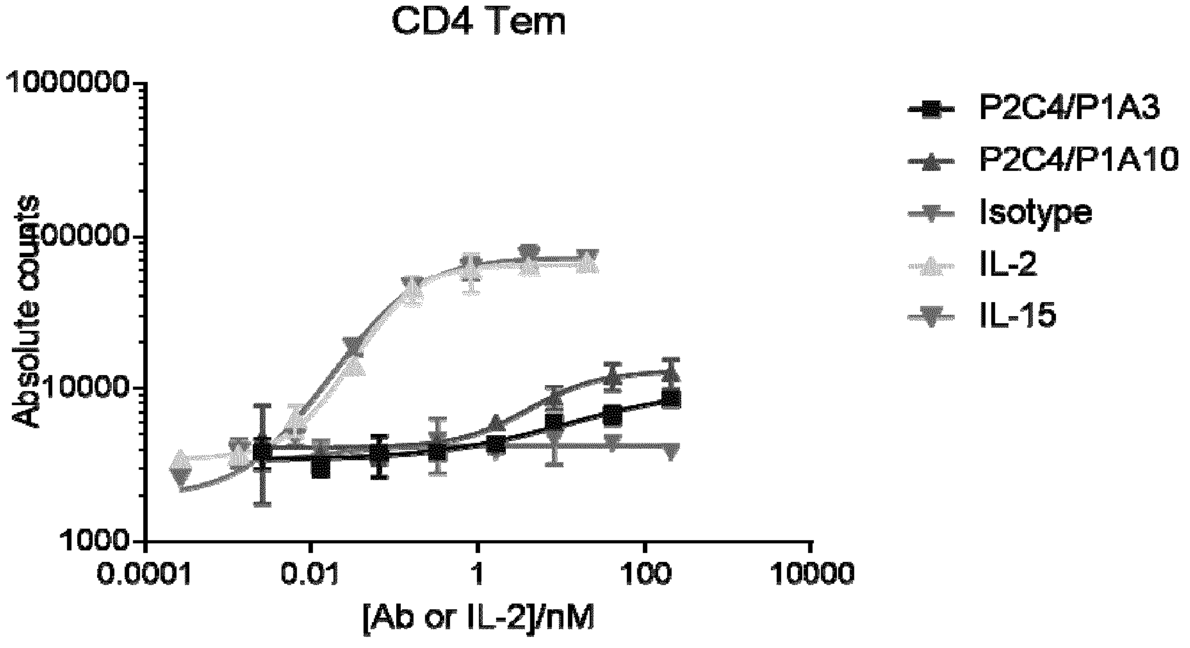
Figure 8F:
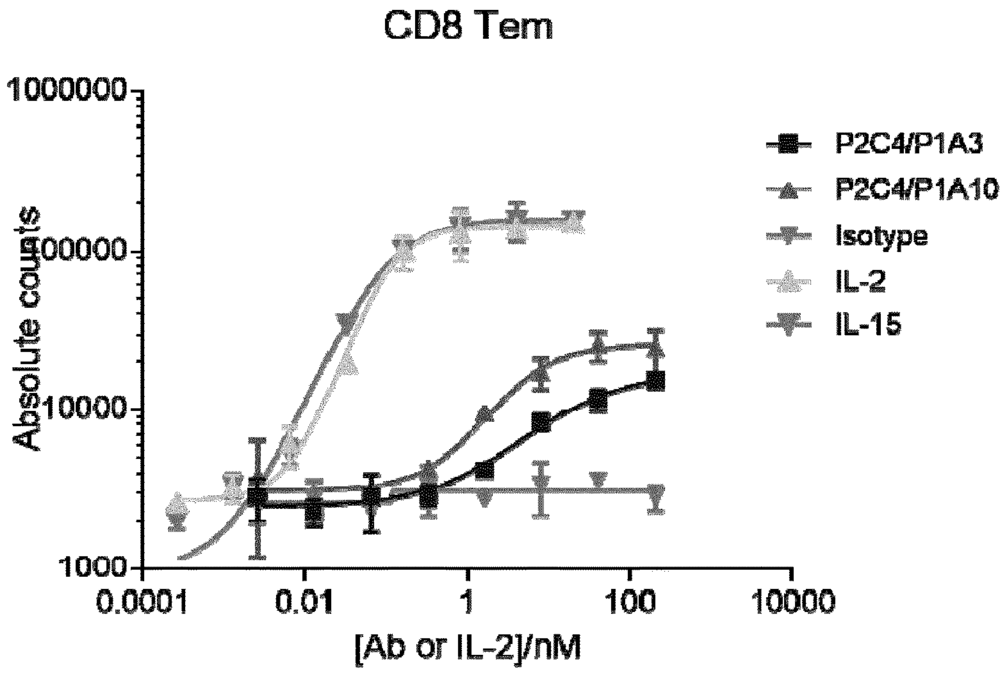
Figure 8G:
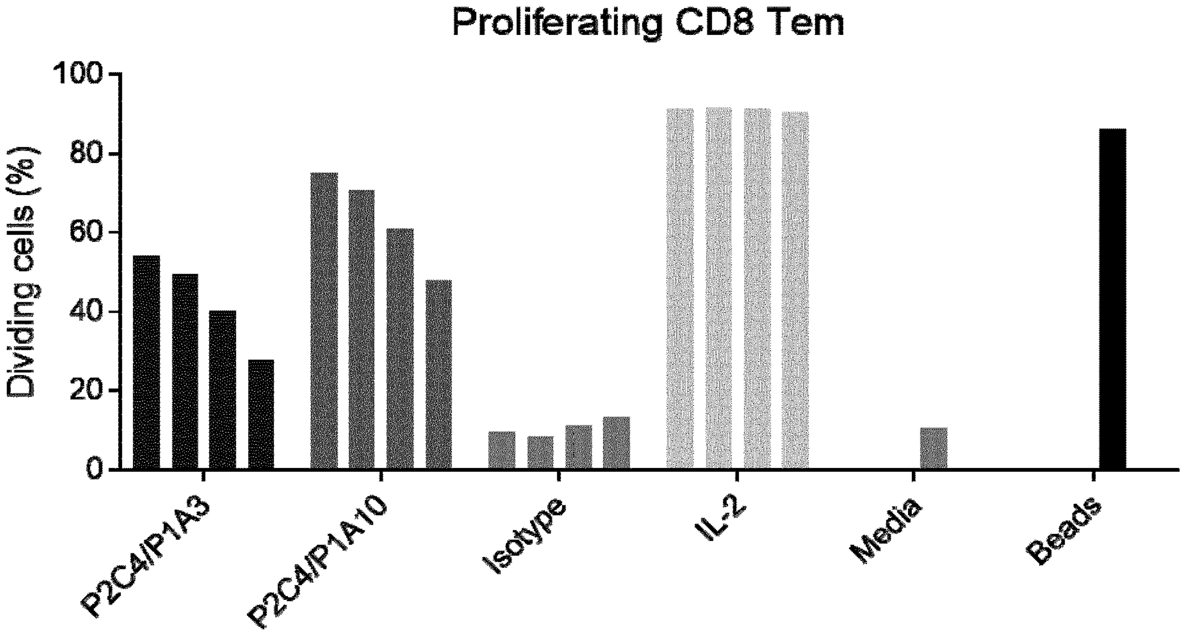

The results are shown in FIGS. 8A to 8G. Both P2C4/P1A3 and P2C4/P1A10 induced dose-dependent proliferation of pre-activated (i.e. anti-CD3/CD28 stimulated) T cells. The effect on CD8+ T cells was more pronounced than the effect on CD4+ T cells. P2C4/P1A10 was a more potent stimulator of proliferation than P2C4/P1A3. Both P2C4/P1A3 and P2C4/P1A10 did not induce significant proliferation of Tregs, with numbers similar to that of the isotype control-treated cells (see e.g. FIG. 8C). The ratio of CD8 to Treg cells indicated that both P2C4/P1A3 and P2C4/P1A10 preferentially expand CD8 T cells over Tregs, and to a greater extent than IL-2 or IL-15 (FIG. 8D). Stimulation of the CD4+ and CD8+ T effector memory T cell subsets was also dose-dependent (FIGS. 8E and 8F). A high percentage of dividing CD8+ T effector memory cells was detected following stimulation with P2C4/P1A10 or P2C4/P1A3 (FIG. 8G).

Pre-expanded human Treg cells were stimulated with P2C4/P1A3, P2C4/P1A10, isotype control antibody, IL-2 or IL-15. After four days, cells were stained with CD3, CD4, CD8, Foxp3 and CD25 and assessed by flow cytometry to determine absolute counts using counting beads. Treg cells were defined as CD3+ CD4+ CD25+ Foxp3+ cells.

Figure 8H:
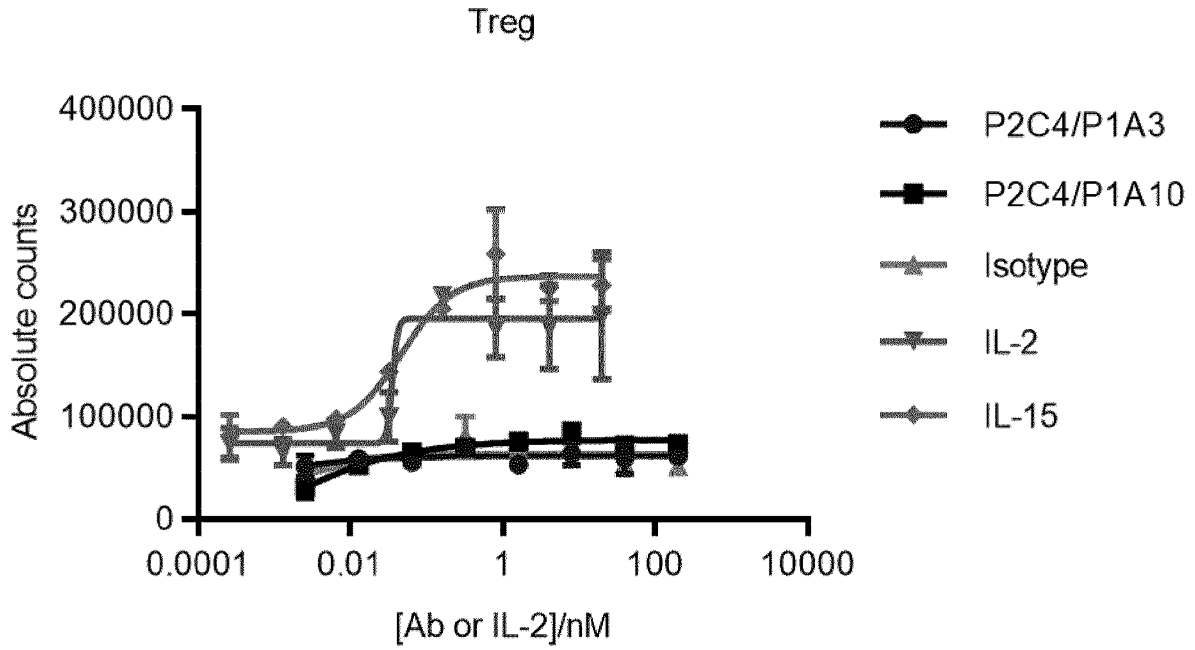
Figure 9A:
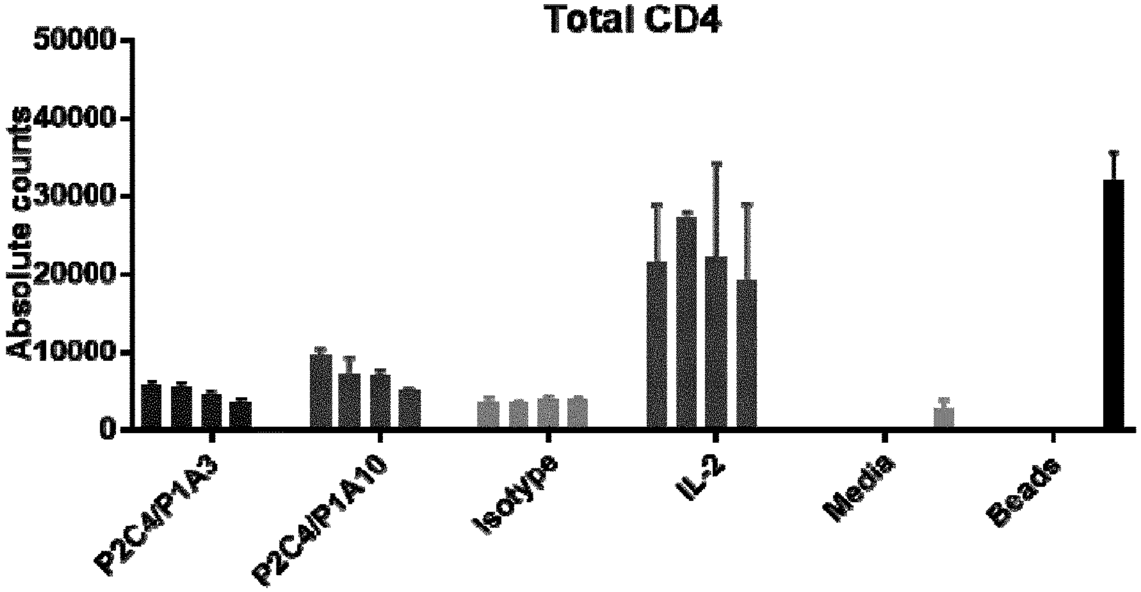
FIGS. 9A to 9I. Bar charts showing analysis of proliferation of pre-activated, T cell subsets in response to treatment of human PBMCs with bispecific IL-2Rβ- and γc-binding antibodies or IL-2. Unstimulated cells (media) and anti-CD3/CD28 bead-stimulated controls (beads) are indicated. (9A) Absolute numbers of CD4+ T cells. (9B) Absolute numbers of CD8+ T cells. (9C) Absolute numbers of Tregs. (9C) Absolute numbers of naïve CD8+ T cells. (9E) Absolute numbers of naïve CD4+ T cells. (9F) Absolute numbers of central memory CD8+ T cells. (9G) Absolute numbers of central memory CD4+ T cells. (9H) Absolute numbers of effector memory CD8+ T cells. (9I) Absolute numbers of effector memory CD4+ T cells.
Figure 9B:
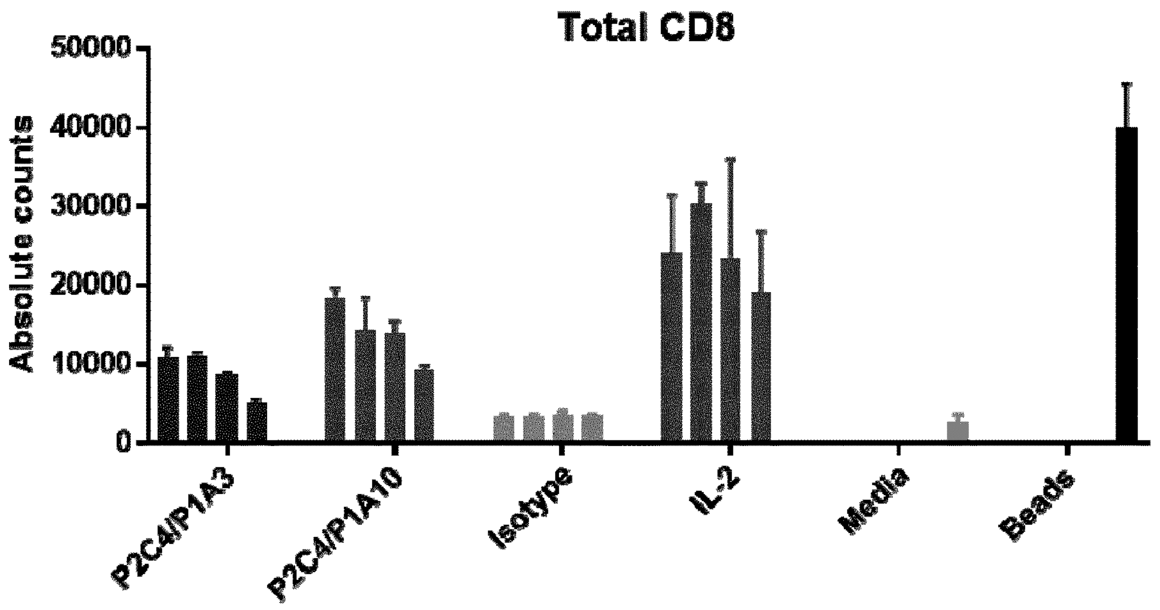
Figure 9C:
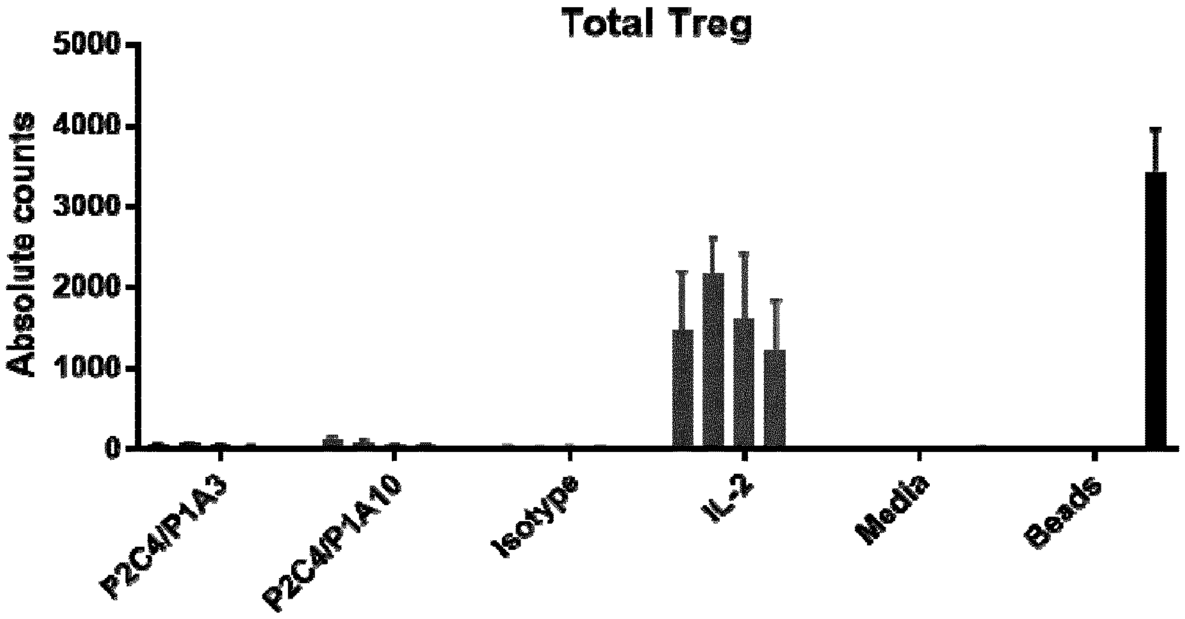
Figure 9D:
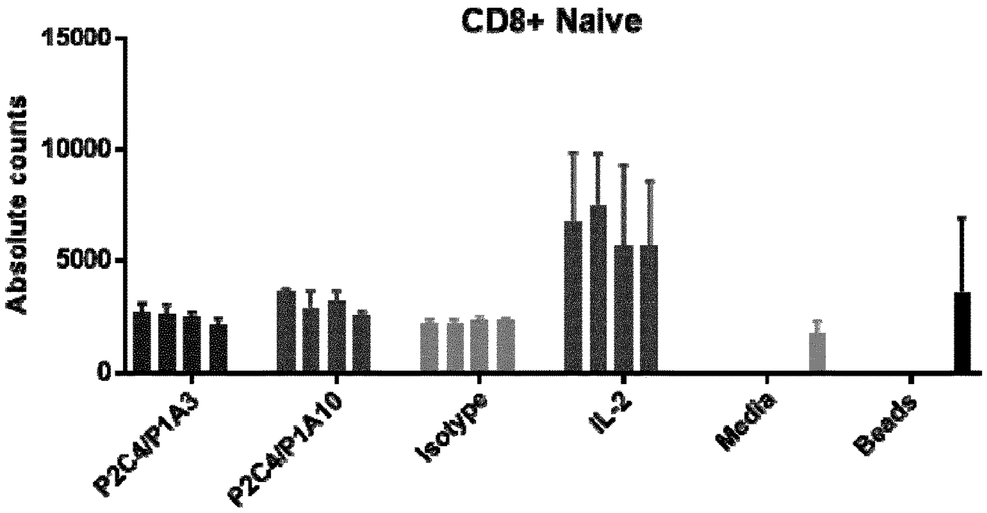
Figure 9E:
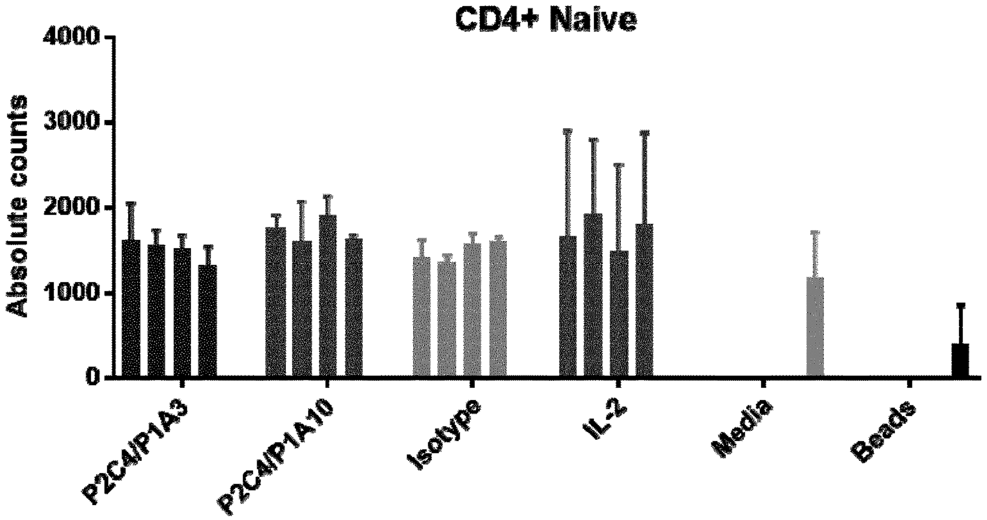
Figure 9F:
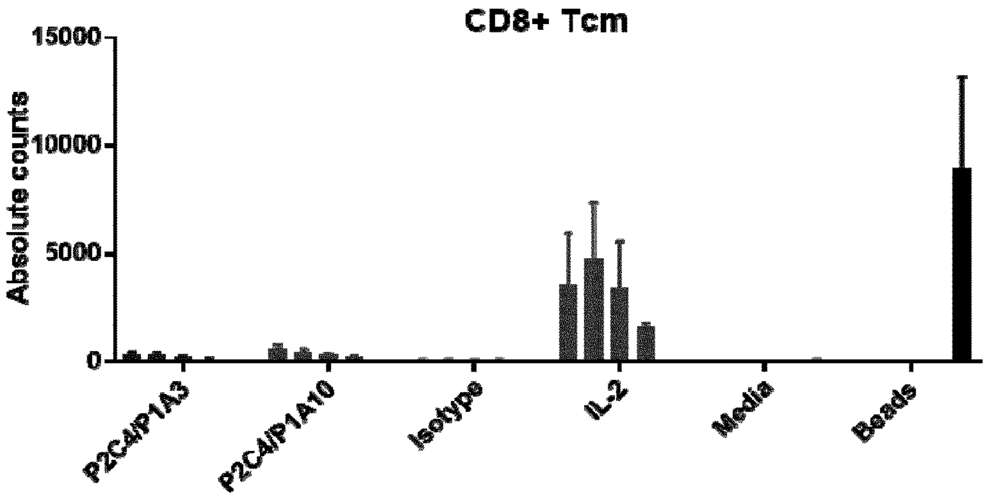
Figure 9G:
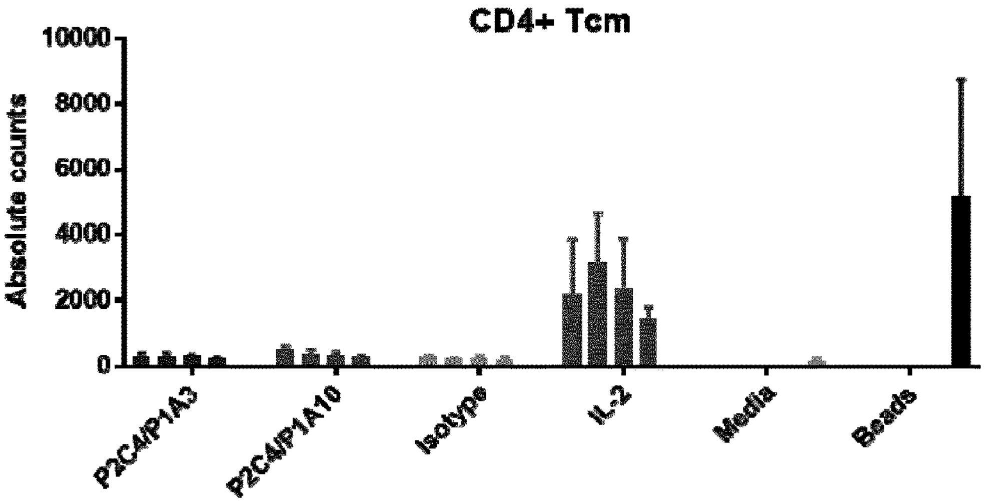
Figure 9H:
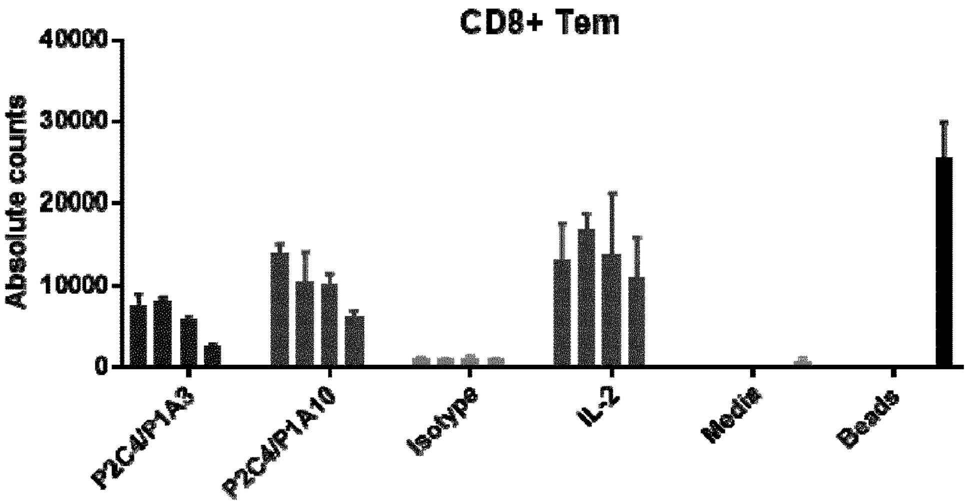
Figure 9I:
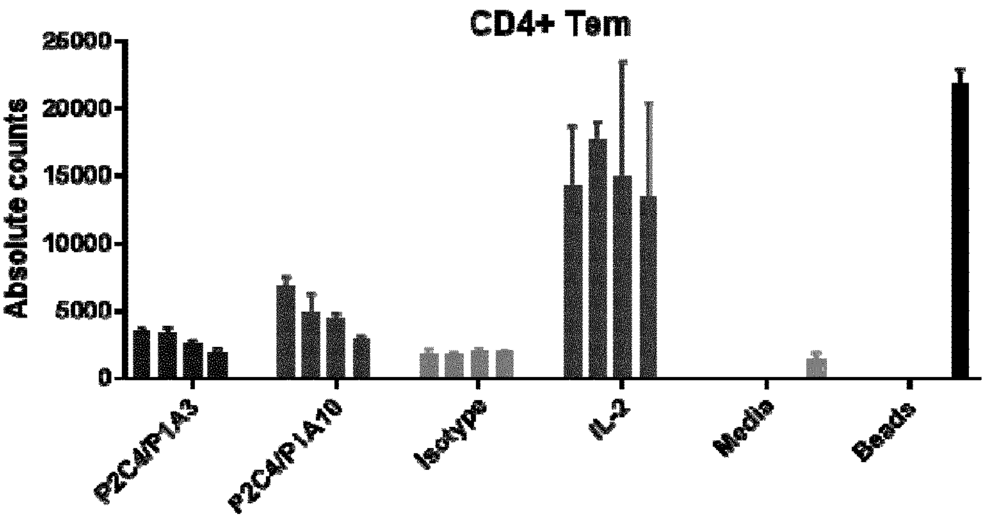

The results are shown in FIG. 8H. A dose-dependent trend in the number of Treg cells was detected following stimulation with IL-2 and IL-15, but not following treatment with P2C4/P1A3 or P2C4/P1A10, indicating that neither antibody sustains nor expands Treg numbers in vitro.

3.3 Analysis of the effect on primary human PBMCs

To determine whether the same stimulatory effect for P2C4/P1A3 and Gigkaine could be observed in stimulated human PBMCs. PBMCs were isolated and pre-activated with anti-CD3/CD28 beads for three days. Cells were then rested in fresh media for a day before labelling with CellTrace Violet, Cells were seeded at 400 000 per well and treated with P2C4/P1A3, P2C4/P1A10 (200 nM, 40 nM, 8 nM and 1.6 nM), IL-2 (20 nM, 4 nM, 0.8 nM, 0.16 nM) or anti-CD3/CD28 beads. Isotype antibody and untreated control conditions were included as negative controls. After four days, cells were stained with T cell markers CD3, CD4, CD8, CD45RO, CCR7, Foxp3 and CD25 to delineate T cell subsets (see Example 3.2). Counting beads were included to allow absolute cell numbers to be determined by flow cytometry.

The results are shown in FIGS. 9A to 9I. In agreement with the data obtained for treatment of pre-activated primary human T cells, P2C4/P1A3 and P2C4/P1A10 also were found to induce preferential expansion of CD8+ T cells over Tregs, and CD4+ T cell proliferation was additionally observed with P2C4/P1A10-treated cells, 3.4 Analysis of the Effect on Antigen-Specific T Cells To determine the effects of P2C4/P1A3 and P2C4/P1A10 stimulation on antigen-specific T cells (e.g. virus-specific T cells), EBV-specific T cells (EBVSTs) were thawed and rested for a day in fresh media, and subsequently treated with P2C4/P1A3, P2C4/P1A10, IL-2 or anti-CD3/CD28 beads. Isotype antibody and untreated control conditions were included as negative controls. After four days, cells were stained with T cell markers CD3, CD4, CD8, CD45RA, CCR7, Foxp3 and CD25 to delineate T cell subsets, and CD56 to enable detection of NK cells.

Counting beads were included to allow absolute cell numbers to be determined by flow cytometry.

Figure 10A:
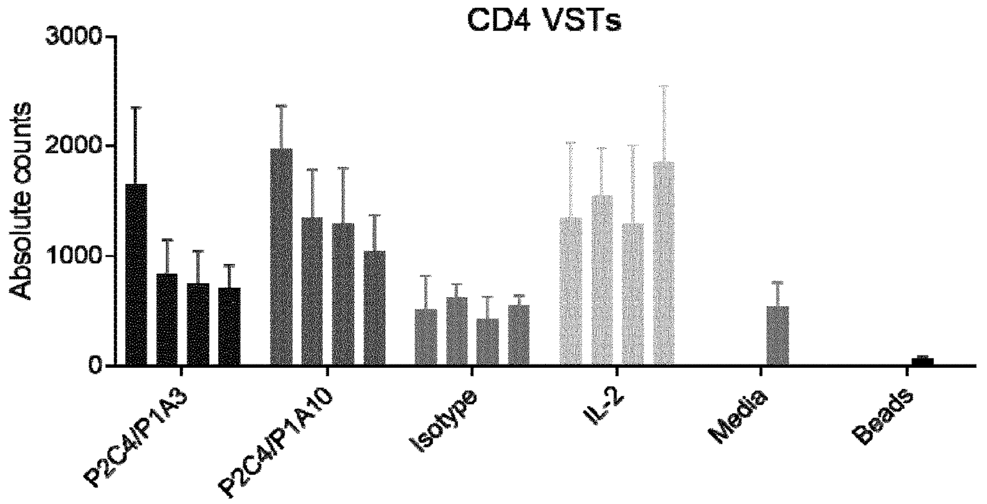
FIGS. 10A to 10G. Bar charts and graphs showing analysis of proliferation of antigen-specific T cells in response to treatment with bispecific IL-2Rβ- and γc-binding antibodies or the indicated cytokines. Unstimulated cells (media) and anti-CD3/CD28 bead-stimulated controls (beads) are indicated. (10A and 10D) Absolute numbers of CD4+ EBV-specific T cells. (10B and 10E) Absolute numbers of CD8+ EBV-specific T cells. (10C) Absolute numbers of CD56+ EBV-specific T cells. (10F) Percentage of CD8+ EBV-specific T cells which are dividing. (10G) Graphs showing dividing CD8+ EBV-specific T cells as determined by CellTrace Violet staining.
Figure 10B:
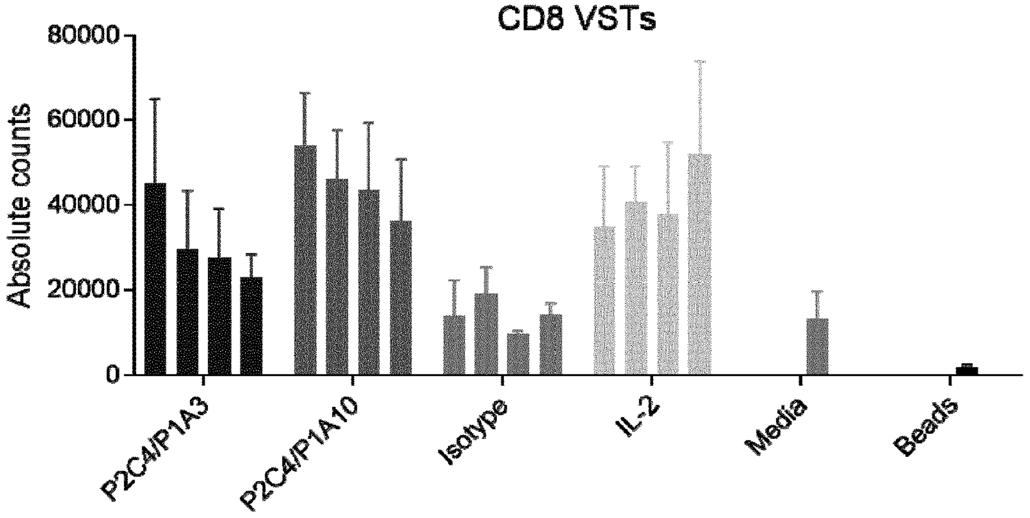
Figure 10C:
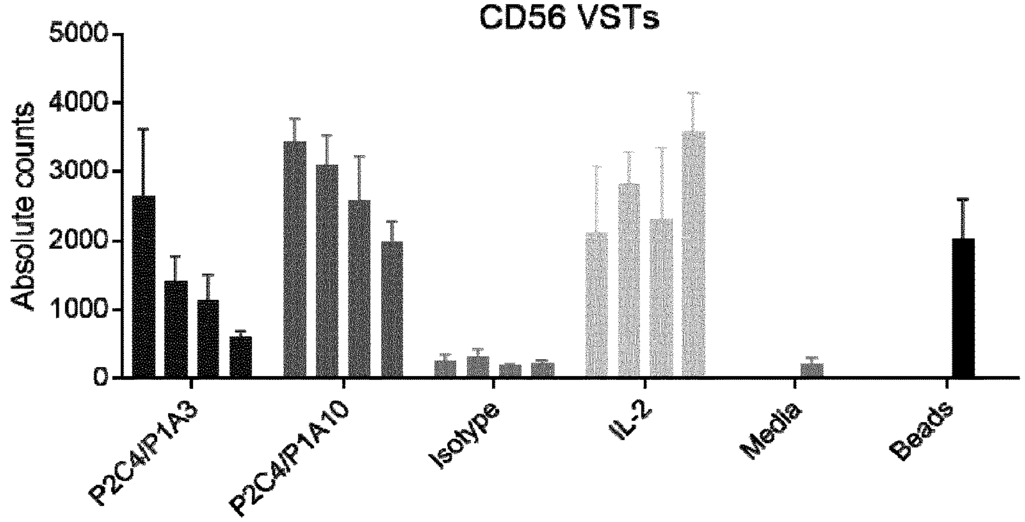
Figure 10D:
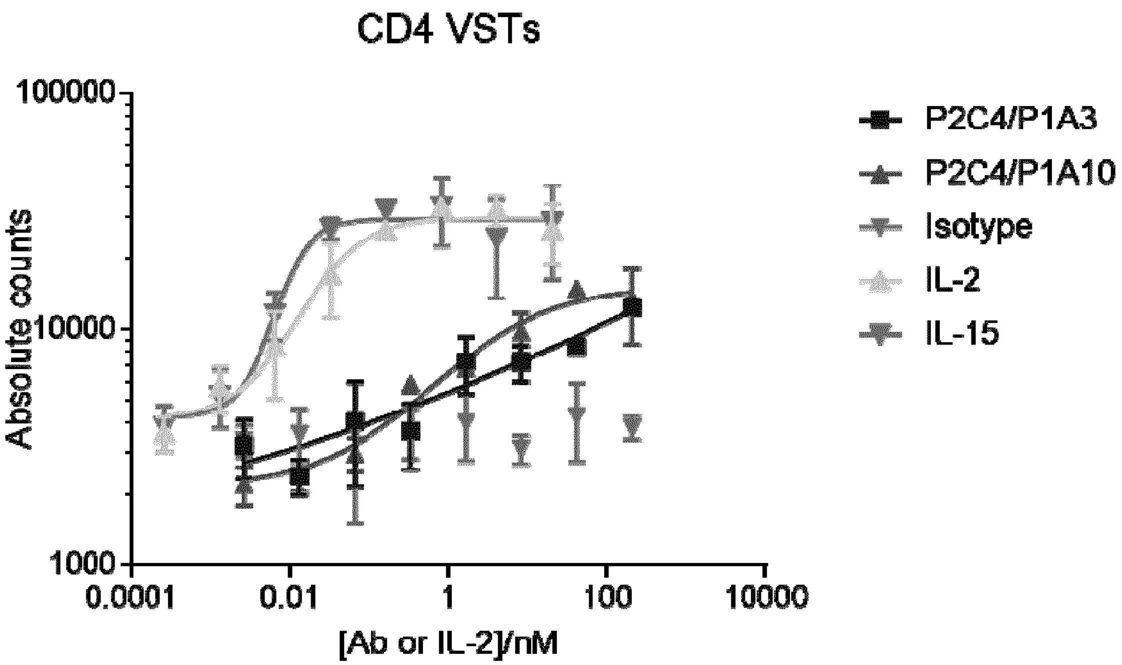
Figure 10E:
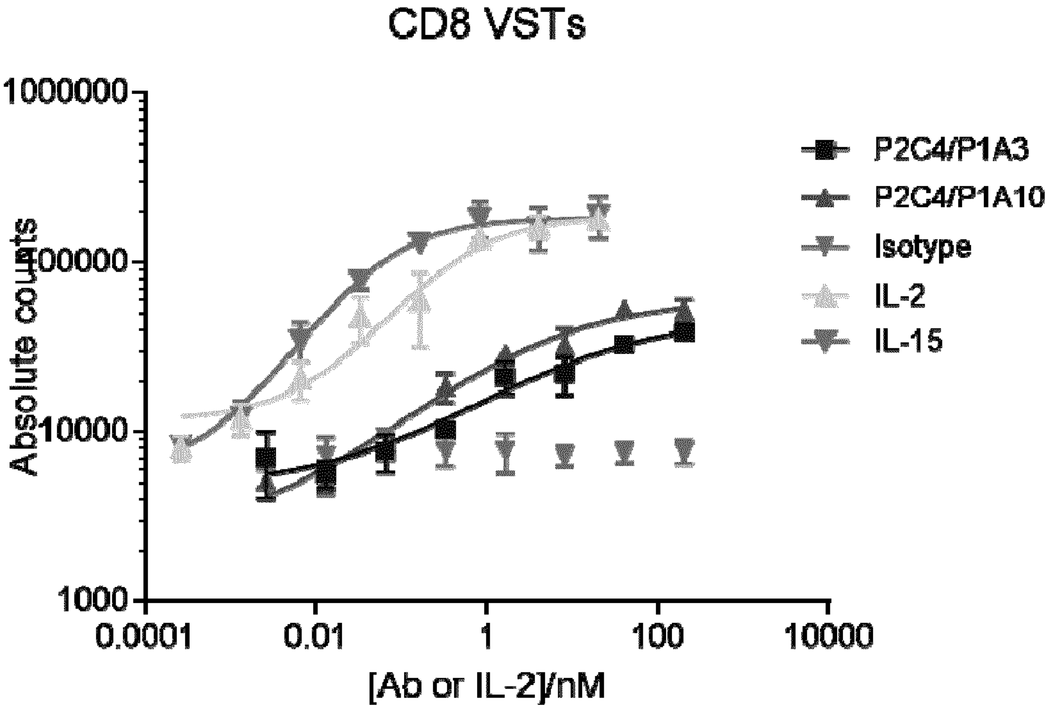
Figure 10F:
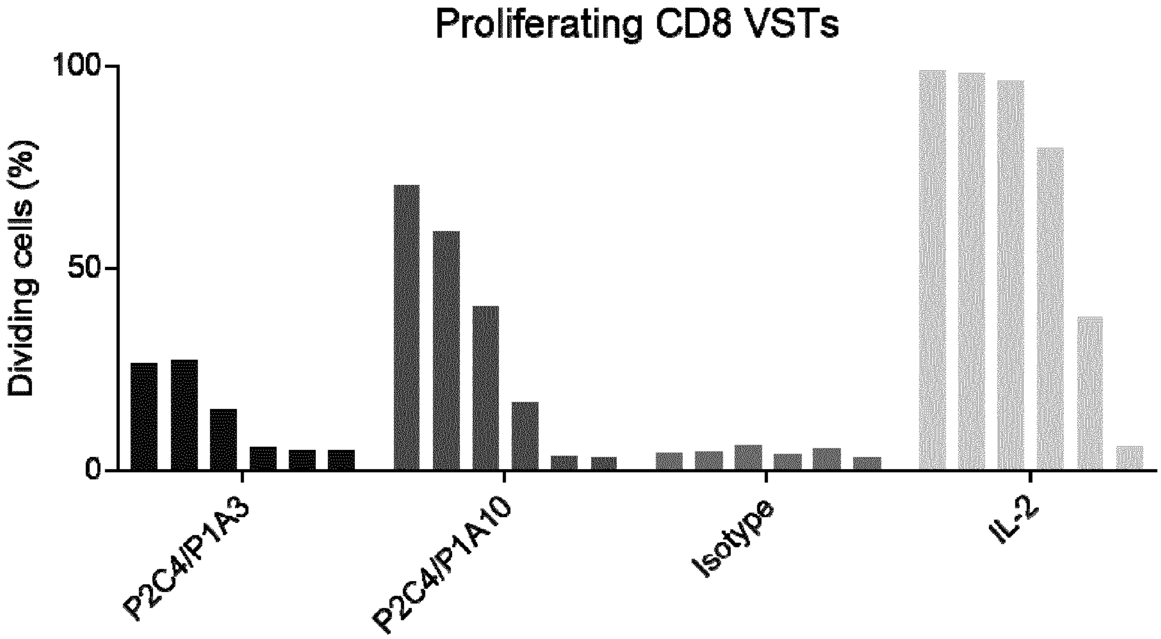
Figure 10G:
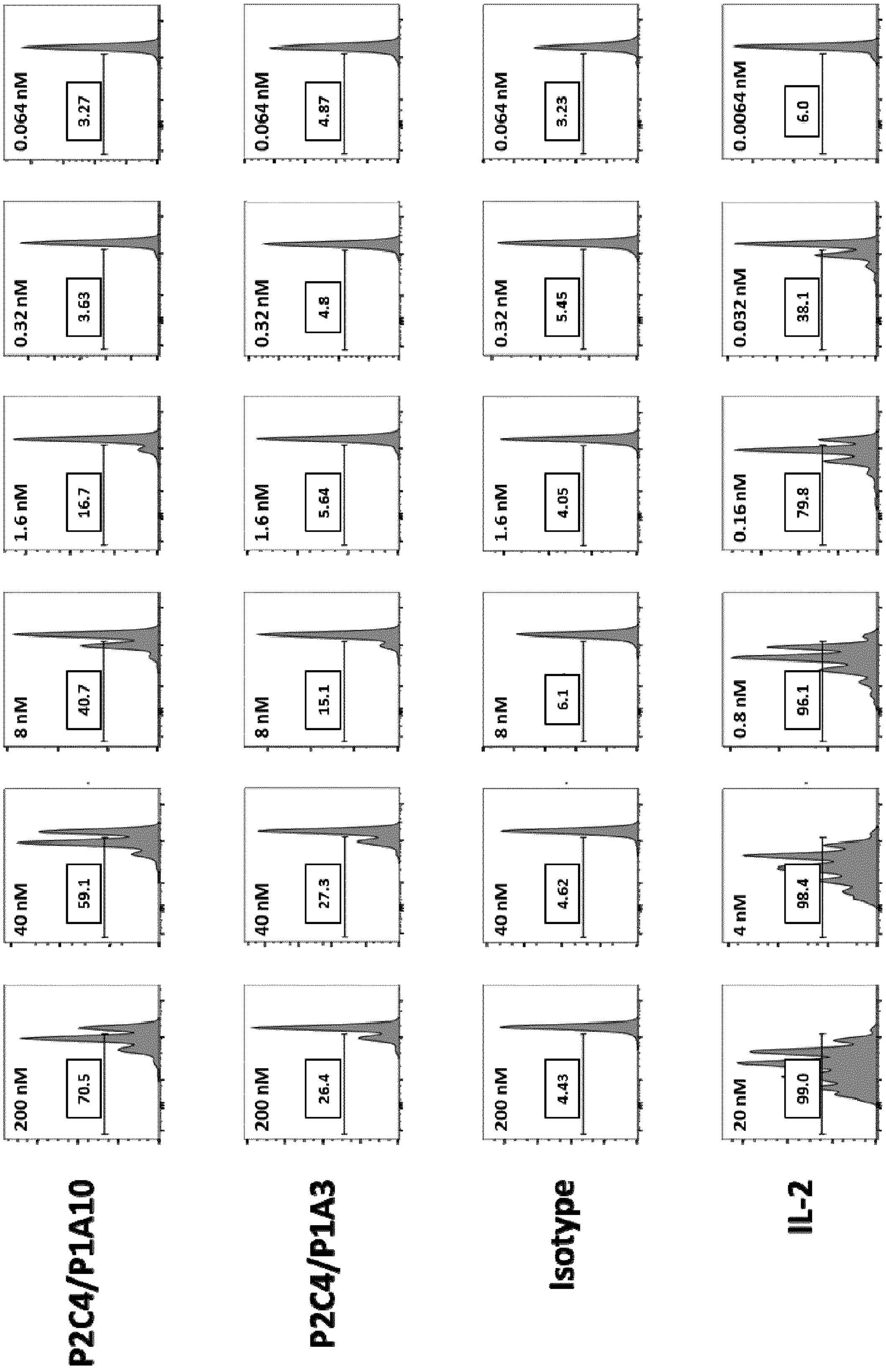

The results are shown in FIGS. 10A to 10G. P2C4/P1A3 and P2C4/P1A10 were found to induce the expansion of both CD4+ and CD8+ virus-specific T cells (FIGS. 10A and 10B). In addition, both antibodies were able to induce the expansion of CD58+ NK cells within the virus-specific T cell population (FIG. 10C). P2C4/P1A3 and P2C4/P1A10 were found to induce proliferation of CD4+ and CD8+ virus-specific T cells in a dose-dependent manner (FIGS. 10D and 10E). A high percentage of dividing CD8+ virus-specific T cells was also detected in response to P2C4/P1A10 and P2C4/P1A3 treatment (FIGS. 10F and 10G).

3.5 Analysis of the Effect on Cynomolgus PBMCs

Frozen cynomolgus PBMCs were thawed and rested overnight in complete media before labelling with Cell Trace Violet and seeded at 200 000 cells per well. Cells were then treated with P2C4/P1A3, P2C4/P1A10, isotype antibody (200 nM, 40 nM, 8 nM, 1.6 nM) or human recombinant IL-2 (20 nM, 4 nM, 0.8 nM, 0.16 nM). Media and anti-CD3/CD28 beads were included as controls. After four days, cells were stained with T cell markers CD3, CD4, CD8, CD28, CD95, Foxp3 and CD25 to delineate cynomolgus T cell subsets:

CD4+ Naïve T cells: CD3+CD4+CD28+CD95−

CD4+ effector memory T cells: CD3+CD4+CD28−CD95+

CD4+ central memory T cells: CD3+CD4+CD28+CD95+

CD8+ Naïve T cells: CD3+CD8+CD28+CD95−

CD8+ effector memory T cells: CD3+CD8+CD28−CD95+

CD8+ central memory T cells: CD3+CD8+CD28+CD95+

Cells were also stained with 0016 and CD20 to respectively identify NK and B cells. Counting beads were included to allow absolute cell numbers to be determined by flow cytometry.

The results are shown in FIGS. 11A to 11K. The effect of proliferation was most pronounced with IL-2 treatment. P2C4/P1A10 induced slight proliferation of CD4+, CD8+ T cells and NK cells in comparison to P2C4/P1A3 and isotype antibody control. Dose-dependent proliferation by P2C4/P1A10 was observed for CD4+ effector memory T cells, CD8+ Naïve T cells, CD8+ effector memory T cells and NK cells. Treg proliferation was observed in cells treated with IL-2 but not P2C4/P1A3 or P2C4/P1A10.

Figure 11A:
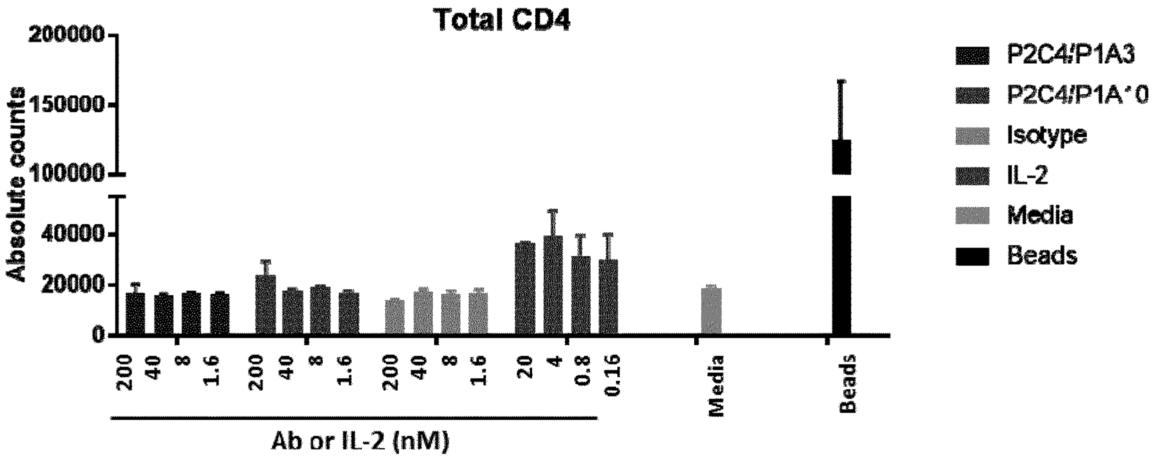
FIG. 11A to 11L. Bar charts showing analysis of proliferation of cynomolgus T cell subsets in response to treatment of cynomolgus PBMCs with bispecific IL-2Rβ- and γc-binding antibodies or IL-2. Unstimulated cells (media) and anti-CD3/CD28 head-stimulated controls (beads) are indicated. (11A) Absolute numbers of CD4+ T cells. (11B) Absolute numbers of CD8+ T cells. (11C) Absolute numbers of Tregs. (11D) Absolute numbers of naïve CD4+ T cells. (11E) Absolute numbers of effector memory CD4+ T cells. (11F) Absolute numbers of central memory CD4+ T cells. (11G) Absolute numbers of naïve CD8+ T cells. (11H) Absolute numbers of effector memory CD8+ T cells. (11I) Absolute numbers of central memory CD8+ T cells. (11J) Absolute numbers of NK cells. (11K) Absolute numbers of B cells. (11L) Ratio of the absolute number of CD8+ T cells to the absolute number of CD4+ T cells.
Figure 11B:
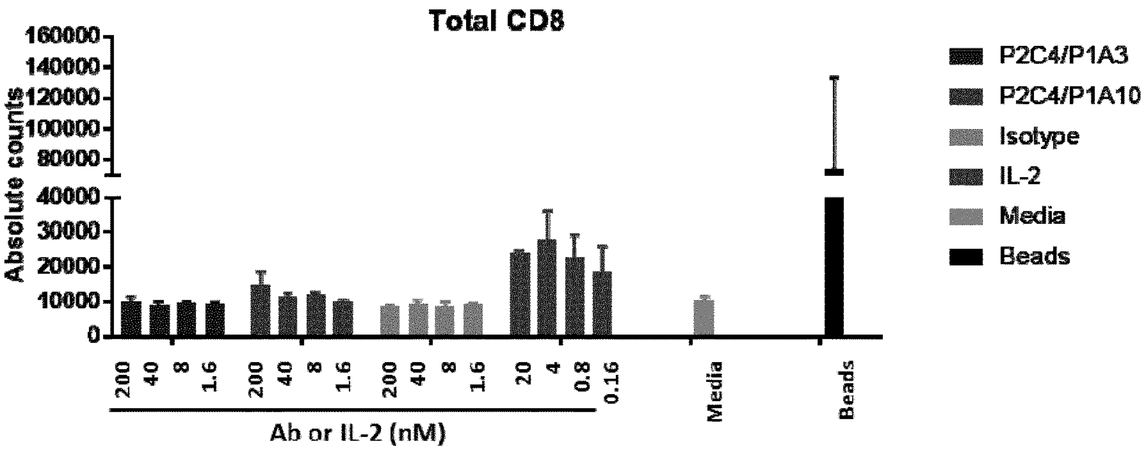
Figure 11C:
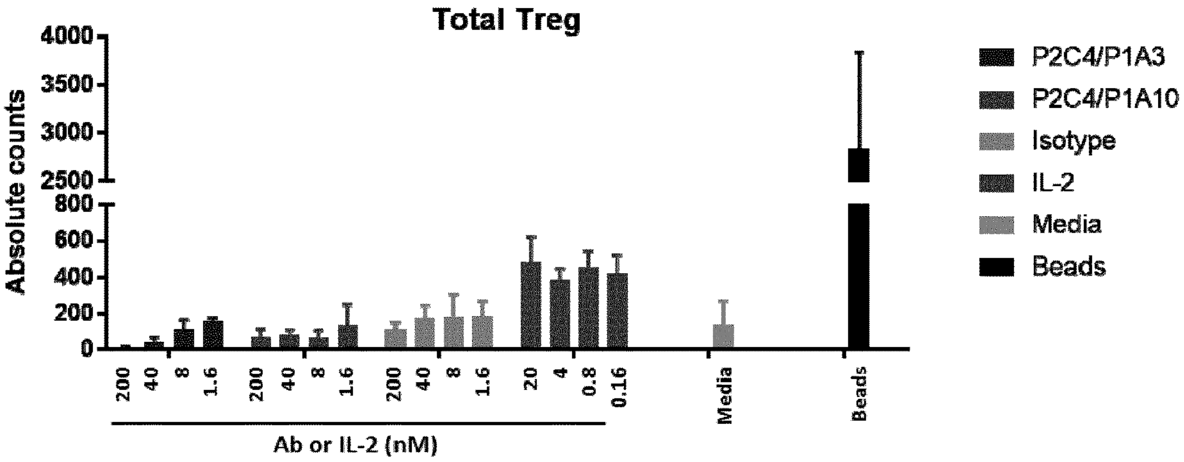
Figure 11D:
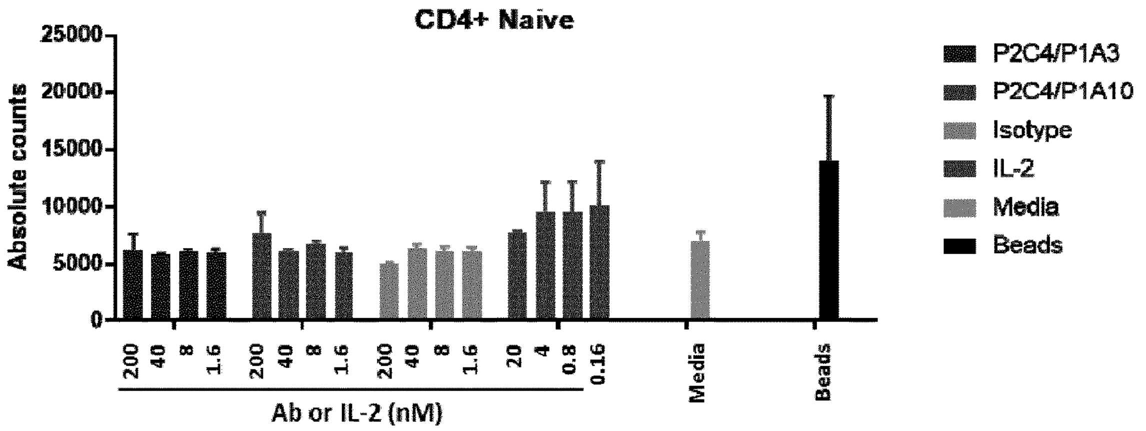
Figure 11E:
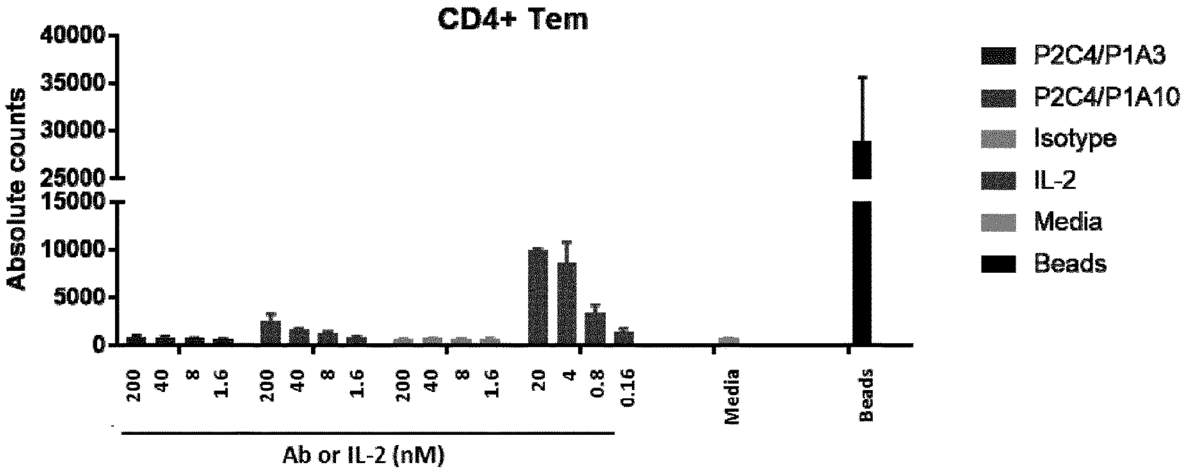
Figure 11F:
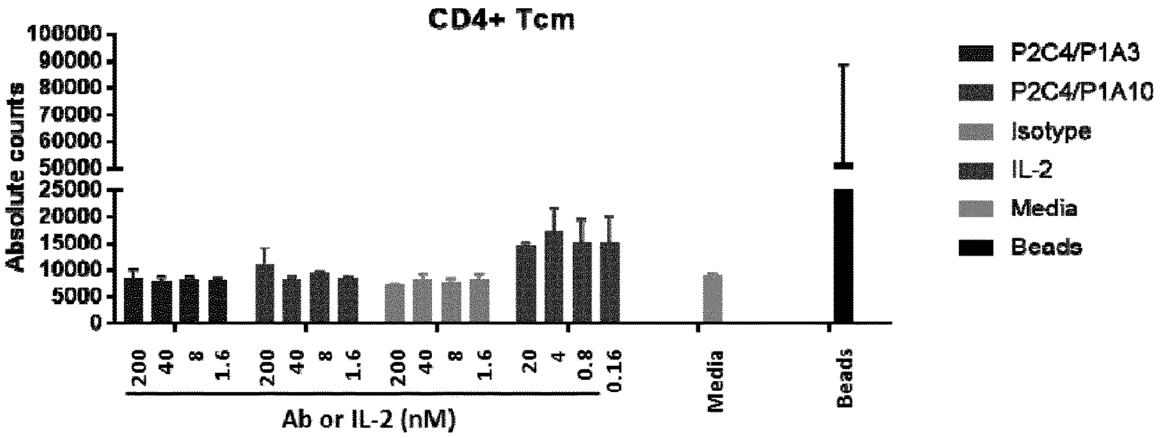
Figure 11G:
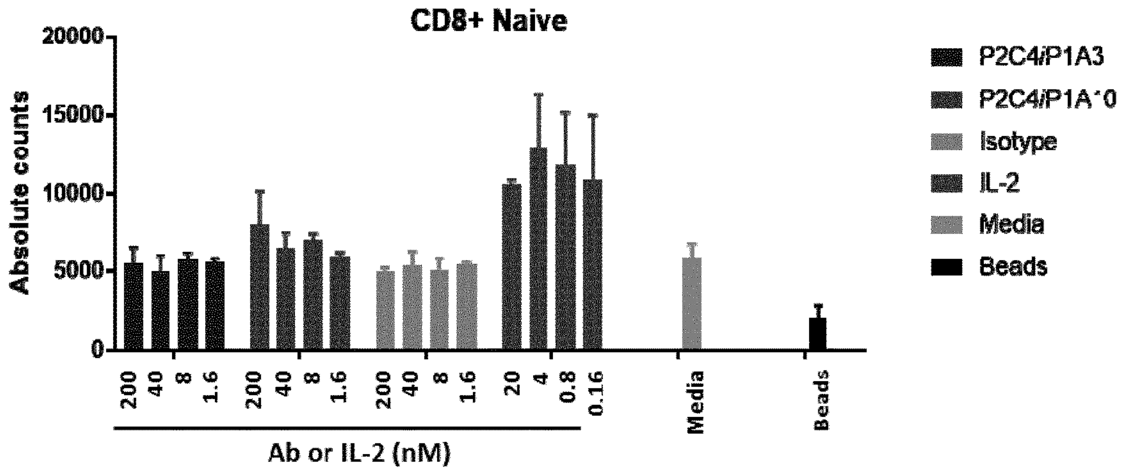
Figure 11H:
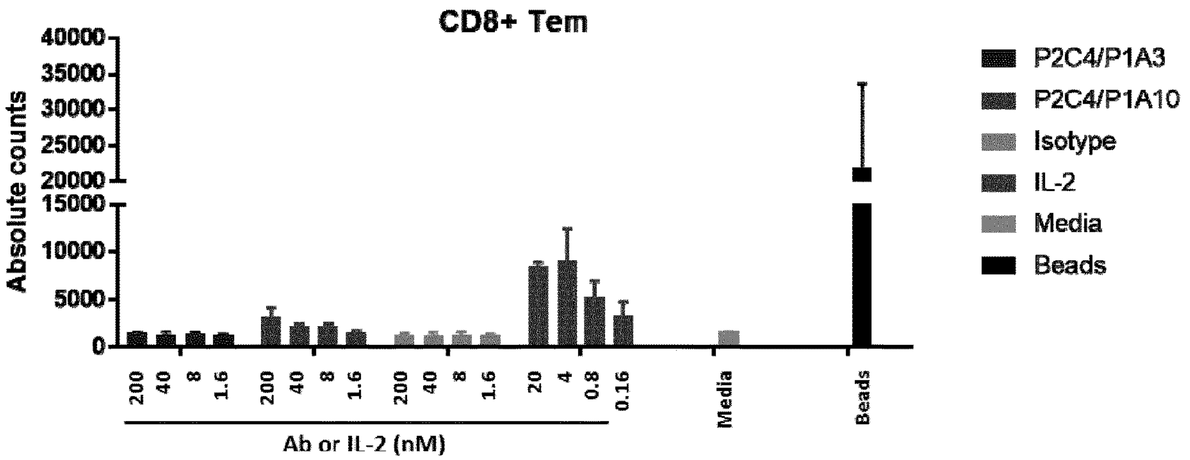
Figure 11I:
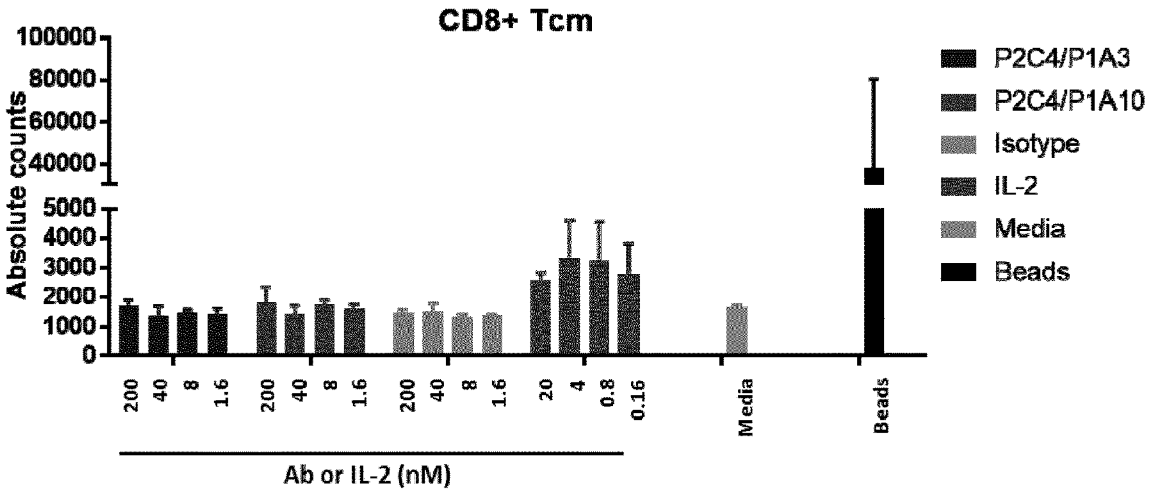
Figure 11J:
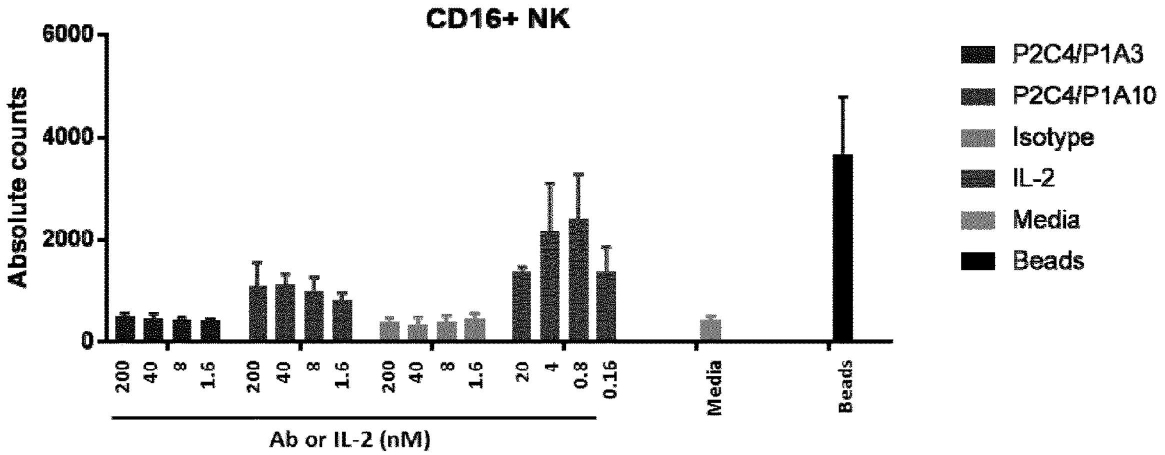
Figure 11K:
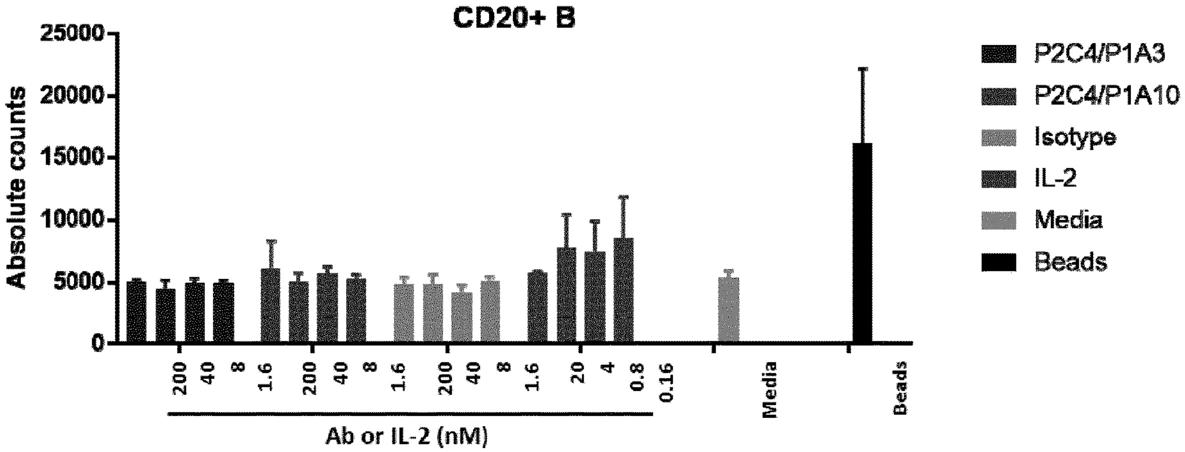
Figure 11L:
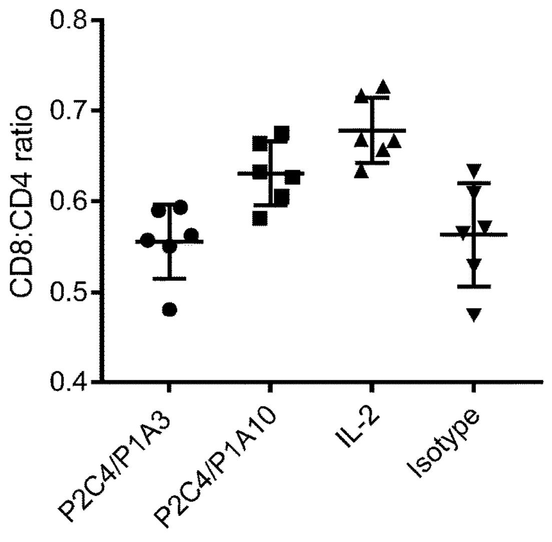

FIG. 11L shows the ratio of the absolute number of CD8+ T cells to the absolute number of CD4+ T cells from directly stimulated cynomolgus PBMCs treated with P2C4/P1A3, P2C4/P1A10, isotype antibody or IL-2. The ratio of CD8 to CD4 T cells indicated that P2C4/P1A10 and IL-2 preferentially expand CD8 over CD4 T cells to a greater extent than P2C4/P1A3 and isotype antibody control.

3.6 Analysis of the Effect on Pre-Activated Cynomolgus PBMCs

Frozen cynomolgus PBMCs were thawed and rested overnight in complete media before pre-activation for three days with CD3/CD2/CD28 non-human primate T cell activating beads at a beads:cells ratio of 1:2. Cells were then rested in fresh media for a day before labelling with Cell Trace Violet. Cells were seeded at 180 000 per well and treated with P2C4/P1A3, P2C4/P1A10, isotype antibody (200 nM, 40 nM, 8 nM, 1.6 nM) or human recombinant IL-2 (20 nM, 4 nM, 0.8 nM, 0.16 nM). Media and anti-CD3/CD28 beads were included as controls. After four days, cells were stained with T cell markers CD3, CD4, CD8, CD28, CD95, Foxp3 and CD25 to delineate T cell subsets, as above.

Counting beads were included to allow absolute cell numbers to be determined by flow cytometry.

The results are shown in FIGS. 12A to 12I. P2C4/P1A3 and P2C4/P1A10 induced the proliferation of both CD4+ and CD8+ T cells but not Treg. P2C4/P1A10 induced the proliferation of all CD4+ and CD8+ T cell subsets. Dose-dependent proliferation was observed in both CD4+ and CD8+ effector memory and central memory T cells under P2C4/P1A3 treatment.

Figure 12A:
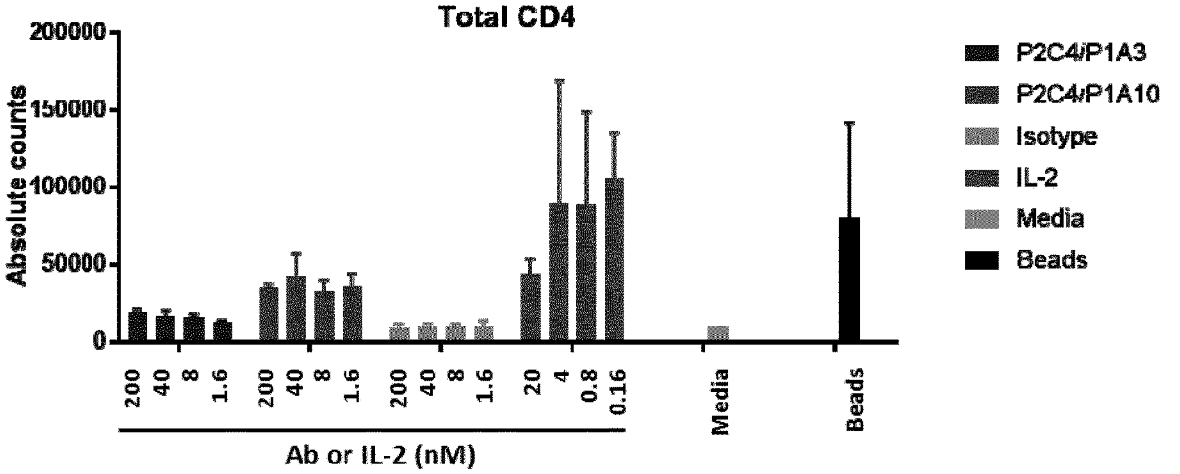
FIG. 12A to 12M. Bar charts showing analysis of proliferation of pre-activated cynomolgus T cell subsets in response to treatment of cynomolgus PBMCs with bispecific IL-2Rβ- and γc-binding antibodies or IL-2. Unstimulated cells (media) and anti-CD3/CD28 bead-stimulated controls (beads) are indicated. (12A) Absolute numbers of CD4+ T cells. (12B) Absolute numbers of CD8+ T cells. (12C) Absolute numbers of Tregs. (12D) Absolute numbers of naïve CD4+ T cells. (12E) Absolute numbers of effector memory CD4+ T cells. (12F) Absolute numbers of central memory CD4+ T cells. (12G) Absolute numbers of naïve CD8+ T cells. (12H) Absolute numbers of effector memory CD8+ T cells. (12I) Absolute numbers of central memory CD8+ T cells. (12J) Ratio of the absolute number of CD8+ T cells to the absolute number of CD4+ T cells. (12K) Percentage of effector memory CD4+ T cells which are dividing. (12L) Percentage of central memory CD4+ T cells which are dividing. (12M) Percentage of effector memory CD8+ T cells which are dividing. (12N) Percentage of central memory CD8+ T cells which are dividing.
Figure 12B:
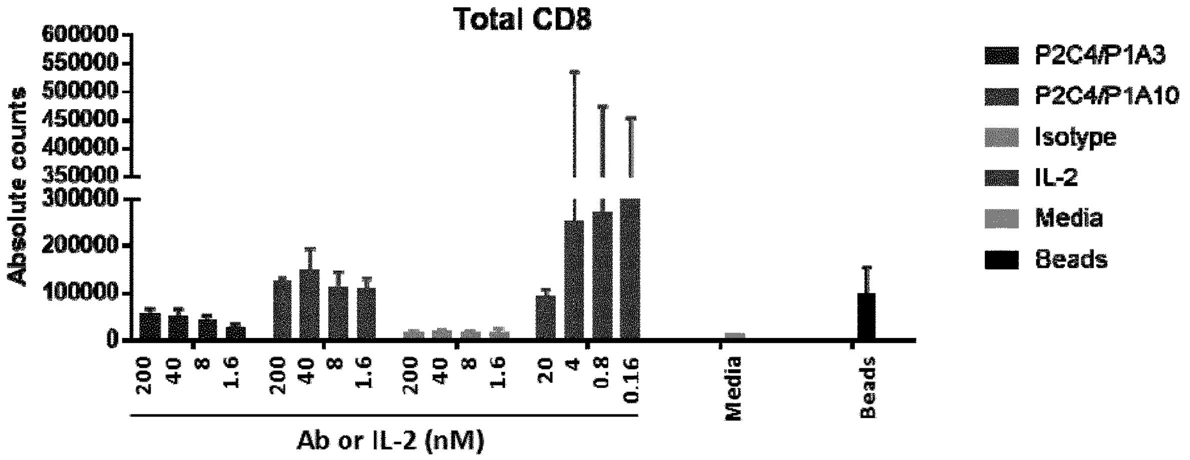
Figure 12C:
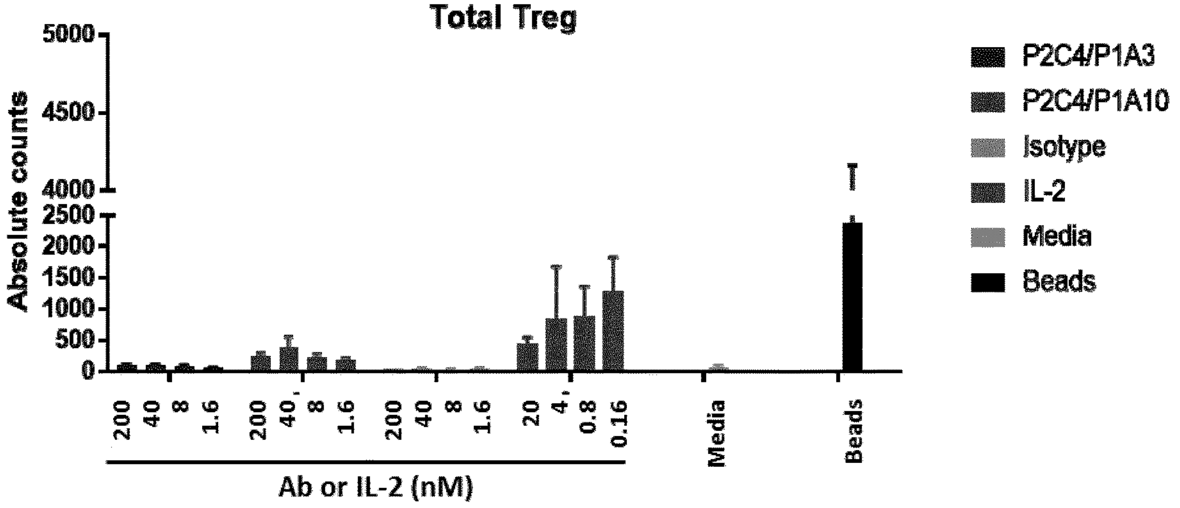
Figure 12D:
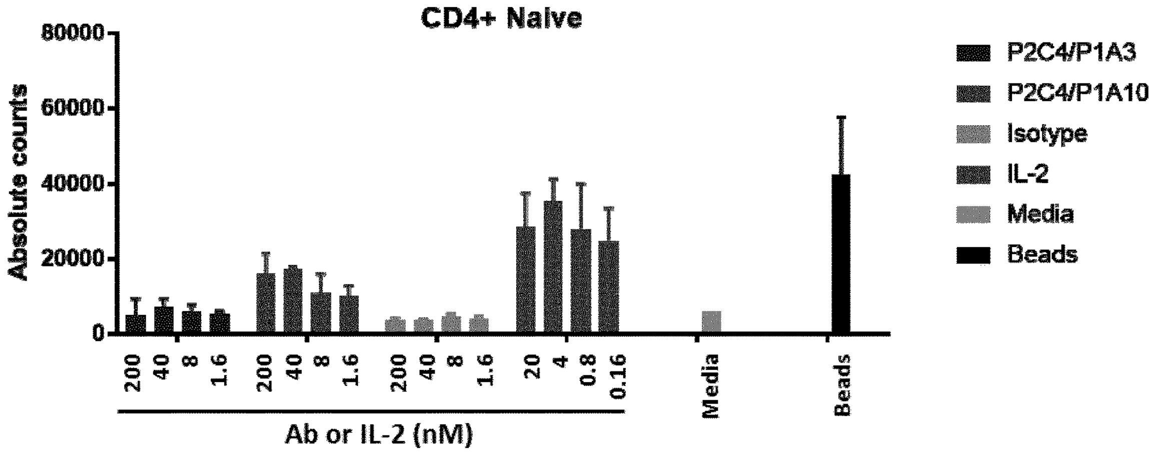
Figure 12E:
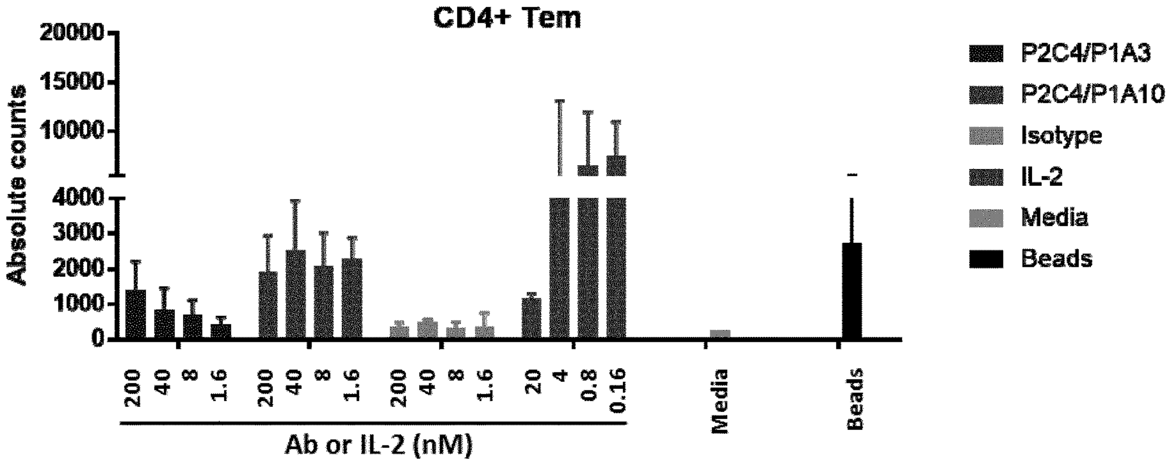
Figure 12F:
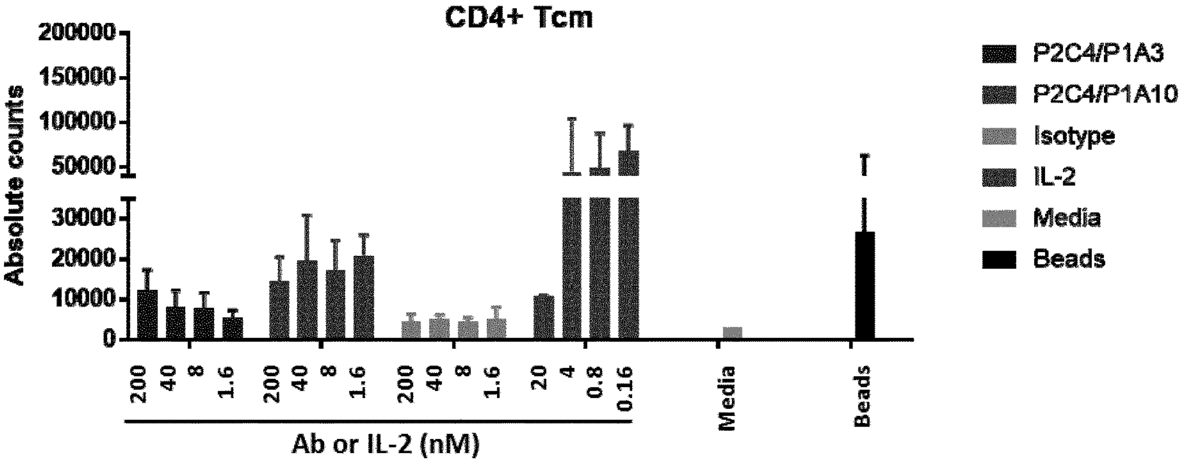
Figure 12G:
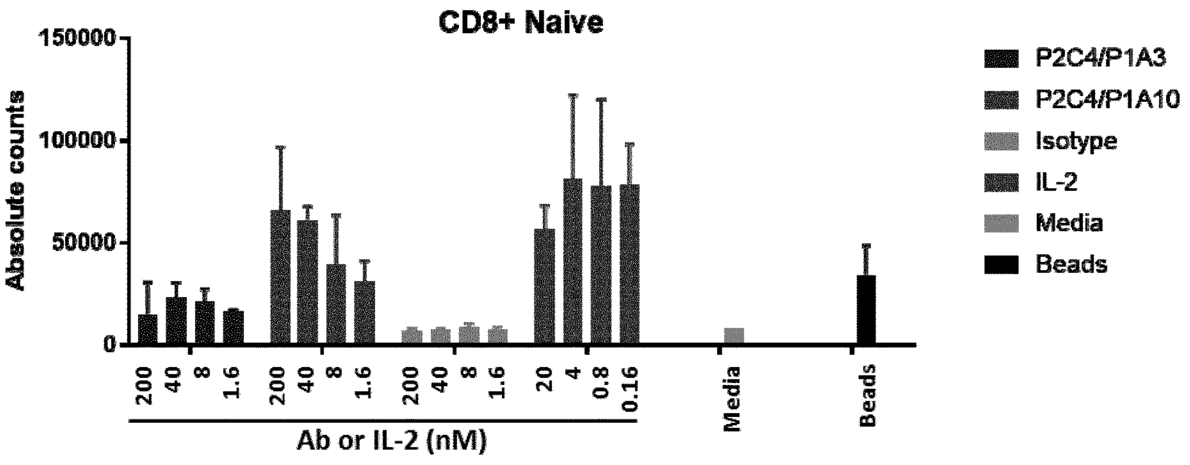
Figure 12H:
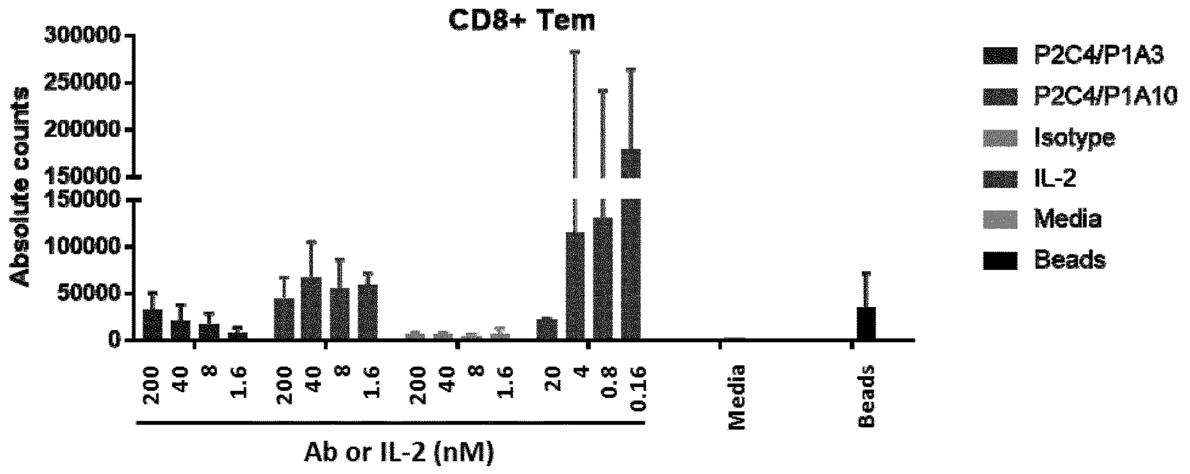
Figure 12I:
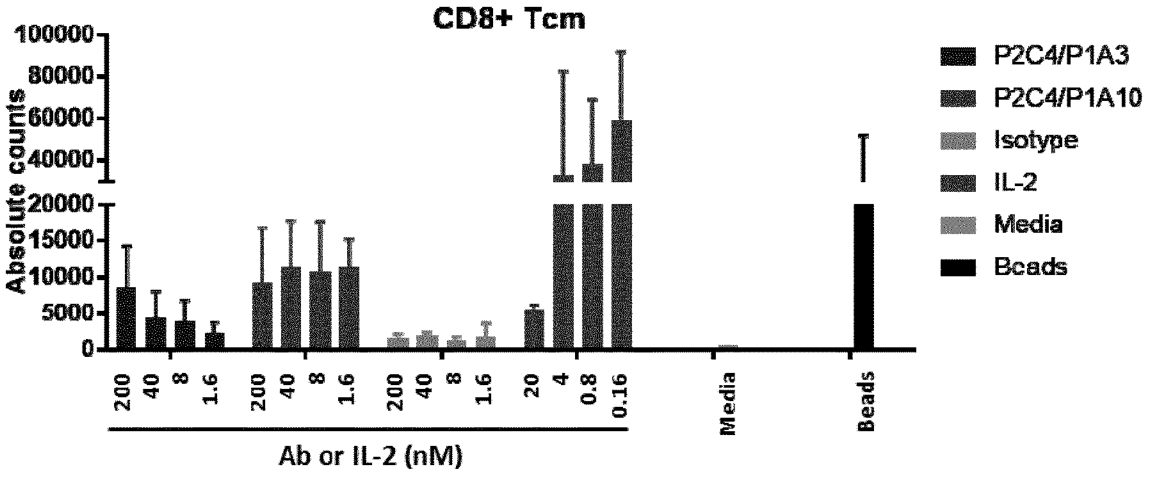
Figure 12J:
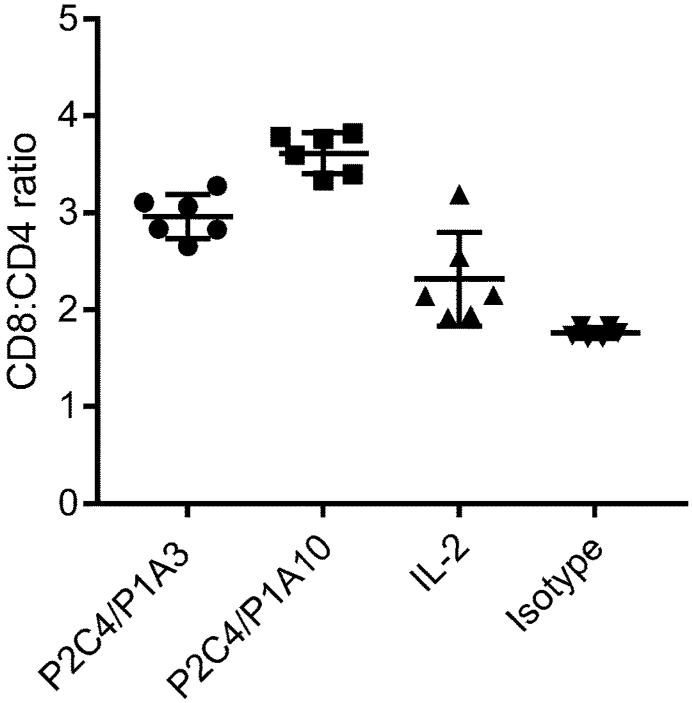
Figure 12K:
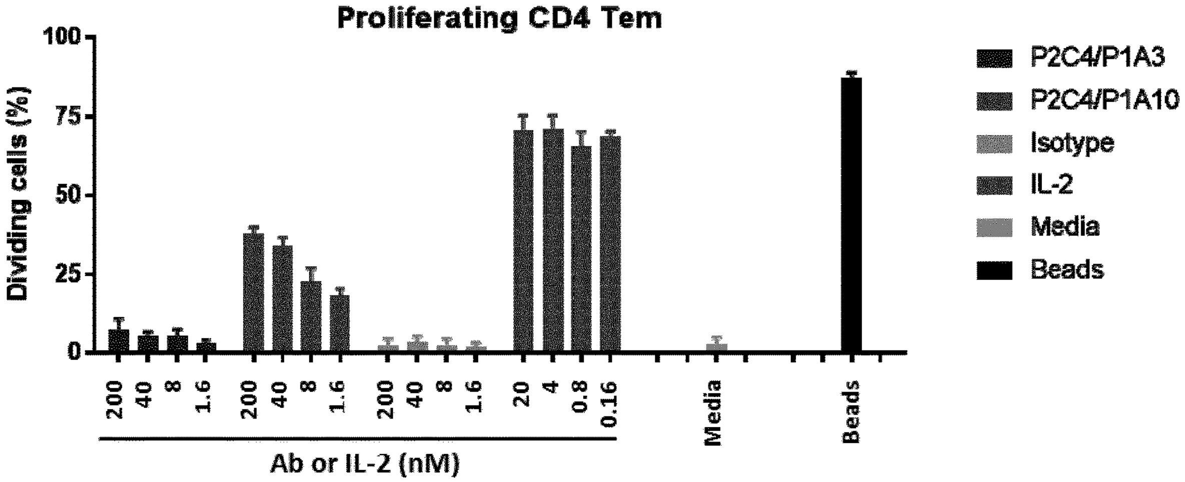
Figure 12L:
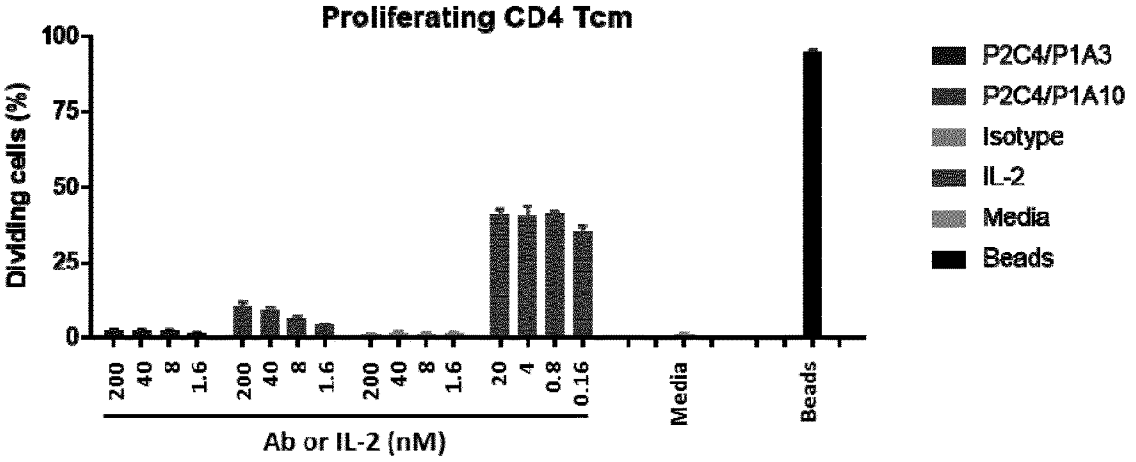
Figure 12M:
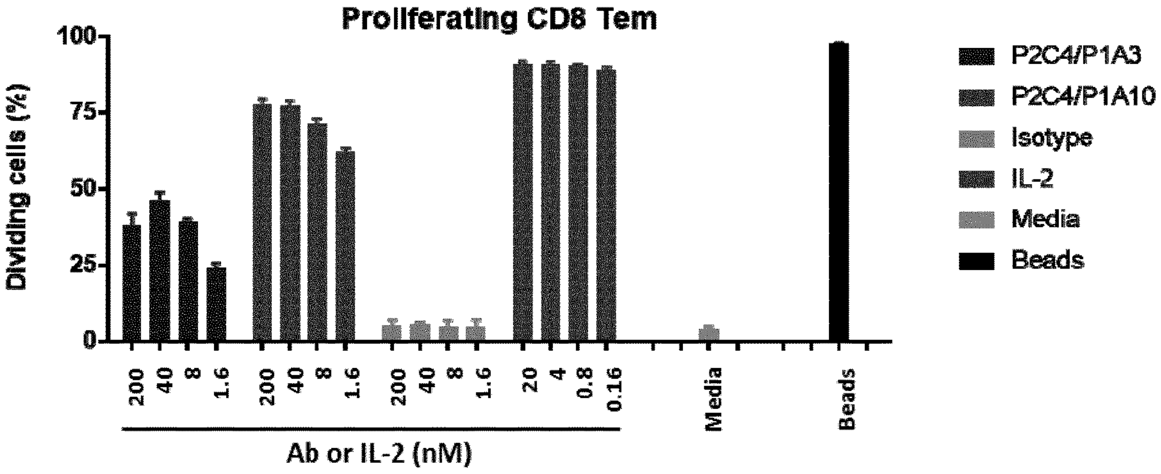
Figure 12N:
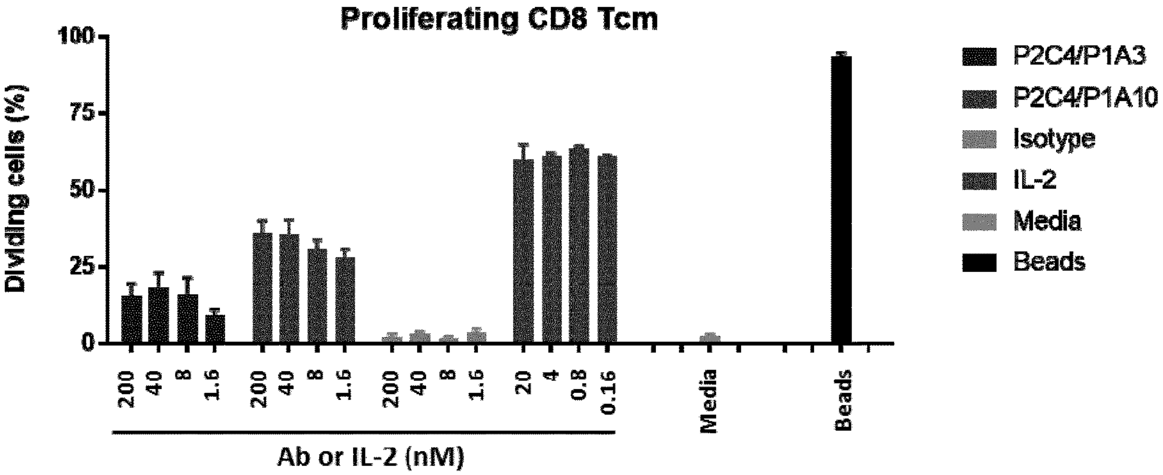

FIG. 12J shows the ratio of the absolute number of CD8+ T cells to the absolute number of CD4+ T cells from pre-activated cynomolgus PBMCs treated with P2C4/P1A3, P2C4/P1A10, isotype antibody or IL-2. The ratio of CD8 to CD4 T cells indicate that P2C4/P1A3 and P2C4/P1A10 preferentially expand CD8 over CD4 T cells to a greater extent than IL-2 and isotype antibody control.

FIGS. 12K to 12N show analysis of proliferation of CD8+ and CD4+ T cells. A high percentage of dividing CD8+ T effector memory and CD8+ T central memory cells were detected following stimulation with P2C4/P1A10 or P2C4/

P1A3. In addition, P2C4/P1A10 also induced a high percentage of dividing CD4+ T effector memory and CD4+ T central memory cells.

3.7 Analysis of the Effect on Pre-Activated Human NK Cells

To determine the effects of IL-2Rβ- and γc-binding bispecific antibodies on human NK cells, primary NK cells were isolated from human PBMCs and pre-activated for three days with irradiated K562-4-1BBL-CD64-CD86 cell line. Cells were labelled with CellTrace™ Violet for tracking of cell proliferation, then treated with P2C4/P1A3, P2C4/P1A10, IL-2 and IL-15. Isotype antibody and no treatment wells were included as negative controls. After five days, cells were stained for CD56 and CD16 NK cell markers. Counting beads were also added to determine the absolute cell numbers, and samples were analysed by flow cytometry.

The results are shown in FIGS. 27A to 27D. P2C4/P1A3 and P2C4/P1A10 were both found to induce proliferation of activated NK cells. Both the CD56+CD16+ and CD56+CD16-NK subsets were found to proliferate in response to P2C4/P1A3 and P2C4/P1A10 treatment in a dose-dependent manner, as shown by the dose-dependent increase in absolute counts of both types of NK cells (27A, 27B) and the percentages of the corresponding proliferating NK cell subsets illustrated by CellTrace™ Violet (CTV)-diluted cells (27C, 27D).

3.8 Analysis of the Effect on CAR-T Cells

To determine the effects of IL-2Rβ- and γc-binding bispecific antibodies on CAR-T cells, primary T cells were isolated from human PBMCs and then transduced with the CAR construct so that the CAR is expressed. After 24 days of cell expansion, cells were labelled with CellTrace™ Violet for tracking of cell proliferation, then treated with P2C4/P1A3, P2C4/P1A10, isotype antibody or IL-2. After five days, cells were stained for CAR expression and T cell markers to identify the T cell subsets. Counting beads were also added to determine the absolute cell numbers, and samples were analysed by flow cytometry.

The results are shown in FIGS. 28A to 28D. P2C4/P1A3 and P2C4/P1A10 both induce proliferation of CAR-T cells. The antibodies were found to induce expansion of the CD4+ and CD8+ CAR-T cells in a dose-dependent manner, as shown by the dose-dependent increase in absolute counts of CD4+ (28A) and CD8+ (28B) CAR-T cell subsets. A greater percentage of CD8+CAR-T cells were found to be proliferating (28D) compared to CD4+ CAR-T cells (28C), determined by CellTrace™ Violet (CTV), suggesting that CD8+ CAR-T cells are more responsive to P2C4/P1A3 and P2C4/P1A10 treatment than CD4+ CAR-T cells.

Example 4: Analysis of Induction of Intracellular Signalling by IL-2Rβ- and γc-Binding Bispecific Antibodies 4.1 Analysis of Induction of STAT5 Phosphorylation in NK Cells NK92 cells were washed and rested in IL-2-free media for 1 h prior to stimulation with various concentrations of P2C4/P1A3, P2C4/P1A10, Isotype control antibody or IL-2 for 30 min. Cells were subsequently fixed, permeabilised and stained for phosphorylated STAT5 using a fluorescently-labelled antibody, and the samples were then analysed by flow cytometry.

Figure 13:
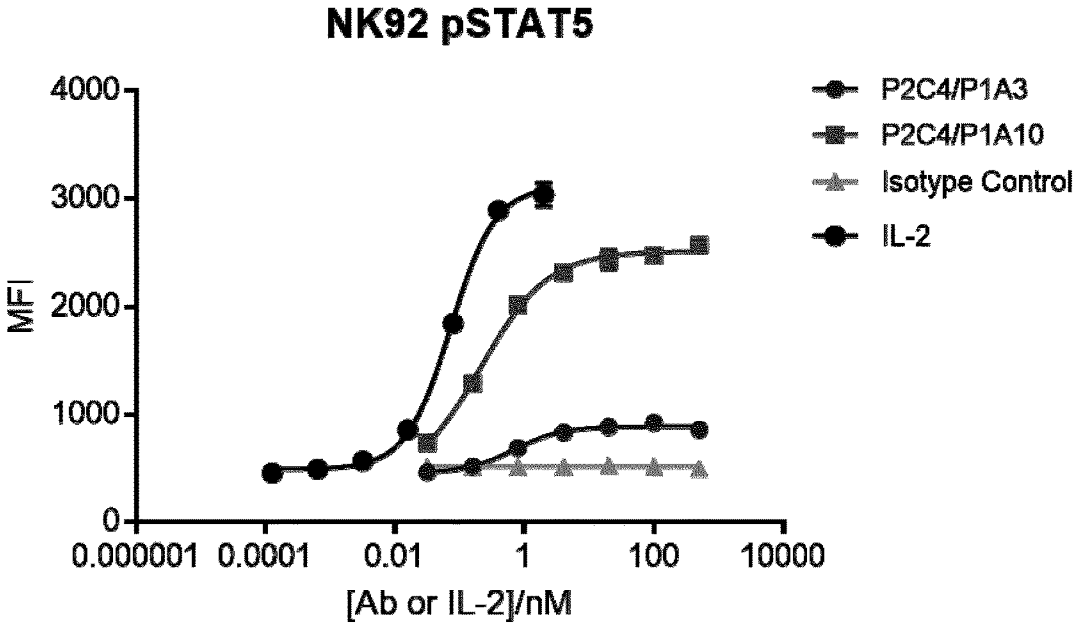
FIG. 13. Graph showing analysis of induction of STAT5 phosphorylation in NK92 cells in response to treatment with bispecific IL-2Rβ- and γc-binding antibodies or IL-2. EC50 values for induction of STAT5 phosphorylation are shown.
Figure 14A:
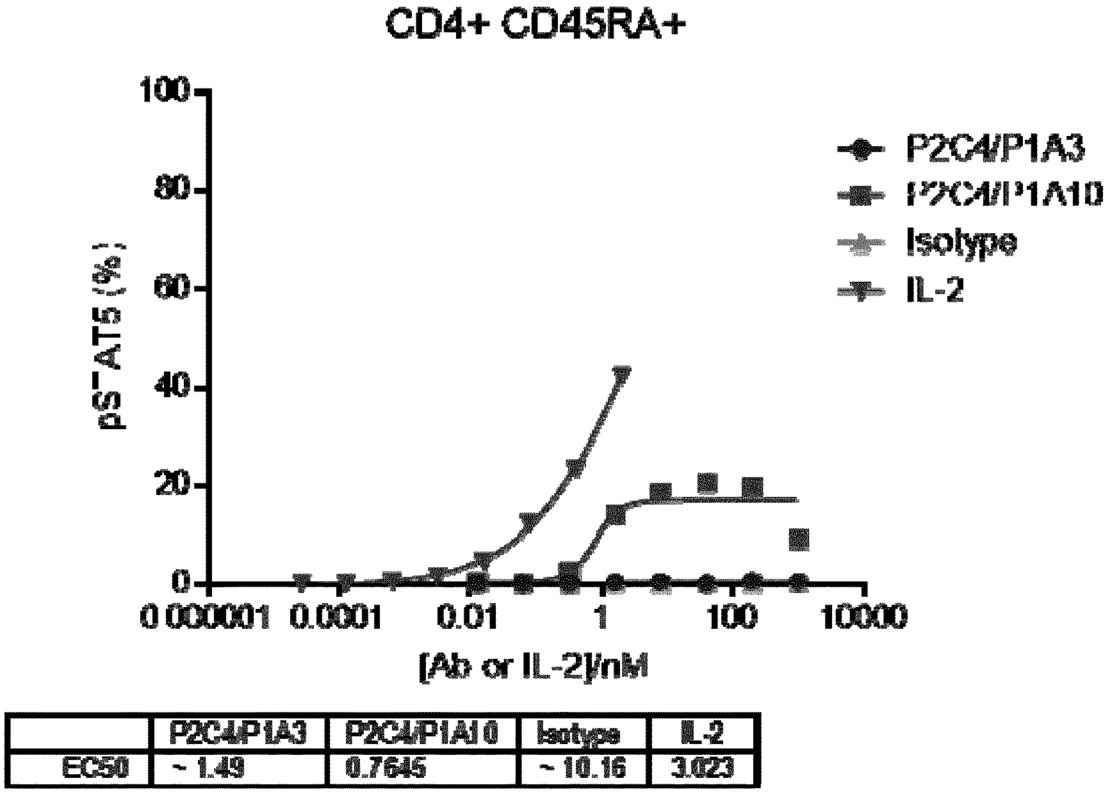
FIGS. 14A to 14H. Graphs showing analysis of induction of STAT5 phosphorylation in human immune cell subsets following treatment of PBMCs with different amounts of bispecific IL-2Rβ- and γc-binding antibodies or IL-2. EC50 values for induction of STAT5 phosphorylation are shown. (14A) Percentage pSTAT5-positive naïve CD4+ T cells. (14B) Percentage pSTAT5-positive memory CD4+ T cells. (14C) Percentage pSTAT5-positive Tregs. (14D) Percentage pSTAT5-positive B cells. (14E) Percentage pSTAT5-positive naïve CD8+ T cells. (14F) Percentage pSTAT5-positive memory CDS+ T cells. (14G) Percentage pSTAT5-positive NK cells, (14H) Percentage pSTAT5-positive monocytes.
Figure 14B:
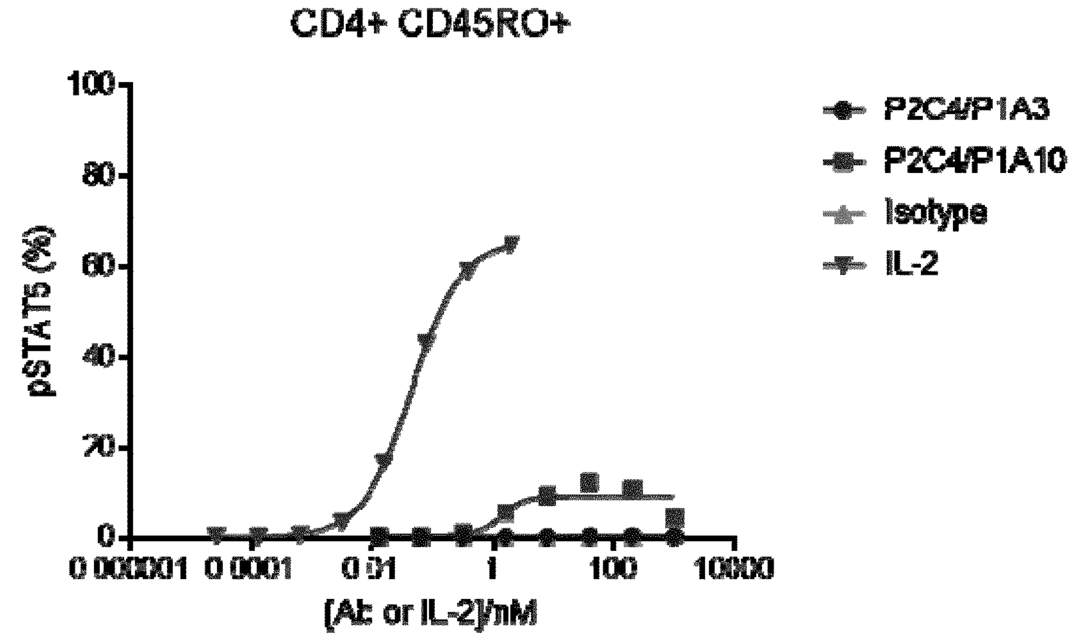
Figure 14C:
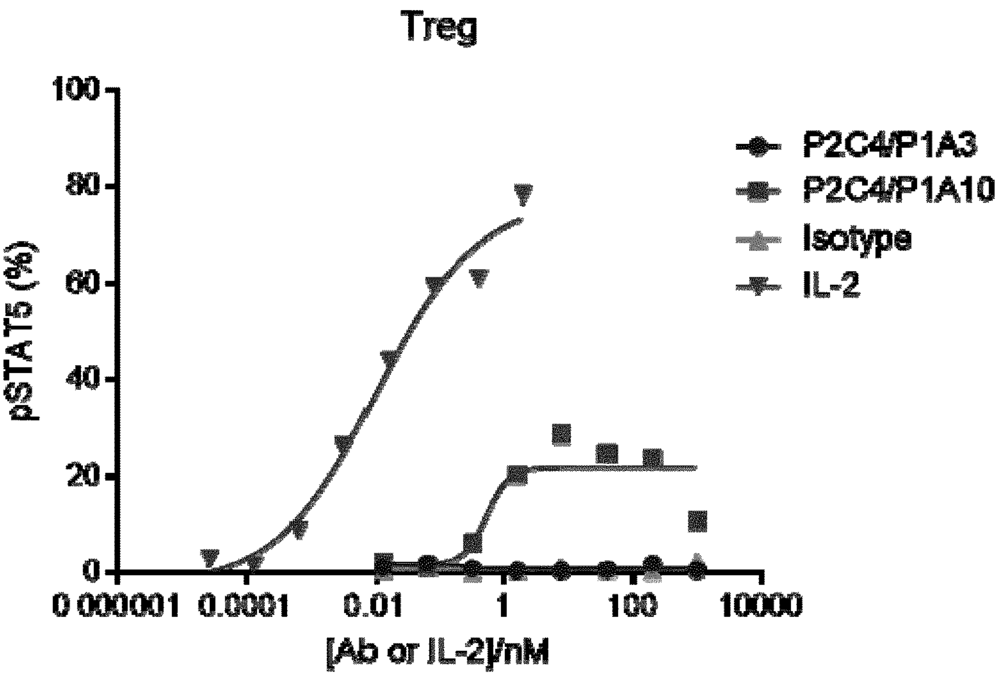
Figure 14D:
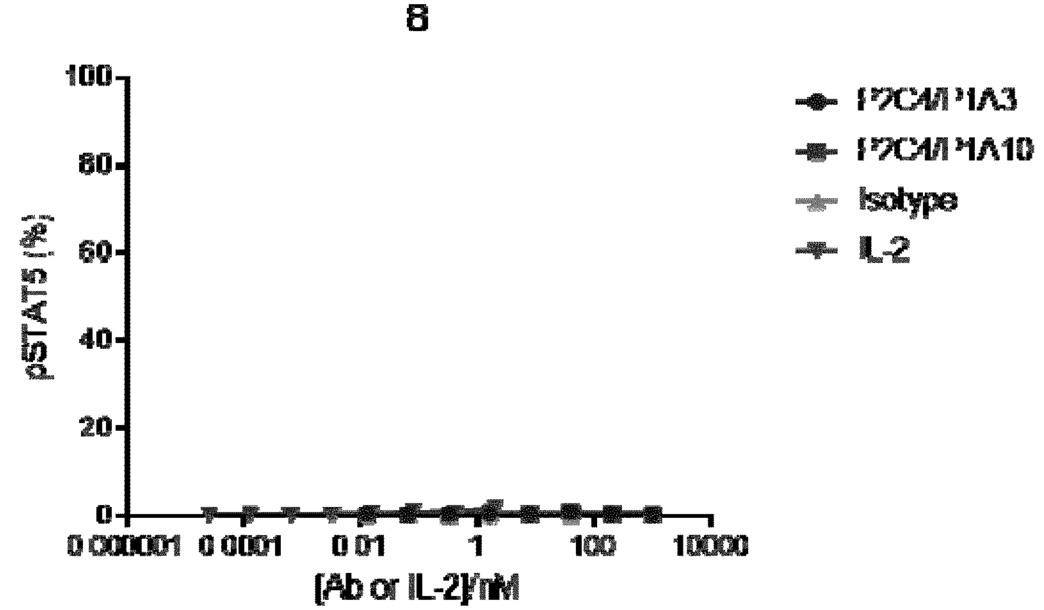
Figure 14E:
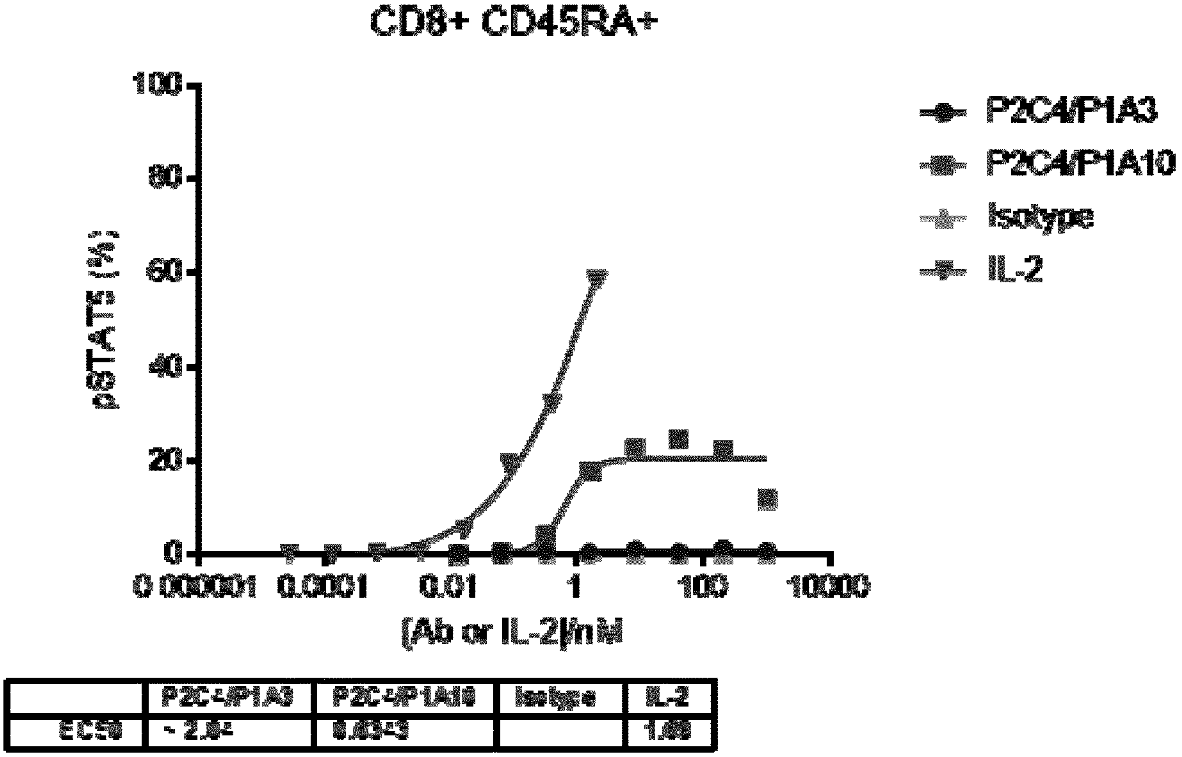
Figure 14F:
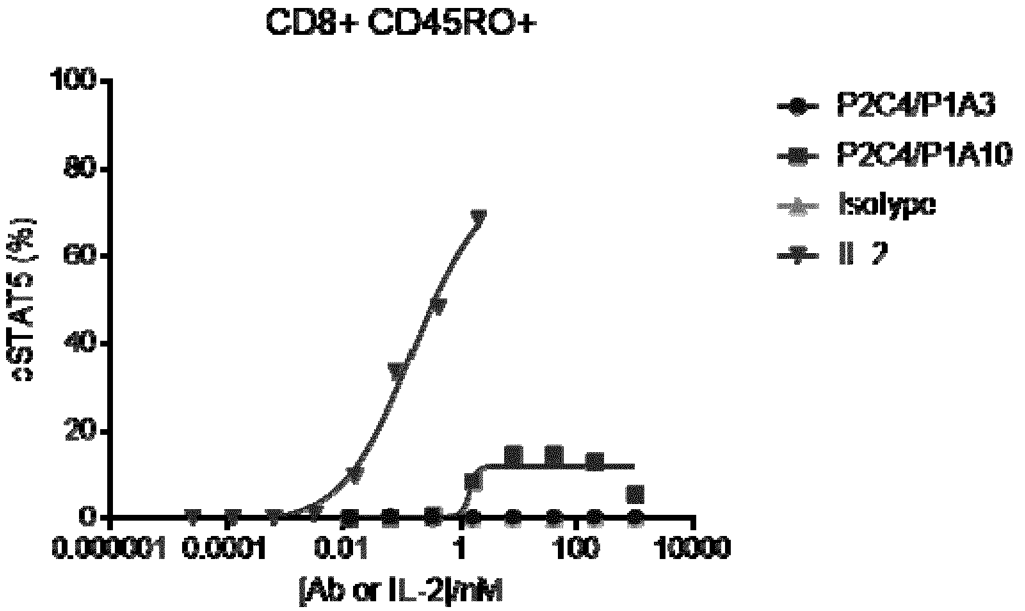
Figure 14G:
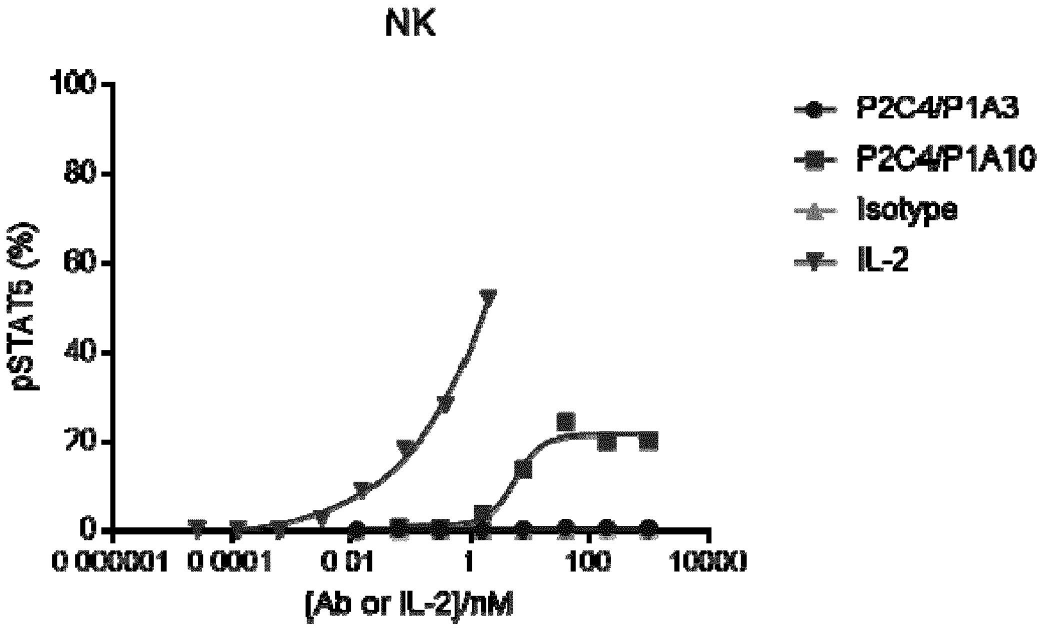
Figure 14H:
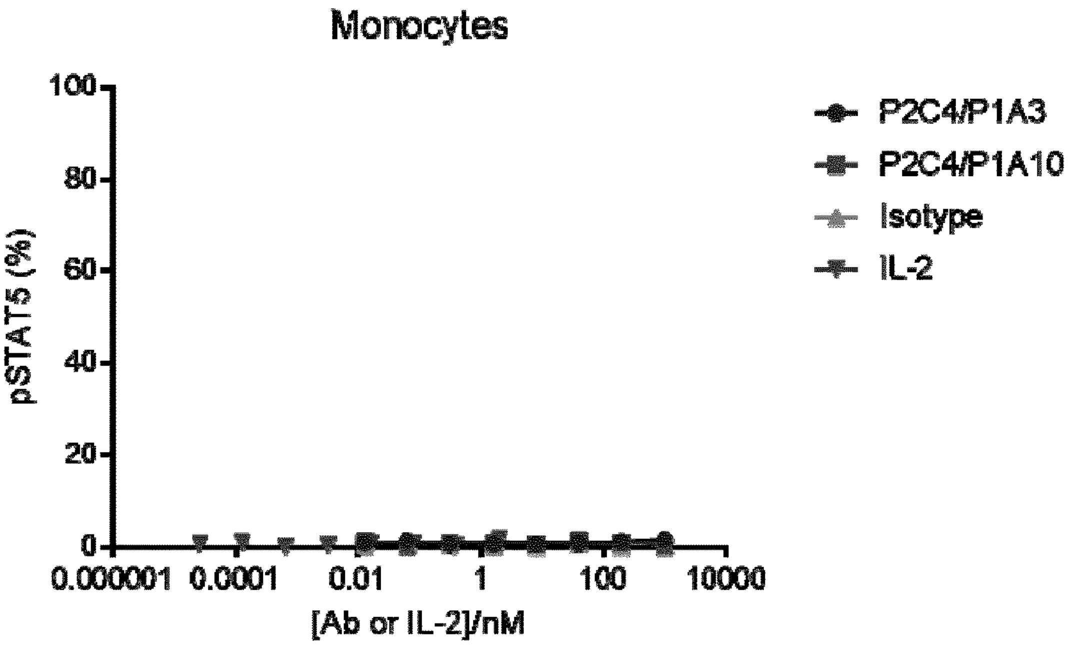

The results are shown in FIG. 13. Both F2C4/P1A3 and P2C4/F1A10 were found to stimulate phosphorylation of STAT5 in NK92 cells in a dose-dependent manner. Activation by P2C4/P1A10 achieved a higher level of STAT5 phosphorylation as compared to activation by P2C4/P1A3.

4.2 Analysis of Induction of STAT5 Phosphorylation in Primary Human Immune Cell Subsets PBMCs were thawed and rested overnight prior to being seeded at 400,000 cells per well in serum-free media. Cells were rested for two hours and subsequently stimulated with B different concentrations of P2C4/P1A3, P2C4/P1A10, isotype control antibody or IL-2. After 30 minutes, cells were analysed by flow cytometry for phosphorylation of STAT5 as well as for immune cell markers CD3, CD4, CD8, CD45 RA, CD45RO, Foxp3, CD25, CD56, CD19 and CD14 to delineate T subsets, B, NK cells and monocytes.

The results are shown in FIGS. 14A to 14H. P2C4/P1A10 induced phosphorylation of STAT5 in several T cell subsets, as well as in NK cells, in a dose-dependent manner. P2C4/P1A3 induced minimal phosphorylation of STAT5. Minimal phosphorylation of STAT5 was also observed in B cells and monocytes.

4.3 Analysis of Induction of STAT5 Phosphorylation in Pre-Activated Primary Human Immune Cell Subsets PBMCs were thawed and rested overnight before pre-activation with anti-CD3/CD28 beads for three days. Cells were then rested in fresh media for a day before seeding at 200 000 per well in serum-free media Cells were rested for two hours and subsequently stimulated with 8 different concentrations of P2C4/P1A3, P2C4/P1A10, isotype control antibody or IL-2. After 30 minutes, cells were analysed by flow cytometry for phosphorylation of STAT5 as well as for immune cell markers CD3, CD4, CD8, and CD56 to delineate T subsets and NK cells.

Figure 15A:
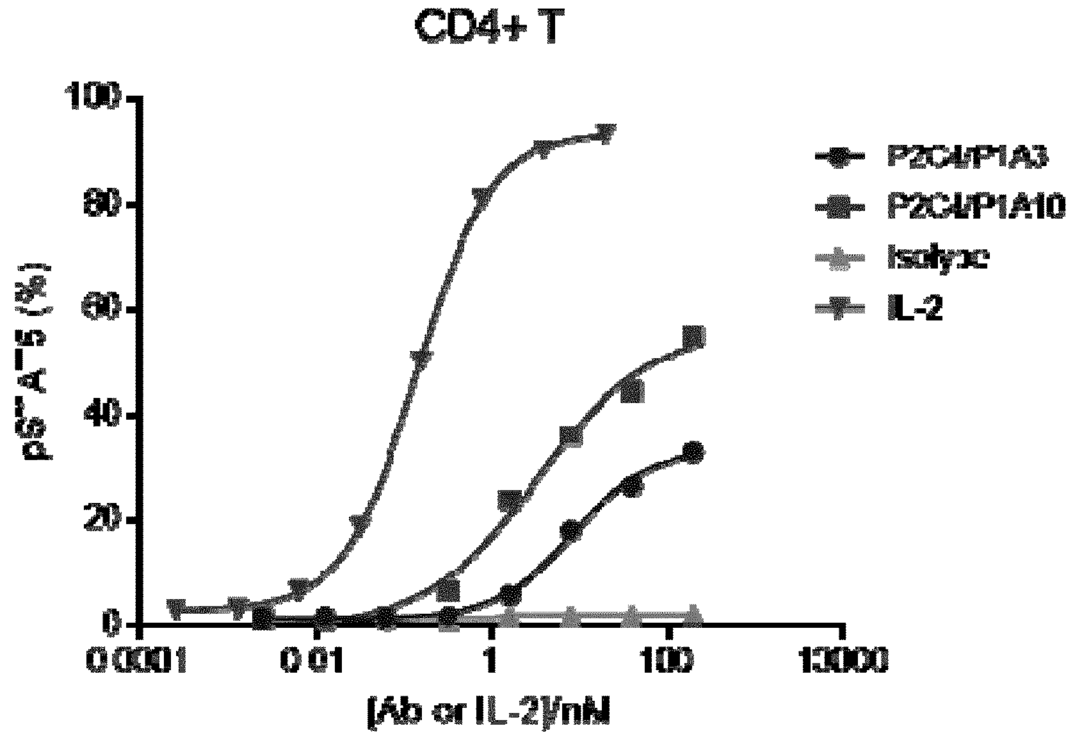
FIGS. 15A to 15C. Graphs showing analysis of induction of STAT5 phosphorylation in human immune cell subsets following treatment of pre-activated PBMCs with different amounts of bispecific IL-2Rβ- and γc-binding antibodies or IL-2. EC50 values for induction of STAT5 phosphorylation are shown. (15A) Percentage pSTAT5-positive CD4+ T cells. (15B) Percentage pSTAT5-positive CD8+ T cells. (15C) Percentage pSTAT5-positive NK cells.
Figure 15B:
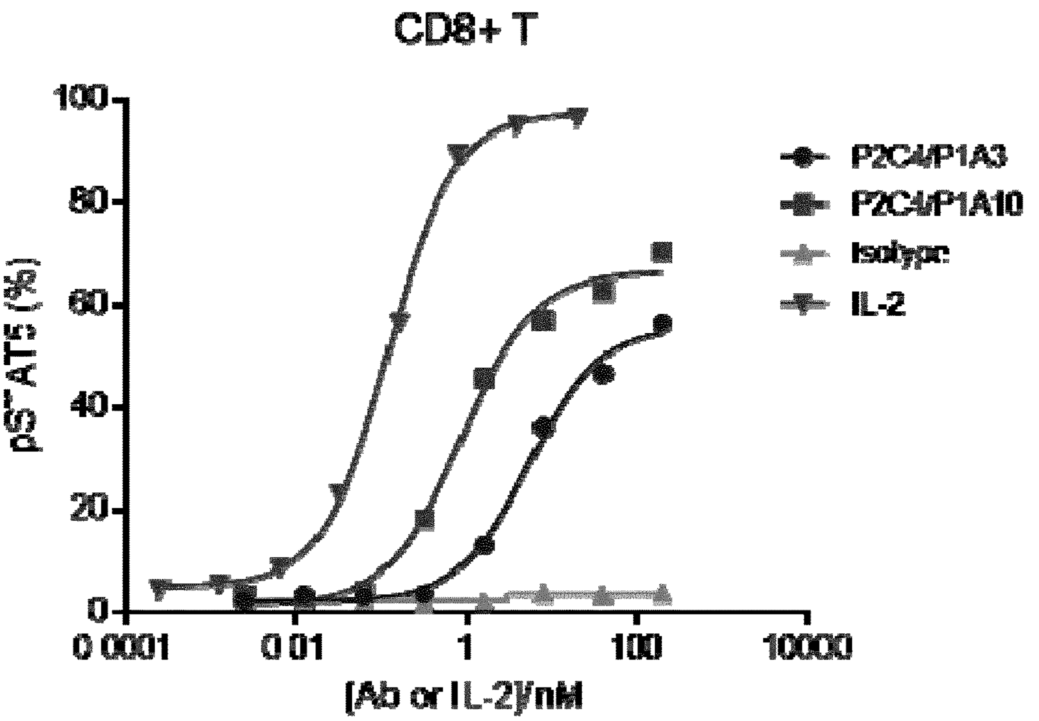
Figure 15C:
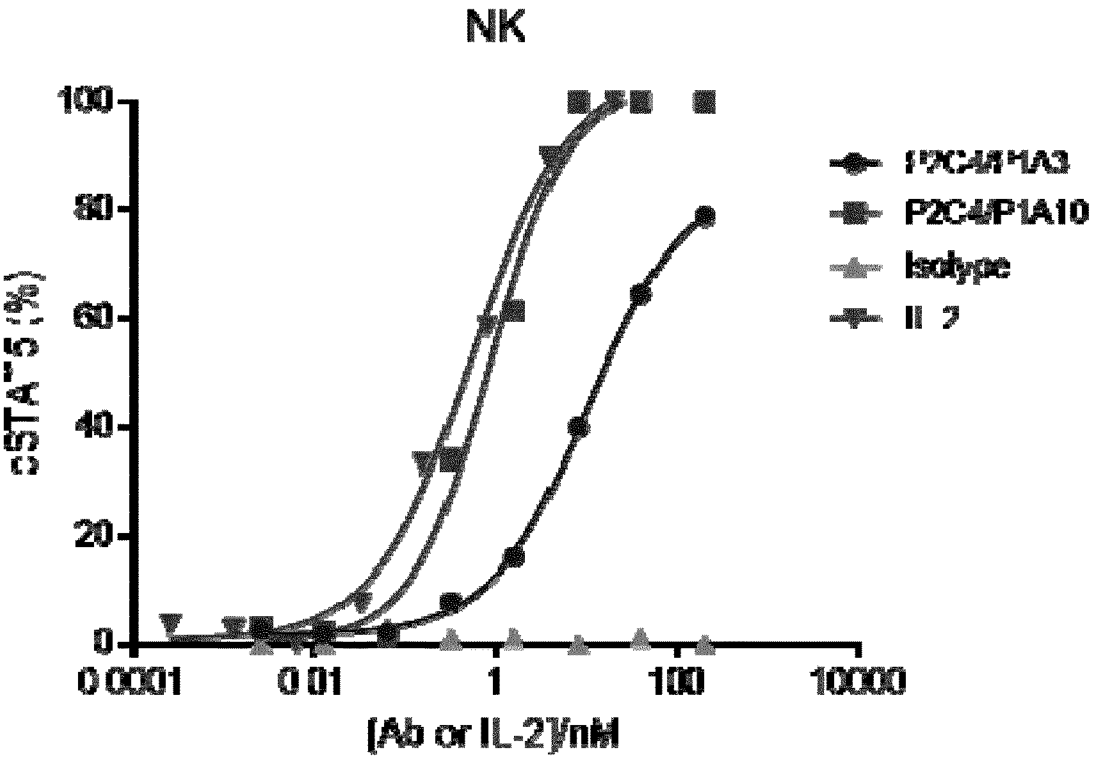

The results are shown in FIGS. 15A to 15C. Both P2C4/F1A10 and F2C4/P1A3 induced the phosphorylation of STAT5 within pre-activated CD4+, CD8+ T cell subsets and NK cells in a dose-dependent manner, and to a greater extent than within non-activated cells.

4.4 Analysis of the Kinetics of Induction of STAT5 Phosphorylation in NK Cells

NK92 cells were rested in serum-free media and treated with P2C4/P1A3, P2C4/P1A10, isotype control antibody at 100 nM or IL-2 at 20 nM for 5, 10, 20, 30, 60 and 120 min. Cells were harvested at the indicated time points for assessment of STAT5 phosphorylation (Y694) via western blotting. Total STAT5 and actin were included as controls.

Figure 16:
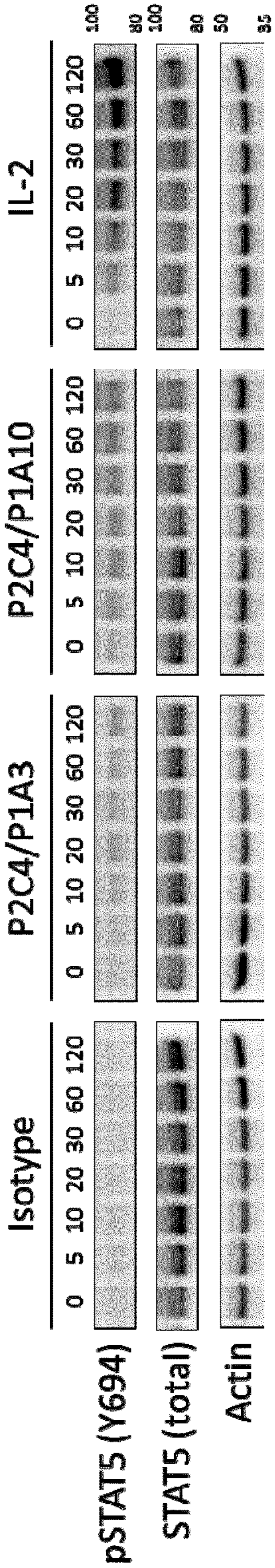
FIG. 16. Western blot showing kinetics of induction of STAT5 phosphorylation in NK92 cells following treatment with bispecific IL-2Rβ- and γc-binding antibodies or IL-2. Total STAT5 and actin were included as controls.
Figure 17A:
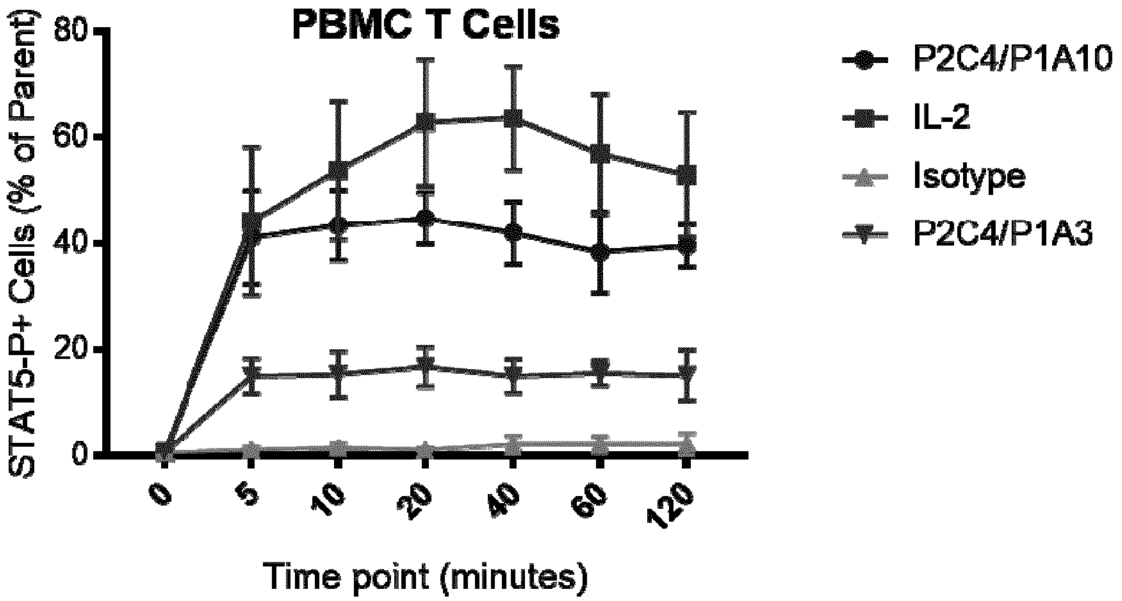
FIGS. 17A to 17E. Graphs showing kinetics of induction of STAT5 phosphorylation in human immune cell subsets following treatment of PBMCs with bispecific IL-2Rβ- and γc-binding antibodies or IL-2, (17A) Percentage pSTAT5-positive T cells. (17B) Percentage pSTAT5-positive CD8+ T cells. (17C) Percentage pSTAT5-positive CD4+ T cells. (17D) Percentage pSTAT5-positive monocytes. (17E) Percentage pSTAT5-positive B cells.
Figure 17B:
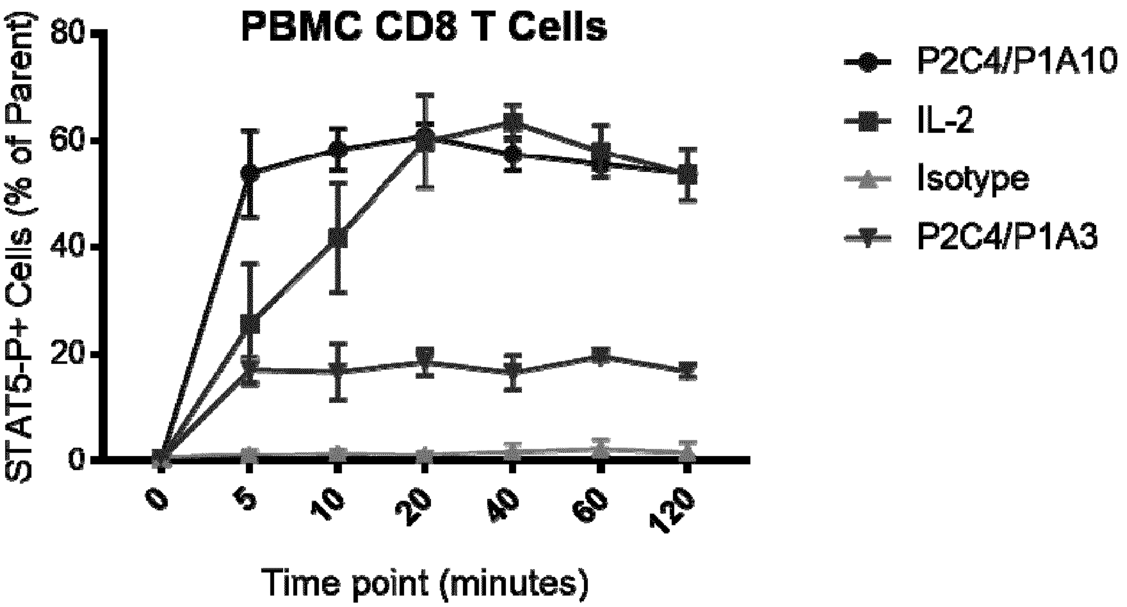
Figure 17C:
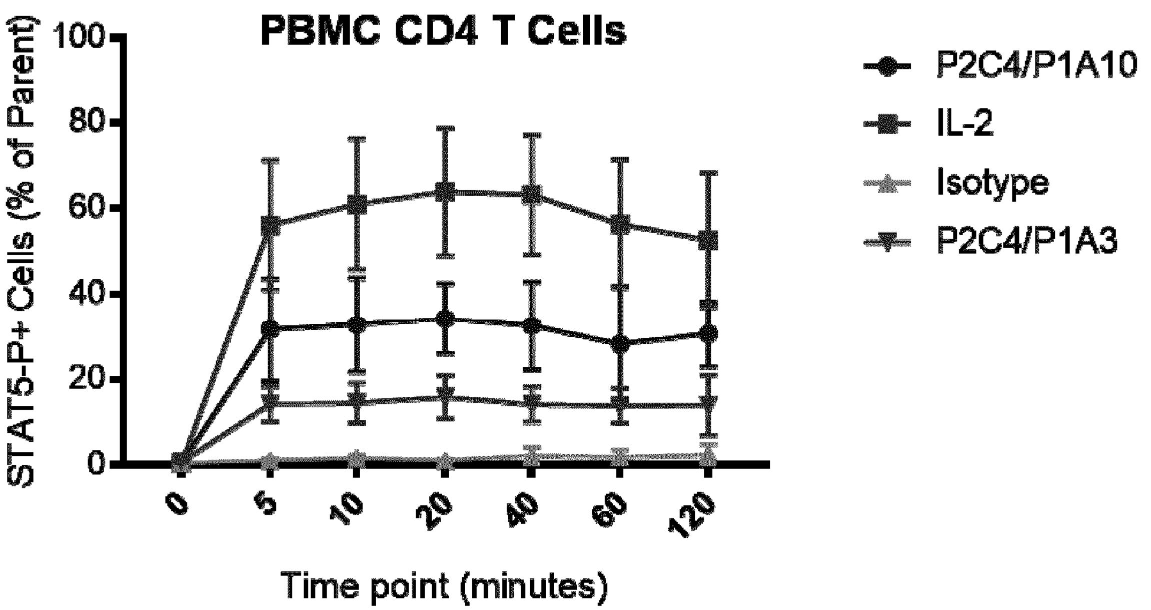
Figure 17D:
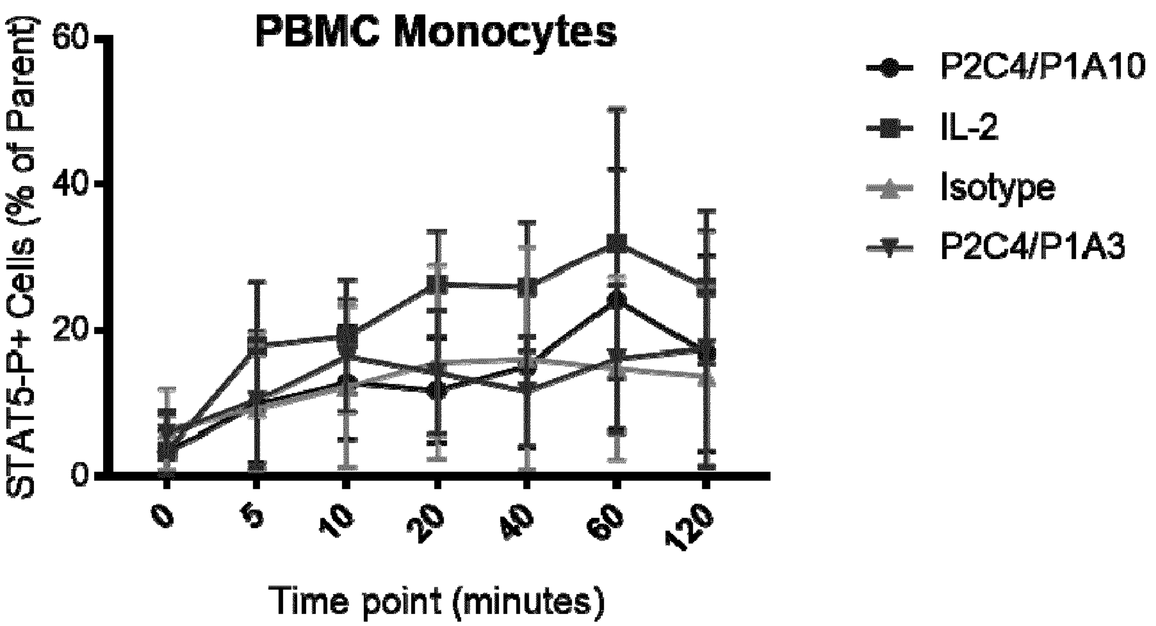
Figure 17E:
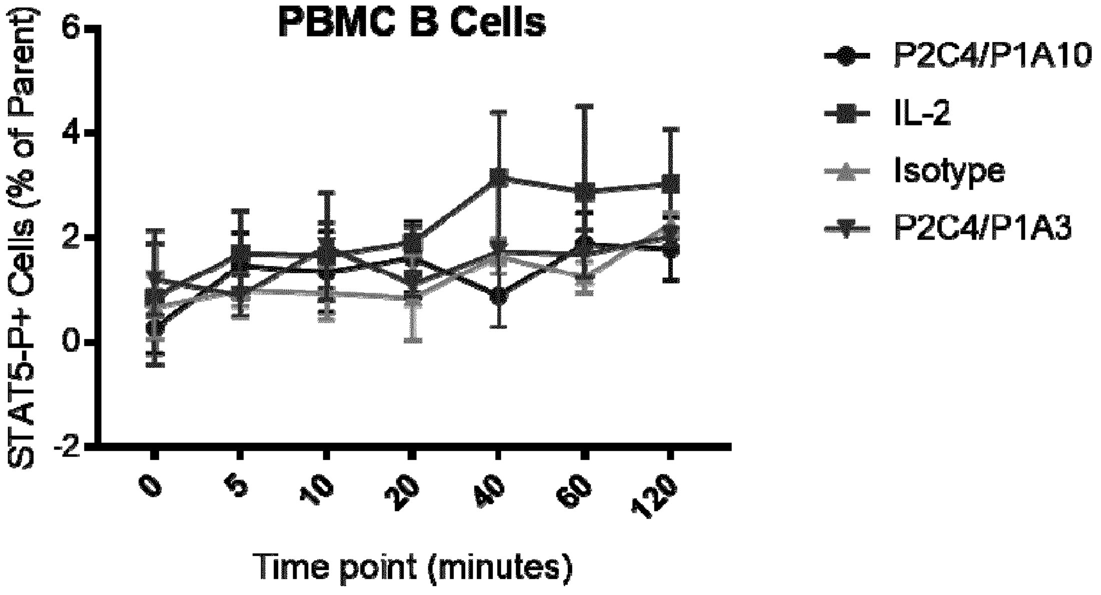

P2C4/P1A3 and P2C4/F1A10 were able to induce pSTAT5 in a time-dependent manner in comparison to isotype antibody treatment (FIG. 16).

4.5 Analysis of the Kinetics of Induction of STAT5 Phosphorylation in Primary Human Immune Cell Subsets Freshly isolated human PBMCs were stimulated with 50 nM P2C4/P1A3, P2C4/P1A10, isotype control antibody or 2 nM IL-2 in a reverse time course of 0, 5, 10, 20, 40, 60 and 120 min. Cells were then fixed, permeabilised and stained with CD3, CD4, CD8, CD14, CD19 and pSTAT5 (4694) for the identification of immune cell subsets. The data are presented as mean percentage of pSTAT5-positive cells of the PBMC subsets from 3 donors.

The results are shown in FIGS. 17A to 17E. Both P2C4/P1A3 and P2C4/P1A10 induced STAT5 phosphorylation in T cells. Maximal stimulation was achieved by both antibodies at the 5 min time point. P2C4/P1A10 also stimulated a higher percentage of pSTAT5-positive cells than P2C4/P1A3 over the time course of 2 h. Stimulation of PBMCs with P2C4/P1A3 and P2C4/P1A10 did not result in a significantly greater percentage of pSTAT5-positive monocytes and B cells as compared to the isotype control antibody.

4.6 Analysis of the Kinetics of Induction of STAT5 Phosphorylation in Antigen-Specific T Cells EBV-specific T cells were thawed and rested in fresh media, and subsequently stimulated with 50 nM P2C4/P1A3, P2C4/P1A10, isotype control antibody or 2 nM IL-2 in a reverse time course of 0, 5, 10, 20, 40, 60 and 120 min. Cells were then fixed, permeabilised and stained with CD3, CD4, CD8 and pSTAT5 (Y694) for the identification of EBV-specific T cell subsets. The data are presented as mean percentage of pSTAT5-positive cells of the virus-specific T cell subsets from 3 donors.

Figure 18A:
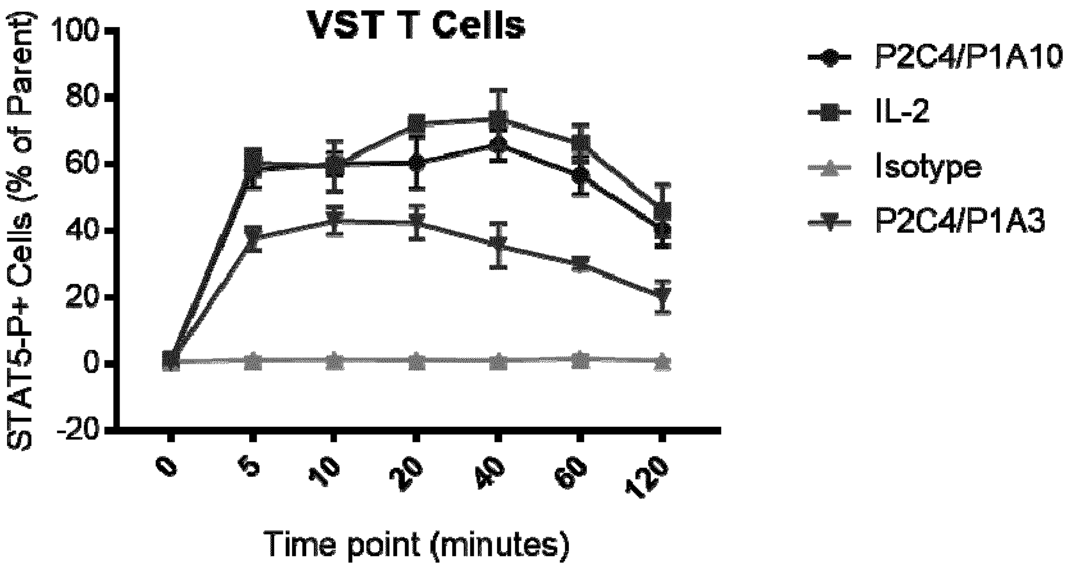
FIGS. 18A to 18C. Graphs showing kinetics of induction of STAT5 phosphorylation in antigen-specific T cells following treatment of with bispecific IL-2Rβ- and γc-binding antibodies or IL-2. (18A) Percentage pSTAT5-positive EBV-specific T cells. (18B) Percentage pSTAT5-positive CD8+ EBV-specific T cells, (18C) Percentage pSTAT5-positive CD4+ EBV-specific T cells.
Figure 18B:
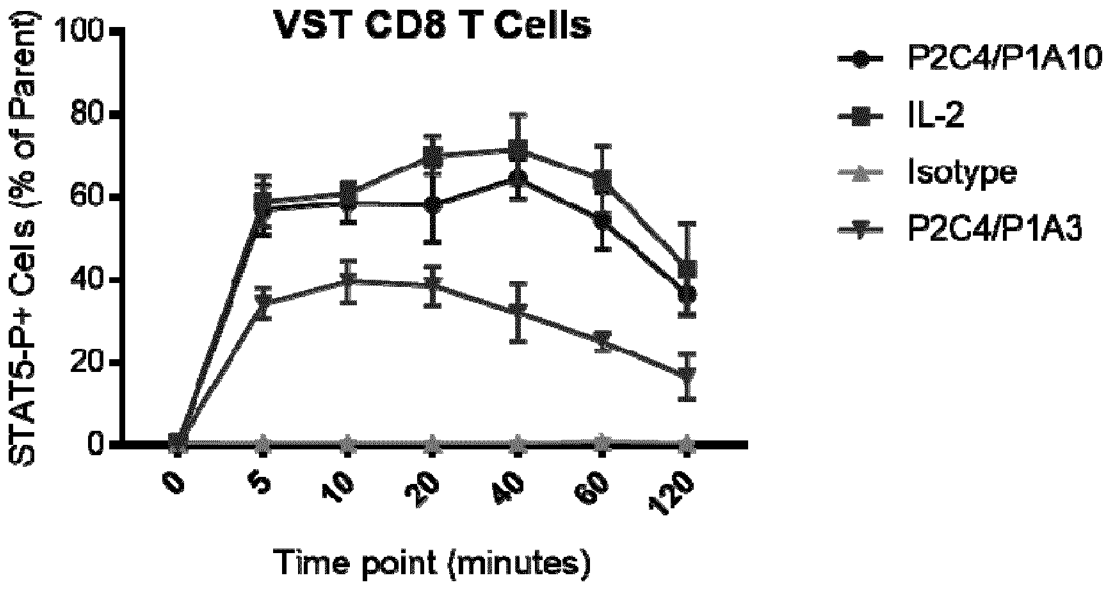
Figure 18C:
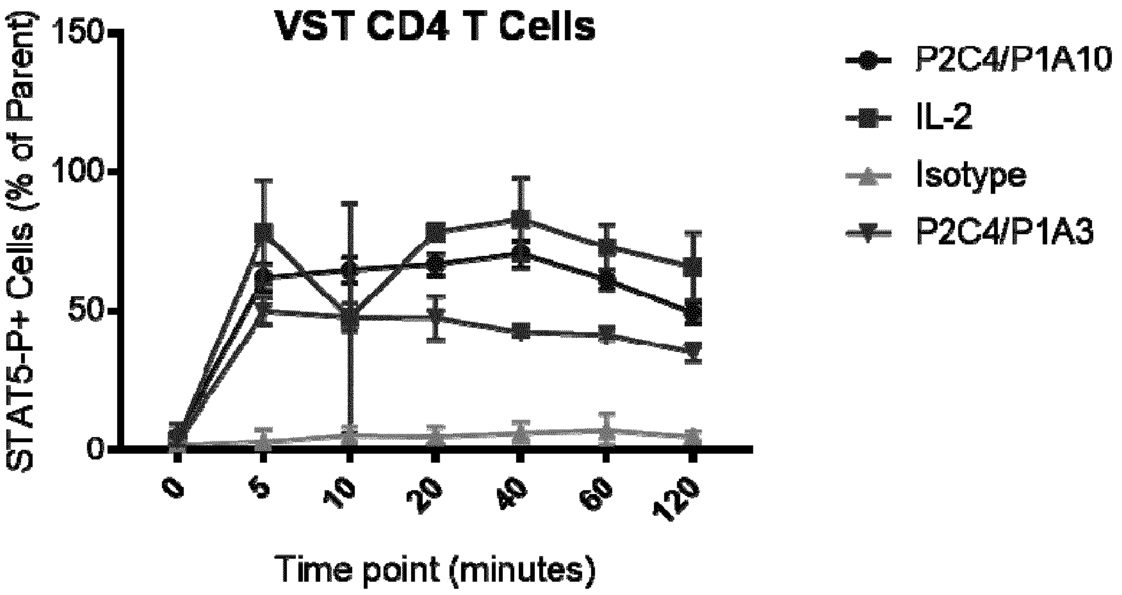

The results are shown in FIGS. 18A to 18C. Similar to the data obtained using human PBMCs (Example 4.5), both P2C4/P1A3 and P2C4/P1A10 stimulated STAT5 phosphorylation in EBV-specific T cells, and P2C4/P1A10 induced higher percentage of STAT5-positive cells than P2C4/P1A3 over the time course of 2 h.

4.7 Effects on Other Cytokine Receptors

To assess whether P2C4/P1A3 or P2C4/P1A10 binding of IL-2Ry prevents IL-4 signalling through the IL-4 receptor, THP-1 cells were treated with P2C4/P1A3, P2C4/P1A10, isotype Control antibody (100 nM) or IL-2 (20 nM), with or without IL-4 (200 ng/mL) for 30 minutes. Cell lysates were assessed by western blotting to determine phosphorylation of STAT6 (Y641). Total STAT6 and actin were included as controls.

Figure 19:
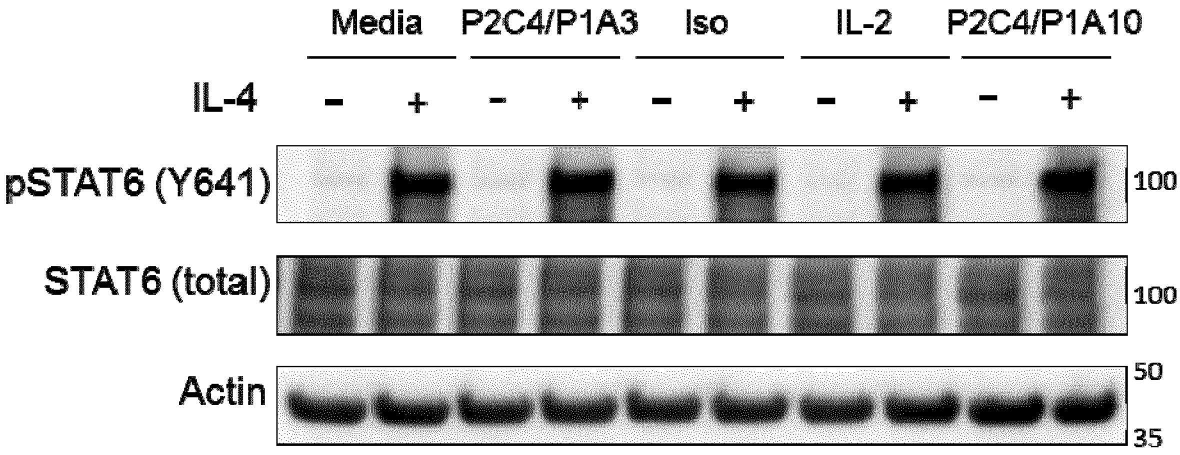
FIG. 19. Western blot showing induction of STAT6 phosphorylation by IL-4 in THP-1 cells following treatment with bispecific IL-2Rβ- and γc-binding antibodies, isotype control antibody, or IL-4. Total STAT6 and actin were included as controls.
Figure 20A:
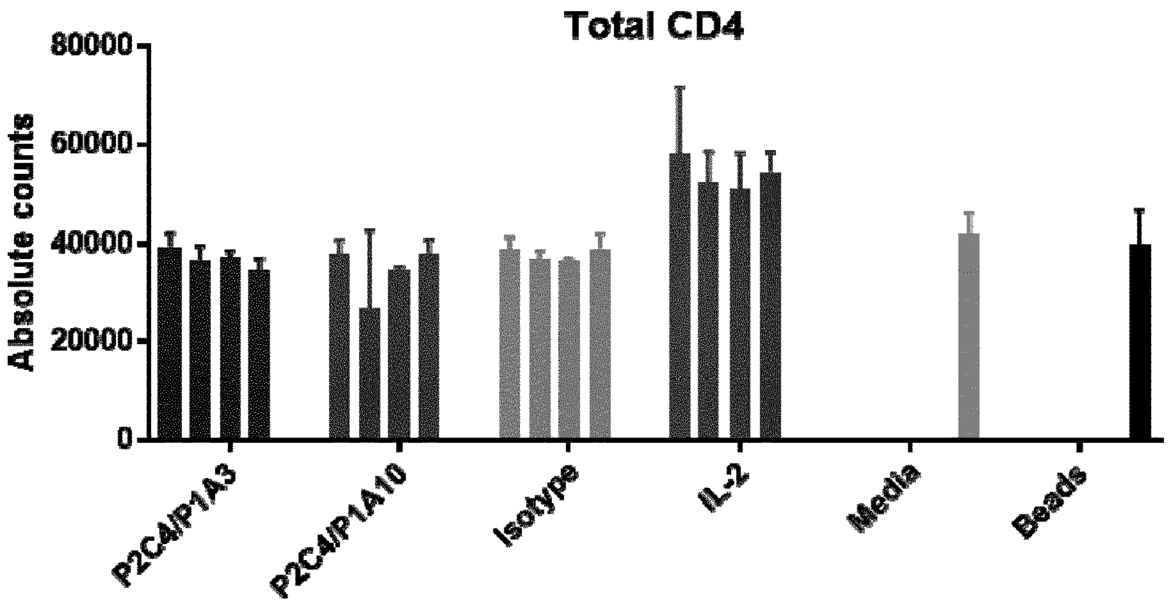
FIGS. 20A to 20K. Bar charts showing analysis of proliferation of immune cell subsets in response to treatment of freshly-obtained, non-activated human PBMCs with bispecific IL-2Rβ- and γc-binding antibodies or IL-2. Unstimulated cells (media) and anti-CD3/CD28 bead-stimulated controls (beads) are indicated. (20A) Absolute numbers of CD4+ T cells. (20B) Absolute numbers of CD8+ T cells. (20C) Absolute numbers of Tregs. (20D) Absolute numbers of NK cells. (20E) Absolute numbers of B cells. (20F) Absolute numbers of naïve CD4+ T cells. (20G) Absolute numbers of naïve CD8+ T cells. (20H) Absolute numbers of central memory CD4+ T cells. (20I) Absolute numbers of central memory CD8+ T cells. (20J) Absolute numbers of effector memory CD4+ T cells. (20K) Absolute numbers of effector memory CD8+ T cells.
Figure 20B:
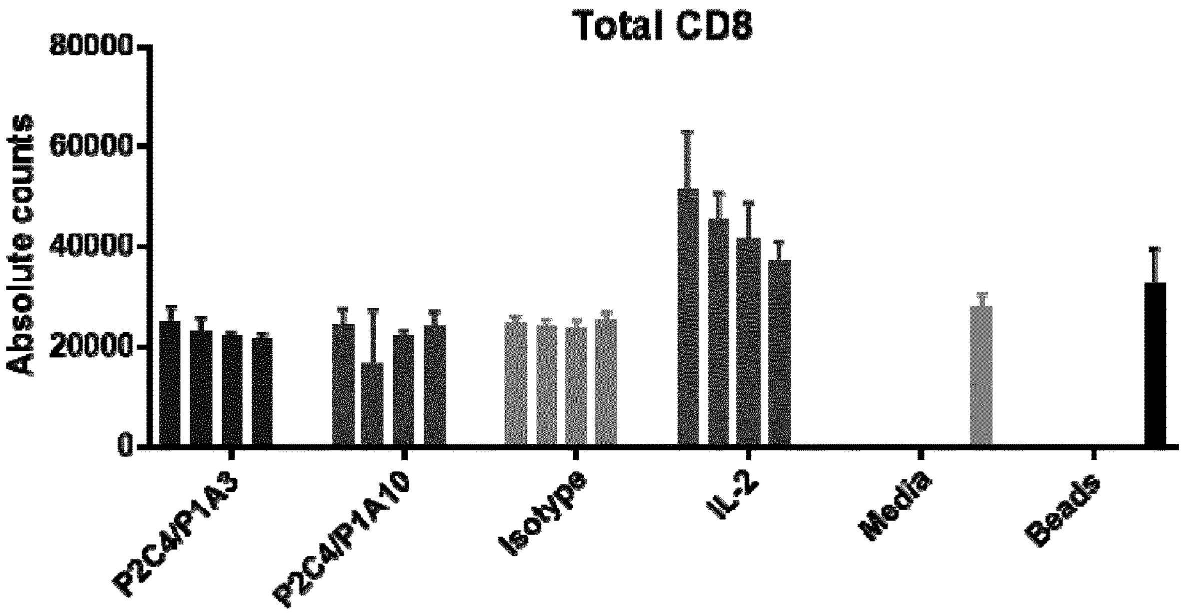
Figure 20C:
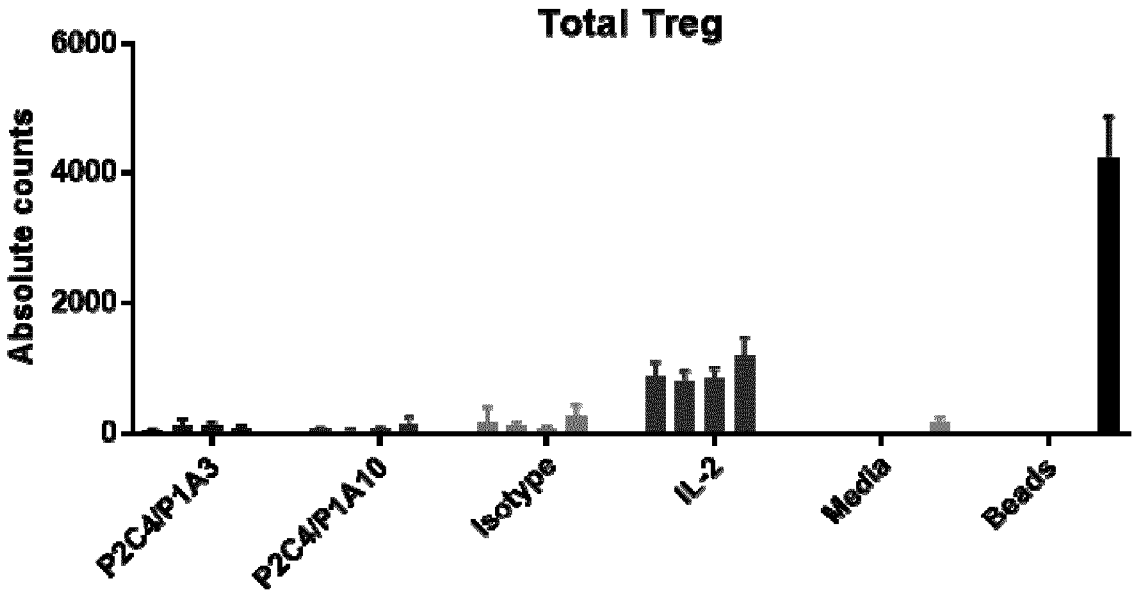
Figure 20D:
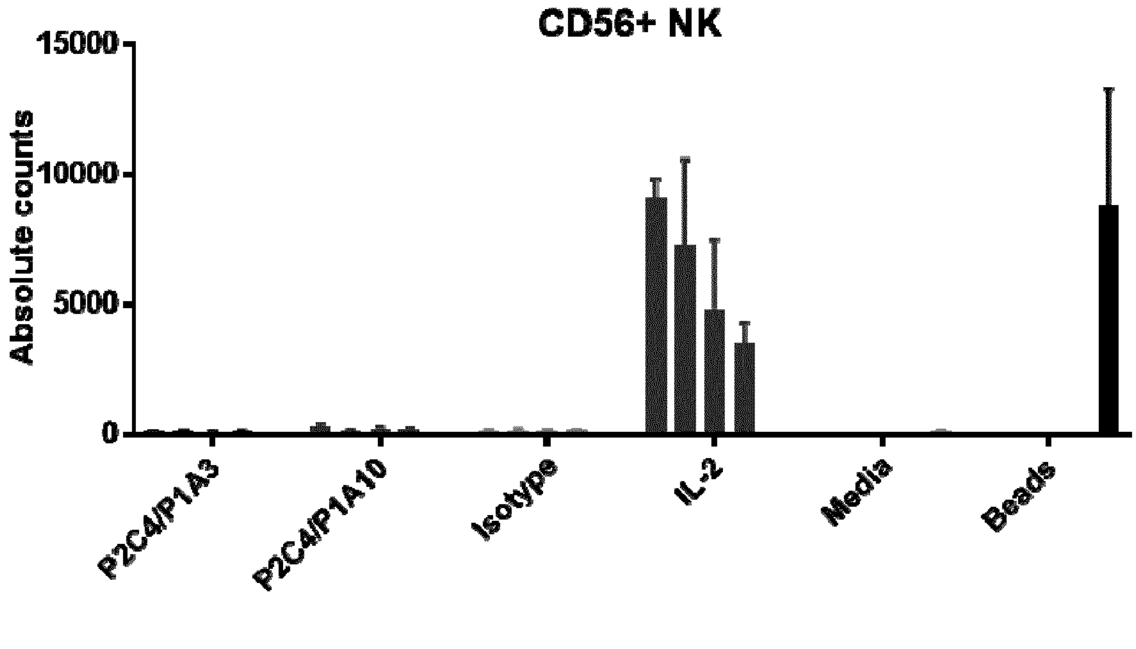
Figure 20E:
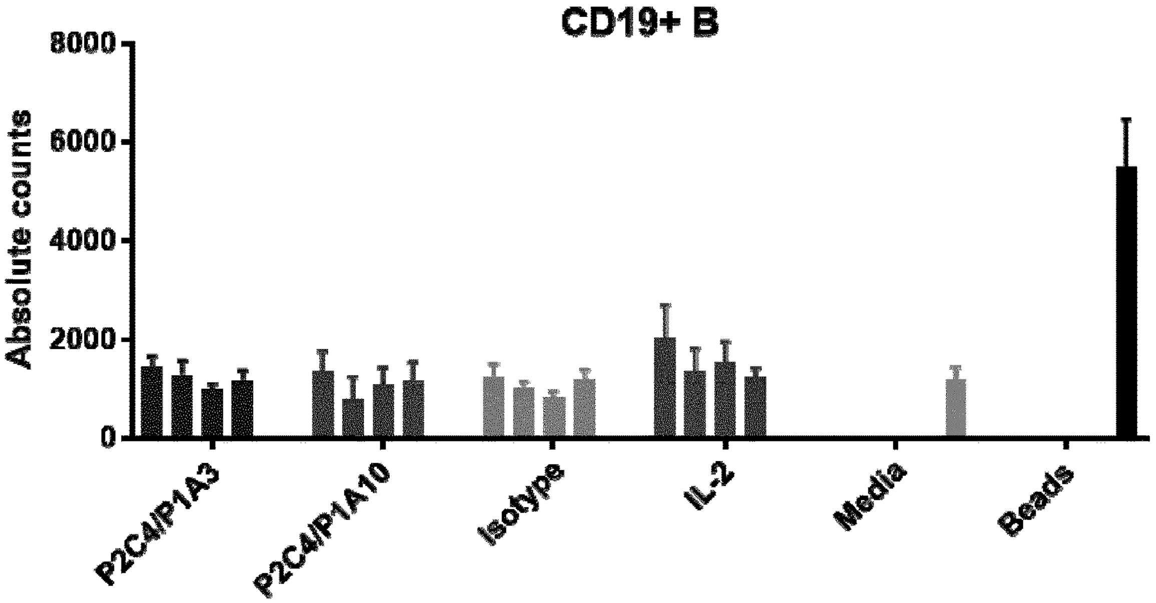
Figure 20F:
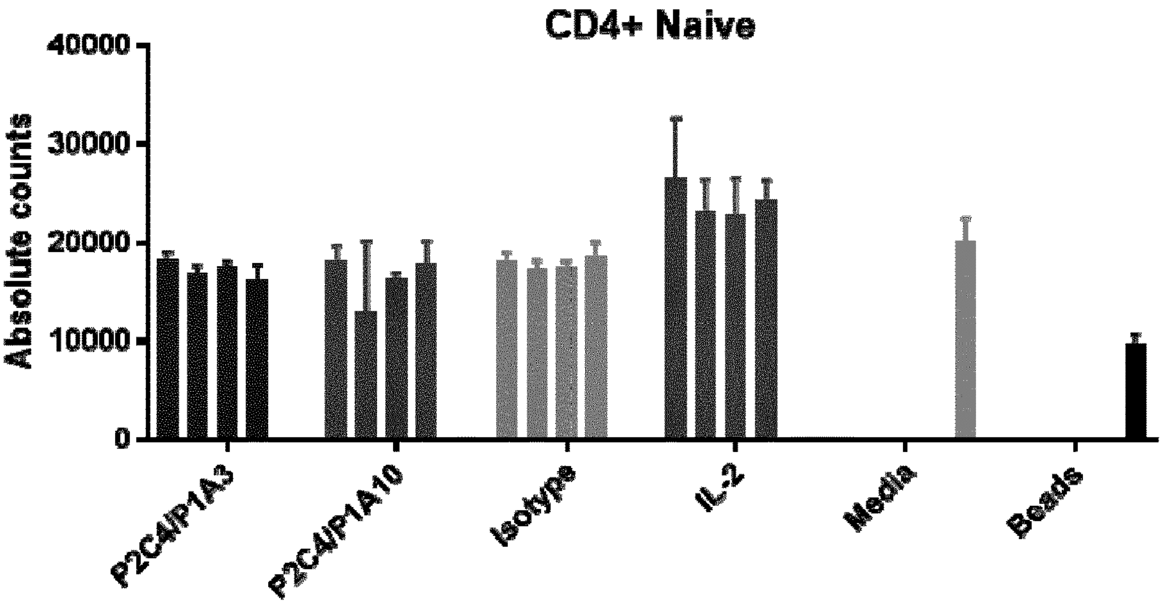
Figure 20G:
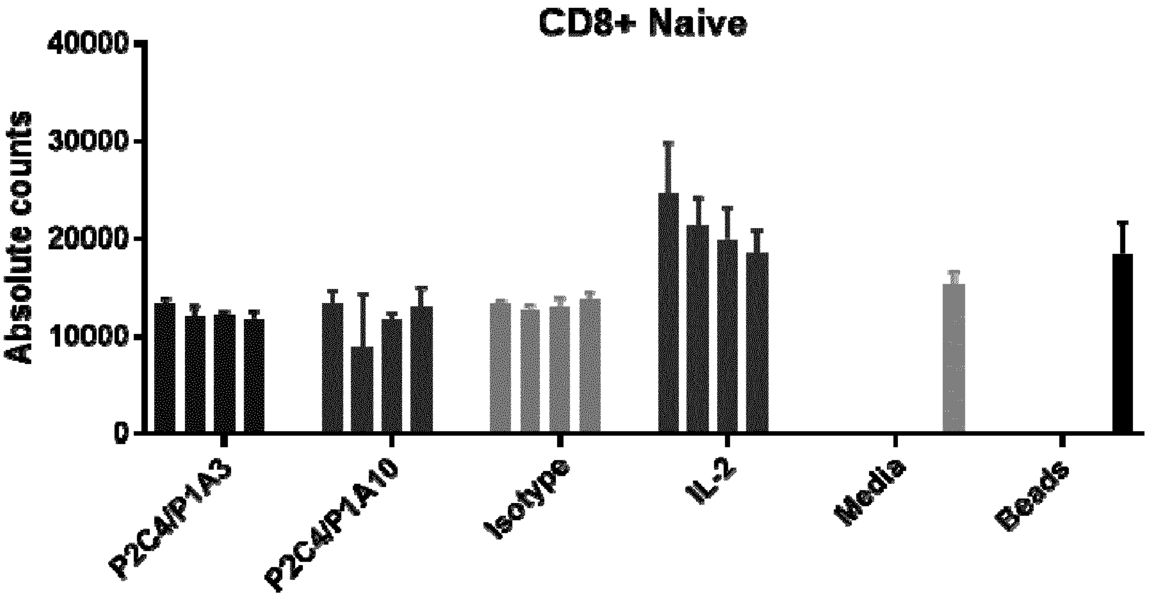
Figure 20H:
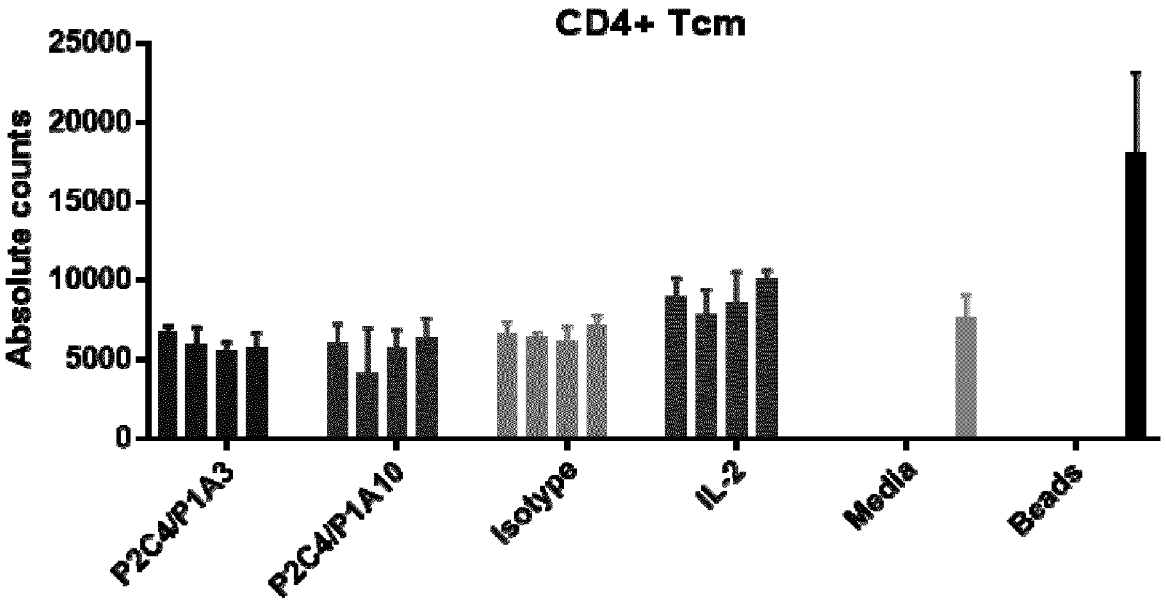
Figure 20I:
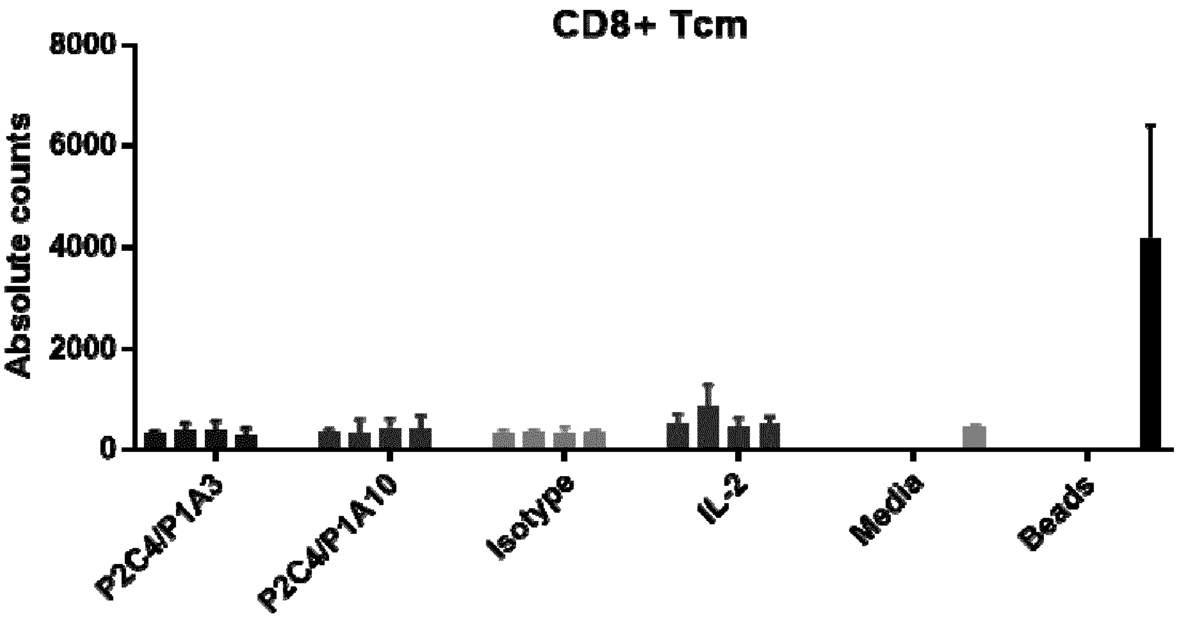
Figure 20J:
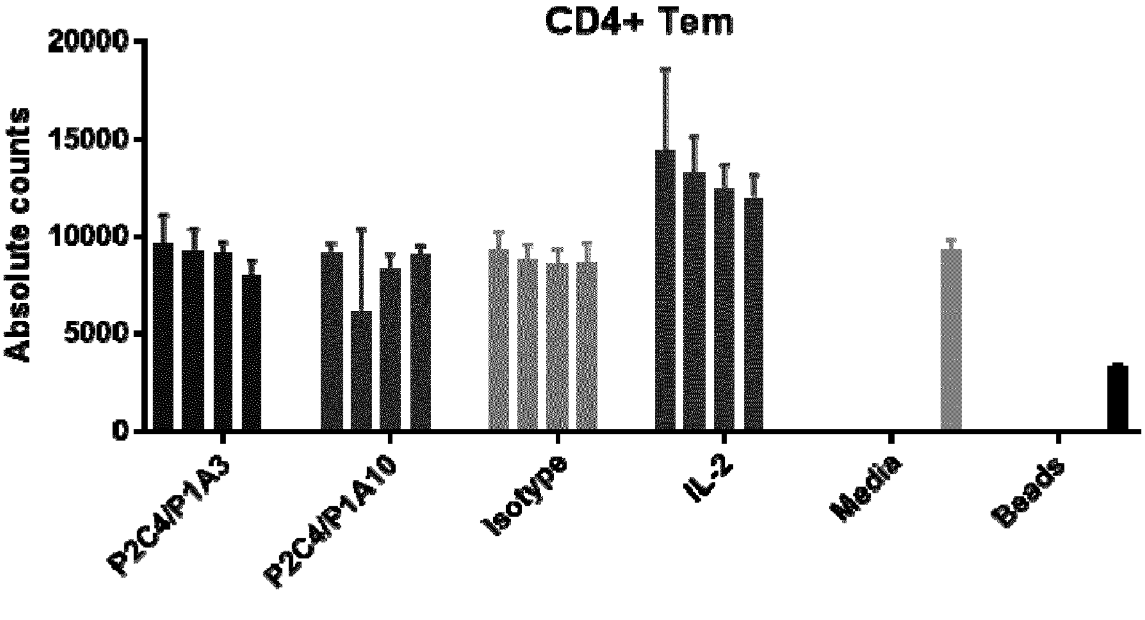
Figure 20K:
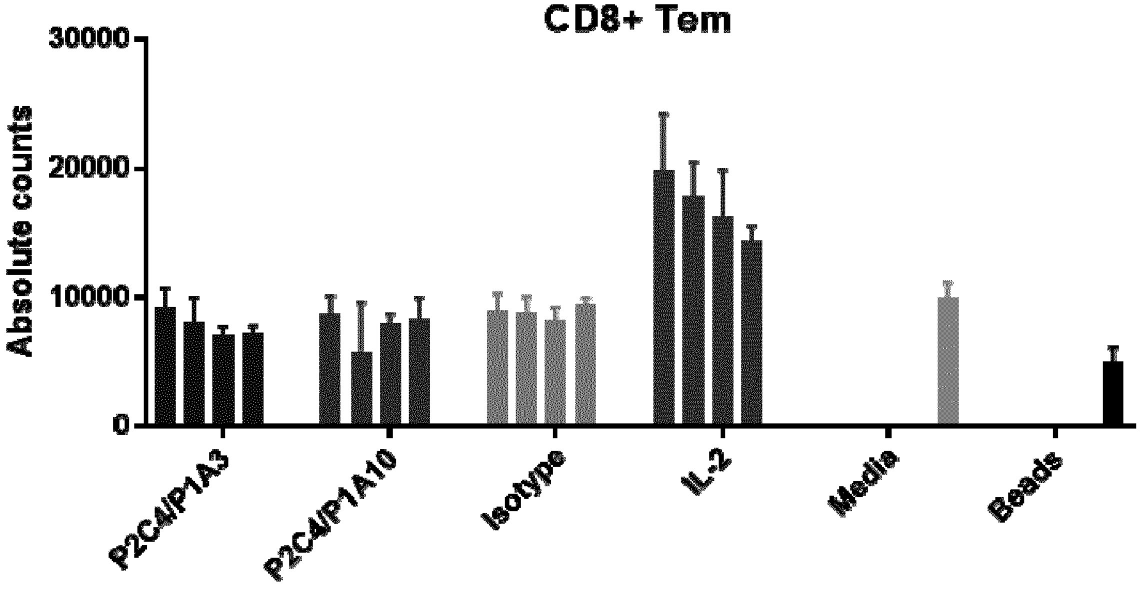

IL-4 induced pSTAT6 to a similar extent between different conditions, even in the presence of P2C4/P1A3/P2C4/P1A10 (FIG. 19). This suggests that despite binding to IL-2Rγ, P2C4/P1A3 and P2C4/P1A10 do not affect IL-4-mediated signalling.

Example 5: Analysis of Toxicity—Induction of Proliferation of Non-Activated Immune Cells 5.1 Analysis of Stimulation of Proliferation by Non-Activated PBMCs To measure the effects of P2C4/P1A3 and P2C4/P1A10 on non-activated, freshly-obtained PBMCs, PBMCs were isolated and directly treated with P2C4/P1A3, P2C4/P1A10 (200 nM, 40 nM, 8 nM and 1.6 nM), IL-2 (20 nM, 4 nM, 0.8 nM and 0.16 nM) or anti-CD3/CD28 beads as positive control. Isotype antibody and untreated control conditions were included as negative controls. After four days, cells were stained with T cell markers CD3, CD4, CD8, CD45RO, CCR7, Foxp3 and CD25 to for the delineation of T cell subsets, and with CD19 and CD56 for the identification of B cells and NK cells, respectively. Counting beads were included to enable absolute cell numbers to be determined by flow cytometry.

The results of the analysis are shown in FIGS. 20A to 20K. P2C4/P1A3 and P2C4/P1A10 did not induce significant proliferation of non-activated PBMCs as compared to isotype control antibody. This was observed for all T cell subsets including CD4, CD8, Treg, naïve, T central memory (Tcm) and T effector memory cells (Tem), as well as NK cells. This contrasts with IL-2, which stimulated expansion of T and NK cells even at lower doses. Minimal proliferation was also observed for B cells in response to treatment with IL-2.

T cell activation requires three signals (1) TCR-(CD3)/MHC interaction, (2) co-stimulation i.e. CD28 and (3) cytokine signalling i.e. IL-2. As P2C4/P1A3 and P2C4/P1A10 do not induce proliferation of T cells under direct stimulation, this indicated that signals (1) and (2) are required before T cells become responsive to the antibodies, in agreement with the results obtained with preactivated cells.

These data suggest that P2C4/P1A3 and P2C4/P1A10 preferentially expand activated T cells, and may be associated with reduced toxicity as compared to treatment with IL-2 (which expands both activated and non-activated cells).

5.2 Analysis of Stimulation of Proliferation by Non-Activated T Cells

Human T cells were isolated and directly treated with P2C4/P1A3, P2C4/P1A10, IL-2 or anti-CD3/CD28 beads. Isotype antibody and untreated control conditions were included as negative controls. After four days, cells were stained with T cell markers CD3, CD4, CD8, CD45RA, CCR7, Foxp3 and CD25 to delineate T cell subsets. Counting beads were included to enable absolute cell numbers to be determined by flow cytometry.

Figure 21A:
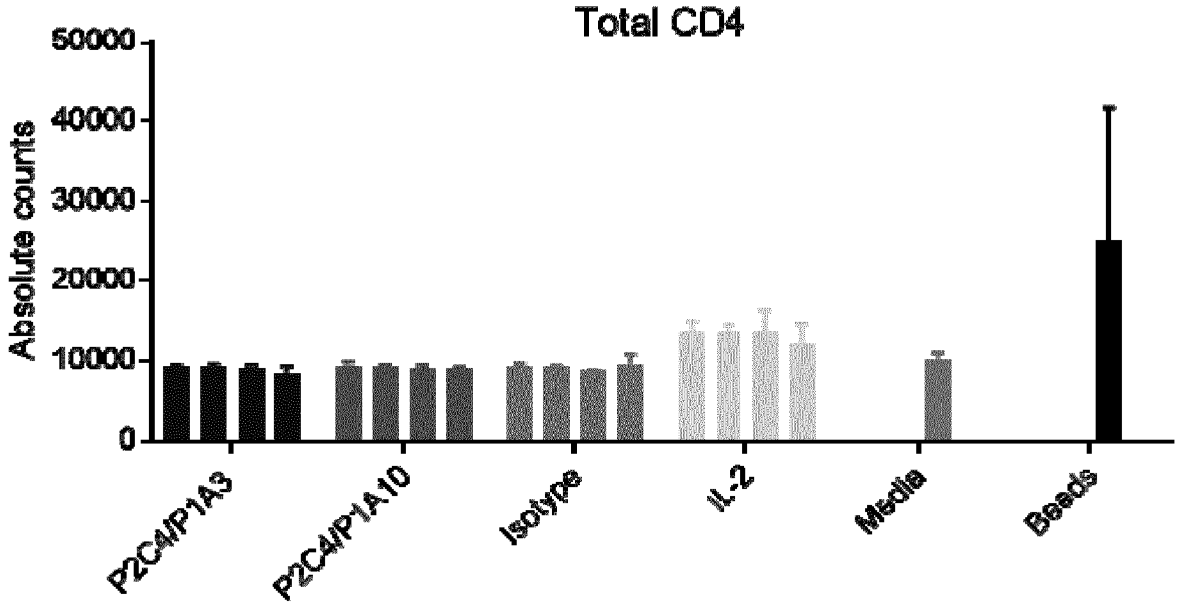
FIGS. 21A to 21C. Bar charts showing analysis of proliferation of immune cell subsets in response to treatment of non-activated human T cells with bispecific IL-2Rβ- and γc-binding antibodies or IL-2. Unstimulated cells (media) and anti-CD3/CD28 bead-stimulated controls (beads) are indicated. (21A) Absolute numbers of CD4+ T cells, (21B) Absolute numbers of CD8+ T cells. (21C) Absolute numbers of Tregs.
Figure 21B:
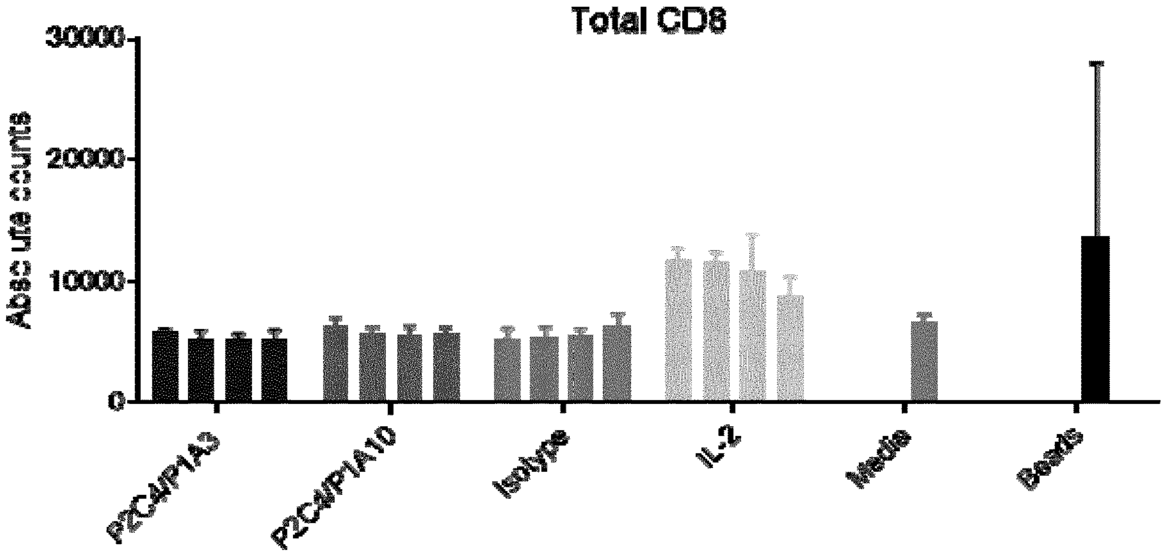
Figure 21C:
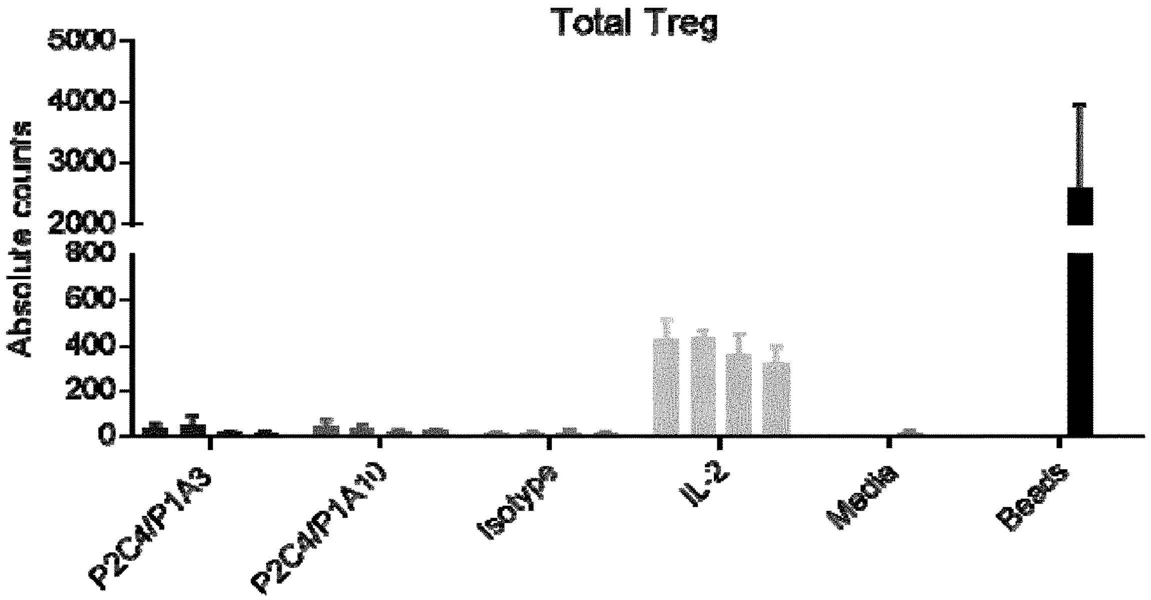

The results are shown in FIGS. 21A to 21C. Similar to the observation with direct stimulation of human PBMCs, P2C4/P1A3 and P2C4/P1A10 did not induce proliferation of T cells without pre-activation, indicating that antigen recognition/CD3 activation and co-stimulation signals are required before T cells become responsive to these antibodies. This contrasts with IL-2, which indiscriminately expanded T cells even at low doses.

Example 6: Analysis of Pharmacokinetics in Non-Human Primates

A simple pharmacokinetics (PK) study was performed to measure the clearance of P2C4/P1A3 in non-human primates, 3 cynomolgus macaques were injected with a single dose of 1 mg/kg, 5 mg/kg and 10 mg/kg P2C4/P1A3 and blood collection was done at pre-dose, 1 h, 24 h, 72 h and 120 h post-antibody injection time-points. Plasma is obtained from the collected blood and a sandwich ELISA were performed to measure the levels of P2C4/P1A3.

Sandwich ELISA was performed using waited anti-human CH2 antibody, and detection of P2C4/P1A3 was by using anti-human Fc-HRP. An ELISA standard curve was derived using purified P2C4/P1A3 for calculation of the absolute concentration of antibody in blood.

Figure 22:
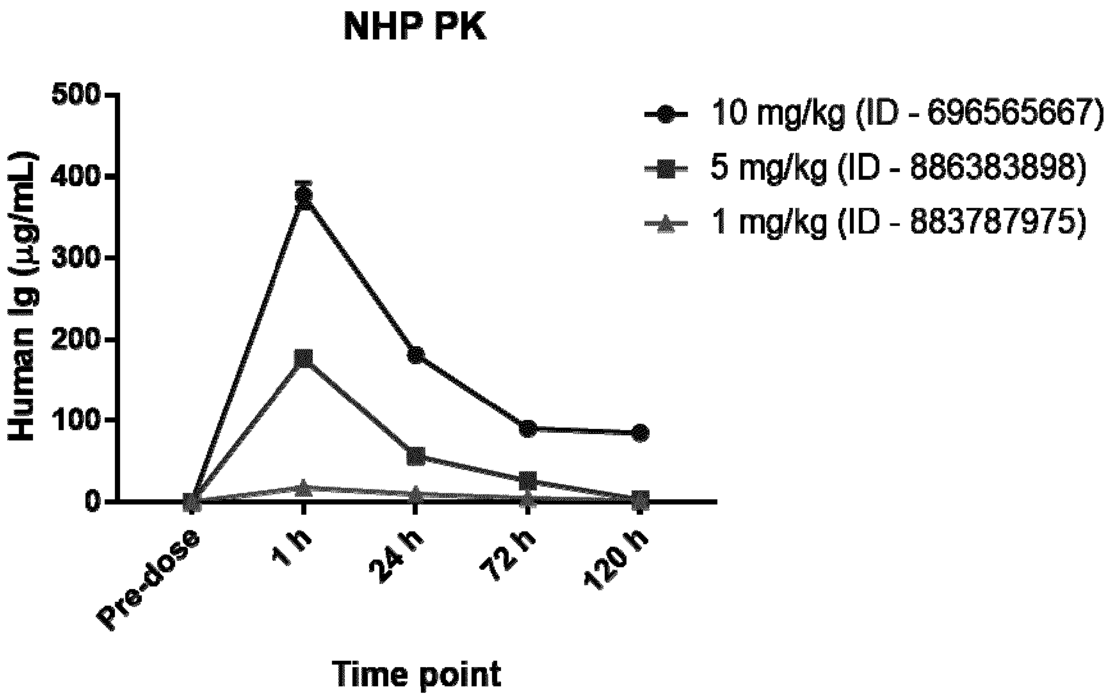
FIG. 22. Graph showing levels of bispecific IL-2Rβ/γc antibody (P2C4:P1A3) in the serum of cynomolgus macaques at the indicated time point, following administration of the indicated amount of antibody, as determined by ELISA.

The results are shown in FIG. 22. Maximum blood antibody levels were detected at 1 h post antibody dosing, and remained in the system up to 120 h.

IL-2 is known to have a much shorter serum half-life—see e.g. Skrombolas and Frelinger, Expert Rev Clin Immunol. (2014)10(2): 207-217, which reports that a study of the serum half-life of IL-2 introduced intravenously found a bi-phasic event with phase I (biodistribution throughout the body) resulting in $t_{1/2}$ of approximately 7 min and phase II (extravasation from plasma into tissue) at approximately 60 min.

Example 7: Analysis of IL-2Rβ and γc Expression on Human PBMCs and Antigen-Specific T Cells Human PBMCs were thawed and rested overnight in cell culture media. The cells were then activated using anti-CD3/CD28 beads.

After three days, cells were rested in media for a day before staining with commercially available anti-IL-2Rβ or γc antibodies plus antibodies for markers of human immune subsets. Cells were then analysed by flow cytometry to determine the expression of IL-2Rβ and γc before (−) and after (+) pre-activation. Normalized Median Fluorescence Intensity (nMFI) was calculated by subtracting MFI values for the "fluorescence-minus one" (FMO) control.

Figure 23A:
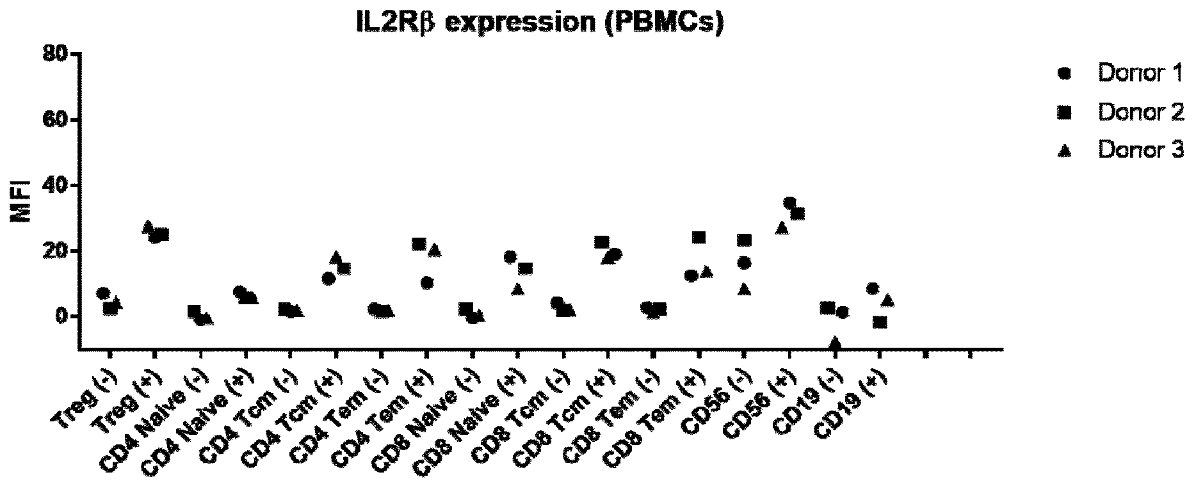
FIGS. 23A and 23B. Graphs showing expression of (23A) IL-2Rβ and (23B) γc on human immune cell subsets with or without activation using anti-CD3/CD28. The graphs show normalized median fluorescence Intensity (nMFI) of antibody staining for IL-2Rβ and γc as determined by flow cytometry.
Figure 23B:
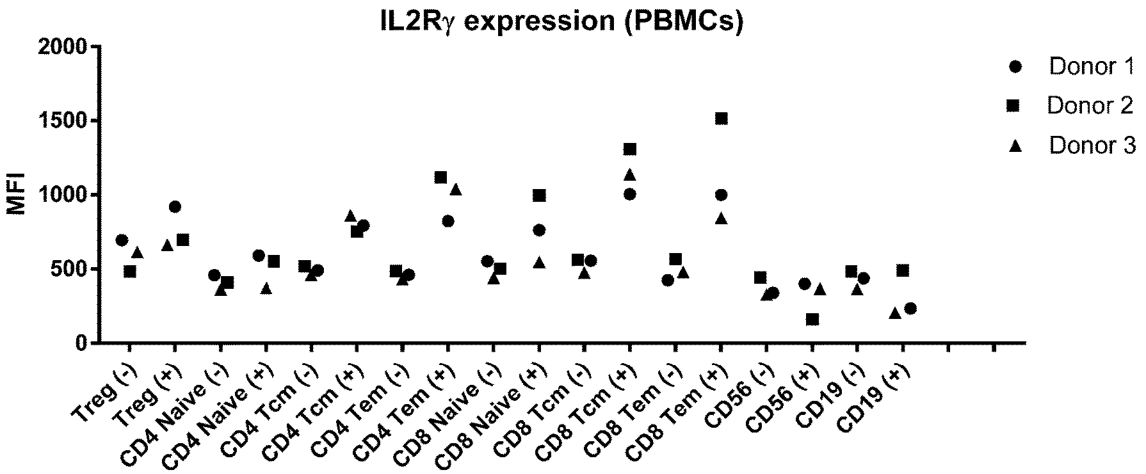

The results are shown in FIGS. 23A and 23B. Activation of human PBMCs with anti-CD3/CD28 was shown to upregulate surface expression of both IL-2Rβ and γc across three different donor samples, particularly on T cell subsets.

In a separate experiment, EBV-specific, immune cells were thawed and rested in fresh media overnight prior to being stained with commercially available anti-IL-2Rβ or γc antibodies plus antibodies for markers of human T cell subsets and NK cells. Cells were then analysed by flow cytometry to determine the expression of IL-2Rβ and γc. Normalized Median Fluorescence Intensity (nMFI) was calculated by subtracting MFI values for the "fluorescence-minus one" (FMO) control.

Figure 24A:
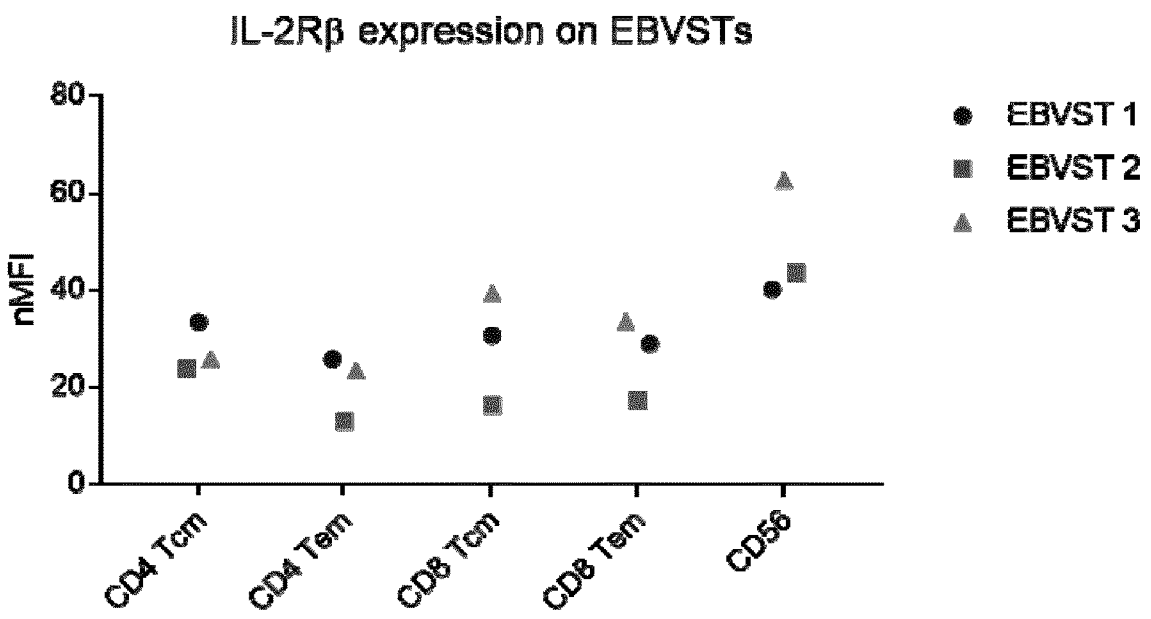
FIGS. 24A and 24B. Graphs showing expression of (24A) IL-2Rβ and (24B) γc on EBV-specific immune cell subsets. The graphs show normalized median fluorescence Intensity (nMFI) of antibody staining for IL-2Rβ and γc as determined by flow cytometry.
Figure 24B:
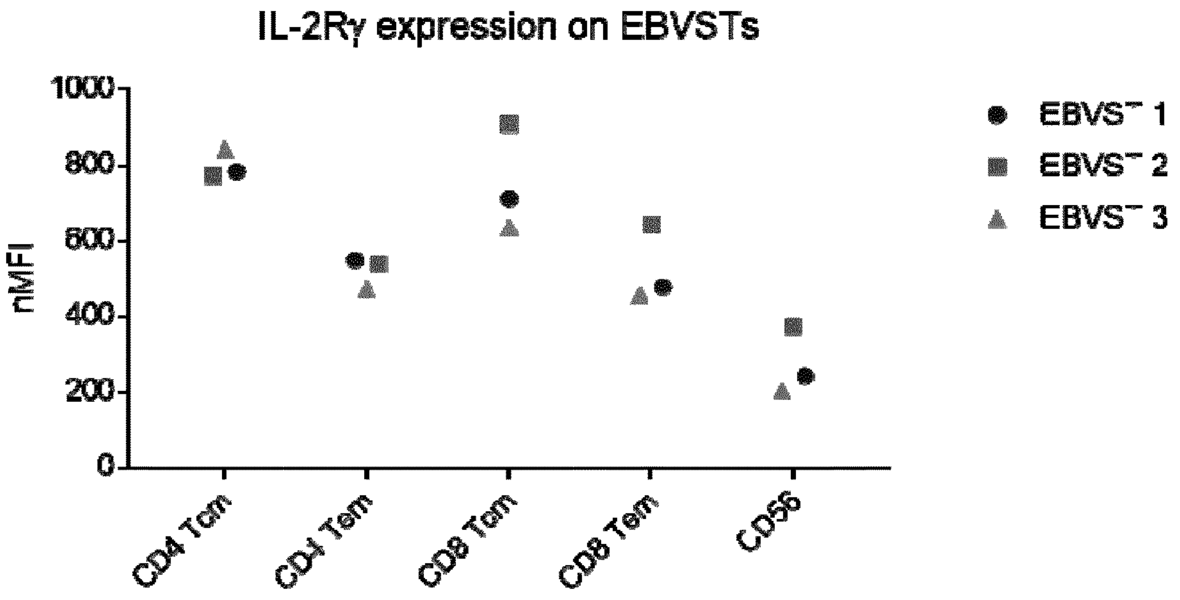

The results are shown in FIGS. 24A and 24B. Expression of IL-2Rβ and γc was detected on different immune cell subsets within the EBV-specific T cells derived from three different donors.

Example 8: Production of Anti-IL-2Rβ/γc Antibody P2C4/P1A10 in Duobody Format

P2C4/P1A10 was made in the Duobody format. Briefly, monospecific anti-IL-2Rβ P2C4 IgG1-K409R and anti-γc P1A10 IgG1-F405L antibodies were produced and purified, mixed, then subjected to reduction with 75 mM 2-MEA at pH 8.5, 31° C. for 5 h. 2-MEA was removed by dialysis, and the antibodies were left to re-oxidise at 4° C., The fully formed bispecific Duobody were purified by anion exchange chromatography.

Example 9: Analysis of the Effect of Anti-IL-2Rβ/γc Antibodies on Anti-Cancer Immune Responses Example 8.4 of WO 2017/021540 A1 reports the ability of CD8+ T cells expanded by treatment with bispecific agonist anti-IL-2Rβ and -γc antibodies to kill cancer cells. Specifically, T cells expanded from PBMCs obtained from EBV seropositive donors by culture in presence of P2C4:P1A3 are shown to kill LCLs.

Example 12 and FIGS. 41 and 42 of WO 2017/021540 A1 demonstrate the ability of bispecific agonist anti-IL-2Rβ and -γc antibodies to stimulate proliferation of T cells and NK cells in vivo in cynomolgus macaques.

In the present Example, bispecific agonist anti-IL-2Rβ and -γc antibodies are shown to promote an anti-cancer immune response in vivo.

Tumours are established by subcutaneous injection of mice with LCLs. Specifically, EBV-transformed lymphoblastoid B-cell line (LCLs) was mixed with Matrigel and injected subcutaneously to the right flank of NSG mice.

Figure 25:
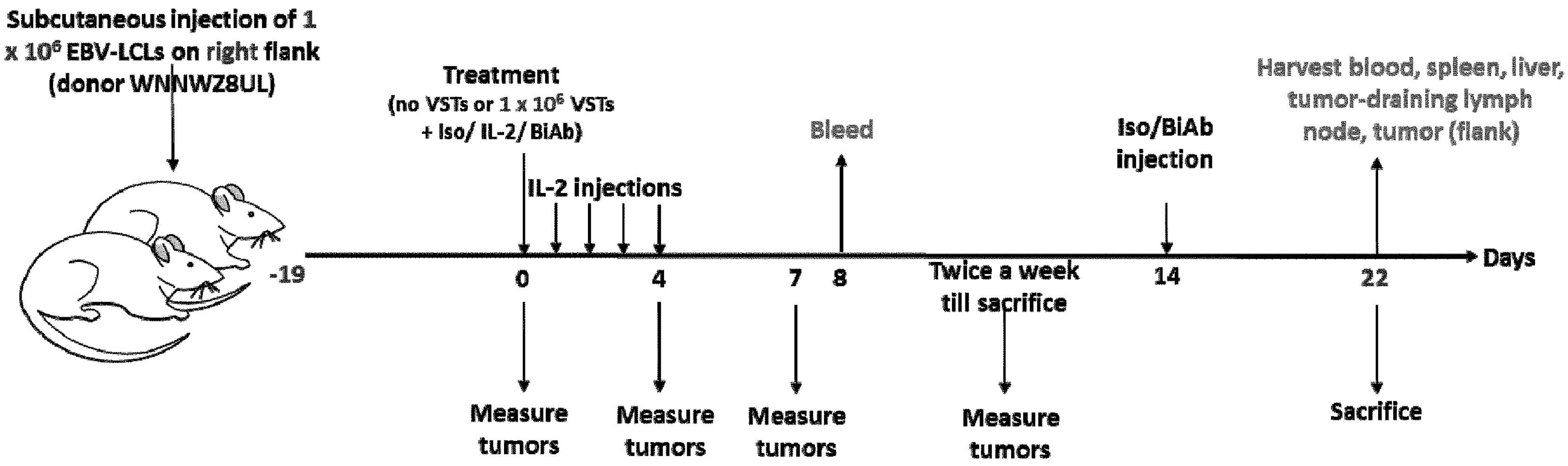
FIG. 25. Schedule of administration of VSTs with or without bispecific IL-2Rβ- and γc-binding antibodies (BiAb), isotype control antibody or IL-2 to murine EBV-LCL tumour model.

Mice were subsequently administered with autologous EBV-specific CTLs (VSTs), with or without P2C4/P1A3, P2C4/P1A10, isotype control antibody, or IL-2, at 19 days post-tumour inoculation. IL-2 treatments were given at 40 000 U/kg, intra-peritoneally (i.p.) consecutively for 5 days for a total of 5 doses. Antibody treatments were given at 5 mg/kg, i.p. every 14 days, for a total of 2 doses. The administration schedule is shown in FIG. 25.

Figure 26A:
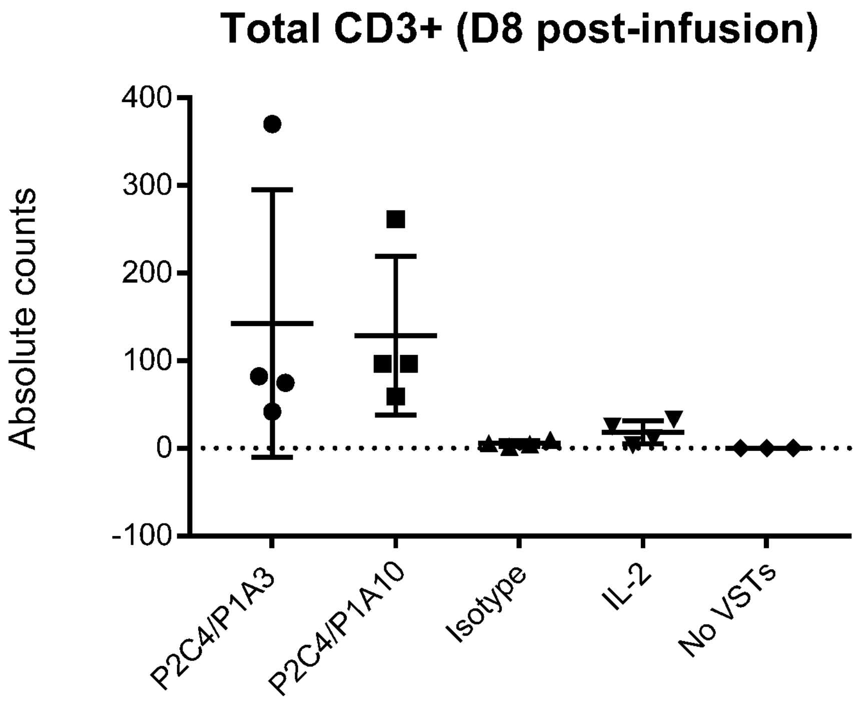
FIGS. 26A to 26I. Graphs showing analysis of proliferation of T cell subsets and PD-1 expression in an in vivo murine EBV-LCL tumour model following treatment with VSTs and bispecific IL-2Rβ- and γc-binding antibodies, isotype control antibody, or IL-2. (26A) Absolute numbers of CD3+ T cells at 8 days post-VST treatment. (26B) Absolute numbers of CD3+CD4+ T cells at 8 days post-VST treatment. (26C) Absolute numbers of CD3+CD8+ T cells at 8 days post-VST treatment. (26D) Absolute numbers of CD3+, CD3+CD4+ and CD3+CD8+ T cells, and CD3 T cell PD-1 expression analysed by MFI, from blood at 22 days post-VST treatment. (26E) Absolute numbers of CD3+, CD3+CD4+ and CD3+CD8+ T cells, and CD3 T cell PD-1 expression analysed by MFI, from the spleen at 22 days post-VST treatment. (26F) Absolute numbers of CD3+, CD3+CD4+ and CD3+CD8+ T cells, and CD3 T cell PD-1 expression analysed by MFI, from the liver at 22 days post-VST treatment. (26G) Absolute numbers of CD3+, CD3+CD4+ and CD3+CD8+ T cells, and CD3 T cell PD-1 expression analysed by MFI, from tumour-draining lymph nodes at 22 days post-VST treatment. (26H) Absolute numbers of CD3+, CD3+CD4+ and CD3+CD8+ T cells, and CD3 T cell PD-1 expression analysed by MFI, from tumour at 22 days post-VST treatment. (26I) Total organ tumour load shown by the absolute total number of CD19+ cells in spleen, liver, tumour-draining lymph node and tumour.
Figure 26B:
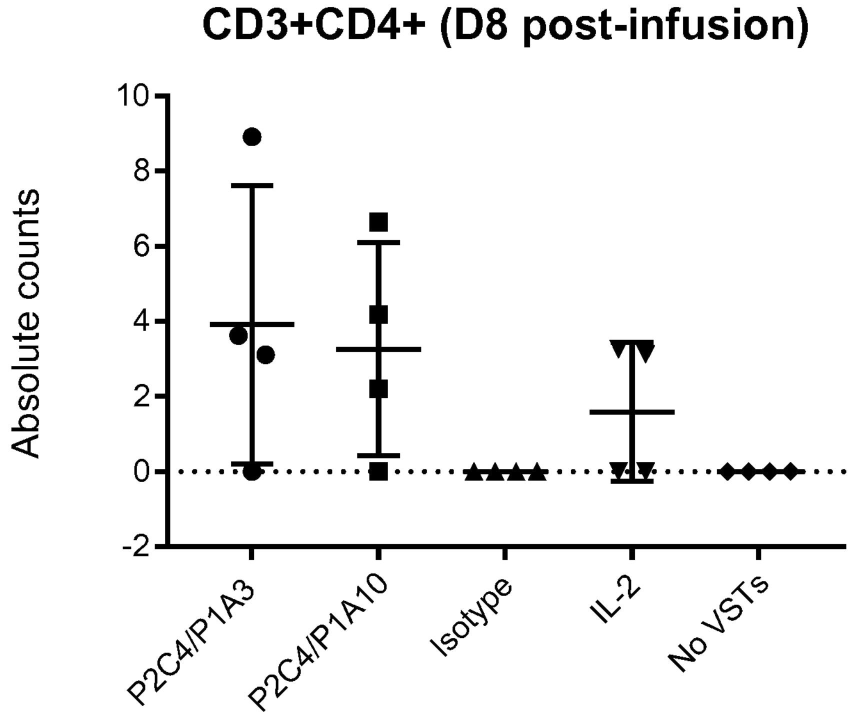
Figure 26C:
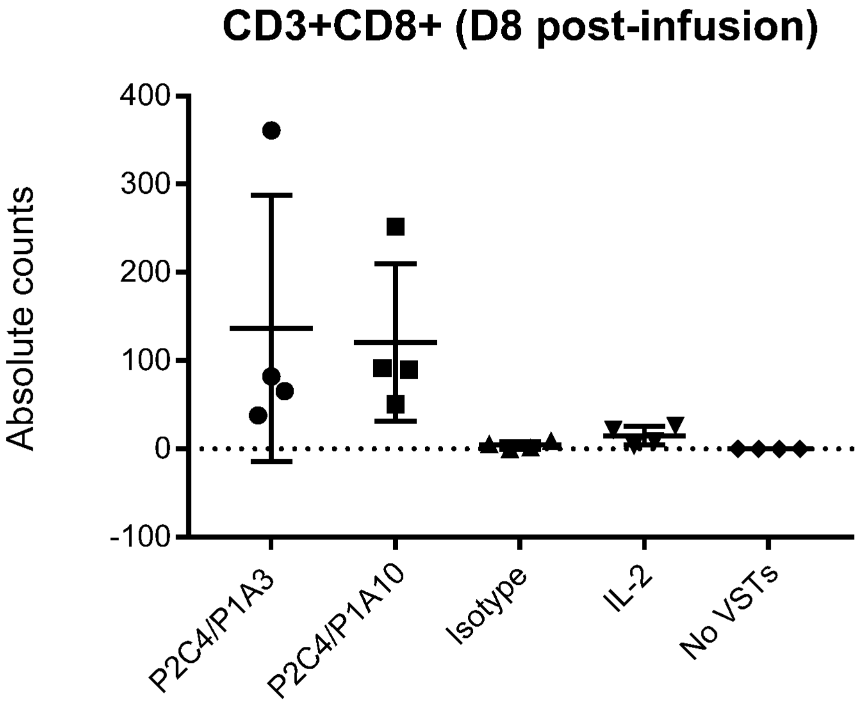
Figure 26D:
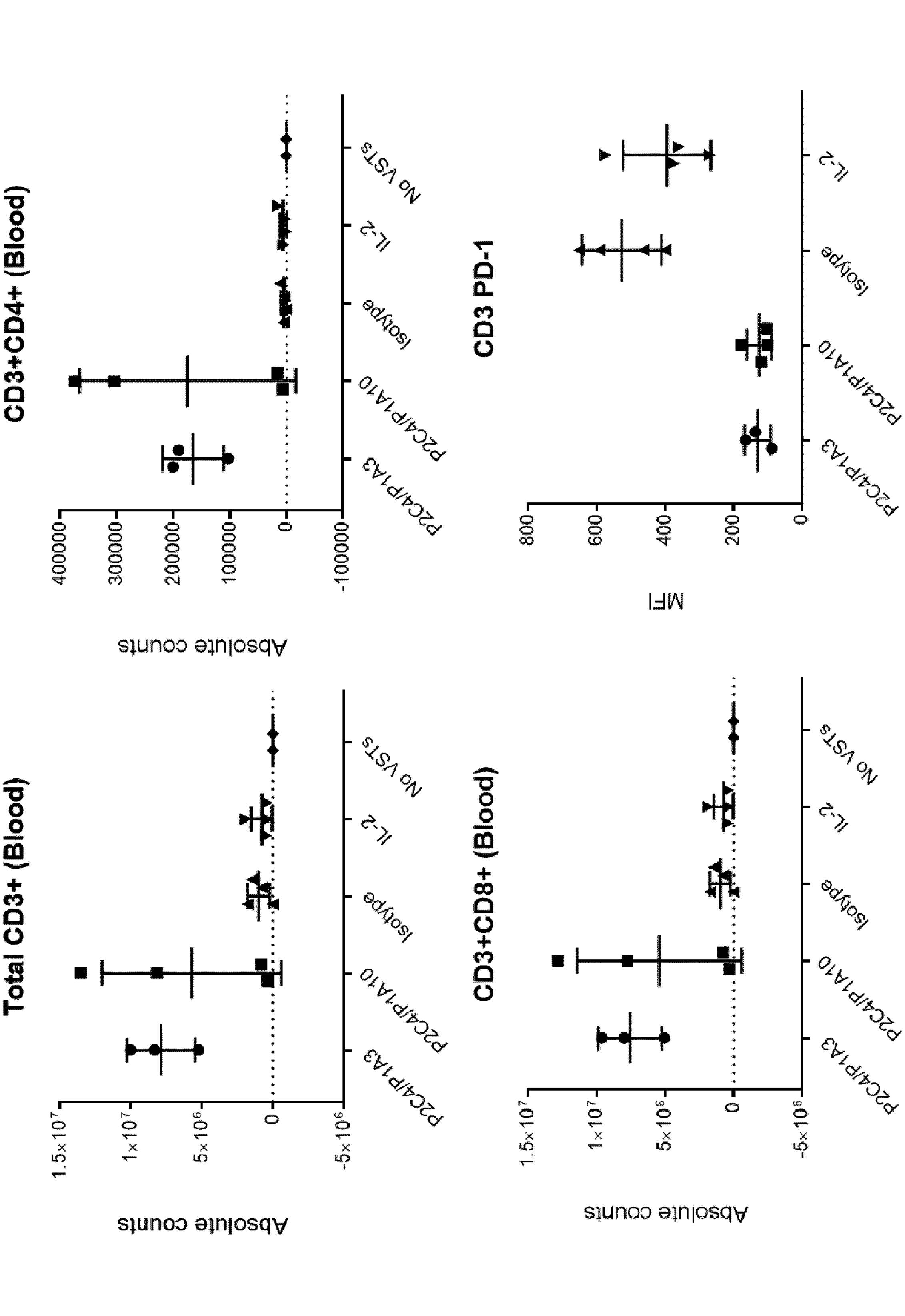
Figure 26E:
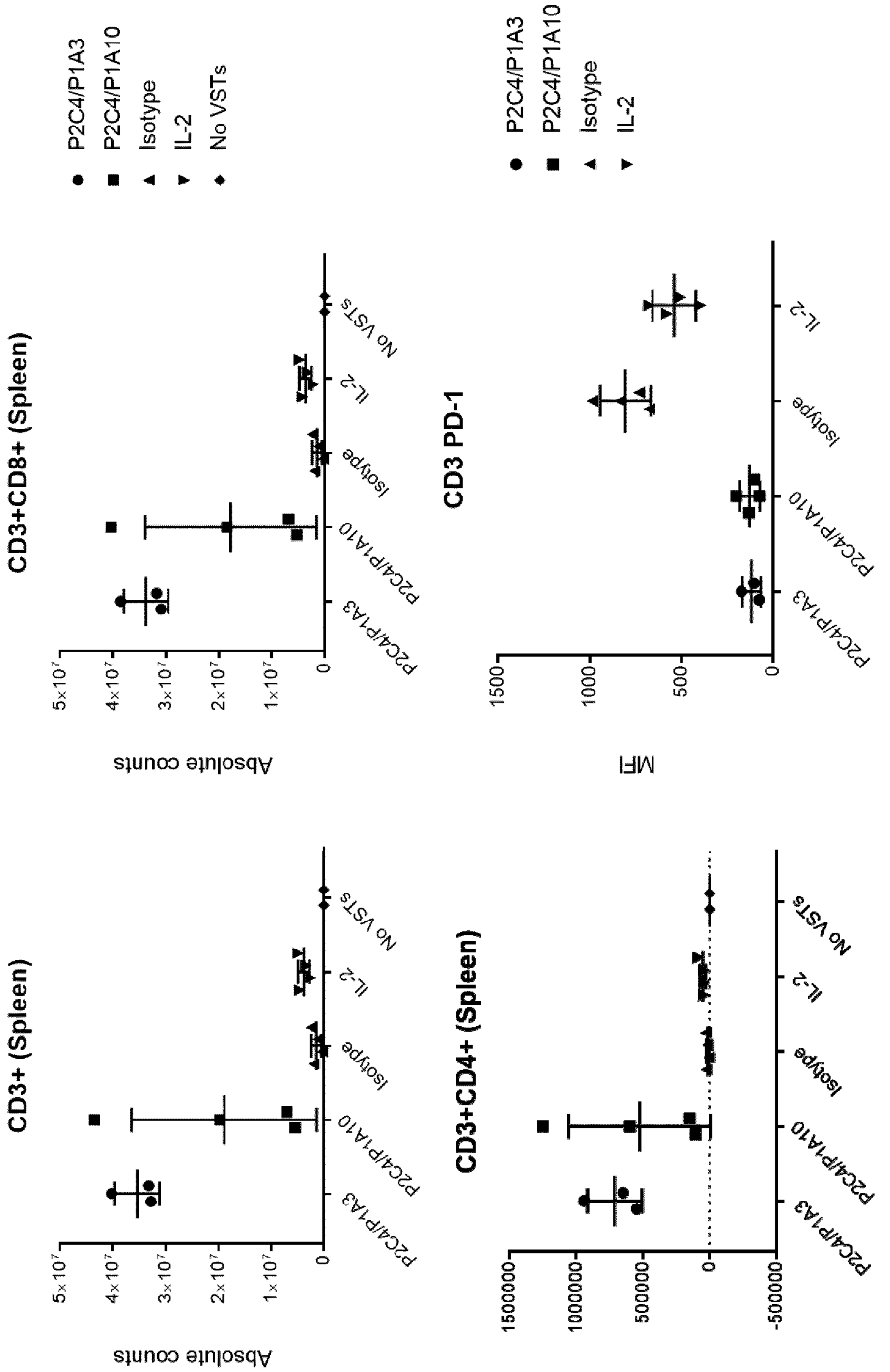
Figure 26F:
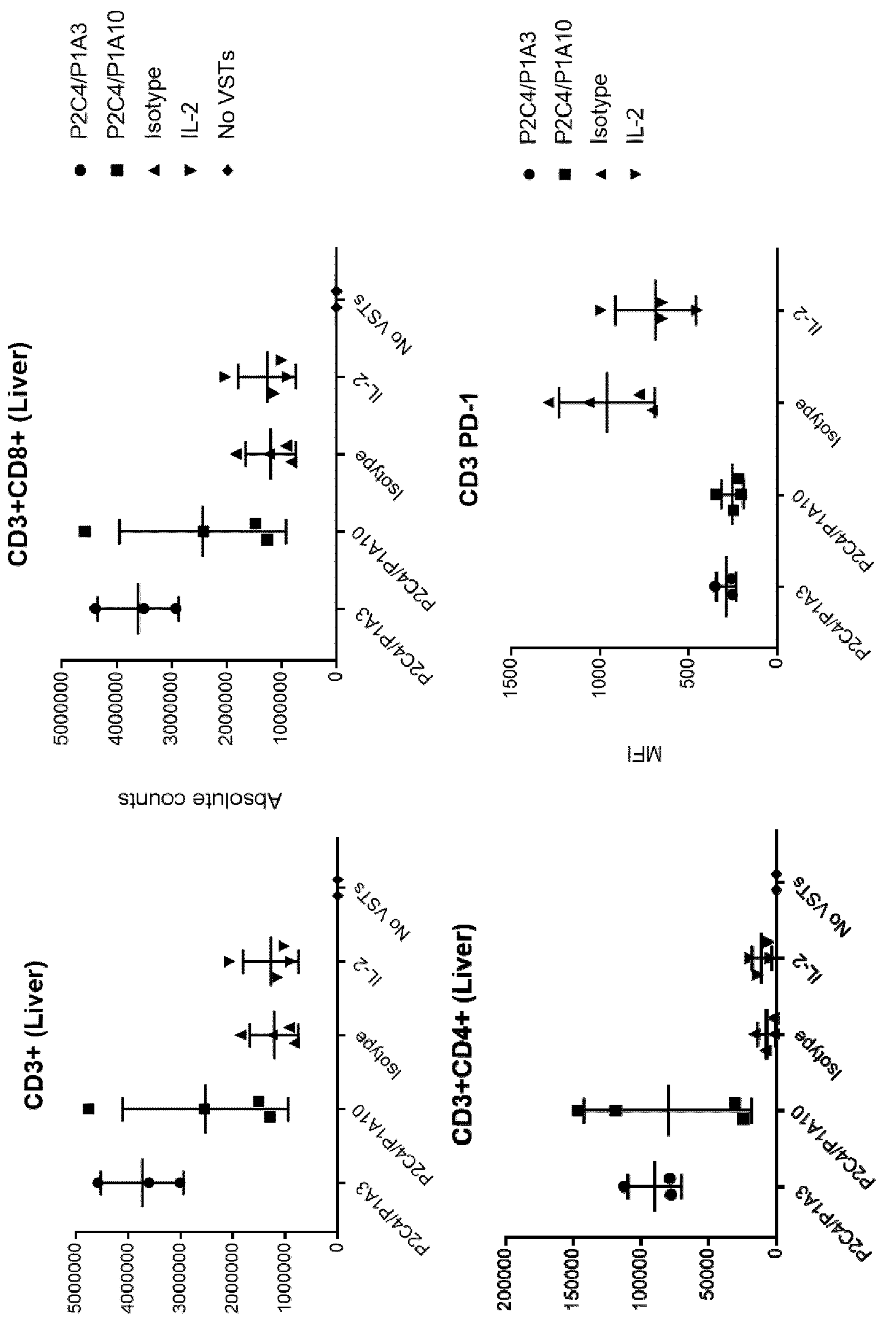
Figure 26G:
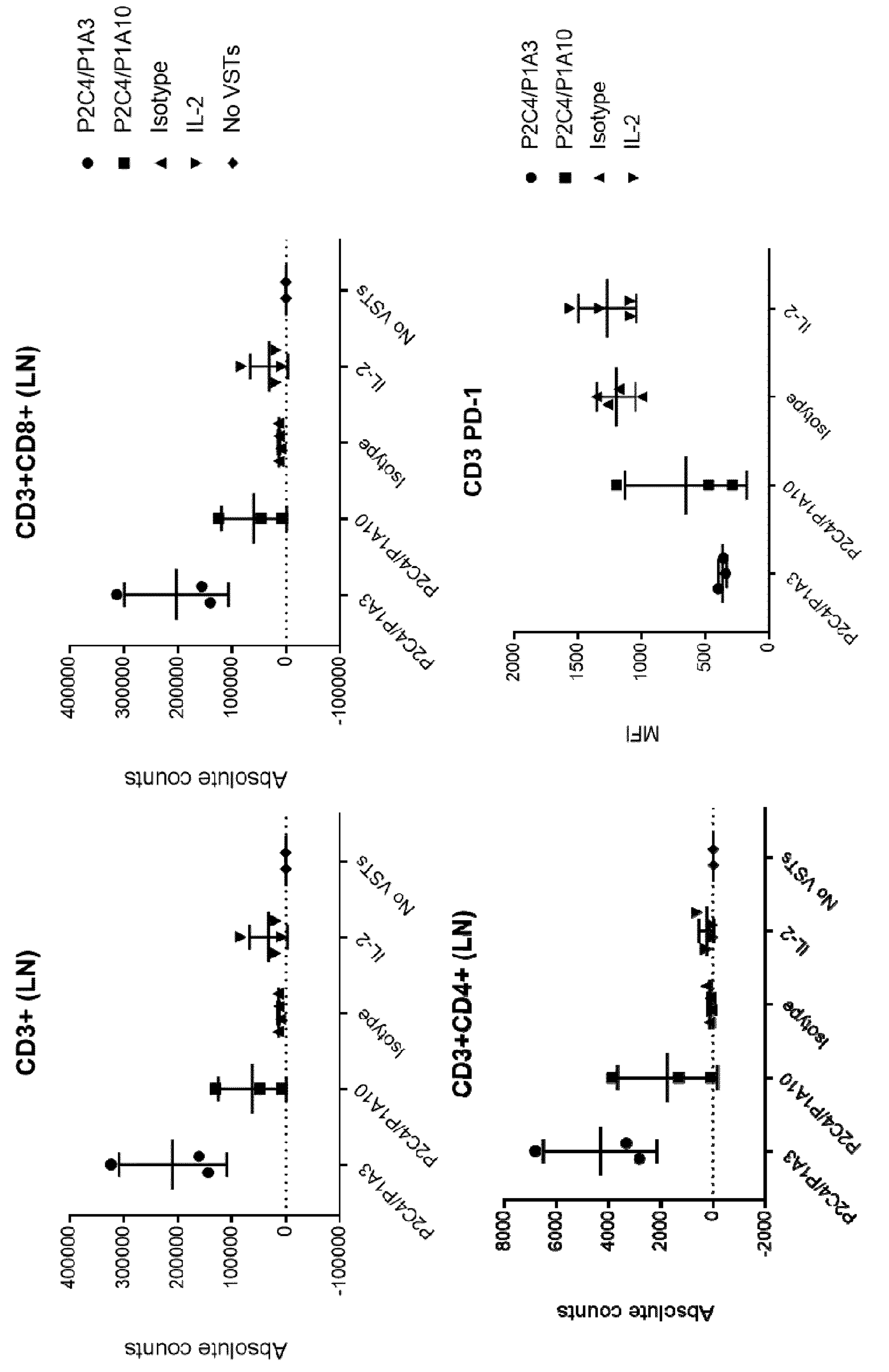
Figure 26H:
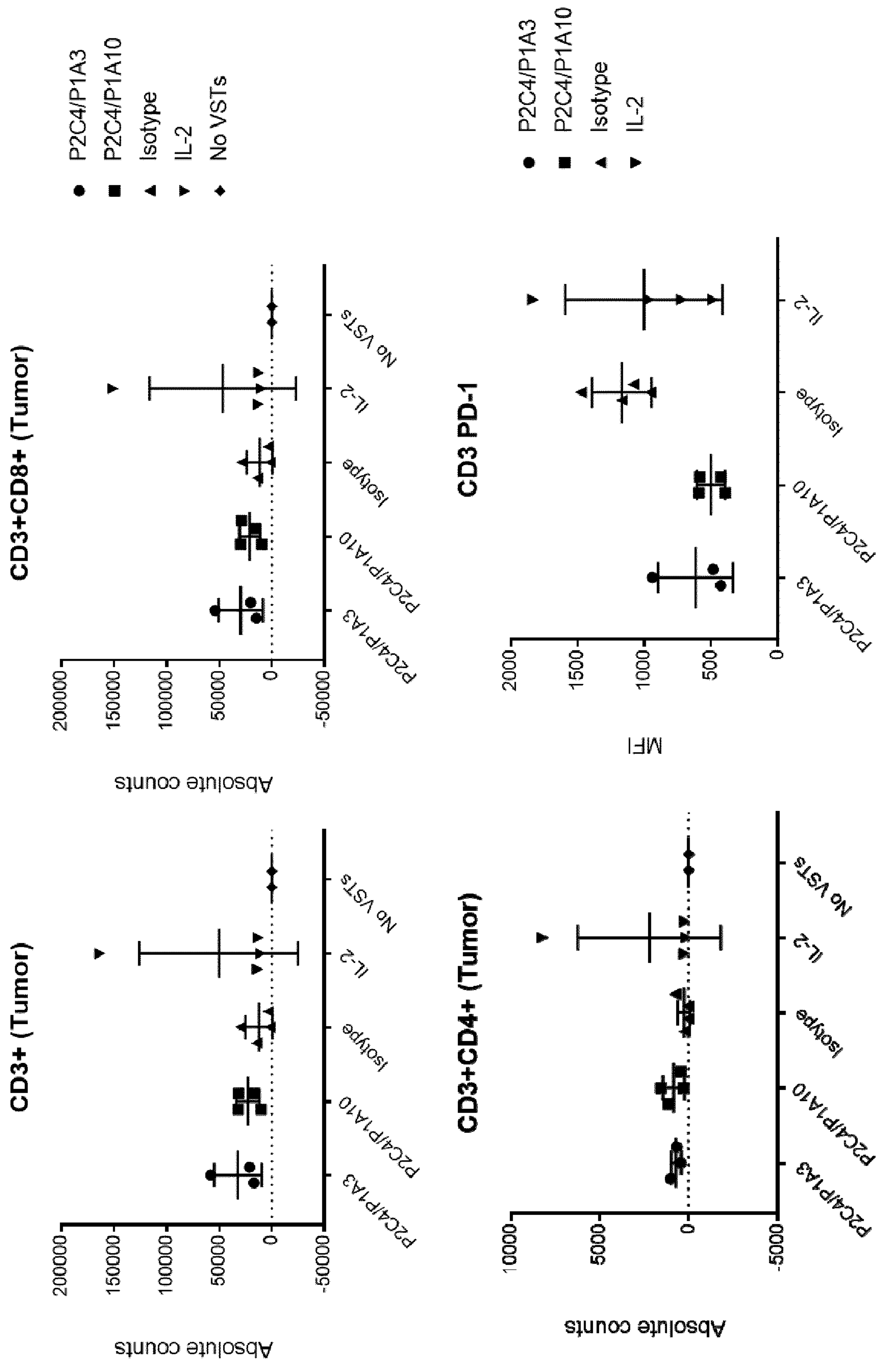

Mouse blood was collected at 8 days post-VST treatment and flow cytometric analysis showed elevated numbers of total human CD3, CD4 and CD8 T cells in mice treated with P2C4/P1A3 and P2C4/P1A10 as compared to mice treated with isotype control antibody or IL-2. The results are shown in FIGS. 26A to 26C.

At the end of the experiment, mice were euthanised at 22 days post-VST treatment and blood, spleen, liver, tumour-draining lymph node and flank tumour were harvested for flow cytometric analysis.

The results are shown in FIGS. 26D to 26H. Similar to results at 8 days post-VST treatment, mice treated with P2C4/P1A3 and P2C4/P1A10 had elevated numbers of total human CD3, CD4 and CD8 T cells in blood and organs. CD3 T cells from mice treated with P2C4/P1A3 and P2C4/P1A10 also had lower expression of PD-1 as compared to cells from mice treated with IL-2 and isotype control antibody.

Figure 26I:
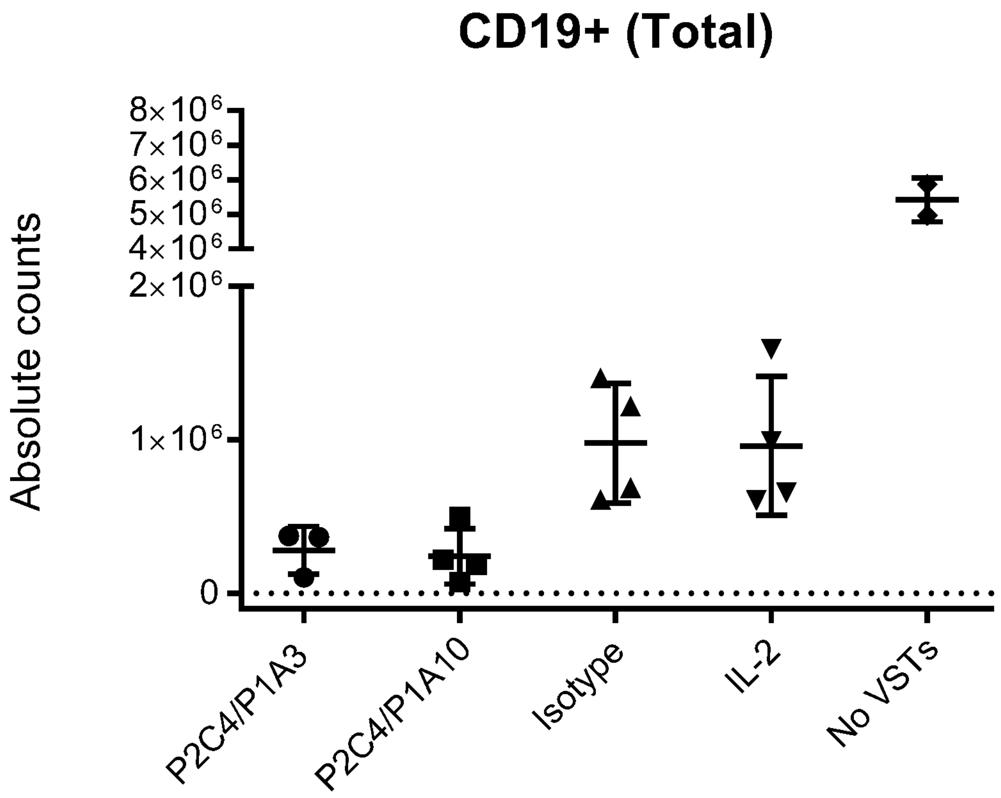
Figure 27A:
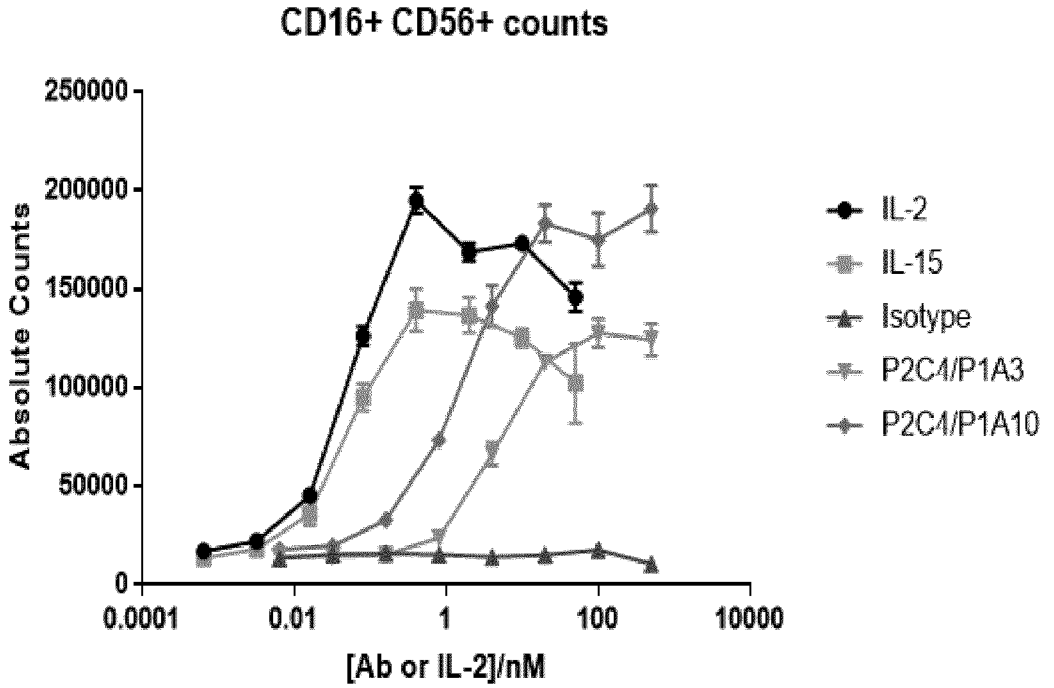
FIGS. 27A to 27D Graphs showing analysis of proliferation of pre-activated human NK cells following treatment with different amounts of bispecific IL-2Rβ- and γc-binding antibodies or the indicated cytokines. Isotype antibody was used as a control. (27A) Absolute numbers of CD16+CD56+ NK cells. EC50 values are shown. (27B) Absolute numbers of CD15−CD56+ NK cells. (27C) Percentage of dividing cells that are CD16+CD56+, determined by CellTrace™ Violet (CTV). EC50 values are shown. (27D) Percentage of dividing cells that are CD16−CD56+, determined by CTV. EC50 values are shown.
Figure 27B:
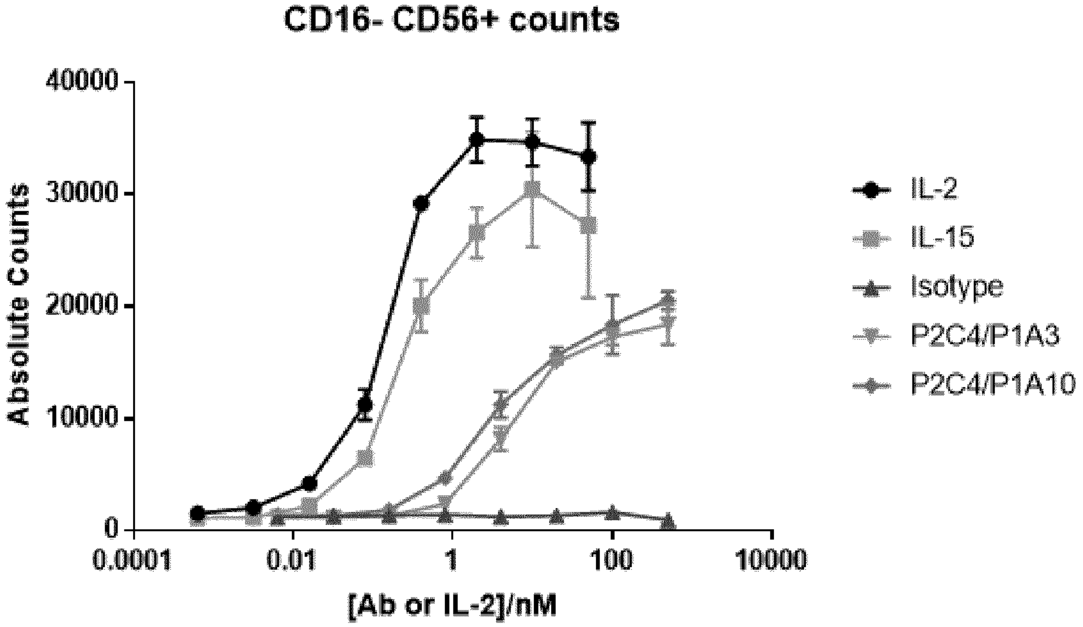
Figure 27C:
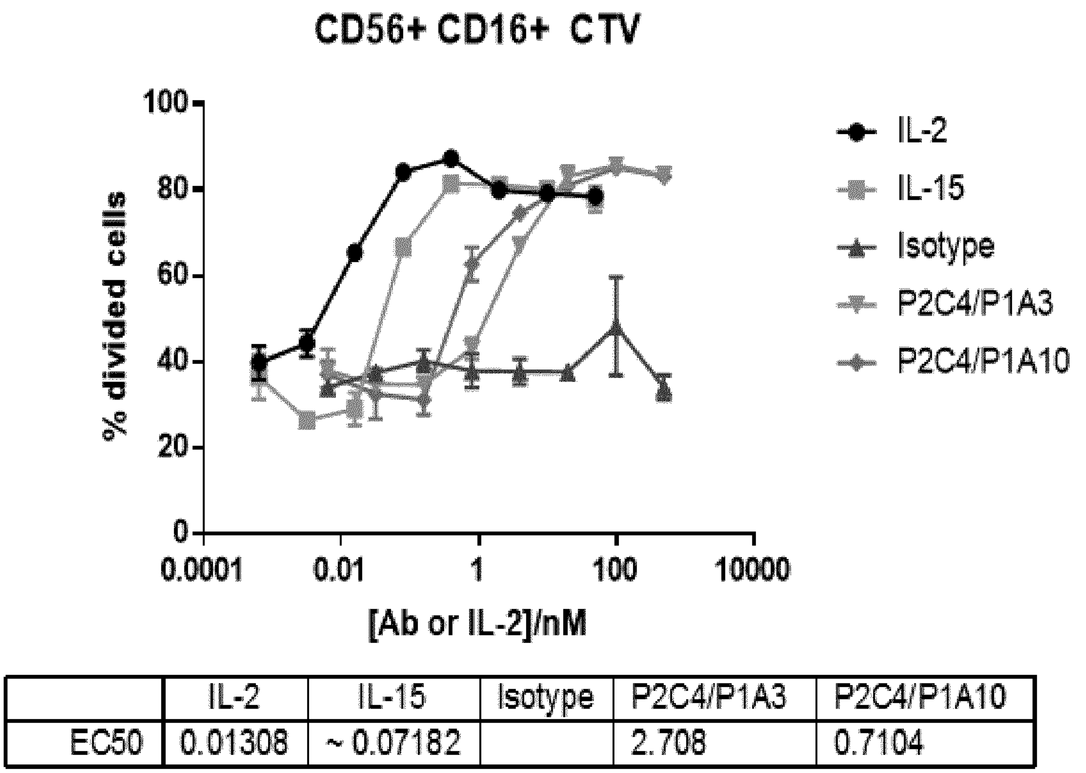
Figure 27D:
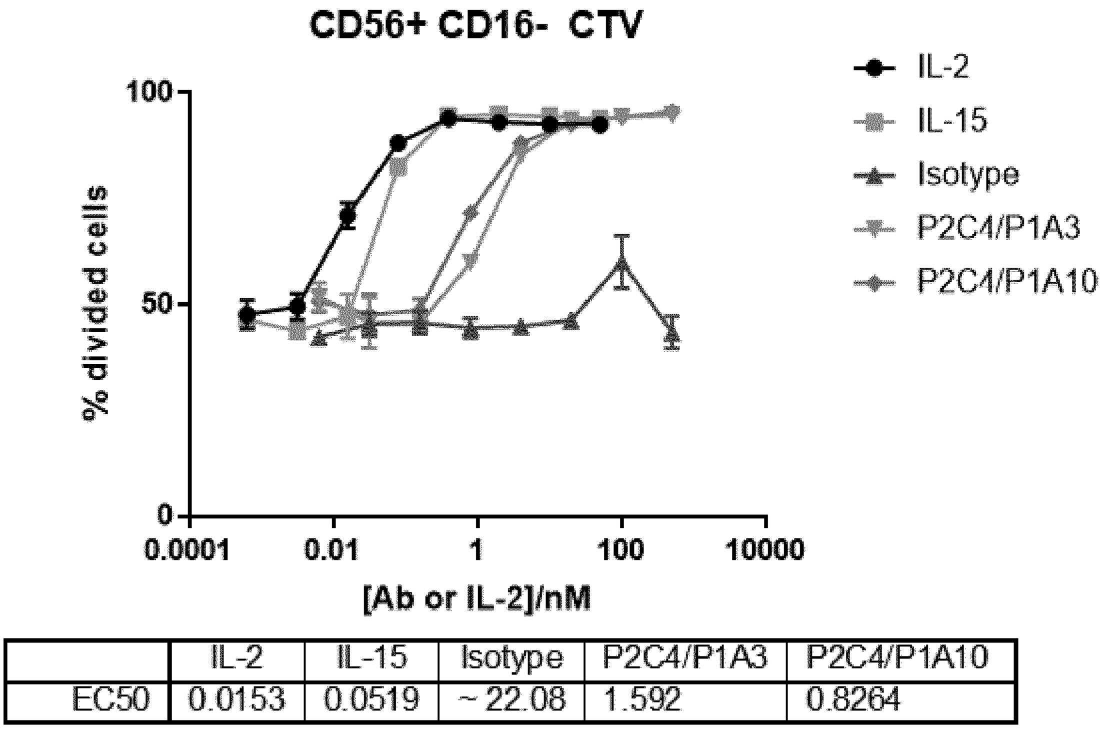
Figure 28A:
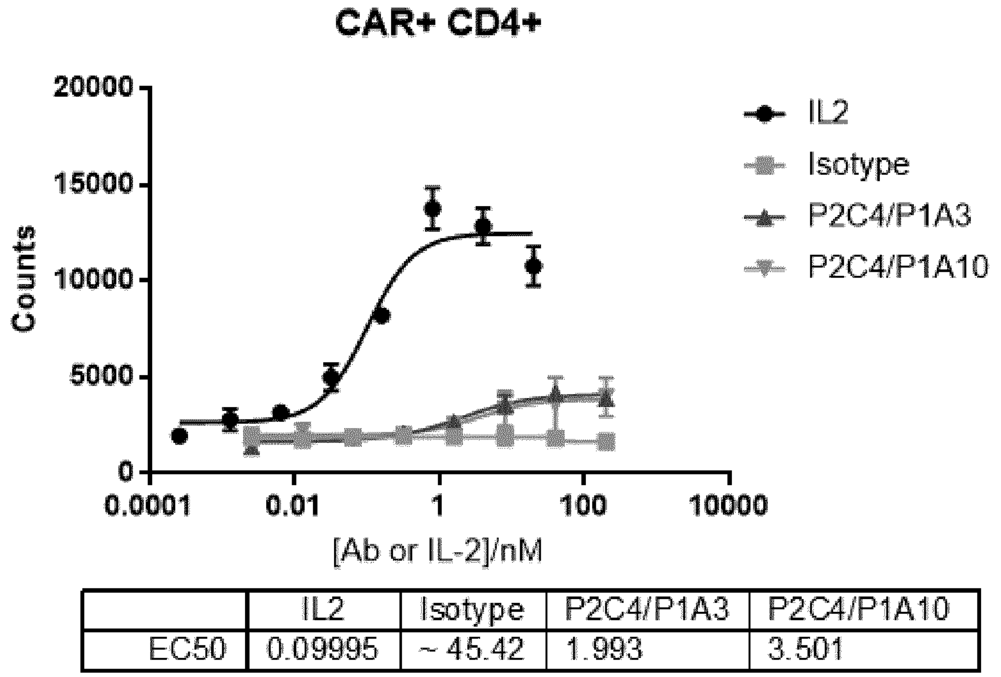
FIGS. 28A to 28D. Graphs showing analysis of proliferation of CAR-T cells following treatment with different amounts of bispecific IL-2Rβ- and γc-binding antibodies or IL-2. Isotype antibody was used as a control. EC50 values are shown for 28A-D. (28A) Absolute numbers of CD4+ CAR-T cells. (28B) Absolute numbers of CD4+ CAR-T cells. (28C) Percentage of dividing CAR-T cells that are CD4+, determined by CellTrace™ Violet (CTV). (28D) Percentage of dividing CAR-T cells that are CD8+, determined by CTV.
Figure 28B:
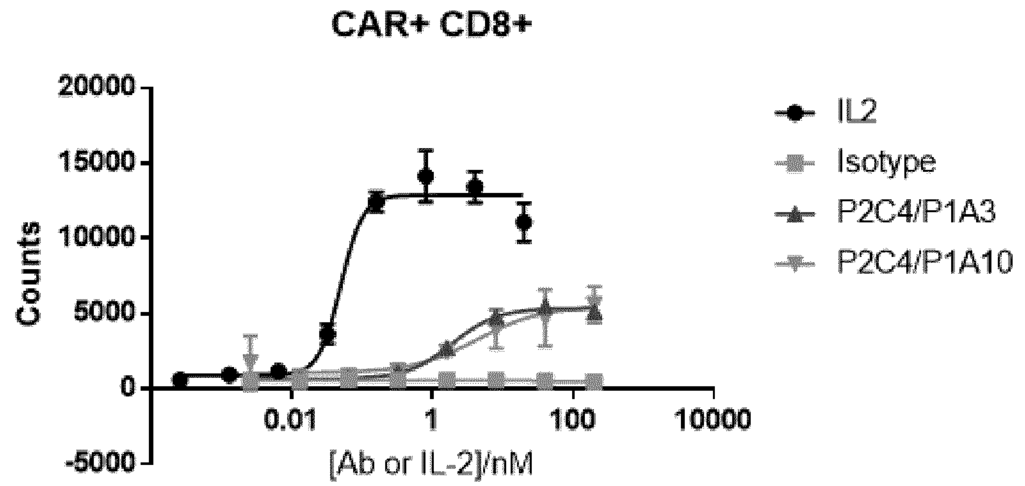
Figure 28C:
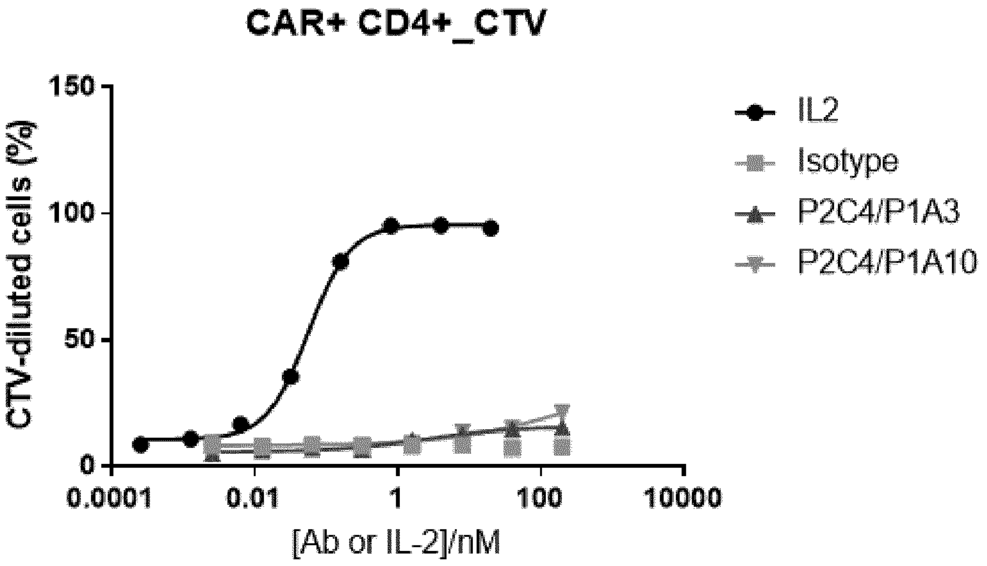
Figure 28D:
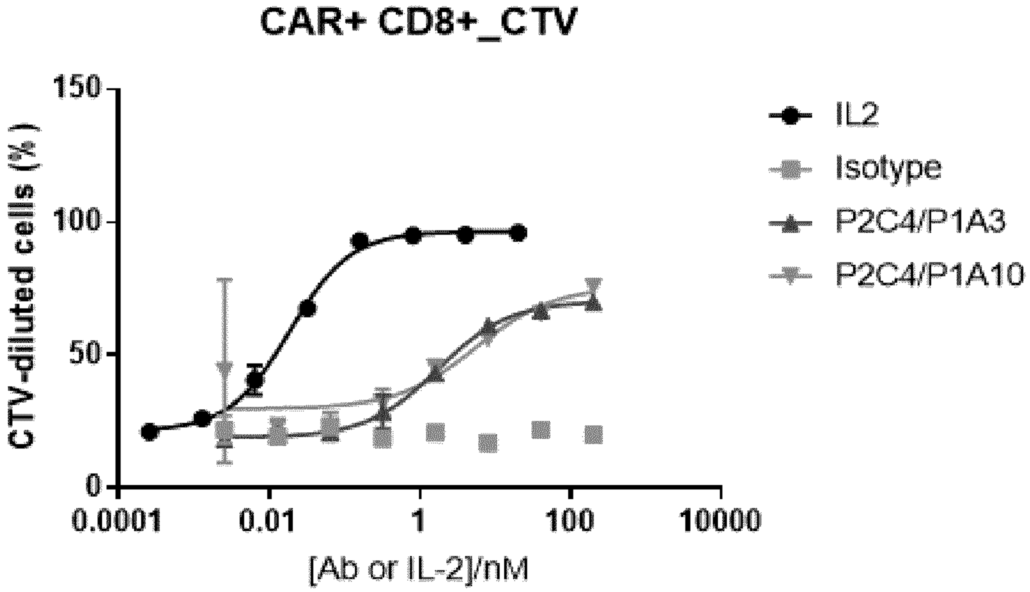

Total organ tumour load in mice was calculated from the total numbers of CD19+ cells in spleen, liver, flank tumour and tumour-draining lymph node (FIG. 26I). Mice treated with P2C4/P1A3 and P2C4/P1A10 had lower total organ tumour burden as compared to mice treated with isotype control antibody, IL-2 or no VSTs.

Example 10: Analysis of the Effect of Anti-IL-2Rβ/γc Antibodies on Anti-Cancer Immune Responses in the Presence of Tregs In the present Example, bispecific agonist anti-IL-2Rβ and -γc antibodies are shown to promote an anti-cancer immune response in vivo, without accompanying increases in immunosuppressive regulatory T cells (Tregs) in a mouse model of EBV-BLCL metastatic lymphoma.

Tumours are established by subcutaneous injection of mice with LCLs. Specifically, EBV-transformed B lymphoblastoid cell lines (LCLs) was mixed with Matrigel and injected subcutaneously to the right flank of NSG mice.

Figure 29:
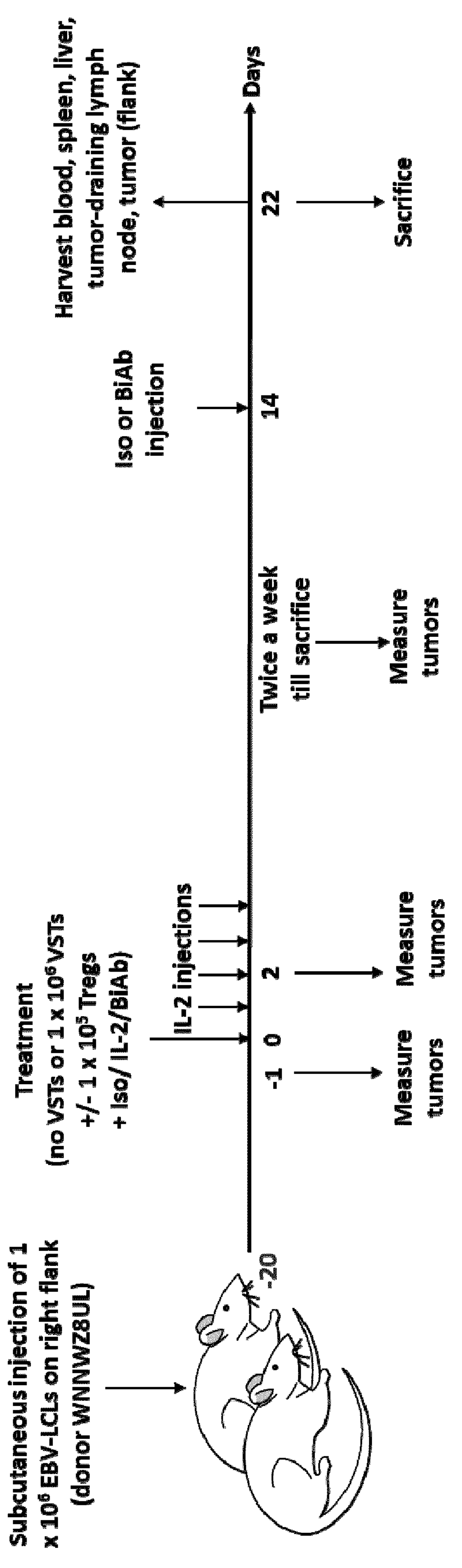
FIG. 29. Schedule of administration of VSTs and Tregs with or without bispecific IL-2Rβ- and γc-binding antibodies (BiAb), isotype control antibody (iso) or IL-2 to murine EBV-BLCL tumour model.

Mice were subsequently administered with autologous EBV-specific CTLs (VSTs) and Tregs, with or without P2C4/P1A3, P2C4/P1A10, isotype control antibody, or IL-2, at 20 days post-tumour inoculation. IL-2 treatments were given at 40 000 U/kg, intra-peritoneally (i.p.) consecutively for 5 days for a total of 5 doses. Antibody treatments were given at 5 mg/kg, i.p. every 14 days, for a total of 2 doses. The administration schedule is shown in FIG. 29.

Figure 30A:
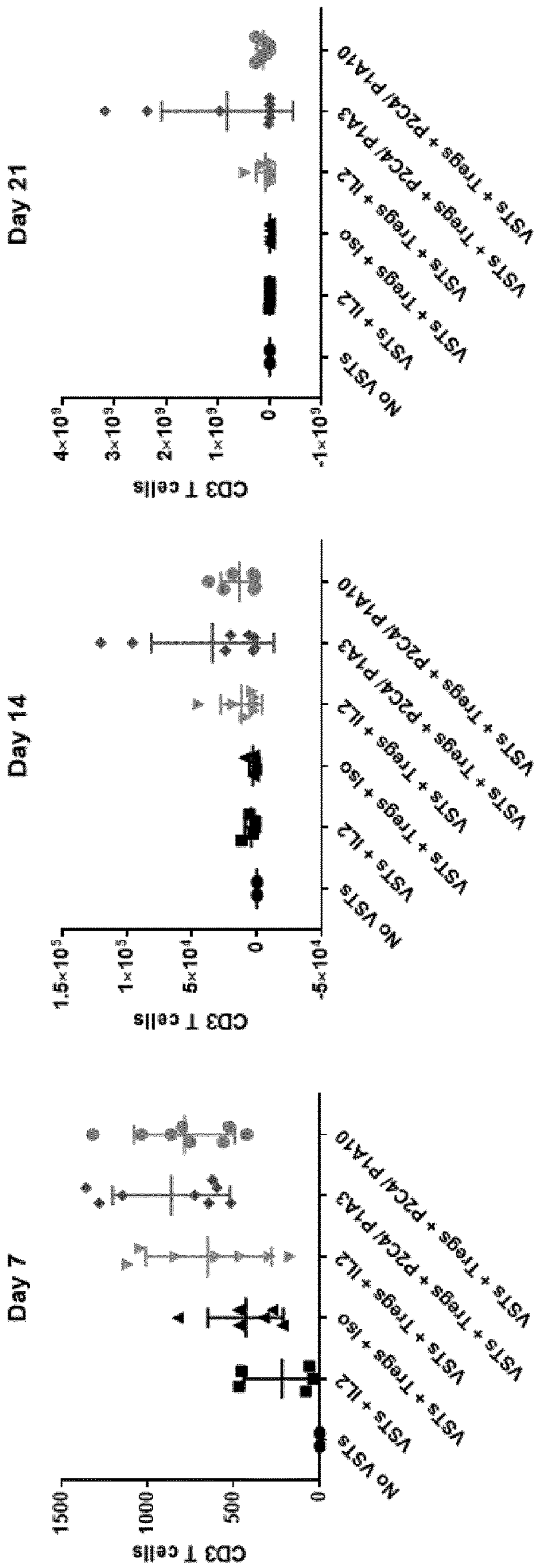
FIGS. 30A to 30K. Graphs showing analysis of proliferation of T cell subsets in an in vivo murine EBV-BLCL tumour model following treatment with VSTs and Tregs plus bispecific IL-2Rβ- and γc-binding antibodies, isotype control antibody (Iso), or IL-2. (30A) Absolute numbers of CD3+ T cells at 7, 14 and 21 clays post-treatment. (30B) Absolute numbers of CD3+, CD3+CD4+ and CD3+CD8+ T cells from the spleen at 22 days post-treatment. (30C) Absolute numbers of CD3+, CD3+CD4+ and CD3+CD8+ T cells from the liver at 22 days post-treatment. (30D) Absolute numbers of CD3+, CD3+CD4+ and CD3+CD8+ T cells from tumour-draining lymph node at 22 days post-treatment. (30E) Absolute numbers of CD3+, CD3+CD4+ and CD3+ CD8+ T cells from injection site at 22 days post-treatment. (30F) Ratio of the absolute number of CD8+ T cells to the absolute number of Tregs in spleen, liver and tumour-draining lymph node at 22 days post-treatment. (30G) Total number of CD3+, CD3+CD4+ and CD3+CD8+ T cells pooled from spleen, liver, tumour-draining lymph node and injection site. (30H) Ratio of the total number of CD8+ T cells to the total number of Tregs pooled from spleen, liver, tumour-draining lymph node, and injection site at 22 days post-treatment. (30I) Absolute numbers of EBV-BLCL tumour cells from spleen, liver and lymph node(s) at 22 days post-treatment. (30J) Total organ tumour load shown by the absolute total number of CD19+ tumour cells in spleen, liver, and tumour-draining lymph node. (30K) Total number of CD107a+, IFN-γ+ and perforin+ CD8 T cells pooled from spleen, liver, tumour-draining lymph node, and injection site at 22 days post-treatment.
Figure 30B:
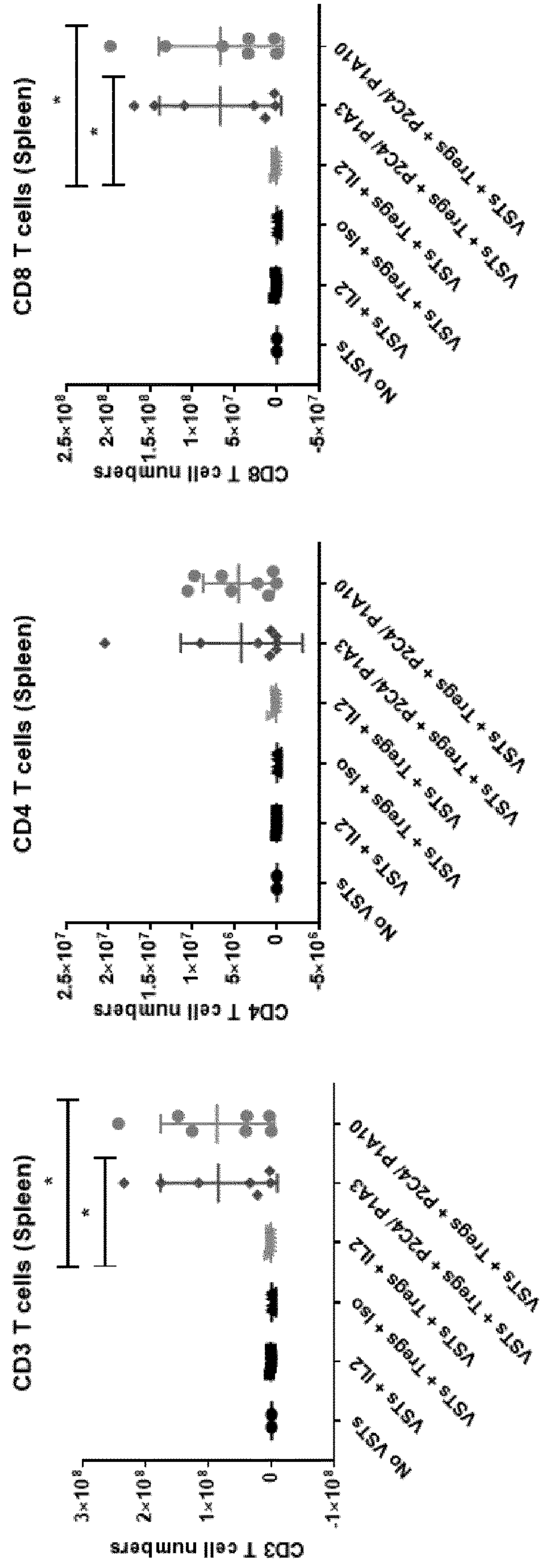
Figure 30C:
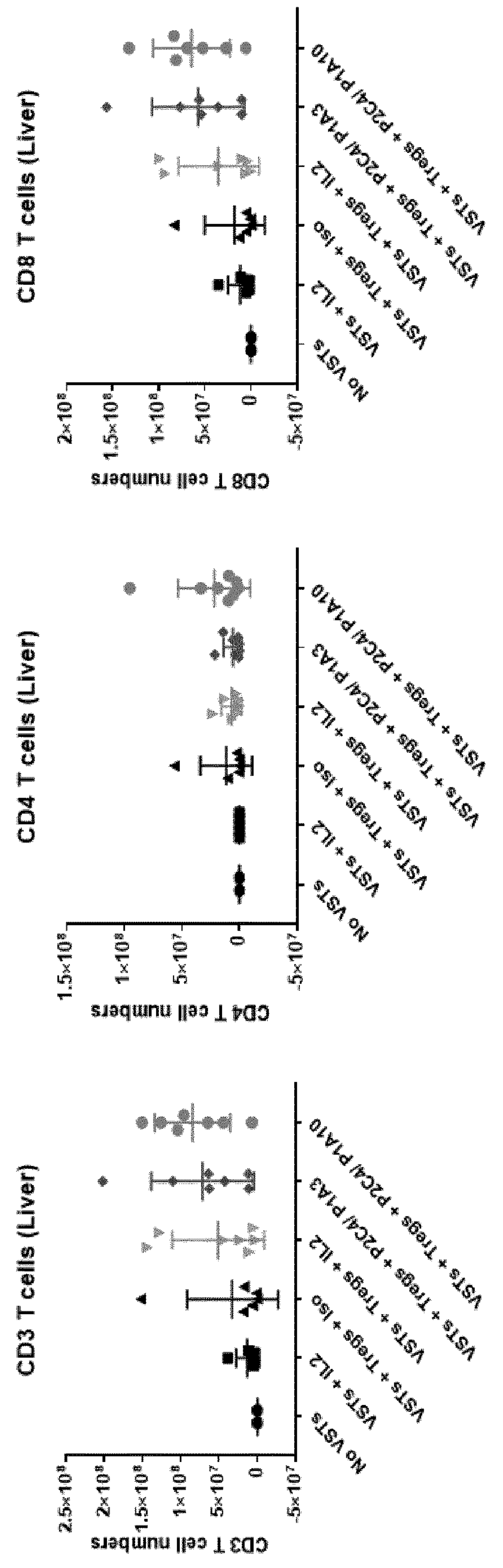
Figure 30D:
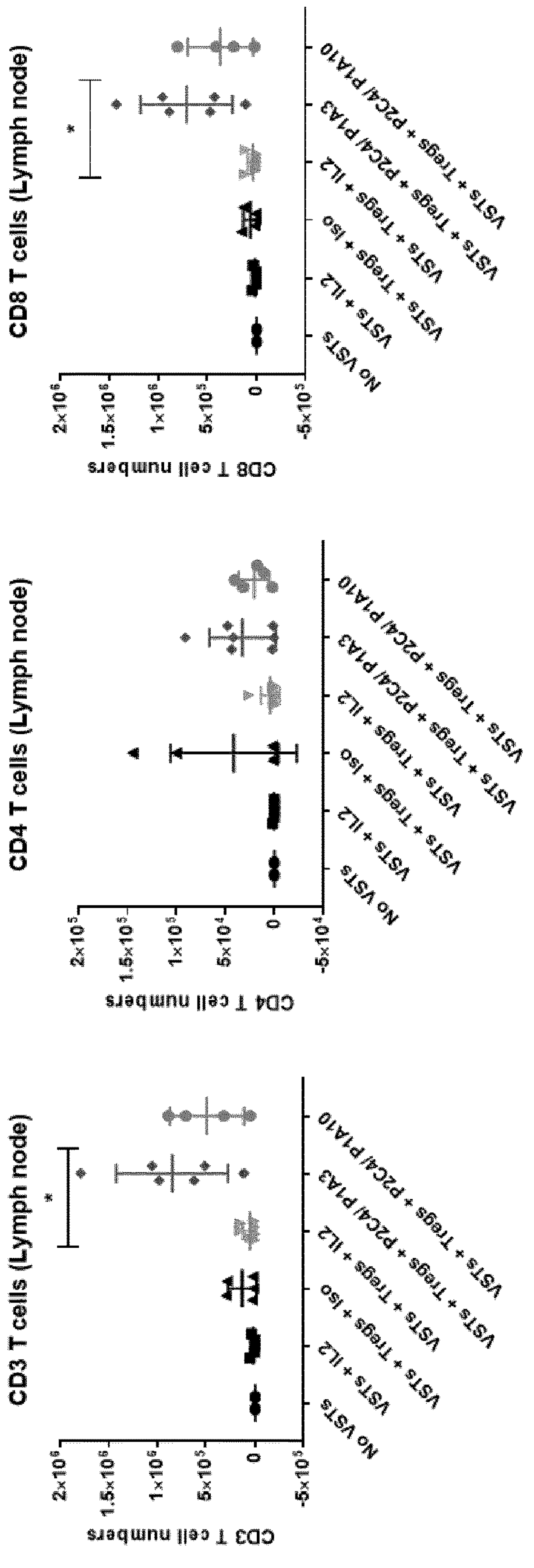
Figure 30E:
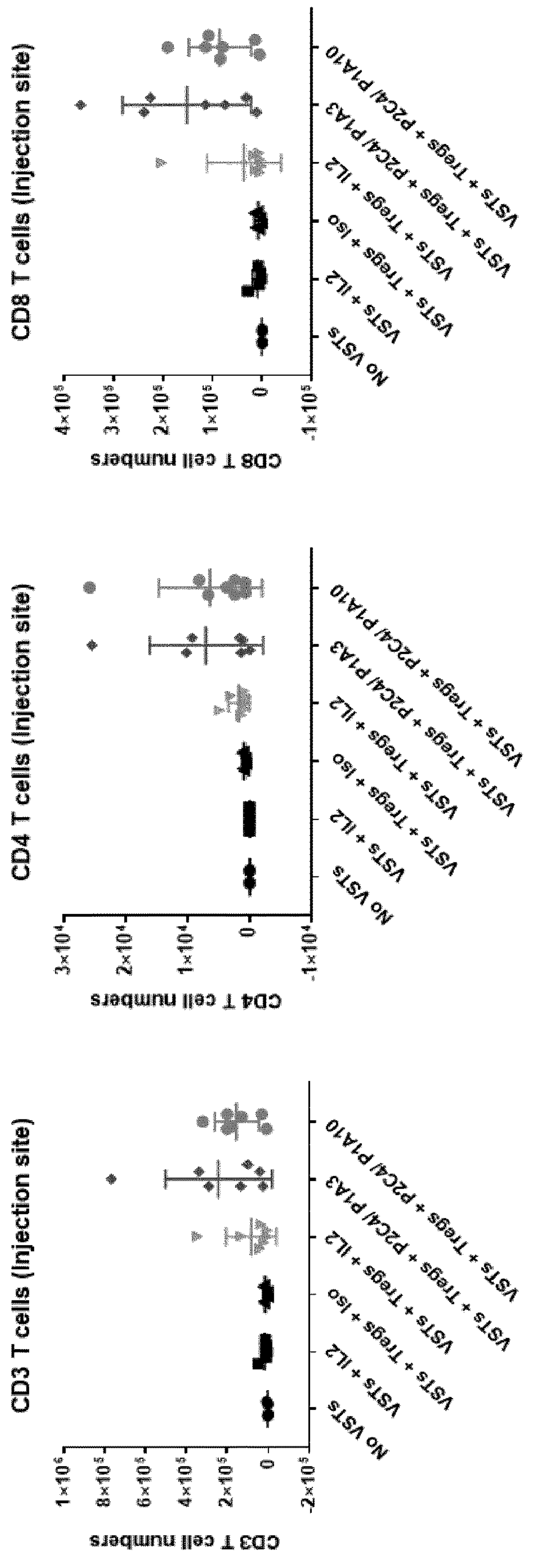

Analysis of peripheral blood collected from mice at 7, 14 and 21 days post-treatment showed that slightly higher numbers of circulating VSTs were detected in mice which received bispecific anti-IL-2Rβ and -yc antibodies compared to isotype (Iso) or IL-2, as shown in FIG. 30A.

At the end of the experiment, mice were euthanised at 22 days post-treatment and spleen, liver, tumour-draining lymph node and injection site were harvested for flow cytometric analysis. The results are shown in FIGS. 30B to 30E. Mice treated with P2C4/P1A3 and P2C4/P1A10 were found to have elevated numbers of total human CD3, CD4 and CD8 T cells in spleen (30B), liver (30C), tumour-draining lymph node(s) (30D) and injection site (30E). **, $p<0.01$; $p<0.05$.

Figure 30F:
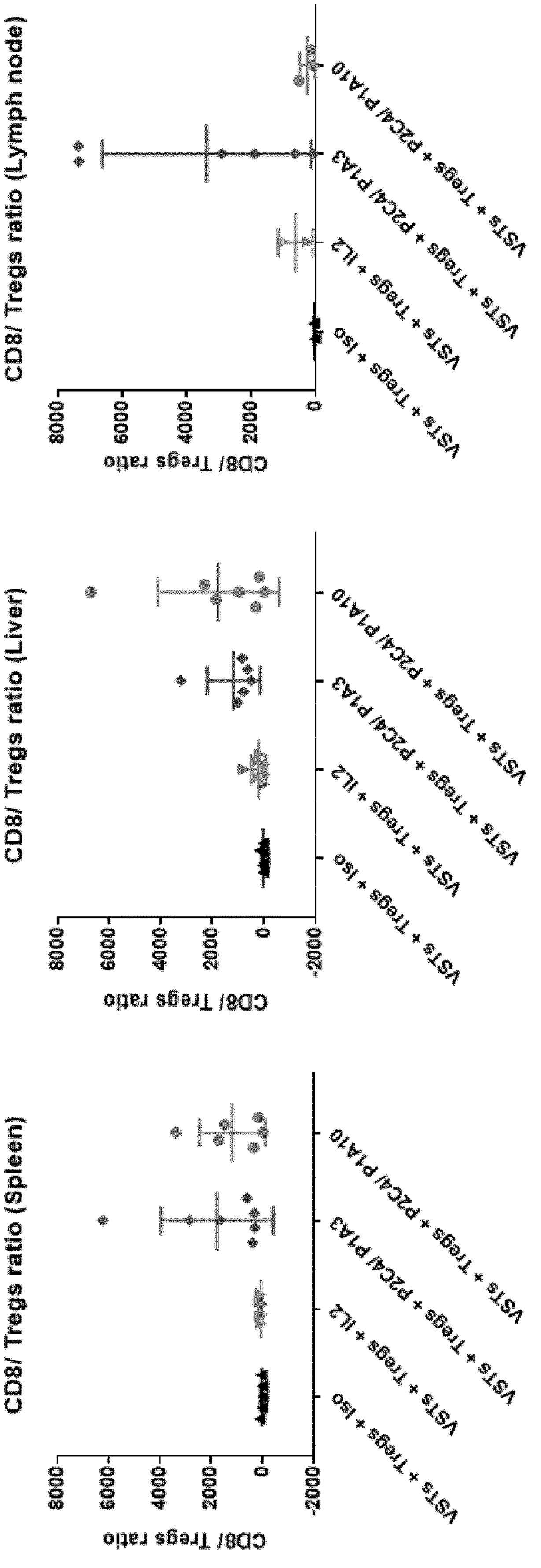

The ratio of CD8 cells to Tregs has been shown to be predictive of a favourable outcome in multiple tumour types (de Leeuw R J et al. Clin Cancer Res 2012; 18:3022-9). FIG. 30F shows that the spleen, liver and lymph node(s) of mice treated with P2C4/P1A3 or P2C4/P1A10 were found to demonstrate higher CD8/Treg ratios compared to the same organs from mice treated with IL-2. This shows that P2C4/P1A3 and P2C4/P1A10 preferentially expand CD8 T cells over Tregs, compared to the effect seen with IL-2.

Figure 30G:
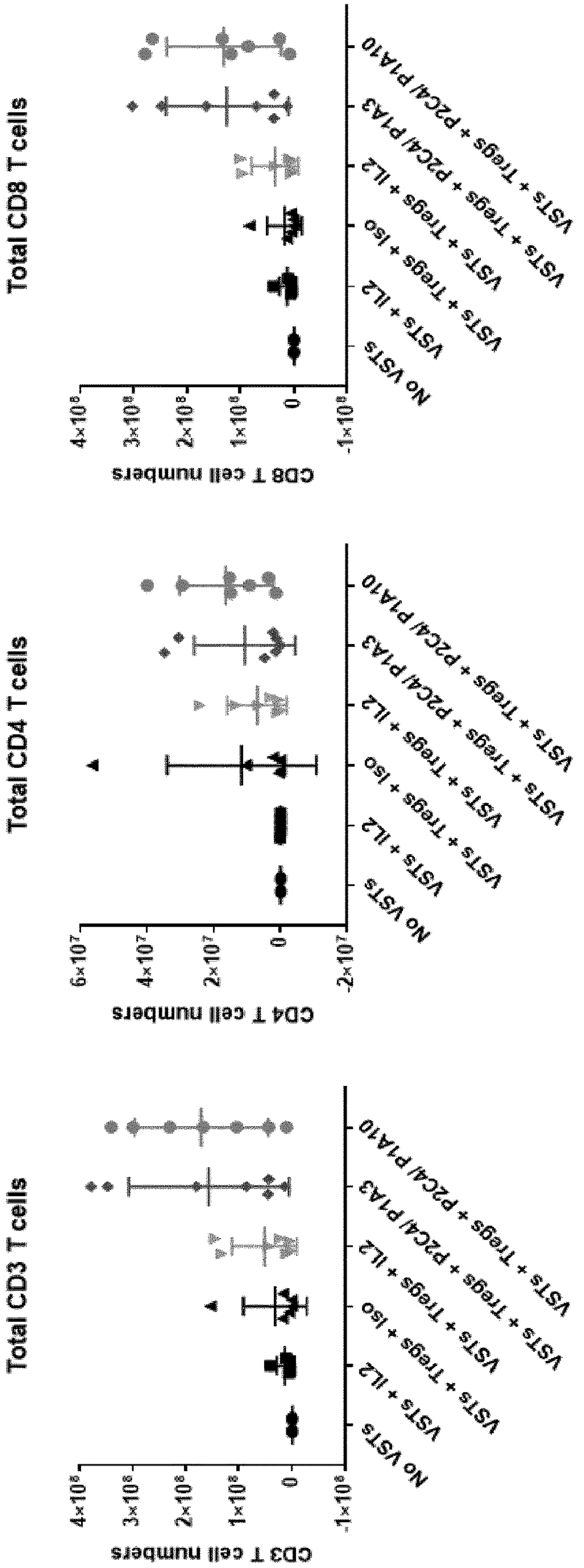
Figure 30H:
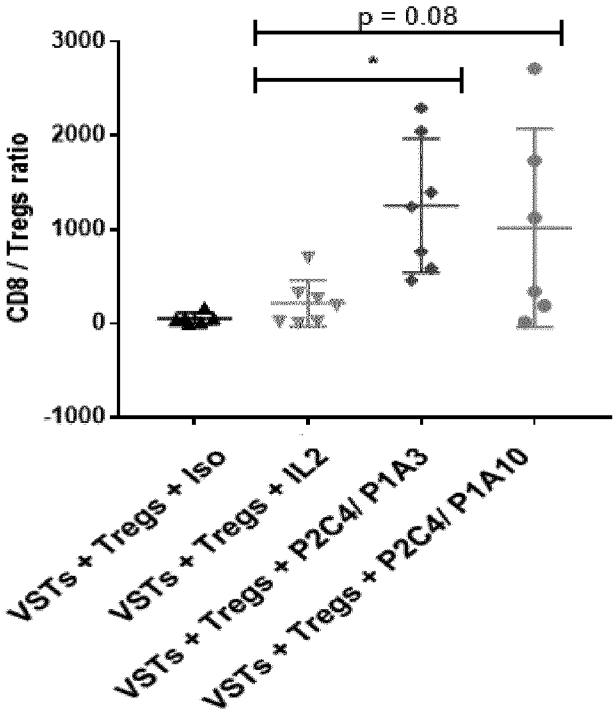

The numbers of CD3, CD4 and CD8 T cells from spleen, liver, tumour-draining lymph node and injection site were pooled to provide total numbers of cells. The results are shown in FIG. 30G. The total pooled CD8/Treg ratio is shown in FIG. 30H. The total CD8/Treg ratio of mice treated with P2C4/P1A3 or P2C4/P1A10 was found to be higher than the total CD8/Treg ratio from mice treated with isotype (Iso) or IL-2. *, p<0.05.

Figure 30I:
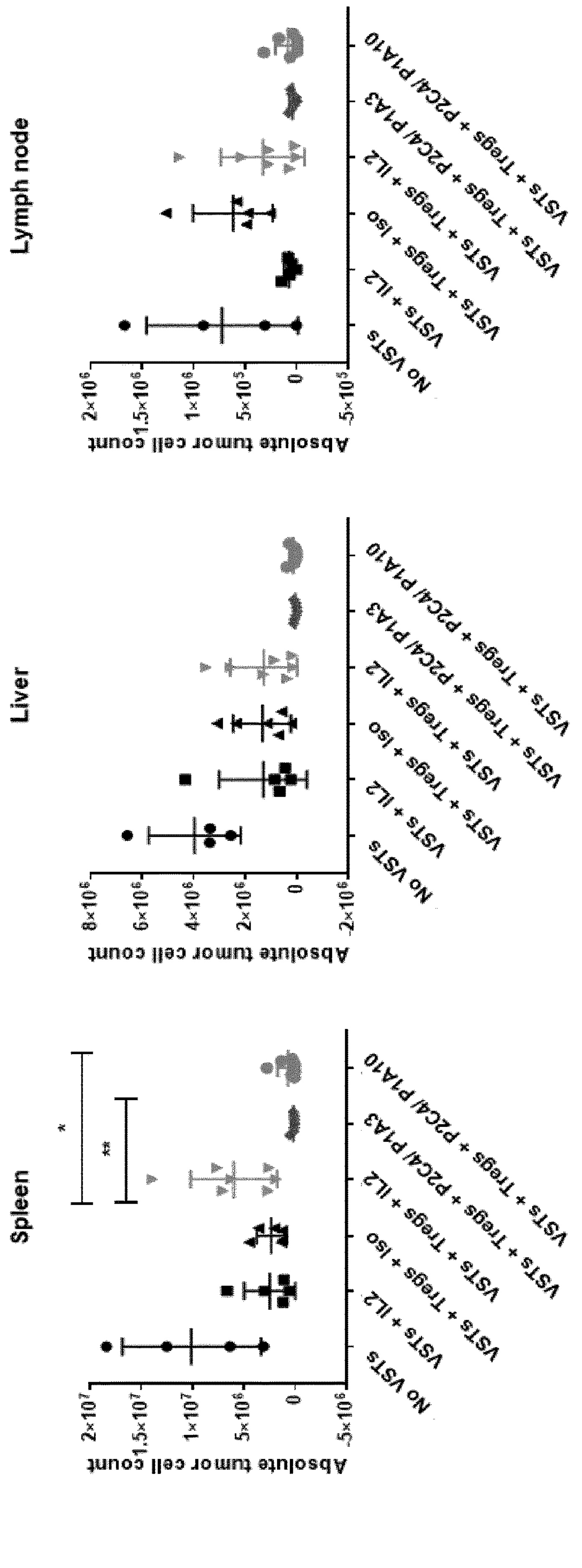

The numbers of EBV-BLCLs present in the spleen, liver and lymph node(s) at the end of the experiment were also analysed. The results are shown in FIG. 30I. Mice treated with P2C4/P1A3 and P2C4/P1A10 were found to have reduced numbers of EBV-BLCL tumour cells compared to mice treated with IL-2, **, p<0.01; *, p<0.05.

Figure 30J:
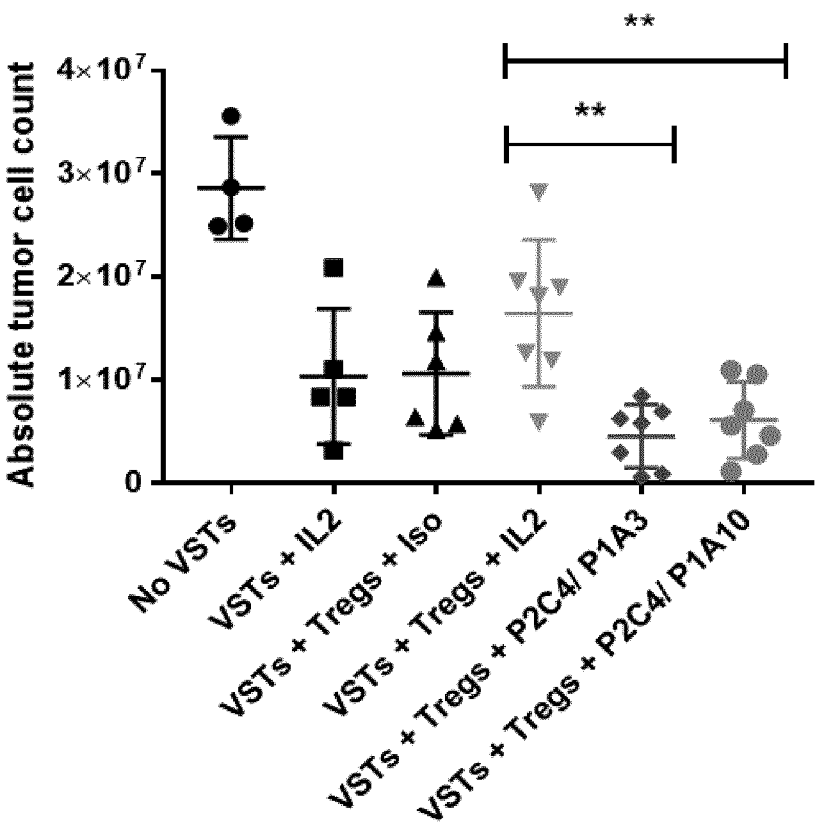

Total organ tumour load in mice was calculated from the total numbers of CD19+ tumour cells found in spleen, liver, and tumour-draining lymph node. The results are shown in FIG. 30J. Mice treated with P2C4/P1A3 and P2C4/P1A10 were found to have lower total organ tumour burden as compared to mice treated with isotype control antibody, IL-2 or no VSTs. **, p<0.01.

Figure 30K:
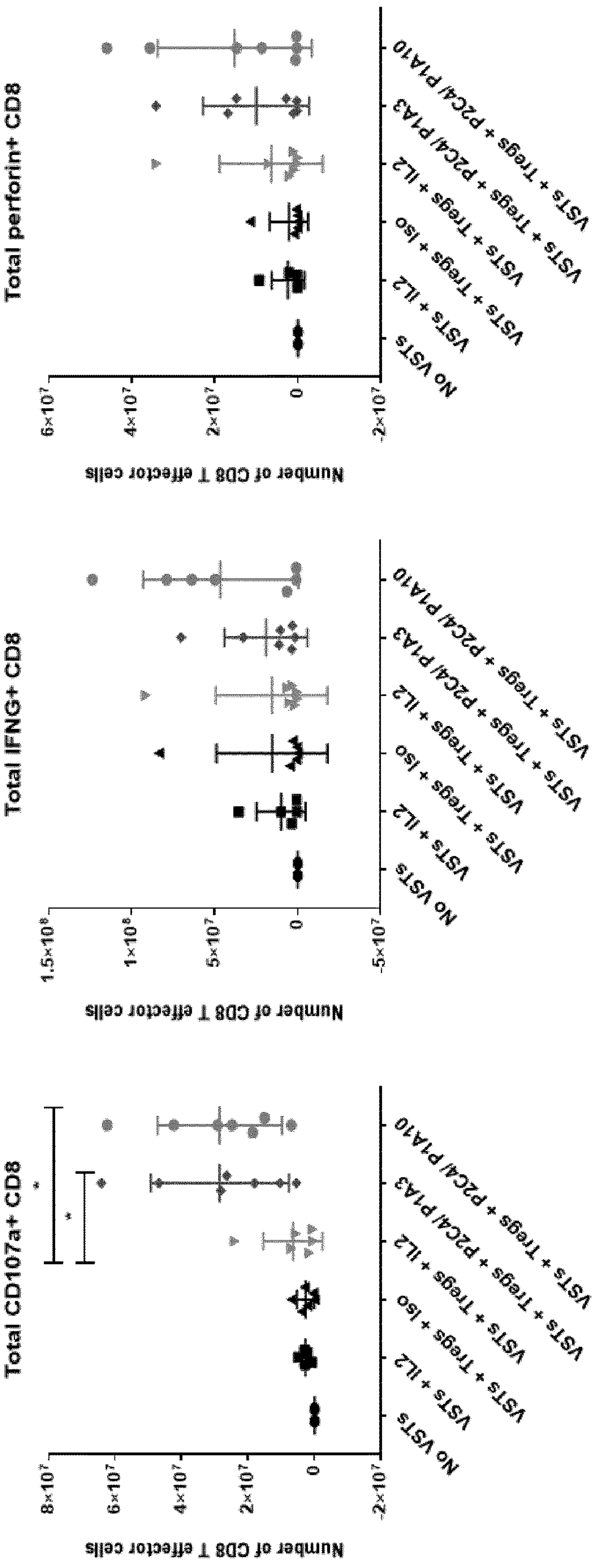

Next, the cytolytic activity of the expanded CD8 T cells was assessed by identifying the total) number of CD8 T cells from spleen, liver, tumour-draining lymph node and injection site secreting the effector molecules interferon-γ (IFN-γ), CD107a and perforin. The results are shown in FIG. 30K. Higher numbers of effector molecule-secreting CD8 T cells were found to be present following treatment with P2C4/P1A3 and P2C4/P1A10 compared to treatment with IL-2. *, P<0.05.

In conclusion, bispecific anti-IL-2Rβ and -γc antibodies were shown to provide sustained expansion of CD8 T cells in vivo without accompanying increases in Tregs, leading to improved tumour control.

Example 11: Analysis of the Effect of Anti-IL-2Rβ/γc Antibodies on Survival

A murine model of metastatic lymphoma is generated by intravenous injection of EBV-BLCLs to investigate the effect of bispecific agonist anti-IL-2Rβ and -γc antibodies versus IL-2 on survival. Mice treated with anti-IL-2Rβ and -γc antibodies are found to have improved survival as compared to mice not treated with anti-IL-2Rβ and -γc antibodies.

The invention claimed is:

1. An antigen-binding molecule which is capable of binding to CD122 and common γ chain (CD132) comprising:

(a) an antigen-binding molecule which is capable of binding to CD122, comprising:
 a heavy chain variable (VH) region incorporating the following CDRs:
  HC-CDR1 having the amino acid sequence of SEQ ID NO:103
  HC-CDR2 having the amino acid sequence of SEQ ID NO:116
  HC-CDR3 having the amino acid sequence of SEQ ID NO:128; and
 a light chain variable (VL) region incorporating the following CDRs:
  LC-CDR1 having the amino acid sequence of SEQ ID NO:145
  LC-CDR2 having the amino acid sequence of SEQ ID NO:162
  LC-CDR3 having the amino acid sequence of SEQ ID NO:177; and (b) an antigen-binding molecule which is capable of binding to CD132, comprising:
 a VH region incorporating the following CDRs:
  HC-CDR1 having the amino acid sequence of SEQ ID NO:196
  HC-CDR2 having the amino acid sequence of SEQ ID NO:204
  HC-CDR3 having the amino acid sequence of SEQ ID NO:212; and
 a VL region incorporating the following CDRs:
  LC-CDR1 having the amino acid sequence of SEQ ID NO:227
  LC-CDR2 having the amino acid sequence of SEQ ID NO:238
  LC-CDR3 having the amino acid sequence of SEQ ID NO:248.

2. The antigen-binding molecule according to claim 1, wherein the antigen-binding molecule which is capable of binding to CD122 comprises:
 a VH region comprising an amino acid sequence having at least 85% sequence identity to SEQ ID NO:1; and
 a VL region comprising an amino acid sequence having at least 85% sequence identity to SEQ ID NO:35.

3. The antigen-binding molecule according to claim 1, wherein the antigen-binding molecule which is capable of binding to CD132 comprises:
 a VH region comprising an amino acid sequence having at least 85% sequence identity to SEQ ID NO:71; and
 a VL region comprising an amino acid sequence having at least 85% sequence identity to SEQ ID NO:89.

4. The antigen-binding molecule according to claim 1, which is capable of reducing expression of PD-1 by T cells.

5. A nucleic acid encoding an antigen-binding molecule which is capable of binding to CD122 and common γ chain (CD132), comprising:

(a) an antigen-binding molecule which is capable of binding to CD122, comprising:
 a heavy chain variable (VH) region incorporating the following CDRs:
  HC-CDR1 having the amino acid sequence of SEQ ID NO:103
  HC-CDR2 having the amino acid sequence of SEQ ID NO:116
  HC-CDR3 having the amino acid sequence of SEQ ID NO:128; and
 a light chain variable (VL) region incorporating the following CDRs:
  LC-CDR1 having the amino acid sequence of SEQ ID NO:145
  LC-CDR2 having the amino acid sequence of SEQ ID NO:162

LC-CDR3 having the amino acid sequence of SEQ ID NO:177; and (b) an antigen-binding molecule which is capable of binding to CD132, comprising:

a VH region incorporating the following CDRs:

HC-CDR1 having the amino acid sequence of SEQ ID NO:196

HC-CDR2 having the amino acid sequence of SEQ ID NO:204

HC-CDR3 having the amino acid sequence of SEQ ID NO:212; and a VL region incorporating the following CDRs:

LC-CDR1 having the amino acid sequence of SEQ ID NO:227

LC-CDR2 having the amino acid sequence of SEQ ID NO:238

LC-CDR3 having the amino acid sequence of SEQ ID NO:248.

6. The nucleic acid according to claim 5, wherein the antigen-binding molecule which is capable of binding to CD122 comprises:

a VH region comprising an amino acid sequence having at least 85% sequence identity to SEQ ID NO:1; and a VL region comprising an amino acid sequence having at least 85% sequence identity to SEQ ID NO:35.

7. The nucleic acid according to claim 5, wherein the antigen-binding molecule which is capable of binding to CD132 comprises:

a VH region comprising an amino acid sequence having at least 85% sequence identity to SEQ ID NO:71; and a VL region comprising an amino acid sequence having at least 85% sequence identity to SEQ ID NO:89.

8. The nucleic acid according to claim 5, wherein the antigen-binding molecule which is capable of binding to CD122 and CD132 is capable of reducing expression of PD-1 by T cells.

9. A method of treating a cancer comprising administering to a subject a therapeutically effective amount of an antigen-binding molecule which is capable of binding to CD122 and common γ chain (CD132), comprising:

(a) an antigen-binding molecule which is capable of binding to CD122, comprising:

a heavy chain variable (VH) region incorporating the following CDRs:

HC-CDR1 having the amino acid sequence of SEQ ID NO:103

HC-CDR2 having the amino acid sequence of SEQ ID NO:116

HC-CDR3 having the amino acid sequence of SEQ ID NO:128; and a light chain variable (VL) region incorporating the following CDRs:

LC-CDR1 having the amino acid sequence of SEQ ID NO:145

LC-CDR2 having the amino acid sequence of SEQ ID NO:162

LC-CDR3 having the amino acid sequence of SEQ ID NO:177; and (b) an antigen-binding molecule which is capable of binding to CD132, comprising:

a VH region incorporating the following CDRs:

HC-CDR1 having the amino acid sequence of SEQ ID NO:196

HC-CDR2 having the amino acid sequence of SEQ ID NO:204

HC-CDR3 having the amino acid sequence of SEQ ID NO:212; and a VL region incorporating the following CDRs:

LC-CDR1 having the amino acid sequence of SEQ ID NO:227

LC-CDR2 having the amino acid sequence of SEQ ID NO:238

LC-CDR3 having the amino acid sequence of SEQ ID NO:248.

10. The method according to claim 9, wherein the antigen-binding molecule which is capable of binding to CD122 comprises:

a VH region comprising an amino acid sequence having at least 85% sequence identity to SEQ ID NO:1; and a VL region comprising an amino acid sequence having at least 85% sequence identity to SEQ ID NO:35.

11. The method according to claim 9, wherein the antigen-binding molecule which is capable of binding to CD132 comprises:

a VH region comprising an amino acid sequence having at least 85% sequence identity to SEQ ID NO:71; and a VL region comprising an amino acid sequence having at least 85% sequence identity to SEQ ID NO:89.

12. The method according to claim 9, wherein the antigen-binding molecule which is capable of binding to CD122 and CD132 is capable of reducing expression of PD-1 by T cells.

13. The method according to claim 9, wherein the cancer is selected from the group consisting of: colon cancer, colon carcinoma, colorectal cancer, nasopharyngeal carcinoma, cervical carcinoma, oropharyngeal carcinoma, gastric carcinoma, hepatocellular carcinoma, head and neck cancer, head and neck squamous cell carcinoma (HNSCC), oral cancer, laryngeal cancer, prostate cancer, lung cancer, small cell lung cancer, non-small cell lung cancer, bladder cancer, urothelial carcinoma, melanoma, advanced melanoma, renal cell carcinoma, ovarian cancer and mesothelioma.

14. The method according to claim 9, wherein the antigen binding molecule is administered in combination with a therapeutically effective amount of an antibody or antigen-binding fragment thereof capable of inhibiting signalling mediated by an immune checkpoint protein.

15. The method according to claim 14, wherein the immune checkpoint protein is PD-1, CTLA-4, LAG-3, TIM-3, VISTA, TIGIT or BTLA.

* * * * *